(12) United States Patent
Li et al.

(10) Patent No.: US 9,695,166 B2
(45) Date of Patent: Jul. 4, 2017

(54) PYRAZOLOPYRIDINE PYRAZOLOPYRIMIDINE AND RELATED COMPOUNDS

(71) Applicant: Global Blood Therapeutics, Inc., South San Francisco, CA (US)

(72) Inventors: Zhe Li, South San Francisco, CA (US); Qing Xu, South San Francisco, CA (US); Chul Yu, South San Francisco, CA (US); Calvin Yee, South San Francisco, CA (US); Stephen L. Gwaltney, II, South San Francisco, CA (US); Brian W. Metcalf, South San Francisco, CA (US); Steven Richards, South San Francisco, CA (US); Matthew A. Lardy, South San Francisco, CA (US); Lina Setti, South San Francisco, CA (US); Hing Sham, South San Francisco, CA (US)

(73) Assignee: Global Blood Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 14/703,848

(22) Filed: May 4, 2015

(65) Prior Publication Data

US 2015/0315198 A1  Nov. 5, 2015

Related U.S. Application Data

(60) Provisional application No. 61/988,551, filed on May 5, 2014.

(51) Int. Cl.
| | |
|---|---|
| C07D 471/04 | (2006.01) |
| C07D 487/04 | (2006.01) |
| C07D 519/00 | (2006.01) |
| A61K 31/437 | (2006.01) |
| A61K 31/4162 | (2006.01) |

(52) U.S. Cl.
CPC ......... *C07D 471/04* (2013.01); *C07D 487/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 2006/0211720 A1 | 9/2006 | Glunz et al. | |
| 2009/0234117 A1* | 9/2009 | Kashiwagi | C07D 487/04 544/118 |
| 2010/0331297 A1 | 12/2010 | Bulawa et al. | |
| 2012/0029002 A1 | 2/2012 | Straub et al. | |
| 2012/0088758 A1 | 4/2012 | Hangeland et al. | |
| 2014/0073573 A1 | 3/2014 | Herold et al. | |

FOREIGN PATENT DOCUMENTS

| | | |
|---|---|---|
| IT | 1380428 B1 * | 9/2010 |
| WO | WO-2009/062118 | 5/2009 |
| WO | WO-2011/153588 | 12/2011 |
| WO | WO 2012/066061 A1 * | 5/2012 |
| WO | WO-2013/106254 | 7/2013 |
| WO | WO-2015/022547 | 2/2015 |

OTHER PUBLICATIONS

Taliani et al, J. Med. Chem. 2010, 53, pp. 3954-3963.*
Bocci et al, Chemical Abstracts DN 152:215307, 2010 (Abstract of IT 1380428).*
Baraldi et al., "New 2-Arylpyrazolo[4,3-c]quinoline Derivatives as Potent and Selective Human A3 Adenosine Receptor Antagonists", Journal of Medicinal Chemistry, 2005, vol. 48, pp. 5001-5008.
Bas et al., "A Randomized Trial of Icatibant in ACE-Inhibitor-Induced Angioedema", The New England Journal of Medicine, 2015, 372:418-425.
Bourzat et al., "New method of synthesis of pyrazolo[4,3-c]pyridines", Tetrahedron (1973), 29(2), 441-7.
Clermont et al, "Effects of Plasma Kallikrein on Retinal Vascular Functions in Diabetes", Abstract 5035, ARVO 2010, Fort Lauderdale, Florida.
Losol et al., "Molecular Genetic Mechanisms of Chronic Urticaria", Allergy Asthma Immunol. Res., 2014, vol. 61, pp. 13-21.
Murashima et el., "Preparation of Novel Heteroisoindoles from Nitropyridines and Nitropyridones", Heterocycles, 2002, vol. 58, No. 1, pp. 301-310.
Nzeako et al., "Hereditary Angioedema: a Broad Review for Clinicians FREE", Arch Intern Med., 2001, 161(20):2417-2429.
PCT International Search Report and Written Opinion for PCT/US15/29166 dated Jul. 24, 2015.
PCT International Search Report and Written Opinion for PCT/US15/29115 dated Oct. 23, 2015.
Phipps et al, "Plasma Kallikrein Mediates Angiotensin II Type 1 Receptor-Stimulated Retinal Vascular Permeability", Hypertension, 2009, 53:175-181.
Riad et al., "The Role of the Renal Kallikrein-Kinin System in Diabetic Nephropathy", Current Opinion in Nephrology and Hypertension, 2007, 16(1):22-26.
Storini et al, "Selective Inhibition of Plasma Kallikrein Protects Brain from Reperfusion Injury", The Journal of Pharmacology and Experimental Therapeutics, 2006, 318(2):849-854.

* cited by examiner

*Primary Examiner* — Zinna Northington Davis
(74) *Attorney, Agent, or Firm* — Knobbe, Martens, Olson & Bear, LLP

(57) ABSTRACT

In one aspect this invention relates generally to compounds of Formula:

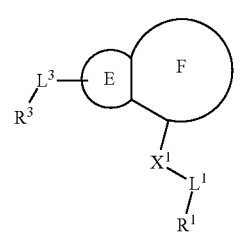

and sub-formulas thereof, or a tautomer of each thereof, a pharmaceutically acceptable salt of each thereof, or a pharmaceutically acceptable solvate of each of the foregoing, where $X^1$, $L^1$, $L^3$, and $R^3$ are described herein.

40 Claims, No Drawings

PYRAZOLOPYRIDINE PYRAZOLOPYRIMIDINE AND RELATED COMPOUNDS

REFERENCE TO RELATED APPLICATIONS

This application claims priority to U.S. provisional application No. 61/988,551 filed May 5, 2014, the content of which is incorporated herein in its entirety by reference.

FIELD OF THE INVENTION

This invention relates generally to compounds of Formula I and subformulas thereof, pharmaceutical compositions comprising the same, and uses thereof.

STATE OF THE ART

Plasma prekallikrein (PK) is an abundant serine protease zymogen in blood that is converted to its catalytically active form, plasma kallikrein (PK), by coagulation factor XIIa (1), and contributes to the innate inflammatory response and intrinsic cascade of blood coagulation (2). The mechanisms that lead to the activation of this pathway in vivo include interactions with poly-phosphates released from activated platelets and deficiency of C1 inhibitor (C1-INH), the primary physiological inhibitor of plasma kallikrein (3,4). PK-mediated cleavage of high-molecular weight kininogen generates the nonapeptide bradykinin (BK), which activates the bradykinin 2 receptor. Subsequent cleavage of BK by carboxypeptidases generates des-Arg$^9$-BK, which activates the B1 receptor. Both B1 and B2 receptors are expressed by vascular, glial, and neuronal cell types, with the highest levels of retinal expression detected in the ganglion cell layer and inner and outer nuclear layers (5, 6). Activation of B1 and B2 receptors causes vasodilation and increases vascular permeability (7-9). Bradykinin and its binding to B2 receptor have been demonstrated to be responsible for most of the symptoms of hereditary angioedema (HAE) (10).

SUMMARY OF THE INVENTION

In one aspect, provided herein is a compound of formula I-Y:

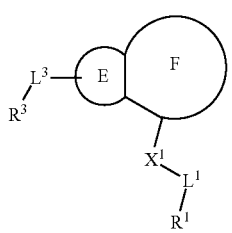

I-Y or a or a tautomer thereof, a pharmaceutically acceptable salt of each thereof, or a pharmaceutically acceptable solvate of each of the foregoing, wherein E and F together are an optionally substituted bicyclic heteroaryl, preferably containing 1-5 nitrogen atoms, or E is an optionally substituted heterocyclyl and F is an optionally substituted heteroaryl; and $X^1$, $L^1$, $L^3$, $R^1$, $R^2$ and $R^3$ are described herein. In some embodiments, $X^1$ is O, S, SO, $SO_2$, and $NR^{15}$, preferably $NR^{15}$, more preferably —NH—;

$R^{15}$ is hydrogen or an amino protective group;
each of $L^1$ and $L^3$ independently is $-(L^{11})_m(CO)_n(L^{12})_o-$ or $-(L^{11})_m$

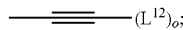

$L^{11}$ and $L^{12}$ each independently are optionally substituted $C_1$-$C_3$ alkylene or optionally substituted $C_1$-$C_3$ heteroalkylene provided that $-X^1-L^1$ does not contain an —O—CO—, —S—CO—, —CO—S—, —S—CO— and such other esterase hydrolyzable moieties in the chain joining $R^1$ to the rest of the compound;
each of m, n, and o is 0 or 1;
each of $R^1$ and $R^3$ is independently:
optionally substituted $C_6$-$C_{10}$ aryl,
optionally substituted 5-10 membered heteroaryl,
optionally substituted 4-15 membered heterocyclyl, or
optionally substituted $C_3$-$C_8$ cycloalkyl.

In one embodiment, E is a five membered ring. In another embodiment, F is a six membered ring. In another embodiment, E contains 3 non-bridging ring atoms, the central or middle ring atom of which is attached to $L_3$-$R_3$.

In various embodiments, provided herein are compounds of Formula I, I-X and I-i and sub-formulas thereof, a tautomer of each thereof, a pharmaceutically acceptable salt of each of the above, or a pharmaceutically acceptable solvate of each of the foregoing, where Formulas I, I-X, and I-I are shown below:

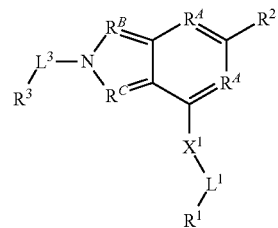

I-X

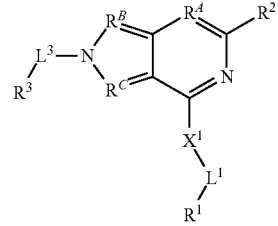

I

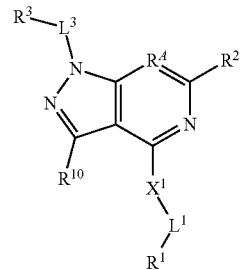

I-i and where $X^1$, $L^1$, $L^3$, $R^A$, $R^B$, $R^C$, $R^1$, $R^2$ and $R^3$ are described herein.

In one aspect, this invention provides a pharmaceutical composition comprising an effective amount of a compound of Formula I, or sub-formulas thereof, and optionally at least one pharmaceutical excipient.

In another aspect, this invention provides a method for inhibiting plasma kallikrein activity in a subject, the method comprising administering to the subject an effective amount of the compound of Formula I, or a pharmaceutical composition thereof.

In another aspect, this invention provides a method for treating a disorder or a disease in a subject mediated by plasma kallikrein, by administering an effective amount of the compound of Formula I, or a pharmaceutical composition thereof, to a patient. Non-limiting disease or disorders include reducing or preventing blood loss, such as, perioperative blood loss due to a surgical procedure performed on the patient In another aspect, provided herein is a method of treating hereditary angioedema comprising administering to a patient in need thereof a therapeutically effective amount of a compound provided herein, or a pharmaceutically acceptable composition provided herein.

In yet another aspect, this invention provides a method for synthesizing the compound of Formula I, or sub-formulas thereof.

DETAILED DESCRIPTION

It is to be understood that this invention is not limited to particular embodiments described. It is also to be understood that the terminology used herein is for the purpose of describing particular embodiments only, and is not intended to be limiting, since the scope of the present invention will be limited only by the appended claims.

Definitions

Unless defined otherwise, all technical and scientific terms used herein have the same meaning as commonly understood by one of ordinary skill in the art to which this invention belongs. As used herein the following terms have the following meanings.

It must be noted that as used herein and in the appended claims, the singular forms "a", "an", and "the" include plural referents unless the context clearly dictates otherwise. Thus, for example, reference to "an excipient" includes a plurality of excipients.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations. Each numerical parameter should at least be construed in light of the number of reported significant digits and by applying ordinary rounding techniques.

As used herein, $C_m$-$C_n$, such as $C_1$-$C_{10}$, $C_1$-$C_6$, or $C_1$-$C_4$ when used before a group refers to that group containing m to n carbon atoms.

The term "alkyl" refers to monovalent saturated aliphatic hydrocarbyl groups having from 1 to 25 carbon atoms (i.e., $C_1$-$C_{25}$ alkyl) or 1 to 6 carbon atoms (i.e., $C_1$-$C_6$ alkyl), or 1 to 4 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). Alkyl substituted with a substituent refers to an alkyl group that is substituted with up to 5, preferably up to 4, and still more preferably up to 3 substituents, and includes alkyl groups substituted with 1 or 2 substituents. The term "alkyl" encompasses the term "cycloalkyl" described below.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

The terms "alkylene" alone or as part of another substituent means a divalent radical derived from an alkyl or cycloalkyl group as exemplified by —$CH_2CH_2CH_2CH_2$—. For alkylene groups, no orientation of the linking group is implied.

The term "alkenyl" refers to monovalent aliphatic hydrocarbyl groups having from 2 to 25 carbon atoms or 2 to 6 carbon atoms and 1 or more, preferably 1, carbon carbon double bond. Examples of alkenyl include vinyl, allyl, dimethyl allyl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Alkynyl" refers to straight or branched monovalent hydrocarbyl groups having from 2 to 6 carbon atoms and preferably 2 to 3 carbon atoms and having at least 1 and preferably from 1to 2 sites of acetylenic (—C≡C—) unsaturation. Examples of such alkynyl groups include acetylenyl (—C≡CH), and propargyl (—CH$_2$C≡CH). C$_x$ alkynyl refers to an alkynyl group having x number of carbon atoms.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

The term "alkoxy" refers to —O-alkyl, where alkyl is as defined above.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group CH$_3$C(O)—.

"Acylamino" refers to the groups —NR$^{300}$C(O)alkyl, —NR$^{300}$C(O)substituted alkyl, —NR$^{300}$C(O)cycloalkyl, —NR$^{300}$C(O)substituted cycloalkyl, —N R$^{300}$C(O)alkenyl, —NR$^{300}$C(O)substituted alkenyl, alkoxy, substituted alkoxy-NR$^{300}$C(O)alkynyl, —NR$^{300}$C(O)substituted alkynyl, —NR$^{300}$C(O)aryl, —NR$^{300}$C(O)substituted aryl, —NR$^{300}$C(O)heteroaryl, —NR$^{300}$C(O)substituted heteroaryl, —NR$^{300}$C(O)heterocyclic, and —NR$^{300}$C(O)substituted heterocyclic wherein R$^{300}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Substituted amino" refers to the group —NR$^{310}$R$^{320}$ where R$^{310}$ and R$^{320}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein R$^{310}$ and R$^{320}$ are optionally joined, together with the nitrogen bound thereto to form a heterocyclic or substituted heterocyclic group, provided that R$^{310}$ and R$^{320}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When R$^{310}$ is hydrogen and R$^{320}$ is alkyl, the substituted amino group is sometimes referred to herein as alkylamino. When R$^{310}$ and R$^{320}$ are alkyl, the substituted amino group is sometimes referred to herein as dialkylamino. When referring to a monosubstituted amino, it is meant that either R$^{310}$ or R$^{320}$ is hydrogen but not both. When referring to a disubstituted amino, it is meant that neither R$^{310}$ nor R$^{320}$ are hydrogen.

"Aminocarbonyl" refers to the group —C(O)NR$^{330}$R$^{340}$ where R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where R$^{330}$ and R$^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{330}$R$^{340}$ where R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{330}$ and R$^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{300}$C(O) NR$^{330}$R$^{340}$ where R$^{300}$ is hydrogen or alkyl and R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{330}$ and R$^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{300}$C(S)NR$^{330}$R$^{340}$ where R$^{300}$ is hydrogen or alkyl and R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O) NR$^{330}$R$^{340}$ where R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{330}$R$^{340}$ where R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{330}$R$^{340}$ where R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{330}$ and R$^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{300}$—SO$_2$NR$^{330}$R$^{340}$ where R$^{300}$ is hydrogen or alkyl and R$^{330}$ and R$^{340}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{330}$ and R$^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{350}$)NR$^{330}$R$^{340}$ where R$^{330}$, R$^{340}$, and R$^{350}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{330}$ and R$^{340}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aryl" refers to a monovalent, aromatic mono- or bicyclic ring having 6-10 ring carbon atoms. Examples of aryl include phenyl and naphthyl. The condensed ring may or may not be aromatic provided that the point of attachment is at an aromatic carbon atom. For example, and without limitation, the following is an aryl group:

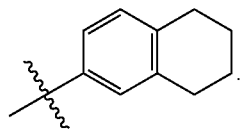 [SMILES: *c1ccc2c(c1)CCCC2]

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{300}$—C(O)O-alkyl, —NR$^{300}$—C(O)O-substituted alkyl, —NR$^{300}$—C(O)O-alkenyl, —NR$^{300}$—C(O)O-substituted alkenyl, —NR$^{300}$—C(O)O-alkynyl, —NR$^{300}$—C(O)O-substituted alkynyl, —NR$^{300}$—C(O)O-aryl, —NR$^{300}$—C(O)O-substituted aryl, —NR$^{300}$—C(O)O-cycloalkyl, —NR$^{300}$—C(O)O-substituted cycloalkyl, —NR$^{300}$—C(O)O-heteroaryl, —NR$^{300}$—C(O)O-substituted heteroaryl, —NR$^{300}$—C(O)O-heterocyclic, and —NR$^{300}$—C(O)O-substituted heterocyclic wherein R$^{300}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "cycloalkyl" refers to a monovalent, preferably saturated, hydrocarbyl mono-, bi-, or tricyclic ring having 3-12 ring carbon atoms. While cycloalkyl, refers preferably to saturated hydrocarbyl rings, as used herein, it also includes rings containing 1-2 carbon-carbon double bonds. Nonlimiting examples of cycloalkyl include cyclopropyl, cyclobutyl, cyclopentyl, cyclohexyl, cycloheptyl, adamentyl, and the like. The condensed rings may or may not be non-aromatic hydrocarbyl rings provided that the point of attachment is at a cycloalkyl carbon atom. For example, and without limitation, the following is a cycloalkyl group:

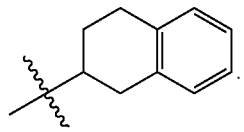

defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{360}$C(=NR$^{360}$)N(R$^{360}$)$_2$ where each R$^{360}$ is independently selected from the group consisting of hydrogen, alkyl, substituted alkyl, aryl, substituted aryl, heteroaryl, substituted heteroaryl, heterocyclic, and substituted heterocyclic and two R$^{360}$ groups attached to a common guanidino nitrogen atom are optionally joined together with the nitrogen bound thereto to form a heterocyclic or substituted heterocyclic group, provided that at least one R$^{360}$ is not hydrogen, and wherein said substituents are as defined herein.

The term "heteroaryl" refers to a monovalent, aromatic mono-, bi-, or tricyclic ring having 2-16 ring carbon atoms and 1-8 ring heteroatoms selected preferably from N, O, S, and P and oxidized forms of N, S, and P, provided that the ring contains at least 5 ring atoms. Nonlimiting examples of heteroaryl include furan, imidazole, oxadiazole, oxazole, pyridine, quinoline, and the like. The condensed rings may or may not be a heteroatom containing aromatic ring provided that the point of attachment is a heteroaryl atom. For example, and without limitation, the following is a heteroaryl group:

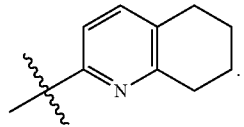

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

The term "heterocyclyl" or heterocycle refers to a non-aromatic, mono-, bi-, or tricyclic ring containing 2-12 ring carbon atoms and 1-8 ring heteroatoms selected preferably from N, O, S, and P and oxidized forms of N, S, and P, provided that the ring contains at least 3 ring atoms. While heterocyclyl preferably refers to saturated ring systems, it also includes ring systems containing 1-3 double bonds, provided that the ring is non-aromatic. Nonlimiting examples of heterocyclyl include, azalactones, oxazoline, piperidinyl, piperazinyl, pyrrolidinyl, tetrahydrofuranyl, and tetrahydropyranyl. The condensed rings may or may not contain a non-aromatic heteroatom containing ring provided that the point of attachment is a heterocyclyl group. For example, and without limitation, the following is a heterocyclyl group:

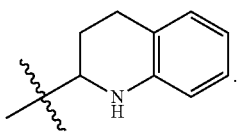 [SMILES: *C1CCc2ccccc2N1]

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Non-limiting examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

The term "hydrolyzing" refers to breaking an $R^H$—O—CO—, $R^H$—O—CS—, or an $R^H$—O—SO$_2$— moiety to an $R^H$—OH, preferably by adding water across the broken bond. A hydrolyzing is performed using various methods well known to the skilled artisan, non limiting examples of which include acidic and basic hydrolysis.

The terms "alkenylene" and "arylene" alone or as part of another substituent means a divalent radical derived from an alkenyl or aryl group, respectively. For, alkenylene and arylene linking groups are contemplated to be used together with, or instead of, alkylene linking groups in some embodiments; no orientation of the linking group is implied.

The term "halo" refers to F, Cl, Br, and I.

The term "nitro" refers to —NO$_2$.

The term "cyano" refers to —CN.

The term "oxo" refers to a C=O group, and to a substitution of 2 geminal hydrogen atoms with a C=O group.

"Spiro ring systems" refers to bicyclic ring systems that have a single ring carbon atom common to both rings.

"Sulfinyl" refers to the divalent group —SO—.

"Sulfonyl" refers to the divalent group —S(O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

An "amino-protecting group," as used herein, is attached to a nitrogen atom. An amino protecting group is well known in the art and includes those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable amino protecting groups include carbamates such as methyl carbamate, ethyl carbamate, 9-fluorenylmethyl carbamate (Fmoc), benzyl carbamate (Cbz), t-butyl carbamate (BOC), 9-(2-sulfo)fluorenylmethyl carbamate, 9-(2,7-dibromo)fluorenylmethyl carbamate, 2,7-di-t-butyl-[9-(10,10-dioxo-10, 10,10,10-tetrahydrothioxanthyl)]methyl carbamate (DBD-Tmoc), 4-methoxyphenacyl carbamate (Phenoc), 2,2,2-trichloroethyl carbamate (Troc); amides such as formamide, acetamide, chloroacetamide, trichloroacetamide, trifluoroacetamide, phenylacetamide; N-phthalimide, N-dithiasuccinimide (Dts), N-2,3-diphenylmaleimide, N-2,5-dimethylpyrrole, N-benzylamine, N-triphenylmethylamine (Tr); eneamines such as N-1,1-dimethylthiomethyleneamine, N-benzylideneamine, N-p-methoxybenzylideneamine; enamides such as benzenesulfenamide, o-nitrobenzenesulfenamide (Nps), 2,4-dinitrobenzenesulfenamide, pentachlorobenzenesulfenamide; and sulfonamides such as p-toluenesulfonamide (Ts), benzenesulfonamide, 2,3,6,-trimethyl-4-methoxybenzenesulfonamide (Mtr).

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (NO) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The group may be substituted with one or more substituents, such as e.g., 1, 2, 3, 4 or 5 substituents. Preferably, the substituents are selected from the functional groups provided herein. In certain more preferred embodiments, "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, NO$_2$, —N$_2$+, —CO$_2$R$^{100}$, —OR$^{100}$, —SR$^{100}$, —SOR$^{100}$, —SO$_2$R$^{100}$, —NR$^{100}$R$^{102}$, —CONR$^{101}$R$^{102}$, —SO$_2$NR$^{101}$R$^{102}$, C$_1$-C$_6$alkyl, C$_1$-C$_6$ haloalkyl, C$_1$-C$_6$ alkoxy, —CR$^{100}$=C(R$^{100}$)$_2$, —CCR$^{100}$, C$_3$-C$_{10}$ cycloalkyl, C$_3$-C$_{10}$ heterocyclyl, C$_6$-C$_{12}$ aryl and C$_2$-C$_{12}$ heteroaryl, wherein each R$^{100}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each alkyl, cycloalkyl, heterocyclyl, aryl, or heteroaryl is optionally substituted with 1-3 halo, 1-3 C$_1$-C$_6$ alkyl, 1-3 C$_1$-C$_6$ haloalkyl or 1-3 C$_1$-C$_6$ alkoxy groups. Preferably, the substituents are selected from the group consisting of chloro, fluoro, —OCH$_3$, methyl, ethyl, iso-propyl, cyclopropyl, vinyl, ethynyl, —CO$_2$H, —CO$_2$CH$_3$, —OCF$_3$, —CF$_3$, —OCHF$_2$.

R$^{101}$ and R$^{102}$ independently is hydrogen; C$_1$-C$_8$ alkyl, optionally substituted with —CO$_2$H or an ester thereof, C$_1$-C$_6$ alkoxy, oxo, —CR$^{103}$=C(R$^{103}$)$_2$, —CCR, C$_3$-C$_{10}$ cycloalkyl, C$_3$-C$_{10}$ heterocyclyl, C$_6$-C$_{12}$ aryl, or C$_2$-C$_{12}$ heteroaryl, wherein each R$^{103}$ independently is hydrogen or C$_1$-C$_8$ alkyl; C$_3$-C$_{12}$ cycloalkyl; C$_3$-C$_{10}$ heterocyclyl; C$_6$-C$_{12}$ aryl; or C$_2$-C$_{12}$ heteroaryl; wherein each cycloalkyl, heterocyclyl, aryl, or heteroaryl is optionally substituted with 1-3 alkyl groups or 1-3 halo groups, or R$^{101}$ and R$^{102}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

The term "pharmaceutically acceptable" refers to safe and non-toxic for in vivo, preferably, human administration. The term "pharmaceutically acceptable salt" refers to a salt that is pharmaceutically acceptable. The term "salt" refers to an ionic compound formed between an acid and a base. When the compound provided herein contains an acidic functionality, such salts include, without limitation, alkai metal, alkaline earth metal, and ammonium salts. As used herein, ammonium salts include, salts containing protonated nitrogen bases and alkylated nitrogen bases. Exemplary, and non-limiting cations useful in pharmaceutically acceptable salts include Na, K, Rb, Cs, NH$_4$, Ca, Ba, imidazolium, and ammonium cations based on naturally occurring amino acids. When the compounds utilized herein contain basic functionality, such salts include, without limitation, salts of organic acids, such as caroboxylic acids and sulfonic acids, and mineral acids, such as hydrogen halides, sulfuric acid, phosphoric acid, and the likes. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the likes.

As used herein, the term "treatment" or "treating" means any treatment of a disease or condition in a patient, including one or more of:

preventing or protecting against the disease or condition, that is, causing the clinical symptoms not to develop, for example, in a subject at risk of suffering from such a disease or condition, thereby substantially averting onset of the disease or condition;

inhibiting the disease or condition, that is, arresting or suppressing the development of clinical symptoms; and/or relieving the disease or condition that is, causing the regression of clinical symptoms.

Compounds

In one aspect, this invention provides a compound of formula I-X, I, or I-i:

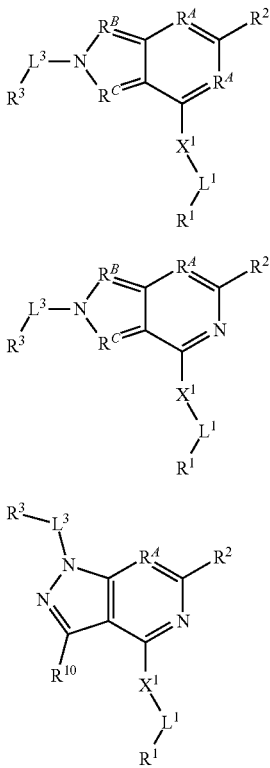

or a tautomer thereof, a pharmaceutically acceptable salt of each thereof, or a pharmaceutically acceptable solvate of each of the foregoing, wherein each of $R^A$, $R^B$ and $R^C$ independently is N or $CR^{10}$, preferably if one of $R^B$ and $R^C$ is N, the other is $CR^{10}$;

$R^{10}$ is hydrogen, halo, preferably fluoro, hydroxy, optionally substituted $C_1$-$C_6$, preferably $C_1$-$C_4$ alkoxy, or an optionally substituted $C_1$-$C_6$ alkyl, preferably with a single hydroxy or a carboxyl ester thereof, $CO_2H$ or a hydroxy ester thereof, $CON(R^{25})_2$, or $SO_2N(R^{25})_2$, more preferably, $R^{10}$ is —$CH_2OH$;

each $R^{25}$ is independently hydrogen or $C_1$-$C_6$ alkyl optionally substituted with 1-5 halo, preferably fluoro groups, or the two $R^{25}$ groups together with the nitrogen atom they are bonded to forms a: 4-15 membered heterocycle containing up to 5 ring heteroatoms, wherein the heteroatom is selected from the group consisting of O, N, S, and oxidized forms of N and S; preferably, a 4-7 membered heterocycle containing 2, or more preferably, a single, ring heteroatoms; wherein the heterocycle is optionally substituted, preferably, with 1-3, more preferably a single, group selected from optionally substituted $C_1$-$C_6$ alkyl, preferably $C_1$-$C_6$ alkyl;

$X^1$ is O, S, SO, $SO_2$, and $NR^{15}$, preferably $NR^{15}$, more preferably —NH—;

$R^{15}$ is hydrogen or an amino protective group;

each of $L^1$ and $L^3$ independently is -$(L^{11})_m(CO)_n(L^{12})_o$- or $(L^{11})_m$

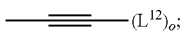

$L^{11}$ and $L^{12}$ each independently are optionally substituted $C_1$-$C_3$ alkylene or $C_1$-$C_3$ heteroalkylene provided that —$X^1L^1$ does not contain an —O—CO—, —S—CO—, —CO—S—, —S—CO— and such other esterase hydrolyzable moieties in the chain joining $R^1$ to the rest of the compound;

each of m, n, and o is 0 or 1;

each of $R^1$ and $R^3$ is independently $C_6$-$C_{10}$ aryl, 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S, or a $C_3$-$C_8$ cycloalkyl, wherein the aryl, heteroaryl, heterocyclyl, or cycloalkyl group is optionally substituted, preferably, with 1-3 substituents selected from =O, substituted amino, preferably $NR^{60}R^{61}$, or —$NH_2$, —$C_1$-$C_6$ alkylamino, aminocarbonylamino, aminocarbonyl, acylamino, carboxylic acid or an ester thereof, substituted sulfonyl, —CN,

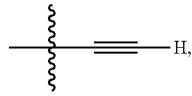

vinyl, halo, optionally substituted $C_1$-$C_6$ alkoxy, —OH, —O—$C_3$-$C_8$ cycloalkyl, —O-(5-10 membered heteroaryl as defined above), —O-(4-15 membered heterocyclyl as defined above) —O—$C_6$-$C_{10}$ aryl, optionally substituted $C_1$-$C_6$alkyl, preferably substituted with an amino or 1-5 fluoro groups, more preferably methyl, $C_6$-$C_{10}$ aryl, 5-10 membered heteroaryl optionally substituted with a halo group, 4-15 membered heterocyclyl, and $C_3$-$C_8$ cycloalkyl substituents, and/or where adjacent positions on a substituted aryl, heteroaryl, heterocyclyl, or cyckloalkyl of $R^1$ and $R^3$ are substituted with $R^{50}$ and $R^{51}$ substituents, such that, for an aryl, $R^{50}$ and $R^{51}$ together with the intervening atoms form an optionally substituted 5-6 membered heteroaryl containing up to 2 heteroatoms, an optionally substituted 5-6 membered heterocycle containing up to 2 heteroatoms, or an optionally substituted 5-6 membered cycloalkyl group;

for a heteroaryl, $R^{50}$ and $R^{51}$ together with the intervening atoms form an optionally substituted phenyl, an optionally substituted 5-6 membered heterocycle containing up to 2 heteroatoms, or an optionally substituted 5-6 membered cycloalkyl group;

for a heterocyclyl, $R^{50}$ and $R^{51}$ together with the intervening atoms form an optionally substituted phenyl, an optionally substituted 5-6 membered heteroaryl containing up to 2 heteroatoms, or an optionally substituted 5-6 membered cycloalkyl group;

for a cycloalkyl, $R^{50}$ and $R^{51}$ together with the intervening atoms form an optionally substituted phenyl, an optionally substituted 5-6 membered heteroaryl containing up to 2 heteroatoms, or an optionally substituted 5-6 membered heterocyle containing up to 2 heteroatoms;

preferably for an aryl, $R^{50}$ and $R^{51}$ together with the intervening atoms form a 5-6 membered heteroaryl containing up to 2 heteroatoms, a 5-6 membered heterocycle containing up to 2 heteroatoms, or a 5-6 membered cycloalkyl group each optionally substituted with 1-3 halo, —$NH_2$, and/or $C_1$-$C_6$ alkyl group;

preferably for a heteroaryl, $R^{50}$ and $R^{51}$ together with the intervening atoms form a phenyl, a 5-6 membered heterocycle containing up to 2 heteroatoms, or a 5-6 membered cycloalkyl group each optionally substituted with 1-3 halo, —NH$_2$, and/or C$_1$-C$_6$ alkyl group;

preferably for a heterocyclyl, R$^{50}$ and R$^{51}$ together with the intervening atoms form a phenyl, a 5-6 membered heteroaryl containing up to 2 heteroatoms, or a 5-6 membered cycloalkyl group each optionally substituted with 1-3 halo, —NH$_2$, and/or C$_1$-C$_6$ alkyl group;

preferably for a cycloalkyl, R$^{50}$ and R$^{51}$ together with the intervening atoms form a phenyl, a 5-6 membered heteroaryl containing up to 2 heteroatoms, or a 5-6 membered heterocyle containing up to 2 heteroatoms each optionally substituted with 1-3 halo, —NH$_2$, and/or C$_1$-C$_6$ alkyl group;

each R$^{60}$ and R$^{61}$ independently is selected from hydrogen, optionally substituted C$_1$-C$_6$ alkyl, optionally substituted C$_3$-C$_8$ cycloalkyl, optionally substituted 4-15 membered heterocyclyl, or R$^{60}$ and R$^{61}$ together with the nitrogen atom they are bonded to form an optionally substituted 4-15 membered heterocyclyl;

R$^2$ is hydrogen, -halo O—R$^{30}$, —NR$^{31}$R$^{32}$, —CO$_2$R$^{30}$, —CONR$^{31}$R$^{32}$, C$_6$-C$_{10}$ aryl, COR$^{30}$, cyano, a 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S, or a C$_3$-C$_8$ cycloalkyl, wherein the aryl, heteroaryl, heterocyclyl, or cycloalkyl group is optionally substituted;

R$^{30}$ is hydrogen, optionally substituted C$_1$-C$_6$ alkyl, C$_3$-C$_8$ cycloalkyl, C$_6$-C$_{10}$ aryl, a 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S;

R$^{31}$ is hydrogen, optionally substituted C$_1$-C$_6$ alkyl, or an amino protecting group; or R$^{32}$ and R$^{31}$ together with the nitrogen atom they are bonded to forms an optionally substituted 4-15 membered heterocyclyl containing up to 5 ring heteroatoms, wherein the heteroatom is selected from the group consisting of O, N, S, and oxidized forms of N and S; and R$^{32}$ is hydrogen or optionally substituted C$_1$-C$_6$ alkyl.

In one embodiment, L$^1$ and L$^3$ independently is -(L$^{11}$)$_m$(CO)$_n$(L$^{12}$)$_o$-.

In one embodiment, each of R$^1$ and R$^3$ is independently C$_6$-C$_{10}$ aryl, 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S, or a C$_3$-C$_8$ cycloalkyl, wherein the aryl, heteroaryl, heterocyclyl, or cycloalkyl group is optionally substituted, preferably, with 1-3 substituents selected from amino or —NH$_2$, halo, C$_1$-C$_6$ alkoxy, —O—C$_3$-C$_8$ cycloalkyl, —O-(5-10 membered heteroaryl as defined above), —O-(4-15 membered heterocyclyl as defined above) —O—C$_6$-C$_{10}$ aryl, optionally substituted C$_1$-C$_6$alkyl preferably methyl, C$_6$-C$_{10}$ aryl, and 5-10 membered heteroaryl optionally substituted with a halo group, 4-15 membered heterocyclyl, and C$_3$-C$_8$ cycloalkyl substituents, and/or where adjacent positions on a substituted aryl, heteroaryl, heterocyclyl, or cyckloalkyl of R$^1$ and R$^3$ are substituted with R$^{50}$ and R$^{51}$ substituents, In another embodiment, the optionally substituted C$_1$-C$_6$ alkoxy is preferably substituted with 1-5, more preferably, 2-3 fluoro groups; —OCHF$_2$, —OCF$_3$, -oxo, carboxylic acid or an ester thereof.

In another embodiment, R$^2$ is hydrogen, —O—R$^{30}$, —NR$^{31}$R$^{32}$, C$_6$-C$_{10}$ aryl, a 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S, or a C$_3$-C$_8$ cycloalkyl, wherein the aryl, heteroaryl, heterocyclyl, or cycloalkyl group is optionally substituted.

In another embodiment, R$^{30}$ is optionally substituted C$_1$-C$_6$ alkyl, C$_3$-C$_8$ cycloalkyl, C$_6$-C$_{10}$ aryl, a 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S;

In another embodiment, R$^{31}$ is hydrogen or an amino protecting group; or R$^{30}$ and R$^{31}$ together with the nitrogen atom they are bonded to forms an optionally substituted 4-15 membered heterocyclyl containing up to 5 ring heteroatoms, wherein the heteroatom is selected from the group consisting of O, N, S, and oxidized forms of N and S; and In another embodiment, R$^{32}$ is optionally substituted C$_1$-C$_6$ alkyl.

In some embodiments, provided herein are compounds and intermediates where the X$^1$-L$^1$-R$^1$ moiety in compounds of formula I-X, I or I-i are replaced with a halo, preferably, chloro, group or an NH$_2$ group.

In some embodiments, R$^A$ is N. In some embodiments, R$^A$ is CR$^{10}$, preferably CH. In some embodiments, R$^B$ is N. In some embodiments, R$^B$ is CR$^{10}$, preferably CH. In some embodiments, R$^C$ is N. In some embodiments, R$^C$ is CR$^{10}$, preferably CH. Preferably if one of R$^B$ and R$^C$ is N, the other is CR$^{10}$, preferably CH.

In some embodiments, R$^{10}$ is hydrogen. In some embodiments, R$^{10}$ is halo, preferably fluoro. In some embodiments, R$^{10}$ is hydroxy. In some embodiments, R$^{10}$ is optionally substituted C$_1$-C$_6$, preferably C$_1$-C$_4$ alkoxy. In some embodiments, R$^{10}$ is an optionally substituted C$_1$-C$_6$ alkyl, such as —CH$_2$—, preferably with a single hydroxy or a carboxyl ester thereof, CO$_2$H or a hydroxy ester thereof, CON(R$^{25}$)$_2$, or SO$_2$N(R$^{25}$)$_2$. More preferably, R$^{10}$ is —CH$_2$OH.

In some embodiments, each R$^{25}$ is hydrogen. In some embodiments, each R$^{25}$ is C$_1$-C$_6$ alkyl, such as methyl, ethyl, propyl or butyl, optionally substituted with 1-5 halo, preferably fluoro groups. In some embodiments, two R$^{25}$ groups together with the nitrogen atom they are bonded to form a: 4-15 membered heterocycle containing up to 5 ring heteroatoms, wherein the heteroatom is selected from the group consisting of O, N, S, and oxidized forms of N and S; preferably, a 4-7 membered heterocycle containing 2, or more preferably, a single, ring heteroatoms; wherein the heterocycle is optionally substituted, preferably, with 1-3, more preferably a single, group selected from optionally substituted C$_1$-C$_6$ alkyl, preferably C$_1$-C$_6$ alkyl, such as methyl, ethyl, propyl or butyl;

In some embodiments, X$^1$ is O. In some embodiments, X$^1$ is S. In some embodiments, X$^1$ is SO. In some embodiments, X$^1$ is SO$_2$. In some embodiments, X$^1$ is preferably NR$^{15}$ and more preferably —NH—.

In some embodiments, $R^{15}$ is hydrogen. In some embodiments, $R^{15}$ is an amino protective group.

In some embodiments, each $L^1$ and $L^3$ is independently is -$(L^{11})_m(CO)_n(L^{12})_o$-. In some embodiments, $L^1$ is —CH$_2$—. In some embodiments, $L^1$ is —CHR$^{70}$—, wherein $R^{70}$ is hydrogen or optionally substituted $C_1$-$C_6$ alkyl. In some embodiments, $L^1$ is —CHMe-. In some embodiments, $L^1$ is —CO—. In some embodiments, $L^3$ is —CH$_2$—. In some embodiments, $L^3$ is —CHR$^{70}$-. In some embodiments, $L^3$ is —CHMe-.

In some embodiments, $R^{70}$ is hydrogen. In some embodiment, $R^{70}$ is optionally substituted $C_1$-$C_6$ alkyl, preferably methyl.

In some embodiments, $L^{11}$ and/or $L^{12}$ are optionally substituted $C_1$-$C_3$ alkylene. In some embodiments, $L^{11}$ and/or $L^{12}$ are $C_1$-$C_3$ heteroalkylene provided that —$X^1$-$L^1$ does not contain an —O—CO—, —S—CO—, —CO—S—, —S—CO— and such other esterase hydrolyzable moieties in the chain joining $R^1$ to the rest of the compound.

In some embodiments, m is 0. In some embodiments, m is 1. In some embodiments, n is 0. In some embodiments, n is 1. In some embodiments, o is 0. In some embodiments, o is 1.

In some embodiments, $R^1$ is an optionally substituted $C_6$-$C_{10}$ aryl. In some embodiments, $R^1$ is an optionally substituted 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S. In some embodiment, $R^1$ is substituted with 1-5, preferably, 1-4, more preferably, 1-3 substituents. In some embodiments, the substituents are selected from: —NH$_2$; NHCH$_3$; =O; O—R$^{30}$; cyano;

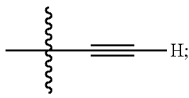

optionally substituted heteroaryl, preferably, an optionally substituted 5-6 membered heteroaryl; optionally substituted $C_1$-$C_6$ alkyl, preferably $C_1$-$C_3$ alkyl optionally substituted with 1-5 halo, or an amino group; optionally substituted $C_1$-$C_6$ alkoxy; halo; $C_3$-$C_8$, preferably $C_3$-$C_4$ cycloalkyl; . In some embodiments, $R^1$ is a $C_3$-$C_8$ cycloalkyl.

In some embodiments, $R^3$ is a substituted $C_6$-$C_{10}$ aryl. In some embodiments, $R^3$ is an unsubstituted $C_6$-$C_{10}$ aryl. In some embodiments, $R^3$ is an optionally substituted 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S. In some embodiments, $R^3$ is a $C_3$-$C_8$ cycloalkyl. In some embodiment, $R^3$ is substituted with 1-5, preferably, 1-4, more preferably, 1-3 substituents. In some embodiments, the substituents are selected from: $C_1$-$C_6$ alkyl, optionally substituted with 1-5 halo, preferably fluoro substituents, optionally substituted 5-10 membered heteroaryl containing up to 3 ring heteroatoms, wherein the heteroatom is selected from the group consisting of O, N, S, and oxidized forms of N and S, optionally substituted $C_6$-$C_{10}$ aryl, 4-15 membered heterocyclyl containing up to 5 ring heteroatoms, wherein the heteroatom is selected from the group consisting of O, N, S, and oxidized forms of N and S; halo, preferably, fluoro; hydroxy; oxo; —NR$^{31}$R$^{32}$,OCH$_3$; NHCH$_3$; =O; O—R$^{30}$;

In some embodiments, the aryl, heteroaryl, heterocyclyl, or cycloalkyl group for $R^1$ or $R^3$ is unsubstituted. In some embodiments, the aryl, heteroaryl, heterocyclyl, or cycloalkyl group for $R^1$ or $R^3$ is substituted, preferably, with 1-3 substituents selected from amino or —NH$_2$, halo, $C_1$-$C_6$ alkoxy, —O—$C_3$-$C_8$ cycloalkyl, —O-(5-10 membered heteroaryl as defined herein), —O-(4-15 membered heterocyclyl as defined herein), —O—$C_6$-$C_{10}$ aryl, optionally substituted $C_1$-$C_6$alkyl preferably methyl, $C_6$-$C_{10}$ aryl, and 5-10 membered heteroaryl optionally substituted with a halo group, 4-15 membered heterocyclyl, and $C_3$-$C_8$ cycloalkyl substituents.

In some embodiments, $R^3$ is $C_6$-$C_{10}$ aryl or 5-10 membered heteroaryl optionally substituted with 1-2 $C_1$-$C_6$ alkyl groups.

In some embodiments, $R^3$ is pyridyl optionally substituted with 1-2 substituents, preferably, a single substituent, selected from amino, halo, $C_1$-$C_6$ alkoxy, —O—$C_3$-$C_8$ cycloalkyl, —O-(5-10 membered heteroaryl), —O—$C_6$-$C_{10}$ aryl, optionally substituted $C_1$-$C_6$ alkyl, preferably, methyl, $C_6$-$C_{10}$ aryl, 5-10 membered heteroaryl, a 4-15 membered heterocyclyl, and $C_3$-$C_8$ cycloalkyl substituents.

In some embodiments, adjacent positions on the substituted aryl, heteroaryl, heterocyclyl, or cyckloalkyl are substituted with $R^{50}$ and $R^{51}$ substituents. In some embodiments, for an aryl, $R^{50}$ and $R^{51}$ together with the intervening atoms form a 5-6 membered heteroaryl containing up to 2 heteroatoms, a 5-6 membered heterocycle containing up to 2 heteroatoms, or a 5-6 membered cycloalkyl group each optionally substituted with 1-3 halo, —NH$_2$, and/or $C_1$-$C_6$ alkyl group, such as methyl, ethyl, propyl or butyl. In some embodiments, for a heteroaryl, $R^{50}$ and $R^{51}$ together with the intervening atoms form a phenyl, a 5-6 membered heterocycle containing up to 2 heteroatoms, or a 5-6 membered cycloalkyl group each optionally substituted with 1-3 halo, —NH$_2$, and/or $C_1$-$C_6$ alkyl group, such as methyl, ethyl, propyl or butyl. In some embodiments, for a heterocyclyl, $R^{50}$ and $R^{51}$ together with the intervening atoms form a phenyl, a 5-6 membered heteroaryl containing up to 2 heteroatoms, or a 5-6 membered cycloalkyl group each optionally substituted with 1-3 halo, —NH$_2$, and/or $C_1$-$C_6$ alkyl group, such as methyl, ethyl, propyl or butyl. In some embodiments, for a cycloalkyl, $R^{50}$ and $R^{51}$ together with the intervening atoms form a phenyl, a 5-6 membered heteroaryl containing up to 2 heteroatoms, or a 5-6 membered heterocyle containing up to 2 heteroatoms each optionally substituted with 1-3 halo, —NH$_2$, and/or $C_1$-$C_6$ alkyl group, such as methyl, ethyl, propyl or butyl.

In some embodiments, $R^2$ is hydrogen. In some embodiments, $R^2$ is —O—R$^{30}$, where $R^{30}$ is as defined above. In some embodiments, $R^2$ is —NR$^{31}$R$^{32}$, where $R^{31}$ and $R^{32}$ are as defined above. In some embodiments, $R^2$ is —NHR$^{32}$. In some embodiments, $R^2$ is $C_6$-$C_{10}$ aryl. In some embodiments, $R^2$ is NMe$_2$. In some embodiments, $R^2$ is CN. In some embodiments, $R^2$ is COOH. In some embodiments, $R^2$ is CONR$^{31}$R$^{32}$, where $R^{31}$ and $R^{32}$ are defined as above. In some embodiments, $R^2$ is a 5-10 membered heteroaryl containing up to 3 ring heteroatoms, wherein the heteroatom is selected from the group consisting of O, N, S, and oxidized forms of N and S, a 4-15 membered heterocyclyl containing up to 5 ring heteroatoms, wherein the heteroatom is selected from the group consisting of O, N, S, and oxidized forms of N and S. In some embodiments, $R^2$ is $C_3$-$C_8$ cycloalkyl. In some embodiments, the aryl, heteroaryl, heterocyclyl, or cycloalkyl group is substituted. In some embodiments, the aryl, heteroaryl, heterocyclyl, or cycloalkyl group is unsubstituted.

In some embodiments, $R^2$ is selected from the group of structures shown below:

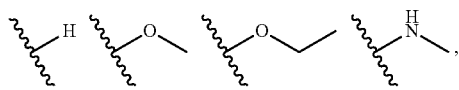

OH, CN, COOH, $NMe_2$.

In some embodiments, $R^{30}$ is hydrogen. In some embodiments, $R^{30}$ is optionally substituted $C_1$-$C_6$ alkyl, such as methyl, ethyl, propyl or butyl. In some embodiments, $R^{30}$ is optionally substituted $C_3$-$C_8$ cycloalkyl. In some embodiments, $R^{30}$ is optionally substituted $C_6$-$C_{10}$ aryl. In some embodiments, $R^{30}$ is optionally substituted 5-10 membered heteroaryl containing up to 3 ring heteroatoms, wherein the heteroatom is selected from the group consisting of O, N, S, and oxidized forms of N and S. In some embodiments, $R^{30}$ is optionally substituted 4-15 membered heterocyclyl containing up to 5 ring heteroatoms, wherein the heteroatom is selected from the group consisting of O, N, S, and oxidized forms of N and S.

In some embodiments, $R^{31}$ is optionally substituted $C_1$-$C_6$ alkyl. In some embodiments, $R^{31}$ is hydrogen. In some embodiments, $R^{31}$ is an amino protecting group. In some embodiments, $R^{30}$ and $R^{31}$ together with the nitrogen atom they are bonded to form an optionally substituted 4-15 membered heterocyclyl containing up to 5 ring heteroatoms, wherein the heteroatom is selected from the group consisting of O, N, S, and oxidized forms of N and S.

In some embodiments, $R^{32}$ is hydrogen. In some embodiments, $R^{32}$ is a substituted $C_1$-$C_6$ alkyl, such as methyl, ethyl, propyl or butyl. In some embodiments, $R^{32}$ is an unsubstituted $C_1$-$C_6$ alkyl, such as methyl, ethyl, propyl or butyl.

In some embodiments, -$L^3$-$R^3$ is selected from the group consisting of the structures shown below:

60

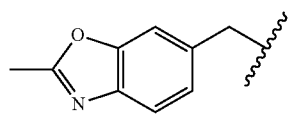

61

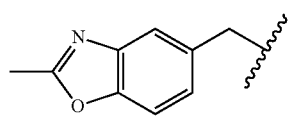

62

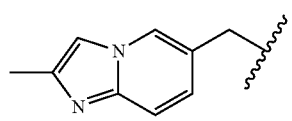

63

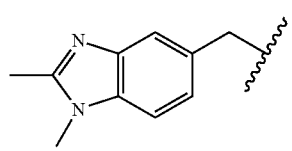

64

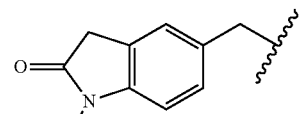

65

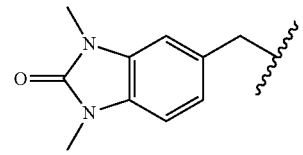

66

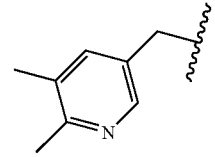

67

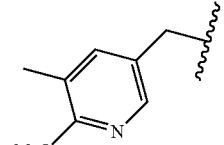

68

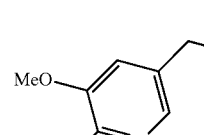

69

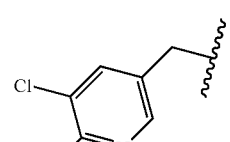

70

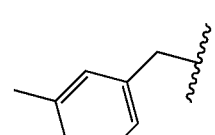

71

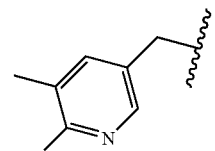

72

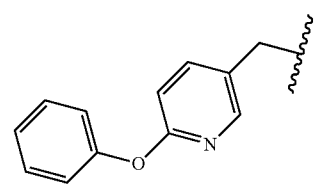

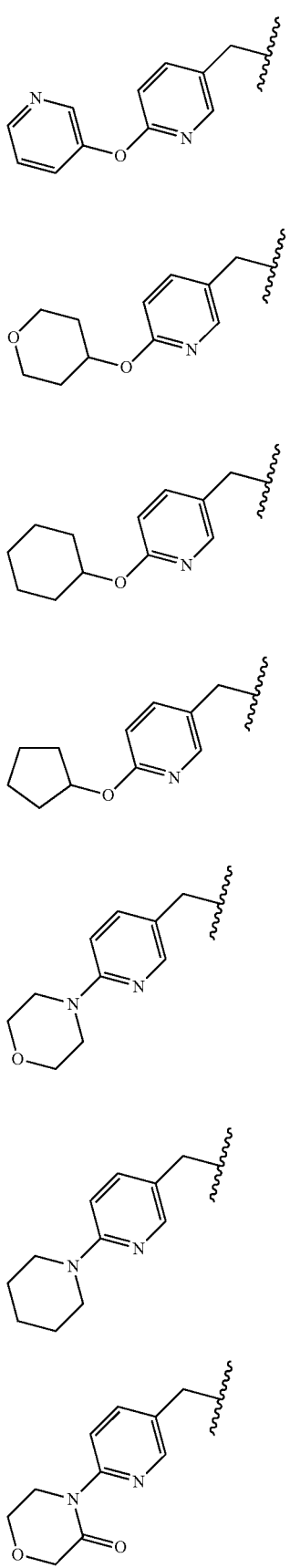
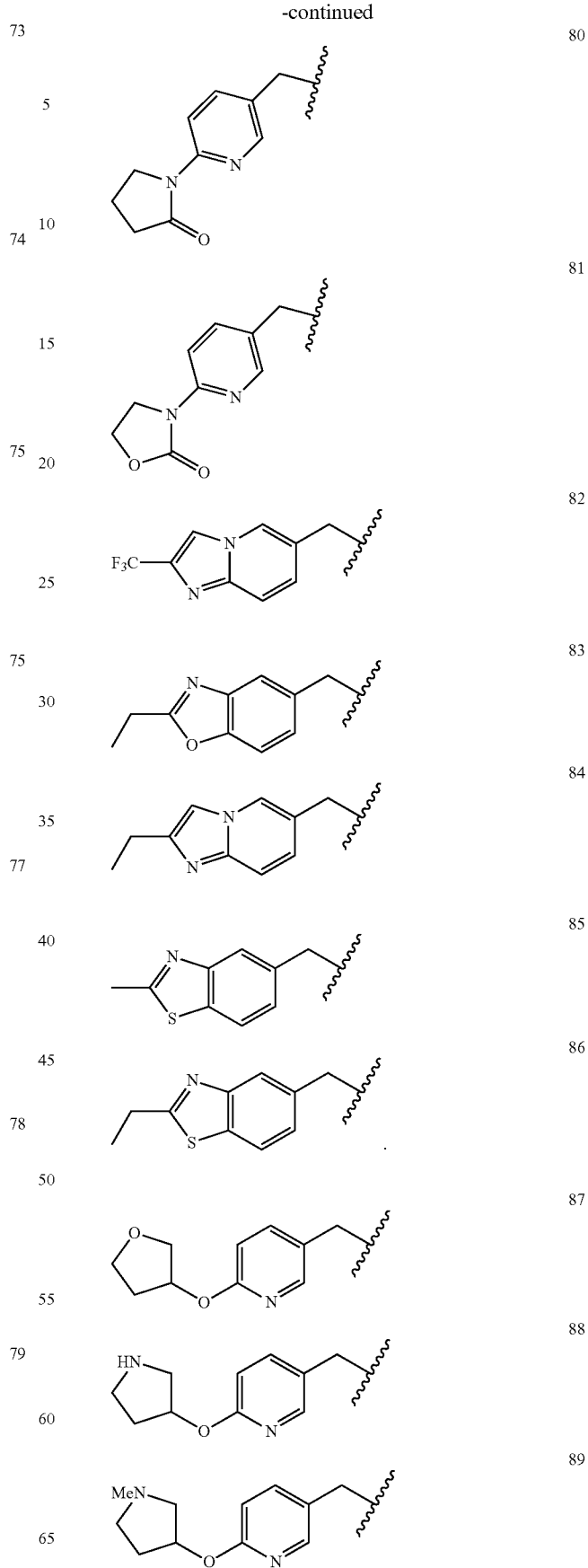

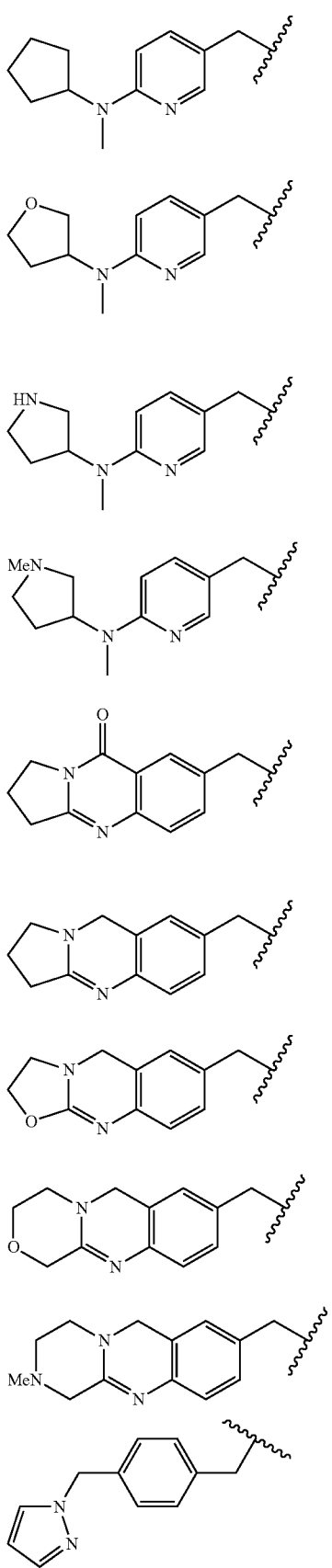
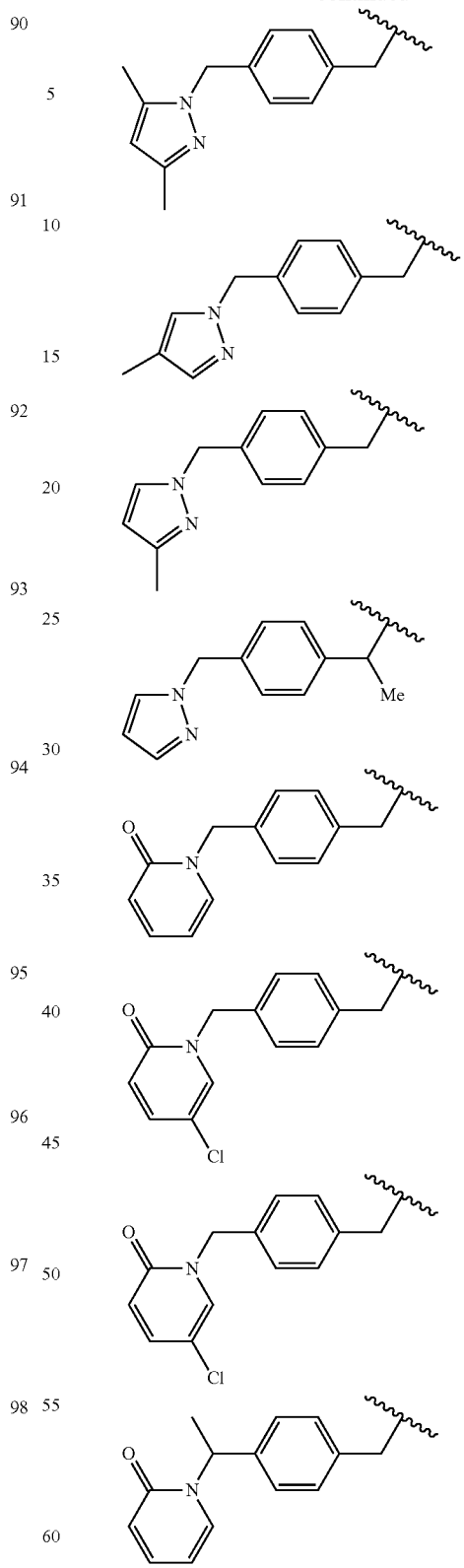
Certain illustrative and nonlimiting substituents for R³ and substituents thereof are provided as above.
In some embodiments, -L³-R³ is selected from the group consisting of the structures shown below:

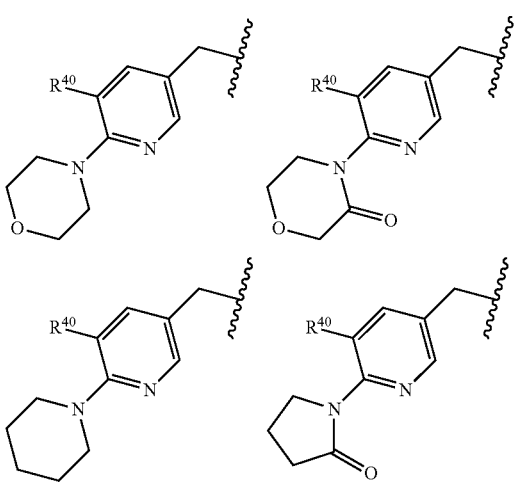
wherein $R^{40}$ is hydrogen or an optional substituent as defined above.
In some embodiments, $-L^1-R^1$ is selected from the group consisting of the structures shown below:
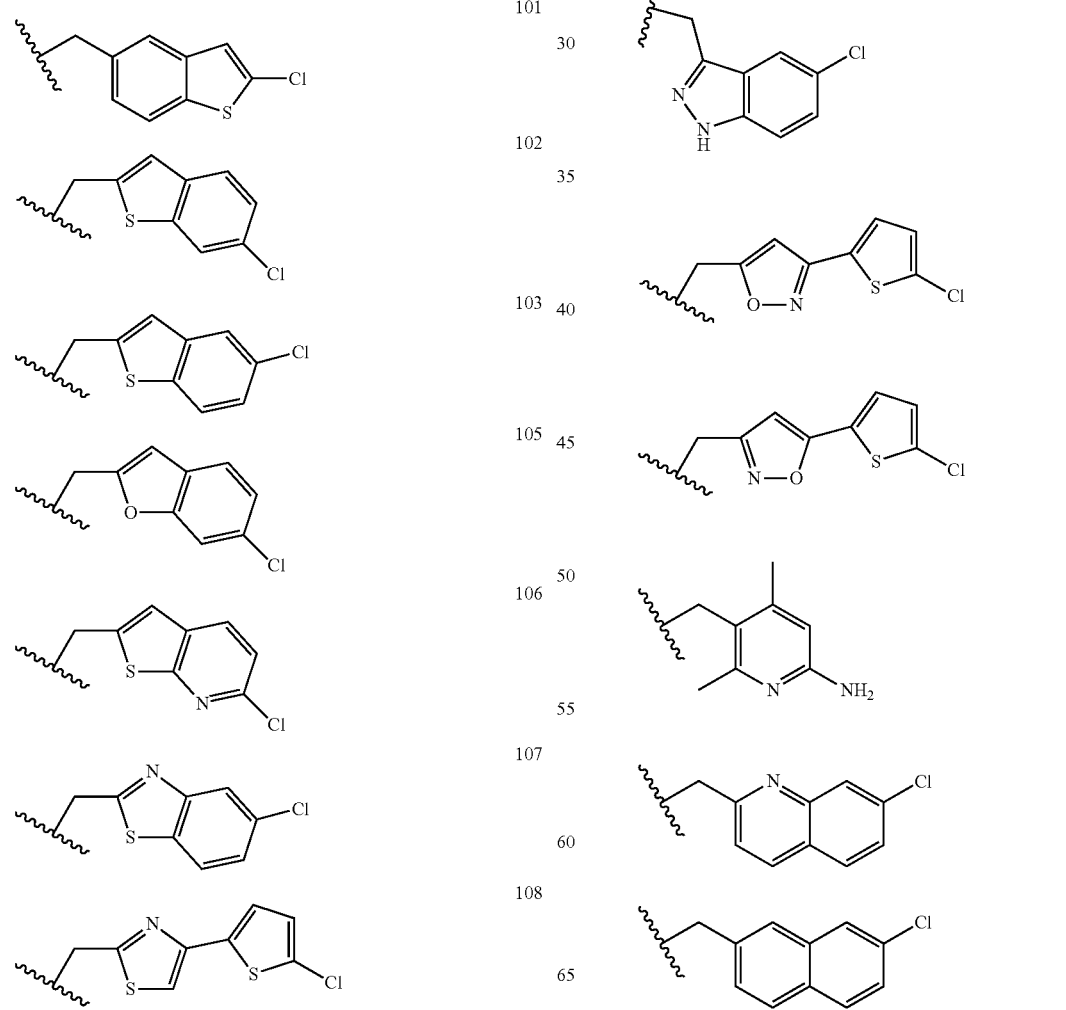

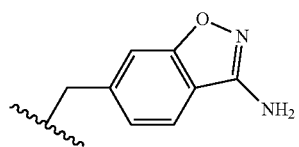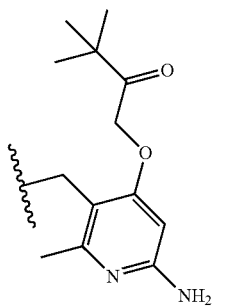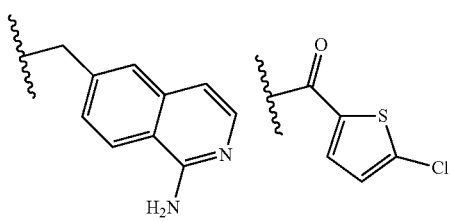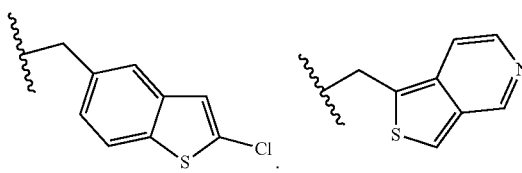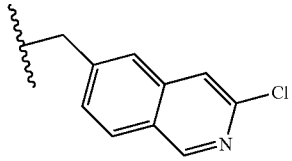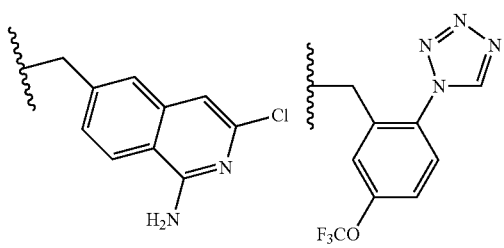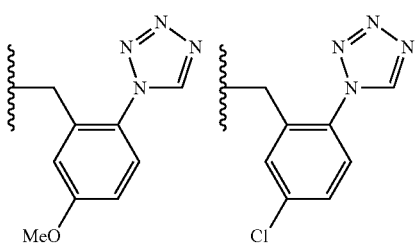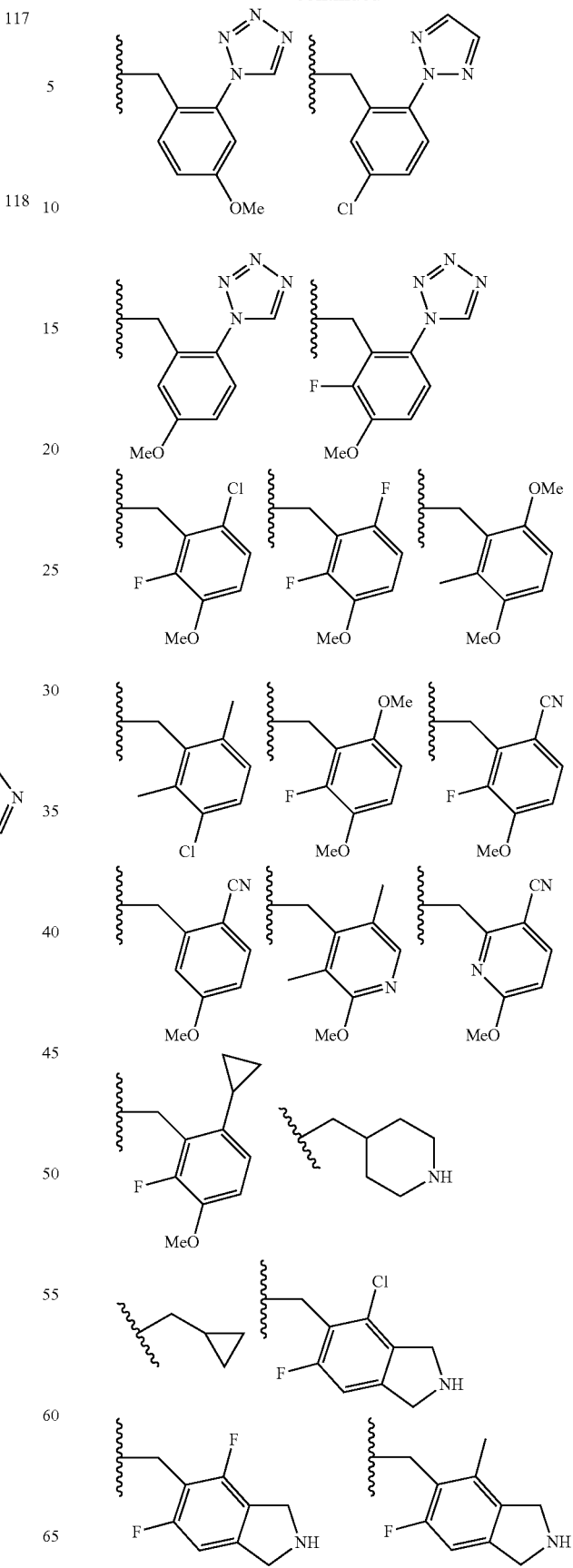

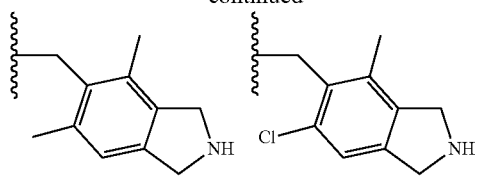
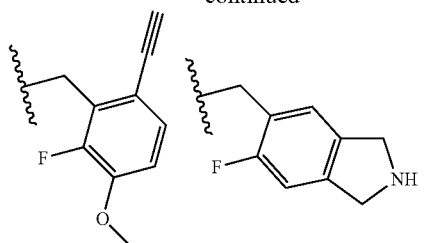
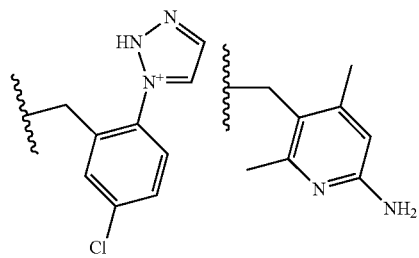
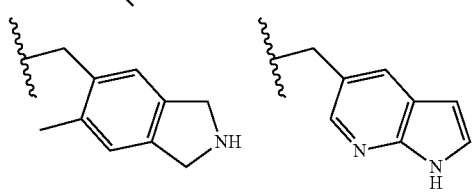
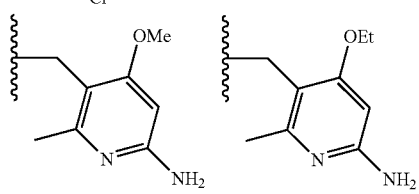
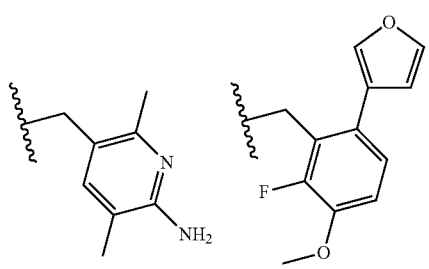
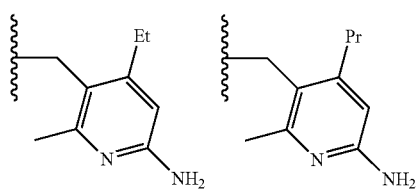
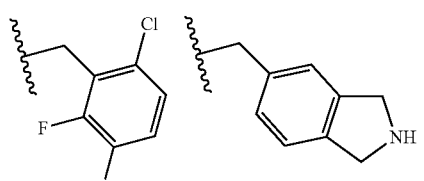
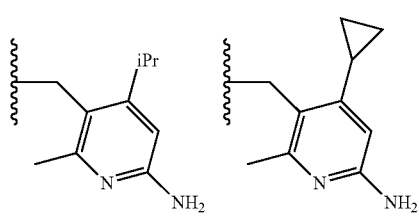
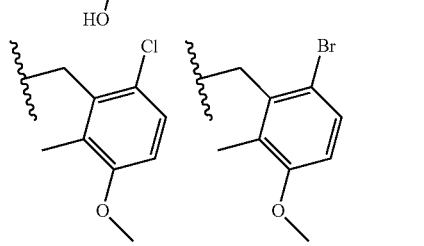
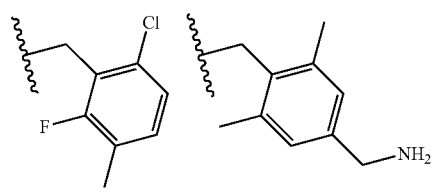
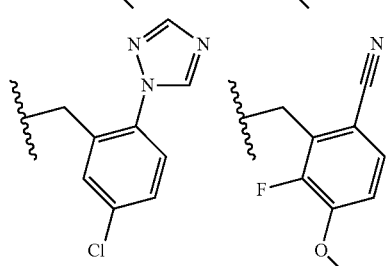
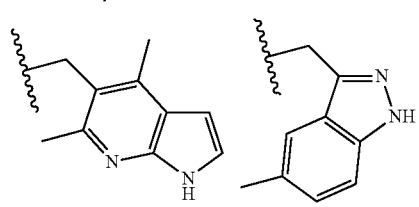
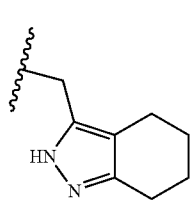
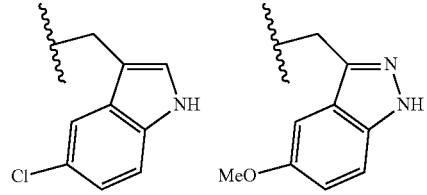
Certain illustrative and nonlimiting substituents for $R^1$ and substituents thereof are provided as above.
In some embodiments the compound of formula I is of formula I-A where any of the variables can be defined as described above for formula I:

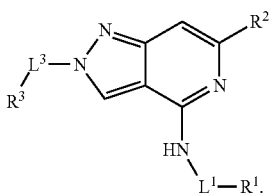

I-A

In some embodiment, provided herein is a compound of formula:

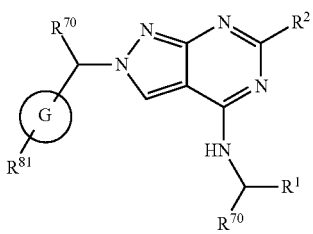

wherein G is optionally substituted $C_6$-$C_{10}$ aryl, optionally substituted heteroaryl, or optionally substituted heterocyclyl; $R^{81}$ is hydrogen, optionally substituted alkyl, preferably optionally substituted methyl, ethyl, or propyl, more preferably optionally substituted methyl; and the remaining variables are defined as in any aspect and embodiment herein.

In some embodiment, provided herein is a compound of formula:

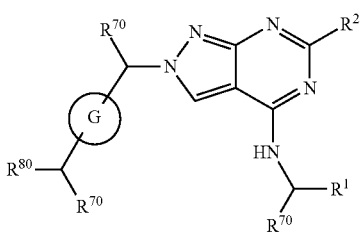

wherein G is optionally substituted $C_6$-$C_{10}$ aryl, optionally substituted heteroaryl, or optionally substituted heterocyclyl; $R^{80}$ is, hydrogen, halo, optionally substituted $C_1$-$C_6$ alkyl, hydroxy, oxo, or optionally substituted heteroaryl; and the remaining variables are defined as in any aspect and embodiment herein.

In some embodiment, provided herein is a compound of formula:

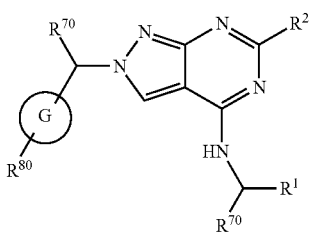

wherein the variables are defined as in any aspect and embodiment herein.

In some embodiments the compound of formula I is of formula I-B where any of the variables can be defined as described above for Formula I:

I-B

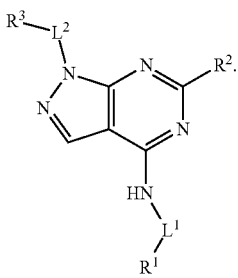

In some embodiments the compound of formula I is of formula I-C where any of the variables can be defined as described above for Formula I:

I-C

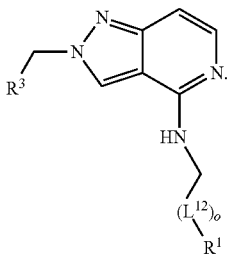

In some embodiments, o is 0. In some embodiments, o is 1.

In some embodiments the compound of formula I is of formula I-D where any of the variables can be defined as described above for Formula I:

I-D

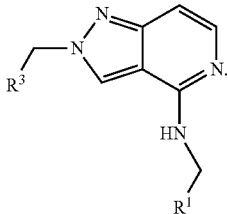

In some embodiments the compound of formula I is of formula I-E where any of the variables can be defined as described above for Formula I:

I-E

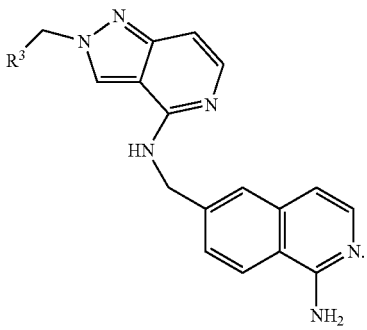

In some embodiments, the compound of formula I is of formula I-F where any of the variables can be defined as described above for Formula I:

I-F

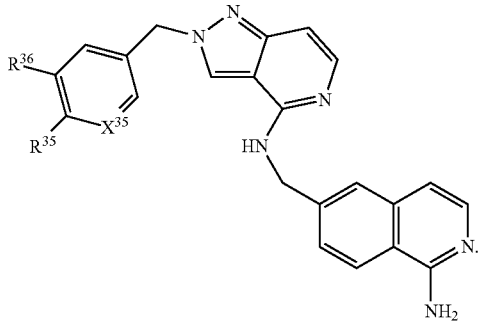

In some embodiments, $X^{35}$ is N. In some embodiments, $X^{35}$ is CH.

In some embodiments, $R^{35}$ is methyl substituted with a 5 membered heteroaryl containing 2 nitrogen atoms. In some embodiments, $R^{35}$ is $C_1$-$C_6$ alkoxy preferably methoxy. In some embodiments, $R^{35}$ is halo, preferably chloro or fluoro. In some embodiments, $R^{35}$ is —O-(6 membered heteroaryl containing a single nitrogen atom). In some embodiments, $R^{35}$ is —O-(6 membered heterocyclyl containing a single nitrogen atom).

Preferably, in some embodiments, $R^{36}$ is hydrogen. In some embodiments, $R^{36}$ is methyl. In some embodiments, $R^{35}$ and $R^{36}$ together with the intervening carbon atoms form a 5 membered heteroaryl containing 1-2 nitrogen atoms, which heteroaryl ring is substituted with 1-2, $C_1$-$C_6$ alkyl, preferably methyl groups.

In some embodiments, the compound of formula I is of formula I-G:

I-G

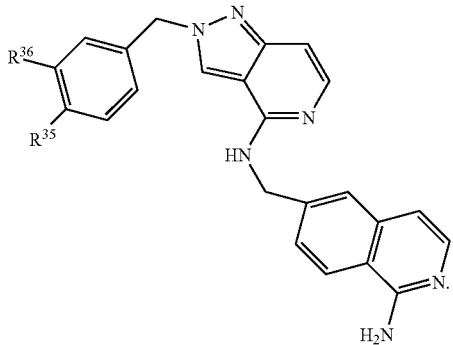

In some embodiments of the compound of formula I-G, $R^{35}$ is methyl substituted with a 5 membered heteroaryl containing 2 nitrogen atoms. In some embodiments of the compound of formula I-G, $R^{35}$ is —O-(6 membered heteroaryl containing a single nitrogen atom). In some embodiments of the compound of formula I-G, $R^{35}$ is —O-(6 membered heterocyclyl containing a single nitrogen atom).

In some embodiments of the compound of formula I-G, $R^{36}$ is hydrogen. In some embodiments of the compound of formula I-G, $R^{35}$ and $R^{36}$ together with the intervening carbon atoms form a 5 membered heteroaryl containing 1-2 nitrogen atoms, which heteroaryl ring is substituted with 1-2, $C_1$-$C_6$ alkyl, preferably methyl groups.

In some embodiments, the compound of formula I is of formula I-H:

I-H

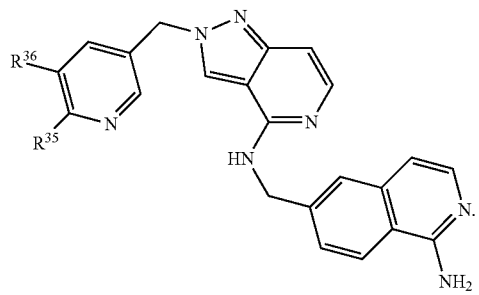

In some embodiments of the compound of formula I-H, $R^{35}$ is $C_1$-$C_6$ alkoxy preferably methoxy, or halo, preferably chloro or fluoro.

In some embodiments of the compound of formula I-H, $R^{35}$ is —O-(6 membered heteroaryl containing a single nitrogen atom). In some embodiments of the compound of formula I-H, $R^{35}$ is —O-(6 membered heterocyclyl containing a single nitrogen atom).

In some embodiments of the compound of formula I-H, $R^{36}$ is hydrogen. In some embodiments of the compound of formula I-H, $R^{36}$ is methyl.

In some embodiments, the compound of formula I is of formula I-I:

I-I

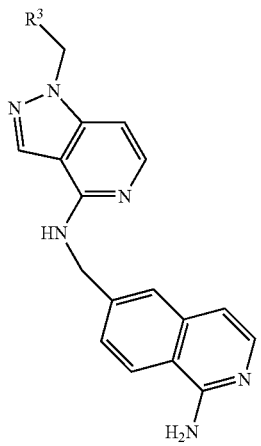

In some embodiments of the compound of formula I-H, $R^3$ is defined as above.

In some embodiments, the compound of formula I is of formula I-J:

I-J

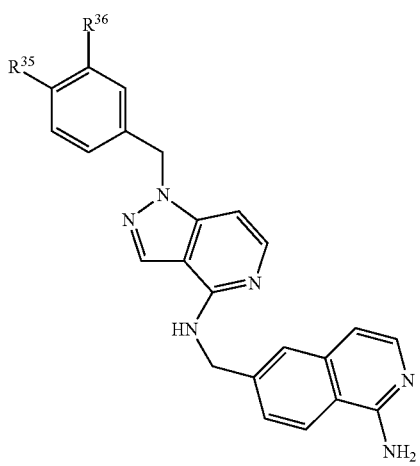

In some embodiments of the compound of formula I-J, $R^{35}$ is methyl substituted with a 5 membered heteroaryl containing 2 nitrogen atoms.

In some embodiments of the compound of formula I-J, $R^{36}$ is hydrogen. In some embodiments of the compound of formula I-J, $R^{35}$ and $R^{36}$ together with the intervening carbon atoms form a 5 membered heteroaryl containing 1-2 nitrogen atoms, which heteroaryl ring is substituted with 1-2, $C_1$-$C_6$ alkyl, preferably methyl groups.

In some embodiments, the compound of formula I is

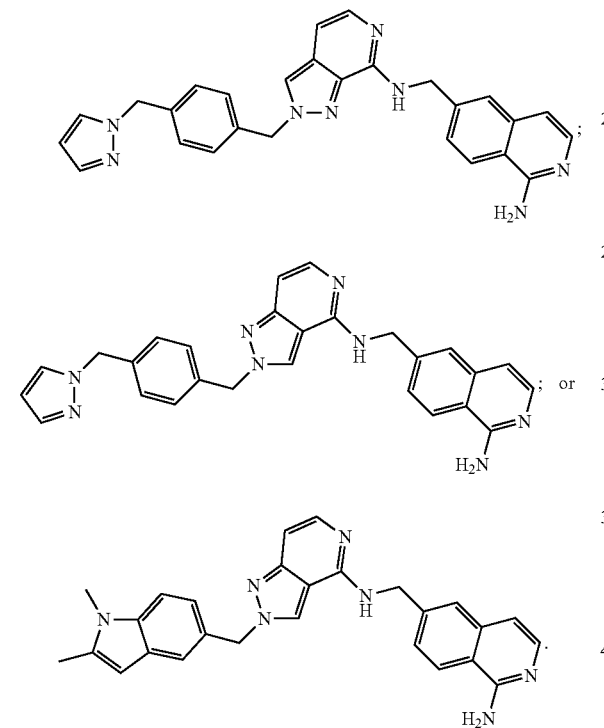

In another embodiment, the compound provided is of formula:

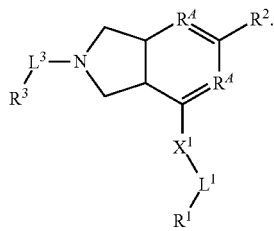

In another embodiment, the compound provided is of formula:

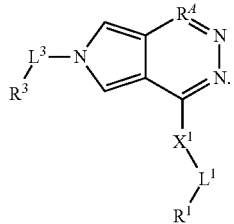

In another embodiment, the compound provided is of formula:

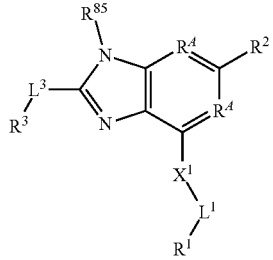

wherein $R^{85}$ is hydrogen or optionally substituted $C_1$-$C_6$ alkyl.

In some embodiments, the compound of formula I is selected from Table I below, which tabulates kallikrein inhibitory activity of the compounds. In other embodiments, compounds provided herein are selected from those disclosed in the Examples section below. The compounds inhibit KLKB1 with $pIC_{50}$(-log($IC_{50}$)) in the range of about 3-about 9. Preferred compounds inhibit KLKB1 with $pIC_{50}$ in the range of about 6-about 9. Preferred compounds inhibited KLKB1 with $pIC_{50}$ in the range of about 8-about 9.

TABLE 1

| Entry # | Example # | IUPAC Name |
|---|---|---|
| 1 | 12 | 6-{[(2-{[4-(1H-pyrazol-1-ylmethyl)phenyl]methyl}-2H-pyrazolo[4,3-c]pyridin-4-yl)amino]methyl}isoquinolin-1-amine |
| 2 | 13 | 6-{[[(1-{[4-(1H-pyrazol-1-ylmethyl)phenyl]methyl}-1H-pyrazolo[4,3-c]pyridin-4-yl)amino]methyl}isoquinolin-1-amine |
| 3 | 16 | 6-{[[(2-{[4-(1H-pyrazol-1-ylmethyl)phenyl]methyl}-2H-pyrazolo[3,4-c]pyridin-7-yl)amino]methyl}isoquinolin-1-amine |
| 4 | 17 | 6-{[[(1-{[4-(1H-pyrazol-1-ylmethyl)phenyl]methyl}-1H-pyrazolo[3,4-c]pyridin-7-yl)amino]methyl}isoquinolin-1-amine |
| 5 | 18 | N-[2-(4-chlorophenoxy)ethyl]-2-{[4-(1H-pyrazol-1-ylmethyl)phenyl]methyl}-2H-pyrazolo[4,3-c]pyridin-4-amine |
| 6 | 21 | 6-[({2-[(1,2-dimethyl-1H-indol-5-yl)methyl]-2H-pyrazolo[4,3-c]pyridin-4-yl}amino)methyl]isoquinolin-1-amine |
| 7 | 22 | 6-[({1-[(1,2-dimethyl-1H-indol-5-yl)methyl]-1H-pyrazolo[4,3-c]pyridin-4-yl}amino)methyl]isoquinolin-1-amine |
| 8 | 25 | 6-{[[(2-{[4-(1H-pyrazol-1-ylmethyl)phenyl]methyl}-2H-pyrazolo[3,4-d]pyrimidin-4-yl)amino]methyl}isoquinolin-1-amine |
| 9 | 26 | 6-{[[(1-{[4-(1H-pyrazol-1-ylmethyl)phenyl]methyl}-1H-pyrazolo[3,4-d]pyrimidin-4-yl)amino]methyl}isoquinolin-1-amine |

TABLE 1-continued

| Entry # | Example # | IUPAC Name |
|---|---|---|
| 10 | 27 | 6-[({2-[(1-methyl-1H-indazol-6-yl)methyl]-2H-pyrazolo[4,3-c]pyridin-4-yl}amino)methyl]isoquinolin-1-amine |
| 11 | 28 | 6-[({1-[(1-methyl-1H-indazol-6-yl)methyl]-1H-pyrazolo[4,3-c]pyridin-4-yl}amino)methyl]isoquinolin-1-amine |
| 12 | 29 | 6-{[(2-{[4-(pyridin-2-yloxy)phenyl]methyl}-2H-pyrazolo[4,3-c]pyridin-4-yl)amino]methyl}isoquinolin-1-amine |
| 13 | 30 | 6-{[(1-{[4-(pyridin-2-yloxy)phenyl]methyl}-1H-pyrazolo[4,3-c]pyridin-4-yl)amino]methyl}isoquinolin-1-amine |
| 14 | 31 | N-[(5-chloro-1H-indazol-3-yl)methyl]-2-{[4-(1H-pyrazol-1-ylmethyl)phenyl]methyl}-2H-pyrazolo[4,3-c]pyridin-4-amine |
| 15 | 32 | 6-[({2-[(2-methyl-1,3-benzoxazol-6-yl)methyl]-2H-pyrazolo[4,3-c]pyridin-4-yl}amino)methyl]isoquinolin-1-amine |
| 16 | 33 | 6-[({2-[(2-methyl-1,3-benzoxazol-5-yl)methyl]-2H-pyrazolo[4,3-c]pyridin-4-yl}amino)methyl]isoquinolin-1-amine |
| 17 | 34 | 6-{[(2-{[6-(oxan-4-yloxy)pyridin-3-yl]methyl}-2H-pyrazolo[4,3-c]pyridin-4-yl)amino]methyl}isoquinolin-1-amine |
| 18 | 35 | 6-[({2-[(6-methoxy-5-methylpyridin-3-yl)methyl]-2H-pyrazolo[4,3-c]pyridin-4-yl}amino)methyl]isoquinolin-1-amine |
| 19 | 36 | 6-[({2-[(5,6-dimethylpyridin-3-yl)methyl]-2H-pyrazolo[4,3-c]pyridin-4-yl}amino)methyl]isoquinolin-1-amine |
| 20 | 38 | 6-{[(2-{[4-(1H-pyrazol-1-ylmethyl)phenyl]methyl}-2H-pyrazolo[4,3-c]pyridin-4-yl)amino]methyl}-1,2-benzoxazol-3-amine |
| 21 | 39 | N-[(5-chloro-1,3-benzothiazol-2-yl)methyl]-2-{[4-(1H-pyrazol-1-ylmethyl)phenyl]methyl}-2H-pyrazolo[4,3-c]pyridin-4-amine |
| 22 | 40 | N-[(5-chloro-1H-1,3-benzodiazol-2-yl)methyl]-2-{[4-(1H-pyrazol-1-ylmethyl)phenyl]methyl}-2H-pyrazolo[4,3-c]pyridin-4-amine |
| 23 | 41 | 4,6-dimethyl-5-{[(2-{[4-(1H-pyrazol-1-ylmethyl)phenyl]methyl}-2H-pyrazolo[3,4-d]pyrimidin-4-yl)amino]methyl}pyridin-2-amine |
| 24 | 42 | N-[(2-chloro-1-benzothiophen-5-yl)methyl]-2-{[4-(1H-pyrazol-1-ylmethyl)phenyl]methyl}-2H-pyrazolo[4,3-c]pyridin-4-amine |
| 25 | 43 | N-[(3-methoxyphenyl)methyl]-2-{[4-(1H-pyrazol-1-ylmethyl)phenyl]methyl}-2H-pyrazolo[3,4-d]pyrimidin-4-amine |
| 26 | 44 | N-[(4-methoxyphenyl)methyl]-2-{[4-(1H-pyrazol-1-ylmethyl)phenyl]methyl}-2H-pyrazolo[3,4-d]pyrimidin-4-amine |
| 27 | 47 | N-[(6-amino-2,4-dimethylpyridin-3-yl)methyl]-2-{[4-(1H-pyrazol-1-ylmethyl)phenyl]methyl}-2H-indazol-4-amine |
| 28 | 48 | N-[(3-chloro-4-methoxyphenyl)methyl]-2-{[4-(1H-pyrazol-1-ylmethyl)phenyl]methyl}-2H-pyrazolo[3,4-d]pyrimidin-4-amine |
| 29 | 49 | N-[(3,4-dimethoxyphenyl)methyl]-2-{[4-(1H-pyrazol-1-ylmethyl)phenyl]methyl}-2H-pyrazolo[3,4-d]pyrimidin-4-amine |
| 30 | 50 | N-[(3,4-dichlorophenyl)methyl]-2-{[4-(1H-pyrazol-1-ylmethyl)phenyl]methyl}-2H-pyrazolo[3,4-d]pyrimidin-4-amine |
| 31 | 51 | N-[(3,5-dichlorophenyl)methyl]-2-{[4-(1H-pyrazol-1-ylmethyl)phenyl]methyl}-2H-pyrazolo[3,4-d]pyrimidin-4-amine |
| 32 | 52 | N-[(3,5-dimethoxyphenyl)methyl]-2-{[4-(1H-pyrazol-1-ylmethyl)phenyl]methyl}-2H-pyrazolo[3,4-d]pyrimidin-4-amine |
| 33 | 53 | N-[(5-chloro-2-methoxyphenyl)methyl]-2-{[4-(1H-pyrazol-1-ylmethyl)phenyl]methyl}-2H-pyrazolo[3,4-d]pyrimidin-4-amine |
| 34 | 55 | N-[(4-chloro-3-methoxyphenyl)methyl]-2-{[4-(1H-pyrazol-1-ylmethyl)phenyl]methyl}-2H-pyrazolo[3,4-d]pyrimidin-4-amine |
| 35 | 61 | 4-methoxy-6-methyl-5-{[(2-{[4-(1H-pyrazol-1-ylmethyl)phenyl]methyl}-2H-pyrazolo[4,3-c]pyridin-4-yl)amino]methyl}pyridin-2-amine |
| 36 | 62 | N-[(2,5-dimethoxyphenyl)methyl]-2-{[4-(1H-pyrazol-1-ylmethyl)phenyl]methyl}-2H-pyrazolo[3,4-d]pyrimidin-4-amine |
| 37 | 64 | N-[(3-chloro-5-methoxyphenyl)methyl]-2-{[4-(1H-pyrazol-1-ylmethyl)phenyl]methyl}-2H-pyrazolo[3,4-d]pyrimidin-4-amine |
| 38 | 66 | N-[(5-methoxy-1H-indazol-3-yl)methyl]-2-{[4-(1H-pyrazol-1-ylmethyl)phenyl]methyl}-2H-pyrazolo[3,4-d]pyrimidin-4-amine |
| 39 | 67 | N-(1H-indazol-3-ylmethyl)-2-{[4-(1H-pyrazol-1-ylmethyl)phenyl]methyl}-2H-pyrazolo[3,4-d]pyrimidin-4-amine |
| 40 | 68 | N-[(2-methoxy-4-methylphenyl)methyl]-2-{[4-(1H-pyrazol-1-ylmethyl)phenyl]methyl}-2H-pyrazolo[3,4-d]pyrimidin-4-amine |
| 41 | 69 | N-[(4-chloro-2-methoxyphenyl)methyl]-2-{[4-(1H-pyrazol-1-ylmethyl)phenyl]methyl}-2H-pyrazolo[3,4-d]pyrimidin-4-amine |
| 42 | 70 | N-[(6-chloro-2-fluoro-3-methoxyphenyl)methyl]-2-{[4-(1H-pyrazol-1-ylmethyl)phenyl]methyl}-2H-pyrazolo[3,4-d]pyrimidin-4-amine |
| 43 | 72 | N-[(2-methoxy-5-methylphenyl)methyl]-2-{[4-(1H-pyrazol-1-ylmethyl)phenyl]methyl}-2H-pyrazolo[3,4-d]pyrimidin-4-amine |
| 44 | 77 | N-[(6-methoxy-2,4-dimethylpyridin-3-yl)methyl]-2-{[4-(1H-pyrazol-1-ylmethyl)phenyl]methyl}-2H-pyrazolo[3,4-d]pyrimidin-4-amine |
| 45 | 78 | 2-(2-{[(2-{[4-(1H-pyrazol-1-ylmethyl)phenyl]methyl}-2H-pyrazolo[3,4-d]pyrimidin-4-yl)amino]methyl}phenyl)acetic acid |
| 46 | 82 | 2-(5-methoxy-2-{[(2-{[4-(1H-pyrazol-1-ylmethyl)phenyl]methyl}-2H-pyrazolo[3,4-d]pyrimidin-4-yl)amino]methyl}phenoxy)acetic acid |
| 47 | 83 | 2-(2-{[(2-{[4-(1H-pyrazol-1-ylmethyl)phenyl]methyl}-2H-pyrazolo[3,4-d]pyrimidin-4-yl)amino]methyl}phenoxy)acetic acid |
| 48 | 86 | N-[(5-methoxy-3-methylpyridin-2-yl)methyl]-2-{[4-(1H-pyrazol-1-ylmethyl)phenyl]methyl}-2H-pyrazolo[3,4-d]pyrimidin-4-amine |

TABLE 1-continued

| Entry # | Example # | IUPAC Name |
|---|---|---|
| 49 | 92 | 6-methoxy-2-methyl-3-{[(2-{[4-(1H-pyrazol-1-ylmethyl)phenyl]methyl}-2H-pyrazolo[3,4-d]pyrimidin-4-yl)amino]methyl}pyridin-4-ol |
| 50 | 97 | 5-chloro-7-{[(2-{[4-(1H-pyrazol-1-ylmethyl)phenyl]methyl}-2H-pyrazolo[3,4-d]pyrimidin-4-yl)amino]methyl}-2,3-dihydro-1,3-benzoxazol-2-one |
| 51 | 102 | 5-chloro-7-{[(2-{[4-(1H-pyrazol-1-ylmethyl)phenyl]methyl}-2H-pyrazolo[3,4-d]pyrimidin-4-yl)oxy]methyl}-1-benzofuran-2-carbonitrile |
| 52 | 104 | N,4,6-trimethyl-5-{[(2-{[4-(1H-pyrazol-1-ylmethyl)phenyl]methyl}-2H-pyrazolo[3,4-d]pyrimidin-4-yl)amino]methyl}pyridin-2-amine |
| 53 | 106 | N,N,4,6-tetramethyl-5-{[(2-{[4-(1H-pyrazol-1-ylmethyl)phenyl]methyl}-2H-pyrazolo[3,4-d]pyrimidin-4-yl)amino]methyl}pyridin-2-amine |
| 54 | 107 | N-{[5-methoxy-2-(1H-1,2,3,4-tetrazol-1-yl)phenyl]methyl}-2-{[4-(1H-pyrazol-1-ylmethyl)phenyl]methyl}-2H-pyrazolo[3,4-d]pyrimidin-4-amine |
| 55 | 108 | 3,6-dimethyl-5-{[(2-{[4-(1H-pyrazol-1-ylmethyl)phenyl]methyl}-2H-pyrazolo[3,4-d]pyrimidin-4-yl)amino]methyl}pyridin-2-amine |
| 56 | 110 | 2-{[4-(1H-pyrazol-1-ylmethyl)phenyl]methyl}-N-(1,2,3,4-tetrahydroisoquinolin-7-ylmethyl)-2H-pyrazolo[3,4-d]pyrimidin-4-amine |
| 57 | 111 | 2-{[4-(1H-pyrazol-1-ylmethyl)phenyl]methyl}-N-{[2-(1H-1,2,3,4-tetrazol-1-yl)-5-(trifluoromethoxy)phenyl]methyl}-2H-pyrazolo[3,4-d]pyrimidin-4-amine |
| 58 | 113 | 2-{[4-(1H-pyrazol-1-ylmethyl)phenyl]methyl}-N-(1,2,3,4-tetrahydroisoquinolin-6-ylmethyl)-2H-pyrazolo[3,4-d]pyrimidin-4-amine |
| 59 | 117 | N-[(2-fluoro-3,6-dimethoxyphenyl)methyl]-2-{[4-(1H-pyrazol-1-ylmethyl)phenyl]methyl}-2H-pyrazolo[3,4-d]pyrimidin-4-amine |
| 60 | 119 | N-[(3-bromo-2,6-dimethylphenyl)methyl]-2-{[4-(1H-pyrazol-1-ylmethyl)phenyl]methyl}-2H-pyrazolo[3,4-d]pyrimidin-4-amine |
| 61 | 120 | N-[(2-methoxy-3,5-dimethylpyridin-4-yl)methyl]-2-{[4-(1H-pyrazol-1-ylmethyl)phenyl]methyl}-2H-pyrazolo[3,4-d]pyrimidin-4-amine |
| 62 | 121 | N-[(3-methoxy-2,6-dimethylphenyl)methyl]-2-{[4-(1H-pyrazol-1-ylmethyl)phenyl]methyl}-2H-pyrazolo[3,4-d]pyrimidin-4-amine |
| 63 | 122 | 3-fluoro-4-methoxy-2-{[(2-{[4-(1H-pyrazol-1-ylmethyl)phenyl]methyl}-2H-pyrazolo[3,4-d]pyrimidin-4-yl)amino]methyl}benzonitrile |
| 64 | 127 | N-{[6-chloro-2-fluoro-3-(trifluoromethoxy)phenyl]methyl}-2-{[4-(1H-pyrazol-1-ylmethyl)phenyl]methyl}-2H-pyrazolo[3,4-d]pyrimidin-4-amine |
| 65 | 131 | N-[(3,6-dimethoxy-2-methylphenyl)methyl]-2-{[4-(1H-pyrazol-1-ylmethyl)phenyl]methyl}-2H-pyrazolo[3,4-d]pyrimidin-4-amine |
| 66 | 132 | N-[(6-ethynyl-2-fluoro-3-methoxyphenyl)methyl]-2-{[4-(1H-pyrazol-1-ylmethyl)phenyl]methyl}-2H-pyrazolo[3,4-d]pyrimidin-4-amine |
| 67 | 133 | N-[(6-ethyl-2-fluoro-3-methoxyphenyl)methyl]-2-{[4-(1H-pyrazol-1-ylmethyl)phenyl]methyl}-2H-pyrazolo[3,4-d]pyrimidin-4-amine |
| 68 | 139 | N-[(6-bromo-3-methoxy-2-methylphenyl)methyl]-2-{[4-(1H-pyrazol-1-ylmethyl)phenyl]methyl}-2H-pyrazolo[3,4-d]pyrimidin-4-amine |
| 69 | 140 | N-[(6-cyclopropyl-2-fluoro-3-methoxyphenyl)methyl]-2-{[4-(1H-pyrazol-1-ylmethyl)phenyl]methyl}-2H-pyrazolo[3,4-d]pyrimidin-4-amine |
| 70 | 147 | N-{[2-fluoro-6-(furan-3-yl)-3-methoxyphenyl]methyl}-2-{[4-(1H-pyrazol-1-ylmethyl)phenyl]methyl}-2H-pyrazolo[3,4-d]pyrimidin-4-amine |
| 71 | 148 | N-{[4-(aminomethyl)phenyl]methyl}-2-{[4-(1H-pyrazol-1-ylmethyl)phenyl]methyl}-2H-pyrazolo[3,4-d]pyrimidin-4-amine |
| 72 | 160 | N-[(5-methyl-1-benzofuran-4-yl)methyl]-2-{[4-(1H-pyrazol-1-ylmethyl)phenyl]methyl}-2H-pyrazolo[3,4-d]pyrimidin-4-amine |
| 73 | 161 | N-[(5-methyl-1-benzofuran-6-yl)methyl]-2-{[4-(1H-pyrazol-1-ylmethyl)phenyl]methyl}-2H-pyrazolo[3,4-d]pyrimidin-4-amine |
| 74 | 162 | N-{[3-(aminomethyl)phenyl]methyl}-2-{[4-(1H-pyrazol-1-ylmethyl)phenyl]methyl}-2H-pyrazolo[3,4-d]pyrimidin-4-amine |
| 75 | 170 | N-{[2-fluoro-3-methoxy-6-(1H-1,2,3,4-tetrazol-1-yl)phenyl]methyl}-2-{[4-(1H-pyrazol-1-ylmethyl)phenyl]methyl}-2H-pyrazolo[3,4-d]pyrimidin-4-amine |
| 76 | 171 | N-{[2-fluoro-3-methoxy-6-(oxetan-3-ylmethoxy)phenyl]methyl}-2-{[4-(1H-pyrazol-1-ylmethyl)phenyl]methyl}-2H-pyrazolo[3,4-d]pyrimidin-4-amine |
| 77 | 172 | hexyl N-(4,6-dimethyl-5-{[(2-{[4-(1H-pyrazol-1-ylmethyl)phenyl]methyl}-2H-pyrazolo[3,4-d]pyrimidin-4-yl)amino]methyl}pyridin-2-yl)carbamate |
| 78 | 173 | N-{[4-(aminomethyl)-2,6-dimethylphenyl]methyl}-2-{[4-(1H-pyrazol-1-ylmethyl)phenyl]methyl}-2H-pyrazolo[3,4-d]pyrimidin-4-amine |
| 79 | 174 | N-{[2-(aminomethyl)-4,6-dimethylphenyl]methyl}-2-{[4-(1H-pyrazol-1-ylmethyl)phenyl]methyl}-2H-pyrazolo[3,4-d]pyrimidin-4-amine |
| 80 | 178 | 1-({4-[(4-{[(6-amino-2,4-dimethylpyridin-3-yl)methyl]amino}-2H-pyrazolo[3,4-d]pyrimidin-2-yl)methyl]phenyl}methyl)-N,N-dimethyl-1H-pyrazole-4-carboxamide |
| 81 | 179 | 4,6-dimethyl-5-[({2-[(4-{[4-(morpholine-4-carbonyl)-1H-pyrazol-1-yl]methyl}phenyl)methyl]-2H-pyrazolo[3,4-d]pyrimidin-4-yl}amino)methyl]pyridin-2-amine |
| 82 | 182 | 1-({4-[(4-{[(6-amino-2,4-dimethylpyridin-3-yl)methyl]amino}-2H-pyrazolo[3,4-d]pyrimidin-2-yl)methyl]phenyl}methyl)-1H-pyrazole-3-carboxylic acid |
| 83 | 183 | 1-({4-[(4-{[(6-amino-2,4-dimethylpyridin-3-yl)methyl]amino}-2H-pyrazolo[3,4-d]pyrimidin-2-yl)methyl]phenyl}methyl)-N,N-dimethyl-1H-pyrazole-3-carboxamide |
| 84 | 184 | 1-({4-[(4-{[(6-amino-2,4-dimethylpyridin-3-yl)methyl]amino}-2H-pyrazolo[3,4-d]pyrimidin-2-yl)methyl]phenyl}methyl)-N,N-dimethyl-1H-pyrazole-5-carboxamide |

TABLE 1-continued

| Entry # | Example # | IUPAC Name |
|---|---|---|
| 85 | 186 | 4,6-dimethyl-5-[({2-[(4-{[4-(trifluoromethyl)-1H-pyrazol-1-yl]methyl}phenyl)methyl]-2H-pyrazolo[3,4-d]pyrimidin-4-yl}amino)methyl]pyridin-2-amine |
| 86 | 187 | 5-({[2-({4-[(4-chloro-1H-pyrazol-1-yl)methyl]phenyl}methyl)-2H-pyrazolo[3,4-d]pyrimidin-4-yl]amino}methyl)-4,6-dimethylpyridin-2-amine |
| 87 | 190 | N-[(5-chloro-1H-indazol-3-yl)methyl]-2-({4-[(3,5-dimethyl-1H-pyrazol-1-yl)methyl]phenyl}methyl)-2H-pyrazolo[3,4-d]pyrimidin-4-amine |
| 88 | 195 | N-[(7-chloronaphthalen-2-yl)methyl]-2-({4-[(4-methyl-1H-pyrazol-1-yl)methyl]phenyl}methyl)-2H-pyrazolo[3,4-d]pyrimidin-4-amine |
| 89 | 196 | N-[(7-chloroquinolin-2-yl)methyl]-2-({4-[(4-methyl-1H-pyrazol-1-yl)methyl]phenyl}methyl)-2H-pyrazolo[3,4-d]pyrimidin-4-amine |
| 90 | 197 | N-[(5-chloro-1H-indazol-3-yl)methyl]-2-({4-[(4-methyl-1H-pyrazol-1-yl)methyl]phenyl}methyl)-2H-pyrazolo[3,4-d]pyrimidin-4-amine |
| 91 | 198 | N-[(2,6-difluoro-3-methoxyphenyl)methyl]-2-({4-[(4-methyl-1H-pyrazol-1-yl)methyl]phenyl}methyl)-2H-pyrazolo[3,4-d]pyrimidin-4-amine |
| 92 | 199 | N-{[4-methoxy-2-(1H-1,2,3,4-tetrazol-1-yl)phenyl]methyl}-2-({4-[(4-methyl-1H-pyrazol-1-yl)methyl]phenyl}methyl)-2H-pyrazolo[3,4-d]pyrimidin-4-amine |
| 93 | 200 | N-{[5-methoxy-2-(1H-1,2,3,4-tetrazol-1-yl)phenyl]methyl}-2-({4-[(4-methyl-1H-pyrazol-1-yl)methyl]phenyl}methyl)-2H-pyrazolo[3,4-d]pyrimidin-4-amine |
| 94 | 201 | N-[(6-chloro-2-fluoro-3-methoxyphenyl)methyl]-2-({4-[(4-fluoro-1H-pyrazol-1-yl)methyl]phenyl}methyl)-2H-pyrazolo[3,4-d]pyrimidin-4-amine |
| 95 | 202 | 2-({4-[(4-fluoro-1H-pyrazol-1-yl)methyl]phenyl}methyl)-N-{[5-methoxy-2-(1H-1,2,3,4-tetrazol-1-yl)phenyl]methyl}-2H-pyrazolo[3,4-d]pyrimidin-4-amine |
| 96 | 203 | N-[(6-cyclopropyl-2-fluoro-3-methoxyphenyl)methyl]-2-({4-[(4-methyl-1H-pyrazol-1-yl)methyl]phenyl}methyl)-2H-pyrazolo[3,4-d]pyrimidin-4-amine |
| 97 | 204 | N-[(6-chloro-2-fluoro-3-methoxyphenyl)methyl]-2-({4-[(4-methyl-1H-pyrazol-1-yl)methyl]phenyl}methyl)-2H-pyrazolo[3,4-d]pyrimidin-4-amine |
| 98 | 205 | N-[(6-chloro-2-fluoro-3-methoxyphenyl)methyl]-2-({4-[(3,5-dimethyl-1H-pyrazol-1-yl)methyl]phenyl}methyl)-2H-pyrazolo[3,4-d]pyrimidin-4-amine |
| 99 | 208 | 2-({[2-({4-[(3,5-dimethyl-1H-pyrazol-1-yl)methyl]phenyl}methyl)-2H-pyrazolo[3,4-d]pyrimidin-4-yl]amino}methyl)-3-fluoro-4-methoxybenzonitrile |
| 100 | 213 | 1-({4-[(4-{[(6-amino-2,4-dimethylpyridin-3-yl)methyl]amino}-1H-pyrazolo[3,4-d]pyrimidin-1-yl)methyl]phenyl}methyl)-1,2-dihydropyridin-2-one |
| 101 | 214 | 1-({4-[(4-{[(6-amino-2,4-dimethylpyridin-3-yl)methyl]amino}-2H-pyrazolo[3,4-d]pyrimidin-2-yl)methyl]phenyl}methyl)-1,2-dihydropyridin-2-one |
| 102 | 215 | 1-({4-[(4-{[(5-chloro-1H-indazol-3-yl)methyl]amino}-2H-pyrazolo[3,4-d]pyrimidin-2-yl)methyl]phenyl}methyl)-1,2-dihydropyridin-2-one |
| 103 | 216 | 1-({4-[(4-{[(4-methoxyphenyl)methyl]amino}-2H-pyrazolo[3,4-d]pyrimidin-2-yl)methyl]phenyl}methyl)-1,2-dihydropyridin-2-one |
| 104 | 217 | 1-[(4-{[4-({[5-chloro-2-(1H-1,2,3,4-tetrazol-1-yl)phenyl]methyl}amino)-2H-pyrazolo[3,4-d]pyrimidin-2-yl]methyl}phenyl)methyl]-1,2-dihydropyridin-2-one |
| 105 | 219 | 1-({4-[(4-{[(5-methoxy-1H-indazol-3-yl)methyl]amino}-2H-pyrazolo[3,4-d]pyrimidin-2-yl)methyl]phenyl}methyl)-1,2-dihydropyridin-2-one |
| 106 | 220 | 1-{[4-({4-[(1H-indazol-3-ylmethyl)amino]-2H-pyrazolo[3,4-d]pyrimidin-2-yl}methyl)phenyl]methyl}-1,2-dihydropyridin-2-one |
| 107 | 221 | 1-({4-[(4-{[(7-chloronaphthalen-2-yl)methyl]amino}-2H-pyrazolo[3,4-d]pyrimidin-2-yl)methyl]phenyl}methyl)-1,2-dihydropyridin-2-one |
| 108 | 223 | 1-({4-[(4-{[(6-amino-4-methoxy-2-methylpyridin-3-yl)methyl]amino}-2H-pyrazolo[4,3-c]pyridin-2-yl)methyl]phenyl}methyl)-1,2-dihydropyridin-2-one |
| 109 | 224 | 1-({4-[(4-{[(5-methyl-1H-indazol-3-yl)methyl]amino}-2H-pyrazolo[3,4-d]pyrimidin-2-yl)methyl]phenyl}methyl)-1,2-dihydropyridin-2-one |
| 110 | 225 | 1-({4-[(4-{[(5-chloro-1-methyl-1H-indazol-3-yl)methyl]amino}-2H-pyrazolo[3,4-d]pyrimidin-2-yl)methyl]phenyl}methyl)-1,2-dihydropyridin-2-one |
| 111 | 226 | 1-({4-[(4-{[(5-chloro-1H-indol-3-yl)methyl]amino}-2H-pyrazolo[3,4-d]pyrimidin-2-yl)methyl]phenyl}methyl)-1,2-dihydropyridin-2-one |
| 112 | 227 | 1-({4-[(4-{[(7-chloroquinolin-2-yl)methyl]amino}-2H-pyrazolo[3,4-d]pyrimidin-2-yl)methyl]phenyl}methyl)-1,2-dihydropyridin-2-one |
| 113 | 232 | 1-({4-[(4-{[(6-chloro-1-benzofuran-2-yl)methyl]amino}-2H-pyrazolo[3,4-d]pyrimidin-2-yl)methyl]phenyl}methyl)-1,2-dihydropyridin-2-one |
| 114 | 233 | 1-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one |
| 115 | 235 | 1-({4-[(4-{[(2-amino-4,6-dimethylpyrimidin-5-yl)methyl]amino}-2H-pyrazolo[3,4-d]pyrimidin-2-yl)methyl]phenyl}methyl)-1,2-dihydropyridin-2-one |
| 116 | 240 | 1-{[4-({4-[(4,5,6,7-tetrahydro-1H-indazol-3-ylmethyl)amino]-2H-pyrazolo[3,4-d]pyrimidin-2-yl}methyl)phenyl]methyl}-1,2-dihydropyridin-2-one |
| 117 | 241 | 1-({4-[(4-{[(6,6-dimethyl-4,5,6,7-tetrahydro-1H-indazol-3-yl)methyl]amino}-2H-pyrazolo[3,4-d]pyrimidin-2-yl)methyl]phenyl}methyl)-1,2-dihydropyridin-2-one |
| 118 | 242 | 1-[(4-{[4-({[4-(5-chlorothiophen-2-yl)-1,3-thiazol-2-yl]methyl}amino)-2H-pyrazolo[3,4-d]pyrimidin-2-yl]methyl}phenyl)methyl]-1,2-dihydropyridin-2-one |
| 119 | 245 | 1-{[4-({4-[({7-chloroimidazo[1,2-a]pyridin-2-yl}methyl)amino]-2H-pyrazolo[3,4-d]pyrimidin-2-yl}methyl)phenyl]methyl}-1,2-dihydropyridin-2-one |

TABLE 1-continued

| Entry # | Example # | IUPAC Name |
|---|---|---|
| 120 | 246 | 1-{[4-({4-[({6-chloroimidazo[1,2-a]pyridin-2-yl}methyl)amino]-2H-pyrazolo[3,4-d]pyrimidin-2-yl}methyl)phenyl]methyl}-1,2-dihydropyridin-2-one |
| 121 | 247 | 1-[(4-{[4-({[4-methoxy-2-(1H-1,2,3,4-tetrazol-1-yl)phenyl]methyl}amino)-2H-pyrazolo[3,4-d]pyrimidin-2-yl]methyl}phenyl)methyl]-1,2-dihydropyridin-2-one |
| 122 | 248 | 1-({4-[(4-{[(2,5-dichlorophenyl)methyl]amino}-2H-pyrazolo[3,4-d]pyrimidin-2-yl)methyl]phenyl}methyl)-1,2-dihydropyridin-2-one |
| 123 | 249 | 1-({4-[(4-{[(5,5-dimethyl-4,5,6,7-tetrahydro-1H-indazol-3-yl)methyl]amino}-2H-pyrazolo[3,4-d]pyrimidin-2-yl]methyl}phenyl)methyl)-1,2-dihydropyridin-2-one |
| 124 | 250 | 1-[(4-{[4-({1H,4H,5H,7H-pyrano[3,4-c]pyrazol-3-ylmethyl}amino)-2H-pyrazolo[3,4-d]pyrimidin-2-yl]methyl}phenyl)methyl]-1,2-dihydropyridin-2-one |
| 125 | 251 | 1-{[4-({4-[({6-methoxyimidazo[1,2-a]pyridin-2-yl}methyl)amino]-2H-pyrazolo[3,4-d]pyrimidin-2-yl}methyl)phenyl]methyl}-1,2-dihydropyridin-2-one |
| 126 | 252 | 1-[(4-{[4-({[5-chloro-2-(1H-1,2,3-triazol-1-yl)phenyl]methyl}amino)-2H-pyrazolo[3,4-d]pyrimidin-2-yl]methyl}phenyl)methyl]-1,2-dihydropyridin-2-one |
| 127 | 253 | 1-[(4-{[4-({[5-chloro-2-(2H-1,2,3-triazol-2-yl)phenyl]methyl}amino)-2H-pyrazolo[3,4-d]pyrimidin-2-yl]methyl}phenyl)methyl]-1,2-dihydropyridin-2-one |
| 128 | 254 | 1-({4-[(4-{[(2-fluoro-3-methoxyphenyl)methyl]amino}-2H-pyrazolo[3,4-d]pyrimidin-2-yl)methyl]phenyl}methyl)-1,2-dihydropyridin-2-one |
| 129 | 255 | 1-({4-[(4-{[(2,6-difluoro-3-methoxyphenyl)methyl]amino}-2H-pyrazolo[3,4-d]pyrimidin-2-yl)methyl]phenyl}methyl)-1,2-dihydropyridin-2-one |
| 130 | 256 | 1-({4-[(4-{[(2,3,6-trifluorophenyl)methyl]amino}-2H-pyrazolo[3,4-d]pyrimidin-2-yl)methyl]phenyl}methyl)-1,2-dihydropyridin-2-one |
| 131 | 257 | 1-({4-[(4-{[(2-chloro-6-fluoro-3-methylphenyl)methyl]amino}-2H-pyrazolo[3,4-d]pyrimidin-2-yl)methyl]phenyl}methyl)-1,2-dihydropyridin-2-one |
| 132 | 258 | 1-({4-[(4-{[(2,6-difluoro-4-methoxyphenyl)methyl]amino}-2H-pyrazolo[3,4-d]pyrimidin-2-yl)methyl]phenyl}methyl)-1,2-dihydropyridin-2-one |
| 133 | 259 | 1-({4-[(4-{[(6-chloro-2-fluoro-3-methylphenyl)methyl]amino}-2H-pyrazolo[3,4-d]pyrimidin-2-yl)methyl]phenyl}methyl)-1,2-dihydropyridin-2-one |
| 134 | 260 | 1-[(4-{[4-({[5-chloro-2-(1H-1,2,4-triazol-1-yl)phenyl]methyl}amino)-2H-pyrazolo[3,4-d]pyrimidin-2-yl]methyl}phenyl)methyl]-1,2-dihydropyridin-2-one |
| 135 | 262 | 1-{[4-({4-[({5-methyl-1H,4H,5H,6H,7H-pyrazolo[4,3-c]pyridin-3-yl}methyl)amino]-2H-pyrazolo[3,4-d]pyrimidin-2-yl}methyl)phenyl]methyl}-1,2-dihydropyridin-2-one |
| 136 | 268 | 7-chloro-2-({[2-({4-[(2-oxo-1,2-dihydropyridin-1-yl)methyl]phenyl}methyl)-2H-pyrazolo[3,4-d]pyrimidin-4-yl]amino}methyl)imidazo[1,2-a]pyridine-3-carbonitrile |
| 137 | 271 | 4-methoxy-2-({[2-({4-[(2-oxo-1,2-dihydropyridin-1-yl)methyl]phenyl}methyl)-2H-pyrazolo[3,4-d]pyrimidin-4-yl]amino}methyl)benzonitrile |
| 138 | 274 | 1-({4-[(4-{[(6-chloro-1,3-benzoxazol-2-yl)methyl]amino}-2H-pyrazolo[3,4-d]pyrimidin-2-yl)methyl]phenyl}methyl)-1,2-dihydropyridin-2-one |
| 139 | 275 | 1-{[4-({4-[(2,3-dihydro-1H-isoindol-5-ylmethyl)amino]-2H-pyrazolo[3,4-d]pyrimidin-2-yl}methyl)phenyl]methyl}-1,2-dihydropyridin-2-one |
| 140 | 276 | 1-[(4-{[4-({[5-fluoro-2-(morpholin-4-yl)phenyl]methyl}amino)-2H-pyrazolo[3,4-d]pyrimidin-2-yl]methyl}phenyl)methyl]-1,2-dihydropyridin-2-one |
| 141 | 277 | 5-({[2-({4-[(2-oxo-1,2-dihydropyridin-1-yl)methyl]phenyl}methyl)-2H-pyrazolo[3,4-d]pyrimidin-4-yl]amino}methyl)-2,3-dihydro-1H-indol-2-one |
| 142 | 278 | 1-[(4-{[4-({[5-methoxy-2-(1H-1,2,3,4-tetrazol-1-yl)phenyl]methyl}amino)-2H-pyrazolo[3,4-d]pyrimidin-2-yl]methyl}phenyl)methyl]-1,2-dihydropyridin-2-one |
| 143 | 284 | 5-chloro-3-({[2-({4-[(2-oxo-1,2-dihydropyridin-1-yl)methyl]phenyl}methyl)-2H-pyrazolo[3,4-d]pyrimidin-4-yl]amino}methyl)-1H-indole-2-carbonitrile |
| 144 | 285 | 5-chloro-7-({[2-({4-[(2-oxo-1,2-dihydropyridin-1-yl)methyl]phenyl}methyl)-2H-pyrazolo[3,4-d]pyrimidin-4-yl]amino}methyl)-2,3-dihydro-1,3-benzoxazol-2-one |
| 145 | 286 | 1-{[4-({4-[({6-methyl-1H,4H,5H,6H,7H-pyrazolo[3,4-c]pyridin-3-yl}methyl)amino]-2H-pyrazolo[3,4-d]pyrimidin-2-yl}methyl)phenyl]methyl}-1,2-dihydropyridin-2-one |
| 146 | 291 | 1-{[4-({4-[({6-chloro-[1,2,4]triazolo[1,5-a]pyridin-2-yl}methyl)amino]-2H-pyrazolo[3,4-d]pyrimidin-2-yl}methyl)phenyl]methyl}-1,2-dihydropyridin-2-one |
| 147 | 295 | 6-methoxy-2-({[2-({4-[(2-oxo-1,2-dihydropyridin-1-yl)methyl]phenyl}methyl)-2H-pyrazolo[3,4-d]pyrimidin-4-yl]amino}methyl)pyridine-3-carbonitrile |
| 148 | 296 | 1-{[4-({4-[({7-chloro-[1,2,4]triazolo[1,5-a]pyridin-2-yl}methyl)amino]-2H-pyrazolo[3,4-d]pyrimidin-2-yl}methyl)phenyl]methyl}-1,2-dihydropyridin-2-one |
| 149 | 298 | 4-chloro-2-({[2-({4-[(2-oxo-1,2-dihydropyridin-1-yl)methyl]phenyl}methyl)-2H-pyrazolo[3,4-d]pyrimidin-4-yl]amino}methyl)benzonitrile |

TABLE 1-continued

| Entry # | Example # | IUPAC Name |
|---|---|---|
| 150 | 299 | 1-{[4-({4-[(1,2,3,4-tetrahydroisoquinolin-6-ylmethyl)amino]-2H-pyrazolo[3,4-d]pyrimidin-2-yl}methyl)phenyl]methyl}-1,2-dihydropyridin-2-one |
| 151 | 300 | 1-{[4-({4-[(1,2,3,4-tetrahydroisoquinolin-7-ylmethyl)amino]-2H-pyrazolo[3,4-d]pyrimidin-2-yl}methyl)phenyl]methyl}-1,2-dihydropyridin-2-one |
| 152 | 301 | 1-[(4-{[4-({[2-fluoro-5-(trifluoromethoxy)phenyl]methyl}amino)-2H-pyrazolo[3,4-d]pyrimidin-2-yl]methyl}phenyl)methyl]-1,2-dihydropyridin-2-one |
| 153 | 302 | 1-[(4-{[4-({[2-chloro-5-(difluoromethoxy)phenyl]methyl}amino)-2H-pyrazolo[3,4-d]pyrimidin-2-yl]methyl}phenyl)methyl]-1,2-dihydropyridin-2-one |
| 154 | 303 | 1-[(4-{[4-({[2-(1H-1,2,3,4-tetrazol-1-yl)-5-(trifluoromethoxy)phenyl]methyl}amino)-2H-pyrazolo[3,4-d]pyrimidin-2-yl]methyl}phenyl)methyl]-1,2-dihydropyridin-2-one |
| 155 | 304 | 1-[(4-{[4-({[6-chloro-2-fluoro-3-(trifluoromethoxy)phenyl]methyl}amino)-2H-pyrazolo[3,4-d]pyrimidin-2-yl]methyl}phenyl)methyl]-1,2-dihydropyridin-2-one |
| 156 | 305 | 1-({4-[(4-{[(6-ethynyl-2-fluoro-3-methoxyphenyl)methyl]amino}-2H-pyrazolo[3,4-d]pyrimidin-2-yl)methyl]phenyl}methyl)-1,2-dihydropyridin-2-one |
| 157 | 308 | 1-({4-[(4-{[(5-chlorothiophen-2-yl)methyl]amino}-2H-pyrazolo[3,4-d]pyrimidin-2-yl)methyl]phenyl}methyl)-1,2-dihydropyridin-2-one |
| 158 | 309 | 3-fluoro-4-methoxy-2-(({[2-({4-[(2-oxo-1,2-dihydropyridin-1-yl)methyl]phenyl}methyl)-2H-pyrazolo[3,4-d]pyrimidin-4-yl]amino}methyl)benzonitrile |
| 159 | 319 | 1-({4-[(4-{[(6-fluoro-2,3-dihydro-1H-isoindol-5-yl)methyl]amino}-2H-pyrazolo[3,4-d]pyrimidin-2-yl)methyl]phenyl}methyl)-1,2-dihydropyridin-2-one |
| 160 | 320 | 1-[(4-{[4-({[4-(aminomethyl)-2,6-dimethylphenyl]methyl}amino)-2H-pyrazolo[3,4-d]pyrimidin-2-yl]methyl}phenyl)methyl]-1,2-dihydropyridin-2-one |
| 161 | 321 | 1-[(4-{[4-({[2-(aminomethyl)-4,6-dimethylphenyl]methyl}amino)-2H-pyrazolo[3,4-d]pyrimidin-2-yl]methyl}phenyl)methyl]-1,2-dihydropyridin-2-one |
| 162 | 323 | 1-({4-[(4-{[(4,6-dimethyl-2,3-dihydro-1H-isoindol-5-yl)methyl]amino}-2H-pyrazolo[3,4-d]pyrimidin-2-yl)methyl]phenyl}methyl)-1,2-dihydropyridin-2-one |
| 163 | 330 | 1-({4-[(4-{[(6-fluoro-4-methyl-2,3-dihydro-1H-isoindol-5-yl)methyl]amino}-2H-pyrazolo[3,4-d]pyrimidin-2-yl)methyl]phenyl}methyl)-1,2-dihydropyridin-2-one |
| 164 | 335 | 1-({4-[(4-{[(6-amino-2,4-dimethylpyridin-3-yl)methyl]amino}-2H-pyrazolo[3,4-d]pyrimidin-2-yl)methyl]phenyl}methyl)-5-(trifluoromethyl)-1,2-dihydropyridin-2-one |
| 165 | 336 | 1-({4-[(4-{[(6-amino-2,4-dimethylpyridin-3-yl)methyl]amino}-2H-pyrazolo[3,4-d]pyrimidin-2-yl)methyl]phenyl}methyl)-5-fluoro-1,2-dihydropyridin-2-one |
| 166 | 337 | 1-({4-[(4-{[(6-amino-2,4-dimethylpyridin-3-yl)methyl]amino}-2H-pyrazolo[3,4-d]pyrimidin-2-yl)methyl]phenyl}methyl)-5-chloro-1,2-dihydropyridin-2-one |
| 167 | 338 | 5-chloro-1-({4-[(4-{[(4-methoxyphenyl)methyl]amino}-2H-pyrazolo[3,4-d]pyrimidin-2-yl)methyl]phenyl}methyl)-1,2-dihydropyridin-2-one |
| 168 | 340 | 5-chloro-1-({4-[(4-{[(5-chloro-3-methylpyridin-2-yl)methyl]amino}-2H-pyrazolo[3,4-d]pyrimidin-2-yl)methyl]phenyl}methyl)-1,2-dihydropyridin-2-one |
| 169 | 344 | 5-chloro-1-({4-[(4-{[(5-methoxy-3-methylpyridin-2-yl)methyl]amino}-2H-pyrazolo[3,4-d]pyrimidin-2-yl)methyl]phenyl}methyl)-1,2-dihydropyridin-2-one |
| 170 | 345 | 5-chloro-1-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one |
| 171 | 346 | 5-chloro-1-({4-[(4-{[(2,6-difluoro-3-methoxyphenyl)methyl]amino}-2H-pyrazolo[3,4-d]pyrimidin-2-yl)methyl]phenyl}methyl)-1,2-dihydropyridin-2-one |
| 172 | 347 | 5-chloro-1-({4-[(4-{[(2-fluoro-3-methoxyphenyl)methyl]amino}-2H-pyrazolo[3,4-d]pyrimidin-2-yl)methyl]phenyl}methyl)-1,2-dihydropyridin-2-one |
| 173 | 348 | 5-chloro-1-({4-[(4-{[(2-fluoro-5-methoxyphenyl)methyl]amino}-2H-pyrazolo[3,4-d]pyrimidin-2-yl)methyl]phenyl}methyl)-1,2-dihydropyridin-2-one |
| 174 | 349 | 5-chloro-1-({4-[(4-{[(6-chloro-2-fluoro-3-hydroxyphenyl)methyl]amino}-2H-pyrazolo[3,4-d]pyrimidin-2-yl)methyl]phenyl}methyl)-1,2-dihydropyridin-2-one |
| 175 | 350 | 1-({4-[(4-{[(2-amino-4,6-dimethylpyrimidin-5-yl)methyl]amino}-2H-pyrazolo[3,4-d]pyrimidin-2-yl)methyl]phenyl}methyl)-5-chloro-1,2-dihydropyridin-2-one |
| 176 | 351 | 5-chloro-1-({4-[(4-{[(6-methoxy-2,4-dimethylpyridin-3-yl)methyl]amino}-2H-pyrazolo[3,4-d]pyrimidin-2-yl)methyl]phenyl}methyl)-1,2-dihydropyridin-2-one |
| 177 | 352 | 5-chloro-1-({4-[(4-{[(6-hydroxy-2,4-dimethylpyridin-3-yl)methyl]amino}-2H-pyrazolo[3,4-d]pyrimidin-2-yl)methyl]phenyl}methyl)-1,2-dihydropyridin-2-one |

TABLE 1-continued

| Entry # | Example # | IUPAC Name |
|---|---|---|
| 178 | 353 | 5-chloro-1-{[4-({4-[(cyclopropylmethyl)amino]-2H-pyrazolo[3,4-d]pyrimidin-2-yl}methyl)phenyl]methyl}-1,2-dihydropyridin-2-one |
| 179 | 355 | 5-chloro-1-{[4-({4-[(piperidin-4-ylmethyl)amino]-2H-pyrazolo[3,4-d]pyrimidin-2-yl}methyl)phenyl]methyl}-1,2-dihydropyridin-2-one |
| 180 | 359 | 1-{[4-({4-[(azepan-4-ylmethyl)amino]-2H-pyrazolo[3,4-d]pyrimidin-2-yl}methyl)phenyl]methyl}-5-chloro-1,2-dihydropyridin-2-one |
| 181 | 360 | 5-chloro-1-[(4-{[4-({1H-pyrrolo[2,3-b]pyridin-5-ylmethyl}amino)-2H-pyrazolo[3,4-d]pyrimidin-2-yl]methyl}phenyl)methyl]-1,2-dihydropyridin-2-one |
| 182 | 366 | 5-chloro-1-{[4-({4-[({6-methyl-1H-pyrrolo[2,3-b]pyridin-5-yl}methyl)amino]-2H-pyrazolo[3,4-d]pyrimidin-2-yl}methyl)phenyl]methyl}-1,2-dihydropyridin-2-one |
| 183 | 367 | 5-chloro-1-{[4-({4-[({4,6-dimethyl-1H-pyrrolo[2,3-b]pyridin-5-yl}methyl)amino]-2H-pyrazolo[3,4-d]pyrimidin-2-yl}methyl)phenyl]methyl}-1,2-dihydropyridin-2-one |
| 184 | 370 | 5-{[(4-chloro-1-{[4-(1H-pyrazol-1-ylmethyl)phenyl]methyl}-1H-pyrazolo[4,3-c]pyridin-6-yl)amino]methyl}-4,6-dimethylpyridin-2-amine |
| 185 | 371 | 5-{[(6-chloro-2-{[4-(1H-pyrazol-1-ylmethyl)phenyl]methyl}-2H-pyrazolo[3,4-d]pyrimidin-4-yl)amino]methyl}-4,6-dimethylpyridin-2-amine |
| 186 | 373 | 5-{[(6-methoxy-2-{[4-(1H-pyrazol-1-ylmethyl)phenyl]methyl}-2H-pyrazolo[3,4-d]pyrimidin-4-yl)amino]methyl}-4,6-dimethylpyridin-2-amine |
| 187 | 374 | 4-N-[(6-amino-2,4-dimethylpyridin-3-yl)methyl]-6-N,6-N-dimethyl-2-{[4-(1H-pyrazol-1-ylmethyl)phenyl]methyl}-2H-pyrazolo[3,4-d]pyrimidine-4,6-diamine |
| 188 | 375 | 4-{[(6-amino-2,4-dimethylpyridin-3-yl)methyl]amino}-2-{[4-(1H-pyrazol-1-ylmethyl)phenyl]methyl}-2H-pyrazolo[3,4-d]pyrimidine-6-carbonitrile |
| 189 | 379 | 5-({[6-chloro-2-({2-methylimidazo[1,2-a]pyridin-6-yl}methyl)-2H-pyrazolo[4,3-c]pyridin-4-yl]amino}methyl)-4,6-dimethylpyridin-2-amine |
| 190 | 385 | 4-{[(6-amino-2,4-dimethylpyridin-3-yl)methyl]amino}-6-{[4-(1H-pyrazol-1-ylmethyl)phenyl]methyl}-6H-pyrrolo[3,4-d]pyrimidine-7-carboxylic acid |
| 191 | 388 | 4-{[(6-amino-2,4-dimethylpyridin-3-yl)methyl]amino}-2-{[4-(1H-pyrazol-1-ylmethyl)phenyl]methyl}-2H-pyrazolo[3,4-d]pyrimidine-6-carboxylic acid |
| 192 | 389 | 4-{[(6-amino-2,4-dimethylpyridin-3-yl)methyl]amino}-N,N-dimethyl-2-{[4-(1H-pyrazol-1-ylmethyl)phenyl]methyl}-2H-pyrazolo[3,4-d]pyrimidine-6-carboxamide |
| 193 | 393 | 4-{[(4-methoxyphenyl)methyl]amino}-2-({4-[(2-oxo-1,2-dihydropyridin-1-yl)methyl]phenyl}methyl)-2H-pyrazolo[3,4-d]pyrimidine-6-carbonitrile |
| 194 | 399 | 4-{[(6-chloro-2-fluoro-3-methoxyphenyl)methyl]amino}-2-{[4-(1H-pyrazol-1-ylmethyl)phenyl]methyl}-2H-pyrazolo[3,4-d]pyrimidine-6-carboxylic acid |
| 195 | 400 | 4-chloro-3-{[(6-chloro-2-{[4-(1H-pyrazol-1-ylmethyl)phenyl]methyl}-2H-pyrazolo[3,4-d]pyrimidin-4-yl)amino]methyl}-2-fluorophenol |
| 196 | 401 | 1-({4-[({6-amino-2,4-dimethylpyridin-3-yl}methyl)amino]-2-chloro-6H-pyrrolo[3,4-d]pyrimidin-6-yl}methyl]phenyl}methyl)-1,2-dihydropyridin-2-one |
| 197 | 406 | 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidine-6-carboxylic acid |
| 198 | 407 | ethyl 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidine-6-carboxylate |
| 199 | 408 | 6-(azetidine-1-carbonyl)-N-[(6-chloro-2-fluoro-3-methoxyphenyl)methyl]-2-({4-[1-(1H-pyrazol-1-yl)ethyl]phenyl}methyl)-2H-pyrazolo[3,4-d]pyrimidin-4-amine |
| 200 | 409 | 4-{[(6-chloro-2-fluoro-3-methoxyphenyl)methyl]amino}-N,N-dimethyl-2-({4-[1-(1H-pyrazol-1-yl)ethyl]phenyl}methyl)-2H-pyrazolo[3,4-d]pyrimidine-6-carboxamide |
| 201 | 410 | 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidin-6-ol |
| 202 | 411 | N-[(6-chloro-2-fluoro-3-methoxyphenyl)methyl]-6-{[3-(pyrimidin-5-yl)phenyl]methyl}-5H,6H,7H-pyrrolo[3,4-d]pyrimidin-4-amine |
| 203 | 412 | N-[(6-chloro-2-fluoro-3-methoxyphenyl)methyl]-6-{[3-(pyrimidin-5-yl)phenyl]methyl}-6H-pyrrolo[3,4-d]pyrimidin-4-amine |
| 204 | 413 | 6-[(4-chloro-1-methyl-1H-pyrazol-3-yl)methyl]-N-[(6-chloro-2-fluoro-3-methoxyphenyl)methyl]-5H,6H,7H-pyrrolo[3,4-d]pyrimidin-4-amine |
| 205 | 414 | 6-[(4-chloro-1-methyl-1H-pyrazol-3-yl)methyl]-N-[(6-chloro-2-fluoro-3-methoxyphenyl)methyl]-6H-pyrrolo[3,4-d]pyrimidin-4-amine |
| 206 | 415 | 5-[(4-{[(6-chloro-2-fluoro-3-methoxyphenyl)methyl]amino}-6H-pyrrolo[3,4-d]pyrimidin-6-yl)methyl]-4-methoxy-N,N-dimethyl-1,3-thiazol-2-amine |
| 207 | 418 | N-[(6-chloro-2-fluoro-3-methoxyphenyl)methyl]-6-{[2-(propan-2-yl)pyrimidin-5-yl]methyl}-5H,6H,7H-pyrrolo[3,4-d]pyrimidin-4-amine |
| 208 | 419 | N-[(6-chloro-2-fluoro-3-methoxyphenyl)methyl]-6-{[2-(propan-2-yl)pyrimidin-5-yl]methyl}-6H-pyrrolo[3,4-d]pyrimidin-4-amine |
| 209 | 425 | 4-{[(6-chloro-2-fluoro-3-methoxyphenyl)methyl]amino}-2-[(5-methylquinolin-3-yl)methyl]-2H-pyrazolo[3,4-d]pyrimidin-6-ol |
| 210 | 426 | 4-{[(6-chloro-2-fluoro-3-methoxyphenyl)methyl]amino}-2-[(3-methylquinolin-5-yl)methyl]-2H-pyrazolo[3,4-d]pyrimidin-6-ol |
| 211 | 431 | 4-{[(6-chloro-2-fluoro-3-methoxyphenyl)methyl]amino}-2-{[3-methyl-2-(propan-2-yl)imidazo[1,2-a]pyridin-6-yl]methyl}-2H-pyrazolo[3,4-d]pyrimidin-6-ol |

TABLE 1-continued

| Entry # | Example # | IUPAC Name |
|---|---|---|
| 212 | 432 | 4-{[(6-chloro-2-fluoro-3-methoxyphenyl)methyl]amino}-2-[(2-ethyl-1,4-dimethyl-1H-1,3-benzodiazol-6-yl)methyl]-2H-pyrazolo[3,4-d]pyrimidin-6-ol |
| 213 | 433 | 4-{[(6-chloro-2-fluoro-3-methoxyphenyl)methyl]amino}-2-[(6-methylquinolin-3-yl)methyl]-2H-pyrazolo[3,4-d]pyrimidin-6-ol |
| 214 | 434 | 6-chloro-N-[(6-chloro-2-fluoro-3-methoxyphenyl)methyl]-2-[(1-ethyl-1,2,3,4-tetrahydroquinolin-7-yl)methyl]-2H-pyrazolo[3,4-d]pyrimidin-4-amine |
| 215 | 435 | 4-{[(6-chloro-2-fluoro-3-methoxyphenyl)methyl]amino}-2-[(7-methylquinolin-2-yl)methyl]-2H-pyrazolo[3,4-d]pyrimidin-6-ol |
| 216 | 436 | 4-{[(6-chloro-2-fluoro-3-methoxyphenyl)methyl]amino}-2-[(2-methylquinolin-7-yl)methyl]-2H-pyrazolo[3,4-d]pyrimidin-6-ol |
| 217 | 437 | 4-{[(6-chloro-2-fluoro-3-methoxyphenyl)methyl]amino}-2-[(2-ethyl-1-methyl-1H-1,3-benzodiazol-6-yl)methyl]-2H-pyrazolo[3,4-d]pyrimidin-6-ol |
| 218 | 438 | 4-{[(6-chloro-2-fluoro-3-methoxyphenyl)methyl]amino}-2-[(2-ethyl-1-methyl-1H-1,3-benzodiazol-5-yl)methyl]-2H-pyrazolo[3,4-d]pyrimidin-6-ol |
| 219 | 444 | ethyl 4-{[(6-{[(hexyloxy)carbonyl]amino}-2,4-dimethylpyridin-3-yl)methyl]amino}-2-{[4-(1H-pyrazol-1-ylmethyl)phenyl]methyl}-2H-pyrazolo[3,4-d]pyrimidine-6-carboxylate |
| 220 | 446 | 6-(({2-({2-methylimidazo[1,2-a]pyridin-6-yl}methyl)-2H-pyrazolo[4,3-c]pyridin-4-yl]amino}methyl)isoquinolin-1-amine |
| 221 | 447 | 6-[({2-[(1,2-dimethyl-1H-1,3-benzodiazol-5-yl)methyl]-2H-pyrazolo[4,3-c]pyridin-4-yl}amino)methyl]isoquinolin-1-amine |
| 222 | 448 | 6-[({2-[(6-chloro-5-methylpyridin-3-yl)methyl]-2H-pyrazolo[4,3-c]pyridin-4-yl}amino)methyl]isoquinolin-1-amine |
| 223 | 449 | 6-[({2-[(6-fluoro-5-methylpyridin-3-yl)methyl]-2H-pyrazolo[4,3-c]pyridin-4-yl}amino)methyl]isoquinolin-1-amine |
| 224 | 450 | 6-[({2-[(6-phenoxypyridin-3-yl)methyl]-2H-pyrazolo[4,3-c]pyridin-4-yl}amino)methyl]isoquinolin-1-amine |
| 225 | 451 | 6-{[(2-{[6-(pyridin-3-yloxy)pyridin-3-yl]methyl}-2H-pyrazolo[4,3-c]pyridin-4-yl)amino]methyl}isoquinolin-1-amine |
| 226 | 454 | 6-{[(2-{[6-(cyclohexyloxy)pyridin-3-yl]methyl}-2H-pyrazolo[4,3-c]pyridin-4-yl)amino]methyl}isoquinolin-1-amine |
| 227 | 455 | 6-{[(2-{[6-(cyclopentyloxy)pyridin-3-yl]methyl}-2H-pyrazolo[4,3-c]pyridin-4-yl)amino]methyl}isoquinolin-1-amine |
| 228 | 456 | 5-[(4-{[(1-aminoisoquinolin-6-yl)methyl]amino}-2H-pyrazolo[4,3-c]pyridin-2-yl)methyl]-1,3-dimethyl-2,3-dihydro-1H-1,3-benzodiazol-2-one |
| 229 | 457 | 6-[({2-[(5-chloro-6-methoxypyridin-3-yl)methyl]-2H-pyrazolo[4,3-c]pyridin-4-yl}amino)methyl]isoquinolin-1-amine |
| 230 | 459 | 6-{[(2-{[6-(morpholin-4-yl)pyridin-3-yl]methyl}-2H-pyrazolo[4,3-c]pyridin-4-yl)amino]methyl}isoquinolin-1-amine |
| 231 | 460 | 6-{[(2-{[6-(piperidin-1-yl)pyridin-3-yl]methyl}-2H-pyrazolo[4,3-c]pyridin-4-yl)amino]methyl}isoquinolin-1-amine |
| 232 | 463 | 4,6-dimethyl-5-{[(2-{[5-(piperidin-1-yl)pyrazin-2-yl]methyl}-2H-pyrazolo[3,4-d]pyrimidin-4-yl)amino]methyl}pyridin-2-amine |
| 233 | 464 | 5-[(4-{[(6-amino-2,4-dimethylpyridin-3-yl)methyl]amino}-2H-pyrazolo[3,4-d]pyrimidin-2-yl)methyl]-N-cyclopentyl-N-methylpyrazin-2-amine |
| 234 | 468 | 5-[({2-[(2-ethyl-1,3-benzoxazol-5-yl)methyl]-2H-pyrazolo[3,4-d]pyrimidin-4-yl}amino)methyl]-4,6-dimethylpyridin-2-amine |
| 235 | 469 | 1-{5-[(4-{[(1-aminoisoquinolin-6-yl)methyl]amino}-2H-pyrazolo[4,3-c]pyridin-2-yl)methyl]pyridin-2-yl}pyrrolidin-2-one |
| 236 | 470 | 4,6-dimethyl-5-({[2-({2-methylimidazo[1,2-a]pyridin-6-yl}methyl)-2H-pyrazolo[4,3-c]pyridin-4-yl]amino}methyl)pyridin-2-amine |
| 237 | 471 | N-[(2-chloro-1-benzothiophen-5-yl)methyl]-2-({2-methylimidazo[1,2-a]pyridin-6-yl}methyl)-2H-pyrazolo[4,3-c]pyridin-4-amine |
| 238 | 472 | N-[(6-chloro-1-benzofuran-2-yl)methyl]-2-({2-methylimidazo[1,2-a]pyridin-6-yl}methyl)-2H-pyrazolo[4,3-c]pyridin-4-amine |
| 239 | 473 | N-[(5-chloro-1,3-benzothiazol-2-yl)methyl]-2-({2-methylimidazo[1,2-a]pyridin-6-yl}methyl)-2H-pyrazolo[4,3-c]pyridin-4-amine |
| 240 | 474 | N-[(5-chloro-1H-indazol-3-yl)methyl]-2-({2-methylimidazo[1,2-a]pyridin-6-yl}methyl)-2H-pyrazolo[4,3-c]pyridin-4-amine |
| 241 | 475 | 6-[({2-[(5,6-dimethoxypyridin-3-yl)methyl]-2H-pyrazolo[4,3-c]pyridin-4-yl}amino)methyl]isoquinolin-1-amine |
| 242 | 481 | N-{[4-(5-chlorothiophen-2-yl)-1,3-thiazol-2-yl]methyl}-2-({2-methylimidazo[1,2-a]pyridin-6-yl}methyl)-2H-pyrazolo[4,3-c]pyridin-4-amine |
| 243 | 482 | 4,6-dimethyl-5-[({2-[(1-methylpiperidin-4-yl)methyl]-2H-pyrazolo[4,3-c]pyridin-4-yl}amino)methyl]pyridin-2-amine |
| 244 | 483 | 4,6-dimethyl-5-{[(2-{[6-(oxolan-3-yloxy)pyridin-3-yl]methyl}-2H-pyrazolo[4,3-c]pyridin-4-yl)amino]methyl}pyridin-2-amine |
| 245 | 484 | 4,6-dimethyl-5-[({2-[(2-methyl-1,3-benzoxazol-5-yl)methyl]-2H-pyrazolo[4,3-c]pyridin-4-yl}amino)methyl]pyridin-2-amine |
| 246 | 485 | N-[(7-chloroquinolin-2-yl)methyl]-2-({2-methylimidazo[1,2-a]pyridin-6-yl}methyl)-2H-pyrazolo[4,3-c]pyridin-4-amine |
| 247 | 486 | N-[(6-chloro-1-benzothiophen-2-yl)methyl]-2-({2-methylimidazo[1,2-a]pyridin-6-yl}methyl)-2H-pyrazolo[4,3-c]pyridin-4-amine |
| 248 | 487 | N-[(5-chloro-1-benzothiophen-2-yl)methyl]-2-({2-methylimidazo[1,2-a]pyridin-6-yl}methyl)-2H-pyrazolo[4,3-c]pyridin-4-amine |
| 249 | 489 | 4,6-dimethyl-5-[({2-[(2-methyl-1,3-benzoxazol-5-yl)methyl]-2H-pyrazolo[3,4-d]pyrimidin-4-yl}amino)methyl]pyridin-2-amine |

TABLE 1-continued

| Entry # | Example # | IUPAC Name |
|---|---|---|
| 250 | 490 | 4-{5-[(4-{[(1-aminoisoquinolin-6-yl)methyl]amino}-2H-pyrazolo[4,3-c]pyridin-2-yl)methyl]pyridin-2-yl}morpholin-3-one |
| 251 | 491 | N-[(4-chloro-1-benzothiophen-2-yl)methyl]-2-({2-methylimidazo[1,2-a]pyridin-6-yl}methyl)-2H-pyrazolo[4,3-c]pyridin-4-amine |
| 252 | 492 | N-{[2-(5-chlorothiophen-2-yl)-1,3-thiazol-5-yl]methyl}-2-({2-methylimidazo[1,2-a]pyridin-6-yl}methyl)-2H-pyrazolo[4,3-c]pyridin-4-amine |
| 253 | 493 | 1-{[6-amino-2-methyl-3-({[2-({2-methylimidazo[1,2-a]pyridin-6-yl}methyl)-2H-pyrazolo[4,3-c]pyridin-4-yl]amino}methyl)pyridin-4-yl]oxy}-3,3-dimethylbutan-2-one |
| 254 | 494 | 4,6-dimethyl-5-{[(2-{[6-(pyrrolidin-3-yloxy)pyridin-3-yl]methyl}-2H-pyrazolo[4,3-c]pyridin-4-yl)amino]methyl}pyridin-2-amine |
| 255 | 499 | 4,6-dimethyl-5-[({2-[(2-methyl-1,3-benzothiazol-5-yl)methyl]-2H-pyrazolo[3,4-d]pyrimidin-4-yl}amino)methyl]pyridin-2-amine |
| 256 | 500 | 5-[({2-[(2-ethyl-1,3-benzothiazol-5-yl)methyl]-2H-pyrazolo[3,4-d]pyrimidin-4-yl}amino)methyl]-4,6-dimethylpyridin-2-amine |
| 257 | 501 | N-[(3-chloroisoquinolin-6-yl)methyl]-2-({2-methylimidazo[1,2-a]pyridin-6-yl}methyl)-2H-pyrazolo[4,3-c]pyridin-4-amine |
| 258 | 504 | 5-{[(2-{[3-fluoro-4-(1H-pyrazol-1-ylmethyl)phenyl]methyl}-2H-pyrazolo[3,4-d]pyrimidin-4-yl)amino]methyl}-4,6-dimethylpyridin-2-amine |
| 259 | 508 | 4,6-dimethyl-5-{[(2-{[(1r,4r)-4-(1H-pyrazol-1-ylmethyl)cyclohexyl]methyl}-2H-pyrazolo[3,4-d]pyrimidin-4-yl)amino]methyl}pyridin-2-amine |
| 260 | 512 | N-{[5-(5-chlorothiophen-2-yl)-1,2-oxazol-3-yl]methyl}-2-({2-methylimidazo[1,2-a]pyridin-6-yl}methyl)-2H-pyrazolo[4,3-c]pyridin-4-amine |
| 261 | 513 | N-[(7-chloronaphthalen-2-yl)methyl]-2-({2-methylimidazo[1,2-a]pyridin-6-yl}methyl)-2H-pyrazolo[4,3-c]pyridin-4-amine |
| 262 | 518 | tert-butyl 2-(5-methoxy-2-{[(2-{[4-(1H-pyrazol-1-ylmethyl)phenyl]methyl}-2H-pyrazolo[3,4-d]pyrimidin-4-yl)amino]methyl}phenoxy)acetate |
| 263 | 522 | 4,6-dimethyl-5-({[2-({2-methylimidazo[1,2-a]pyridin-6-yl}methyl)-2H-pyrazolo[3,4-d]pyrimidin-4-yl]amino}methyl)pyridin-2-amine |
| 264 | 523 | 5-({[2-({2-ethylimidazo[1,2-a]pyridin-6-yl}methyl)-2H-pyrazolo[3,4-d]pyrimidin-4-yl]amino}methyl)-4,6-dimethylpyridin-2-amine |
| 265 | 524 | 1-({4-[(4-{[(6-amino-2,4-dimethylpyridin-3-yl)methyl]amino}-2H-pyrazolo[3,4-d]pyrimidin-2-yl)methyl]phenyl}methyl)pyrrolidin-2-one |
| 266 | 525 | 4,6-dimethyl-5-{[(2-{[2-(trifluoromethyl)imidazo[1,2-a]pyridin-6-yl]methyl}-2H-pyrazolo[3,4-d]pyrimidin-4-yl)amino]methyl}pyridin-2-amine |
| 267 | 526 | N-[(3-chloroisoquinolin-6-yl)methyl]-2-{[6-(pyrrolidin-3-yloxy)pyridin-3-yl]methyl}-2H-pyrazolo[4,3-c]pyridin-4-amine |
| 268 | 530 | 3-{5-[(4-{[(1-aminoisoquinolin-6-yl)methyl]amino}-2H-pyrazolo[4,3-c]pyridin-2-yl)methyl]pyridin-2-yl}-1,3-oxazolidin-2-one |
| 269 | 535 | N-({6-chlorothieno[2,3-b]pyridin-2-yl}methyl)-2-({2-methylimidazo[1,2-a]pyridin-6-yl}methyl)-2H-pyrazolo[4,3-c]pyridin-4-amine |
| 270 | 536 | 6-({[2-({2-methylimidazo[1,2-a]pyridin-6-yl}methyl)-2H-pyrazolo[4,3-c]pyridin-4-yl]amino}methyl)-1,2-benzoxazol-3-amine |
| 271 | 541 | 3-chloro-6-({[2-({2-methylimidazo[1,2-a]pyridin-6-yl}methyl)-2H-pyrazolo[4,3-c]pyridin-4-yl]amino}methyl)isoquinolin-1-amine |
| 272 | 542 | 5-{[(2-{[3-methoxy-4-(1H-pyrazol-1-ylmethyl)phenyl]methyl}-2H-pyrazolo[3,4-d]pyrimidin-4-yl)amino]methyl}-4,6-dimethylpyridin-2-amine |
| 273 | 543 | 5-[({2-[(2-ethyl-7-methyl-1,3-benzoxazol-5-yl)methyl]-2H-pyrazolo[3,4-d]pyrimidin-4-yl}amino)methyl]-4,6-dimethylpyridin-2-amine |
| 274 | 544 | 5-[({2-[(2-ethyl-1,3-benzothiazol-5-yl)methyl]-2H-pyrazolo[3,4-d]pyrimidin-4-yl}amino)methyl]-4-methoxy-6-methylpyridin-2-amine |
| 275 | 545 | 1-({4-[(4-{[(6-amino-2,4-dimethylpyridin-3-yl)methyl]amino}-2H-pyrazolo[3,4-d]pyrimidin-2-yl)methyl]phenyl}methyl)-3-methyl-1,2,3,4-tetrahydropyrimidine-2,4-dione |
| 276 | 551 | 5-{[(2-{[4-(cyclopentanesulfonyl)phenyl]methyl}-2H-pyrazolo[3,4-d]pyrimidin-4-yl)amino]methyl}-4,6-dimethylpyridin-2-amine |
| 277 | 556 | 7-[(4-{[(6-amino-2,4-dimethylpyridin-3-yl)methyl]amino}-2H-pyrazolo[4,3-c]pyridin-2-yl)methyl]-1H,2H,3H,9H-pyrrolo[2,1-b]quinazolin-9-one |
| 278 | 563 | 12-[(4-{[(6-amino-2,4-dimethylpyridin-3-yl)methyl]amino}-2H-pyrazolo[4,3-c]pyridin-2-yl)methyl]-3,4,9-triazatricyclo[8.4.0.0³,⁷]tetradeca-1(10),4,6,11,13-pentaen-8-one |
| 279 | 564 | 1-({4-[(4-{[(6-amino-2,4-dimethylpyridin-3-yl)methyl]amino}-2H-pyrazolo[3,4-d]pyrimidin-2-yl)methyl]phenyl}methyl)piperidin-2-one |
| 280 | 565 | 4-({4-[(4-{[(6-amino-2,4-dimethylpyridin-3-yl)methyl]amino}-2H-pyrazolo[3,4-d]pyrimidin-2-yl)methyl]phenyl}methyl)morpholin-3-one |
| 281 | 566 | 1-({4-[(4-{[(6-amino-2,4-dimethylpyridin-3-yl)methyl]amino}-2H-pyrazolo[3,4-d]pyrimidin-2-yl)methyl]phenyl}methyl)azepan-2-one |
| 282 | 567 | 5-({[2-({2-ethyl-3-methylimidazo[1,2-a]pyridin-6-yl}methyl)-2H-pyrazolo[3,4-d]pyrimidin-4-yl]amino}methyl)-4,6-dimethylpyridin-2-amine |
| 283 | 572 | N-[(5-chloro-1H-indazol-3-yl)methyl]-2-{[6-(oxolan-3-ylmethyl)pyridin-3-yl]methyl}-2H-pyrazolo[3,4-d]pyrimidin-4-amine |
| 284 | 573 | N-[(6-chloro-2-fluoro-3-methoxyphenyl)methyl]-2-(quinoxalin-6-ylmethyl)-2H-pyrazolo[3,4-d]pyrimidin-4-amine |
| 285 | 575 | 1-({4-[(4-{[(6-chloro-2-fluoro-3-methoxyphenyl)methyl]amino}-2H-pyrazolo[3,4-d]pyrimidin-2-yl)methyl]phenyl}methyl)-3-methyl-1,3-diazinan-2-one |
| 286 | 576 | 1-({4-[(4-{[(6-amino-2,4-dimethylpyridin-3-yl)methyl]amino}-2H-pyrazolo[3,4-d]pyrimidin-2-yl)methyl]phenyl}methyl)-3-methyl-1,3-diazinan-2-one |

TABLE 1-continued

| Entry # | Example # | IUPAC Name |
|---|---|---|
| 287 | 579 | 6-[(4-{[(6-amino-2,4-dimethylpyridin-3-yl)methyl]amino}-2H-pyrazolo[3,4-d]pyrimidin-2-yl)methyl]-1H,2H,3H,9H-pyrrolo[2,1-b]quinazolin-9-one |
| 288 | 580 | 2-[(4-{[(6-amino-2,4-dimethylpyridin-3-yl)methyl]amino}-2H-pyrazolo[3,4-d]pyrimidin-2-yl)methyl]-5-fluorobenzonitrile |
| 289 | 581 | 5-[({2-[(2,4-difluorophenyl)methyl]-2H-pyrazolo[3,4-d]pyrimidin-4-yl}amino)methyl]-4,6-dimethylpyridin-2-amine |
| 290 | 582 | 5-[({2-[(2,4-difluorophenyl)methyl]-2H-pyrazolo[3,4-d]pyrimidin-4-yl}amino)methyl]-4,6-dimethylpyrimidin-2-amine |
| 291 | 583 | 5-{[(2-{[2-methoxy-4-(trifluoromethyl)phenyl]methyl}-2H-pyrazolo[3,4-d]pyrimidin-4-yl)amino]methyl}-4,6-dimethylpyridin-2-amine |
| 292 | 584 | 2-[(4-{[(6-amino-2,4-dimethylpyridin-3-yl)methyl]amino}-2H-pyrazolo[3,4-d]pyrimidin-2-yl)methyl]-5-methoxybenzonitrile |
| 293 | 585 | 4,6-dimethyl-5-[({2-[(2-phenyl-1,3-thiazol-4-yl)methyl]-2H-pyrazolo[3,4-d]pyrimidin-4-yl}amino)methyl]pyridin-2-amine |
| 294 | 586 | N-[(6-chloro-2-fluoro-3-methoxyphenyl)methyl]-2-[(2-phenyl-1,3-thiazol-4-yl)methyl]-2H-pyrazolo[3,4-d]pyrimidin-4-amine |
| 295 | 587 | 5-[({2-[(2,4-dimethoxyphenyl)methyl]-2H-pyrazolo[3,4-d]pyrimidin-4-yl}amino)methyl]-4,6-dimethylpyridin-2-amine |
| 296 | 588 | 5-[({2-[(4-fluoro-2-methoxyphenyl)methyl]-2H-pyrazolo[3,4-d]pyrimidin-4-yl}amino)methyl]-4,6-dimethylpyridin-2-amine |
| 297 | 589 | 5-[({2-[(3-fluoropyridin-2-yl)methyl]-2H-pyrazolo[3,4-d]pyrimidin-4-yl}amino)methyl]-4,6-dimethylpyridin-2-amine |
| 298 | 590 | 4,6-dimethyl-5-[({2-[(2-methylquinolin-6-yl)methyl]-2H-pyrazolo[3,4-d]pyrimidin-4-yl}amino)methyl]pyridin-2-amine |
| 299 | 594 | N-[(6-chloro-2-fluoro-3-methoxyphenyl)methyl]-2-({4-[1-(1H-pyrazol-1-yl)ethyl]phenyl}methyl)-2H-pyrazolo[3,4-d]pyrimidin-4-amine |
| 300 | 595 | N-{[5-methoxy-2-(1H-1,2,3,4-tetrazol-1-yl)phenyl]methyl}-2-({4-[1-(1H-pyrazol-1-yl)ethyl]phenyl}methyl)-2H-pyrazolo[3,4-d]pyrimidin-4-amine |
| 301 | 596 | 4,6-dimethyl-5-({[2-({4-[1-(1H-pyrazol-1-yl)ethyl]phenyl}methyl)-2H-pyrazolo[3,4-d]pyrimidin-4-yl]amino}methyl)pyridin-2-amine |
| 302 | 597 | N-[(6-chloro-2-fluoro-3-methoxyphenyl)methyl]-2-({2-ethyl-3-methylimidazo[1,2-a]pyridin-6-yl}methyl)-2H-pyrazolo[3,4-d]pyrimidin-4-amine |
| 303 | 598 | N-[(2,6-difluoro-3-methoxyphenyl)methyl]-2-({2-ethyl-3-methylimidazo[1,2-a]pyridin-6-yl}methyl)-2H-pyrazolo[3,4-d]pyrimidin-4-amine |
| 304 | 599 | 4,6-dimethyl-5-[({2-[(2-phenyl-1,3-oxazol-4-yl)methyl]-2H-pyrazolo[3,4-d]pyrimidin-4-yl}amino)methyl]pyridin-2-amine |
| 305 | 600 | N-[(6-chloro-2-fluoro-3-methoxyphenyl)methyl]-2-[(2-phenyl-1,3-oxazol-4-yl)methyl]-2H-pyrazolo[3,4-d]pyrimidin-4-amine |
| 306 | 601 | 5-[({2-[(1,2-dimethyl-1H-1,3-benzodiazol-6-yl)methyl]-2H-pyrazolo[3,4-d]pyrimidin-4-yl}amino)methyl]-4,6-dimethylpyridin-2-amine |
| 307 | 602 | 5-[({2-[(2-ethyl-1-methyl-1H-1,3-benzodiazol-6-yl)methyl]-2H-pyrazolo[3,4-d]pyrimidin-4-yl}amino)methyl]-4,6-dimethylpyridin-2-amine |
| 308 | 607 | N-[(6-chloro-2-fluoro-3-methoxyphenyl)methyl]-2-{1-[4-(1H-pyrazol-1-ylmethyl)phenyl]ethyl}-2H-pyrazolo[3,4-d]pyrimidin-4-amine |
| 309 | 608 | N-[(6-chloro-2-fluoro-3-methoxyphenyl)methyl]-1-{1-[4-(1H-pyrazol-1-ylmethyl)phenyl]ethyl}-1H-pyrazolo[3,4-d]pyrimidin-4-amine |
| 310 | 609 | 2-[(4-{[(6-amino-2,4-dimethylpyridin-3-yl)methyl]amino}-2H-pyrazolo[3,4-d]pyrimidin-2-yl)methyl]-5-(trifluoromethyl)benzonitrile |
| 311 | 610 | 2-[(4-{[(6-amino-2,4-dimethylpyridin-3-yl)methyl]amino}-2H-pyrazolo[3,4-d]pyrimidin-2-yl)methyl]pyridine-3-carbonitrile |
| 312 | 611 | 4,6-dimethyl-5-{[(2-{[3-(trifluoromethyl)pyridin-2-yl]methyl}-2H-pyrazolo[3,4-d]pyrimidin-4-yl)amino]methyl}pyridin-2-amine |
| 313 | 612 | 5-({[2-({2,3-dimethylimidazo[1,2-a]pyridin-6-yl}methyl)-2H-pyrazolo[3,4-d]pyrimidin-4-yl]amino}methyl)-4,6-dimethylpyridin-2-amine |
| 314 | 619 | 4,6-dimethyl-5-[({2-[(7-methylquinolin-3-yl)methyl]-2H-pyrazolo[3,4-d]pyrimidin-4-yl}amino)methyl]pyridin-2-amine |
| 315 | 622 | 4,6-dimethyl-5-[({2-[(1-methyl-1,2,3,4-tetrahydroquinolin-7-yl)methyl]-2H-pyrazolo[3,4-d]pyrimidin-4-yl}amino)methyl]pyridin-2-amine |
| 316 | 623 | N-(2,3-dihydro-1H-isoindol-5-ylmethyl)-2-({4-[1-(1H-pyrazol-1-yl)ethyl]phenyl}methyl)-2H-pyrazolo[3,4-d]pyrimidin-4-amine |
| 317 | 624 | 6-[(4-{[(6-chloro-2-fluoro-3-methoxyphenyl)methyl]amino}-2H-pyrazolo[3,4-d]pyrimidin-2-yl)methyl]-1H,2H,3H,9H-pyrrolo[2,1-b]quinazolin-9-one |
| 318 | 628 | 8-[(4-{[(6-chloro-2-fluoro-3-methoxyphenyl)methyl]amino}-2H-pyrazolo[3,4-d]pyrimidin-2-yl)methyl]-2H,3H,5H-[1,3]oxazolo[2,3-b]quinazolin-5-one |
| 319 | 630 | 1-{4-[(4-{[(6-chloro-2-fluoro-3-methoxyphenyl)methyl]amino}-2H-pyrazolo[3,4-d]pyrimidin-2-yl)methyl]phenyl}-1-(1-methyl-1H-pyrazol-3-yl)ethan-1-ol |
| 320 | 633 | 4,6-dimethyl-5-[({2-[(7-methylquinolin-2-yl)methyl]-2H-pyrazolo[3,4-d]pyrimidin-4-yl}amino)methyl]pyridin-2-amine |
| 321 | 634 | 4,6-dimethyl-5-[({2-[(2-methylquinolin-7-yl)methyl]-2H-pyrazolo[3,4-d]pyrimidin-4-yl}amino)methyl]pyridin-2-amine |
| 322 | 635 | N-[(2-methoxy-3,5-dimethylpyridin-4-yl)methyl]-2-({4-[1-(1H-pyrazol-1-yl)ethyl]phenyl}methyl)-2H-pyrazolo[3,4-d]pyrimidin-4-amine |
| 323 | 636 | N-[(2-fluoro-3,6-dimethoxyphenyl)methyl]-2-({4-[1-(1H-pyrazol-1-yl)ethyl]phenyl}methyl)-2H-pyrazolo[3,4-d]pyrimidin-4-amine |
| 324 | 637 | 1-{4-[(4-{[(6-chloro-2-fluoro-3-methoxyphenyl)methyl]amino}-2H-pyrazolo[3,4-d]pyrimidin-2-yl)methyl]phenyl}-1-(1,3-oxazol-2-yl)ethan-1-ol |

TABLE 1-continued

| Entry # | Example # | IUPAC Name |
|---|---|---|
| 325 | 638 | N-[(3-methoxy-2,6-dimethylphenyl)methyl]-2-({4-[1-(1H-pyrazol-1-yl)ethyl]phenyl}methyl)-2H-pyrazolo[3,4-d]pyrimidin-4-amine |
| 326 | 639 | 3-fluoro-4-methoxy-2-({[2-({4-[1-(1H-pyrazol-1-yl)ethyl]phenyl}methyl)-2H-pyrazolo[3,4-d]pyrimidin-4-yl]amino}methyl)benzonitrile |
| 327 | 640 | 5-[({2-benzyl-2H-pyrazolo[3,4-d]pyrimidin-4-yl}amino)methyl]-4,6-dimethylpyridin-2-amine |
| 328 | 641 | N-[(6-chloro-2-fluoro-3-methoxyphenyl)methyl]-2-({4-[(dimethyl-4H-1,2,4-triazol-4-yl)methyl]phenyl}methyl)-2H-pyrazolo[3,4-d]pyrimidin-4-amine |
| 329 | 642 | N-[(6-chloro-2-fluoro-3-methoxyphenyl)methyl]-2-{[3-methoxy-4-(1H-pyrazol-1-ylmethyl)phenyl]methyl}-2H-pyrazolo[3,4-d]pyrimidin-4-amine |
| 330 | 647 | N-[(6-chloro-2-fluoro-3-methoxyphenyl)methyl]-2-({4-[(2-methoxypyridin-3-yl)methyl]phenyl}methyl)-2H-pyrazolo[3,4-d]pyrimidin-4-amine |
| 331 | 648 | 3-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one |
| 332 | 649 | 1-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyrimidin-2-one |
| 333 | 650 | N-[(7-chloroquinolin-2-yl)methyl]-2-({4-[1-(1H-pyrazol-1-yl)ethyl]phenyl}methyl)-2H-pyrazolo[3,4-d]pyrimidin-4-amine |
| 334 | 656 | 5-chloro-1-({3-[(4-{[(6-chloro-2-fluoro-3-methoxyphenyl)methyl]amino}-2H-pyrazolo[3,4-d]pyrimidin-2-yl)methyl]bicyclo[1.1.1]pentan-1-yl}methyl)-1,2-dihydropyridin-2-one |
| 335 | 657 | N-[(6-chloro-2-fluoro-3-methoxyphenyl)methyl]-2-[(3-{[(5-chloropyridin-2-yl)oxy]methyl}bicyclo[1.1.1]pentan-1-yl)methyl]-2H-pyrazolo[3,4-d]pyrimidin-4-amine |
| 336 | 658 | N-[(7-methoxyquinolin-2-yl)methyl]-2-({4-[1-(1H-pyrazol-1-yl)ethyl]phenyl}methyl)-2H-pyrazolo[3,4-d]pyrimidin-4-amine |
| 337 | 659 | N-[(6-methoxy-1-benzofuran-2-yl)methyl]-2-({4-[1-(1H-pyrazol-1-yl)ethyl]phenyl}methyl)-2H-pyrazolo[3,4-d]pyrimidin-4-amine |
| 338 | 660 | N-[(7-chloro-8-fluoroquinolin-2-yl)methyl]-2-({4-[1-(1H-pyrazol-1-yl)ethyl]phenyl}methyl)-2H-pyrazolo[3,4-d]pyrimidin-4-amine |
| 339 | 661 | 1-(1-{4-[(4-{[(6-chloro-2-fluoro-3-methoxyphenyl)methyl]amino}-2H-pyrazolo[3,4-d]pyrimidin-2-yl)methyl]phenyl}ethyl)-1,2-dihydropyridin-2-one |
| 340 | 662 | N-[(6-chloro-1-benzofuran-2-yl)methyl]-2-({4-[1-(1H-pyrazol-1-yl)ethyl]phenyl}methyl)-2H-pyrazolo[3,4-d]pyrimidin-4-amine |
| 341 | 663 | 1-(1-{4-[(4-{[(5-chlorothiophen-2-yl)methyl]amino}-2H-pyrazolo[3,4-d]pyrimidin-2-yl)methyl]phenyl}ethyl)-1,2-dihydropyridin-2-one |
| 342 | 664 | N-[(6-chloro-2-fluoro-3-methoxyphenyl)methyl]-2-({4-[1-(1H-pyrazol-1-yl)propyl]phenyl}methyl)-2H-pyrazolo[3,4-d]pyrimidin-4-amine |
| 343 | 665 | 1-(1-{4-[(4-{[(6-chloro-2-fluoro-3-methoxyphenyl)methyl]amino}-2H-pyrazolo[3,4-d]pyrimidin-2-yl)methyl]phenyl}propyl)-1,2-dihydropyridin-2-one |
| 344 | 669 | N-{4-[(4-{[(6-chloro-2-fluoro-3-methoxyphenyl)methyl]amino}-2H-pyrazolo[3,4-d]pyrimidin-2-yl)methyl]phenyl}-N-methylpyridin-2-amine |
| 345 | 670 | 3-fluoro-4-methoxy-2-{[(2-{[5-methoxy-6-(pyrrolidin-1-yl)pyridin-3-yl]methyl}-2H-pyrazolo[3,4-d]pyrimidin-4-yl)amino]methyl}benzonitrile |
| 346 | 671 | 2-{[(2-{[6-(3,3-difluoropyrrolidin-1-yl)-4-methoxypyridin-3-yl]methyl}-2H-pyrazolo[3,4-d]pyrimidin-4-yl)amino]methyl}-3-fluoro-4-methoxybenzonitrile |
| 347 | 672 | N-[(6-chloro-2-fluoro-3-methoxyphenyl)methyl]-2-{[3-methyl-4-(1H-pyrazol-1-ylmethyl)phenyl]methyl}-2H-pyrazolo[3,4-d]pyrimidin-4-amine |
| 348 | 673 | N-{[5-methoxy-2-(1H-1,2,3,4-tetrazol-1-yl)phenyl]methyl}-2-{[3-methyl-4-(1H-pyrazol-1-ylmethyl)phenyl]methyl}-2H-pyrazolo[3,4-d]pyrimidin-4-amine |
| 349 | 674 | N-[(6-chloro-2-fluoro-3-methoxyphenyl)methyl]-2-({3-methoxy-4-[(4-methyl-1H-pyrazol-1-yl)methyl]phenyl}methyl)-2H-pyrazolo[3,4-d]pyrimidin-4-amine |
| 350 | 675 | N-[(6-chloro-2-fluoro-3-methoxyphenyl)methyl]-2-({4-[(6-methoxypyridin-2-yl)methyl]phenyl}methyl)-2H-pyrazolo[3,4-d]pyrimidin-4-amine |
| 351 | 676 | N-[(6-chloro-2-fluoro-3-methoxyphenyl)methyl]-2-[(4-{[6-(morpholin-4-yl)pyridin-2-yl]methyl}phenyl)methyl]-2H-pyrazolo[3,4-d]pyrimidin-4-amine |
| 352 | 677 | 6-({4-[(4-{[(6-chloro-2-fluoro-3-methoxyphenyl)methyl]amino}-2H-pyrazolo[3,4-d]pyrimidin-2-yl)methyl]phenyl}methyl)-N,N-dimethylpyridin-2-amine |
| 353 | 680 | 1-({4-[(2-chloro-4-{[(6-chloro-2-fluoro-3-methoxyphenyl)methyl]amino}-5H,6H,7H-pyrrolo[3,4-d]pyrimidin-6-yl)methyl]phenyl}methyl)-1,2-dihydropyridin-2-one |
| 354 | 681 | 1-({4-[(4-{[(6-amino-2,4-dimethylpyridin-3-yl)methyl]amino}-2-chloro-5H,6H,7H-pyrrolo[3,4-d]pyrimidin-6-yl)methyl]phenyl}methyl)-1,2-dihydropyridin-2-one |
| 355 | 682 | 2-chloro-N-[(6-chloro-2-fluoro-3-methoxyphenyl)methyl]-6-{[4-(1H-pyrazol-1-ylmethyl)phenyl]methyl}-5H,6H,7H-pyrrolo[3,4-d]pyrimidin-4-amine |
| 356 | 683 | N-[(6-chloro-2-fluoro-3-methoxyphenyl)methyl]-6-{[4-(1H-pyrazol-1-ylmethyl)phenyl]methyl}-5H,6H,7H-pyrrolo[3,4-d]pyrimidin-4-amine |
| 357 | 684 | 1-({4-[(4-{[(6-chloro-2-fluoro-3-methoxyphenyl)methyl]amino}-5H,6H,7H-pyrrolo[3,4-d]pyrimidin-6-yl)methyl]phenyl}methyl)-1,2-dihydropyridin-2-one |
| 358 | 685 | 4,6-dimethyl-5-{[(6-{[4-(1H-pyrazol-1-ylmethyl)phenyl]methyl}-5H,6H,7H-pyrrolo[3,4-d]pyrimidin-4-yl)amino]methyl}pyridin-2-amine |
| 359 | 686 | 1-({4-[(4-{[(6-amino-2,4-dimethylpyridin-3-yl)methyl]amino}-5H,6H,7H-pyrrolo[3,4-d]pyrimidin-6-yl)methyl]phenyl}methyl)-1,2-dihydropyridin-2-one |

TABLE 1-continued

| Entry # | Example # | IUPAC Name |
|---|---|---|
| 360 | 687 | 1-[(4-{[4-({[2-fluoro-5-(trifluoromethoxy)phenyl]methyl}amino)-5H,6H,7H-pyrrolo[3,4-d]pyrimidin-6-yl]methyl}phenyl)methyl]-1,2-dihydropyridin-2-one |
| 361 | 688 | N-[(6-chloro-2-fluoro-3-methoxyphenyl)methyl]-6-{pyrazolo[1,5-a]pyrimidin-3-ylmethyl}-5H,6H,7H-pyrrolo[3,4-d]pyrimidin-4-amine |
| 362 | 689 | N-[(6-chloro-2-fluoro-3-methoxyphenyl)methyl]-6-[(5-phenyl-1,2-oxazol-3-yl)methyl]-5H,6H,7H-pyrrolo[3,4-d]pyrimidin-4-amine |
| 363 | 690 | 3-[(4-{[(6-chloro-2-fluoro-3-methoxyphenyl)methyl]amino}-5H,6H,7H-pyrrolo[3,4-d]pyrimidin-6-yl)methyl]-1-methyl-1,2-dihydroquinolin-2-one |
| 364 | 691 | N-[(6-chloro-2-fluoro-3-methoxyphenyl)methyl]-6-[(1-propyl-1H-imidazol-2-yl)methyl]-5H,6H,7H-pyrrolo[3,4-d]pyrimidin-4-amine |
| 365 | 692 | 2-[(4-{[(6-chloro-2-fluoro-3-methoxyphenyl)methyl]amino}-5H,6H,7H-pyrrolo[3,4-d]pyrimidin-6-yl)methyl]quinolin-4-ol |
| 366 | 694 | 4-chloro-N-[(6-chloro-2-fluoro-3-methoxyphenyl)methyl]-6-{[4-(1H-pyrazol-1-ylmethyl)phenyl]methyl}-6H-pyrrolo[3,4-d]pyridazin-1-amine |
| 367 | 695 | N-[(6-chloro-2-fluoro-3-methoxyphenyl)methyl]-6-{[4-(1H-pyrazol-1-ylmethyl)phenyl]methyl}-6H-pyrrolo[3,4-d]pyridazin-1-amine |
| 368 | 696 | 4,6-dimethyl-5-{[(6-{[4-(1H-pyrazol-1-ylmethyl)phenyl]methyl}-6H-pyrrolo[3,4-d]pyridazin-1-yl)amino]methyl}pyridin-2-amine |
| 369 | 697 | 5-{[(4-chloro-6-{[4-(1H-pyrazol-1-ylmethyl)phenyl]methyl}-6H-pyrrolo[3,4-d]pyridazin-1-yl)amino]methyl}-4,6-dimethylpyridin-2-amine |
| 370 | 698 | 5-[({6-[(2,4-dimethoxyphenyl)methyl]-6H-pyrrolo[3,4-d]pyridazin-1-yl}amino)methyl]-4,6-dimethylpyridin-2-amine |
| 371 | 699 | N-[(6-chloro-2-fluoro-3-methoxyphenyl)methyl]-6-{[2-(2-methoxyethyl)pyrimidin-5-yl]methyl}-5H,6H,7H-pyrrolo[3,4-d]pyrimidin-4-amine |
| 372 | 701 | N-[(6-chloro-2-fluoro-3-methoxyphenyl)methyl]-8-{[4-(1H-pyrazol-1-ylmethyl)phenyl]methyl}-7H-purin-6-amine |
| 373 | 702 | 2-({[8-({4-[(5-chloro-2-oxo-1,2-dihydropyridin-1-yl)methyl]phenyl}methyl)-9-methyl-9H-purin-6-yl]amino}methyl)-3-fluoro-4-methoxybenzonitrile |
| 374 | 707 | 1-({4-[(3-{[(6-bromo-2-fluoro-3-methoxyphenyl)methyl]amino}-1H,4H,5H,6H-pyrrolo[3,4-c]pyrazol-5-yl)methyl]phenyl}methyl)-1,2-dihydropyridin-2-one |

Synthesis of Compounds

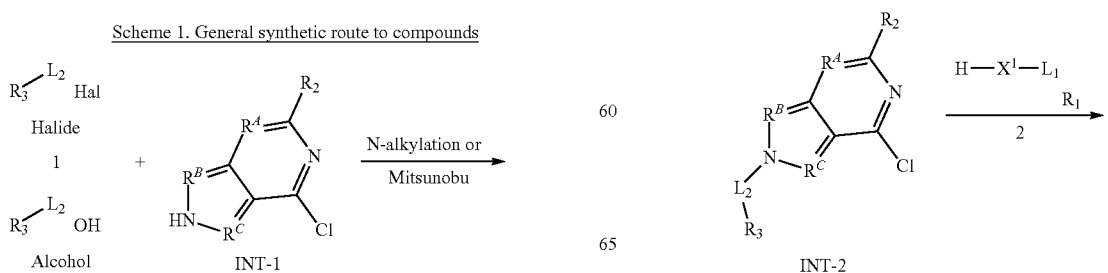

-continued

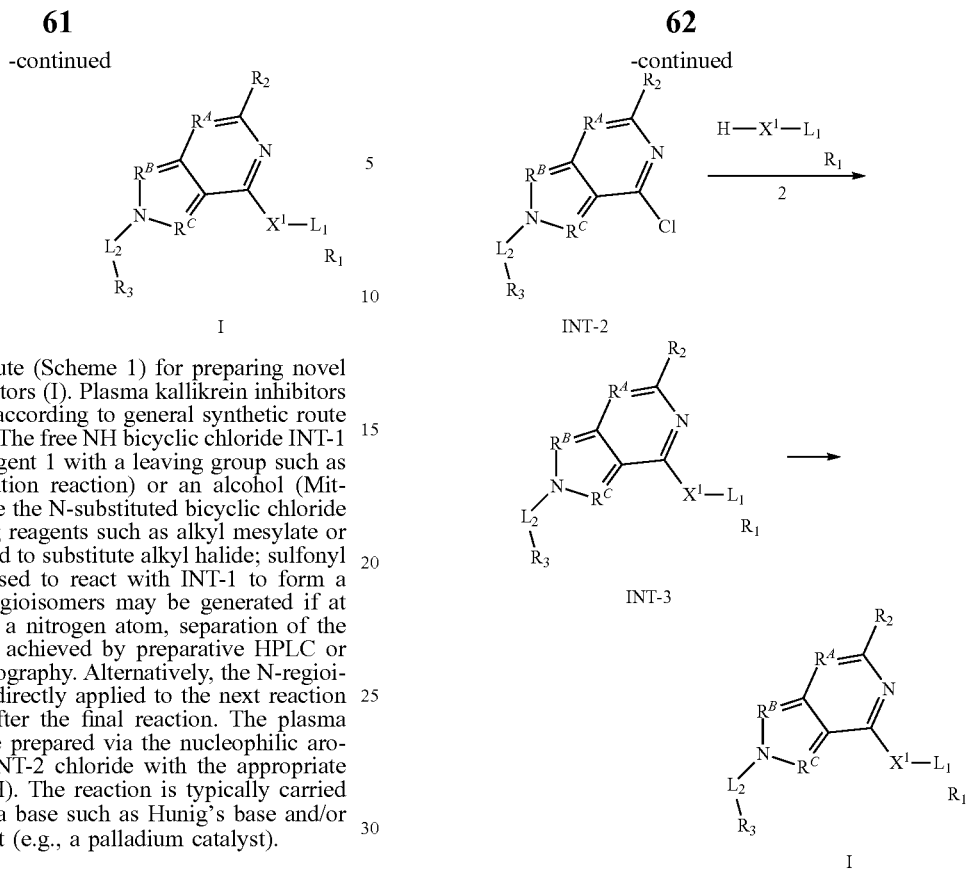

General synthetic route (Scheme 1) for preparing novel plasma kallikrein inhibitors (I). Plasma kallikrein inhibitors (I) can be synthesized according to general synthetic route described in Scheme 1. The free NH bicyclic chloride INT-1 is first reacted with reagent 1 with a leaving group such as an alkyl halide (alkylation reaction) or an alcohol (Mitsunobu reaction) to give the N-substituted bicyclic chloride INT-2. Other alkylating reagents such as alkyl mesylate or tosylate can also be used to substitute alkyl halide; sulfonyl chloride can also be used to react with INT-1 to form a sulfonamide INT-2. Regioisomers may be generated if at least one of B or D is a nitrogen atom, separation of the N-regioisomers can be achieved by preparative HPLC or flash silica gel chromatography. Alternatively, the N-regioisomer mixture can be directly applied to the next reaction and separation done after the final reaction. The plasma kallikrein inhibitors are prepared via the nucleophilic aromatic substitution of INT-2 chloride with the appropriate nucleophile (R1-L1-XH). The reaction is typically carried out in the presence of a base such as Hunig's base and/or Lewis acid or a catalyst (e.g., a palladium catalyst).

General synthetic route (Scheme 2) for preparing novel plasma kallikrein inhibitors (I) with $R^2$ group. One approach to access plasma kallikrein inhibitors (I) with R2 substitution is shown in Scheme 2. Starting from the dichloride INT-1, the mono-chloride INT-3 can be prepared through similar reaction sequence described in Scheme 1. Further reaction of the mono-chloride INT-3 with a nucleophile (such as alkoxide or amine) or a boronate via Suzuki coupling reaction produces the desired kallikrein inhibitor (I).

Scheme 2. General synthetic route to compounds I-Introduction of $R^2$ via dichloride INT-1

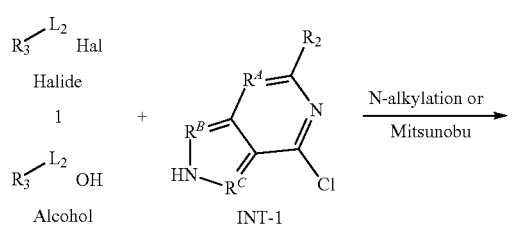

Scheme 3. General synthetic route to compounds with pyrrolo[3,4-c]pyridine core

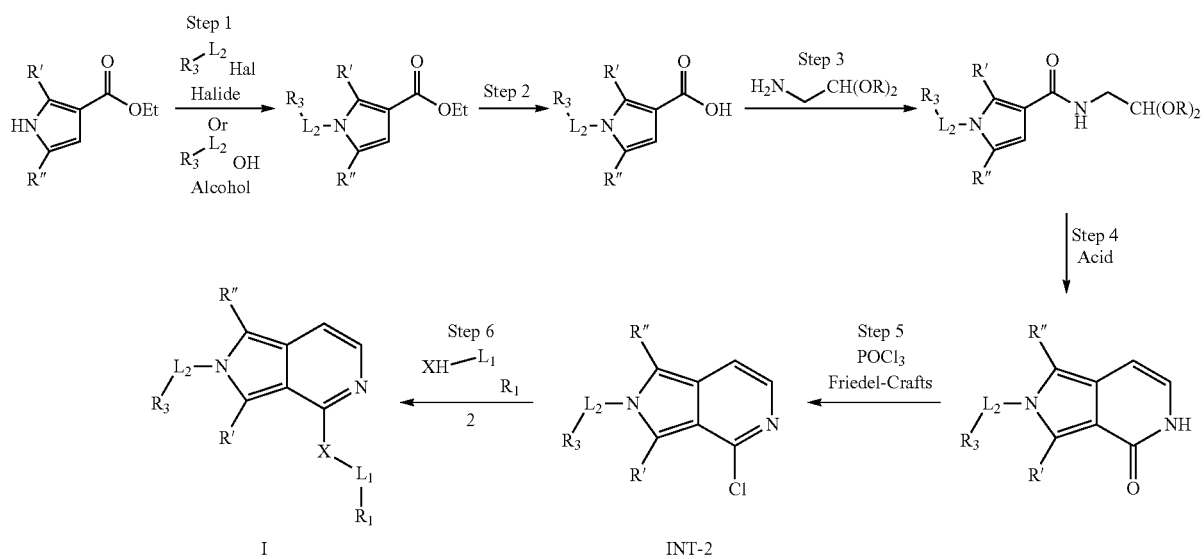

General synthetic route (Scheme 3 & 4) for preparing novel plasma kallikrein inhibitors with a pyrrolopyridine core (I). Plasma kallikrein inhibitors (I) with the pyrrolo[3,4-c]pyridine core can be synthesized according to the general synthetic route described in Schemes 3 & 4. In Scheme 3, pyrrole-3-carboxylic ester is converted to N-substituted analog (step 1) via similar reactions for INT-1 described in Schemes 1 and 2. The ester group is then hydrolyzed under basic or acidic conditions to give the corresponding pyrrole-3-carboxylic acid (step 2), which is coupled with a 1-amine-2-acetal compound [such as 2,2-dimethoxyethan-1-amine or (1,3-dioxolan-2-yl)methanamine] to give amide pyrrole-3-carboxylic amide (step 3). The pyrrole amide is cyclized to produce bicyclic 2,5-dihydro-4H-pyrrolo[3,4-c]pyridin-4-one scaffold (step 4)—this Friedel-Crafts type annulation one intermediate with ethyl 2-isocyanoacetate (step 2) (for a closely related reaction see HETEROCYCLES, Vol. 58, 2002, pp. 301-310) under basic conditions. The N-substituted bicyclic intermediate is obtained by alkylation or Mitsunobu reaction (step 3) using conditions similar to that described for INT-1 in Schemes 1 & 2. After removing the p-methoxybenzyl (PMB) protecting group in step 4, the bicyclic pyridone is treated with a reagent such as $POCl_3$ to form the key chloride INT-2 (step 5). Conversion of INT-2 to kallikrein inhibitors (I) can be achieved via $S_NAr$ reaction under similar conditions described in Schemes 1 & 2. The ester kallikrein inhibitors (I) can be further manipulated to produce other kallikrein inhibitors with carboxylic acid (Ia), amine (Ib), amide (Ic), and C—H (Id) functionalities using standard organic transformations.

Scheme 4. General synthetic route to compounds with pyrrolo[3,4-c]pyridine core

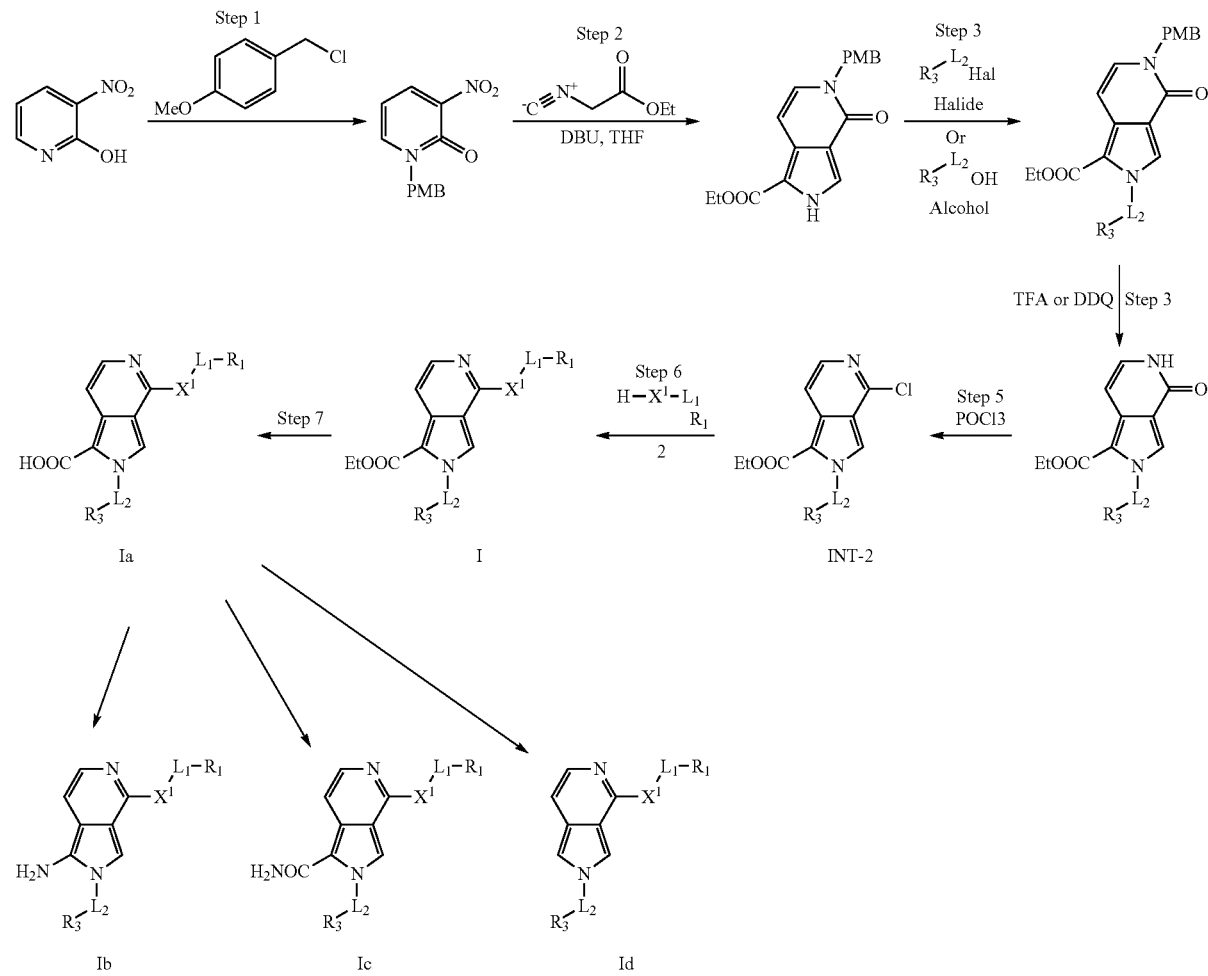

normally takes place under acid-promoted conditions (such as TFA, TsOH, MsOH, $AlCl_3$ etc.) with heating. Reaction of the bicyclic pyrrolo[3,4-c]pyridin-4-one intermediate with chlorinating agents such as $POCl_3$ provides a key intermediate (INT-2, step 5). Finally, INT-2 is transformed to kallikrein inhibitors (I) via $S_NAr$ reaction with appropriate nucleophiles (R1-L1-XH) as described in Schemes 1 & 2.

For the route in Scheme 4, the bicyclic pyrrolopyridine scaffold is constructed via the reaction of 3-nitropyridin-2-

Preparation of INT-2 by general method A—alkylation reaction. In a typical alkylation reaction, a mixture of the NH bicyclic derivative (INT-1) (0.1-2 mmol, 1eq.), alkyl chloride or bromide (1a) (1 to 1.5 eq), and a base such as $Cs_2CO_3$ (2-5 eq.) (catalytic amount of NaI or $Bu_4NI$ may also be added) in DMF or acetonitrile (1 to 10 mL) was stirred at RT or heating up to 120° C. for 0.5-24 h under nitrogen atmosphere. In workup A, water was added to the reaction mixture, the precipitated product was collected, washed with water, and then subjected to preparative HPLC or flash silica gel chromatography purification. In workup B (for products that did not precipitate), diluted HCl or aqueous NH$_4$Cl was added at 0° C. to adjust the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvent mixtures (e.g., ethyl acetate/hexanes).

Preparation of INT-2 by general method B—Mitsunobu reaction: To a solution of NH bicyclic derivative (INT-1) (0.1-2 mmol, 1eq.), (0.1-2 mmol) in THF (1-10 mL) and alcohol (1b) (0.8 to 1.2eq) was added PPh$_3$ (1-1.5eq) in anhydrous THF (1-10 mL), followed by the addition of DIAD or DEAD (1.1 eq) in THF or toluene. The reaction is typically carried out at 0° C. (or RT) and reagents added dropwise. After addition, the reaction is continued at 0° C. (or RT) for up to 48 hours. The mixture was concentrated and the residue was purified by preparative HPLC or flash silica gel chromatography.

Preparation of compound I by general method C—S$_N$Ar reaction: In a typical procedure, a mixture of N-substituted bicyclic chloride (INT-2) (0.1-2 mmol, 1eq.) and a nucleophile such as an amine (2a) (1.2 to 5 eq) in a polar solvent (0.5 to 5 mL) such as n-BuOH, ethylene glycol dimethyl ether, 1-ethoxy-2-(2-ethoxyethoxyl)ethane or DMF was placed in a microwave vial. A Lewis acid (such as ZnCl$_2$) and a base (such as Hunig's base, DIPEA) may also be added to the reaction mixture to facilitate the reaction. The reaction mixture was then heated by either conventional heating or in microwave reactor at elevated temperature between 100 and 250° C. for up to 24 hrs. In workup A, the reaction mixture was concentrated on a rotavap to remove all volatiles, the resulting residue was purified by preparative HPLC or flash silica gel chromatography. In workup B, water was added to the reaction mixture, the precipitated product was collected, washed with water, and then subjected to preparative HPLC or flash silica gel chromatography purification. In workup C (for products that did not precipitate), diluted HCl or aqueous NH$_4$Cl was added at 0° C. to adjusted the pH to ~7, the reaction mixture was partitioned between ethyl acetate or dichloromethane and aqueous sodium chloride and the organic layer separated, dried, and solvent removed under vacuum to afford crude product which was purified by automated silica gel column chromatography using appropriate solvent mixtures (e.g., ethyl acetate/hexanes).

Pharmaceutical Compositions

In further aspects of the invention, provided is a pharmaceutical composition comprising a compound of Formula (I) as provided herein or a pharmaceutically acceptable salt thereof, and at least one pharmaceutically acceptable excipient.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

The concentration of the excipient is one that can readily be determined to be effective by those skilled in the art, and can vary depending on the particular excipient used. The total concentration of the excipients in the solution can be from about 0.001% to about 90% or from about 0.001% to about 10%.

The concentration of compounds provided herein and/or utilized herein can be from about 1 to about 99% by weight in the pharmaceutical compositions provided herein. In certain embodiments, the concentration of compounds provided herein and/or utilized herein in the pharmaceutical composition is about 5% by weight, or alternatively, about 10%, or about 20%, or about 1%, or about 2%, or about 3%, or about 4%, or about 6%, or about 7%, or about 8%, or about 9%, or about 11%, or about 12%, or about 14%, or about 16%, or about 18%, or about 22%, or about 25%, or about 26%, or about 28%, or about 30%, or about 32%, or about 34%, or about 36%, or about 38%, or about 40%, or about 42%, or about 44%, or about 46%, or about 48%, or about 50%, or about 52%, or about 54%, or about 56%, or about 58%, or about 60%, or about 64%, or about 68%, or about 72%, or about 76%, or about 80% by weight.

Compounds and pharmaceutical compositions of this invention maybe used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention. In some embodiments, a compound of this invention can be used as an adjunct to conventional drug therapy of the conditions described herein.

Pharmaceutical compositions can be formulated for different routes of administration, including oral delivery and other routes such as intravenous, intraarterial, pulmonary, rectal, nasal, vaginal, lingual, intramuscular, intraperitoneal, intracutaneous, transdermal, intracranial, and subcutaneous routes. Other dosage forms include tablets, capsules, pills, powders, aerosols, suppositories, parenterals, and oral liquids, including suspensions, solutions and emulsions. All dosage forms may be prepared using methods that are standard in the art (see e.g., Remington's Pharmaceutical Sciences, 16$^{th}$ ed., A. Oslo editor, Easton Pa. 1980).

Methods of Use

In another aspect, this invention provides a method for inhibiting plasma kallikrein activity in a subject, the method comprising administering to the subject an effective amount of the compound of Formula I, or a subformula thereof, or a pharmaceutical composition of any thereof.

Kallikrein inhibitors may have clinical utility in disease states such as hereditary angioedema (HAE), diabetic retinopathy, macular edema and other inflammatory disorders. The contact pathway of blood coagulation, leading to kallikrein production, is activated during acute episodes of swelling of face, extremities, larynx and gastrointestinal tract in HAE patients. Blisters formed during attacks contain high levels of kallikrein which mediates a potent inflammatory response via bradykinin formation. HAE patients are genetically deficient in the physiologic inhibitor of plasma kallikrein and cannot suppress the enzyme's catalytic activity. Further support for the hypothesis that kallikrein inhibition provides therapeutic benefit in HAE is provided by ecallentide (Kalbitor), an injectable peptidic kallikrein inhibitor indicated for treatment of acute attacks. Thus, an oral kallikrein inhibitor may provide benefit during both acute attacks and in prophylactic suppression of bradykinin production in HAE patients. Angioedema induced by treatment with angiotensin-converting-enzyme (ACE) inhibitors accounts for one third of angioedema cases in the emergency room. The largest groups of patients with drug induced angioedema are those treated with ACE inhibitors. Since this angioedema shares a bradykinin dependent mechanism with HAE, kallikrein inhibitors may also be useful for treating this patient population (N Engl J Med 2015; 372:418-425, Jan. 29, 2015).

Plasma kallikrein may have numerous implications in disorders such as (HAE) Nzeako et al., Arch Intern Med., 161, 2417-2429, 2001), retinopathy or diabetic retinopathy (AC Clermont et al, Abstract 5035-0883, ARVO 2010, Fort Lauderdale, Fla.), proliferative and non-proliferative retinopathy, diabetic macular edema (DME), clinically significant macular edema (CSME), cystoid macular edema (CME), CME following cataract extraction, CME induced by cryotherapy, CME induced by uveitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy (JA Phipps et al, Hypertension, 53, 175-181, 2009), retinal trauma, dry and wet aged-related macular degeneration (AMD), ischemic reperfusion injuries (C Storoni et al, JPET, 318, 849-954, 2006), e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), edema, high altitude cerebral edema,cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associate with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, microalbuminuria, albuminuria and proteinuria, vein thrombosis, coagulation from post fibrinolytic treatments, angina, angioedema, sepsis, arthritis (e.g. rheumatoid arthritis, osteoarthritis, infection arthritis), lupus, gout, psoriasis, blood loss during cardiopulmonary bypass, inflammatory bowel, diabetes, diabetic complications, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma).

Plasma kallikrein inhibitors are considered to be useful in the treatment of a wide range of disorders, in particular retinopathy or edema-associated diseases, such as hereditary angioedema, macular edema and brain edema.

Plasma kallikrein inhibitors are considered to be especially useful in the treatment of retinopathy, e.g. retinopathy associated with diabetes and/or hypertension.

Regarding the role of kallikrein in diabetes, the role of the renal kallikreing-kinin system in diabetic nephropathy has been reported (*Current opinion in nephrology and hypertension* 2007; 16(1):22-26). Population based studies have also provided evidence for activation of blood coagulation and increased kallikrein levels in diabetic patients. Since kallikrein mediates retinal vascular dysfunction and induces retinal thickening in rodent model of diabetes, it may be postulated that kallikrein inhibitors will be suitable for use in amelioration of hyperglycemia induced retinopathy and related inflammatory disorders. Since contact with synthetic surfaces activates the blood coagulation system and leads to inflammatory and thrombotic complications, kallikrein inhibitors may also have applicability in extra corporeal membrane oxygenation machines (ECMO) and other bypass equipment. Kallikrein inhibitors may also play a role in reducing reperfusion injury during coronary artery bypass grafting since bradykinin infusion has shown beneficial effects in improved cardiac performance (Rhaleb N E, Yang X P and Carretero A, 2011 *Comprehensive Physiology Review*). Even though kallikrein inhibitors are not currently indicated for non-HAE uses, animal model data is suggestive of potential uses in other clinical scenarios. Plasma kallikrein inhibitors are considered to be especially useful in the treatment of hereditary angioedema.

Plasma kallikrein inhibitors are considered to be especially useful in the treatment of edema formation in diseases, e.g. edema formation related to ischemic reperfusion injuries.

Plasma kallikrein inhibitors are considered to be especially useful in the treatment of macular edema, e.g. macular edema associated with diabetes and/or hypertension.

Plasma kallikrein inhibitors are considered to be especially useful in the prevention and treatment of thrombosis Plasma kallikrein inhibitors are considered to be especially useful in the treatment of intracerebral hemorrhage induced by hyperglycemia in diabetic patients Plasma kallikrein inhibitors are considered to be especially useful in the treatment of retinal vascular permeability induced by angiotensin in hypertensive patients.

In some embodiments, a plasma kallikrein inhibitir is contemplated to have implications and or therapeutically beneficial effects in disorders such as (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet aged-related macular degeneration (AMD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema drug-related (ACE-inhibitors), edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associate with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, microalbuminuria, albuminuria and proteinuria, deep vein thrombosis, coagulation from post fibrinolytic treatments, angina, angioedema, sepsis, arthritis (e.g. rheumatoid arthritis, osteoarthritis, infection arthritis), lupus, gout, psoriasis, blood loss during cardiopulmonary bypass, inflammatory bowel, diabetes, diabetic complications, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma).

Plasma kallikrein inhibitors are also contemplated to be useful in the treatment of a wide range of disorders, in particular retinopathy or edema-associated diseases, such as hereditary angioedema, macular edema and brain edema. Plasma kallikrein inhibitors are also contemplated to be useful in the treatment of retinopathy, e.g. retinopathy associated with diabetes and/or hypertension; hereditary angioedema; edema formation in diseases, e.g. edema formation related to ischemic reperfusion injuries; macular edema, e.g. macular edema associated with diabetes and/or hypertension; .in the prevention and treatment of thrombosis; in the treatment of intracerebral hemorrhage induced by hyperglycemia in diabetic patients.

In some embodiments of the method for treatment, upon administration to the patient, a therapeutically effective amount of the compound of Formula I, or a subformula thereof, reduces protease activity, such as kallikrein activity, for up to 12, 24, 26 or 48 hours after administration.

An effective amount of the compound of Formula I is the amount of the compound of Formula I required to produce a therapeutic effect in vitro or in vivo. In some embodiments the effective amount in vitro is about from 0.1 nM to about 1 mM. In some embodiments the effective amount in vitro is from about 0.1 nM to about 0.5 nM or from 0.5 nM to about 1.0 nM or from about 1.0 nM to about 5.0 nM or from about 5.0 nM to about 10 nM or from about 10 nM to about 50 nM or from about 50 nM to about 100 nM or from about 100 nM to about 500 nM or from about 500 nM to about 1 mM. In some embodiments, the effective amount for an effect in vivo is about 0.1 mg to about 100 mg, or preferably, from about 1 mg to about 50 mg, or more preferably, from about 1 mg to about 25 mg per kg/day. In some other embodiments, the effective amount in vivo is from about 10 mg/kg/day to about 100 mg/kg/day, about 20 mg/kg/day to about 90 mg/kg/day, about 30 mg/kg/day to about 80 mg/kg/day, about 40 mg/kg/day to about 70 mg/kg/day, or about 50 mg/kg/day to about 60 mg/kg/day. In still some other embodiments, the effective amount in vivo is from about 100 mg/kg/day to about 1000 mg/kg/day.

In some preferred embodiments, the compound of Formula I is suitable for once daily administration.

Routes of administration refer to the method for administering a compound of Formula I or a composition thereof to a mammal. Administration can be achieved by a variety of methods. These include but are not limited to subcutaneous, intravenous, transdermal, sublingual, or intraperitoneal injection or oral administration.

In certain aspects, the methods described herein relate to administering the compound of Formula I or compositions thereof in vitro. In other aspects the administration is in vivo. In yet other aspects, the in vivo administration is to a mammal. Mammals include but are not limited to humans and common laboratory research animals such as, for example, mice, rats, dogs, pigs, cats, and rabbits.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Biological Assays:
In-Vitro Plasma Kallikrein Inhibition
Materials

The chromogenic substrate D-Pro-Phe-Arg-pNa, 2HCl (BIOPHEN CS-31(02) from Hyphen BioMed, Neuville-Sur-oise, France) was dissolved in 5 mL deionized water and stored at 4° C. Concentration was determined in the spectrophotometer at 342 nm using an extinction coefficient of 8270. All other chemicals were of analytical grade.

Human plasma kallikrein was purchased from Enzyme Research Labs (South Bend, Ind., USA, batch HPKa 2830). A stock solution of 7 μM in 50% glycerol was stored at −20° C.

Enzyme reactions were conducted in "assay buffer" comprised of 20 mM HEPES at pH 7.4, 150 mM NaCl, 0.1% PEG-8000 and 0.01% Triton X-100.

Both enzyme and substrate were diluted in assay buffer.

The compound solutions as well as the enzyme and the substrate solutions were transferred to 96-well plates (Clear, UV-Star, Flat-bottom, Half-Area plates; cat. No. 675801 Greiner Bio-one, purchased from VWR International, Arlington Heights, Ill., USA) using a Rainin LTS 96-channel pipettor (Rainin, Columbus, Ohio, USA). Plate measurements were conducted using a SPECTROStar Nano reader (BMG Labtech, San Francisco, Calif., USA). The SPECTROStar Nano is a spectrophotometer and absorbance was measured at 405 nm. We used discrete wavelength, precise, kinetic reads of 15 cycles with a 60 sec cycle time.

Determination of $IC_{50}$ values

For the determination of $IC_{50}$ values, the assays were performed at room temperature in 96-well plates with a total assay volume of 85 µl per well.

The test compound was dissolved in 100% DMSO. The compounds were serially diluted in DMSO in a 7 point dose response. For the assays, 66.5 µL of protease solution (protease in assay buffer) was added per well followed by the addition of 8.5 µL of compound in 100% DMSO. The final assay concentration of the human plasma kallikrein was 250 pM. After 30 min incubation at room temperature on an orbital shaker, the reactions were started by the addition of 10 µL substrate solution (in assay buffer, final assay concentration was 600 uM). After the addition of the substrate solution the final DMSO concentration was 10%. The plate went back on the shaker for 5 sec, was spun at 2000 rpm for 5 sec and read on the spectrophotometer. The effect of the compound on the enzymatic activity was obtained from the linear part of the progress curves and determined after 15 minutes. The $IC_{50}$ value was calculated from the plot of rate vs. inhibitor concentration by a 4 parameter logistic equation:

$$y = A + ((B-A)/(1 = ((C/x)\hat{\ }D)))$$

where y is the rate at the inhibitor concentration, x. A is the minimum y value at the highest inhibitor concentration and B is the y value in the absence of inhibitor, C is the $IC_{50}$ value and D is the slope factor. The curve fitting was conducted with the non-linear regression routine of the analysis software XLfit (IDBS, version 5.3.1).

EXAMPLES

Example 1

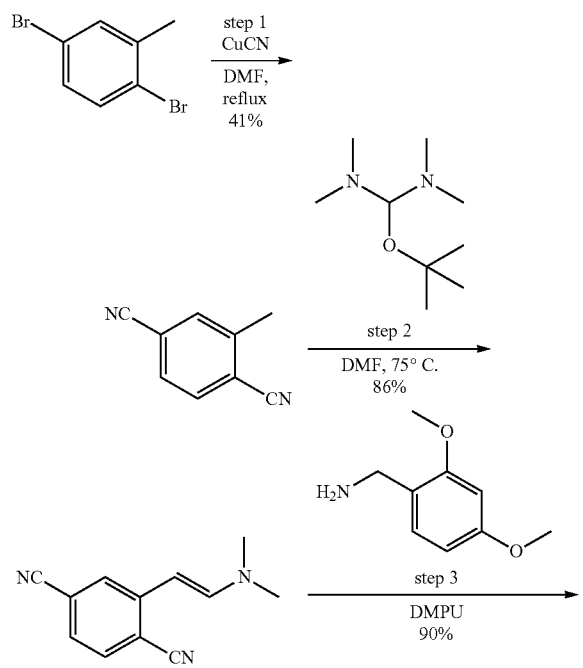

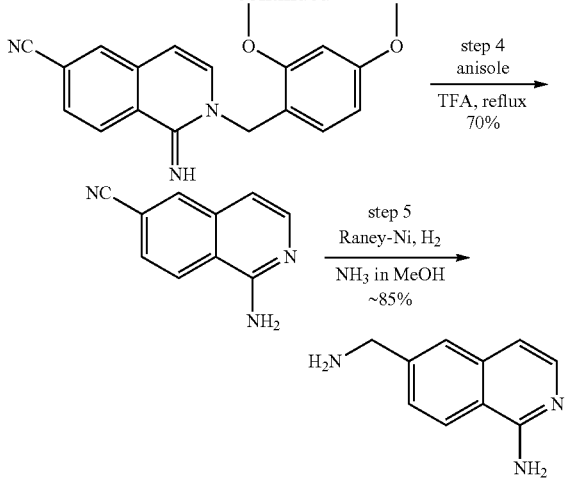

Example 1

Step 1: 2-methylbenzene-1,4-dicarbonitrile

Into a 500-ml round-bottom flask, which was purged and maintained with an inert atmosphere of nitrogen, was placed a solution of 1,4-dibromo-2-methylbenzene (15 g, 60.02 mmol, 1.00 equiv) in n,n-dimethylformamide (200 ml). Cucn (20.4 g, 227.77 mmol, 3.80 equiv) was added to the reaction. The resulting solution was heated to reflux for 6 h, and then it was diluted with 200 ml of ammonia. The solids were filtered out. The resulting solution was extracted with 2×200 ml of ethyl acetate. The combined organic layers were washed with 2×200 ml of brine, dried over anhydrous sodium sulfate and concentrated under vacuum. The residue was applied onto a silica gel column with petroleum ether/ethyl acetate (50/1-30/1) as eluent to provide 3.8 g (45%) of 2-methylbenzene-1,4-dicarbonitrile as a light yellow solid.

Step 2. 2-[(E)-2-(dimethylamino)ethenyl]benzene-1,4-dicarbonitrile

Into a 250-mL round-bottom flask, which was purged and maintained with an inert atmosphere of nitrogen, was placed a solution of 2-methylbenzene-1,4-dicarbonitrile (4 g, 28.14 mmol, 1.00 equiv), [(tert-butoxy)(dimethylamino)methyl]dimethylamine (9.8 g, 56.23 mmol, 2.00 equiv) in N,N-dimethylformamide (50 mL). The resulting solution was stirred overnight at 75° C., and then it was concentrated under vacuum. The resulting mixture was washed with 50 mL of hexane. The solids were collected by filtration. This provided 5.3 g (95%) of 2-[(E)-2-(dimethylamino)ethenyl]benzene-1,4-dicarbonitrile as a yellow solid.

Step 3. 2-[(2,4-dimethoxyphenyl)methyl]-1-imino-1,2,3,4-tetrahydroisoquinoline-6-carbonitrile Into a 250-mL round-bottom flask, was placed a mixture of 2-[(E)-2-(dimethylamino)ethenyl]benzene-1,4-dicarbonitrile (5.4 g, 27.38 mmol, 1.00 equiv), DMPU (15 mL), and (2,4-dimethoxyphenyl)methanamine (7.58 mL). The resulting solution was stirred for 3 h at 140° C., and then it was cooled with an ice bath. The resulting solution was diluted with 200 mL of hexane/EA (2/1). The precipitates were collected by filtration. The solid was dried in an oven under reduced pressure. This provided 7.55 g (86%) of 2-[(2,4- dimethoxyphenyl)methyl]-1-imino-1,2,3,4-tetrahydroisoquinoline-6-carbonitrile as a yellow solid.

Step 4. 1-aminoisoquinoline-6-carbonitrile

Into a 250-mL round-bottom flask, was placed a solution of 2-[(2,5-dimethoxyphenyl)methyl]-1-imino-1,2-dihydroisoquinoline-6-carbonitrile (7.55 g, 23.64 mmol, 1.00 equiv) and anisole (3.9 mL, 1.50 equiv) in trifluoroacetic acid (100 mL). The resulting solution was stirred for 2 days at 70° C. The resulting mixture was concentrated under vacuum. The pH value of the solution was adjusted to 8 with sodium bicarbonate (sat. aq.), and then was extracted with 3×200 mL of ethyl acetate. The combined organic layers were dried over anhydrous sodium sulfate and concentrated under vacuum. The residue was applied onto a silica gel column with dichloromethane/methanol (50/1-30/1) as eluent to yield 2.5 g (63%) of 1-aminoisoquinoline-6-carbonitrile as a yellow solid.

Step 5. 6-(aminomethyl)isoquinolin-1-amine (Example 1). Into a 500-mL round-bottom flask, was placed 6-isocyanoisoquinolin-1-amine (7.9 g, 46.70 mmol, 1.00 equiv), methanol (100 mL), ammonia (100 mL), Raney-Ni (10 g). To the above, hydrogen was introduced. The resulting solution was stirred for 5 h at room temperature. The solids were filtered. The resulting mixture was concentrated under vacuum. The crude product was re-crystallized from methanol:ether in the ratio of 1:20. The solids were collected by filtration. This resulted in 6.5 g (80%) of 6-(aminomethyl)isoquinolin-1-amine as a yellow solid. $^1$H NMR (300 MHz, CD$_3$OD): δ 8.091-8.063 (d, J=8.4 Hz, 1H), 7.732-7.712 (d, J=6.0 Hz, 1H), 7.663 (s, 1H), 7.560-7.494 (m, 1H), 3.965 (s, 1H); MS (ES, m/z): found for C$_{10}$H$_{11}$N$_3$: 174.2 [M+H]+.

Example 2

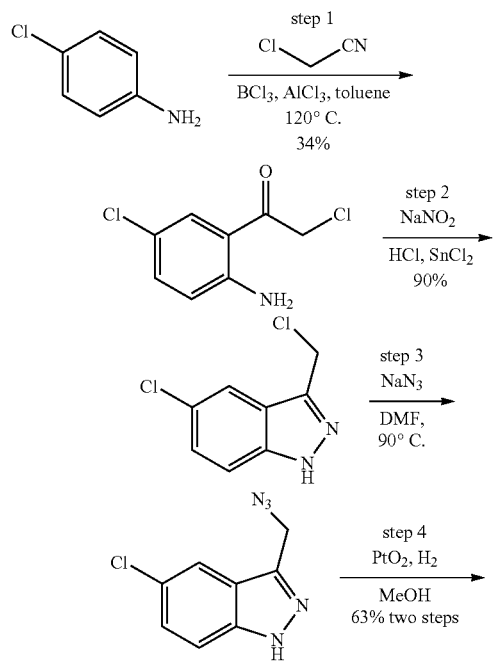

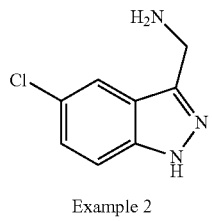

Example 2

Step 1.
1-(2-amino-5-chlorophenyl)-2-chloroethan-1-one

Into a 500-mL round-bottom flask, was placed 4-chloroaniline (20 g, 156.77 mmol, 1.00 equiv) in toluene (172 mL). This was followed by the addition of BCl$_3$ in dichloromethane (1M) (172.4 mL, 1.10 equiv) dropwise with stirring. To this was added ClCH$_2$CN (12 mL, 1.20 equiv), AlCl$_3$ (23 g, 1.10 equiv). The resulting solution was stirred for 24 h at 120° C. in an oil bath. The reaction was then quenched by the addition of 240 mL of 2M hydrogen chloride. The resulting solution was extracted with 3×500 mL of dichloromethane and the organic layers combined and dried over anhydrous sodium sulfate. The solids were filtered out. The resulting mixture was concentrated under vacuum. The crude product was purified by re-crystallization from ethanol/n-hexane. This resulted in 10.8 g (34%) of 1-(2-amino-5-chlorophenyl)-2-chloroethan-1-one as a yellow solid.

Step 2. 5-chloro-3-(chloromethyl)-1H-indazole hydrochloride

Into a 500-mL round-bottom flask, was placed 1-(2-amino-5-chlorophenyl)-2-chloroethan-1-one (9.8 g, 48.03 mmol, 1.00 equiv), hydrogen chloride in H$_2$O (37%) (146.3 mL). This was followed by the addition of a solution of Na NO$_2$ (3.651 g, 52.91 mmol, 1.10 equiv) in water (22.5 mL) dropwise with stirring at −10° C. The mixture was stirred for 2 h. To this was added SnCl$_2$ 2H$_2$O (26 g, 2.40 equiv). The resulting solution was stirred for 1 h at −10° C. in an ice/salt bath. The reaction was then quenched by the addition of 200 mL of water/ice. The solids were collected by filtration. This resulted in 10.8 g (95%) of 5-chloro-3-(chloromethyl)-1H-indazole hydrochloride as a brown solid.

Step 3. 3-(azidomethyl)-5-chloro-1H-indazole

Into a 250-mL round-bottom flask, was placed 5-chloro-3-(chloromethyl)-1H-indazole hydrochloride (10.8 g, 45.47 mmol, 1.00 equiv), N,N-dimethylformamide (91 mL), water (9.4 mL), NaN$_3$ (3.8 g, 58.45 mmol, 1.30 equiv). The resulting solution was stirred for 1 h at 90° C. The resulting mixture was concentrated under vacuum. The resulting solution was diluted with 500 mL of water/ice. The resulting solution was extracted with 3×500 mL of dichloromethane and the organic layers combined and concentrated. This resulted in 9.3 g of 3-(azidomethyl)-5-chloro-1H-indazole as a crude solid.

Step 4. (5-chloro-1H-indazol-3-yl)methanamine (Example 2). Into a 250-mL round-bottom flask, which was purged and maintained with an inert atmosphere of nitrogen, was placed 3-(azidomethyl)-5-chloro-1H-indazole (9.3 g, 44.79 mmol, 1.00 equiv), methanol (147.8 mL), PtO$_2$ (790 mg, 0.08 equiv). To the above, hydrogen was introduced. The resulting solution was stirred for 1 day at room temperature. The solids were filtered out. The resulting mixture was concentrated under vacuum. The resulting solution was diluted with 300 mL of 1M HCl (aq.). The resulting mixture was washed with 2×300 mL of MTBE. The pH value of the solution was adjusted to 10 with sodium hydroxide (2 M). The resulting solution was extracted with 6×500 mL of dichloromethane and the organic layers combined and concentrated under vacuum. This resulted in 5.1 g (63%) of (5-chloro-1H-indazol-3-yl)methanamine as a yellow solid. $^1$H NMR (400 MHz, CD$_3$OD): δ 7.90 (s, 1H), 7.49 (d, J=8.8 Hz, 1H), 7.37 (d, J=8.8 Hz, 1H), 4.14 (s, 2H); MS (ES, m/z) found for C$_8$H$_8$ClN$_3$: 182.0[M+H]$^+$.

Example 3

Synthesis of 5-(aminomethyl)-4,6-dimethylpyridin-2-amine

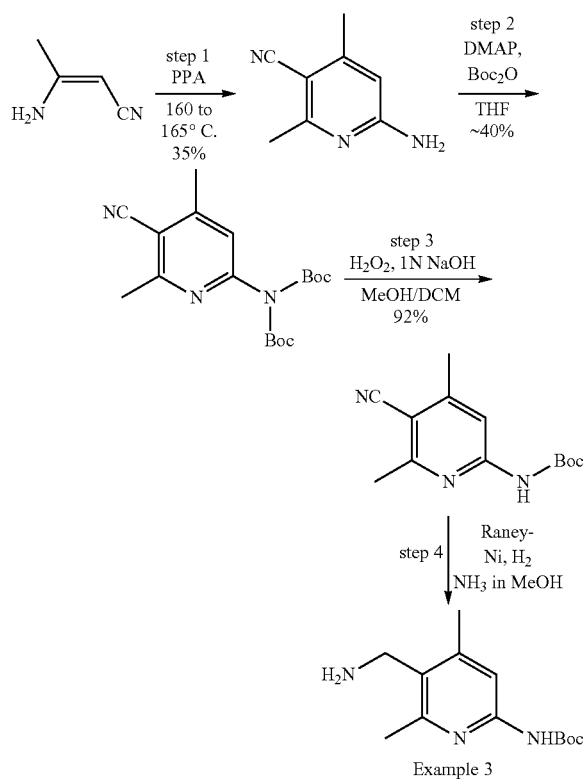

Example 3

Step 1. 6-amino-2,4-dimethylpyridine-3-carbonitrile

Into a 500-mL three neck round-bottom flask, was placed PPA (300 g). This was followed by the addition of (2E)-3-aminobut-2-enenitrile (30 g, 365.39 mmol, 1.00 equiv) at 100° C. The resulting solution was stirred for 3 h at 165° C. The reaction mixture was cooled to 90° C. The reaction was then quenched by the addition of 500 mL of water/ice. The pH value of the solution was adjusted to 9 with sodium hydroxide (10%). The resulting solution was extracted with 3×1500 mL of ethyl acetate and the organic layers combined and dried over anhydrous sodium sulfate and concentrated under vacuum. This resulted in 12.4 g (23%) of 6-amino-2,4-dimethylpyridine-3-carbonitrile as a yellow solid.

Step 2. tert-butyl N-[(tert-butoxy)carbonyl]-N-(5-cyano-4,6-dimethylpyridin-2-yl)carbamate Into a 500-mL round-bottom flask, was placed 6-amino-2,4-dimethylpyridine-3-carbonitrile (12.4 g, 84.25 mmol, 1.00 equiv), 4-dimethylaminopyridine (1.03 g, 8.43 mmol, 0.10 equiv), and tetrahydrofuran (100 mL). This was followed by the addition of a solution of Boc$_2$O (55.0 g, 252.00 mmol, 3.00 equiv) in tetrahydrofuran (100 mL) dropwise with stirring. The resulting solution was stirred overnight at room temperature. The resulting solution was diluted with 200 mL of H$_2$O. The resulting solution was extracted with 4×100 mL of ethyl acetate and the organic layers combined. The resulting mixture was washed with 200 mL of brine. The combined organics were dried over anhydrous sodium sulfate and concentrated under vacuum. The residue was applied onto a silica gel column with ethyl acetate/petroleum ether (1:10) as eluent. This resulted in 13.2 g (45%) of tert-butyl N-[(tert-butoxy)carbonyl]-N-(5-cyano-4,6-dimethylpyridin-2-yl)carbamate as a light yellow solid.

Step 3. tert-butyl N-(5-cyano-4,6-dimethylpyridin-2-yl)carbamate

Into a 250-mL round-bottom flask, was placed tert-butyl N-[(tert-butoxy)carbonyl]-N-(5-cyano-4,6-dimethylpyridin-2-yl)carbamate (7.1 g, 20.44 mmol, 1.00 equiv), methanol (70 mL), dichloromethane (20 mL). This was followed by the addition of H$_2$O$_2$ (2.69 mL, 1.50 equiv) dropwise with stirring. To this was added a solution of sodium hydroxide (1.228 g, 30.70 mmol, 1.50 equiv) in water (10 mL) dropwise with stirring. The resulting solution was stirred for 2 h at 0° C. in a water/ice bath. The reaction was then quenched by the addition of 100 mL of 10% Na$_2$CO$_3$. The resulting solution was extracted with 2×50 mL of ethyl acetate and the organic layers combined and dried over anhydrous sodium sulfate and concentrated under vacuum. The residue was applied onto a silica gel column with ethyl acetate/petroleum ether (1:3) as eluent. This resulted in 3.8 g (75%) of tert-butyl N-(5-cyano-4,6-dimethylpyridin-2-yl)carbamate as a white solid.

Step 4. tert-butyl (5-(aminomethyl)-4,6-dimethylpyridin-2-yl)carbamate (Example 3). Into a 100-mL round-bottom flask, was placed tert-butyl N-(5-cyano-4,6-dimethylpyridin-2-yl)carbamate (3.8 g, 15.37 mmol, 1.00 equiv), NH$_3$/MeOH (10 mL), methanol (20 mL), and Raney-Ni (3.8 g). To the above, hydrogen was introduced. The resulting solution was stirred overnight at room temperature under 1 atm hydrogen. The solids were filtered. The resulting mixture was concentrated under vacuum. This resulted in 3.1975 g (83%) of tert-butyl N-[5-(aminomethyl)-4,6-dimethylpyridin-2-yl]carbamate as a white solid. $^1$H NMR (300 MHz, DMSO-d$_6$): δ: 9.38 (s, 1H), 7.43 (s, 1H), 3.65 (s, 1H), 2.42 (s, 3H), 2.32 (s, 3H), 1.59 (s, 2H), 1.44 (s, 9H); MS (ES, m/z) found for C$_{13}$H$_{21}$N$_3$O$_2$: [M+H]: 252.

Example 4

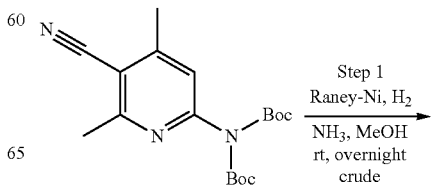

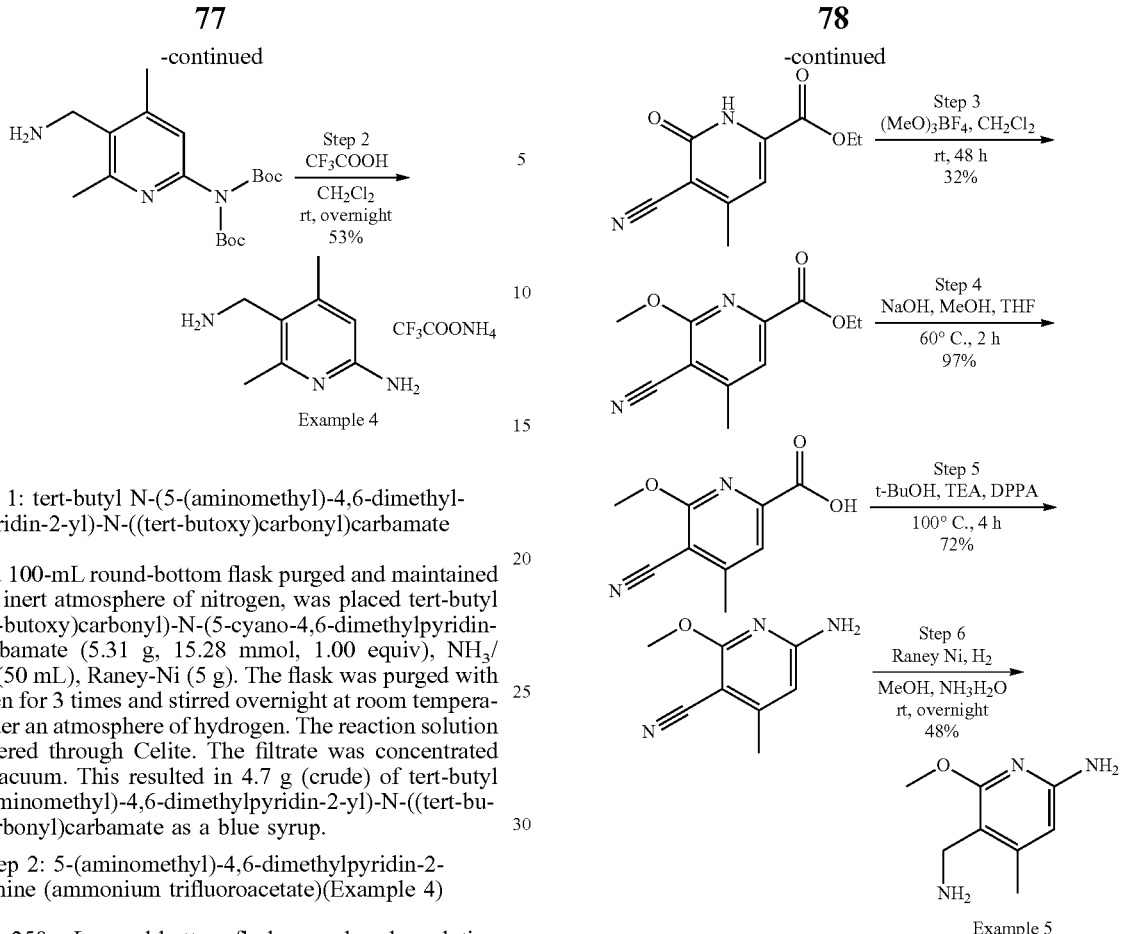

Step 1: tert-butyl N-(5-(aminomethyl)-4,6-dimethyl-pyridin-2-yl)-N-((tert-butoxy)carbonyl)carbamate Into a 100-mL round-bottom flask purged and maintained with an inert atmosphere of nitrogen, was placed tert-butyl N-((tert-butoxy)carbonyl)-N-(5-cyano-4,6-dimethylpyridin-2-yl)carbamate (5.31 g, 15.28 mmol, 1.00 equiv), $NH_3$/MeOH (50 mL), Raney-Ni (5 g). The flask was purged with hydrogen for 3 times and stirred overnight at room temperature under an atmosphere of hydrogen. The reaction solution was filtered through Celite. The filtrate was concentrated under vacuum. This resulted in 4.7 g (crude) of tert-butyl N-(5-(aminomethyl)-4,6-dimethylpyridin-2-yl)-N-((tert-butoxy)carbonyl)carbamate as a blue syrup.

Step 2: 5-(aminomethyl)-4,6-dimethylpyridin-2-amine (ammonium trifluoroacetate)(Example 4)

Into a 250-mL round-bottom flask was placed a solution of tert-butyl N-(5-(aminomethyl)-4,6-dimethylpyridin-2-yl)-N-((tert-butoxy)carbonyl)carbamate (4.7 g, 13.37 mmol, 1.00 equiv) in dichloromethane (100 mL). To which was added TFA (5 mL) dropwise with stirring. The resulting solution was stirred overnight at room temperature. The resulting mixture was concentrated under vacuum. The crude product was purified by Combi-Flash with the following conditions: column C18, 20-45 um, 100 A, 120 g. Mobile phase: solvent A: water contains 0.05% TFA, solvent B: $CH_3CN$. Gradient: 5-28%. Run time: 12 min. Flow rate: 80 mL/min. This resulted in 2.01 g (53%) of 5-(aminomethyl)-4,6-dimethylpyridin-2-amine (ammonium trifluoroacetate) as a light green solid. $^1$H NMR (300 MHz, $CD_3OD$): δ 6.74 (s, 1H), 4.16 (s, 2H), 2.57 (s, 3H), 2.47 (s, 3H). MS (ESI) m/z found for $C_8H_{13}N_3$: 152 $[M+H]^+$.

Example 5

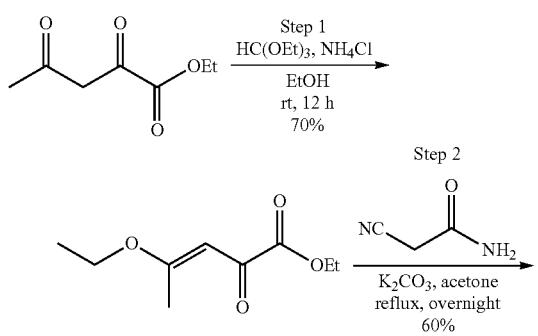

Step 1: Ethyl (3E)-4-ethoxy-2-oxopent-3-enoate

Into a 500-mL round-bottom flask, was placed a mixture of ethyl 2,4-dioxopentanoate (36.50 g, 230.79 mmol, 1.00 equiv), (diethoxymethoxy)ethane (41 mL, 1.10 equiv), $NH_4Cl$ (3.70 g, 69.17 mmol, 0.30 equiv) and ethanol (60 mL). The resulted solution was stirred for 12 h at room temperature. The resulted mixture was concentrated under vacuum and diluted with 500 mL of ether. The solids were filtered out. The filtrate was concentrated under vacuum. This resulted in 30.20 g (70%) of ethyl (3E)-4-ethoxy-2-oxopent-3-enoate as yellow oil. MS (ESI) m/z found for $C_9H_{14}O_4$: 187 $[M+H]^+$.

Step 2: Ethyl 5-cyano-4-methyl-6-oxo-1,6-dihydropyridine-2-carboxylate

Into an 1000-mL round-bottom flask, was placed a mixture of ethyl (3E)-4-ethoxy-2-oxopent-3-enoate (30.00 g, 161.11 mmol, 1.00 equiv), 2-cyanoacetamide (12.00 g, 142.73 mmol, 10.88 equiv), potassium carbonate (21.00 g, 151.94 mmol, 0.94 equiv) and acetone (400 mL). The resulted solution was refluxed overnight. The resulted mixture was concentrated under vacuum and diluted with 350 mL of 1 M HCl aqueous solution. The solids were collected by filtration. This resulted in 20.00 g (60%) of ethyl 5-cyano-4-methyl-6-oxo-1,6-dihydropyridine-2-carboxylate as white solid. MS (ESI) m/z found for $C_{10}H_{10}N_2O_3$: 207 $[M+H]^+$.

Step 3: Ethyl 5-cyano-6-methoxy-4-methylpyridine-2-carboxylate

Into a 50-mL round-bottom flask, was placed a mixture of ethyl 5-cyano-4-methyl-6-oxo-1,6-dihydropyridine-2-carboxylate (200 mg, 0.97 mmol, 1.00 equiv), (MeO)$_3$BF$_4$ (200 mg, 1.40 equiv) and dichloromethane (10 mL). The resulted solution was stirred for 48 h at room temperature. To the reaction solution was added 7.5 mL of 1 M NaOH aqueous solution. Then it was extracted with 3×10 mL of dichloromethane. The organic layers were combined, dried over anhydrous sodium sulfate and concentrated under vacuum. This resulted in 68.5 mg (32%) of ethyl 5-cyano-6-methoxy-4-methylpyridine-2-carboxylate as white solid. MS (ESI) m/z found for $C_{11}H_{12}N_2O_3$: 221 [M+H]$^+$.

Step 4: 5-cyano-6-methoxy-4-methylpyridine-2-carboxylic acid

Into a 100-mL round-bottom flask, was placed a mixture of ethyl 5-cyano-6-methoxy-4-methylpyridine-2-carboxylate (1.0 g, 4.54 mmol, 1.00 equiv), 1 M NaOH aqueous solution (2 mL), methanol (20 mL) and tetrahydrofuran (20 mL). The resulted solution was stirred for 2 h at 60° C. The reaction mixture was concentrated under vacuum and acidified with 1 M HCl aqueous solution to pH=4. The solids were collected by filtration. This resulted in 850 mg (97%) of 5-cyano-6-methoxy-4-methylpyridine-2-carboxylic acid as white solids. MS (ESI) m/z found for $C_9H_8N_2O_3$: 193 [M+H]$^+$.

Step 5: 6-amino-2-methoxy-4-methylpyridine-3-carbonitrile

Into a 250-mL round-bottom flask, was placed a mixture of 5-cyano-6-methoxy-4-methylpyridine-2-carboxylic acid (4.60 g, 23.94 mmol, 1.00 equiv), TEA (11.25 mL) and tBuOH (150 mL), to which was added DPPA (7.5 mL) with stirring. The resulted mixture was stirred for 4 h at 100° C. The resulted mixture was concentrated under vacuum. The residue was purified by silica gel column chromatography eluted with ethyl acetate and petroleum ether (1:3). This resulted in 2.80 g (72%) of 6-amino-2-methoxy-4-methylpyridine-3-carbonitrile as light yellow solid. MS (ESI) m/z found for $C_8H_9N_3O$: 164 [M+H]$^+$.

Step 6: 5-(aminomethyl)-6-methoxy-4-methylpyridin-2-amine (Example 5)

Into a 250-mL round-bottom flask, was placed a mixture of 6-amino-2-methoxy-4-methylpyridine-3-carbonitrile (2.50 g, 15.32 mmol, 1.00 equiv) in methanol, ammonia (100 mL) and Raney Ni (2.00 g). The above mixture was stirred overnight at room temperature with hydrogen stream bubbling through the reaction solution. The solids were filtered out. The filtrate was concentrated under vacuum. The residue was purified by silica gel column chromatography eluted with ethyl acetate and methanol (1:0-0:1). This resulted in 1.22 g (48%) of 5-(aminomethyl)-6-methoxy-4-methylpyridin-2-amine as light red solids. $^1$H NMR (300 MHz, DMSO-d): δ 5.83 (s, 1H), 5.56 (s, 2H), 3.74 (s, 3H), 3.49 (s, 2H), 2.14 (s, 3H). MS (ESI) m/z found for $C_8H_{13}N_3O$: 151 [M+H-NH$_3$]$^+$.

Examples 6, 7, 8

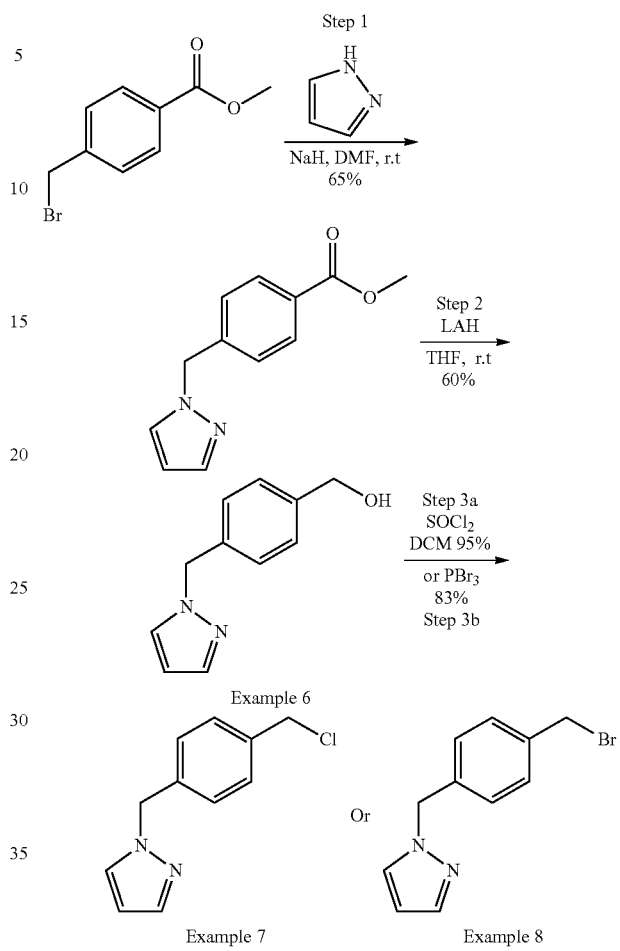

Step 1. methyl 4-(1H-pyrazol-1-ylmethyl)benzoate

Into a 500-mL 3-necked round-bottom flask, which was purged and maintained with an inert atmosphere of nitrogen, was placed 1H-pyrazole (6.2 g, 91.07 mmol, 1.00 equiv) in N,N-dimethylformamide (100 mL). This was followed by the addition of NaH (60%) (5.5 g, 137.50 mmol, 1.51 equiv) in several batches at 0° C. The mixture was stirred for 1 h at 0° C. To this was added a solution of methyl 4-(bromomethyl)benzoate (21 g, 91.67 mmol, 1.01 equiv) in N,N-dimethylformamide (100 mL) dropwise with stirring at 0° C. The resulting solution was stirred for 5 h at room temperature. The reaction was then quenched by the addition of 100 mL of water/ice. The resulting solution was extracted with 2×200 mL of ethyl acetate and the organic layers combined. The resulting mixture was washed with 3×200 mL of brine. The organic layer was concentrated under vacuum. This resulted in 13 g (66%) of methyl 4-(1H-pyrazol-1-ylmethyl)benzoate as yellow oil.

Step 2. (4-((1H-pyrazol-1-yl)methyl)phenyl)methanol (Example 6.). Into a 250-mL 3-necked round-bottom flask, which was purged and maintained with an inert atmosphere of nitrogen, was placed methyl 4-(1H-pyrazol-1-ylmethyl)benzoate (8 g, 37.00 mmol, 1.00 equiv) in tetrahydrofuran (100 mL). This was followed by the addition of LiAlH$_4$ (1.69 g, 44.53 mmol, 1.20 equiv) in several batches at 0° C. The resulting solution was stirred for 30 min at 0° C. and for an additional 3 h at room temperature. The reaction was then quenched by the addition of 1.7 mL of water, 1.7 mL of 15% NaOH, and 5.1 mL of water. The solids were filtered. The resulting solution was extracted with 2×200 mL of ethyl acetate and the organic layers combined and concentrated under vacuum. The residue was applied onto a silica gel column with ethyl acetate/petroleum ether (1:40-1:4) as eluent. This resulted in 3.9 g (56%) of [4-(1H-pyrazol-1-ylmethyl)phenyl]methanol as a yellow oil.

Step 3a. 1-(4-(chloromethyl)benzyl)-1H-pyrazole (Example 7). Into a 50-mL round-bottom flask, which was purged and maintained with an inert atmosphere of nitrogen, was placed [4-(1H-pyrazol-1-ylmethyl)phenyl]methanol (328 mg, 1.74 mmol, 1.00 equiv) in dichloromethane (1.2 mL). This was followed by the addition of thionyl chloride (0.13 mL, 1.00 equiv) dropwise with stirring at 0° C. The resulting solution was stirred for 0.5 h at room temperature. The resulting mixture was concentrated under vacuum. This resulted in 360 mg (100%) of 1-[[4-(chloromethyl)phenyl]methyl]-1H-pyrazole as a brown oil.

Step 3b. 1-(4-(bromomethyl)benzyl)-1H-pyrazole (Example 8). Into a 500-mL round-bottom flask, was placed [4-(1H-pyrazol-1-ylmethyl)phenyl]methanol (4.5 g, 23.91 mmol, 1.00 equiv) in dichloromethane (150 mL). This was followed by the addition of PBr3 (13 g, 48.03 mmol, 2.01 equiv) dropwise with stirring at 0° C. The resulting solution was stirred for 1 h at room temperature. The pH value of the solution was adjusted to 8 with sodium bicarbonate (sat. aq.). The resulting solution was extracted with 2×200 mL of ethyl acetate and the organic layers combined and concentrated under vacuum. The residue was applied onto a silica gel column with ethyl acetate/petroleum ether (30%) as eluent. This resulted in 5 g (83%) of 1-[[4-(bromomethyl)phenyl]methyl]-1H-pyrazole as a white solid.

Example 9

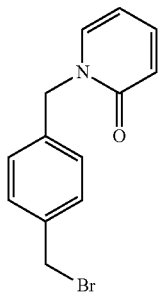

1-(4-(bromomethyl)benzyl)pyridin-2(1H)-one

Into a 2000-mL 4-necked round-bottom flask purged and maintained with an inert atmosphere of nitrogen, were placed pyridin-2-ol (5 g, 52.58 mmol, 1.00 equiv), 1,4-bis(bromomethyl)benzene (82.7 g, 313.31 mmol, 6.00 equiv) and dixoane (830 mL). This was followed by the addition of NaH (2.53 g, 68.52 mmol, 1.30 equiv, 65%) in several batches at room temperature. The resulting solution was stirred for 1 h at 70° C. in an oil bath. The reaction was then quenched by the addition of 3 mL of water. The resulted mixture was concentrated under vacuum. The crude product was purified by silica gel column chromatography eluted with ethyl acetate/ petroleum ether (1:4 to 1:1). This resulted in 10.5 g (72%) of 1-[[4-(bromomethyl)phenyl]methyl]-1,2-dihydropyridin-2-one as white solid. $^1$H NMR (300 MHz, CD$_3$OD): δ 7.72 (d, J=6.6 Hz, 1H), 7.58-7.52 (m, 1H), 7.42 (d, J=8.1 Hz, 2H), 7.31-(d, J=8.1 Hz, 2H), 6.61 (d, J=9.3 Hz, 1H), 6.44-6.39 (m, 1H), 5.21 (s, 2H), 4.56 (s, 2H). MS (ESI) m/z found for C$_{13}$H$_{12}$BrNO: 498 [M+H]$^+$.

Examples 12, 13

Example 8

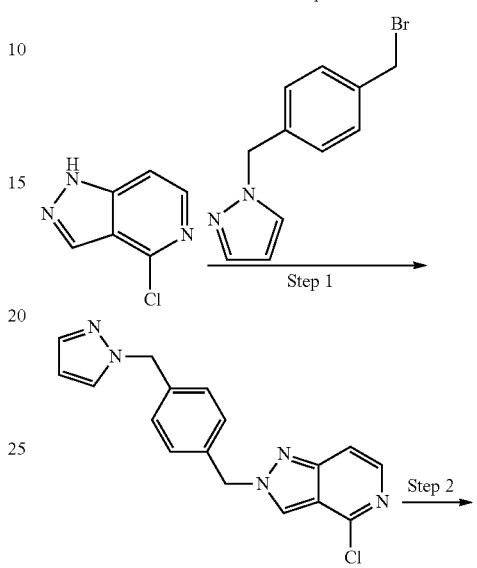

Example 10

+

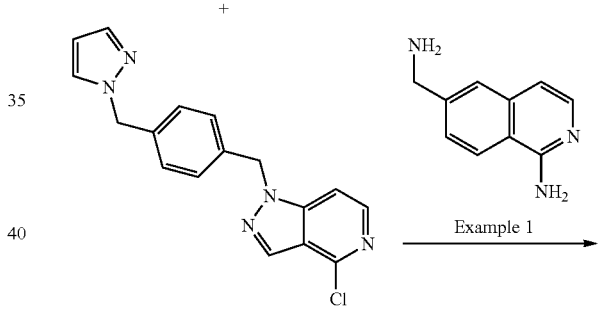

Example 11

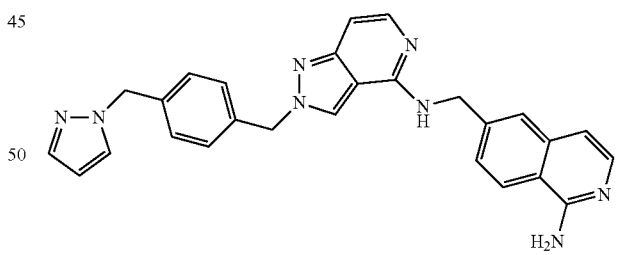

Example 12

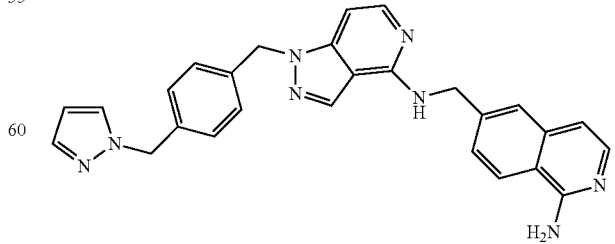

Example 13

Examples 10, 11

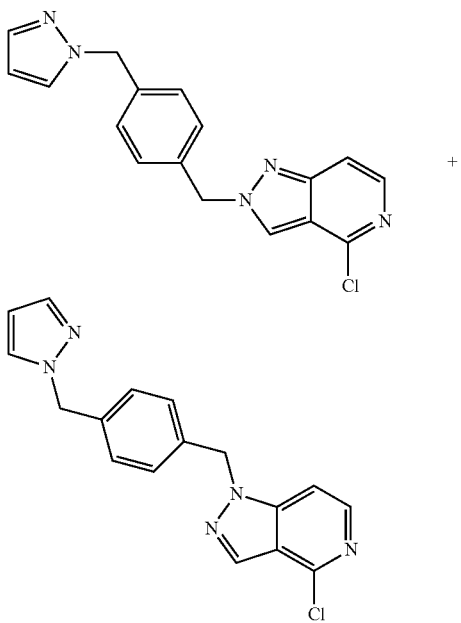

Step 1. 1-(4-((1H-pyrazol-1-yl)methyl)benzyl)-4-chloro-1H-pyrazolo[4,3-c]pyridine and 2-(4-((1H-pyrazol-1-yl)methyl)benzyl)-4-chloro-2H-pyrazolo[4,3-c]pyridine To a solution of 4-chloro-1H-pyrazolo[4,3-c]pyridine (150.00 mg; 0.98 mmol; 1.00 eq.) and 1-(4-(bromomethyl)benzyl)-1H-pyrazole (245.29 mg; 0.98 mmol; 1.00 eq.) in DMF (2 mL) was added Cs$_2$CO$_3$ (636.6 mg, 1.95 mmol). After stirring at room temperature for 2 h, the mixture was diluted with water and was extracted with EtOAc, the organic layer was combined, dried and concentrated to give crude product, which was purified by column chromatography to give a mixture of two isomers. The mixture was purified by preparative HPLC again to give 1-(4-((1H-pyrazol-1-yl)methyl)benzyl)-4-chloro-1H-pyrazolo[4,3-c]pyridine (75 mg) and 2-(4-((1H-pyrazol-1-yl)methyl)benzyl)-4-chloro-2H-pyrazolo[4,3-c]pyridine (74 mg).

Example 12

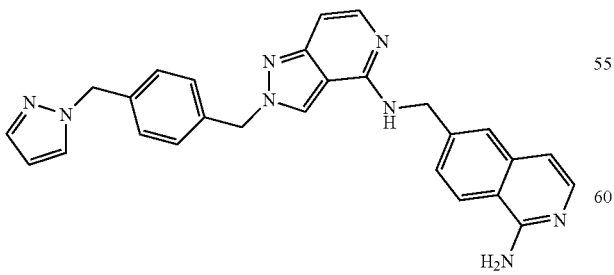

Step 2a. 6-(((2-(4-((1H-pyrazol-1-yl)methyl)benzyl)-2H-pyrazolo[4,3-c]pyridin-4-yl)amino)methyl)isoquinolin-1-amine.

To a suspension of 2-(4-((1H-pyrazol-1-yl)methyl) benzyl)-4-chloro-2H-pyrazolo[4,3-c]pyridine (18.00 mg; 0.06 mmol; 1.00 eq.) in nBuOH (0.8 mL) was added 6-(aminomethyl)isoquinolin-1-amine (38.52 mg; 0.22 mmol; 4.00 eq.). After heating in a microwave reactor at 200° C. for 30 min, HPLC showed the reaction was complete and the mixture was diluted with water and acetonitrile and then purified by preparative HPLC to give 6-(((2-(4-((1H-pyrazol-1-yl)methyl)benzyl)-2H-pyrazolo[4,3-c]pyridin-4-yl)amino)methyl)isoquinolin-1-amine (7 mg). $^1$H NMR (400 MHz, DMSO-d$_6$) δ 8.59 (s, 1H), 8.26 (d, J=8.6 Hz, 1H), 7.78 (dd, J=2.3, 0.7 Hz, 1H), 7.72-7.63 (m, 2H), 7.58-7.39 (m, 3H), 7.34-7.23 (m, 2H), 7.23-7.11 (m, 2H), 6.95 (d, J=6.3 Hz, 1H), 6.75-6.69 (m, 1H), 6.23 (dd, J=2.2, 1.8 Hz, 1H), 5.57 (s, 2H), 5.30 (s, 2H), 4.82 (d, J=5.4 Hz, 2H). MS (M+H)+ found for C$_{27}$H$_{24}$N$_8$: 461.2.

Example 13

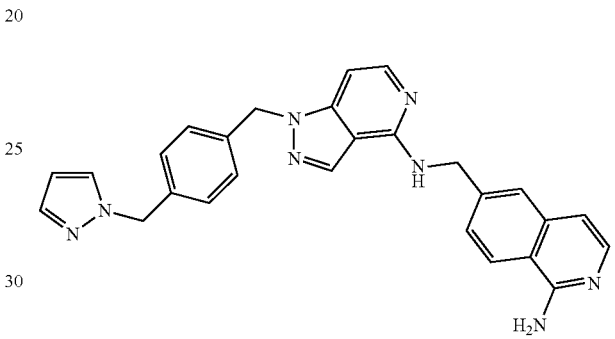

Step 2b. 6-(((1-(4-((1H-pyrazol-1-yl)methyl)benzyl)-1H-pyrazolo[4,3-c]pyridin-4-yl)amino)methyl)isoquinolin-1-amine.

To a suspension of 1-(4-((1H-pyrazol-1-yl)methyl) benzyl)-4-chloro-1H-pyrazolo[4,3-c]pyridine (20.00 mg; 0.06 mmol; 1.00 eq.) in n-BuOH (1 mL) was added 6-(aminomethyl)isoquinolin-1-amine (42.80 mg; 0.25 mmol; 4.00 eq.) and the reaction was heated in a microwave reactor for 30 min., HPLC showed all starting material had been consumed. The mixture was cooled and diluted with ACN/water and was purified by preparative HPLC to give 6-(((1-(4-((1H-pyrazol-1-yl)methyl)benzyl)-1H-pyrazolo[4,3-c]pyridin-4-yl)amino)methyl)isoquinolin-1-amine. $^1$H NMR (400 MHz, DMSO-d$_6$) δ 8.27-8.18 (m, 2H), 8.04 (s, 1H), 7.75 (dd, J=2.2, 0.7 Hz, 1H), 7.71-7.63 (m, 3H), 7.56-7.49 (m, 1H), 7.40 (dd, J=1.8, 0.7 Hz, 1H), 7.19-7.09 (m, 4H), 6.93 (d, J=6.2 Hz, 1H), 6.82 (dd, J=6.2, 1.0 Hz, 1H), 6.22 (dd, J=2.3, 1.8 Hz, 1H), 5.49 (s, 2H), 5.26 (s, 2H), 4.82 (d, J=5.8 Hz, 2H). MS (M+H)+ found for C$_{27}$H$_{24}$N$_8$: 461.2.

Example 8

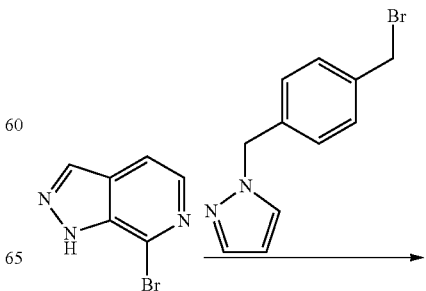

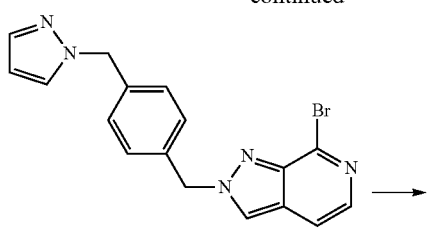

Example 14

+

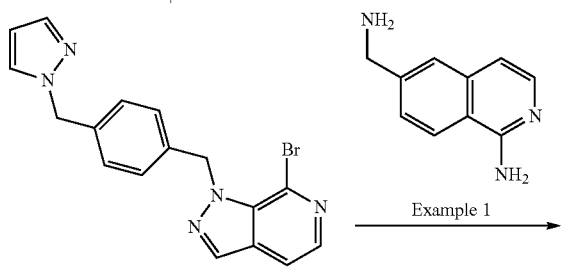

Example 15

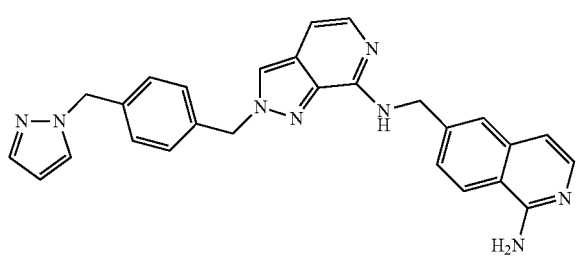

Example 16

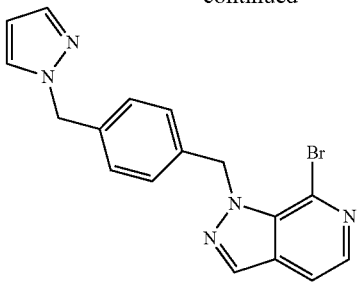

Step 1. 2-(4-((1H-pyrazol-1-yl)methyl)benzyl)-7-bromo-2H-pyrazolo[3,4-c]pyridine and 1-(4-((1H-pyrazol-1-yl)methyl)benzyl)-7-bromo-1H-pyrazolo[3,4-c]pyridine To a solution of 7-bromo-1H-pyrazolo[3,4-c]pyridine (150.00 mg; 0.76 mmol; 1.00 eq.) and 1-(4-(bromomethyl)benzyl)-1H-pyrazole (190.23 mg; 0.76 mmol; 1.00 eq.) in DMF (2 mL) was added $Cs_2CO_3$ and stirred at room temperature for 2 h, then it was diluted with Sat. $NaHCO_3$ and the aqueous layer was extracted with EtOAc, organic layers were combined and dried over $Na_2SO_4$, concentrated to give crude product, which was purified by preparative HPLC to give 2-(4-((1H-pyrazol-1-yl)methyl)benzyl)-7-bromo-2H-pyrazolo[3,4-c]pyridine (88 mg) and 1-(4-((1H-pyrazol-1-yl)methyl)benzyl)-7-bromo-1H-pyrazolo[3,4-c]pyridine (75 mg).

Example 16

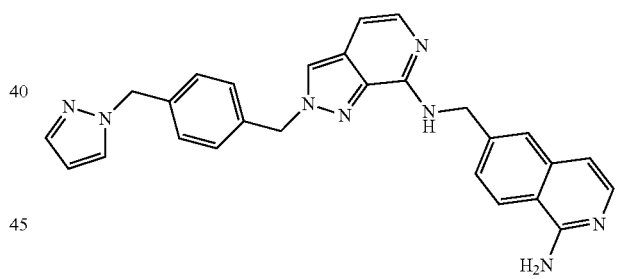

Step 2a. 6-(((2-(4-((1H-pyrazol-1-yl)methyl)benzyl)-2H-pyrazolo[3,4-c]pyridin-7-yl)amino)methyl)isoquinolin-1-amine To a suspension of 2-(4-((1H-pyrazol-1-yl)methyl)benzyl)-7-bromo-2H-pyrazolo[3,4-c]pyridine (18.00 mg; 0.05 mmol; 1.00 eq.) in n-BuOH (0.8 mL) was added 6-(aminomethyl)isoquinolin-1-amine (33.87 mg; 0.20 mmol; 4.00 eq.) After heating at 200° C. for 25 min in a microwave reactor, the mixture was cooled and diluted with water and acetonitrile. The mixture was purified by preparative HPLC to give 6-(((2-(4-((1H-pyrazol-1-yl)methyl)benzyl)-2H-pyrazolo[3,4-c]pyridin-7-yl)amino)methyl)isoquinolin-1-amine (7 mg). $^1$H NMR (400 MHz, DMSO-$d_6$) δ 8.32 (s, 1H), 8.20 (d, J=8.7 Hz, 1H), 7.87 (s, 1H), 7.78 (dd, J=2.3, 0.7 Hz, 1H), 7.66 (d, J=6.2 Hz, 1H), 7.63 (s, 1H), 7.54 (dd, J=8.7, 1.7 Hz, 1H), 7.46 (s, 2H), 7.41 (dd, J=1.9, 0.7 Hz, 1H), 7.34 (d, J=6.2 Hz, 1H), 7.29-7.14 (m, 4H), 6.96-6.89

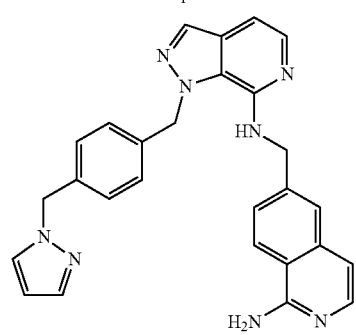

Example 17

Examples 14, 15

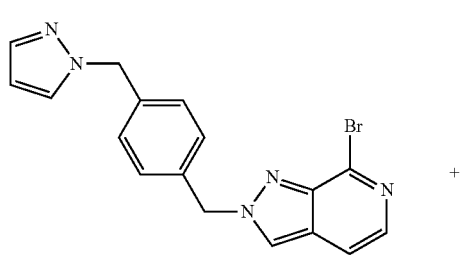

+

(m, 1H), 6.73 (d, J=6.2 Hz, 1H), 6.23 (dd, J=2.3, 1.8 Hz, 1H), 5.61 (s, 2H), 5.29 (s, 2H), 4.78 (d, J=6.0 Hz, 2H). MS (M+H)+ found for $C_{27}H_{24}N_8$: 461.1.

Example 17

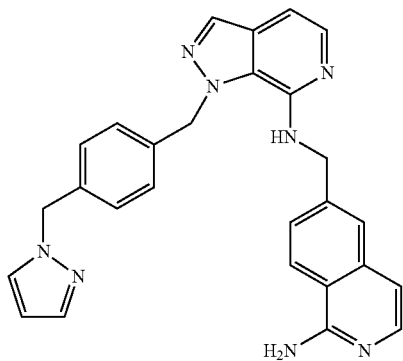 [SMILES: Nc1nccc2cc(CNc3nccc4cnn(Cc5ccc(Cn6cccn6)cc5)c34)ccc12]

Step 2b. 6-(((1-(4-((1H-pyrazol-1-yl)methyl)benzyl)-1H-pyrazolo[3,4-c]pyridin-7-yl)amino)methyl)isoquinolin-1-amine To a solution of 1-(4-((1H-pyrazol-1-yl)methyl)benzyl)-7-bromo-1H-pyrazolo[3,4-c]pyridine (18.00 mg; 0.05 mmol; 1.00 eq.) in n-BuOH (0.7 mL) was added 6-(aminomethyl)isoquinolin-1-amine (33.87 mg; 0.20 mmol; 4.00 eq.). The mixture was heated at 200° C. in microwave reactor for 25 min, then cooled and purified by preparative HPLC to give 6-(((1-(4-((1H-pyrazol-1-yl)methyl)benzyl)-1H-pyrazolo[3,4-c]pyridin-7-yl)amino)methyl)isoquinolin-1-amine (2 mg). $^1$H NMR (400 MHz, DMSO-$d_6$) δ 8.35 (d, J=8.6 Hz, 1H), 8.04 (s, 1H), 7.74 (dd, J=2.3, 0.5 Hz, 1H), 7.62 (d, J=6.9 Hz, 1H), 7.55-7.46 (m, 3H), 7.44-7.38 (m, 1H), 7.15-7.06 (m, 3H), 7.00 (d, J=8.1 Hz, 2H), 6.92 (t, J=6.0 Hz, 2H), 6.22 (t, J=2.1 Hz, 1H), 5.97 (s, 2H), 5.26 (d, J=12.9 Hz, 2H), 4.81 (d, J=5.4 Hz, 2H), 1.33-1.19 (m, 1H), 0.85 (t, J=7.3 Hz, 1H). MS (M+H)+ found for $C_{27}H_{24}N_8$: 461.2.

Example 18

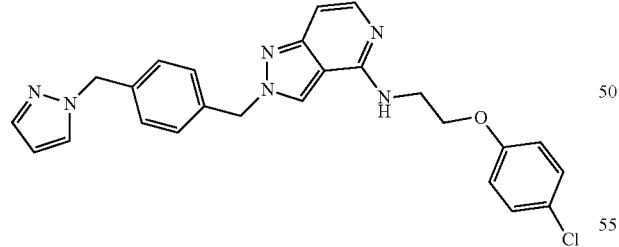

2-(4-((1H-pyrazol-1-yl)methyl)benzyl)-N-(2-(4-chlorophenoxy)ethyl)-2H-pyrazolo[4,3-c]pyridin-4-amine To a mixture of 2-(4-((1H-pyrazol-1-yl)methyl)benzyl)-4-chloro-2H-pyrazolo[4,3-c]pyridine (10.00 mg; 0.03 mmol; 1.00 eq.)(Example 10) in n-BuOH (0.8 mL) was added 2-(4-chlorophenoxyl)ethanamine (21.20 mg; 0.12 mmol; 4.00 eq.), then the mixture was heated in microwave reactor for 25 min. HPLC showed the reaction was complete and the mixture was diluted with water and acetonitrile and purified by prep HPLC to give 2-(4-((1H-pyrazol-1-yl)methyl)benzyl)-N-(2-(4-chlorophenoxyl)ethyl)-2H-pyrazolo[4,3-c]pyridin-4-amine. $^1$H NMR (400 MHz, DMSO-$d_6$) δ 12.37 (s, 1H), 8.79 (s, 1H), 7.78 (dd, J=2.3, 0.7 Hz, 1H), 7.49-7.39 (m, 2H), 7.36-7.26 (m, 4H), 7.23-7.16 (m, 2H), 7.00-6.88 (m, 3H), 6.23 (dd, J=2.2, 1.8 Hz, 1H), 5.60 (s, 2H), 5.30 (s, 2H), 4.21 (t, J=5.2 Hz, 2H), 3.85 (d, J=5.7 Hz, 2H). MS (M+H)+ found for $C_{25}H_{23}ClN_6O$: 460.2.

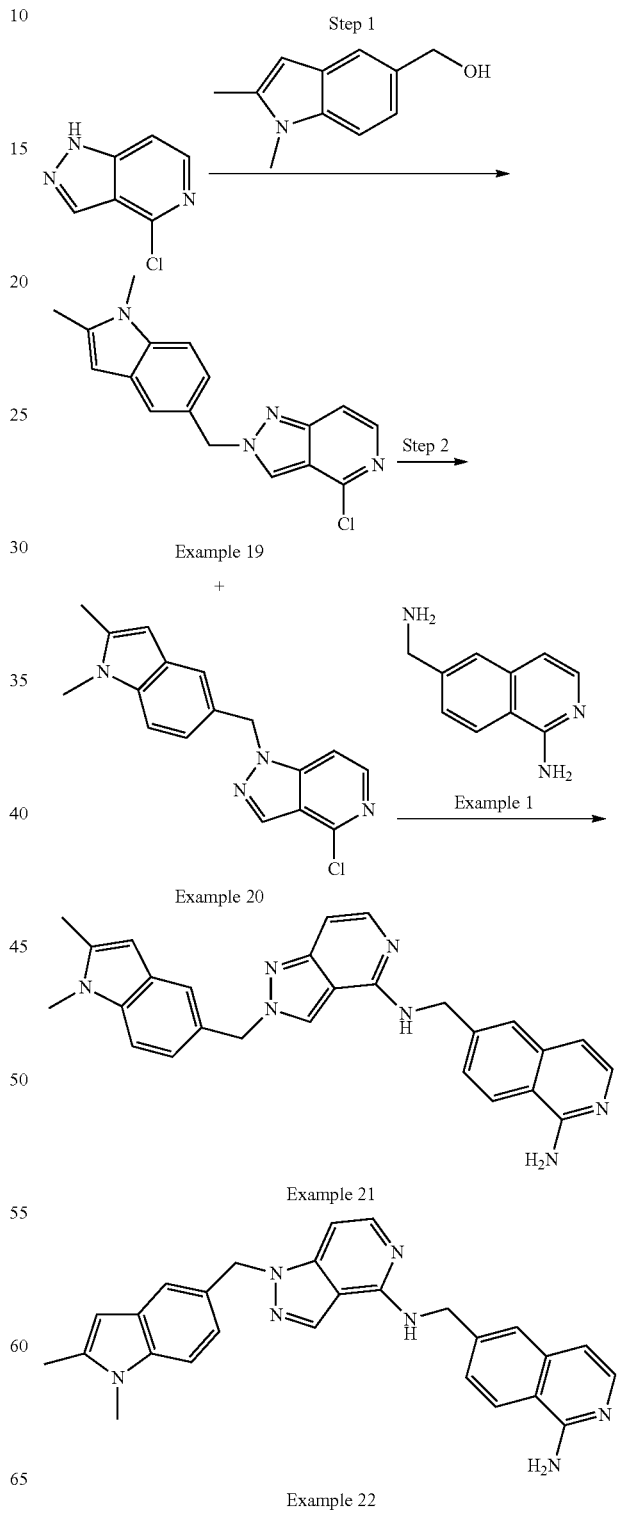

Examples 19, 20

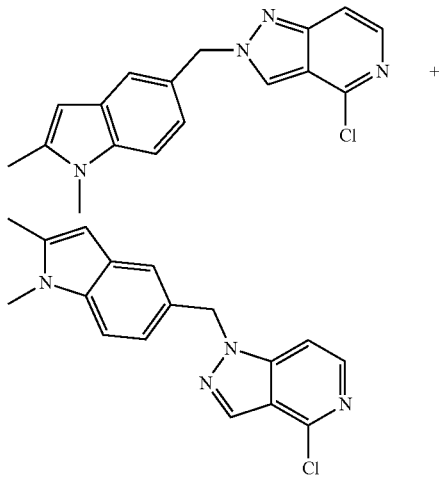

Step 1. 4-chloro-2-((1,2-dimethyl-1H-indol-5-yl)methyl)-2H-pyrazolo[4,3-c]pyridine and 4-chloro-1-((1,2-dimethyl-1H-indol-5-yl)methyl)-1H-pyrazolo[4,3-c]pyridine To a solution of (1,2-dimethyl-1H-indol-5-yl)methanol (300.00 mg; 1.71 mmol; 1.00 eq.) and 4-chloro-1H-pyrazolo[4,3-c]pyridine (262.92 mg; 1.71 mmol; 1.00 eq.) in THF (2 mL) was added triphenylphosphine (polymer supported, 1.71 g; 2.05 mmol; 1.20 eq.) and diisopropyl (E)-1,2-diazadicarboxylate (0.40 ml; 2.05 mmol; 1.20 eq.) at 0° C. and was stirred at rt for 15 h, then it was concentrated and was purified by column to give 4-chloro-2-((1,2-dimethyl-1H-indol-5-yl)methyl)-2H-pyrazolo[4,3-c]pyridine (132 mg) and 4-chloro-1-((1,2-dimethyl-1H-indol-5-yl)methyl)-1H-pyrazolo[4,3-c]pyridine (230 mg).

Example 21

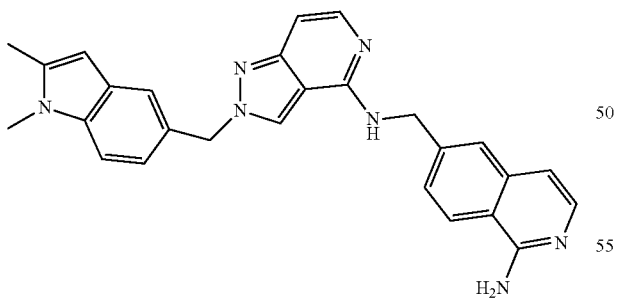

Step 2 6-(((2-((1,2-dimethyl-1H-indol-5-yl)methyl)-2H-pyrazolo[4,3-c]pyridin-4-yl)amino)methyl)isoquinolin-1-amine To a solution of 4-chloro-2-((1,2-dimethyl-1H-indol-5-yl)methyl)-2H-pyrazolo[4,3-c]pyridine (132.00 mg; 0.42 mmol; 1.00 eq.) in n-BuOH (1 mL) was added 6-(aminomethyl)isoquinolin-1-amine (441.42 mg; 2.55 mmol; 6.00 eq.) and the mixture was heated at 200° C. for 25 min in a microwave synthesizer. The mixture was cooled and purified by preparatory HPLC to give 6-(((2-((1,2-dimethyl-1H-indol-5-yl)methyl)-2H-pyrazolo[4,3-c]pyridin-4-yl)amino)methyl)isoquinolin-1-amine (16 mg). $^1$H NMR (400 MHz, DMSO-$d_6$) δ 8.34 (d, J=0.9 Hz, 1H), 8.07 (d, J=8.6 Hz, 1H), 7.76-7.72 (m, 1H), 7.70 (d, J=5.8 Hz, 1H), 7.53 (d, J=1.6 Hz, 1H), 7.50 (d, J=6.4 Hz, 1H), 7.48-7.42 (m, 1H), 7.39 (dd, J=8.6, 1.7 Hz, 1H), 7.35 (dt, J=8.4, 0.7 Hz, 1H), 7.08 (dd, J=8.4, 1.7 Hz, 1H), 6.82-6.76 (m, 1H), 6.67 (s, 2H), 6.62 (dd, J=6.3, 0.9 Hz, 1H), 6.22-6.16 (m, 1H), 5.56 (s, 2H), 4.74 (d, J=5.7 Hz, 2H), 3.62 (s, 3H), 2.37 (d, J=1.0 Hz, 3H). MS (M+H)+ found for $C_{27}H_{25}N_7$: 448.1.

Example 22

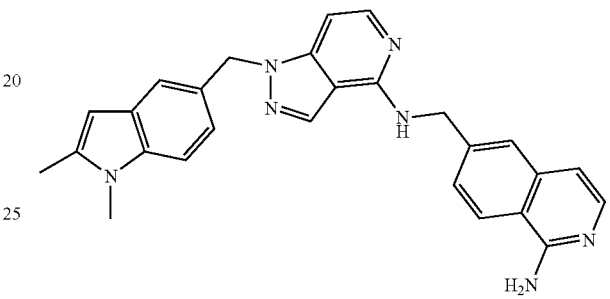

Step 2b. 6-(((1-((1,2-dimethyl-1H-indol-5-yl)methyl)-2H-pyrazolo[4,3-c]pyridin-4-yl)amino)methyl)isoquinolin-1-amine To a solution of 4-chloro-1-((1,2-dimethyl-1H-indol-5-yl)methyl)-1H-pyrazolo[4,3-c]pyridine (32.00 mg; 0.1 mmol; 1.00 eq.) in n-BuOH (1 mL) was added 6-(aminomethyl)isoquinolin-1-amine (107 mg; 0.62 mmol; 6.00 eq.) and the mixture was heated at 200° C. for 25 min. The mixture was cooled and purified by preparatory HPLC to give 6-(((1-((1,2-dimethyl-1H-indol-5-yl)methyl)-2H-pyrazolo[4,3-c]pyridin-4-yl)amino)methyl)isoquinolin-1-amine (3 mg). $^1$H NMR (400 MHz, DMSO-$d_6$) δ 8.22 (d, J=0.9 Hz, 1H), 8.09 (d, J=8.6 Hz, 1H), 7.91 (t, J=6.0 Hz, 1H), 7.71 (d, J=5.8 Hz, 1H), 7.66 (d, J=6.1 Hz, 1H), 7.56 (dd, J=1.5, 0.7 Hz, 1H), 7.42 (dd, J=8.6, 1.8 Hz, 1H), 7.33-7.23 (m, 2H), 6.98 (dd, J=8.4, 1.7 Hz, 1H), 6.81 (t, J=1.0 Hz, 1H), 6.80 (t, J=0.9 Hz, 1H), 6.69 (s, 2H), 6.16-6.10 (m, 1H), 5.52 (s, 2H), 4.79 (d, J=5.9 Hz, 2H), 3.59 (s, 3H), 2.34 (d, J=1.0 Hz, 3H). MS (M+H)+ found for $C_{27}H_{25}N_7$: 448.1.

Examples 25, 26

Example 8

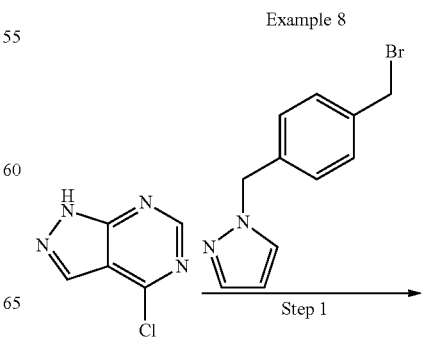

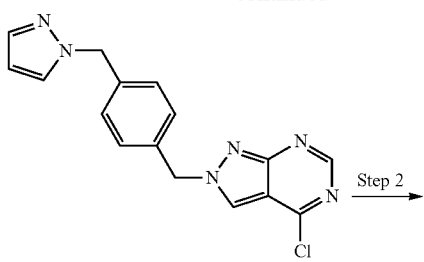

Example 23

+

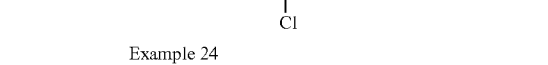

Example 24

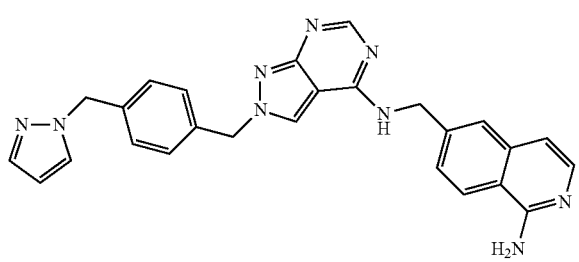

Example 25

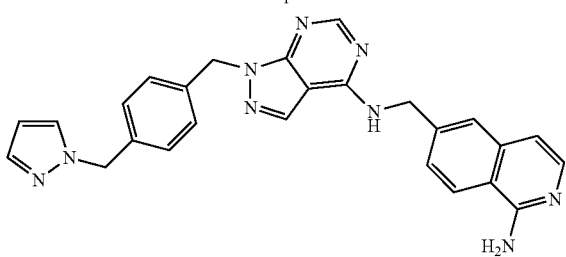

Example 26

Examples 23, 24

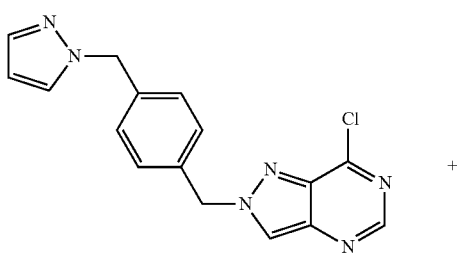

+

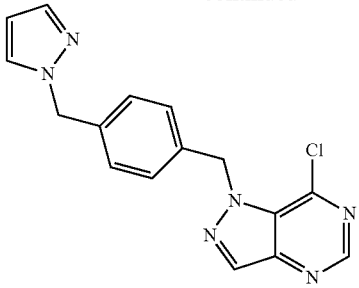

Step 1 To a suspension of 4-chloro-1H-pyrazolo[3,4-d]pyrimidine (0.31 g; 2.00 mmol; 1.00 eq.) and 1-{[4-(bromomethyl)phenyl]methyl}-1H-pyrazole (0.50 g; 2.00 mmol; 1.00 eq.) in DMF (3 mL) was added cesium carbonate (1.30 g; 4.00 mmol; 2.00 eq.). The mixture was stirred for 2 hr at room temperature, then it was diluted with water and the resulting precipitates were collected by filtration to give a mixture of two isomers. This mixture was used in next reaction without purification.

Examples 25, 26

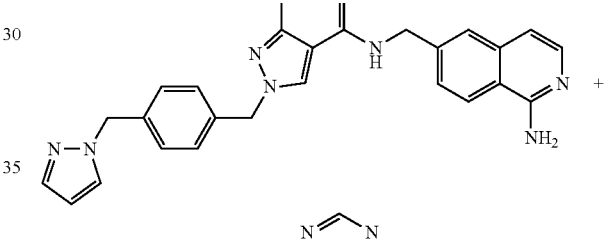

Step 2a. 6-(((2-(4-((1H-pyrazol-1-yl)methyl)benzyl)-2H-pyrazolo[3,4-d]pyrimidin-4-yl)amino)methyl)isoquinolin-1-amine and 6-(((1-(4-((1H-pyrazol-1-yl)methyl)benzyl)-1H-pyrazolo[3,4-d]pyrimidin-4-yl)amino)methyl)isoquinolin-1-amine A solution of the above mixture of regio isomers (120.00 mg; 0.37 mmol; 1.00 eq.) and 6-(aminomethyl)isoquinolin-1-amine (192.01 mg; 1.11 mmol; 3.00 eq.) in n-BuOH (1.5 mL) was heated at 180° C. in a microwave synthesizer for 25 min, then it was cooled and purified by prep HPLC to give 6-(((2-(4-((1H-pyrazol-1-yl)methyl)benzyl)-2H-pyrazolo[3,4-d]pyrimidin-4-yl)amino)methyl)isoquinolin-1-amine (13 mg, $^1$H NMR (400 MHz, DMSO-$d_6$) δ 8.72 (d, J=5.9 Hz, 1H), 8.37 (s, 1H), 8.23-8.06 (m, 2H), 7.81-7.70 (m, 2H), 7.56 (s, 1H), 7.45-7.34 (m, 2H), 7.33-7.23 (m, 2H), 7.19 (d, J=7.9 Hz, 2H), 6.86-6.79 (m, 1H), 6.72 (s, 2H), 6.23 (dd, J=2.3, 1.8 Hz, 1H), 5.52 (d, J=7.9 Hz, 2H), 5.30 (s, 2H), 4.82 (d, J=5.6 Hz, 2H). MS (M+H)+ found for $C_{26}H_{23}N_9$: 462.1) and 6-(((1-(4-((1H-pyrazol-1-yl)methyl)benzyl)-1H-pyrazolo[3,4-d]pyrimidin-4-yl)amino)methyl)isoquinolin- 1-amine (18 mg, ¹H NMR (400 MHz, DMSO-d₆) δ 8.87 (t, J=5.9 Hz, 1H), 8.26 (s, 1H), 8.19-8.09 (m, 2H), 7.78-7.70 (m, 2H), 7.58 (d, J=1.7 Hz, 1H), 7.46-7.37 (m, 2H), 7.21-7.09 (m, 4H), 6.87-6.80 (m, 1H), 6.71 (s, 2H), 6.22 (dd, J=2.3, 1.8 Hz, 1H), 5.46 (s, 2H), 5.26 (s, 2H), 4.86 (d, J=6.1 Hz, 2H), MS (M+H)+ found for C₂₆H₂₃N₉: 462.1).

Example 27

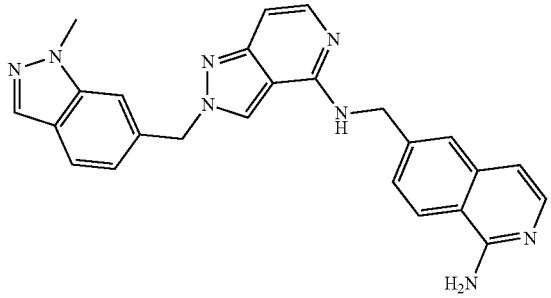 [SMILES: Cn1ncc2ccc(Cn3cc4c(NCc5ccc6c(N)nccc6c5)nccc4n3)cc21]

6-(((2-((1-methyl-1H-indazol-6-yl)methyl)-2H-pyrazolo[4,3-c]pyridin-4-yl)amino)methyl)isoquinolin-1-amine 6-(((2-((1-methyl-1H-indazol-6-yl)methyl)-2H-pyrazolo[4,3-c]pyridin-4-yl)amino)methyl)isoquinolin-1-amine was synthesized in a manner similar to Example 21 using (1-methyl-1H-indazol-6-yl)methanol to replace (1,2-dimethyl-1H-indol-5-yl)methanol. ¹H NMR (400 MHz, DMSO-d₆) δ 8.44 (d, J=1.0 Hz, 1H), 8.15-8.08 (m, 1H), 8.04 (d, J=1.0 Hz, 1H), 7.95 (s, 1H), 7.77 (dd, J=1.7, 0.8 Hz, 1H), 7.70 (d, J=5.9 Hz, 1H), 7.63 (dt, J=8.7, 0.9 Hz, 1H), 7.57 (s, 1H), 7.51 (d, J=6.4 Hz, 1H), 7.41 (ddd, J=12.1, 8.6, 1.7 Hz, 2H), 6.90-6.78 (m, 3H), 6.65 (dd, J=6.4, 0.9 Hz, 1H), 5.66 (s, 2H), 4.76 (d, J=5.4 Hz, 2H), 4.01 (s, 3H). MS (M+H)+ found for C₂₅H₂₂N₈: 435.1.

Example 28

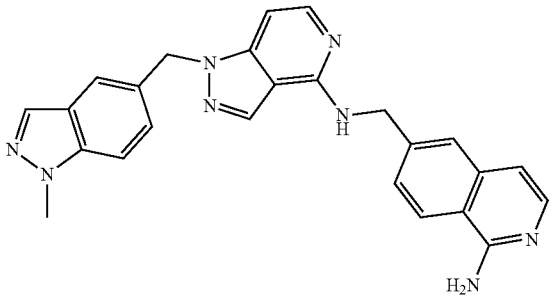 [SMILES: Cn1ncc2cc(Cn3ncc4c(NCc5ccc6c(N)nccc6c5)nccc43)ccc21]

6-(((1-((1-methyl-1H-indazol-6-yl)methyl)-1H-pyrazolo[4,3-c]pyridin-4-yl)amino)methyl)isoquinolin-1-amine 6-(((1-((1-methyl-1H-indazol-6-yl)methyl)-1H-pyrazolo[4,3-c]pyridin-4-yl)amino)methyl)isoquinolin-1-amine was synthesized in a manner similar to Example 22 using (1-methyl-1H-indazol-6-yl)methanol to replace (1,2-dimethyl-1H-indol-5-yl)methanol. ¹H NMR (400 MHz, DMSO-d₆) δ 8.25 (d, J=0.9 Hz, 1H), 8.12 (d, J=8.1 Hz, 2H), 8.02-7.92 (m, 2H), 7.70 (d, J=5.9 Hz, 1H), 7.68 (d, J=6.1 Hz, 1H), 7.64-7.57 (m, 2H), 7.55 (dt, J=8.7, 1.0 Hz, 1H), 7.44 (dd, J=8.6, 1.8 Hz, 1H), 7.29 (dd, J=8.7, 1.6 Hz, 1H), 6.90-6.78 (m, 4H), 5.60 (s, 2H), 4.80 (d, J=5.9 Hz, 2H), 3.98 (s, 3H). MS (M+H)+ found for C₂₅H₂₂N₈: 435.1.

Example 29

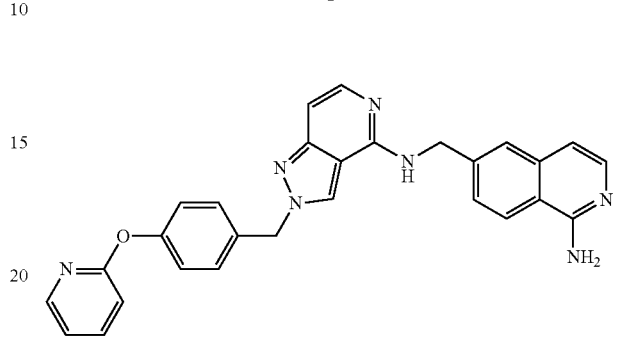

6-(((2-(4-(pyridin-2-yloxy)benzyl)-2H-pyrazolo[4,3-c]pyridin-4-yl)amino)methyl)isoquinolin-1-amine 6-(((2-(4-(pyridin-2-yloxy)benzyl)-2H-pyrazolo[4,3-c]pyridin-4-yl)amino)methyl)isoquinolin-1-amine was synthesized in a manner similar to Example 21 using (4-(pyridin-2-yloxy)phenyl)methanol to replace (1,2-dimethyl-1H-indol-5-yl)methanol. ¹H NMR (400 MHz, DMSO-d₆) δ 8.54 (d, J=0.9 Hz, 1H), 8.16-8.06 (m, 3H), 7.99 (s, 1H), 7.62-7.56 (m, 1H), 7.87-7.79 (m, 1H), 7.75-7.67 (m, 1H), 7.61-7.56 (m, 1H), 7.52 (d, J=6.4 Hz, 1H), 7.45 (dd, J=8.6, 1.8 Hz, 1H), 7.40-7.33 (m, 2H), 7.15-7.07 (m, 2H), 7.07-6.95 (m, 1H), 6.89-6.79 (m, 2H), 6.66 (dd, J=6.4, 0.9 Hz, 1H), 5.59 (s, 2H), 4.79 (d, J=5.2 Hz, 2H). MS (M+H)+ found for C₂₈H₂₃N₇O: 474.1.

Example 30

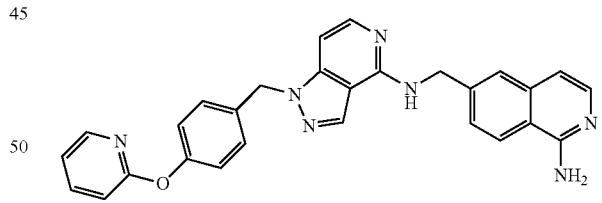

6-(((1-(4-(pyridin-2-yloxy)benzyl)-1H-pyrazolo[4,3-c]pyridin-4-yl)amino)methyl)isoquinolin-1-amine 6-(((1-(4-(pyridin-2-yloxy)benzyl)-1H-pyrazolo[4,3-c]pyridin-4-yl)amino)methyl)isoquinolin-1-amine was synthesized in a manner similar to Example 22 using (4-(pyridin-2-yloxy)phenyl)methanol to replace (1,2-dimethyl-1H-indol-5-yl)methanol. ¹H NMR (400 MHz, DMSO-d₆) δ 8.27 (d, J=0.9 Hz, 1H), 8.13 (d, J=12.1 Hz, 1H), 8.10-8.07 (m, 1H), 7.97 (t, J=5.9 Hz, 1H), 7.81 (ddd, J=8.3, 7.2, 2.0 Hz, 1H), 7.71 (dd, J=6.0, 0.9 Hz, 2H), 7.61-7.56 (m, 1H), 7.44 (dd, J=8.6, 1.7 Hz, 1H), 7.30-7.21 (m, 2H), 7.08 (ddd, J=7.2, 4.9, 0.9 Hz, 1H), 7.06-7.01 (m, 2H), 6.98 (dt, J=8.3, 0.9 Hz, 1H), 6.89 (dd, J=6.2, 0.9 Hz, 1H), 6.82 (dd, J=6.0, 0.8 Hz, 1H), 6.71 (s, 2H), 5.52 (s, 2H), 4.81 (d, J=5.9 Hz, 2H). MS (M+H)+ found for $C_{28}H_{23}N_7O$: 474.1.

Example 31

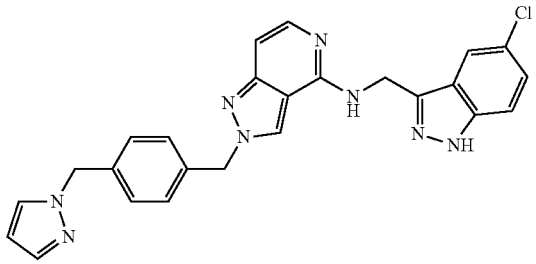 [SMILES: Clc1ccc2[nH]nc(CNc3nccc4nn(Cc5ccc(Cn6cccn6)cc5)cc34)c2c1]

2-(4-((1H-pyrazol-1-yl)methyl)benzyl)-N-((5-chloro-1H-indazol-3-yl)methyl)-2H-pyrazolo[4,3-c]pyridin-4-amine 2-(4-((1H-pyrazol-1-yl)methyl)benzyl)-N-((5-chloro-1H-indazol-3-yl)methyl)-2H-pyrazolo[4,3-c]pyridin-4-amine was synthesized in a manner similar to Example 12 using (5-chloro-1H-indazol-3-yl)methanamine (Example 2) to replace 6-(aminomethyl)isoquinolin-1-amine. $^1$H NMR (400 MHz, Methanol-$d_4$) δ 8.57 (s, 1H), 8.44 (d, J=5.6 Hz, 1H), 7.85-7.78 (m, 1H), 7.67 (dd, J=2.3, 0.7 Hz, 1H), 7.55-7.49 (m, 2H), 7.48 (dd, J=2.0, 0.7 Hz, 1H), 7.41-7.33 (m, 3H), 7.34-7.24 (m, 2H), 7.24-7.12 (m, 2H), 6.94 (dd, J=7.1, 0.9 Hz, 1H), 6.30 (dd, J=2.0 Hz, 1H), 5.57 (s, 2H), 5.33 (s, 2H), 5.05 (s, 2H). MS (M+H)+ found for $C_{25}H_{21}ClN_8$: 469.0, 471.1.

Example 32

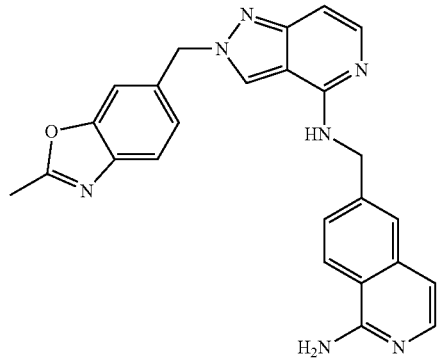 [SMILES: Cc1nc2ccc(Cn3cc4c(NCc5ccc6c(N)nccc6c5)nccc4n3)cc2o1]

6-(((2-((2-methylbenzo[d]oxazol-6-yl)methyl)-2H-pyrazolo[4,3-c]pyridin-4-yl)amino)methyl)isoquinolin-1-amine 6-(((2-((2-methylbenzo[d]oxazol-6-yl)methyl)-2H-pyrazolo[4,3-c]pyridin-4-yl)amino)methyl)isoquinolin-1-amine was synthesized in a manner similar to Example 21 using (2-methylbenzo[d]oxazol-6-yl)methanol to replace (1,2-dimethyl-1H-indol-5-yl)methanol. $^1$H NMR (400 MHz, Methanol-$d_4$) δ 8.61 (d, J=0.9 Hz, 1H), 8.35 (s, 1H), 8.30 (dt, J=8.7, 0.7 Hz, 1H), 7.81 (d, J=1.5 Hz, 1H), 7.70 (dd, J=8.6, 1.8 Hz, 1H), 7.63 (t, J=0.7 Hz, 2H), 7.61-7.55 (m, 1H), 7.47 (d, J=6.9 Hz, 1H), 7.39 (dd, J=8.1, 1.6 Hz, 1H), 7.12-7.05 (m, 1H), 6.91 (dd, J=6.9, 0.9 Hz, 1H), 5.74 (s, 2H), 4.94 (s, 2H), 2.63 (s, 3H). MS (M+H)+ found for $C_{25}H_{21}N_7O$: 436.1.

Example 33

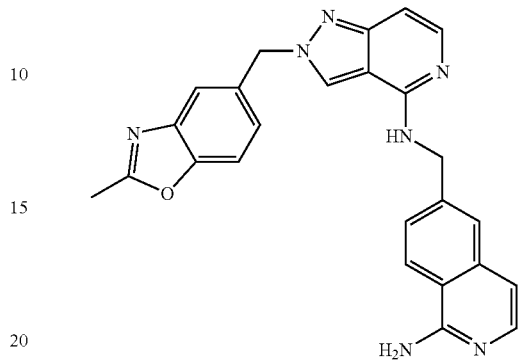

6-(((2-((2-methylbenzo[d]oxazol-5-yl)methyl)-2H-pyrazolo[4,3-c]pyridin-4-yl)amino)methyl)isoquinolin-1-amine 6-(((2-((2-methylbenzo[d]oxazol-5-yl)methyl)-2H-pyrazolo[4,3-c]pyridin-4-yl)amino)methyl)isoquinolin-1-amine was synthesized in a manner similar to Example 21 using (2-methylbenzo[d]oxazol-5-yl)methanol to replace (1,2-dimethyl-1H-indol-5-yl)methanol. $^1$H NMR (400 MHz, Methanol-$d_4$) δ 8.67 (d, J=0.9 Hz, 1H), 8.34 (d, J=8.6 Hz, 1H), 8.28 (s, 1H), 7.85 (d, J=1.6 Hz, 1H), 7.73 (dd, J=8.6, 1.8 Hz, 1H), 7.65 (dd, J=1.8, 0.7 Hz, 2H), 7.62-7.53 (m, 2H), 7.48-7.37 (m, 1H), 7.17-7.04 (m, 1H), 6.96 (dd, J=7.0, 0.9 Hz, 1H), 5.74 (s, 2H), 4.96 (s, 2H), 2.63 (s, 3H). MS (M+H)+ found for $C_{25}H_{21}N_7O$: 436.1.

Example 34

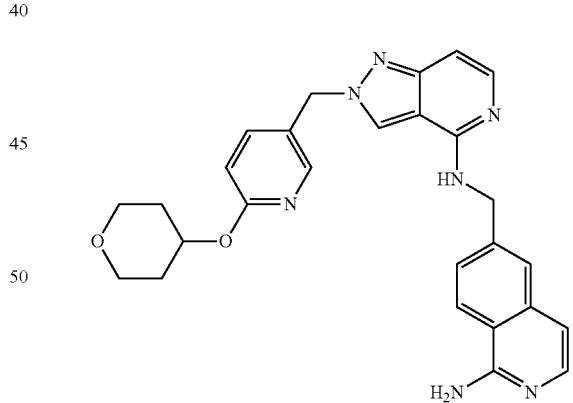

6-(((2-((6-((tetrahydro-2H-pyran-4-yl)oxy)pyridin-3-yl)methyl)-2H-pyrazolo[4,3-c]pyridin-4-yl)amino)methyl)isoquinolin-1-amine 6-(((2-((6-((tetrahydro-2H-pyran-4-yl)oxy)pyridin-3-yl)methyl)-2H-pyrazolo[4,3-c]pyridin-4-yl)amino)methyl)isoquinolin-1-amine was synthesized in a manner similar to Example 21 using (6-((tetrahydro-2H-pyran-4-yl)oxy)pyridin-3-yl)methanol to replace (1,2-dimethyl-1H-indol-5-yl)methanol. $^1$H NMR (400 MHz, Methanol-$d_4$) δ 8.52-8.47 (m, 1H), 8.23-8.16 (m, 2H), 7.74 (s, 1H), 7.69 (dd, J=8.6, 2.5

Hz, 1H), 7.66-7.59 (m, 2H), 7.51 (d, J=6.7 Hz, 1H), 7.02 (dd, J=6.5, 0.8 Hz, 1H), 6.82 (dd, J=6.7, 0.9 Hz, 1H), 6.78 (dd, J=8.6, 0.7 Hz, 1H), 5.54 (s, 2H), 5.20 (tt, J=8.4, 4.0 Hz, 1H), 4.90 (s, 2H), 4.57 (s, 1H), 3.93 (dt, J=11.7, 4.6 Hz, 2H), 3.59 (ddd, J=11.9, 9.0, 3.0 Hz, 2H), 2.04 (ddd, J=13.4, 4.9, 2.9 Hz, 2H), 1.72 (dtd, J=13.0, 8.8, 4.0 Hz, 2H). MS (M+H)+ found for $C_{27}H_{27}N_7O_2$: 482.1.

Example 35

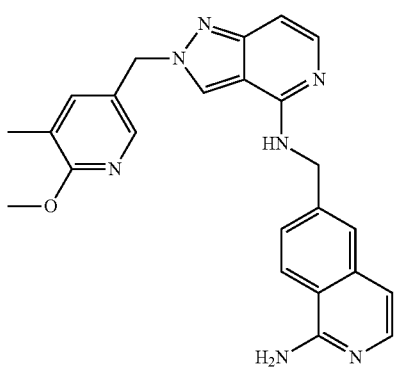 [SMILES: COc1ncc(Cn2cc3c(NCc4ccc5c(N)nccc5c4)nccc3n2)cc1C]

6-(((2-((6-methoxy-5-methylpyridin-3-yl)methyl)-2H-pyrazolo[4,3-c]pyridin-4-yl)amino)methyl)iso-quinolin-1-amine 6-(((2-((6-methoxy-5-methylpyridin-3-yl)methyl)-2H-pyrazolo[4,3-c]pyridin-4-yl)amino)methyl)isoquinolin-1-amine was synthesized in a manner similar to Example 21 using (6-methoxypyridin-3-yl)methanol to replace (1,2-dimethyl-1H-indol-5-yl)methanol. $^1$H NMR (400 MHz, Methanol-$d_4$) δ 8.49 (d, J=0.9 Hz, 2H), 8.22 (dd, J=8.6, 0.8 Hz, 1H), 8.05 (dd, J=2.4, 0.9 Hz, 1H), 7.76 (d, J=1.6 Hz, 1H), 7.72-7.58 (m, 2H), 7.55-7.47 (m, 2H), 7.09-7.00 (m, 1H), 6.84 (dd, J=6.8, 0.9 Hz, 1H), 5.51 (s, 3H), 4.90 (s, 2H), 3.93 (s, 3H), 2.15 (t, J=0.8 Hz, 3H). MS (M+H)+ found for $C_{24}H_{23}N_7O$: 426.1.

Example 36

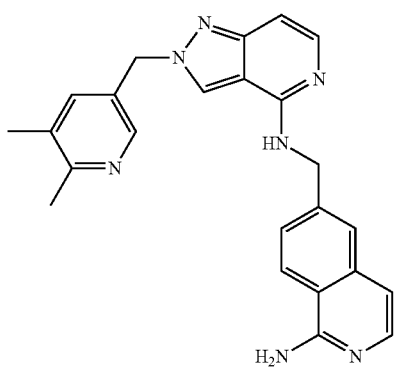 [SMILES: Cc1cc(Cn2cc3c(NCc4ccc5c(N)nccc5c4)nccc3n2)cnc1C]

6-(((2-((5,6-dimethylpyridin-3-yl)methyl)-2H-pyrazolo[4,3-c]pyridin-4-yl)amino)methyl)isoquinolin-1-amine 6-(((2-((5,6-dimethylpyridin-3-yl)methyl)-2H-pyrazolo[4,3-c]pyridin-4-yl)amino)methyl)isoquinolin-1-amine was synthesized in a manner similar to Example 21 using (5,6-dimethylpyridin-3-yl)methanol to replace (1,2-dimethyl-1H-indol-5-yl)methanol. $^1$H NMR (400 MHz, Methanol-$d_4$) δ 8.57 (d, J=0.9 Hz, 1H), 8.39 (s, 1H), 8.31-8.23 (m, 2H), 7.80 (d, J=1.6 Hz, 1H), 7.68 (dd, J=8.6, 1.8 Hz, 1H), 7.63-7.56 (m, 2H), 7.49 (d, J=6.8 Hz, 1H), 7.11-7.04 (m, 1H), 6.86 (dd, J=6.8, 0.9 Hz, 1H), 5.61 (s, 2H), 4.93 (s, 2H), 2.48 (s, 3H), 2.30 (q, J=0.6 Hz, 3H). MS (M+H)+ found for $C_{24}H_{23}N_7$: 410.1.

Example 38

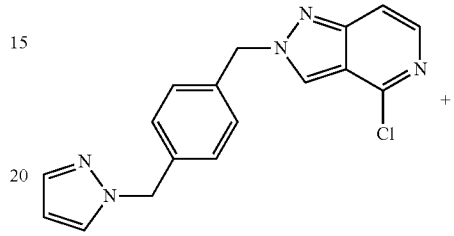

Example 10

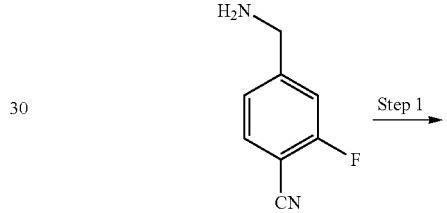

Step 1

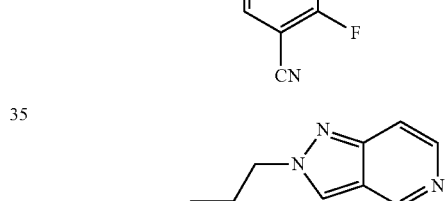

Step 2

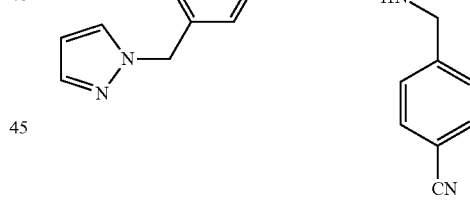

Example 37

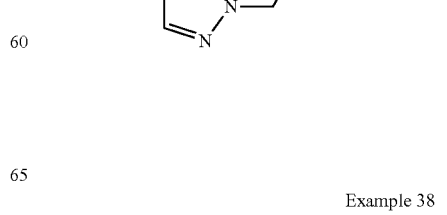

Example 38

Example 37

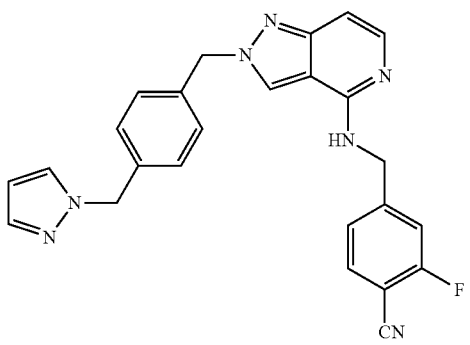 [SMILES: N#Cc1ccc(CNc2nccc3nn(Cc4ccc(Cn5cccn5)cc4)cc23)cc1F]

Step 1. 4-(((2-(4-((1H-pyrazol-1-yl)methyl)benzyl)-2H-pyrazolo[4,3-c]pyridin-4-yl)amino)methyl)-2-fluorobenzonitrile To a suspension of 2-(4-((1H-pyrazol-1-yl)methyl)benzyl)-4-chloro-2H-pyrazolo[4,3-c]pyridine (50.00 mg; 0.15 mmol; 1.00 eq.) in n-BuOH (0.6 mL) was added 4-(aminomethyl)-2-fluorobenzonitrile (69.56 mg; 0.46 mmol; 3.00 eq.) and the mixture was heated at 200° C. in a microwave synthesizer for 25 min. The mixture was cooled and diluted with ACN/water, and purified by prep HPLC to give 4-(((2-(4-((1H-pyrazol-1-yl)methyl)benzyl)-2H-pyrazolo[4,3-c]pyridin-4-yl)amino)methyl)-2-fluorobenzonitrile (33 mg).

Example 38

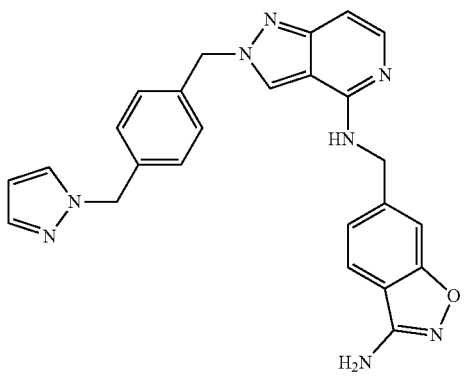 [SMILES: Nc1noc2cc(CNc3nccc4nn(Cc5ccc(Cn6cccn6)cc5)cc34)ccc12]

Step 2. 6-(((2-(4-((1H-pyrazol-1-yl)methyl)benzyl)-2H-pyrazolo[4,3-c]pyridin-4-yl)amino)methyl)benzo[d]isoxazol-3-amine To a suspension of N-hydroxyacetamide (14.16 mg; 0.19 mmol; 2.50 eq.) in DMF (0.5 mL) was added potassium carbonate (41.64 mg; 0.30 mmol; 4.0 eq.) and 1 drop of water. The mixture was stirred for 10 min. A solution of 4-(((2-(4-((1H-pyrazol-1-yl)methyl)benzyl)-2H-pyrazolo[4,3-c]pyridin-4-yl)amino)methyl)-2-fluorobenzonitrile (33.00 mg; 0.08 mmol; 1.00 eq.)(Example 37) in DMF (0.5 mL) was added and the mixture was heated at 70° C. for 3 h, cooled and diluted with water and ACN, purified by prep HPLC to give 6-(((2-(4-((1H-pyrazol-1-yl)methyl)benzyl)-2H-pyrazolo[4,3-c]pyridin-4-yl)amino)methyl)benzo[d]isoxazol-3-amine (19 mg). $^1$H NMR (400 MHz, Methanol-$d_4$) δ 8.47 (d, J=0.9 Hz, 1H), 7.71 (dd, J=8.2, 0.7 Hz, 1H), 7.68 (dd, J=2.3, 0.7 Hz, 1H), 7.53-7.46 (m, 2H), 7.38 (dq, J=1.5, 0.7 Hz, 1H), 7.36-7.30 (m, 2H), 7.30-7.24 (m, 1H), 7.24-7.17 (m, 2H), 6.84 (dd, J=6.8, 0.9 Hz, 1H), 6.31 (dd, J=2.0 Hz, 1H), 5.57 (s, 2H), 5.34 (s, 2H), 4.83 (s, 2H). MS (M+H)+ found for $C_{25}H_{22}N_8O$: 451.1.

Example 39

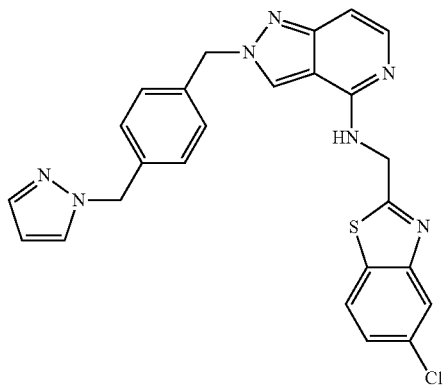 [SMILES: Clc1ccc2sc(CNc3nccc4nn(Cc5ccc(Cn6cccn6)cc5)cc34)nc2c1]

2-(4-((1H-pyrazol-1-yl)methyl)benzyl)-N-((5-chlorobenzo[d]thiazol-2-yl)methyl)-2H-pyrazolo[4,3-c]pyridin-4-amine 2-(4-((1H-pyrazol-1-yl)methyl)benzyl)-N-((5-chlorobenzo[d]thiazol-2-yl)methyl)-2H-pyrazolo[4,3-c]pyridin-4-amine was synthesized in a manner similar to Example 12 using (5-chlorobenzo[d]thiazol-2-yl)methanamine to replace 6-(aminomethyl)isoquinolin-1-amine. $^1$H NMR (400 MHz, Methanol-$d_4$) δ 8.44 (d, J=0.9 Hz, 1H), 7.92 (dd, J=2.1, 0.5 Hz, 1H), 7.88 (dd, J=8.6, 0.5 Hz, 1H), 7.68 (dd, J=2.3, 0.7 Hz, 1H), 7.57 (d, J=6.6 Hz, 1H), 7.50 (dd, J=2.0, 0.7 Hz, 1H), 7.39 (dd, J=8.6, 2.0 Hz, 1H), 7.36-7.30 (m, 2H), 7.26-7.18 (m, 2H), 6.85 (dd, J=6.6, 0.9 Hz, 1H), 6.31 (dd, J=2.0 Hz, 1H), 5.59 (s, 2H), 5.35 (s, 2H), 5.12 (s, 2H). MS (M+H)+ found for $C_{25}H_{20}ClN_7S$: 486.1.

Example 40

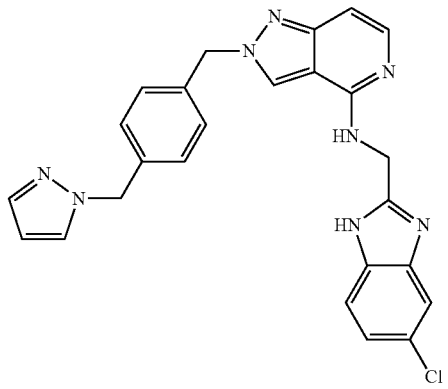 [SMILES: Clc1ccc2[nH]c(CNc3nccc4nn(Cc5ccc(Cn6cccn6)cc5)cc34)nc2c1]

2-(4-((1H-pyrazol-1-yl)methyl)benzyl)-N-((5-chloro-1H-benzo[d]imidazol-2-yl)methyl)-2H-pyrazolo[4,3-c]pyridin-4-amine 2-(4-((1H-pyrazol-1-yl)methyl)benzyl)-N-((5-chloro-1H-benzo[d]imidazol-2-yl)methyl)-2H-pyrazolo[4,3-c]pyridin- 4-amine was synthesized similar to Example 12 using (5-chloro-1H-benzo[d]imidazol-2-yl)methanamine to replace 6-(aminomethyl)isoquinolin-1-amine. $^1$H NMR (400 MHz, Methanol-d$_4$) δ 8.50-8.40 (m, 1H), 8.37 (s, 1H), 7.70-7.61 (m, 1H), 7.54 (d, J=6.8 Hz, 1H), 7.50 (dd, J=2.0, 0.6 Hz, 1H), 7.49 (dd, J=2.0, 0.7 Hz, 1H), 7.46 (dd, J=8.6, 0.6 Hz, 1H), 7.35-7.26 (m, 2H), 7.27-7.10 (m, 3H), 6.87 (dd, J=6.8, 0.9 Hz, 1H), 6.34-6.27 (m, 1H), 5.58 (s, 2H), 5.34 (s, 2H), 4.97 (s, 2H).MS (M+H)+ found for C$_{25}$H$_{21}$ClN$_8$: 469.1.

Example 41

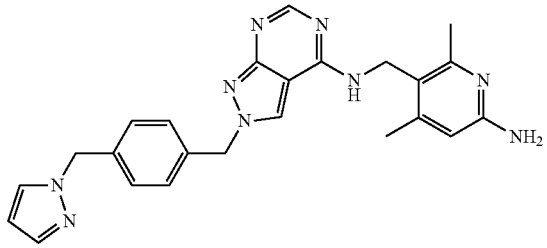 [SMILES: Cc1cc(N)nc(C)c1CNc1ncnc2nn(Cc3ccc(Cn4cccn4)cc3)cc12]

2-(4-((1H-pyrazol-1-yl)methyl)benzyl)-N-((6-amino-2,4-dimethylpyridin-3-yl)methyl)-2H-pyrazolo[3,4-d]pyrimidin-4-amine Prepared as in Example 335 except substituting (4-((1H-pyrazol-1-yl)methyl)phenyl)methanol for 1-{[4-(hydroxymethyl)phenyl]methyl}-5-(trifluoromethyl)-1,2-dihydropyridin-2-one gave 2-(4-((1H-pyrazol-1-yl)methyl)benzyl)-N-((6-amino-2,4-dimethylpyridin-3-yl)methyl)-2H-pyrazolo[3,4-d]pyrimidin-4-amine as a white solid. $^1$H NMR (400 MHz, CD$_3$OD) δ 8.32 (s, 1H), 8.22 (s, 1H), 7.68 (d, J=2.3 Hz, 1H), 7.50 (d, J=2.0 Hz, 1H), 7.36-7.30 (m, 2H), 7.24-7.18 (m, 2H), 6.68 (s, 1H), 6.32 (t, J=2.2 Hz, 1H), 5.52 (s, 2H), 5.34 (s, 2H), 4.69 (s, 2H), 2.58 (s, 3H), 2.46-2.42 (m, 3H). MS (M+H)$^+$ found for C$_{24}$H$_{25}$N$_9$: 440.2.

Example 42

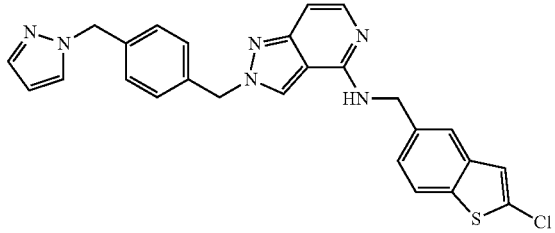 [SMILES: Clc1cc2cc(CNc3nccc4nn(Cc5ccc(Cn6cccn6)cc5)cc34)ccc2s1]

2-(4-((1H-pyrazol-1-yl)methyl)benzyl)-N-((2-chlorobenzo[b]thiophen-5-yl)methyl)-2H-pyrazolo[4,3-c]pyridin-4-amine Into a 30-mL bottle was placed 1-[[4-([4-chloro-2H-pyrazolo[4,3-c]pyridin-2-yl]methyl) phenyl]methyl]-1H-pyrazole (113 mg, 0.35 mmol, 1.00 equiv) (Example 10), (2-chloro-1-benzothiophen-5-yl)methanamine (103 mg, 0.52 mmol, 1.50 equiv), 1-ethoxy-2-(2-ethoxyethoxyl)eth-ane (12 mL), dichlorozinc (714 mg, 5.24 mmol, 10.00 equiv) and diisopropanyl ethyl amine (1.35 g, 10.45 mmol, 20.00 equiv). The resulting solution was stirred 4 h at 120° C. The crude product was purified by reverse phase medium pressure column chromatography with the following conditions (IntelFlash-1): column, silica gel; mobile phase, dichloromethane/ ethyl acetate/ methanol/ 20% ammonia aqueous solution (ratio 4:4:1:0.2) within 30 min; detector UV wavelength: 254 nm. The crude product was purified by Prep-HPLC with the following conditions: column, Bridge C18; mobile phase, acetonitrile/water (0.05% NH4OH, 10 mM NH4HCO3) gradient from 56% to 61% within 5 min, flow rate: 20 mL/min; detector UV wavelength: 254 nm. This resulted in 29.7 mg (18%) of N-[(2-chloro-1-benzothiophen-5-yl)methyl]-2-[[4-(1H-pyrazol-1-ylmethyl)phenyl]methyl]-2H-pyrazolo[4,3-c]pyridin-4-amine as a white solid. $^1$H NMR (300 MHz, CD$_3$OD): δ 8.37 (s, 1H), 7.75-7.68 (m, 3H), 7.60 (br, 1H), 7.50 (s, 1H), 7.40 (d, J=8.4 Hz, 1H), 7.37 (br, 2H), 7.32-7.21 (m, 3H), 6.75 (d, J=7.5 Hz, 1H), 5.62 (s, 2H), 5.35 (s, 2H), 4.85 (s, 2H). MS (ESI) m/z found for C$_{26}$H$_{21}$ClN$_6$S: 485 [M+H]$^+$.

Example 43

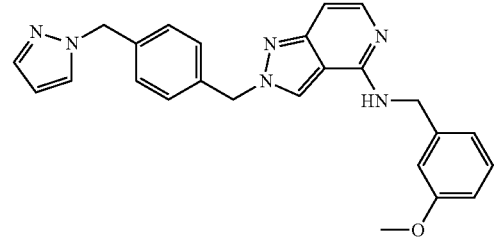 [SMILES: COc1cccc(CNc2nccc3nn(Cc4ccc(Cn5cccn5)cc4)cc23)c1]

N-[(3-methoxyphenyl)methyl]-2-{[4-(1H-pyrazol-1-ylmethyl)phenyl]methyl}-2H-pyrazolo[3,4-d]pyrimidin-4-amine Into a 8-mL sealed tube, was placed a solution of 2-(4-((1H-pyrazol-1-yl)methyl)benzyl)-4-chloro-2H-pyrazolo[3,4-d]pyrimidine (400 mg, 1.00 equiv, crude)(Example 23) in 2-ethoxyethyl ether (5 mL), to which were added (3-methoxyphenyl)methanamine (338 mg, 2.46 mmol, 2.00 equiv) and zinc dichloride (1.68 g, 12.32 mmol, 10.00 equiv) sequentially. The resulting solution was stirred for 3 h at 120° C. The reaction mixture was diluted with 8 mL of DMSO. The residue was purified by silica gel column chromatography eluted with ethyl acetate/petroleum ether/ methanol (1:5:0 to 0:0:1). The crude product was further purified by Prep-HPLC with the following conditions: column, Waters X-bridge RP18, 19×150 mm, 5 um; Mobile phase, CH$_3$CN/H$_2$O (0.05% NH$_3$.H$_2$O) gradient from 30% to 41% in 5 min; Flow rate: 20 mL/min; Detector UV length: 254 nm. This resulted in 38.8 mg (7%) of 2-(4-((1H-pyrazol-1-yl)methyl)benzyl)-N-(3-methoxybenzyl)-2H-pyrazolo[3,4-d]pyrimidin-4-amine as a white solid. $^1$H NMR (300 MHz, DMSO-d$_6$): δ 8.55 (m, 1H), 8.30 (s, 1H), 8.13 (s, 1H), 7.73 (d, J=1.8 Hz, 1H), 7.37 (d, J=1.8 Hz, 1H), 7.25-7.13 (m, 5H), 6.84-6.74 (m, 3H), 6.19 (t, J=2.1 Hz, 1H), 5.46 (s, 2H), 5.25 (s, 2H), 4.60 (d, J=6.0 Hz, 2H), 3.65 (s, 3H). MS (ESI) m/z found for C$_{24}$H$_{23}$N$_7$O: 426 [M+H]$^+$.

Example 44

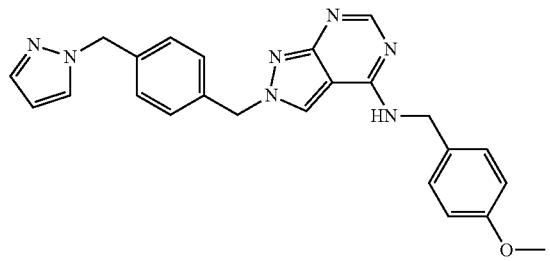 [SMILES: COc1ccc(CNc2ncnc3nn(Cc4ccc(Cn5cccn5)cc4)cc23)cc1]

N-[(4-methoxyphenyl)methyl]-2-{[4-(1H-pyrazol-1-ylmethyl)phenyl]methyl}-2H-pyrazolo[3,4-d]pyrimidin-4-amine Into a 8-mL sealed tube, was placed a solution of 2-(4-((1H-pyrazol-1-yl)methyl)benzyl)-4-chloro-2H-pyrazolo[3,4-d]pyrimidine (400 mg, 1.00 equiv, crude)(Example 23) in 2-ethoxyethyl ether (5 mL), (4-methoxyphenyl)methanamine (338 mg, 2.46 mmol, 2.00 equiv), zinc dichloride (1.68 g, 12.32 mmol, 10.00 equiv). The resulting solution was stirred for 3 h at 120° C. The resulting solution was diluted with 8 mL of DMSO. The residue was purified by silica gel column chromatography eluted with ethyl acetate/petroleum ether/methanol (1:5:0 to 0:0:1). The crude product was further purified by Prep-HPLC with the following conditions: column, Waters X-bridge RP18, 19×150 mm, 5 um; mobile phase, CH$_3$CN/H$_2$O (0.05% NH$_3$.H$_2$O) gradient from 30% to 41% in 5 min; flow rate: 20 mL/min; detector UV wavelength: 254 nm. This resulted in 17.3 mg (3%) of 2-(4-((1H-pyrazol-1-yl)methyl)benzyl)-N-(4-methoxybenzyl)-2H-pyrazolo[3,4-d]pyrimidin-4-amine as a light yellow solid. $^1$H NMR (300 MHz, DMSO-d$_6$): δ 8.56 (m, 1H), 8.34 (s, 1H), 8.20 (s, 1H), 7.80 (d, J=1.8 Hz, 1H), 7.45 (d, J=1.8 Hz, 1H), 7.31-7.20 (m, 6H), 6.88 (d, J=8.7 Hz, 2H), 6.26 (t, J=2.1 Hz, 1H), 5.53 (s, 2H), 5.32 (s, 2H), 4.62 (d, J=5.7 Hz, 2H), 3.72 (s, 3H). MS (ESI) m/z found for C$_{24}$H$_{23}$N$_7$O: 426 [M+H]$^+$.

Example 47

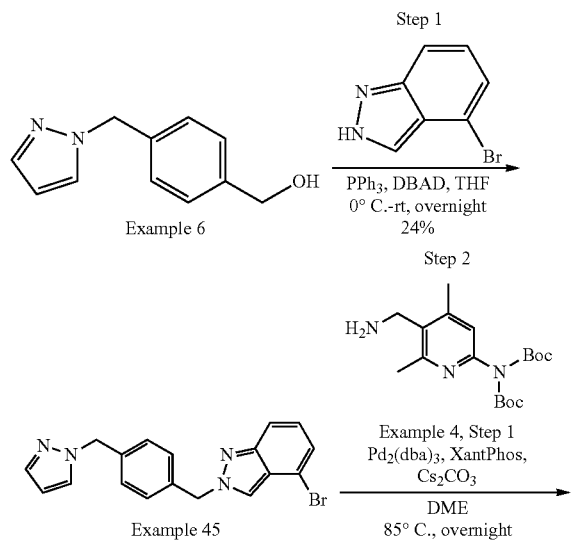

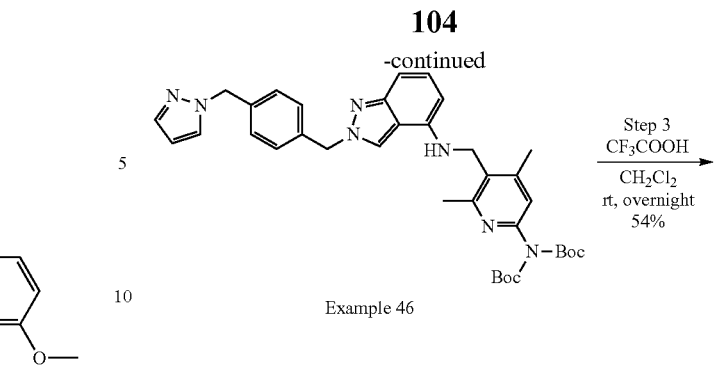

Example 46

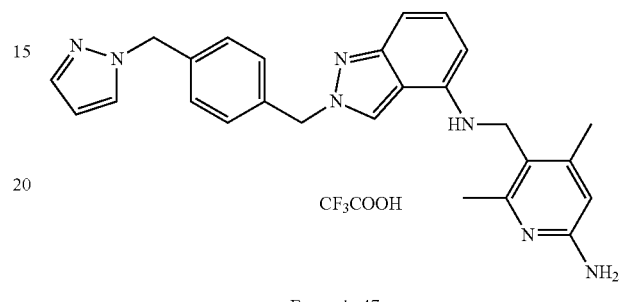

Example 47

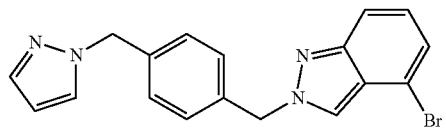 [SMILES: Brc1cccc2nn(Cc3ccc(Cn4cccn4)cc3)cc12]

Example 45

Step 1: 2-(4-((1H-pyrazol-1-yl)methyl)benzyl)-4-bromo-2H-indazole

Into a 250-mL 3-necked round-bottom flask purged and maintained with an inert atmosphere of nitrogen, were placed (4-((1H-pyrazol-1-yl)methyl)phenyl)methanol (600 mg, 3.19 mmol, 1.00 equiv)(Example 6), 4-bromo-2H-indazole (625 mg, 3.17 mmol, 1.00 equiv), tetrahydrofuran (40 mL), and triphenyl phosphine (1 g, 3.81 mmol, 1.20 equiv). To the stirred solution was added a solution of DBAD (881 mg, 3.83 mmol, 1.20 equiv) in THF (20 mL) dropwise at 0° C. The resulting solution was stirred overnight at room temperature. The reaction mixture was diluted with 100 mL of ethyl acetate and washed with 1×100 mL of brine. The resulting mixture was dried over anhydrous sodium sulfate and concentrated under vacuum. The crude product was purified by Prep-HPLC with the following conditions: column, Waters Atlantis T3, 5 um, 19×150 mm; Mobile phase: CH$_3$CN/H$_2$O (0.05% TFA) gradient from 65 to 70% in 7 min; flow rate: 20 mL/min. This resulted in 290 mg (24%) of 2-(4-((1H-pyrazol-1-yl)methyl)benzyl)-4-bromo-2H-indazole as white solid. $^1$H NMR (300 MHz, DMSO-d$_6$): δ 8.55 (s, 1H), 7.79 (d, J=1.8 Hz, 1H), 7.60 (d, J=8.7 Hz, 1H), 7.43 (s, 1H), 7.34-7.26 (m, 3H), 7.20-7.13 (m, 3H), 6.24 (t, J=1.8 Hz, 1H), 5.63 (s, 2H), 5.30 (s, 2H). MS (ESI) m/z found for C$_{18}$H$_{15}$BrN$_4$: 367 [M+H]$^+$.

Example 46

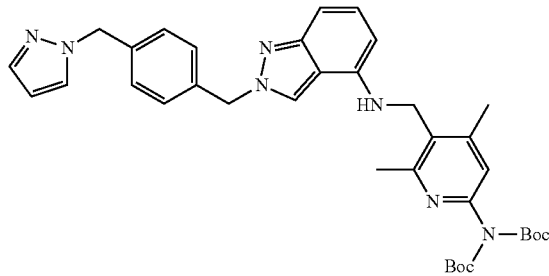 [SMILES: Cc1cc(N(C(=O)OC(C)(C)C)C(=O)OC(C)(C)C)nc(C)c1CNc1cccc2nn(Cc3ccc(Cn4cccn4)cc3)cc12]

Step 2. tert-butyl N-[(tert-butoxy)carbonyl]-N-(4,6-dimethyl-5-{[(2-{[4-(1H-pyrazol-1-ylmethyl)phenyl]methyl}-2H-indazol-4-yl)amino]methyl}pyridin-2-yl)carbamate Into a 50-mL 3-necked round-bottom flask purged and maintained with an inert atmosphere of nitrogen, were placed 2-(4-((1H-pyrazol-1-yl)methyl)benzyl)-4-bromo-2H-indazole (100 mg, 0.27 mmol, 1.00 equiv)(Example 45), tert-butyl N-(5-(aminomethyl)-4,6-dimethylpyridin-2-yl)-N-((tert-butoxy)carbonyl)carbamate (105 mg, 0.30 mmol, 1.10 equiv)(Example 4, Step 1), ethylene glycol dimethyl ether (10 mL), Cs$_2$CO$_3$ (264 mg, 0.81 mmol, 3.00 equiv), Pd$_2$(dba)$_3$.CHCl$_3$ (14 mg, 0.01 mmol, 0.05 equiv) and Xant-Phos (31 mg, 0.05 mmol, 0.20 equiv). The resulting solution was stirred overnight at 85° C. The reaction mixture was cooled to room temperature and was added 50 mL of water. The mixture was extracted with 3×20 mL of ethyl acetate and the organic layers were combined. The mixture was dried over anhydrous sodium sulfate and concentrated under vacuum. The crude product was purified by Prep-HPLC with the following conditions: column, Waters Atlantis T3, 5 um, 19×150 mm; mobile phase, CH$_3$CN/H$_2$O (0.05% TFA) gradient from 60% to 65% in 7 min; flow rate: 20 mL/min. This resulted in 30 mg (17%) of tert-butyl N-((tert-butoxy)carbonyl)-N-(4,6-dimethyl-5-(((2-((4-(1H-pyrazol-1-ylmethyl)phenyl)methyl)-2H-indazol-4-yl)amino)methyl)pyridin-2-yl)carbamate as white solid. MS (ESI) m/z found for C$_{36}$H$_{43}$N$_7$O$_4$: 638 [M+H]$^+$.

Example 47

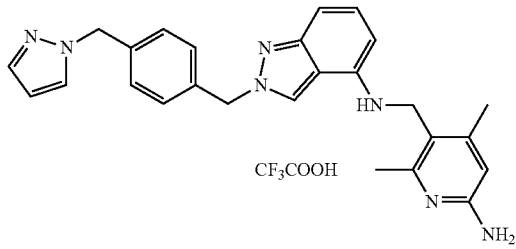 [SMILES: Cc1cc(N)nc(C)c1CNc1cccc2nn(Cc3ccc(Cn4cccn4)cc3)cc12 ; "CF3COOH"]

Step 3: N-[(6-amino-2,4-dimethylpyridin-3-yl)methyl]-2-{[4-(1H-pyrazol-1-ylmethyl)phenyl]methyl}-2H-indazol-4-amine Into a 50-mL round-bottom flask purged and maintained with an inert atmosphere of nitrogen, was placed a solution of tert-butyl N-((tert-butoxy)carbonyl)-N-(4,6-dimethyl-5-(((2-((4-(1H-pyrazol-1-ylmethyl)phenyl)methyl)-2H-indazol-4-yl)amino)methyl)pyridin-2-yl)carbamate (30 mg, 0.05 mmol, 1.00 equiv)(Example 46) in dichloromethane (10 mL). To which was added trifluoroacetic acid (1 mL) dropwise with stirring. The resulting solution was stirred overnight at room temperature. The resulting mixture was concentrated under vacuum. The crude product was purified by Prep-HPLC with the following conditions: column, Waters Atlantis T3, 19×150 mm, 5 um; mobile phase, CH$_3$CN/H$_2$O (0.05% TFA) gradient from 27% to 32% in 7 min; flow rate: 20 mL/min; Detector UV wavelength: 254 nm. This resulted in 14.5 mg (54%) of 2-(4-((1H-pyrazol-1-yl)methyl)benzyl)-N-((6-amino-2,4-dimethylpyridin-3-yl)methyl)-2H-indazol-4-amine (TFA salt) as white solid. $^1$H NMR (300 MHz, DMSO-d$_6$): δ 13.38 (br, 1H), 8.26 (s, 1H), 7.78 (s, 1H), 7.58 (br, 2H), 7.43 (s, 1H), 7.26 (d, J=8.1 Hz, 2H), 7.18 (d, J=8.4 Hz, 2H), 7.06-7.01 (m, 1H), 6.81 (d, J=8.7 Hz, 1H), 6.68 (s, 1H), 6.24 (t, J=2.1 Hz, 1H), 6.03 (d, J=7.2 Hz, 1H), 5.86 (m, 1H), 5.51 (s, 2H), 5.30 (s, 2H), 4.13 (d, J=3.0 Hz, 2H), 2.45 (s, 3H), 2.34 (s, 3H). MS (ESI) m/z found for C$_{26}$H$_{27}$N$_7$: 438 [M+H-TFA]$^+$.

Example 48

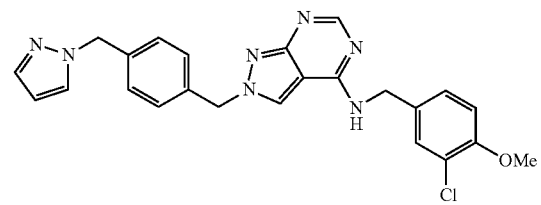 [SMILES: COc1ccc(CNc2ncnc3nn(Cc4ccc(Cn5cccn5)cc4)cc23)cc1Cl]

2-(4-((1H-pyrazol-1-yl)methyl)benzyl)-N-(3-chloro-4-methoxybenzyl)-2H-pyrazolo[3,4-d]pyrimidin-4-amine Into a 8-mL vial, was placed a solution of 1-((4-((4-chloro-2H-pyrazolo[3,4-d]pyrimidin-2-yl)methyl)phenyl)methyl)-1H-pyrazole (400 mg, crude, 1.23 mmol, 1.00 equiv)(Example 23) in 1-ethoxy-2-(2-ethoxyethoxyl)ethane (5 mL), zinc dichloride (1.68 mg, 12.30 mmol, 10.00 equiv) and (3-chloro-4-methoxyphenyl)methanamine (410 mg, 2.40 mmol, 2.00 equiv). The resulted solution was stirred for 3 h at 120° C. The reaction mixture was cooled to room temperature and diluted with 5 mL of DMSO. The residue was purified by silica gel column chromatography eluted with EA:PE:MeOH (1:5:0 to 0:0:1). The crude product was further purified by Prep-HPLC with the following conditions. Column: Waters X-bridge RP18, 19×150 mm, 5 um; mobile phase: H$_2$O (0.05% ammonia) and acetonitrile with a gradient of 39% to 44% acetonitrile in 5 min; flow rate: 20 mL/min; detector UV wavelength: 254 nm and 220 nm. This resulted in 31 mg (5%) of 2-(4-((1H-pyrazol-1-yl)methyl)benzyl)-N-(3-chloro-4-methoxybenzyl)-2H-pyrazolo[3,4-d]pyrimidin-4-amine as white solid. $^1$H NMR (300 MHz, DMSO-d$_6$): δ 8.61 (br, 1H), 8.34 (s, 1H), 8.20 (s, 1H), 7.79 (d, J=1.8 Hz, 1H), 7.44 (s, 1H), 7.39 (s, 1H), 7.31-7.19 (m, 5H), 7.09 (d, J=8.7 Hz, 1H), 6.25 (t, J=2.1 Hz, 1H), 5.53 (s, 2H), 5.32 (s, 2H), 4.62 (d, J=6.0 Hz, 2H), 3.82 (s, 3H). MS (ESI) m/z found for C$_{24}$H$_{22}$ClN$_7$O: 460 [M+H]$^+$.

Example 49

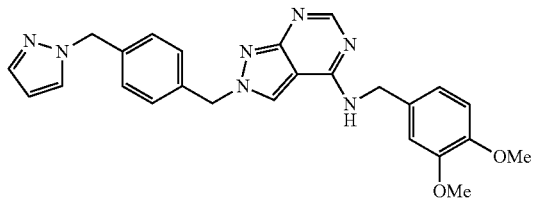 [SMILES: COc1ccc(CNc2ncnc3nn(Cc4ccc(Cn5cccn5)cc4)cc23)cc1OC]

2-(4-((1H-pyrazol-1-yl)methyl)benzyl)-N-(3,4-dimethoxybenzyl)-2H-pyrazolo[3,4-d]pyrimidin-4-amine Into a 8-mL round-bottom flask, were placed a solution of 2-(4-((1H-pyrazol-1-yl)methyl)benzyl)-4-chloro-2H-pyrazolo[3,4-d]pyrimidine (400 mg, 1.00 equiv)(Example 23) in 2-ethoxyethyl ether (5 mL), (3,4-dimethoxyphenyl)methanamine (417 mg, 2.49 mmol, 2.00 equiv) and zinc dichloride (1.68 g, 12.32 mmol, 10.00 equiv). The resulted solution was stirred for 3 h at 120° C. The reaction solution was diluted with 8 mL of DMSO. The residue was purified by silica gel column chromatography eluted with ethyl acetate/petroleum ether/methanol (1:5:0-0:0:1). The crude product was further purified by Prep-HPLC with the following conditions: column, Waters X-bridge RP18, 19×150 mm, 5 um; mobile phase, $CH_3CN/H_2O$ (0.05% $NH_3.H_2O$) gradient from 31% to 36% in 5.5 min; flow rate: 20 mL/min; Detector UV wave length, 254 nm, 220 nm. This resulted in 17 mg (3%) of 2-(4-((1H-pyrazol-1-yl)methyl)benzyl)-N-(3,4-dimethoxybenzyl)-2H-pyrazolo[3,4-d]pyrimidin-4-amine as white solid. $^1$H NMR (300 MHz, DMSO-$d_6$): δ 8.54 (m, 1H), 8.35 (s, 1H), 8.21 (s, 1H), 7.79 (d, J=1.8 Hz, 1H), 7.44 (d, J=1.2 Hz, 1H), 7.29 (d, J=8.1 Hz, 2H), 7.20 (d, J=8.1 Hz, 2H), 6.98 (s, 1H), 6.90-6.86 (m, 2H), 6.25 (t, J=2.1 Hz, 1H), 5.52 (s, 2H), 5.31 (s, 2H), 4.61 (d, J=5.7 Hz, 2H), 3.71 (s, 6H). MS (ESI) m/z found for $C_{25}H_{25}N_7O_2$: 456 [M+H]$^+$.

Example 50

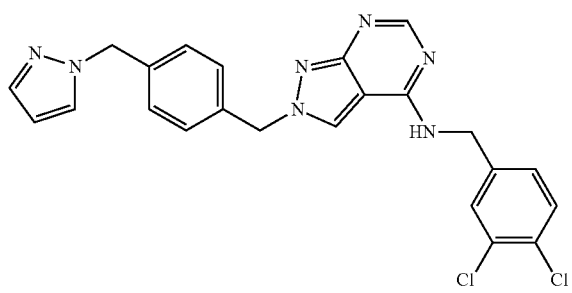 [SMILES: Clc1ccc(CNc2ncnc3nn(Cc4ccc(Cn5cccn5)cc4)cc23)cc1Cl]

2-(4-((1H-pyrazol-1-yl)methyl)benzyl)-N-(3,4-dichlorobenzyl)-2H-pyrazolo[3,4-d]pyrimidin-4-amine Into a 8-mL round-bottom flask, were placed a solution of 2-(4-((1H-pyrazol-1-yl)methyl)benzyl)-4-chloro-2H-pyrazolo[3,4-d]pyrimidine (400 mg, 1.00 equiv, crude) (Example 23) in 2-ethoxyethyl ether (5 mL), (3,4-dichlorophenyl)methanamine (437 mg, 2.48 mmol, 2.00 equiv) and zinc dichloride (1.68 g, 12.32 mmol, 10.00 equiv). The resulted solution was stirred for 3 h at 120° C. The reaction solution was diluted with 8 mL of DMSO. The residue was purified by silica gel column chromatography eluted with ethyl acetate /petroleum ether/methanol (1:5:0 to 0:0:1). The crude product was purified by Prep-HPLC with the following conditions: column, Waters X-bridge RP18, 19×150 mm, 5 um; mobile phase, $CH_3CN/H_2O$ (0.05% $NH_3.H_2O$) gradient from 45% to 50% in 5.5 min; flow rate: 20 mL/min; detector UV wavelength, 254 nm, 220 nm. This resulted in 43.7 mg (7%) of 2-(4-((1H-pyrazol-1-yl)methyl)benzyl)-N-(3,4-dichlorobenzyl)-2H-pyrazolo[3,4-d]pyrimidin-4-amine as white solid. $^1$H NMR (300 MHz, DMSO-$d_6$): δ 8.69 (m, 1H), 8.35 (s, 1H), 8.20 (s, 1H), 7.80 (d, J=1.8 Hz, 1H), 7.57 (d, J=8.1 Hz, 2H), 7.44 (d, J=1.5 Hz, 1H), 7.34-7.30 (m, 3H), 7.21 (d, J=8.1 Hz, 2H), 6.25 (t, J=2.1 Hz, 1H), 5.55 (s, 2H), 5.32 (s, 2H), 4.69 (d, J=5.7 Hz, 2H). MS (ESI) m/z found for $C_{23}H_{19}Cl_2N_7$: 464 [M+H]$^+$.

Example 51

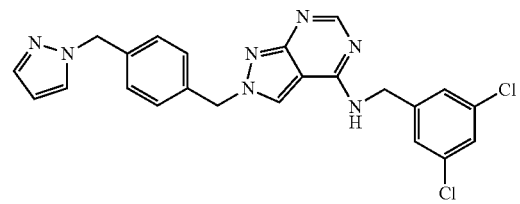 [SMILES: Clc1cc(Cl)cc(CNc2ncnc3nn(Cc4ccc(Cn5cccn5)cc4)cc23)c1]

2-(4-((1H-pyrazol-1-yl)methyl)benzyl)-N-(3,5-dichlorobenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (400 mg, 1.00 equiv)(Example 23) in 1-ethoxy-2-(2-ethoxyethoxy)ethane (5 mL), (3,5-dichlorophenyl)methanamine (422 mg, 2.40 mmol, 2.00 equiv) and zinc dichloride (1.68 g, 12.32 mmol, 10.00 equiv). The resulted solution was stirred for 3 h at 120° C. The reaction mixture was cooled to room temperature and diluted with 5 mL of DMSO. The residue was purified by silica gel column chromatography eluted with EA:PE:MeOH (1:5:0 to 0:0:1). The crude product was purified by Prep-HPLC with the following conditions. Column: Waters X-bridge RP18, 19×150 mm, 5 um; mobile phase: water (it contains 0.05% ammonia) and acetonitrile with a gradient 56% to 61% acetonitrile in 5 min; flow rate: 20 mL/min; detector UV wavelength: 254 nm and 220 nm. This resulted in 108.2 mg (19%) of 2-(4-((1H-pyrazol-1-yl)methyl)benzyl)-N-(3,5-dichlorobenzyl)-2H-pyrazolo[3,4-d]pyrimidin-4-amine as white solid. $^1$H NMR (300 MHz, DMSO-$d_6$): δ 8.70 (br, 1H), 8.36 (s, 1H), 8.21 (s, 1H), 7.80 (d, J=1.5 Hz, 1H), 7.49 (s, 1H), 7.44 (s, 1H), 7.39 (d, J=1.8 Hz, 2H), 7.32 (d, J=8.1 Hz, 2H), 7.21 (d, J=8.1 Hz, 2H), 6.25 (t, J=2.1 Hz, 1H), 5.55 (s, 2H), 5.32 (s, 2H), 4.71 (d, J=6.0 Hz, 2H). MS (ESI) m/z found for $C_{23}H_{19}Cl_2N_7$: 464 [M+H]$^+$.

Example 52

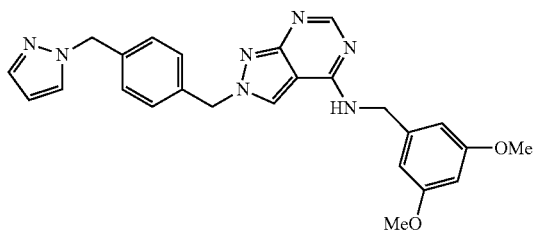 [SMILES: COc1cc(CNc2ncnc3nn(Cc4ccc(Cn5cccn5)cc4)cc23)cc(OC)c1]

2-(4-((1H-pyrazol-1-yl)methyl)benzyl)-N-(3,5-dimethoxybenzyl)-2H-pyrazolo[3,4-d]pyrimidin-4-amine Into a 8-mL round-bottom flask, were placed a solution of 2-(4-((1H-pyrazol-1-yl)methyl)benzyl)-4-chloro-2H-pyrazolo[3,4-d]pyrimidine (400 mg, 1.00 equiv)(Example 23) in 2-ethoxyethyl ether (5 mL), (3,5-dimethoxyphenyl)methanamine (418 mg, 2.50 mmol, 2.00 equiv) and zinc dichloride (1.68 g, 12.32 mmol, 10.00 equiv). The resulted solution was stirred for 3 h at 120° C. The reaction solution was diluted with 8 mL of DMSO. The residue was purified by silica gel column chromatography eluted with ethyl acetate/ petroleum ether/ methanol (1:5:0 to 0:0:1). The crude product was purified by Prep-HPLC with the following conditions: column, Waters X-bridge RP18, 19×150 mm, 5 um; mobile phase, $CH_3CN/H_2O$ (0.05% $NH_3.H_2O$) gradient from 36% to 41% in 5.5 min; flow rate: 20 mL/min; detector UV wavelength: 254 nm. This resulted in 34.8 mg (6%) of 2-(4-((1H-pyrazol-1-yl)methyl)benzyl)-N-(3,5-dimethoxybenzyl)-2H-pyrazolo[3,4-d]pyrimidin-4-amine as a white solid. $^1$H NMR (300 MHz, DMSO-$d_6$): δ 8.58 (m, 1H), 8.37 (s, 1H), 8.20 (s, 1H), 7.80 (d, J=2.4 Hz, 1H), 7.44 (s, 1H), 7.30 (d, J=8.1 Hz, 2H), 7.21 (d, J=8.1 Hz, 2H), 6.49 (s, 2H), 6.38 (t, J=2.1 Hz, 1H), 6.25 (t, J=2.1 Hz, 1H), 5.53 (s, 2H), 5.32 (s, 2H), 4.62 (d, J=5.7 Hz, 2H), 3.70 (s, 6H). MS (ESI) m/z found for $C_{25}H_{25}N_7O_2$: 456 [M+H]$^+$.

Example 53

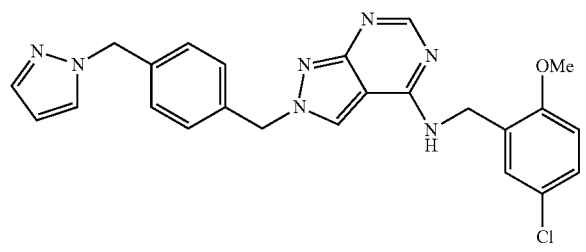 [SMILES: COc1ccc(Cl)cc1CNc1ncnc2nn(Cc3ccc(Cn4cccn4)cc3)cc12]

2-(4-((1H-pyrazol-1-yl)methyl)benzyl)-N-(5-chloro-2-methoxybenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (75 mg, 0.23 mmol, 1.00 equiv)(Example 23) in 1-ethoxy-2-(2-ethoxyethoxy)ethane (5 mL), (5-chloro-2-methoxyphenyl)methanamine (79 mg, 0.46 mmol, 2.00 equiv) and zinc dichloride (313 mg, 2.30 mmol, 10.00 equiv). The resulted solution was stirred for 3 h at 120° C. The reaction mixture was cooled to room temperature and diluted with 5 mL of DMSO. The residue was purified by silica gel column chromatography eluted with ethyl acetate/ petroleum ether/ methanol (1:5:0 to 0:0:1). The crude product was further purified by Prep-HPLC with the following conditions. Column: Waters X-bridge RP18, 19×150 mm, 5 um; mobile phase: $H_2O$ (0.05% ammonia) and acetonitrile with a gradient of 42% to 47% acetonitrile in 5.5 min; flow rate: 20 mL/min; detector UV wavelength: 254 nm and 220 nm. This resulted in 47.5 mg (45%) of 2-(4-((1H-pyrazol-1-yl)methyl)benzyl)-N-(5-chloro-2-methoxybenzyl)-2H-pyrazolo[3,4-d]pyrimidin-4-amine as white solid. $^1$H NMR (300 MHz, DMSO-$d_6$): δ 8.52 (br, 1H), 8.40 (s, 1H), 8.19 (s, 1H), 7.80 (d, J=1.8 Hz, 1H), 7.45 (s, 1H), 7.33-7.20 (m, 6H), 7.04 (d, J=8.7 Hz, 1H), 6.26 (s, 1H), 5.55 (s, 2H), 5.33 (s, 2H), 4.64 (d, J=5.4 Hz, 2H), 3.83 (s, 3H). MS (ESI) m/z found for $C_{24}H_{22}ClN_7O$: 460 [M+H]$^+$.

Example 54

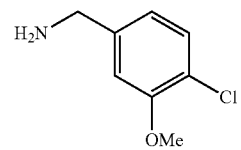 [SMILES: COc1cc(CN)ccc1Cl]

(4-chloro-3-methoxyphenyl)methanamine

Into a 250-mL 3-necked round-bottom flask purged and maintained with an inert atmosphere of nitrogen, was placed a solution of 4-chloro-3-methoxybenzonitrile (980 mg, 5.85 mmol, 1.00 equiv) in tetrahydrofuran (100 mL) with stirring at 0° C., to which was added 2M $BH_3$-$Me_2$S tetrahydrofuran solution (12 mL, 4.00 equiv) dropwise with stirring at 0° C. in 10 min. The resulted mixture was stirred for 5 min at 0° C. and then refluxed for 1 h. The reaction was quenched by the addition of 7 mL of methanol. The resulted mixture was concentrated under vacuum. The crude product was purified by Combi-Flash with the following conditions. Column: C18, 20-45 um, 100 Å, 120 g; mobile phase: water (it contains 0.05% ammonia and 10 mM $NH_4HCO_3$) and acetonitrile with a gradient of 35% to 65% acetonitrile in 10 min; flow rate: 60 mL/min; detector UV wavelength: 254 nm and 220 nm. This resulted in 100 mg (10%) of (4-chloro-3-methoxyphenyl)methanamine as colorless oil. MS (ESI) m/z found for $C_8H_{10}ClNO$: 172 [M+H]$^+$.

Example 55

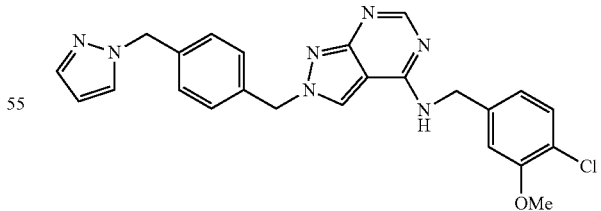

2-(4-((1H-pyrazol-1-yl)methyl)benzyl)-N-(4-chloro-3-methoxybenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]

pyrimidine (75 mg, 0.23 mmol, 1.00 equiv)(Example 23) in 1-ethoxy-2-(2-ethoxyethoxy)ethane (5 mL), (4-chloro-3-methoxyphenyl)methanamine (79 mg, 0.46 mmol, 2.00 equiv) and zinc dichloride (313 mg, 2.30 mmol, 10.00 equiv). The resulted solution was stirred for 3 h at 120° C. The reaction mixture was cooled to room temperature and diluted with 5 mL of DMSO. The residue was purified by silica gel column chromatography eluted with EA:PE:MeOH (1:5:0 to 0:0:1). The crude product was purified by Prep-HPLC with the following conditions. Column: Waters X-ridge RP18, 19×150 mm, 5 um; mobile phase: water (it contains 0.05% ammonia) and acetonitrile with a gradient of 40% to 45% in 5.5 min; flow rate: 20 mL/min; detector UV wavelength: 254 nm and 220 nm. This resulted in 21.3 mg (20%) of 2-(4-((1H-pyrazol-1-yl)methyl)benzyl)-N-(4-chloro-3-methoxybenzyl)-2H-pyrazolo[3,4-d]pyrimidin-4-amine as white solid. $^1$H NMR (300 MHz, DMSO-d$_6$): δ 8.65 (br, 1H), 8.37 (s, 1H), 8.21 (s, 1H), 7.80 (d, J=2.1 Hz, 1H), 7.45 (s, 1H), 7.36-7.16 (m, 6H), 6.91 (d, J=7.8 Hz, 1H), 6.26 (t, J=1.8 Hz, 1H), 5.54 (s, 2H), 5.32 (s, 2H), 4.69 (d, J=5.7 Hz, 2H), 3.82 (s, 3H). MS (ESI) m/z found for $C_{24}H_{22}ClN_7O$: 460 [M+H]$^+$.

Example 58

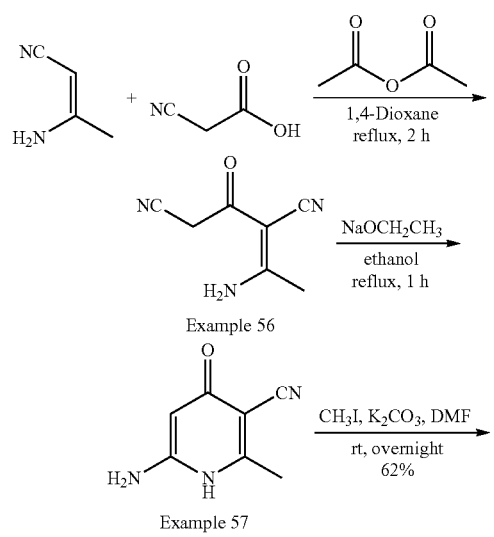

Example 56

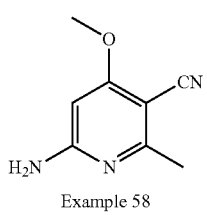

Example 57

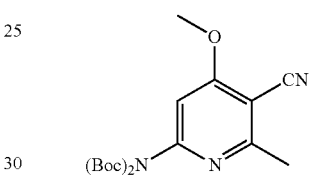

Example 58

6-amino-4-methoxy-2-methylpyridine-3-carbonitrile Into a 500-mL 3-necked round-bottom flask, was placed a mixture of 1,4-Dioxane (300 mL), acetyl acetate (44.77 g, 438.54 mmol, 1.20 equiv), 2-cyanoacetic acid (37.1 g, 436.16 mmol, 1.20 equiv) and (2Z)-3-aminobut-2-enenitrile (30 g, 365.39 mmol, 1.00 equiv). The resulted solution was heated to reflux for 2 h. The reaction mixture was cooled to room temperature with a water/ice bath. The solids were collected by filtration. This resulted in 23.2 g (crude) of (2Z)-2-(1-aminoethylidene)-3-oxopentanedinitrile as a yellow solid that was taken on directly to the next reaction.
Into a 500-mL round-bottom flask, was placed a mixture of ethanol (300 mL), (2Z)-2-(1-aminoethylidene)-3-oxopentanedinitrile (23.0 g, 154.21 mmol, 1.00 equiv)(Example 56) and ethoxysodium (11.0 g, 161.65 mmol, 1.05 equiv). The resulted mixture was heated to reflux for 1 h. The reaction mixture was cooled to room temperature with a water/ice bath. The resulted mixture was concentrated under vacuum. This resulted in 20.5 g (crude) of 6-amino-2-methyl-4-oxo-1,4-dihydropyridine-3-carbonitrile as a yellow solid that was used crude.
Into a 500-mL 3-necked round-bottom flask, was placed a mixture of K$_2$CO$_3$ (27.74 g, 199.26 mmol, 1.50 equiv) (Example 57) and 6-amino-2-methyl-4-oxo-1,4-dihydropyridine-3-carbonitrile (20 g, 134.09 mmol, 1.00 equiv) in N,N-dimethylformamide (200 mL) with stirring at 0° C., to which was added iodomethane (22.86 g, 161.06 mmol, 1.20 equiv) dropwise. The resulted solution was stirred overnight at room temperature. The reaction was then quenched by the addition of 500 mL of water/ice. The solids were collected by filtration. This resulted in 13.5 g (62%) of 6-amino-4-methoxy-2-methylpyridine-3-carbonitrile as a yellow solid. MS (ESI) m/z 164 [M+H]$^+$ Example 59

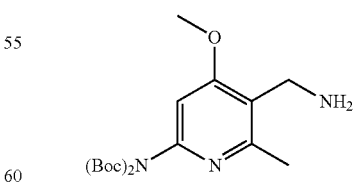

tert-butyl N-[(tert-butoxy)carbonyl]-N-(5-cyano-4-methoxy-6-methylpyridin-2-yl)carbamate Into a 500-mL round-bottom flask, was placed a mixture of 6-amino-4-methoxy-2-methylpyridine-3-carbonitrile (13.00 g, 79.67 mmol, 1.00 equiv)(Example 58), (Boc)$_2$O (51.68 g, 236.79 mmol, 3.00 equiv) and 4-dimethylaminopyridine (970 mg, 7.94 mmol, 0.10 equiv) in THF (250 mL). The resulted solution was stirred overnight at room temperature. The resulted mixture was concentrated under vacuum. The residue was purified by silica gel column eluted with ethyl acetate/petroleum ether (1:100-1:30). This resulted in 17.2 g (59%) of tert-butyl N-[(tert-butoxy)carbonyl]-N-(5-cyano-4-methoxy-6-methylpyridin-2-yl)carbamate as a white solid. $^1$H NMR (300 MHz, DMSO-d$_6$): δ 7.30 (s, 1H), 3.97 (s, 3H), 2.51 (s, 3H), 1.46 (s, 18H). MS (ESI) m/z 364 [M+H]$^+$ Example 60 tert-butyl N-[5-(aminomethyl)-4-methoxy-6-methylpyridin-2-yl]-N-[(tert-butoxy)carbonyl]carbamate Into a 500-mL round-bottom flask, was placed a mixture of methanol (200 mL), ammonia (20 mL), tert-butyl N-[(tert-butoxy)carbonyl]-N-(5-cyano-4-methoxy-6-methylpyridin-2-yl)carbamate (13.00 g, 35.77 mmol, 1.00 equiv) (Example 59) and Raney/Ni (5.0 g). The flask was purged with hydrogen for three times. Then it was stirred overnight at room temperature under hydrogen atmosphere (with a balloon). The solids were filtered out. The filtrate was concentrated under vacuum. This resulted in 13.1 g (crude) of tert-butyl N-[5-(aminomethyl)-4-methoxy-6-methylpyridin-2-yl]-N-[(tert-butoxy)carbonyl]carbamate as a white solid. $^1$H NMR (300 MHz, DMSO-d$_6$): δ 6.92 (s, 1H), 3.82 (s, 3H), 3.64 (s, 2H), 2.41 (s, 3H), 1.42 (s, 18H). MS (ESI) m/z 368 [M+H]$^+$ Example 61

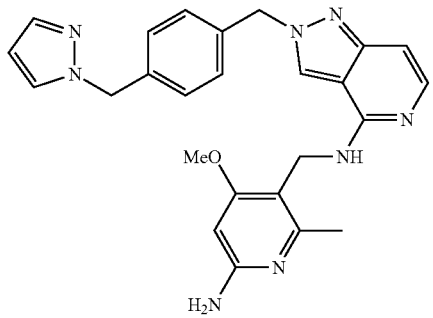 [SMILES: COc1cc(N)nc(C)c1CNc1nccc2nn(Cc3ccc(Cn4cccn4)cc3)cc12]

2-(4-((1H-pyrazol-1-yl)methyl)benzyl)-N-((6-amino-4-methoxy-2-methylpyridin-3-yl)methyl)-2H-pyrazolo[4,3-c]pyridin-4-amine Into a 8-mL vial, were placed 1-[[4-([4-chloro-2H-pyrazolo[4,3-c]pyridin-2-yl]methyl)phenyl]methyl]-1H-pyrazole (100 mg, 0.31 mmol, 1.00 equiv)(Example 23), (1-ethoxy-2-(2-ethoxyethoxyl)ethane (6 mL), tert-butyl N-[5-(aminomethyl)-4-methoxy-6-methylpyridin-2-yl]-N-[(tert-butoxy)carbonyl]carbamate (170 mg, 0.46 mmol, 1.50 equiv)(Example 60), and zinc dichloride (421 mg, 3.09 mmol, 10.00 equiv). The resulted solution was stirred for 3 h at 120° C. . The crude product was purified by flash column chromatography eluted with DCM/EA/MeOH/ concentrated ammonia aqueous solution (4:4:1:0.2). The crude product was further purified by Prep-HPLC with the following conditions: column, Waters XBridge RP18 19*150 mm; mobile phase, CH3CN/water (0.05% NH$_4$OH, 10 mM NH$_4$HCO$_3$) gradient from 31% to 36% with a 25-min run time, flow rate: 20 mL/min; detector UV wavelength: 254 nm. This resulted in 22.7 mg (16%) of 4-methoxy-6-methyl-5-[[(2-[[4-(1H-pyrazol-1-ylmethyl)phenyl]methyl]-2H-pyrazolo[4,3-c]pyridin-4-yl)amino]methyl]pyridin-2-amine as white solid. $^1$H NMR (300 MHz, CD$_3$OD): 8.37 (s, 1H), 7.68-7.62 (m, 2H), 7.51 (s, 1H), 7.34-7.20 (m, 4H), 6.72 (d, J=13.2 Hz, 1H), 6.33 (s, 1H), 6.09 (s, 1H), 5.57 (s, 2H), 5.35 (s, 2H), 4.50 (s, 2H), 3.81 (s, 2H), 2.34 (s, 3H). MS (ESI) m/z found for C$_{25}$H$_{26}$N$_8$O: 455 [M+H].$^+$.

Example 62

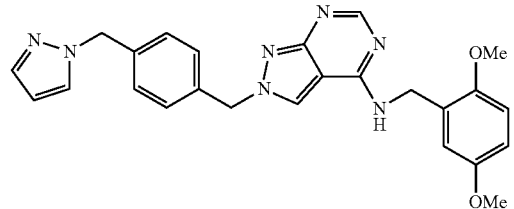 [SMILES: COc1ccc(OC)c(CNc2ncnc3nn(Cc4ccc(Cn5cccn5)cc4)cc23)c1]

2-(4-((1H-pyrazol-1-yl)methyl)benzyl)-N-(2,5-dimethoxybenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (75 mg, 0.23 mmol, 1.00 equiv)(Example 23) in 1-ethoxy-2-(2-ethoxyethoxyl)ethane (5 mL), (2,5-dimethoxyphenyl)methanamine (77 mg, 0.46 mmol, 2.00 equiv) and zinc dichloride (313 mg, 2.30 mmol, 10.00 equiv). The resulting solution was stirred for 3 h at 120° C. The reaction mixture was cooled to room temperature and diluted with 5 mL of DMSO. The residue was purified by silica gel column chromatography eluted with EA:PE:MeOH (1:5:0 to 0:0:1). The crude product was purified by Prep-HPLC with the following conditions. Column: Waters X-bridge RP18, 19×150 mm, 5 um; mobile phase: water (0.05% ammonia) and acetonitrile with a gradient of 37% to 42% acetonitrile in 5.5 min; flow rate: 20 mL/min; detector UV wavelength: 254 nm and 220 nm. This resulted in 18.9 mg (18%) of 2-(4-((1H-pyrazol-1-yl)methyl)benzyl)-N-(2,5-dimethoxybenzyl)-2H-pyrazolo[3,4-d]pyrimidin-4-amine as white solid. $^1$H NMR (300 MHz, DMSO-d): 6 8.47-8.44 (br, 1H), 8.40 (s, 1H), 8.19 (s, 1H), 7.80 (d, J=2.1 Hz, 1H), 7.45 (d, J=1.5 Hz, 1H), 7.31 (d, J=7.8 Hz, 2H), 7.22 (d, J=8.1 Hz, 2H), 6.95-6.91 (m, 1H), 6.81-6.80 (m, 2H), 6.26 (t, J=1.8 Hz, 1H), 5.54 (s, 2H), 5.32 (s, 2H), 4.62 (d, J=5.7 Hz, 2H), 3.77 (s, 3H), 3.64 (s, 3H). MS (ESI) m/z found for C$_{25}$H$_{25}$N$_7$O$_2$: 456 [M+H]$^+$.

Example 63

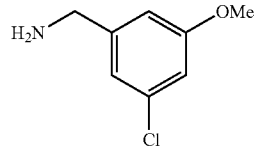 [SMILES: COc1cc(Cl)cc(CN)c1]

(3-chloro-5-methoxyphenyl)methanamine

Into a 250-mL 3-necked round-bottom flask purged and maintained with an inert atmosphere of nitrogen, was placed a solution of 3-chloro-5-methoxybenzonitrile (1 g, 5.97 mmol, 1.00 equiv) in tetrahydrofuran (100 mL) with stirring at 0° C., to which was added 2M BH$_3$-Me$_2$S tetrahydrofuran solution (12.3 mL, 4.00 equiv) dropwise with stirring at 0° C. in 10 min. The resulted mixture was stirred for 5 min at 0° C. The reaction solution was refluxed for 1 h. The reaction was then quenched by the addition of 7 mL of methanol. The resulting mixture was concentrated under vacuum. The crude product was purified by Combi-Flash with the following conditions. Column: C18, 20-45 um, 100 Å, 120 g; mobile phase: water (it contains 0.05% ammonia and 10 mM NH$_4$HCO$_3$) and acetonitrile with a gradient of 30% to 65% acetonitrile in 12 min; flow rate: 60 mL/min; detector UV wavelength: 254 nm and 220 nm. This resulted in 100 mg (10%) of (3-chloro-5-methoxyphenyl)methanamine as yellow oil. MS (ESI) m/z found for C$_8$H$_{10}$ClNO: 172 [M+H]$^+$.

Example 64

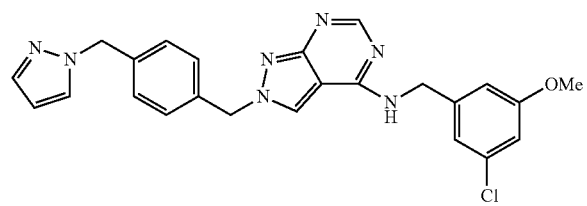 [SMILES: COc1cc(Cl)cc(CNc2ncnc3nn(Cc4ccc(Cn5cccn5)cc4)cc23)c1]

2-(4-((1H-pyrazol-1-yl)methyl)benzyl)-N-(3-chloro-5-methoxybenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (75 mg, 0.23 mmol, 1.00 equiv)(Example 23) in 1-ethoxy-2-(2-ethoxyethoxy)ethane (5 mL), (3-chloro-5-methoxyphenyl)methanamine (79 mg, 0.46 mmol, 2.00 equiv)(Example 63) and zinc dichloride (313 mg, 2.30 mmol, 10.00 equiv). The resulting solution was stirred for 3 h at 120° C. The reaction mixture was cooled to room temperature and diluted with 5 mL of DMSO. The residue was purified by silica gel column chromatography eluted with EA:PE:MeOH (1:5:0 to 0:0:1). The crude product was purified by Prep-HPLC with the following conditions. Column: Waters X-bridge RP18, 19×150 mm, 5 um; mobile phase: water (0.05% ammonia) and acetonitrile with a gradient of 42% to 48% acetonitrile in 5 min; flow rate: 20 mL/min; detector UV wavelength: 254 nm and 220 nm. This resulted in 45.3 mg (43%) of 2-(4-((1H-pyrazol-1-yl)methyl)benzyl)-N-(3-chloro-5-methoxybenzyl)-2H-pyrazolo[3,4-d]pyrimidin-4-amine as white solid. $^1$H NMR (300 MHz, DMSO-d$_6$): δ 8.67 (br, 1H), 8.37 (s, 1H), 8.21 (s, 1H), 7.80 (d, J=2.1 Hz, 1H), 7.45 (s, 1H), 7.31 (d, J=8.1 Hz, 2H), 7.22 (d, J=7.8 Hz, 2H), 6.96-6.89 (m, 3H), 6.26 (t, J=1.8 Hz, 1H), 5.55 (s, 2H), 5.32 (s, 2H), 4.67 (d, J=5.7 Hz, 2H), 3.75 (s, 3H). MS (ESI) m/z found for C$_{24}$H$_{22}$ClN$_7$O: 460 [M+H]$^+$.

Example 65

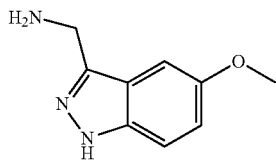

(5-methoxy-1H-indazol-3-yl)methanamine Into a 250-mL round-bottom flask, was placed a mixture of 5-methoxy-1H-indazole-3-carbonitrile (600 mg, 3.46 mmol, 1.00 equiv), methanol (100 mL), Raney-nickel (200 mg) and concentrated ammonia (2 mL, aqueous solution). The flask was purged with hydrogen for 3 times. Then it was stirred overnight at room temperature under hydrogen atmosphere (with a balloon). Afterwards, the mixture was filtered. The filtrate was concentrated under vacuum. The residue was purified by silica gel column chromatography eluted with EA/DCM/MeOH/NH4OH (4:4:1:0.2). This resulted in 240 mg (39%) of (5-methoxy-1H-indazol-3-yl)methanamine as a brown solid. MS (ESI) m/z 178 [M+H]$^+$.

Example 66

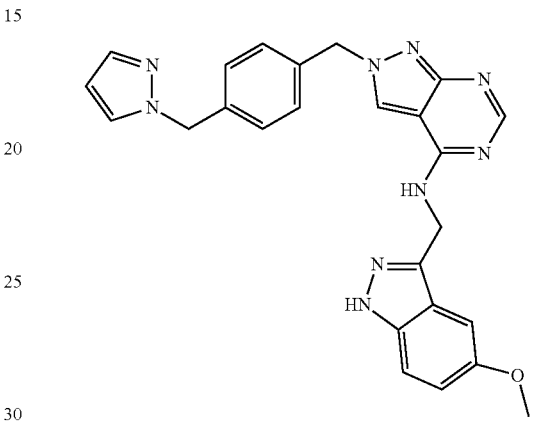

2-(4-((1H-pyrazol-1-yl)methyl)benzyl)-N-((5-methoxy-1H-indazol-3-yl)methyl)-2H-pyrazolo[3,4-d]pyrimidin-4-amine Into a 30-mL vial, were placed 1-[[4-([4-chloro-2H-pyrazolo[3,4-d]pyrimidin-2-yl]methyl)phenyl]methyl]-1H-pyrazole (120 mg, 0.37 mmol, 1.00 equiv)(Example 23), (5-methoxy-1H-indazol-3-yl)methanamine (98 mg, 0.55 mmol, 1.50 equiv)(Example 65), 1-ethoxy-2-(2-ethoxyethoxyl)ethane (12 mL), dichlorozinc (504 mg, 3.70 mmol, 10.00 equiv) and diisopropanyl ethyl amine (956 mg, 7.40 mmol, 20.00 equiv). The resulted solution was stirred for 3 h at 120° C. The crude product was purified by medium pressure column chromatography with the following conditions: column, silica gel; mobile phase, dichloromethane/ ethyl acetate/ methanol/ 20% ammonia aqueous solution (ratio 4:4:1:0.2) within 30 min; detector UV wavelength: 254 nm. The resulting mixture was concentrated under vacuum. The crude product was further purified by Prep-HPLC with the following conditions: Column, Bridge C18; mobile phase, ACN/water (0.05% NH4OH, 10 mM NH4HCO3) from 32% to 37% within 5 min, flow rate: 20 mL/min; Detector, 254 nm. This resulted in 62.9 mg (37%) of N-[(5-methoxy-1H-indazol-3-yl)methyl]-2-[[4-(1H-pyrazol-1-ylmethyl)phenyl]methyl]-2H-pyrazolo[3,4-d]pyrimidin-4-amine as a white solid. $^1$H NMR (300 MHz, CD$_3$OD): δ 8.37 (s, 1H), 8.24 (s, 1H), 7.68 (s, 1H), 7.51 (s, 1H), 7.44 (d, J=18.3 Hz, 1H), 7.38 (d, J=21.3 Hz, 2H), 7.22-7.16 (m, 3H), 7.05 (d, J=11.4 Hz, 1H), 6.33 (s, 1H), 5.52 (s, 2H), 5.35 (s, 2H), 5.12 (s, 2H), 3.75 (s, 3H). MS (ESI) m/z found for C$_{25}$H$_{23}$N$_9$O: 466 [M+H]$^+$.

Example 67

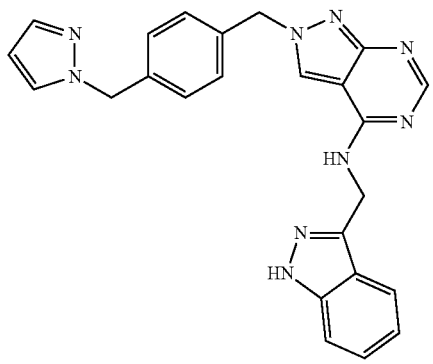 [SMILES: c1ccc2c(CNc3ncnc4nn(Cc5ccc(Cn6cccn6)cc5)cc34)n[nH]c2c1]

N-((1H-indazol-3-yl)methyl)-2-(4-((1H-pyrazol-1-yl)methyl)benzyl)-2H-pyrazolo[3,4-d]pyrimidin-4-amine Into a 8-mL vial, were placed 1-[[4-([4-chloro-2H-pyrazolo[3,4-d]pyrimidin-2-yl]methyl]phenyl]methyl]-1H-pyrazole (85 mg, 0.26 mmol, 1.00 equiv)(Example 23), 1H-indazol-3-ylmethanamine (57.8 mg, 0.39 mmol, 1.5 equiv), 1-ethoxy-2-(2-ethoxyethoxy)ethane (6 mL), zinc dichloride (357 mg, 2.62 mmol, 10.00 equiv) and DIEA (676 mg, 5.23 mmol, 20.00 equiv). The resulted solution was stirred for 3 h at 120° C. The crude product was purified by flash column chromatography eluted with DCM/EA/MeOH/ concentrated ammonia aqueous solution (4:4:1:0.2). The crude product was further purified by Prep-HPLC with the following conditions: column, Waters XBridge RP18 19*150 mm; mobile phase, CH3CN/water (0.05% NH$_4$OH, 10 mM NH$_4$HCO$_3$) gradient from 25% to 30% with a 25-min run time, flow rate: 20 mL/min; detector UV wavelength: 254 nm. This resulted in 43.7 mg (38%) of N-(1H-indazol-3-ylmethyl)-2-[[4-(1H-pyrazol-1-ylmethyl)phenyl]methyl]-2H-pyrazolo[3,4-d]pyrimidin-4-amine as white solid. $^1$H NMR (300 MHz, CD$_3$OD): 8.35 (s, 1H), 8.24 (s, 1H), 7.78 (d, J=8.1 Hz, 1H), 7.68 (s, 1H), 7.52-7.49 (m, 2H), 7.29-7.41 (m, 3H), 7.22 (d, J=8.1 Hz, 2H), 7.08-7.13 (m, 1H), 6.31-6.33 (s, 1H), 5.52 (s, 2H), 5.39 (s, 2H), 5.16 (s, 2H). MS (ESI) m/z found for C$_{24}$H$_{21}$N$_9$: 436 [M+H]$^+$.

Example 68

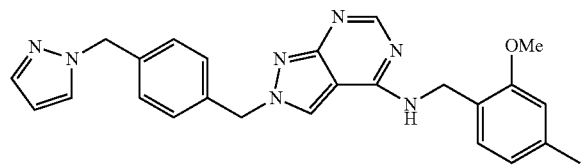 [SMILES: COc1cc(C)ccc1CNc1ncnc2nn(Cc3ccc(Cn4cccn4)cc3)cc12]

2-(4-((1H-pyrazol-1-yl)methyl)benzyl)-N-(2-methoxy-4-methylbenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (150 mg, 0.46 mmol, 1.00 equiv)(Example 23) in 1-ethoxy-2-(2-ethoxyethoxy)ethane (5 mL), (2-methoxy-4-methylphenyl)methanamine (140 mg, 0.93 mmol, 2.00 equiv) and zinc dichloride (630 mg, 4.62 mmol, 10.00 equiv). The reaction solution was stirred for 3 h at 120° C. The resulting solution was diluted with 5 mL of DMSO at room temperature. The residue was purified by silica gel column chromatography eluted with EA:PE:MeOH (1:5:0 to 0:0:1). The crude product was purified by Prep-HPLC with the following conditions. Column: Waters X-bridge RP18, 19×150 mm, 5 um; mobile phase: water (0.05% ammonia) and acetonitrile with a gradient of 41% to 46% acetonitrile in 5.5 min; flow rate: 20 mL/min; detector UV wavelength: 254 nm and 220 nm. This resulted in 15.2 mg (7%) of 2-(4-((1H-pyrazol-1-yl)methyl)benzyl)-N-(2-methoxy-4-methylbenzyl)-2H-pyrazolo[3,4-d]pyrimidin-4-amine as white solid. $^1$H NMR (300 MHz, DMSO-d$_6$): δ 8.40 (br, 1H), 8.38 (s, 1H), 8.16 (s, 1H), 7.80 (d, J=2.1 Hz, 1H), 7.44 (d, J=1.5 Hz, 1H), 7.33 (d, J=7.2 Hz, 2H), 7.21 (d, J=7.8 Hz, 2H), 7.07 (d, J=7.5 Hz, 1H), 6.83 (s, 1H), 6.68 (d, J=8.1 Hz, 1H), 6.25 (t, J=2.1 Hz, 1H), 5.52 (s, 2H), 5.32 (s, 2H), 4.59 (d, J=5.7 Hz, 2H), 3.80 (s, 3H), 2.28 (s, 3H). MS (ESI) m/z found for C$_{25}$H$_{25}$N$_7$O: 440 [M+H]$^+$.

Example 69

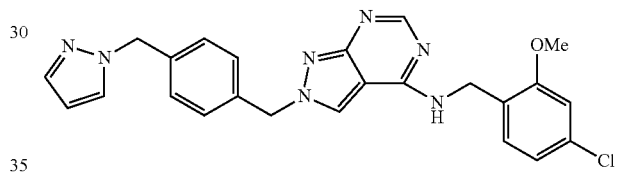

2-(4-((1H-pyrazol-1-yl)methyl)benzyl)-N-(4-chloro-2-methoxybenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (150 mg, 0.46 mmol, 1.00 equiv)(Example 23) in 1-ethoxy-2-(2-ethoxyethoxy)ethane (5 mL), (4-chloro-2-methoxyphenyl)methanamine (158 mg, 0.92 mmol, 2.00 equiv) and zinc dichloride (630 mg, 4.62 mmol, 10.00 equiv). The resulting solution was stirred for 3 h at 120° C. The resulting solution was diluted with 5 mL of DMSO at room temperature. The residue was purified by silica gel column chromatography eluted with EA:PE:MeOH (1:5:0 to 0:0:1). The crude product was purified by Prep-HPLC with the following conditions. Column: Waters X-bridge RP18, 19×150 mm, 5 um; mobile phase: water (0.05% ammonia) and acetonitrile with a gradient of 42% to 48% acetonitrile in 5.5 min; flow rate: 20 mL/min; detector UV wavelength: 254 nm and 220 nm. This resulted in 9.8 mg (5%) of 2-(4-((1H-pyrazol-1-yl)methyl)benzyl)-N-(4-chloro-2-methoxybenzyl)-2H-pyrazolo[3,4-d]pyrimidin-4-amine as white solid. $^1$H NMR (300 MHz, DMSO-d$_6$): δ 8.50 (br, 1H), 8.38 (s, 1H), 8.17 (s, 1H), 7.80 (d, J=1.5 Hz, 1H), 7.44 (d, J=1.2 Hz, 1H), 7.31 (d, J=8.1 Hz, 2H), 7.23-7.17 (m, 3H), 7.08 (d, J=2.1 Hz, 1H), 6.94 (dd, J=7.8, 1.8 Hz, 1H), 6.25 (t, J=2.1 Hz, 1H), 5.54 (s, 2H), 5.32 (s, 2H), 4.60 (d, J=5.4 Hz, 2H), 3.85 (s, 3H). MS (ESI) m/z found for C$_{24}$H$_{22}$ClN$_7$O: 460 [M+H]$^+$.

Example 70

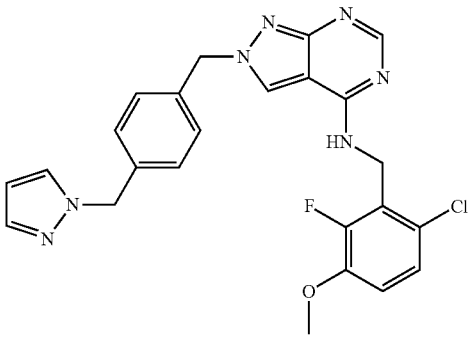 [SMILES: COc1ccc(Cl)c(CNc2ncnc3nn(Cc4ccc(Cn5cccn5)cc4)cc23)c1F]

2-(4-((1H-pyrazol-1-yl)methyl)benzyl)-N-(6-chloro-2-fluoro-3-methoxybenzyl)-2H-pyrazolo[3,4-d]pyrimidin-4-amine 2-(4-((1H-pyrazol-1-yl)methyl)benzyl)-N-(6-chloro-2-fluoro-3-methoxybenzyl)-2H-pyrazolo[3,4-d]pyrimidin-4-amine was synthesized in a manner similar to Example 335. $^1$H NMR (400 MHz, Methanol-$d_4$) δ 8.29 (s, 1H), 8.20 (s, 1H), 7.64 (d, J=2.3 Hz, 1H), 7.48 (d, J=1.9 Hz, 1H), 7.27 (d, J=7.9 Hz, 2H), 7.23-7.12 (m, 3H), 7.07 (t, J=8.9 Hz, 1H), 6.29 (t, J=2.2 Hz, 1H), 5.46 (s, 2H), 5.28 (s, 2H), 4.84 (s, 2H), 3.85 (s, 3H). MS (M+H)+ found for $C_{24}H_{21}Cl_2FN_7O$: 477.8.

Example 71

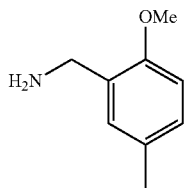

(2-methoxy-5-methylphenyl)methanamine Into a 250-mL 3-necked round-bottom flask purged and maintained with an inert atmosphere of nitrogen, was placed a solution of 2-methoxy-5-methylbenzonitrile (1 g, 6.79 mmol, 1.00 equiv) in tetrahydrofuran (100 mL) with stirring at 0° C., to which was added 2M BH$_3$-Me$_2$S in tetrahydrofuran solution (12 mL, 4.00 equiv) dropwise with stirring at 0° C. in 10 min. The resulting mixture was stirred for 5 min at 0° C. and refluxed for 1 h. The reaction was then quenched by the addition of 7 mL of methanol. The reaction mixture was concentrated under vacuum. The crude product was purified by Combi-Flash with the following conditions. Column: C 18, 20-45 um, 100 Å, 120 g; mobile phase: water (it contains 0.05% ammonia and 10 mM NH$_4$HCO$_3$) and acetonitrile with a gradient of 30% to 65% acetonitrile in 12 min; flow rate: 60 mL/min; detector UV wavelength: 254 nm and 220 nm. This resulted in 100 mg (10%) of (2-methoxy-5-methylphenyl)methanamine as white solid. MS (ESI) m/z found for C9H13NO: 152 [M+H]$^+$.

Example 72

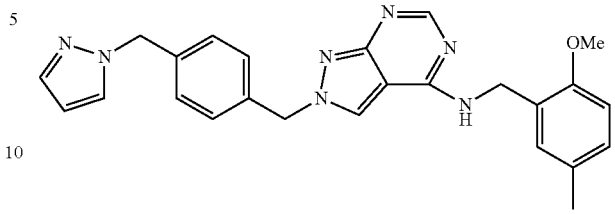

2-(4-((1H-pyrazol-1-yl)methyl)benzyl)-N-(2-methoxy-5-methylbenzyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (195 mg, 0.60 mmol, 1.00 equiv)(Example 23) in DMF (5 mL), (2-methoxy-5-methylphenyl)methanamine (100 mg, 0.66 mmol, 1.10 equiv)(Example 71) and DIEA (774 mg, 6.00 mmol, 10.00 equiv). The resulting solution was stirred for 3 h at room temperature. The crude product was purified by Prep-HPLC with the following conditions. Column: Waters X-bridge RP18, 19 x 150 mm, 5 um; mobile phase: water (0.05% ammonia) and acetonitrile with a gradient of 39% to 44% acetontrile in 5.5 min; flow rate: 20 mL/min; detector UV wavelength: 254 nm and 220 nm. This resulted in 9.8 mg (3%) of 2-(4-((1H-pyrazol-1-yl)methyl)benzyl)-N-(2-methoxy-5-methylbenzyl)-2H-pyrazolo[3,4-d]pyrimidin-4-amine as white solid. $^1$H NMR (300 MHz, DMSO-$d_6$): δ 8.39 (br, 2H), 8.18 (s, 1H), 7.80 (d, J=1.5 Hz, 1H), 7.44 (d, J=1.2 Hz, 1H), 7.31 (d, J=7.8 Hz, 2H), 7.21 (d, J=7.8 Hz, 2H), 7.02 (m, 2H), 6.90 (m, 1H), 6.25 (t, J=1.8 Hz, 1H), 5.53 (s, 2H), 5.32 (s, 2H), 4.61 (d, J=5.7 Hz, 2H), 3.77 (s, 3H), 2.17 (s, 3H). MS (ESI) m/z found for $C_{25}H_{25}N_7O$: 440 [M+H]$^+$.

Example 77

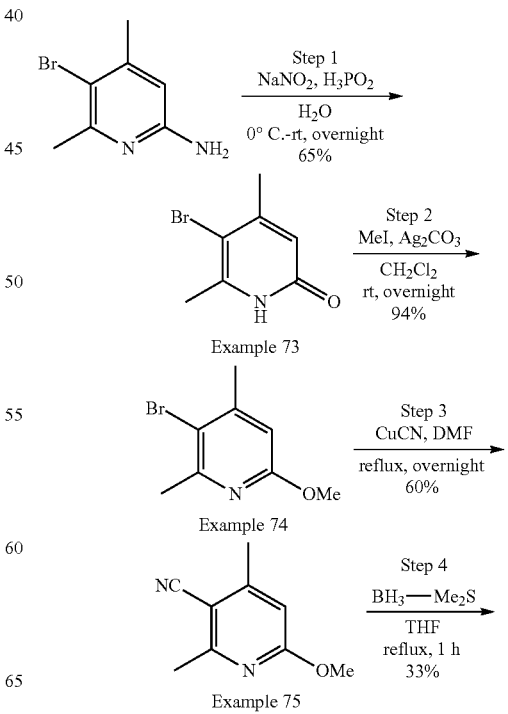

-continued

Step 5

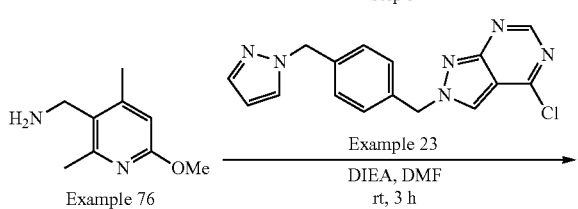

Example 23
DIEA, DMF
rt, 3 h
9%

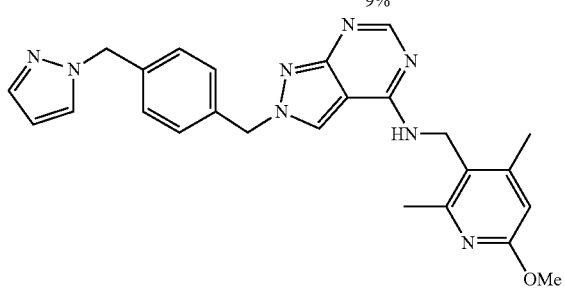

Example 77

Example 73

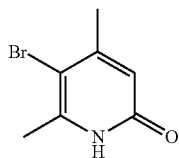

Step 1:
5-bromo-4,6-dimethyl-1,2-dihydropyridin-2-one

Into a 250-mL 3-necked round-bottom flask purged and maintained with an inert atmosphere of nitrogen, was placed a solution of $H_3PO_2$ (25 mL, 50%, 8.00 equiv) in water (55 mL) with stirring at 0° C., to which was added 5-bromo-4,6-dimethylpyridin-2-amine (6 g, 29.84 mmol, 1.00 equiv). This was followed by the addition of $NaNO_2$ (2.4 g, 34.78 mmol, 1.17 equiv) in water (12 mL) at 0° C. The resulting solution was stirred for additional 30 min at 0° C. The reaction solution was stirred for 3 h at room temperature. The pH value of the aqueous phase was adjusted to 6-7 with saturated $NaHCO_3$ aqueous solution. The solids were collected by filtration. The cake was washed with 20 mL of water. This resulted in 3.90 g (65%) of 5-bromo-4,6-dimethyl-1,2-dihydropyridin-2-one as white solid. MS (ESI) m/z found for $C_7H_8BrNO$: 202 $[M+H]^+$.

Example 74

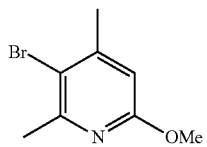

Step 2: 3-bromo-6-methoxy-2,4-dimethylpyridine Into a 500-mL 3-necked round-bottom flask purged and maintained with an inert atmosphere of nitrogen, was placed a mixture of 5-bromo-4,6-dimethyl-1,2-dihydropyridin-2-one (3.90 g, 19.30 mmol, 1.00 equiv)(Example 73), dichloromethane (150 mL) and $Ag_2CO_3$ (7.34 g, 0.0266 mol, 1.40 equiv) with stirring, to which was added MeI (28.4 g, 0.2 mol, 10.50 equiv). The resulting solution was stirred overnight at room temperature. The solids were collected by filtration and the cake was washed with 50 mL of $CH_2Cl_2$. The filtrate was concentrated under vacuum. This resulted in 3.91 g (94%) of 3-bromo-6-methoxy-2,4-dimethylpyridine as brown oil. MS (ESI) m/z found for: $C_8H_{10}BrNO$: 216 $[M+H]^+$.

Example 75

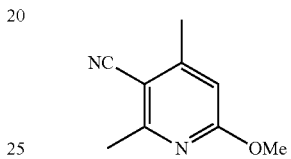

Step 3: 6-methoxy-2,4-dimethylpyridine-3-carbonitrile Into a 100-mL 3-necked round-bottom flask purged and maintained with an inert atmosphere of nitrogen, was placed a mixture of 3-bromo-6-methoxy-2,4-dimethylpyridine (1 g, 4.63 mmol, 1.00 equiv)(Example 74), N,N-dimethylformamide (30 mL) and CuCN (414 mg, 1.00 equiv). The resulting solution was refluxed overnight. The reaction mixture was cooled to room temperature. The resulted solution was diluted with 100 mL of water. The solids were filtered out. The filtrate was extracted with EA (40 mL×3) and washed with 1×100 mL of brine. The resulting mixture was dried over anhydrous sodium sulfate and concentrated under vacuum. The residue was purified by silica gel column chromatography eluted with EA:PE (1:3). This resulted in 450 mg (60%) of 6-methoxy-2,4-dimethylpyridine-3-carbonitrile as brown oil. MS (ESI) m/z found for $C_9H_{10}N_2O$: 163 $[M+H]^+$.

Example 76

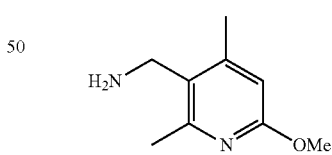

Step 4:
(6-methoxy-2,4-dimethylpyridin-3-yl)methanamine

Into a 100-mL 3-necked round-bottom flask purged and maintained with an inert atmosphere of nitrogen, was placed 6-methoxy-2,4-dimethylpyridine-3-carbonitrile (450 mg, 2.77 mmol, 1.00 equiv)(Example 75) in tetrahydrofuran (10 mL) with stirring at 0° C., to which was added 10M $BH_3\text{-}Me_2S$ solution in tetrahydrofuran (1.11 mL, 4.00 equiv) dropwise with stirring at 0° C. The resulting solution was refluxed for 1 h. The reaction was then quenched by the addition of 10 mL of methanol at 0° C. The mixture was stirred for 1 h at room temperature and then concentrated under vacuum. The crude product was purified by Combi-Flash with the following conditions. Column: C 18, 20-45 um, 100 Å, 120 g; mobile phase: water (0.05% ammonia and 10 mM NH$_4$HCO$_3$) and acetonitrile with a gradient of 30% to 60% acetonitrile in 10 min; flow rate: 60 mL/min; detector UV wavelength: 254 nm and 220 nm. This resulted in 150 mg (33%) of (6-methoxy-2,4-dimethylpyridin-3-yl)methanamine as yellow solids.

Example 77

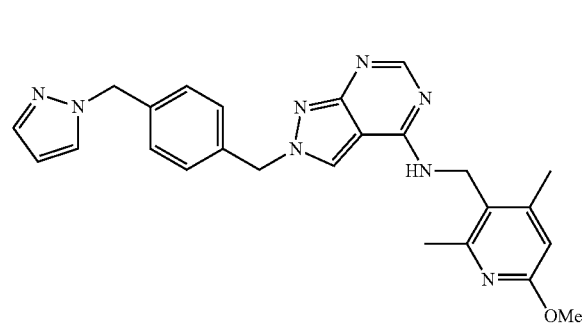 [SMILES: COc1cc(C)c(CNc2ncnc3nn(Cc4ccc(Cn5cccn5)cc4)cc23)c(C)n1]

Step 5: 2-(4-((1H-pyrazol-1-yl)methyl)benzyl)-N-((6-methoxy-2,4-dimethylpyridin-3-yl)methyl)-2H-pyrazolo[3,4-d]pyrimidin-4-amine Into a 8-mL vial, was placed a solution of 2-(4-((1H-pyrazol-1-yl)methyl)benzyl)-4-chloro-2H-pyrazolo[3,4-d]pyrimidine (266 mg, 0.82 mmol, 1.00 equiv)(Example 76) in N,N-dimethylformamide (5 mL), (6-methoxy-2,4-dimethylpyridin-3-yl)methanamine (150 mg, 0.90 mmol, 1.10 equiv) and DIEA (1.06 g, 8.20 mmol, 10.00 equiv). The resulting solution was stirred for 3 h at room temperature. The crude product was purified by Prep-HPLC with the following conditions. Column: Waters X-bridge RP18, 19×150 mm, 5 um; mobile phase: water (0.05% ammonia) and acetonitrile with a gradient of 35% to 40% acetonitrile in 5.5 min; flow rate: 20 mL/min; detector UV wavelength: 254 nm and 220 nm. This resulted in 34.5 mg (8%) of 2-(4-((1H-pyrazol-1-yl)methyl)benzyl)-N-((6-methoxy-2,4-dimethylpyridin-3-yl)methyl)-2H-pyrazolo[3,4-d]pyrimidin-4-amine as white solid. $^1$H NMR (300 MHz, DMSO-d$_6$): δ 8.26 (br, 2H), 8.04 (m, 1H), 7.79 (d, J=1.8 Hz, 1H), 7.44 (d, J=1.5 Hz, 1H), 7.29 (d, J=8.1 Hz, 2H), 7.20 (d, J=8.4 Hz, 2H), 6.53 (s, 1H), 6.25 (m, 1H), 5.49 (s, 2H), 5.31 (s, 2H), 4.60 (d, J=4.2 Hz, 2H), 3.80 (s, 3H), 2.44 (s, 3H), 2.28 (s, 3H). MS (ESI) m/z found for C$_{25}$H$_{26}$N$_8$O: 455 [M+H]$^+$.

Example 78

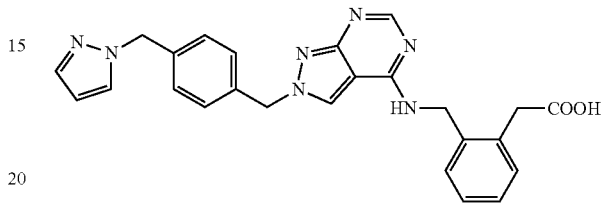

2-(2-((2-(4-((1H-pyrazol-1-yl)methyl)benzyl)-2H-pyrazolo[3,4-d]pyrimidin-4-ylamino)methyl)phenyl)acetic acid Into a 8-mL vial, was placed a solution of 2-(4-((1H-pyrazol-1-yl)methyl)benzyl)-4-chloro-2H-pyrazolo[3,4-d]pyrimidine (537 mg, 1.65 mmol, 1.00 equiv)(Example 23) in N,N-dimethylformamide (5 mL), 2-(2-(aminomethyl)phenyl)acetic acid (300 mg, 1.82 mmol, 1.10 equiv) and DIEA (2.13 g, 16.5 mmol, 10.00 equiv). The resulting solution was stirred overnight at 60° C. The crude product was purified by Prep-HPLC with the following conditions. Column: Waters X-bridge RP18, 19×150 mm, 5 um; mobile phase: water (it contains 0.05% ammonia and 10 mM NH$_4$HCO$_3$) and acetonitrile with a gradient of 10% to 20% acetonitrile in 5.5 min; flow rate: 20 mL/min; detector UV wavelength: 254 nm and 220 nm. This resulted in 16.9 mg (2%) of 2-(2-((2-(4-((1H-pyrazol-1-yl)methyl)benzyl)-2H-pyrazolo[3,4-d]pyrimidin-4-ylamino)methyl)phenyl)acetic acid as white solid. $^1$H NMR (300 MHz, DMSO-d$_6$): δ 9.24 (br, 1H), 8.39 (s, 1H), 8.20 (s, 1H), 7.79 (s, 1H), 7.44 (s, 1H), 7.30-7.18 (m, 8H), 6.25 (s, 1H), 5.51 (s, 2H), 5.51 (s, 2H), 5.31 (s, 2H), 4.70 (s, 2H), 3.61 (s, 2H). MS (ESI) m/z found for C$_{25}$H$_{23}$N$_7$O$_2$: 454 [M+H]$^+$.

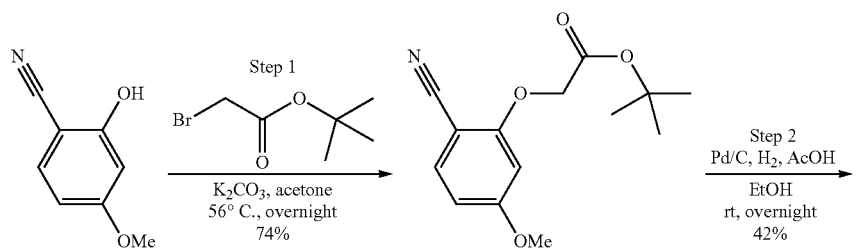

Example 79

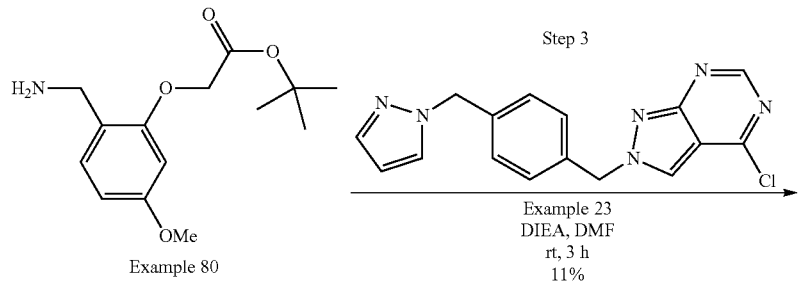

Example 80

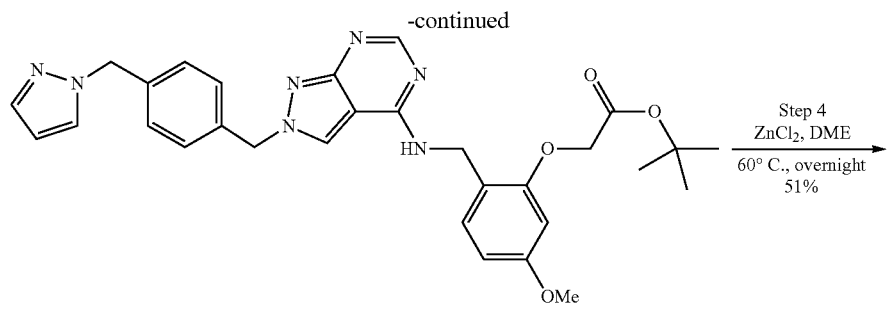

Example 81

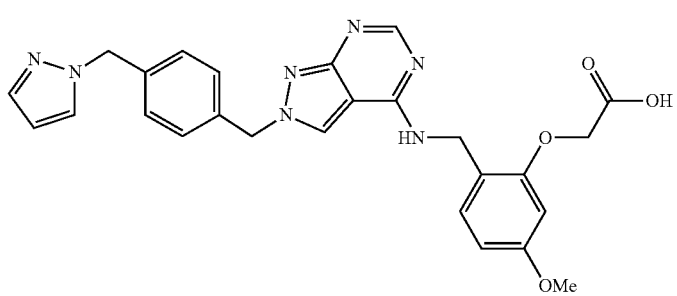

Example 82

Example 79

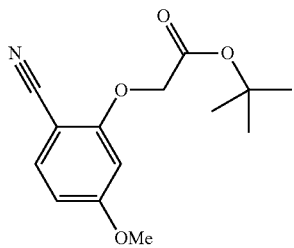 [SMILES: COc1ccc(C#N)c(OCC(=O)OC(C)(C)C)c1]

Step 1: tert-butyl 2-(2-cyano-5-methoxyphenoxy)acetate

Into a 250-mL 3-necked round-bottom flask purged and maintained with an inert atmosphere of nitrogen, was placed a mixture of 2-hydroxy-4-methoxybenzonitrile (2 g, 13.41 mmol, 1.00 equiv), acetone (80 mL), tert-butyl 2-bromoacetate (2.87 g, 14.71 mmol, 1.10 equiv) and $K_2CO_3$ (3.7 g, 26.77 mmol, 2.00 equiv). The resulting solution was stirred overnight at 56° C. The reaction mixture was cooled to room temperature. The solids were filtered out. The filtrate was concentrated under vacuum. The residue was added with 100 mL of EA and washed with 100 mL of brine. The resulting mixture was dried over anhydrous sodium sulfate and concentrated under vacuum. This resulted in 2.60 g (74%) of tert-butyl 2-(2-cyano-5-methoxyphenoxy)acetate as brown solid. MS (ESI) m/z found for: $C_{14}H_{17}NO$: 4264 $[M+H]^+$.

Example 80

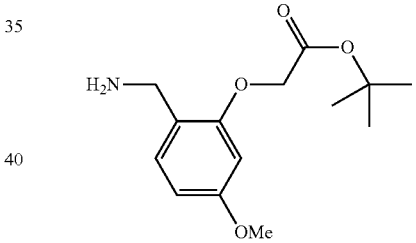

Step 2: tert-butyl 2-(2-(aminomethyl)-5-methoxyphenoxy)acetate Into a 250-mL round-bottom flask, was placed a mixture of tert-butyl 2-(2-cyano-5-methoxyphenoxy)acetate (2.6 g, 9.88 mmol, 1.00 equiv)(Example 79), ethanol (100 mL) and AcOH (5 mL). The flask was purged with nitrogen for three times. This was followed by the addition of 5% palladium on carbon (260 mg, 0.10 equiv). The flask was purged with hydrogen for three times. The resulting solution was stirred overnight at room temperature. The solids was filtered out over Celite. The filtrate was concentrated under vacuum. The residue was diluted with 30 mL of water. The pH value of the aqueous phase was adjusted to 9 with saturated aqueous $NaHCO_3$ solution. The resulting mixture was extracted with EA (30 mL×3) and washed with 1×100 mL of brine. The resulting mixture was dried over anhydrous sodium sulfate and concentrated under vacuum. This resulted in 1.10 g (42%) of tert-butyl 2-(2-(aminomethyl)-5-methoxyphenoxy)acetate as yellow oil. MS (ESI) m/z found for $C_{14}H_{21}NO_4$: 268 $[M+H]^+$.

Example 81

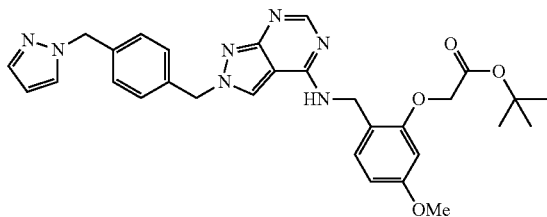 [SMILES: COc1ccc(CNc2ncnc3nn(Cc4ccc(Cn5cccn5)cc4)cc23)c(OCC(=O)OC(C)(C)C)c1]

Step 3: tert-butyl 2-(2-((2-(4-((1H-pyrazol-1-yl)methyl)benzyl)-2H-pyrazolo[3,4-d]pyrimidin-4-ylamino)methyl)-5-methoxyphenoxy)acetate Into a 8-mL vial, was placed a solution of 2-(4-((1H-pyrazol-1-yl)methyl)benzyl)-4-chloro-2H-pyrazolo[3,4-d]pyrimidine (220 mg, 0.68 mmol, 1.00 equiv)(Example 23) in N,N-dimethylformamide (5 mL), tert-butyl 2-(2-(aminomethyl)-5-methoxyphenoxy)acetate (200 mg, 0.75 mmol, 1.10 equiv)(Example 80) and DIEA (903 mg, 6.99 mmol, 10.00 equiv). The resulting solution was stirred for 3 h at room temperature. The crude product was purified by Prep-HPLC with the following conditions. Column: Waters X-bridge RP18, 19 x 150 mm, 5 um; mobile phase: water (0.05% ammonia) and acetonitrile with a gradient of 30% to 50% acetonitrile in 5.5 min; flow rate: 20 mL/min; detector UV wavelength: 254 nm and 220 nm. This resulted in 40 mg (11%) of tert-butyl 2-(2-((2-(4-((1H-pyrazol-1-yl)methyl)benzyl)-2H-pyrazolo[3,4-d]pyrimidin-4-ylamino)methyl)-5-methoxyphenoxy)acetate as white solid. $^1$H NMR (300 MHz, DMSO-$d_6$): δ 8.37 (s, 1H), 8.35 (m, 1H), 8.18 (s, 1H), 7.79 (d, J=1.8 Hz, 1H), 7.44 (d, J=1.5 Hz, 1H), 7.29 (d, J=8.1 Hz, 2H), 7.20 (d, J=8.1 Hz, 2H), 7.13 (d, J=9.3 Hz, 1H), 6.50-6.48 (m, 2H), 6.25 (t, J=2.1 Hz, 1H), 5.52 (s, 2H), 5.32 (s, 2H), 4.72 (s, 2H), 4.62 (d, J=5.1 Hz, 2H), 3.70 (s, 3H), 1.40 (s, 9H). MS (ESI) m/z found for $C_{30}H_{33}N_7O_4$: 556 [M+H]$^+$.

Example 82

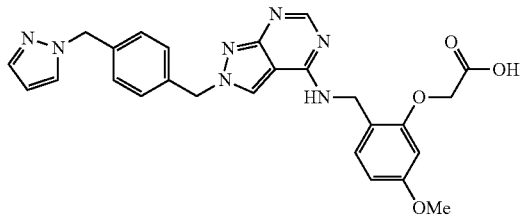 [SMILES: COc1ccc(CNc2ncnc3nn(Cc4ccc(Cn5cccn5)cc4)cc23)c(OCC(=O)O)c1]

Step 4: 2-(2-((2-(4-((1H-pyrazol-1-yl)methyl)benzyl)-2H-pyrazolo[3,4-d]pyrimidin-4-ylamino)methyl)-5-methoxyphenoxy)acetic acid Into a 8-mL vial, was placed a solution of tert-butyl 2-(2-((2-(4-((1H-pyrazol-1-yl)methyl)benzyl)-2H-pyrazolo[3,4-d]pyrimidin-4-ylamino)methyl)-5-methoxyphenoxy)acetate (31 mg, 0.06 mmol, 1.00 equiv)(Example 81) in ethylene glycol dimethyl ether (3 mL) and zinc dichloride (76 mg, 0.56 mmol, 10.00 equiv). The resulting solution was stirred overnight at 60° C. The resulting mixture was concentrated under vacuum. The crude product was purified by Prep-HPLC with the following conditions. Column: Waters X-bridge RP18, 19×150 mm, 5 um; mobile phase: water (0.05% ammonia and 10 mM NH$_4$HCO$_3$) and acetonitrile with a gradient of 10% to 20% acetonitrile in 5.5 min; flow rate: 20 mL/min; detector UV wavelength: 254 nm and 220 nm. This resulted in 14.3 mg (51%) of 2-(2-((2-(4-((1H-pyrazol-1-yl)methyl)benzyl)-2H-pyrazolo[3,4-d]pyrimidin-4-ylamino)methyl)-5-methoxyphenoxy) acetic acid as white solid. $^1$H NMR (300 MHz, DMSO-$d_6$): δ 8.63 (br, 1H), 8.18 (s, 1H), 7.78 (s, 1H), 7.43 (s, 1H), 7.22-7.16 (m, 6H), 6.57 (br, 1H), 6.45-6.44 (m, 1H), 6.25 (s, 1H), 5.48 (s, 2H), 5.30 (s, 2H), 4.60-4.54 (m, 4H), 3.71 (s, 3H). MS (ESI) m/z found for $C_{26}H_{25}N_7O_4$: 500 [M+H]$^+$.

Example 83

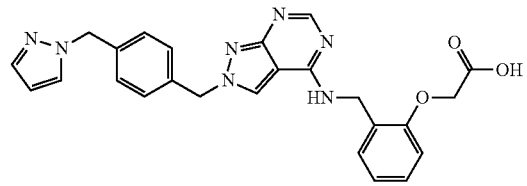 [SMILES: O=C(O)COc1ccccc1CNc1ncnc2nn(Cc3ccc(Cn4cccn4)cc3)cc12]

2-(2-((2-(4-((1H-pyrazol-1-yl)methyl)benzyl)-2H-pyrazolo[3,4-d]pyrimidin-4-ylamino)methyl)phenoxy)acetic acid 2-(2-((2-(4-((1H-pyrazol-1-yl)methyl)benzyl)-2H-pyrazolo[3,4-d]pyrimidin-4-ylamino)methylphenoxy)acetic acid was prepared in a similar manner as Example 82. $^1$H NMR (300 MHz, DMSO-$d_6$): δ 9.71 (br, 1H), 8.64 (br, 1H), 8.18 (s, 1H), 7.78 (s, 1H), 7.44 (s, 1H), 7.24-7.19 (m, 6H), 6.98-6.86 (m, 2H), 6.25 (s, 1H), 5.49 (s, 2H), 5.30 (s, 2H), 4.69 (s, 2H), 4.55 (s, 2H). MS (ESI) m/z found for $C_{25}H_{23}N_7O_3$: 470 [M+H]$^+$.

Example 84

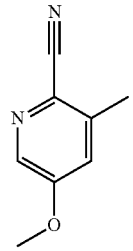

5-methoxy-3-methylpyridine-2-carbonitrile 5-bromo-3-methylpyridine-2-carbonitrile (500.00 mg; 2.54 mmol; 1.00 eq.) was dissolved in DMF (1 ml). Copper iodide (96.66 mg; 0.51 mmol; 0.20 eq.) and methanol (1 ml) were added. The mixture was stirred and sodium hydride (60%; 111.65 mg; 2.79 mmol; 1.10 eq.) was added. The reaction was heated in a bath at 110° C. After 23 h, the mixture was cooled and taken up in ethyl acetate (50 ml) and brine (30 ml). The phases were separated and the aqueous phase was extracted with more ethyl acetate (2×30 ml). The combined organic phases were washed with brine, dried over sodium sulfate and evaporated to a dark liquid which was purified by silica gel chromatography (ethyl acetate/hexanes gradient) to give 5-methoxy-3-methylpicolinonitrile (130 mg) as a white solid. $^1$H NMR (400 MHz, CDCl$_3$) δ 8.21 (d, J=2.7 Hz, 1H), 7.07 (dd, J=2.5, 1.0 Hz, 1H), 3.91 (s, 3H), 2.54 (s, 3H). MS (M+H)$^+$ found for C$_8$H$_8$N$_2$O: 149.

Example 85

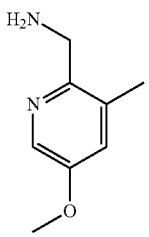

(5-methoxy-3-methylpyridin-2-yl)methanamine 5-methoxy-3-methylpyridine-2-carbonitrile (0.13 g; 0.88 mmol; 1.00 eq.)(Example 84) was dissolved in 7M ammonia/methanol (5 ml) and ethanol (5 ml). Raney Ni (>52 mg) which had been rinsed with ethanol 3x was added, the flask was charged with H$_2$ and stirred vigorously. After 17 h the reaction was purged w/ N$_2$, filtered through Celite and evaporated to a residue of (5-methoxy-3-methylpyridin-2-yl)methanamine which was carried on without further purification. MS (M+H)$^+$ found for C$_8$H$_{12}$N$_2$O: 153.

Example 86

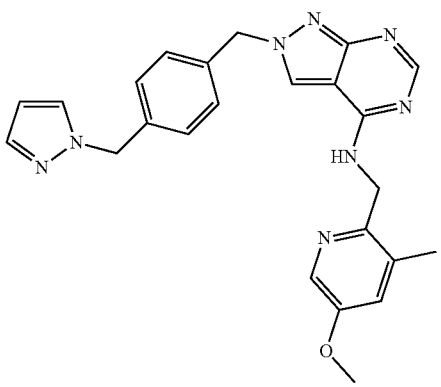 [SMILES: COc1cnc(CNc2ncnc3nn(Cc4ccc(Cn5cccn5)cc4)cc23)c(C)c1]

2-(4-((1H-pyrazol-1-yl)methyl)benzyl)-N-((5-methoxy-3-methylpyridin-2-yl)methyl)-2H-pyrazolo[3,4-d]pyrimidin-4-amine 1-{[4-({4-chloro-2H-pyrazolo[3,4-d]pyrimidin-2-yl}methyl)phenyl]methyl}-1H-pyrazole (50.00 mg; 0.15 mmol; 1.00 eq.)(Example 23) was partly suspended in 1-butanol (3 ml) and Hunig's base (53.63 ul; 0.31 mmol; 2.00 eq.) (5-methoxy-3-methylpyridin-2-yl)methanamine (36.82 mg; 0.17 mmol; 1.10 eq.)(Example 85) was added and the reaction heated in a microwave reactor at 110° C. for 30 min. More (5-methoxy-3-methylpyridin-2-yl)methan-amine (35 mg; 0.16 mmol; 1.05 eq.) was added and the reaction was heated further in the microwave at 100° C. for 30 m. The reaction was diluted with acetonitrile (6 ml) and evaporated to a residue which was purified by reverse phase chromatography (acetonitrile gradient with 0.1% aqueous formic acid, Waters XSelect CSH column) to give 2-(4-((1H-pyrazol-1-yl)methyl)benzyl)-N-((5-methoxy-3-methylpyridin-2-yl)methyl)-2H-pyrazolo[3,4-d]pyrimidin-4-amine (6 mg) as a tan solid. $^1$H NMR (400 MHz, CD$_3$OD) δ 8.02 (d, J=2.8 Hz, 1H), 7.68 (d, J=2.3 Hz, 1H), 7.50 (d, J=1.9 Hz, 1H), 7.37-7.29 (m, 2H), 7.26 (d, J=2.7 Hz, 1H), 7.24-7.18 (m, 2H), 6.35-6.28 (m, 1H), 5.53 (s, 2H), 5.34 (s, 2H), 4.79 (s, 2H), 3.86 (s, 3H), 2.38 (s, 3H). MS (M+H)$^+$ found for C$_{24}$H$_{24}$N$_8$O: 441.2.

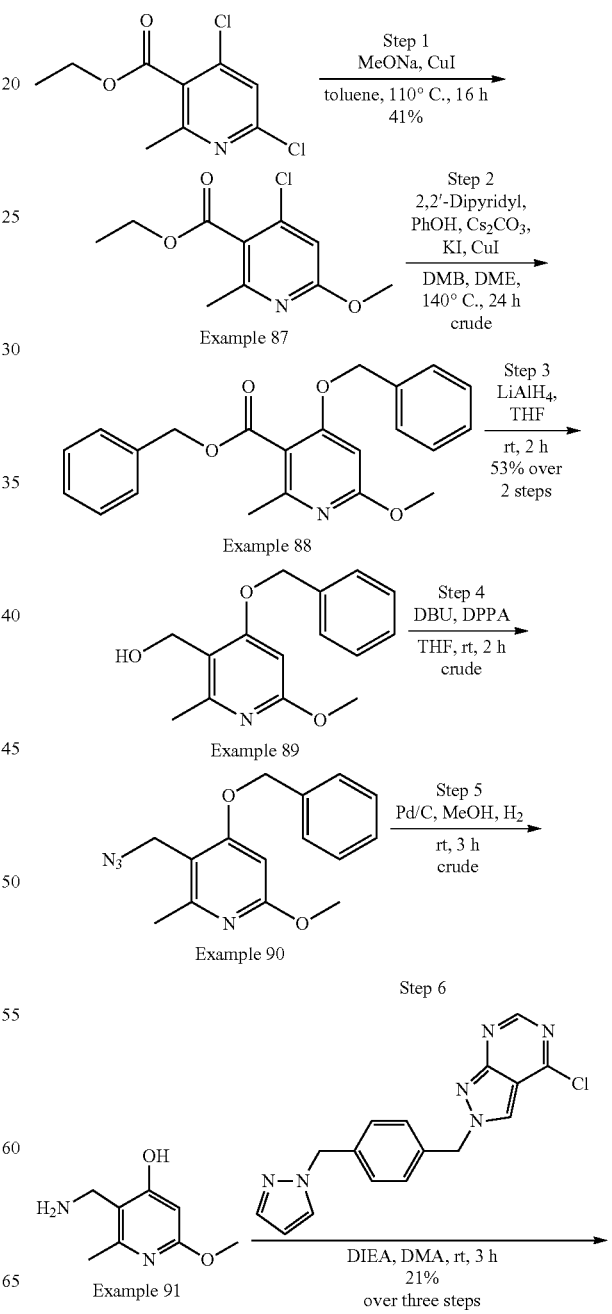

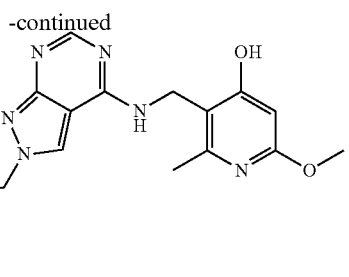

Example 92

Example 87

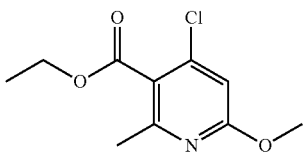

Step 1: ethyl
4-chloro-6-methoxy-2-methylnicotinate

Into a 500-mL round-bottom flask, was placed a mixture of ethyl 4,6-dichloro-2-methylpyridine-3-carboxylate (10.0 g, 42.72 mmol, 1.00 equiv), toluene (200 mL), MeONa (4.60 g, 2.00 equiv), CuI (800 mg, 4.20 mmol, 0.10 equiv). The reaction mixture was stirred at 110° C. for 16 h. The mixture was concentrated under vacuum. The residue was applied onto a silica gel column eluted with ethyl acetate/petroleum ether (1:5). This resulted in 4.00 g (41%) of ethyl 4-chloro-6-methoxy-2-methylpyridine-3-carboxylate as a colorless liquid. LC-MS (ESI) m/z: found for $C_{10}H_{12}ClNO_3$: 230[M+H]$^+$.

Example 88

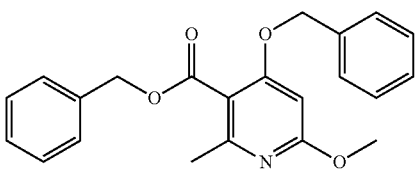 [SMILES: COc1cc(OCc2ccccc2)c(C(=O)OCc2ccccc2)c(C)n1]

Step 2: benzyl 4-(benzyloxy)-6-methoxy-2-methylnicotinate Into a 50-mL round-bottom flask, was placed a mixture of ethyl 4-chloro-6-methoxy-2-methylpyridine-3-carboxylate (2 g, 8.71 mmol, 1.00 equiv)(Example 87), phenylmethanol (9.4 g, 86.93 mmol, 10.00 equiv), xylene (18 mL), ethylene glycol dimethyl ether (2 mL), Cs$_2$CO$_3$ (5.7 g, 17.49 mmol, 2.00 equiv), CuI (170 mg, 0.89 mmol, 0.10 equiv), KI (1.4 g, 1.00 equiv) and 2-(pyridin-2-yl)pyridine (160 mg, 1.02 mmol, 0.12 equiv). The reaction mixture was stirred at 140° C. for 24 h. The reaction mixture was cooled to 25° C. with a water bath and diluted with 50 mL of EA. Then it was filtered over Celite and the filtrate was concentrated under vacuum. This resulted in 2.50 g (crude) of benzyl 4-(benzyloxy)-6-methoxy-2-methylnicotinate as a yellow liquid, which was used in the next step without further purification.

Example 89

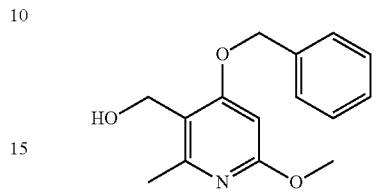

Step 3: (4-(benzyloxy)-6-methoxy-2-methylpyridin-3-yl) methanol Into a 100-mL round-bottom flask, was placed benzyl 4-(benzyloxy)-6-methoxy-2-methylpyridine-3-carboxylate (4.0 g, 11.01 mmol, 1.00 equiv)(Example 88) in tetrahydrofuran (23 mL) with stirring at 0° C., to which was added 2.40 M LiAlH4 THF solution (23 mL, 5.00 equiv) dropwise. The resulting solution was stirred for 2 h at 25° C. The reaction was then quenched by the addition of 4 mL of water and 8 mL of 20% sodium hydroxide aqueous solution. The mixture was then dried over anhydrous sodium sulfate. The residue was applied onto a silica gel column eluted with ethyl acetate/petroleum ether (1:5). This resulted in 1.50 g (53%) of (4-(benzyloxy)-6-methoxy-2-methylpyridin-3-yl) methanol as a yellow liquid. LC-MS (ESI) m/z found for $C_{15}H_{17}NO_3$: 260[M+H]$^+$.

Example 90

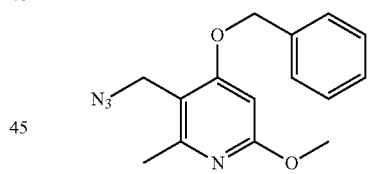

Step 4: 3-(azidomethyl)-4-(benzyloxy)-6-methoxy-2-methylpyridine

Into a 50-mL round-bottom flask, was placed a mixture of [4-(benzyloxy)-6-methoxy-2-methylpyridin-3-yl]methanol (650 mg, 2.51 mmol, 1.00 equiv)(Example 89), tetrahydrofuran (6.5 mL) and DBU (570 mg, 3.74 mmol, 1.50 equiv). The resulting solution was stirred for 10 min at 25° C., to which was added DPPA (830 mg, 3.02 mmol, 1.20 equiv). The resulting solution was stirred for 2 h at 25° C. The reaction mixture was extracted with 10 mL of EA and washed with 3×5 mL of water. The organic phase was dried over anhydrous sodium sulfate and concentrated under vacuum. This resulted in 800 mg (crude) of 3-(azidomethyl)-4-(benzyloxy)-6-methoxy-2-methylpyridine as a yellow liquid. LC-MS (ESI) m/z found for $C_{15}H_{16}N_4O_2$: 285[M+H]$^+$.

Example 91

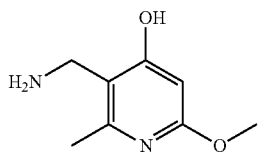

Step 5: 3-(aminomethyl)-6-methoxy-2-methylpyridin-4-ol

Into a 250-mL round-bottom flask, was placed a mixture of 3-(azidomethyl)-4-(benzyloxy)-6-methoxy-2-methylpyridine (350 mg, 1.23 mmol, 1.00 equiv)(Example 90), methanol (35 mL) and 10% palladium on carbon (0.35 g). The reaction solution was purged with hydrogen for 3 times and stirred at 25° C. for 3 h under hydrogen atmosphere. The solids were filtered out and concentrated under vacuum. This resulted in 201 mg (crude) of 3-(aminomethyl)-6-methoxy-2-methylpyridin-4-ol as an off-white solid. LC-MS (ESI) m/z found for $C_8H_{12}N_2O_2$: 169[M+H]$^+$.

Example 92

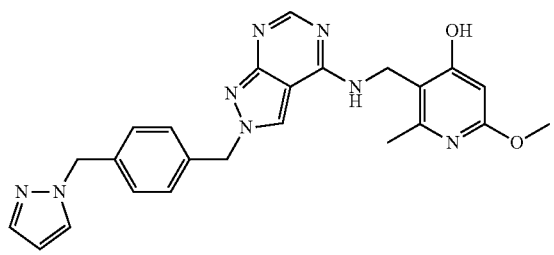 [SMILES: COc1cc(O)c(CNc2ncnc3nn(Cc4ccc(Cn5cccn5)cc4)cc23)c(C)n1]

Step 6: 3-((2-(4-((1H-pyrazol-1-yl)methyl)benzyl)-2H-pyrazolo[3,4-d]pyrimidin-4-ylamino)methyl)-6-methoxy-2-methylpyridin-4-ol Into a 50-mL round-bottom flask, was placed a mixture of 3-(aminomethyl)-6-methoxy-2-methylpyridin-4-ol (100 mg, 0.59 mmol, 1.00 equiv)(Example 91), 1-[[4-([4-chloro-2H-pyrazolo[3,4-d]pyrimidin-2-yl]methyl)phenyl]methyl]-1H-pyrazole (155 mg, 0.48 mmol, 0.80 equiv)(Example 23), DMA (4 mL) and DIEA (230 mg, 1.78 mmol, 3.00 equiv). The resulting solution was stirred for 3 h at 25° C. The solids were filtered out. The liquid was purified by Prep-HPLC with the following conditions. Column: Waters Sunfire C18, 19*150 mm, 5 μm; mobile phase: water (with 0.1% TFA) and acetronitile with a gradient of 10% to 30% acetonitrile in 6 min; flow rate: 20 mL/min; detector UV wavelength: 254 nm. It afforded 56 mg (21%) of 6-methoxy-2-methyl-3-[[(2-[[4-(1H-pyrazol-1-ylmethyl)phenyl]methyl]-2H-pyrazolo[3,4-d]pyrimidin-4-yl)amino]methyl]pyridin-4-ol as a white solid. $^1$H NMR (300 MHz, DMSO-d$_6$): δ11.25 (br, 1H), 9.90 (br, 1H), 8.65-8.62 (m, 2H), 7.82 (s, 1H), 7.48 (s, 1H), 7.44-7.32 (m, 2H), 7.23-7.21 (m, 2H), 6.26 (s, 1H), 5.65 (s, 1H), 5.62 (s, 2H), 5.31 (s, 2H), 4.53-4.51 (m, 2H), 3.75 (s, 3H), 2.22 (s, 3H). LC-MS (ESI) m/z found for $C_{24}H_{24}N_8O_2$: 457[M+H]$^+$.

Example 93

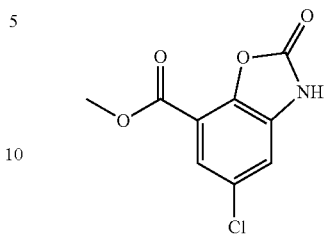

methyl 5-chloro-2-oxo-2,3-dihydrobenzo[d]oxazole-7-carboxylate

Into a 100-mL 3-necked round-bottom flask purged and maintained with an inert atmosphere of nitrogen, was placed a mixture of methyl 3-amino-5-chloro-2-hydroxybenzoate (2 g, 9.92 mmol, 1.00 equiv), tetrahydrofuran (30 mL) and CDI (2.4 g, 14.80 mmol, 1.50 equiv). The resulting solution was refluxed for 3 h. The reaction mixture was cooled to room temperature. Then it was concentrated under vacuum. The residue was extracted with 100 mL of EA. The organic phase was washed with 50 mL of water, 50 mL of 2 M aqueous HCl solution and 100 mL of brine. The organic phase was dried over anhydrous sodium sulfate and concentrated under vacuum. This resulted in 1.75 g (78%) of methyl 5-chloro-2-oxo-2,3-dihydrobenzo[d]oxazole-7-carboxylate as white solid. $^1$H NMR (300 MHz, DMSO-d$_6$): δ 7.48 (s, 1H), 7.39 (s, 1H), 3.90 (s, 3H).

Example 94

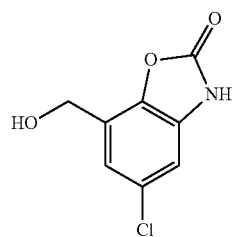 [SMILES: O=c1[nH]c2cc(Cl)cc(CO)c2o1]

5-chloro-7-(hydroxymethyl)-2,3-dihydro-1,3-benzoxazol-2-one

Into a 100-mL 3-necked round-bottom flask purged and maintained with an inert atmosphere of nitrogen, was placed methyl 5-chloro-2-oxo-2,3-dihydro-1,3-benzoxazole-7-carboxylate (700 mg, 3.08 mmol, 1.00 equiv)(Example 93) in tetrahydrofuran (10 mL) with stirring at 0° C., to which was added LiAlH$_4$ (228 mg, 6.01 mmol, 2.00 equiv) in several batches. The resulting solution was stirred for 2 h at room temperature. The reaction was then quenched by the addition of 10 mL of water/ice. The solids were filtered out. The filtrate was extracted with EA (20 mL×3) and washed with 50 mL of brine. The organic phase was dried over anhydrous sodium sulfate and concentrated under vacuum. This resulted in 140 mg (23%) of 5-chloro-7-(hydroxymethyl)-2,3-dihydro-1,3-benzoxazol-2-one as yellow solid. MS (ESI) m/z 198 [M−H]$^−$.

Example 95

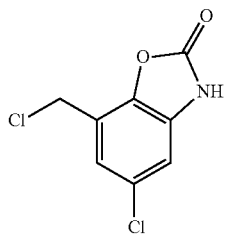 [SMILES: O=c1[nH]c2cc(Cl)cc(CCl)c2o1]

5-chloro-7-(chloromethyl)-2,3-dihydro-1,3-benzoxazol-2-one

Into a 50-mL round-bottom flask purged and maintained with an inert atmosphere of nitrogen, was placed 5-chloro-7-(hydroxymethyl)-2,3-dihydro-1,3-benzoxazol-2-one (140 mg, 0.70 mmol, 1.00 equiv)(Example 94) in dichloromethane (10 mL) with stirring at 0° C., to which was added thionyl chloride (250 mg, 2.10 mmol, 3.00 equiv) at 0° C. The resulting solution was stirred for 2 h at room temperature. The reaction mixture was concentrated under vacuum. This resulted in 130 mg (85%) of 5-chloro-7-(chloromethyl)-2,3-dihydro-1,3-benzoxazol-2-one as yellow solid. MS (ESI) m/z 216 [M−H]⁻.

Example 96

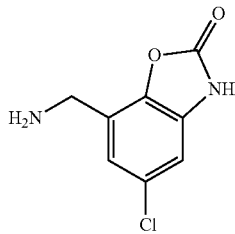 [SMILES: NCc1cc(Cl)cc2[nH]c(=O)oc12]

7-(aminomethyl)-5-chloro-2,3-dihydro-1,3-benzoxazol-2-one Into a 50-mL round-bottom flask purged and maintained with an inert atmosphere of nitrogen, was placed a mixture of 5-chloro-7-(chloromethyl)-2,3-dihydro-1,3-benzoxazol-2-one (120 mg, 0.55 mmol, 1.00 equiv)(Example 95), methanol (5 mL) and 7M ammonia methanol solution (5 mL). The resulting solution was stirred for 2 h at room temperature. The reaction mixture was concentrated under vacuum. This resulted in 80 mg (73%) of 7-(aminomethyl)-5-chloro-2,3-dihydro-1,3-benzoxazol-2-one as yellow solid. MS (ESI) m/z 199 [M+H]⁺.

Example 97

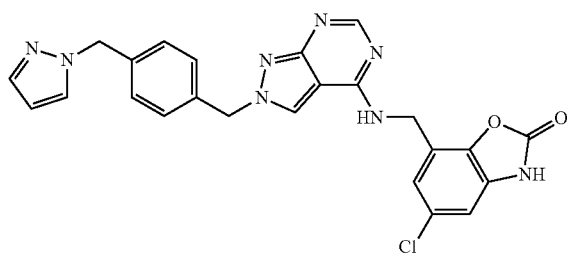 [SMILES: O=c1[nH]c2cc(Cl)cc(CNc3ncnc4nn(Cc5ccc(Cn6cccn6)cc5)cc34)c2o1]

7-((2-(4-((1H-pyrazol-1-yl)methyl)benzyl)-2H-pyrazolo[3,4-d]pyrimidin-4-ylamino)methyl)-5-chlorobenzo[d]oxazol-2(3H)-one Into a 8-mL vial purged and maintained with an inert atmosphere of nitrogen, was placed a solution of 2-(4-((1H-pyrazol-1-yl)methyl)benzyl)-4-chloro-2H-pyrazolo[3,4-d]pyrimidine (58 mg, 0.18 mmol, 1.00 equiv)(Example 23) in N,N-dimethylformamide (5 mL), 7-(aminomethyl)-5-chloro-2,3-dihydro-1,3-benzoxazol-2-one (40 mg, 0.20 mmol, 1.10 equiv)(Example 96) and DIEA (232 mg, 1.80 mmol, 10.00 equiv). The resulting solution was stirred overnight at room temperature. The crude product was purified by Prep-HPLC with the following conditions. Column: Waters X-bridge RP18, 19×150 mm, 5 um; mobile phase: water (0.05% ammonia) and acetonitrile with a gradient of 14% to 19% acetonitrile in 6 min; flow rate: 20 mL/min; detector UV wavelength: 254 nm and 220 nm. This resulted in 7.5 mg (9%) of 7-((2-(4-((1H-pyrazol-1-yl)methyl)benzyl)-2H-pyrazolo[3,4-d]pyrimidin-4-ylamino)methyl)-5-chlorobenzo[d]oxazol-2(3H)-one as white solid. ¹H NMR (300 MHz, DMSO-d): δ 8.66 (br, 1H), 8.36 (s, 1H), 8.22 (s, 1H), 7.79 (d, J=2.1 Hz, 1H), 7.44 (s, 1H), 7.31 (d, J=8.1 Hz, 2H), 7.21 (d, J=8.1 Hz, 2H), 6.98 (m, 2H), 6.25 (t, J=2.1 Hz, 1H), 5.54 (s, 2H), 5.32 (s, 2H), 4.74 (d, J=5.4 Hz, 2H). MS (ESI) m/z found for $C_{24}H_{19}ClN_8O_2$: 487 [M+H]⁺.

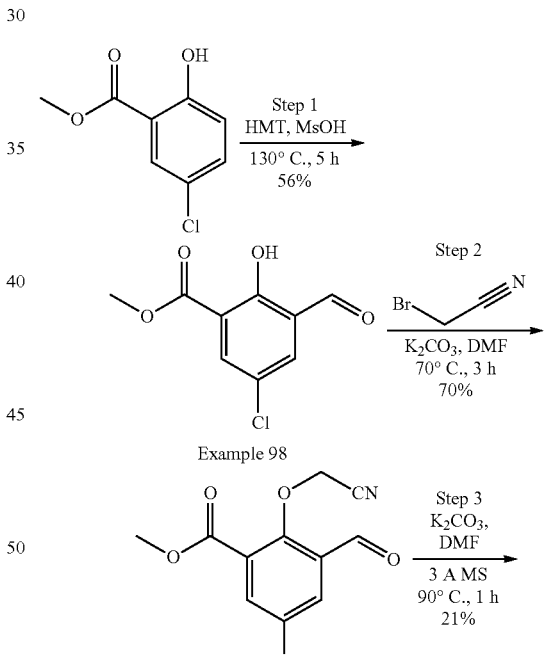

Example 98

Example 99

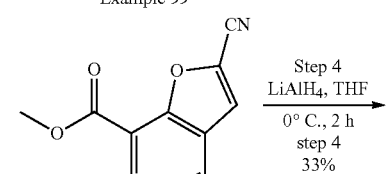

Example 100

137

-continued

Step 5

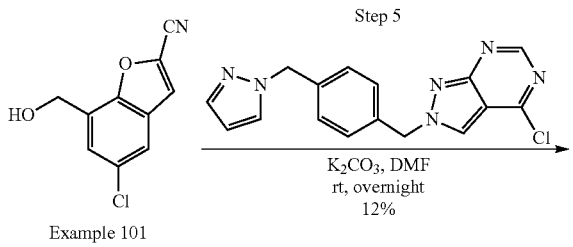

Example 101

K₂CO₃, DMF
rt, overnight
12%

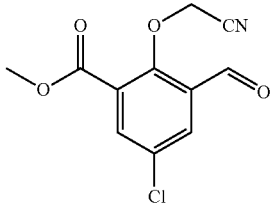

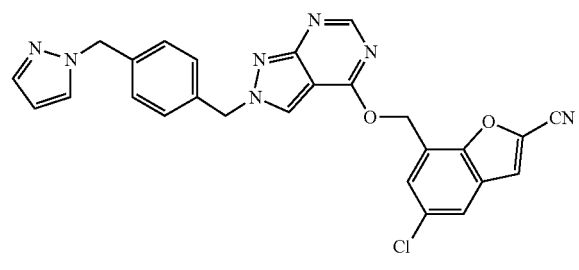

Example 102

Example 98

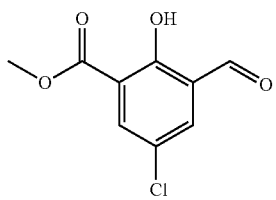

Step 1: methyl 5-chloro-3-formyl-2-hydroxybenzoate

Into a 100-mL 3-necked round-bottom flask purged and maintained with an inert atmosphere of nitrogen, was placed a mixture of MsOH (50 mL) and methyl 5-chloro-2-hydroxybenzoate (5.00 g, 26.80 mmol, 1.00 equiv) at room temperature with stirring at 0° C., to which was added hexamethylenetetramine (7.48 g, 53.36 mmol, 2.00 equiv). The resulting solution was stirred for 5 h at 130° C. in an oil bath. The reaction mixture was cooled to room temperature. The reaction was then quenched by the addition of 50 mL of 1 M HCl aqueous solution. The resulting solution was treated with 200 mL of water and extracted with 3×150 mL of dichloromethane. The organic phase was washed with 150 mL of saturated NaHCO₃ aqueous solution and 2×150 mL of brine. The resulting mixture was dried over anhydrous sodium sulfate and concentrated under vacuum. This resulted in 3.20 g (56%) of methyl 5-chloro-3-formyl-2-hydroxybenzoate as yellow solid. MS (ESI) m/z found for $C_9H_7ClO_4$: 215 $[M+H]^+$.

138

Example 99

Step 2: methyl 5-chloro-2-(cyanomethoxy)-3-formylbenzoate

Into a 250-mL round-bottom flask purged and maintained with an inert atmosphere of nitrogen, was placed a solution of methyl 5-chloro-3-formyl-2-hydroxybenzoate (2.0 g, 9.32 mmol, 1.00 equiv)(Example 98) in N,N-dimethylformamide (100 mL) at room temperature. This was followed by the addition of K₂CO₃ (1.54 g, 11.06 mmol, 1.20 equiv) and 2-bromoacetonitrile (1.67 g, 13.92 mmol, 1.50 equiv). The resulting solution was stirred for 3 h at 70° C. in an oil bath. The reaction mixture was cooled to room temperature and added 150 mL of water. The mixture was extracted with 2×150 mL of ethyl acetate. The organic phase was washed with 2×150 mL of water and 2×150 mL of brine, dried over anhydrous sodium sulfate and concentrated under vacuum. The residue was purified by silica gel column chromatography eluted with ethyl acetate/ petroleum ether (1:6). This resulted in 1.65 g (70%) of methyl 5-chloro-2-(cyanomethoxy)-3-formylbenzoate as white solid.

Example 100

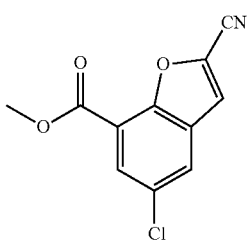 [SMILES: COC(=O)c1cc(Cl)cc2cc(C#N)oc12]

Step 3: methyl 5-chloro-2-cyano-1-benzofuran-7-carboxylate

Into a 250-mL round-bottom flask purged and maintained with an inert atmosphere of nitrogen, was placed a solution of methyl 5-chloro-2-(cyanomethoxy)-3-formylbenzoate (1.65 g, 6.51 mmol, 1.00 equiv)(Example 99) in N,N-dimethylformamide (100 mL) at room temperature. This was followed by the addition of K₂CO₃ (1.79 g, 12.86 mmol, 2.00 equiv) and 3 Å molecular sieves powder (1.00 g). The resulting solution was stirred for 1 h at 90° C. in an oil bath. The reaction mixture was cooled to room temperature and treated with 150 mL of water. Then it was extracted with 2×150 mL of ethyl acetate and washed with 2×150 mL of water and 2×150 mL of brine. The organic phase was dried over anhydrous sodium sulfate and concentrated under vacuum. The residue was purified by silica gel column chromatography eluted with EA: PE (1:15). This resulted in 320 mg (21%) of methyl 5-chloro-2-cyano-1-benzofuran-7-carboxylate as yellow solid. $^1$H NMR (300 MHz, DMSO-$d_6$): δ 8.27 (d, J=2.4 Hz, 1H), 8.18 (s, 1H), 8.04 (d, J=2.1 Hz, 1H), 3.97 (s, 3H).

Example 101

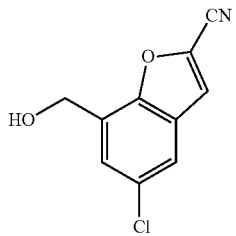 [SMILES: N#Cc1cc2cc(Cl)cc(CO)c2o1]

Step 4: 5-chloro-7-(hydroxymethyl)-1-benzofuran-2-carbonitrile

Into a 100-mL 3-necked round-bottom flask purged and maintained with an inert atmosphere of nitrogen, was placed a solution of methyl 5-chloro-2-cyano-1-benzofuran-7-carboxylate (240 mg, 1.02 mmol, 1.00 equiv)(Example 100) in tetrahydrofuran (80 mL) at room temperature with stirring at 0° C., to which was added LiAlH$_4$ (38.8 mg, 1.02 mmol, 1.00 equiv) in several batches at 0° C. The resulting solution was stirred for 2 h at room temperature. The reaction was then quenched by the addition of 3 mL of water. The solids were filtered out. The filtrate was concentrated under vacuum. The residue was purified by silica gel column chromatography eluted with EA: PE (1:10). This resulted in 70 mg (33%) of 5-chloro-7-(hydroxymethyl)-1-benzofuran-2-carbonitrile as yellow solid. $^1$H NMR (300 MHz, DMSO-$d_6$): δ 8.08 (s, 1H), 7.84 (d, J=2.1 Hz, 1H), 7.58 (d, J=2.1 Hz, 1H), 5.58 (t, J=6.0 Hz, 1H), 4.80 (d, J=6.0 Hz, 2H).

Example 102

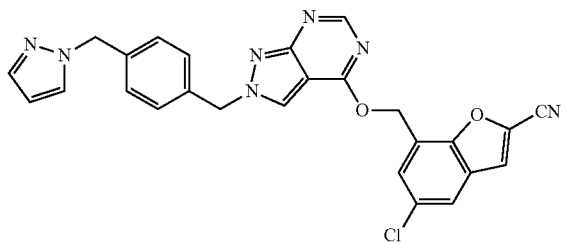 [SMILES: N#Cc1cc2cc(Cl)cc(COc3ncnc4nn(Cc5ccc(Cn6cccn6)cc5)cc34)c2o1]

Step 5: 7-((2-(4-((1H-pyrazol-1-yl)methyl)benzyl)-2H-pyrazolo[3,4-d]pyrimidin-4-yloxy)methyl)-5-chlorobenzofuran-2-carbonitrile Into a 8-mL vial purged and maintained with an inert atmosphere of nitrogen, was placed a solution of 2-(4-((1H-pyrazol-1-yl)methyl)benzyl)-4-chloro-2H-pyrazolo[3,4-d]pyrimidine (39 mg, 0.12 mmol, 1.00 equiv) (Example 23) in N,N-dimethylformamide (3 mL) at room temperature. This was followed by the addition of 5-chloro-7-(hydroxymethyl)-1-benzofuran-2-carbonitrile (25 mg, 0.12 mmol, 1.00 equiv)(Example 101) and K$_2$CO$_3$ (33 mg, 0.24 mmol, 2.00 equiv). The resulting solution was stirred overnight at room temperature. The solids were filtered out. The filtrate was purified by Combi-Flash with the following conditions. Column: C 18, 20-45 um, 100 Å, 120 g; mobile phase: water (0.05% ammonia and 10 mM NH$_4$HCO$_3$) and acetonitrile with a gradient of 10% to 67% acetonitrile in 25 min; flow rate: 60 mL/min; detector UV wavelength: 254 nm and 220 nm. This resulted in 7.2 mg (12%) of 7-((2-(4-((1H-pyrazol-1-yl)methyl)benzyl)-2H-pyrazolo[3,4-d]pyrimidin-4-yloxy)methyl)-5-chlorobenzofuran-2-carbonitrile as yellow solid. $^1$H NMR (300 MHz, DMSO-$d_6$): δ 8.87 (s, 1H), 8.57 (s, 1H), 8.14 (s, 1H), 8.00 (d, J=2.1 Hz, 1H), 7.83 (d, J=2.1 Hz, 1H), 7.78 (d, J=1.8 Hz, 1H), 7.42 (d, J=1.2 Hz, 1H), 7.33 (d, J=8.1 Hz, 2H), 7.18 (d, J=8.1 Hz, 2H), 6.24 (t, J=2.1 Hz, 1H), 5.88 (s, 2H), 5.58 (s, 2H), 5.30 (s, 2H). MS (ESI) m/z found for C$_{26}$H$_{18}$ClN$_7$O$_2$: 496 [M+H]$^+$.

Example 103

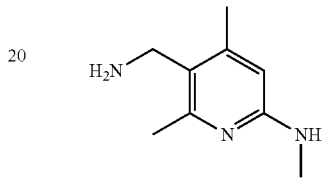

5-(aminomethyl)-N,4,6-trimethylpyridin-2-amine To a solution of LiAlH$_4$ (102 mg, 2.69 mmol, 8.50 equiv) in tetrahydrofuran (20.0 mL) with stirring at 0° C. was added tert-butyl N-[5-(aminomethyl)-4,6-dimethylpyridin-2-yl]-N-[(tert-butoxy)carbonyl]carbamate (111 mg, 0.32 mmol, 1.00 equiv)(Example 4, Step 2). The resulting solution was stirred at 80° C. overnight. The reaction mixture was cooled to room temperature and quenched with 4 mL of ethyl acetate followed by the addition of 1.0 mL of 30% NaOH aqueous solution. The mixture was dried over anhydrous magnesium sulfate. After concentration, it afforded 125 mg (crude) of 5-(aminomethyl)-N,4,6-trimethylpyridin-2-amine as a yellow solid. MS (ESI), m/z found for C$_9$H$_{15}$N$_3$: 166 [M+1]$^+$.

Example 104

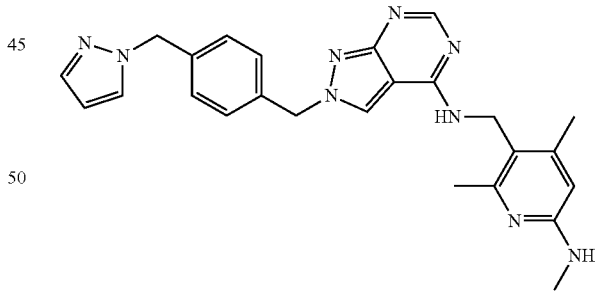

2-(4-((1H-pyrazol-1-yl)methyl)benzyl)-N-((2,4-dimethyl-6-(methylamino)pyridin-3-yl)methyl)-2H-pyrazolo[3,4-d]pyrimidin-4-amine To a solution of 5-(aminomethyl)-N,4,6-trimethylpyridin-2-amine (125 mg crude, 1.20 equiv) (Example 103) in DMA (4.0 mL) were added 1-[[4-([4-chloro-2H-pyrazolo[3,4-d]pyrimidin-2-yl]methyl)phenyl]methyl]-1H-pyrazole (204.5 mg, 0.63 mmol, 1.00 equiv) (Example 23) and DIEA (244 mg, 1.89 mmol, 3.00 equiv). The resulting solution was stirred for 5 h at 50° C. The crude product was purified by Prep-HPLC with the following conditions. Column: Waters XBridge RP18 19*150 mm, 5 μm; mobile phase: CH$_3$CN/water (0.05% NH$_3$.H$_2$O) with a gradient of 30% to 70% acetonitrile in 7 min; flow rate: 20 mL/min; detector UV wavelength: 254 nm. This resulted in 13.3 mg (9%) of N,4,6-trimethyl-5-[[(2-[[4-(1H-pyrazol-1-ylmethyl)phenyl]methyl]-2H-pyrazolo[3,4-d]pyrimidin-4-yl)amino]methyl]pyridin-2-amine as a white solid. $^1$H NMR (300 MHz, DMSO-d$_6$): δ ppm 8.30 (s, 1H), 8.24 (s, 1H), 7.95 (s, 1H), 7.79 (d, J=1.8 Hz, 1H), 7.44 (d, J=1.2 Hz, 1H), 7.30-7.27 (m, 2H), 7.21-7.17 (m, 2H), 6.25-6.24 (m, 1H), 6.18-6.12 (m, 2H), 5.48 (s, 2H), 5.31 (s, 2H), 4.51 (d, J=3.9 Hz, 2H), 2.73 (d, J=4.8 Hz, 3H), 2.50 (d, J=1.5 Hz, 3H), 2.32 (s, 3H). MS (ESI) m/z found for C$_{25}$H$_{27}$N$_9$: 454 [M+H]$^+$.

Example 105

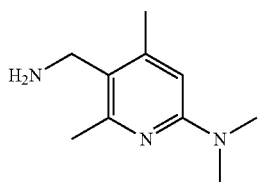

5-(aminomethyl)-N,N,4,6-tetramethylpyridin-2-amine To a solution of LiAlH$_4$ (102 mg, 2.69 mmol, 8.50 equiv) in tetrahydrofuran (20.0 mL) with stirring at 0° C. was added tert-butyl N-[5-(aminomethyl)-4,6-dimethylpyridin-2-yl]-N-[(tert-butoxy)carbonyl]carbamate (111 mg, 0.32 mmol, 1.00 equiv) (Example 4, Step 2). The resulting solution was stirred at 80° C. overnight. The reaction mixture was cooled to room temperature and quenched with 4 mL of ethyl acetate followed with addition of 1.0 mL of 30% NaOH aqueous solution. The mixture was dried over anhydrous magnesium sulfate and stirred vigorously. Then the solids were filtered out and washed with 2×20 mL of tetrahydrofuran. The filtrate was concentrated under vacuum. This resulted in 125 mg (crude) of 5-(aminomethyl)-N,N,4,6-tetramethylpyridin-2-amine as a yellow solid. MS (ESI), m/z found for C$_{10}$H$_{17}$N$_3$: 180 [M+H]$^+$.

Example 106

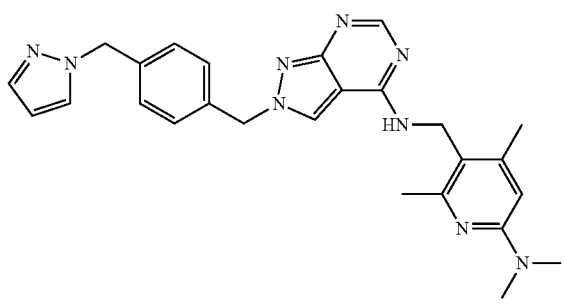 [SMILES: Cc1cc(N(C)C)nc(C)c1CNc1ncnc2nn(Cc3ccc(Cn4cccn4)cc3)cc12]

2-(4-((1H-pyrazol-1-yl)methyl)benzyl)-N-((6-(dimethylamino)-2,4-dimethylpyridin-3-yl)methyl)-2H-pyrazolo[3,4-d]pyrimidin-4-amine To a solution of 5-(aminomethyl)-N,N,4,6-tetramethylpyridin-2-amine (125 mg crude, 1.20 equiv)(Example 105) in DMA (4.0 mL) were added 1-[[4-([4-chloro-2H-pyrazolo[3,4-d]pyrimidin-2-yl]methyl)phenyl]methyl]-1H-pyrazole (204.5 mg, 0.63 mmol, 1.00 equiv)(Example 23) and DIEA (244 mg, 1.89 mmol, 3.00 equiv). The resulting solution was stirred for 5 h at 50° C. The solids were filtered out. The crude product was purified by Prep-HPLC with the following conditions. Column: Waters Atlantis T3 19*150 mm, 51 mm; mobile phase: CH$_3$CN/water (it contains 0.05% TFA) with a gradient of 37% to 67% acetonitrile in 7 min; flow rate: 20 mL/min; detector UV wavelength: 254 nm.

This resulted in 4.1 mg (2.8%) of 2-(4-((1H-pyrazol-1-yl)methyl)benzyl)-N-((6-(dimethylamino)-2,4-dimethylpyridin-3-yl)methyl)-2H-pyrazolo[3,4-d]pyrimidin-4-amine as a light yellow solid. $^1$H NMR (300 MHz, CD$_3$OD): δ ppm 8.64 (s, 1H), 8.29 (s, 1H), 7.66 (d, J=2.1 Hz, 1H), 7.49 (d, J=1.5 Hz, 1H), 7.35-7.32 (m, 2H), 7.20-7.18 (m, 2H), 6.32-6.26 (m, 2H), 5.49 (s, 2H), 5.35 (s, 2H), 5.04 (s, 2H), 3.05 (s, 3H), 2.86 (s, 3H), 2.36 (s, 3H), 2.18 (s, 3H). MS (ESI) m/z found for C$_{26}$H$_{29}$N$_9$: 468 [M+H]$^+$.

Example 107

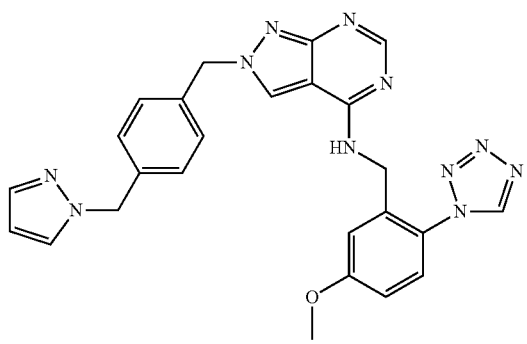 [SMILES: COc1ccc(-n2cnnn2)c(CNc2ncnc3nn(Cc4ccc(Cn5cccn5)cc4)cc23)c1]

2-(4-((1H-pyrazol-1-yl)methyl)benzyl)-N-(5-methoxy-2-(1H-tetrazol-1-yl)benzyl)-2H-pyrazolo[3,4-d]pyrimidin-4-amine 2-(4-((1H-pyrazol-1-yl)methyl)benzyl)-N-(5-methoxy-2-(1H-tetrazol-1-yl)benzyl)-2H-pyrazolo[3,4-d]pyrimidin-4-amine was prepared similar to Example 111. $^1$H NMR (400 MHz, DMSO-d$_6$) δ 9.76 (s, 1H), 8.54 (t, J=5.7 Hz, 1H), 8.29 (s, 1H), 8.07 (s, 1H), 7.81-7.75 (m, 1H), 7.52-7.39 (m, 2H), 7.28 (d, J=8.0 Hz, 2H), 7.19 (d, J=8.1 Hz, 2H), 7.14-7.03 (m, 2H), 6.23 (t, J=2.1 Hz, 1H), 5.51 (s, 2H), 5.30 (s, 2H), 4.44 (d, J=5.6 Hz, 2H), 3.78 (s, 3H). MS (M+H)+ found for C$_{25}$H$_{23}$N$_{11}$O: 494.1.

Example 108

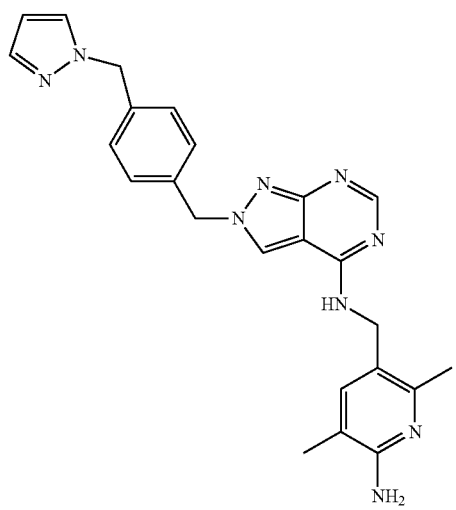 [SMILES: Cc1cc(CNc2ncnc3nn(Cc4ccc(Cn5cccn5)cc4)cc23)c(C)nc1N]

2-(4-((1H-pyrazol-1-yl)methyl)benzyl)-N-((6-amino-2,5-dimethylpyridin-3-yl)methyl)-2H-pyrazolo[3,4-d]pyrimidin-4-amine 1-{[4-({4-chloro-2H-pyrazolo[3,4-d]pyrimidin-2-yl}methyl)phenyl]methyl}-1H-pyrazole (0.10 g; 0.31 mmol; 1.00 eq.)(Example 23) was suspended in 1-butanol (3 ml) and Hunig's base (117.99 ul; 0.68 mmol; 2.20 eq.) 5-(azaniumylmethyl)-3,6-dimethylpyridin-2-aminium dichloride (75.91 mg; 0.34 mmol; 1.10 eq.) (as prepared in WO99/11267, p. 41) was added and the reaction was heated in a microwave reactor at 110° C. for 60 m. The reaction was then evaporated and purified by reverse phase chromatography (acetonitrile gradient with 0.1% aqueous formic acid, Waters XSelect CSH column) to give 2-(4-((1H-pyrazol-1-yl)methyl)benzyl)-N-((6-amino-2,5-dimethylpyridin-3-yl) methyl)-2H-pyrazolo[3,4-d]pyrimidin-4-amine (92 mg) as a white solid. $^1$H NMR (400 MHz, DMSO-d$_6$) δ 10.21 (s, 1H), 8.71 (s, 1H), 8.55 (s, 1H), 7.81 (d, J=2.2 Hz, 1H), 7.77 (s, 1H), 7.65 (s, 2H), 7.44 (d, J=1.8 Hz, 1H), 7.33 (d, J=7.8 Hz, 2H), 7.22 (d, J=7.9 Hz, 2H), 6.25 (t, J=2.1 Hz, 1H), 5.60 (s, 2H), 5.32 (s, 2H), 4.64 (d, J=5.4 Hz, 2H), 2.12 (s, 3H). MS (M+H)$^+$ found for $C_{24}H_{25}N_9$: 440.2.

Example 109

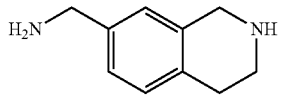

1,2,3,4-tetrahydroisoquinolin-7-ylmethanamine Into a 50-mL round-bottom flask purged and maintained with an inert atmosphere of hydrogen, was placed a mixture of 1,2,3,4-tetrahydroisoquinoline-7-carbonitrile (500 mg, 3.16 mmol, 1.00 equiv), Ni (50 mg) and 10 mL of methanol (it contains 10% of ammonia). The resulted solution was stirred for 4 h at 25° C. The solids were filtered out. The filtrate was concentrated under vacuum. The residue was purified by silica gel column chromatography eluted with dichloromethane and methanol (20:1). This resulted in 210 mg (41%) of 1,2,3,4-tetrahydroisoquinolin-7-ylmethanamine as brown oil. MS (ESI) m/z found for $C_{10}H_{14}N_2$: 163 [M+H]$^+$.

Example 110

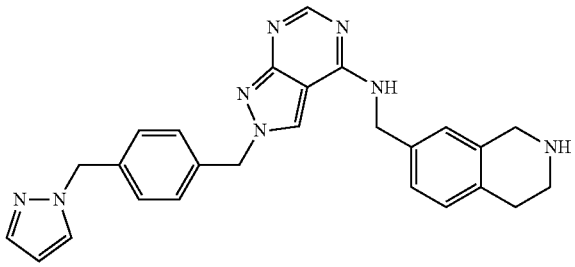 [SMILES: c1cnn(Cc2ccc(Cn3cc4c(NCc5ccc6c(c5)CNCC6)ncnc4n3)cc2)c1]

2-[[4-(1H-pyrazol-1-ylmethyl)phenyl]methyl]-N-(1,2,3,4-tetrahydroisoquinolin-7-ylmethyl)-2H-pyrazolo[3,4-d]pyrimidin-4-amine Into a 10-mL round-bottom flask, was placed a mixture of 1,2,3,4-tetrahydroisoquinolin-7-ylmethanamine (60 mg, 0.37 mmol, 1.20 equiv)(Example 109), DMA (5 mL), DIEA (200 mg, 1.55 mmol, 5.00 equiv) and 1-[[4-([4-chloro-2H-pyrazolo[3,4-d]pyrimidin-2-yl]methyl) phenyl]methyl]-1H-pyrazole (100 mg, 0.31 mmol, 1.00 equiv)(Example 23). The resulted solution was stirred for 2 h at 80° C. The residue was purified by Prep-HPLC with the following conditions. Column: Waters X-bridge RP18 19×150 mm, 5 um; mobile phase: CH$_3$CN/H$_2$O (it contains 0.05% ammonia) with a gradient of acetonitrile from 25% to 35% in 10 min; flow rate: 20 mL/min; detector UV wavelength: 254 nm and 220 nm. This resulted in 76.6 mg (55%) of 2-[[4-(1H-pyrazol-1-ylmethyl)phenyl]methyl]-N-(1,2,3,4-tetrahydroisoquinolin-7-ylmethyl)-2H-pyrazolo[3,4-d]pyrimidin-4-amine as off-white solid. $^1$H NMR (300 MHz, DMSO-d$_6$): δ 9.00 (br, 1H), 8.24 (s, 1H), 7.79 (d, J=2.4 Hz, 1H), 7.43 (s, 1H), 7.18-7.33 (m, 8H), 6.25 (d, J=1.8 Hz, 1H), 5.53 (s, 2H), 5.31 (s, 2H), 5.01 (s, 2H), 4.07 (br, 2H), 3.71 (s, 2H), 2.97 (br, 2H). MS (ESI) m/z found for $C_{26}H_{26}N_8$: 451 [M+H]$^+$.

Example 111

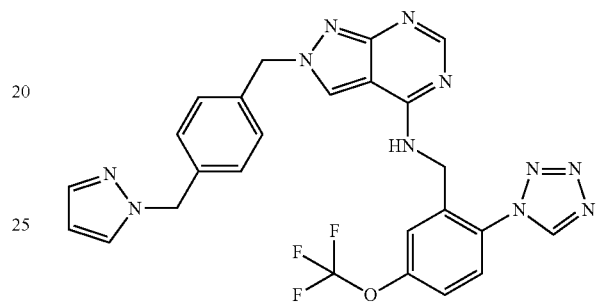

2-(4-((1H-pyrazol-1-yl)methyl)benzyl)-N-(2-(1H-tetrazol-1-yl)-5-(trifluoromethoxy)benzyl)-2H-pyrazolo[3,4-d]pyrimidin-4-amine 2-(4-((1H-pyrazol-1-yl)methyl)benzyl)-N-(2-(1H-tetrazol-1-yl)-5-(trifluoromethoxy)benzyl)-2H-pyrazolo[3,4-d]pyrimidin-4-amine was prepared in a similar manner as Example 170. $^1$H NMR (400 MHz, DMSO-d$_6$) δ 9.89 (s, 1H), 8.62 (t, J=5.8 Hz, 1H), 8.29 (s, 1H), 8.07 (s, 1H), 7.80-7.71 (m, 2H), 7.56 (d, J=7.9 Hz, 2H), 7.42 (d, J=1.7 Hz, 1H), 7.28 (d, J=8.0 Hz, 2H), 7.19 (d, J=8.0 Hz, 2H), 6.23 (t, J=2.0 Hz, 1H), 5.52 (s, 2H), 5.30 (s, 2H), 4.55 (d, J=5.6 Hz, 2H). MS (M+H)+ found for $C_{26}H_{20}F_3N_{10}O_2$: 548.1.

Example 112

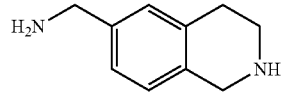 [SMILES: NCc1ccc2c(c1)CCNC2]

1,2,3,4-tetrahydroisoquinolin-6-ylmethanamine

Into a 50-mL round-bottom flask purged and maintained with an inert atmosphere of hydrogen, was placed a mixture of 3-(2-aminoethyl)-4-(chloromethyl)benzonitrile (500 mg, 2.57 mmol, 1.00 equiv), Ni (50 mg) and 10 mL of methanol (it contains 10% of ammonia). The resulted solution was stirred for 4 h at 25° C. The solids were filtered out. The filtrate was concentrated under vacuum. The residue was purified by silica gel column chromatography eluted with dichloromethane and methanol (20:1). This resulted in 230

Example 113

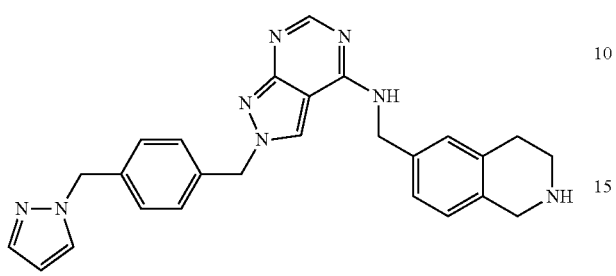

2-[[4-(1H-pyrazol-1-ylmethyl)phenyl]methyl]-N-(1,2,3,4-tetrahydroisoquinolin-6-ylmethyl)-2H-pyrazolo[3,4-d]pyrimidin-4-amine Into a 10-mL round-bottom flask, was placed a mixture of 1,2,3,4-tetrahydroisoquinolin-6-ylmethanamine (60 mg, 0.37 mmol, 1.20 equiv)(Example 112), DMA (5 mL), DIEA (200 mg, 1.55 mmol, 5.00 equiv) and 1-[[4-([4-chloro-2H-pyrazolo[3,4-d]pyrimidin-2-yl]methyl)phenyl]methyl]-1H-pyrazole (100 mg, 0.31 mmol, 1.00 equiv)(Example 23). The resulted solution was stirred for 2 h at 80° C. The resulted mixture was concentrated under vacuum. The residue was purified by silica gel column chromatography eluted with dichloromethane and methanol (1:1). This resulted in 7.0 mg (5%) of 2-[[4-(1H-pyrazol-1-ylmethyl)phenyl]methyl]-N-(1,2,3,4-tetrahydroisoquinolin-6-ylmethyl)-2H-pyrazolo[3,4-d]pyrimidin-4-amine as off-white solid. $^1$H NMR (300 MHz, DMSO-d$_6$): δ 9.05 (br, 1H), 8.27 (br, 4H), 7.79 (d, J=2.1 Hz, 1H), 7.31-7.44 (m, 6H), 7.20 (d, J=8.1 Hz, 2H), 6.25 (t, J=2.1 Hz, 1H), 5.54 (s, 2H), 5.31 (s, 2H), 5.04 (s, 2H), 4.09 (br, 2H), 4.01 (br, 2H), 3.01 (br, 2H). MS (ESI) m/z found for C$_{26}$H$_{26}$N$_8$: 451 [M+H]$^+$.

Example 114

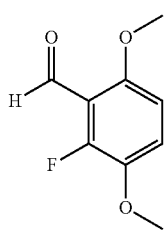

2-fluoro-3,6-dimethoxybenzaldehyde

Into a 500-mL 3-necked round-bottom flask, was placed a solution of 2-fluoro-1,4-dimethoxybenzene (9.4 g, 60.20 mmol, 1.00 equiv) in THF (200 mL). The solution was stirred at −78° C. with stirring, to which was added a solution of n-BuLi/hexane (26.5 mL, 66.3 mmol, 1.10 equiv) dropwise with stirring at −78° C. The resulted solution was stirred for 1 h at −78° C. Then to it was added a solution of N,N-dimethylformamide (8.80 g, 120.40 mmol, 2.00 equiv) in tetrahydrofuran (20 mL) dropwise with stirring at −78° C. After the addition, the reaction solution was allowed to warm up to room temperature and stirred for 2 h. The reaction was quenched by the addition of 100 mL of water. The reaction mixture was extracted with 400 mL of ethyl acetate. The organic layers were combined, washed with 100 mL of brine, dried over anhydrous sodium sulfate and concentrated under vacuum. This resulted in 12.0 g (crude) of 2-fluoro-3,6-dimethoxybenzaldehyde as a yellow solid. LC-MS (ESI) m/z: found for C$_9$H$_9$FO$_3$: 185 [M+H]$^+$.

Example 115

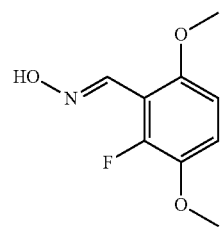

(E)-N-[(2-fluoro-3,6-dimethoxyphenyl)methylidene]hydroxylamine Into a 250-m L round-bottom flask, was placed a mixture of 2-fluoro-3,6-dimethoxybenzaldehyde (12.0 g, 65.2 mmol, 1.00 equiv)(Example 114), ethanol (200 mL), sodium carbonate (10.4 g, 97.8 mmol, 1.50 equiv) and hydroxylamine hydrochloride (13.5 g, 194.3 mmol, 3.00 equiv). The resulted solution was stirred for 0.5 h at room temperature. After concentration under vacuum, the residue was suspended in H$_2$O (100 mL) and extracted with 2×200 mL of ethyl acetate. The organic phase was washed with 3×100 mL of brine, dried over anhydrous sodium sulfate and concentrated under vacuum. This resulted in 12 g (92%) of crude (E)-N-[(2-fluoro-3,6-dimethoxyphenyl)methylidene]hydroxylamine as a white solid.

Example 116

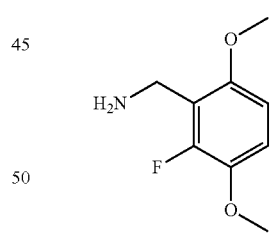

(2-fluoro-3,6-dimethoxyphenyl)methanamine

Into a 500-mL round-bottom flask, was placed a mixture of crude (E)-N-[(2-fluoro-3,6-dimethoxyphenyl)methylidene]hydroxylamine (12.0 g, 60.3 mmol, 1.00 equiv)(Example 115), ethanol (250 mL), ammonia (25 mL) and Raney-Ni (15 g) under nitrogen atmosphere. The reaction mixture was purged with hydrogen for three times. The mixture was stirred for 1 h at room temperature under an atmosphere of hydrogen (balloon). The solids were filtered out through a pad of Celite. The filtrate was concentrated under vacuum. The residue was purified by silica gel column eluted with dichloromethane/methanol=10/1. This resulted in 2.0 g (18%) of (2-fluoro-3,6-dimethoxyphenyl)methanamine as yellow oil. $^1$H NMR (300 MHz, CDCl$_3$): δ 6.81 (t, J=9.0 Hz, 1H), 6.57 (dd, J=9.0 Hz, J=1.8 Hz, 1H), 3.89 (s, 2H), 3.85 (s, 3H), 3.83 (s, 3H).

LC-MS (ESI) m/z: found for C$_9$H$_{12}$FNO$_2$:186 [M+H]$^+$.

Example 117

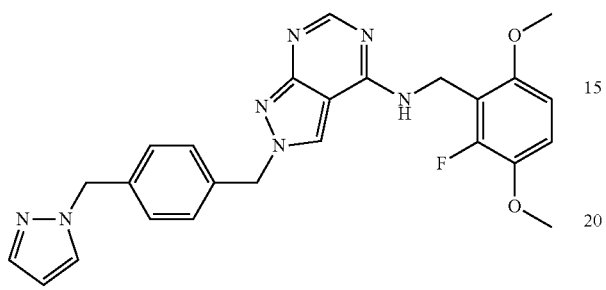

N-[(2-fluoro-3,6-dimethoxyphenyl)methyl]-2-[[4-(1H-pyrazol-1-ylmethyl)phenyl]methyl]-2H-pyrazolo[3,4-d]pyrimidin-4-amine Into an 8-mL vial, was placed a mixture of 1-[[4-([4-chloro-2H-pyrazolo[3,4-d]pyrimidin-2-yl]methyl)phenyl]methyl]-1H-pyrazole (175 mg, 0.54 mmol, 1.00 equiv) (Example 23), DMA (3 mL), DIEA (174 mg, 1.35 mmol, 2.50 equiv) and (2-fluoro-3,6-dimethoxyphenyl)methanamine (100 mg, 0.54 mmol, 1.00 equiv)(Example 116). The resulted solution was stirred for 1 h at 80° C. The crude product (100 mg) was purified by Prep-HPLC with the following conditions: Column: Waters XBridge C18, 19*150 mm, 5 μm; mobile phase: water (it contains 10 mmol NH$_4$HCO$_3$+0.013% NH$_3$·H$_2$O) and acetonitrile with a gradient of 40% to 45% acetonitrile in 8 min; flow rate: 20 mL/min, detector UV wavelength: 254 nm. This resulted in 66.6 mg (26%) of N-[(2-fluoro-3,6-dimethoxyphenyl)methyl]-2-[[4-(1H-pyrazol-1-ylmethyl)phenyl]methyl]-2H-pyrazolo[3,4-d]pyrimidin-4-amine as a white solid. $^1$H NMR (300 MHz, DMSO-d6): δ 8.31 (s, 1H), 8.24 (s, 1H), 8.14 (s, 1H), 7.79 (d, J=2.1 Hz, 1H), 7.44 (d, J=1.5 Hz, 1H), 7.28 (d, J=8.1 Hz, 2H), 7.20 (d, J=8.1 Hz, 2H), 7.10 (t, J=9.0 Hz, 1H), 6.82-6.79 (m, 1H), 6.25 (t, J=2.1 Hz, 1H), 5.50 (s, 2H), 5.31 (s, 2H), 4.63 (d, J=3.0 Hz, 2H), 3.79 (s, 3H), 3.75 (s, 3H). LC-MS (ESI) m/z: found for C$_{25}$H$_{24}$FN$_7$O: 474 [M+H]$^+$.

Example 118

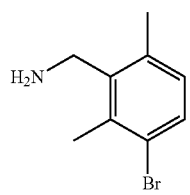

(3-bromo-2,6-dimethylphenyl)methanamine Into a 8-mL sealed tube, was placed a mixture of (2,6-dimethylphenyl)methanamine (100 mg, 0.74 mmol, 1.00 equiv), benzyltrimethylazanium tribroman-2-uide (288 mg, 0.74 mmol, 1.00 equiv), ZnCl$_2$ (121 mg, 0.89 mmol, 1.20 equiv) and AcOH (2.0 mL). The resulted reaction was stirred for 16 hours at 50° C. in an oil bath. The mixture was diluted with 20 mL of 2N sodium hydroxide aqueous solution and extracted with 3×20 mL of ethyl acetate. The organic phase was washed with 1×30 mL of brine, dried over anhydrous sodium sulfate and concentrated under vacuum. This resulted in 165 mg (crude product) of (3-bromo-2,6-dimethylphenyl)methanamine as a yellow oil, which was used directly for the next step reaction without purification. MS (ESI) m/z found for C$_9$H$_{12}$BrN: 255 [M+CH$_3$CN+H]$^+$.

Example 119

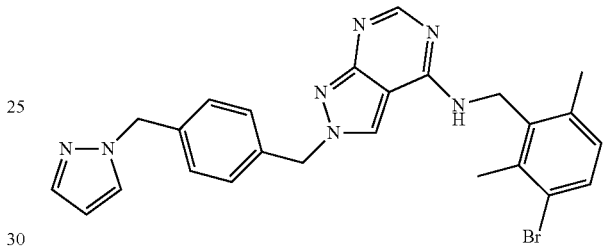

N-[(3-bromo-2,6-dimethylphenyl)methyl]-2-[[4-(1H-pyrazol-1-ylmethyl)phenyl]methyl]-2H-pyrazolo[3,4-d]pyrimidin-4-amine Into a 4-mL vial, was placed a mixture of (3-bromo-2,6-dimethylphenyl)methanamine (50 mg, 0.23 mmol, 1.00 equiv)(Example 118), 1-[4-(4-chloro-2H-pyrazolo[3,4-d]pyrimidin-2-ylmethyl)phenyl]methyl-1H-pyrazole (76 mg, 0.23 mmol, 1.00 equiv)(Example 23), DIEA (303 mg, 2.34 mmol, 10.00 equiv) and DMA (1.0 mL). The resulted mixture was stirred for 2 h at 20° C. The resulting mixture was concentrated under vacuum to give a residue. The crude was directly purified by Prep-HPLC with the following conditions. Column: X Bridge C18, 19*150 mm, 5 um; mobile phase: water (it contains 10 mM NH$_4$HCO$_3$+0.05% NH$_3$.H$_2$O) and acetonitrile with a gradient of 60% to 65% acetonitrile in 8 min; flow rate: 20 mL/min; detector UV wavelength: 220 nm. The collected HPLC fractions were concentrated under reduced pressure and lyophilized to afford 30.9 mg (42%) of N-[(3-bromo-2,6-dimethylphenyl)methyl]-2-[[4-(1H-pyrazol-1-ylmethyl)phenyl]methyl]-2H-pyrazolo[3,4-d]pyrimidin-4-amine as a white solid. $^1$H-NMR (300 MHz, CD$_3$OD): δ 8.34 (s, 1H), 8.23 (s, 1H), 7.68 (d, J=2.4 Hz, 1H), 7.51-7.45 (m, 2H), 7.32 (d, J=7.8 Hz, 2H), 7.21 (d, J=8.1 Hz, 2H), 7.02 (d, J=8.4 Hz, 1H), 6.34-6.32 (m, 1H), 5.51 (s, 2H), 5.35 (s, 2H), 4.81 (s, 2H), 2.47 (s, 3H), 2.37 (s, 3H). MS (ESI) m/z found for C$_{25}$H$_{24}$BrN$_7$: 502 [M+H]$^+$.

Example 120

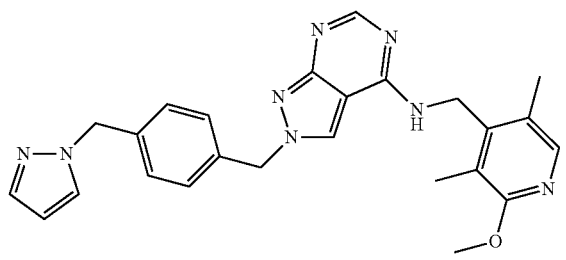 [SMILES: COc1ccc(C)c(CNc2ncnc3nn(Cc4ccc(Cn5cccn5)cc4)cc23)c1C]

N-[(2-methoxy-3,5-dimethylpyridin-4-yl)methyl]-2-
[[4-(1H-pyrazol-1-ylmethyl)phenyl]methyl]-2H-
pyrazolo[3,4-d]pyrimidin-4-amine N-[(2-methoxy-3,5-dimethylpyridin-4-yl)methyl]-2-[[4-(1H-pyrazol-1-ylmethyl)phenyl]methyl]-2H-pyrazolo[3,4-d]pyrimidin-4-amine was prepared in the same manner as Example 119. $^1$H NMR (300 MHz, DMSO-$d_6$): δ 8.27 (s, 2H), 8.12 (brs, 1H), 7.85 (s, 1H), 7.79 (d, J=1.8 Hz, 1H), 7.44 (s, 1H), 7.29 (d, J=7.9 Hz, 2H), 7.20 (d, J=7.9 Hz, 2H), 6.25 (t, J=1.8 Hz, 1H), 5.50 (s, 2H), 5.31 (s, 2H), 4.63 (d, J=4.8 Hz, 2H), 3.85 (s, 3H), 2.22 (s, 3H), 2.17 (s, 3H) ppm. MS (ESI) m/z 455 [M+H]$^+$.

Example 121

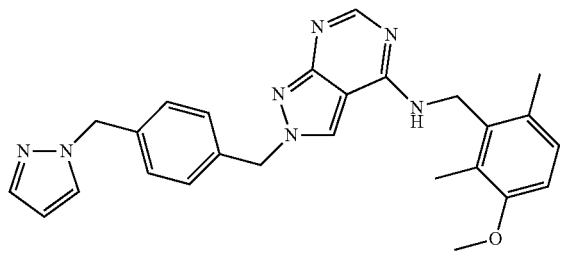

N-[(3-methoxy-2,6-dimethylphenyl)methyl]-2-[[4-(1H-pyrazol-1-ylmethyl)phenyl]methyl]-2H-pyrazolo[3,4-d]pyrimidin-4-amine N-[(3-methoxy-2,6-dimethylphenyl)methyl]-2-[[4-(1H-pyrazol-1-ylmethyl)phenyl]methyl]-2H-pyrazolo[3,4-d]pyrimidin-4-amine was prepared in the same manner as Example 119. $^1$H NMR (300 MHz, CD$_3$OD): δ 8.33 (s, 1H), 8.25 (s, 1H), 7.68 (d, J=2.1 Hz, 1H), 7.51 (d, J=1.5 Hz, 1H), 7.31 (d, J=8.1 Hz, 2H), 7.20 (d, J=8.1 Hz, 2H), 7.05 (d, J=8.4 Hz, 1H), 6.84 (d, J=8.4 Hz, 1H), 6.33-6.32 (m, 1H), 5.50 (s, 2H), 5.35 (s, 2H), 4.73 (s, 2H), 3.81 (s, 3H), 2.31 (s, 3H), 2.22 (s, 3H) ppm. MS (ESI) m/z 454 [M+H]$^+$.

Example 122

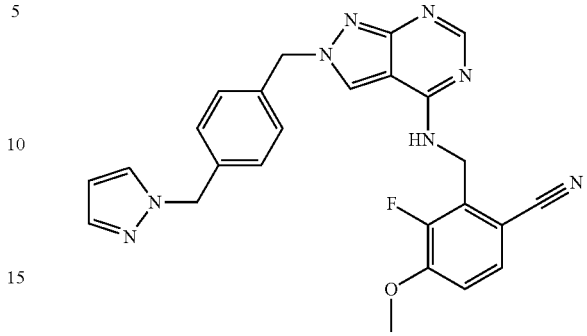

2-(((2-(4-((1H-pyrazol-1-yl)methyl)benzyl)-2H-
pyrazolo[3,4-d]pyrimidin-4-yl)amino)methyl)-3-
fluoro-4-methoxybenzonitrile 2-(4-((1H-pyrazol-1-yl)methyl)benzyl)-N-(6-chloro-2-fluoro-3-methoxybenzyl)-2H-pyrazolo[3,4-d]pyrimidin-4-amine (30.00 mg; 0.06 mmol; 1.00 eq.)(Example 23), Pd$_2$(dba)$_3$ (1.15 mg; 0.00 mmol; 0.02 eq.), 2-(dicyclohexylphosphino)-2',6'-dimethoxy-1,1'-biphenyl (1.03 mg; 0.00 mmol; 0.04 eq.), zinc dicarbonitrile (4.42 mg; 0.04 mmol; 0.60 eq.) in N-Methyl-2-pyrrolidinone (2.00 ml) were in a microwave vial. Bubbled N$_2$ for 2 minutes and capped the vial. Heated the reaction to 150° C. for 2 hours. Filtered thru a plug of Celite. Purified by prep HPLC to afford 2-(((2-(4-((1H-pyrazol-1-yl)methyl)benzyl)-2H-pyrazolo[3,4-d]pyrimidin-4-yl)amino)methyl)-3-fluoro-4-methoxybenzonitrile (3 mgs; 10%). $^1$H NMR (400 MHz, DMSO-$d_6$) δ 8.55 (s, 1H), 8.38 (s, 1H), 7.77 (d, J=2.2 Hz, 1H), 7.48-7.29 (m, 4H), 7.23-7.13 (m, 3H), 6.22 (t, J=2.1 Hz, 1H), 5.63 (s, 2H), 5.42 (s, 2H), 5.29 (s, 2H), 3.94 (s, 3H). MS (M+H)+ found for C$_{25}$H$_{21}$FN$_8$O: 469.1.

Example 123

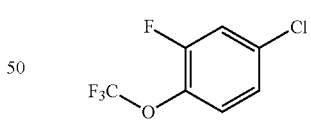

4-chloro-2-fluoro-1-(trifluoromethoxy) benzene Into a 250-mL round-bottom flask, was placed a mixture of 4-bromo-2-fluoro-1-(trifluoromethoxy)benzene (10.0 g, 38.61 mmol, 1.00 equiv), N,N-dimethylformamide (100 mL) and CuCl (38.2 g, 386.1 mmol, 10.00 equiv). The reaction mixture was stirred for 16 h at 150° C. under nitrogen atmosphere. After concentration, the residue was diluted with 100 mL of water and extracted with 3×100 mL of ether. The organic phase was dried over anhydrous sodium sulfate and concentrated under vacuum. This resulted in 2.8 g (34%) of 4-chloro-2-fluoro-1-(trifluoromethoxy)benzene as light yellow oil. $^1$H NMR (300 MHz, CDCl$_3$, ppm): δ 7.27-7.21 (m, 2H), 7.17-7.13 (m, 1H).

Example 124

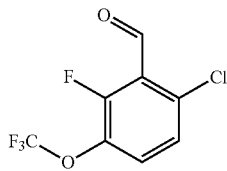 [SMILES: O=Cc1c(Cl)ccc(OC(F)(F)F)c1F]

6-chloro-2-fluoro-3-(trifluoromethoxy) benz aldehyde To a solution of 4-chloro-2-fluoro-1-(trifluoromethoxy)benzene (6.0 g, 27.97 mmol, 1.00 equiv)(Example 123) in tetrahydrofuran (100 mL) with stirring at −78° C. was added 2.0 M LDA (16.8 mL, 33.56 mmol, 1.20 equiv) THF solution dropwise. The reaction solution was stirred for 30 minutes at −78° C. and then DMF (4.1 g, 56.10 mmol, 2.00 equiv) was added dropwise to the solution. The resulted solution was stirred for 1 h at −78° C. The reaction was quenched by the addition of water (50 mL) and then extracted with 3×100 mL of ethyl acetate. The combined organic phase was dried over anhydrous sodium sulfate and concentrated under vacuum to give a residue. The crude was purified by silica gel column eluted with ethyl acetate/petroleum ether (1:5). This resulted in 4.5 g (66%) of 6-chloro-2-fluoro-3-(trifluoromethoxy) benz aldehyde as a light yellow solid.

$^1$H NMR (300 MHz, CDCl$_3$): δ 10.43 (s, 1H), 7.50 (t, J=8.1 Hz, 1H), 7.34 (dd, J=9.0 Hz, J=1.8 Hz).

Example 125

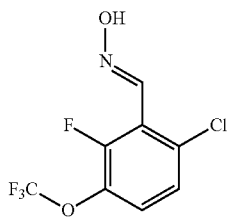 [SMILES: O/N=C/c1c(Cl)ccc(OC(F)(F)F)c1F]

(E)-N-[[6-chloro-2-fluoro-3-(trifluoromethoxy) phenyl]methylidene]hydroxylamine Into an 100-mL round-bottom flask, was placed a mixture of 6-chloro-2-fluoro-3-(trifluoromethoxy) benzaldehyde (4.9 g, 20.20 mmol, 1.00 equiv) (Example 124), ethanol/H$_2$O (60 mL, V/V=5/1), concentrated ammonia (4.2 mL, 60.43 mmol, 3.00 equiv) and sodium carbonate (3.2 g, 30.19 mmol, 1.50 equiv). The mixture was stirred for 16 h at room temperature. Then it was concentrated to give a residue, which was diluted with 100 mL of ethyl acetate and washed with 3×30 mL of brine. The organic phase was dried over anhydrous sodium sulfate and concentrated under vacuum. The residue was purified by silica gel column eluted with ethyl acetate/ petroleum ether (1/1). This resulted in 3.9 g (75%) of (E)-N-[[6-chloro-2-fluoro-3-(trifluoromethoxy)phenyl]methylidene]hydroxylamine as light yellow solids. LC-MS (ESI) m/z: calculated for C$_8$H$_4$ClF$_4$NO$_2$: 256.99; found: 299 [M+H+CH$_3$CN]$^+$. Rt: 1.51 min.

Example 126

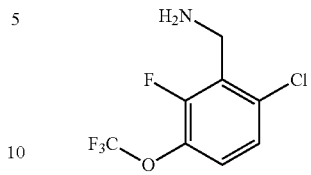

[6-chloro-2-fluoro-3-(trifluoromethoxy)phenyl] methanamine

Into a 100-mL round-bottom flask, was placed a mixture of (E)-N-[[6-chloro-2-fluoro-3-(trifluoromethoxy) phenyl]methylene]hydroxylamine (4.0 g, 15.52 mmol, 1.00 equiv) (Example 125), AcOH (50 mL) and Zn (10.0 g, dust, 152.2 mmol, 10.00 equiv). The mixture was stirred for 16 h at 60° C. After concentration, the residue was diluted with 50 mL of water and then extracted with 3×100 mL of dichloromethane. The organic phase was dried over anhydrous sodium sulfate and concentrated under vacuum. The residue was purified by silica gel column eluted with dichloromethane/ methanol (100/1). This resulted in 2.04 g (54%) of [6-chloro-2-fluoro-3-(trifluoromethoxy)phenyl]methanamine as yellow oil. $^1$H NMR (300 MHz, CDCl$_3$): δ 7.24-7.15 (m, 2H), 4.04 (s, 2H). LC-MS (ESI) m/z: calculated for C$_8$H$_6$ClF$_4$NO: 243.01; found: 285 [M+H+CH$_3$CN]$^+$.

Example 127

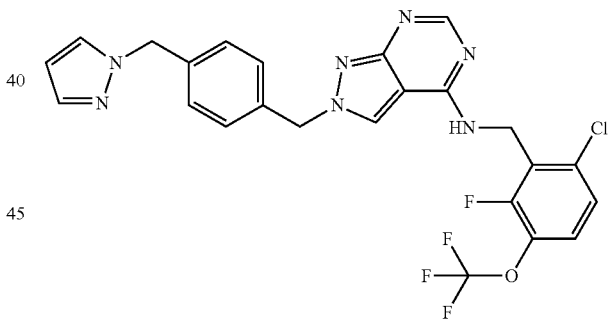

N-[[6-chloro-2-fluoro-3-(trifluoromethoxy)phenyl]methyl]-2-[[4-(1H-pyrazol-1-ylmethyl)phenyl]methyl]-2H-pyrazolo[3,4-d]pyrimidin-4-amine Into an 8-mL vial, was placed a mixture of [6-chloro-2-fluoro-3-(trifluoromethoxy)phenyl]methanamine (90 mg, 0.37 mmol, 1.20 equiv)(Example 126), DMA (2 mL), 1-[4-(4-chloro-2H-pyrazolo[3,4-d]pyrimidin-2-ylmethyl)phenyl]methyl-1H-pyrazole (100 mg, 0.31 mmol, 1.00 equiv)(Example 23) and DIEA (80 mg, 0.62 mmol, 2.00 equiv). The resulted solution was stirred for 2 h at 80° C. The mixture was diluted with 2 mL of methanol. After filtration, the filtrate was purified by Prep-HPLC with the following conditions. Column: Waters XBridge C18, 19*150 mm, 5 µm; mobile phase: water (it contains 10 mmol NH$_4$HCO$_3$+ 0.05% ammonia) and acetonitrile with a gradient of 45% to 55% acetonitrile in 8 min; flow rate: 20 mL/min, detector UV wavelength: 254 nm. This resulted in 66.8 mg (41%) of N-[[6-chloro-2-fluoro-3-(trifluoromethoxy)phenyl]methyl]-2-[[4-(1H-pyrazol-1-ylmethyl)phenyl]methyl]-2H-pyrazolo[3,4-d]pyrimidin-4-amine as a yellow solid. $^1$H NMR (300 MHz, DMSO-$d_6$): δ 8.43 (s, 1H), 8.29 (s, 1H), 8.25 (s, 1H), 7.80 (s, 1H), 7.64 (t, J=8.4 Hz, 1H), 7.51 (d, J=9.0 Hz, 1H), 7.44 (s, 1H), 7.30 (d, J=8.1 Hz, 2H), 7.20 (d, J=7.8 Hz, 1H), 6.25 (s, 1H), 5.52 (s, 2H), 5.32 (s, 2H), 4.81 (d, J=3.3 Hz, 2H). LC-MS (ESI) m/z: calculated for $C_{24}H_{18}ClF_4N_7O$: 531.12; found: 532 [M+H]$^+$.

Example 128

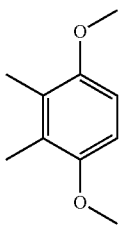

1,4-dimethoxy-2,3-dimethylbenzene

Into a 100-mL 3-necked round-bottom flask, was placed a mixture of 2,3-dimethylbenzene-1,4-diol (2.5 g, 18.09 mmol, 1.00 equiv), DMSO (40 mL) and potassium hydroxide (8.1 g, 144.36 mmol, 8.00 equiv). The mixture was stirred for 10 min. Then MeI (4.5 mL) was added dropwise with stirring at room temperature. The resulted solution was stirred for 2 h at room temperature. The reaction mixture was diluted with 100 mL of TBME, washed with 3×50 mL of brine. The organic phase was dried over anhydrous $Na_2SO_4$ and concentrated under reduced pressure. This resulted in 2.0 g (66%) of 1,4-dimethoxy-2,3-dimethylbenzene as a brown solid. $^1$H NMR (300 MHz, CDCl$_3$): δ 6.68 (s, 2H), 3.80 (s, 6H), 2.18 (s, 6H).

Example 129

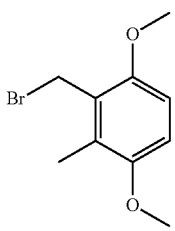

2-(bromomethyl)-1,4-dimethoxy-3-methylbenzene

Into a 50-mL round-bottom flask, was placed a mixture of 1,4-dimethoxy-2,3-dimethylbenzene (1.00 g, 6.02 mmol, 1.00 equiv)(Example 128), CCl$_4$ (20 mL), NBS (1.20 g, 6.74 mmol, 1.10 equiv) and BPO (145 mg, 0.57 mmol, 0.10 equiv). The solution was stirred for 16 h at 80° C. After concentration, the residue was diluted with 50 mL of TBME and washed with 3×20 mL of brine. The organic phase was dried over anhydrous $Na_2SO_4$ and concentrated under reduced pressure. This resulted in 1.20 g (81%) of 2-(bromomethyl)-1,4-dimethoxy-3-methylbenzene as a brown crude solid.

Example 130

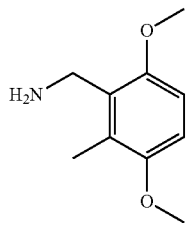

(3,6-dimethoxy-2-methylphenyl)methanamine

Into a 250-mL round-bottom flask, was placed a mixed solution of concentrated ammonia (25 mL) and dioxane (25 mL), to which was added dropwise a solution of 2-(bromomethyl)-1,4-dimethoxy-3-methylbenzene (1.2 g, 4.90 mmol, 1.00 equiv)(Example 129) in dioxane (10 mL) with stirring at room temperature over 0.5 h. The solution was stirred for additional 1 h at room temperature. After concentration, the residue was purified by silica gel column eluted with dichloromethane/methanol (50/1). This resulted in 300 mg (34%) of (3,6-dimethoxy-2-methylphenyl)methanamine as brown solids. LC-MS (ESI) m/z: calculated for $C_{10}H_{15}NO_2$: 181.11; found: 182.1 [M+H]$^+$.

Example 131

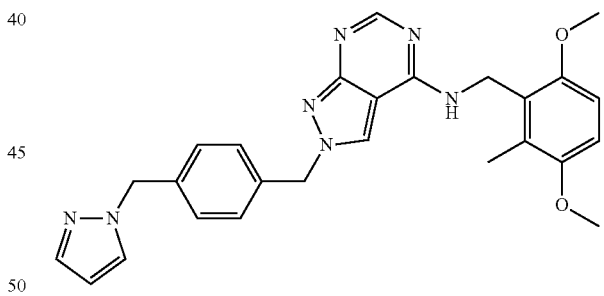

N-[(3,6-dimethoxy-2-methylphenyl)methyl]-2-[[4-(1H-pyrazol-1-ylmethyl)phenyl]methyl]-2H-pyrazolo[3,4-d]pyrimidin-4-amine Into an 8-mL vial, was placed a mixture of 1-[[4-([4-chloro-2H-pyrazolo[3,4-d]pyrimidin-2-yl]methyl)phenyl]methyl]-1H-pyrazole (81 mg, 0.25 mmol, 1.00 equiv)(Example 23), N,N-dimethylformamide (2 mL), (3,6-dimethoxy-2-methylphenyl)methanamine (54 mg, 0.30 mmol, 1.20 equiv)(Example 130) and DIEA (65 mg, 0.50 mmol, 2.00 equiv). The resulted solution was stirred for 1 h at 60° C. After filtration, the filtrate was purified by Prep-HPLC with the following conditions. Column: Sunfire Prep C18, 19*150 mm, 5 μm; mobile phase: water (it contains 0.1% TFA) and acetonitrile with a gradient of 50% to 60% acetonitrile in 8 min; flow rate: 20 mL/min; detector UV wavelength: 254 nm. This resulted in 38 mg (32%) of N-[(3,6-dimethoxy-2-methylphenyl)methyl]-2-[[4-(1H-pyrazol-1-ylmethyl)phenyl]methyl]-2H-pyrazolo[3,4-d]pyrimidin-4-amine as a yellow solid. $^1$H NMR (300 MHz, DMSO-d$_6$): δ 8.32 (s, 1H), 8.25 (s, 1H), 7.99 (s, 1H), 7.79 (s, 1H), 7.44 (s, 1H), 7.28 (d, J=7.8 Hz, 2H), 7.19 (d, J=7.8 Hz, 2H), 6.93-6.83 (m, 2H), 6.25 (s, 1H), 5.48 (s, 2H), 5.31 (s, 2H), 4.63 (d, J=3.6 Hz, 2H), 3.74 (s, 3H), 3.73 (s, 3H), 2.13 (s, 3H). LC-MS (ESI) m/z: calculated for C26H27N7O2: 469.22; found: 470.2 [M+H]$^+$.

Example 132

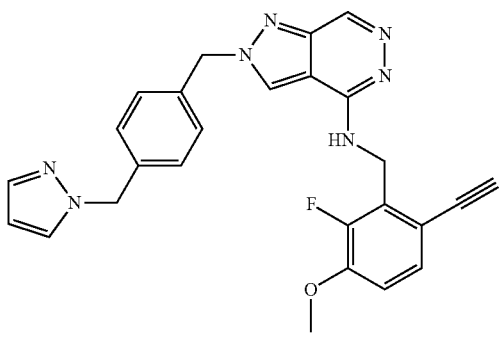 [SMILES: C#Cc1ccc(OC)c(F)c1CNc1nncc2nn(Cc3ccc(Cn4cccn4)cc3)cc12]

Preparation of 2-(4-((1H-pyrazol-1-yl)methyl)benzyl)-N-(6-ethynyl-2-fluoro-3-methoxybenzyl)-2H-pyrazolo[3,4-d]pyrimidin-4-amine 2-(4-((1H-pyrazol-1-yl)methyl)benzyl)-N-(6-ethynyl-2-fluoro-3-methoxybenzyl)-2H-pyrazolo[3,4-d]pyrimidin-4-amine was prepared in a similar manner to Example 147. $^1$H NMR (400 MHz, DMSO-d$_6$) δ 8.29-8.20 (m, 3H), 7.77 (d, J=2.2 Hz, 1H), 7.42 (d, J=1.8 Hz, 1H), 7.38-7.23 (m, 3H), 7.21-7.11 (m, 3H), 6.23 (t, J=2.0 Hz, 1H), 5.48 (s, 2H), 5.29 (s, 2H), 4.75 (dd, J=4.3, 1.9 Hz, 2H), 4.21 (s, 1H), 3.85 (s, 3H). MS (M+H)+ found for C$_{26}$H$_{22}$FN$_7$O: 468.1.

Example 133

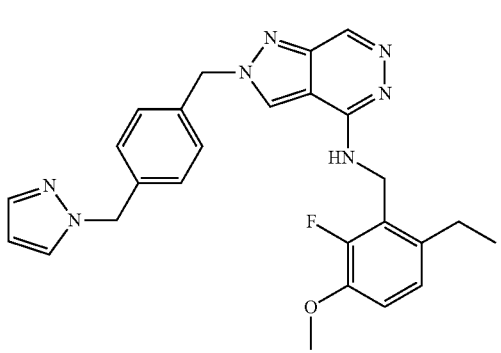 [SMILES: CCc1ccc(OC)c(F)c1CNc1nncc2nn(Cc3ccc(Cn4cccn4)cc3)cc12]

2-(4-((1H-pyrazol-1-yl)methyl)benzyl)-N-(6-ethyl-2-fluoro-3-methoxybenzyl)-2H-pyrazolo[3,4-d]pyrimidin-4-amine To a solution of N-[(6-ethynyl-2-fluoro-3-methoxyphenyl)methyl]-2-{[4-(1H-pyrazol-1-ylmethyl)phenyl]methyl}-2H-pyrazolo[3,4-d]pyrimidin-4-amine (4.00 mg; 0.01 mmol; 1.00 eq.)(Example 132) in EtOH (1 mL) and THF (1 mL) was added Pd(OH)$_2$/C and charged with H$_2$ balloon for 15 min, then the catalyst was filtered odd and the filtrate was lyophilized to give 2-(4-((1H-pyrazol-1-yl)methyl)benzyl)-N-(6-ethyl-2-fluoro-3-methoxybenzyl)-2H-pyrazolo[3,4-d]pyrimidin-4-amine. $^1$H NMR (400 MHz, DMSO-d$_6$) δ 8.28 (s, 1H), 8.24 (s, 2H), 7.77 (d, J=2.2 Hz, 1H), 7.42 (s, 1H), 7.26 (d, J=7.9 Hz, 2H), 7.18 (d, J=7.9 Hz, 2H), 7.02 (dd, J=28.5, 8.5 Hz, 2H), 6.23 (t, J=2.0 Hz, 1H), 5.48 (s, 2H), 5.29 (s, 2H), 4.65 (s, 2H), 3.79 (s, 3H), 2.71-2.53 (m, 2H), 1.06 (t, J=7.5 Hz, 3H). MS (M+H)+ found for C$_{26}$H$_{26}$FN$_7$O: 472.04.

Example 134

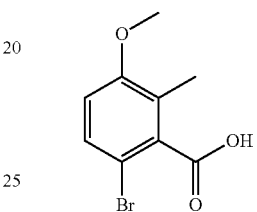

6-bromo-3-methoxy-2-methylbenzoic acid Into a 100-mL round-bottom flask, was placed a mixture of 3-methoxy-2-methylbenzoic acid (5.00 g, 30.09 mmol, 1.00 equiv), AcOH (30 mL) and water (30 mL), followed by Br$_2$ (1.70 mL, 1.10 equiv) dropwise. The resulted solution was stirred for 2 h at 60° C. After concentration, the residue was diluted with 150 mL of ethyl acetate and washed with 3×50 mL of brine. The organic phase was dried over anhydrous Na$_2$SO$_4$ and concentrated under reduced pressure. This resulted in 6.50 g (88%) of 6-bromo-3-methoxy-2-methylbenzoic acid as yellow crude oil. LC-MS (ESI) m/z: calculated for C9H9BrO3: 243.97; found: 245 [M+H]$^+$. Rt: 1.33 min.

Example 135

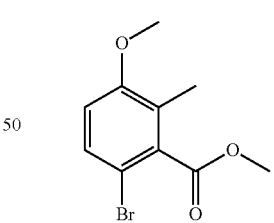

6-bromo-3-methoxy-2-methylbenzoate Into a 50-mL round-bottom flask, was placed a mixture of 6-bromo-3-methoxy-2-methylbenzoic acid (1.0 g, 4.08 mmol, 1.00 equiv)(Example 134), dichloromethane (20 mL), DIEA (1.32 g, 10.21 mmol, 2.50 equiv), HATU (1.87 g, 4.92 mmol, 1.20 equiv) and MeOH (2 mL). The resulted solution was stirred for 4 h at room temperature. The reaction solution was concentrated under reduced pressure and the residue was purified by silica gel column eluted with ethyl acetate/petroleum ether (1/1). This resulted in 1.03 g (97%) of methyl 6-bromo-3-methoxy-2-methylbenzoate as a white solid.

Example 136

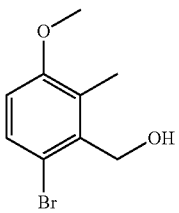

(6-bromo-3-methoxy-2-methylphenyl)methanol

Into a 25-mL round-bottom flask, was placed a solution of methyl 6-bromo-3-methoxy-2-methylbenzoate (770 mg, 2.97 mmol, 1.00 equiv)(Example 135) in tetrahydrofuran (10 mL) with stirring at 0° C., to which was added LiAlH$_4$ (220 mg, 5.80 mmol, 2.00 equiv) in portions. The solution was stirred for 0.5 h at 0° C. and then quenched by the addition of 50 mL of 1 N HCl aqueous solution. The resulted solution was extracted with 200 mL of ethyl acetate. The organic phase was washed with 2×50 mL of brine, dried over anhydrous sodium sulfate and concentrated under vacuum. This resulted in 890 mg of (6-bromo-3-methoxy-2-methylphenyl)methanol as a light yellow crude solid. LC-MS (ESI) m/z: calculated for $C_3H_{11}BrO_2$:229.99. found: 254 [M-17+ $CH_3CN]^+$. Rt: 1.29 min.

Example 137

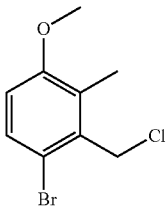

Into a 25-mL round-bottom flask, was placed a solution of (6-bromo-3-methoxy-2-methylphenyl)methanol (230 mg, 1.00 mmol, 1.00 equiv)(Example 136) in dichloromethane (5 mL). This was followed by the addition of thionyl chloride (1.22 mL, 2.00 equiv) dropwise with stirring at 0° C. The resulted solution was stirred for 1 h at 0° C. and then concentrated under vacuum. This resulted in 240 mg (97%) of 1-bromo-2-(chloromethyl)-4-methoxy-3-methylbenzene as a light yellow solid.

Example 138

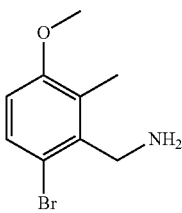

(6-bromo-3-methoxy-2-methylphenyl)methanamine

Into a 25-mL round-bottom flask, was placed a solution of ammonia (5 mL) and dioxane (5 mL). This was followed by the addition of a solution of 1-bromo-2-(chloromethyl)-4-methoxy-3-methylbenzene (240 mg, 0.96 mmol, 1.00 equiv) (Example 137) in dioxane (2 mL) dropwise with stirring. The resulted solution was stirred for 1 h at room temperature and then concentrated under vacuum. The residue was purified by silica gel column eluted with dichloromethane/methanol (50/1). This resulted in 95 mg (43%) of (6-bromo-3-methoxy-2-methylphenyl)methanamine as a yellow solid. LC-MS (ESI) m/z: calculated for C9H12BrNO: 229.01. found: 230 [M+H]$^+$.

Example 139

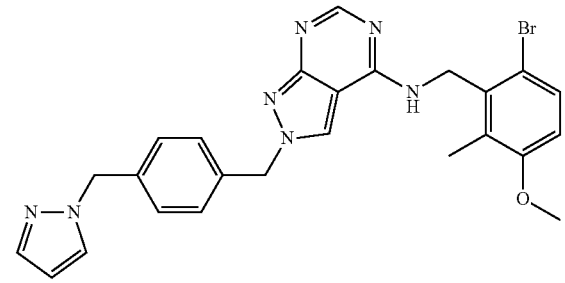 [SMILES: COc1ccc(Br)c(CNc2ncnc3nn(Cc4ccc(Cn5cccn5)cc4)cc23)c1C]

N-[(6-bromo-3-methoxy-2-methylphenyl)methyl]-2-[[4-(1H-pyrazol-1-ylmethyl)phenyl]methyl]-2H-pyrazolo[3,4-d]pyrimidin-4-amine Into an 8-mL vial, was placed a mixture of (6-bromo-3-methoxy-2-methylphenyl)methanamine (85 mg, 0.37 mmol, 1.00 equiv)(Example 138), DIEA (120 mg, 0.93 mmol, 2.50 equiv), 1-[[4-([4-chloro-2H-pyrazolo[3,4-d]pyrimidin-2-yl]methyl)phenyl]methyl]-1H-pyrazole (108 mg, 0.33 mmol, 0.90 equiv)(Example 23) and DMA (2 mL). The resulted solution was stirred for 1 h at 60° C. After filtration, the filtrate was purified by Prep-HPLC with the following conditions. Column: Waters XBridge C18, 19*150 mm, 5 μm; mobile phase: water (it contains 10 mmol NH$_4$HCO$_3$+ 0.05% ammonia) and acetonitrile with a gradient of 45% to 52% acetonitrile in 8 min; flow rate: 20 mL/min; detector UV wavelength: 254 nm. This resulted in 45.6 mg (24%) of N-[(6-bromo-3-methoxy-2-methylphenyl)methyl]-2-[[4-(1H-pyrazol-1-ylmethyl)phenyl]methyl]-2H-pyrazolo[3,4-d]pyrimidin-4-amine as a white solid. $^1$H-NMR (300 MHz, DMSO-d$_6$): δ 8.29 (d, J=8.7 Hz, 2H), 8.12 (s, 1H), 7.79 (d, J=1.8 Hz, 1H), 7.48 (d, J=9.0 Hz, 1H), 7.43 (d, J=1.2 Hz, 1H), 7.29 (d, J=8.1 Hz, 2H), 7.19 (d, J=8.1 Hz, 2H), 6.95 (d, J=9.0 Hz, 1H), 6.25 (t, J=2.1 Hz, 1H), 5.49 (s, 2H), 5.31 (s, 2H), 4.76 (d, J=4.2 Hz, 2H), 3.80 (s, 3H), 2.19 (s, 3H). LC-MS (ESI) m/z: calculated for $C_{25}H_{24}BrN_7O$: 517.12. found: 518 [M+H]$^+$.

Example 140

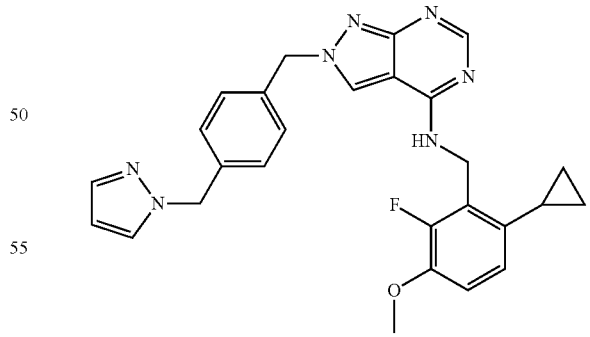

2-(4-((1H-pyrazol-1-yl)methyl)benzyl)-N-(6-cyclopropyl-2-fluoro-3-methoxybenzyl)-2H-pyrazolo[3,4-d]pyrimidin-4-amine 2-(4-((1H-pyrazol-1-yl)methyl)benzyl)-N-(6-cyclopropyl-2-fluoro-3-methoxybenzyl)-2H-pyrazolo[3,4-d]pyrimidin-4-amine was prepared in a similar manner to Example 147. $^1$H NMR (400 MHz, DMSO-d$_6$) δ 8.32-8.21 (m, 3H), 7.77 (d, J=2.1 Hz, 1H), 7.42 (d, J=1.6 Hz, 1H), 7.27 (d, J=7.9 Hz, 2H), 7.18 (d, J=7.9 Hz, 2H), 7.01 (t, J=8.7 Hz, 1H), 6.80 (d, J=8.5 Hz, 1H), 6.23 (q, J=1.6 Hz, 1H), 5.48 (s, 2H), 5.29 (s, 2H), 4.85-4.78 (m, 2H), 3.78 (s, 3H), 1.96 (ddd, J=13.8, 8.6, 5.3 Hz, 1H), 0.86-0.72 (m, 2H), 0.56 (td, J=5.9, 4.2 Hz, 2H). MS (M+H)+ found for $C_{27}H_{26}FN_7O$: 484.04.

Example 141

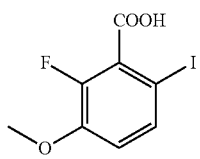

2-fluoro-6-iodo-3-methoxybenzoic acid

Into an 100-mL 3-necked round-bottom flask purged and maintained with an inert atmosphere of nitrogen, was placed a solution of 2-fluoro-4-iodo-1-methoxybenzene (5.00 g, 19.84 mmol, 1.00 equiv) in tetrahydrofuran (40 mL) with stirring at −78° C. This was followed by the addition of LDA (1.8 N, 11 mL, 1.10 equiv, in THF solution) dropwise at −78° C. The resulted solution was stirred for 1h at -78° C. Carbon dioxide was bubbled into the reaction solution with stirring. The reaction mixture was warmed up to room temperature and stirred overnight. Then it was concentrated under vacuum and diluted with sodium hydroxide aqueous solution (30 mL, 4N). The mixture was extracted with 30 mL of ethyl acetate. The pH value of the aqueous phase was adjusted to 2.0 with 2N hydrochloride aqueous solution. The resulted solution was extracted with 3×50 mL of ethyl acetate. The organic layers were combined and concentrated under vacuum. This resulted in 3.10 g (53%) of 2-fluoro-6-iodo-3-methoxybenzoic acid as light yellow solid. LC-MS (ESI) m/z: calculated for $C_8H_6FIO_3$: 296. found: 295[M−1]$^-$.

Example 142

2-fluoro-6-iodo-3-methoxybenzoyl chloride

Into a 50-mL round-bottom flask purged and maintained with an inert atmosphere of nitrogen, was placed a solution 2-fluoro-6-iodo-3-methoxybenzoic acid (3.10 g, 10.47 mmol, 1.00 equiv)(Example 141) and thionyl chloride (10 mL). The resulted solution was stirred 3h at 80° C. in an oil bath. The resulted mixture was concentrated under vacuum. This resulted in 3.10 g (crude) of 2-fluoro-6-iodo-3-methoxybenzoyl chloride as a brown solid.

Example 143

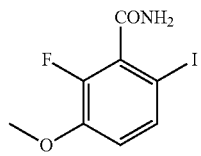

2-fluoro-6-iodo-3-methoxybenzamide

Into an 100-mL round-bottom flask, was placed a solution of ammonia (10 mL) and tetrahydrofuran (15 mL), to which was added of a solution of 2-fluoro-6-iodo-3-methoxybenzoyl chloride (3.10 g, 9.86 mmol, 1.00 equiv)(Example 142) in tetrahydrofuran (5.00 mL) dropwise with stirring at 0° C. The resulted solution was stirred overnight at room temperature. The volatiles were removed under vacuum. The solids were collected by filtration. This resulted in 3.00 g of 2-fluoro-6-iodo-3-methoxybenzamide as yellow solid. LC-MS (ESI) m/z: calculated for $C_8H_7FINO_2$: 295. found: 296 [M+H]$^+$.

Example 144

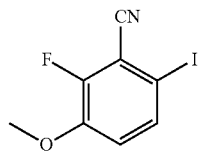

2-fluoro-6-iodo-3-methoxybenzonitrile

Into an 100-mL 3-necked round-bottom flask purged and maintained with an inert atmosphere of nitrogen, was placed a solution of 2-fluoro-6-iodo-3-methoxybenzamide (3.00 g, 10.17 mmol, 1.00 equiv)(Example 143) and N,N-dimethylformamide (30 mL), to which was added thionyl chloride (6.00 g, 5.00 equiv) dropwise with stirring at room temperature. The resulted solution was stirred for 16 h at 115° C. in an oil bath. The reaction was then quenched by the addition of water/ice. The solution was extracted with 3×50 mL of ethyl acetate. The organic phase was concentrated under vacuum. The residue was purified by silica gel column chromatography eluted with ethyl acetate/petroleum ether (1:4). This resulted in 2.50 g (89%) of 2-fluoro-6-iodo-3-methoxybenzonitrile as brown solid. GC-MS (ESI) m/z: calculated for $C_8H_5FINO$: 277. found: 278[M+1].

Example 145

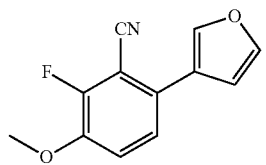 [SMILES: COc1ccc(-c2ccoc2)c(C#N)c1F]

2-fluoro-6-(furan-3-yl)-3-methoxybenzonitrile

Into a 10-mL round-bottom flask purged and maintained with an inert atmosphere of nitrogen, was placed a mixture of 2-fluoro-6-iodo-3-methoxybenzonitrile (300 mg, 1.08 mmol, 1.00 equiv)(Example 144), dioxane (5.00 mL), KOAc (330 mg, 3.36 mmol, 3.00 equiv), Pd(dppf)Cl$_2$ (90 mg, 0.12 mmol, 0.10 equiv) and (furan-3-yl)boronic acid (148 mg, 1.32 mmol, 1.20 equiv). The resulted solution was stirred for 3h at 80° C. in an oil bath. The resulted mixture was concentrated under vacuum. The residue was purified by silica gel column chromatography eluted with ethyl acetate/petroleum ether (1:3). This resulted in 210 mg (89%) of 2-fluoro-6-(furan-3-yl)-3-methoxybenzonitrile as light yellow solid. GC-MS (ESI) m/z: calculated for C$_{12}$H$_8$FNO$_2$: 217. found: 217[M]. Rt: 7.95 min.

Example 146

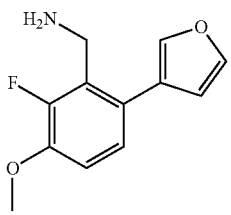 [SMILES: COc1ccc(-c2ccoc2)c(CN)c1F]

[2-fluoro-6-(furan-3-yl)-3-methoxyphenyl]methanamine

Into a 50-mL round-bottom flask, was placed a mixture of methanol (10 mL), Raney Ni (50 mg), 2-fluoro-6-(furan-3-yl)-3-methoxybenzonitrile (210 mg, 0.97 mmol, 1.00 equiv) (Example 145), and concentrated ammonia (1 mL) with stirring under nitrogen atmosphere. The resulted mixture was purged with hydrogen for 3 times and stirred for 2 h at room temperature under nitrogen atmosphere. The solids were filtered out. The filtrate was concentrated under vacuum. This resulted in 190 mg (89%) of [2-fluoro-6-(furan-3-yl)-3-methoxyphenyl]methanamine as a gray crude solid. LC-MS (ESI) m/z: calculated for C$_{12}$H$_{12}$FNO$_2$: 221. found: 222[M+H]$^+$.

Example 147

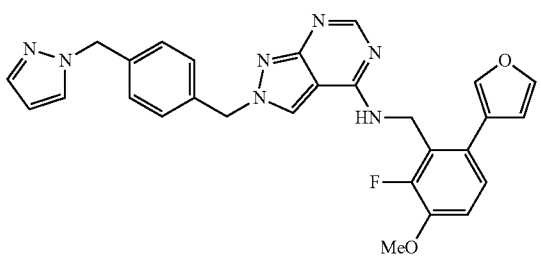 [SMILES: COc1ccc(-c2ccoc2)c(CNc2ncnc3nn(Cc4ccc(Cn5cccn5)cc4)cc23)c1F]

N-[[2-fluoro-6-(furan-3-yl)-3-methoxyphenyl]methyl]-2-[[4-(1H-pyrazol-1-ylmethyl)phenyl]methyl]-2H-pyrazolo[3,4-d]pyrimidin-4-amine Into a 10-mL round-bottom flask, was placed a solution of 1-[[4-([4-chloro-2H-pyrazolo[3,4-d]pyrimidin-2-yl]methyl)phenyl]methyl]-1H-pyrazole (100 mg, 0.31 mmol, 1.00 equiv)(Example 23), DMA (5 mL), DIEA (194 mg, 1.50 mmol, 5.00 equiv) and [2-fluoro-6-(furan-3-yl)-3-methoxyphenyl]methanamine (80 mg, 0.36 mmol, 1.20 equiv)(Example 146). The resulting solution was stirred for 2 h at 80° C. in an oil bath. The reaction mixture was purified by Prep-HPLC with the following conditions. Column: Waters XBridge RP18 19*150 mm, 5 μm; mobile phase: water (it is a buffer of 0.05% ammonia+10 mM NH$_4$HCO$_3$) and acetonitrile with a gradient of 40% to 50% acetonitrile in 8 min; flow rate: 20 mL/min; detector UV wavelength: 254 nm. This resulted in 52 mg (33%) of N-[[2-fluoro-6-(furan-3-yl)-3-methoxyphenyl]methyl]-2-[[4-(1H-pyrazol-1-ylmethyl)phenyl]methyl]-2H-pyrazolo[3,4-d]pyrimidin-4-amine as off-white solid.

$^1$H NMR (300 MHz, DMSO-d$_6$): δ 8.31-8.36 (m, 2H), 8.24 (s, 1H), 7.80 (d, J=1.5 Hz, 1H), 7.71 (d, J=9.6 Hz, 2H), 7.44 (s, 1H), 7.30 (d, J=8.1 Hz, 2H), 7.11-7.23 (m, 4H), 6.66 (s, 1H), 6.25 (s, 1H), 5.51 (s, 2H), 5.31 (s, 2H), 4.60 (m, 2H), 3.88 (s, 3H). LC-MS (ESI) m/z: calculated for C$_{28}$H$_{24}$FN$_7$O$_2$: 509. found: 510[M+H]$^+$.

Example 148

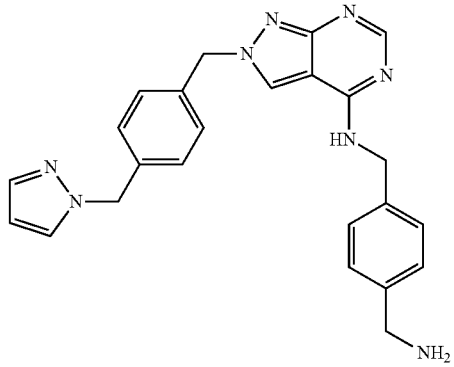 [SMILES: NCc1ccc(CNc2ncnc3nn(Cc4ccc(Cn5cccn5)cc4)cc23)cc1]

2-(4-((1H-pyrazol-1-yl)methyl)benzyl)-N-(4-(aminomethyl)benzyl)-2H-pyrazolo[3,4-d]pyrimidin-4-amine To a mixture of 1-{[4-({4-chloro-2H-pyrazolo[3,4-d]pyrimidin-2-yl}methyl)phenyl]methyl}-1H-pyrazole (50.00 mg; 0.15 mmol; 1.00 eq.)(Example 23) and [4-(aminomethyl)phenyl]methanamine (23.06 mg; 0.17 mmol; 1.10 eq.) in DMF (1 mL) was added Hunig's base-ethylbis(propan-2-yl)amine (0.04 ml; 0.23 mmol; 1.50 eq.). After heated at 80° C. for 1 h, it was cooled and diluted with water and Acetonitrile, and was purified by preparative HPLC to give 2-(4-((1H-pyrazol-1-yl)methyl)benzyl)-N-(4-(aminomethyl)benzyl)-2H-pyrazolo[3,4-d]pyrimidin-4-amine. $^1$H NMR (400 MHz, DMSO-d$_6$) δ 8.67 (t, J=6.0 Hz, 1H), 8.34 (s, 1H), 8.27 (d, J=3.6 Hz, 1H), 8.16 (s, 1H), 7.78 (d, J=2.2 Hz, 1H), 7.42 (d, J=1.8 Hz, 1H), 7.29 (d, J=13.3 Hz, 5H), 7.19 (d, J=7.8 Hz, 2H), 6.24 (t, J=2.0 Hz, 1H), 5.52 (s, 2H), 5.30 (s, 2H), 4.67 (d, J=5.8 Hz, 2H), 3.84 (s, 2H). MS (M+H)+ found for C$_{24}$H$_{24}$N$_8$: 425.1.

Example 149

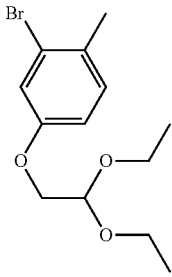 [SMILES: CCOC(COc1ccc(C)c(Br)c1)OCC]

2-bromo-4-(2,2-diethoxyethoxy)-1-methylbenzene

Into a 500-mL round-bottom flask, were placed a mixture of 3-bromo-4-methylphenol (7 g, 37.43 mmol, 1.00 equiv), potassium carbonate (10.5 g, 75.97 mmol, 2.00 equiv), N,N-dimethylformamide (70 mL) and 2-bromo-1,1-diethoxyethane (8.9 g, 45.16 mmol, 1.20 equiv). The resulted solution was stirred overnight at 90° C. The resulted solution was diluted with 350 mL of H$_2$O. The resulted mixture was extracted with 3×350 mL of ethyl acetate. The organic phase was dried over anhydrous sodium sulfate and concentrated under vacuum. This resulted in 6.90 g (61%) of 2-bromo-4-(2,2-diethoxyethoxy)-1-methylbenzene as yellow oil. LC-MS (ESI) m/z: calculated for C$_{13}$H$_{19}$BrO$_3$: 302 found: 213 [M+H]+. Rt: 1.747 min.

Example 150, 151

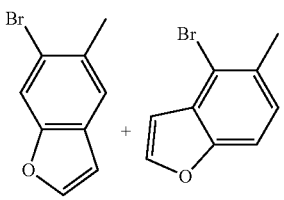

6-bromo-5-methyl-1-benzofuran and
4-bromo-5-methyl-1-benzofuran

Into a 500-mL round-bottom flask, was placed a mixture of 2-bromo-4-(2,2-diethoxyethoxy)-1-methylbenzene (6 g, 19.79 mmol, 1.00 equiv)(Example 149), PPA (6.5 g, 3.00 equiv) and toluene (240 mL). The resulted solution was refluxed for 2 h. The resulted mixture was concentrated under vacuum. The resulted solution was diluted with 200 mL of H$_2$O, and then extracted with 3×200 mL of ethyl acetate. The organic layers were combined and concentrated under vacuum. This resulted in 4.8 g of 6-bromo-5-methyl-1-benzofuran and 4-bromo-5-methyl-1-benzofuran as black crude oil. GC-MS (ESI) m/z: calculated for C$_9$H$_7$BrO: 210 found: 210 [M]+.

Example 152, 153

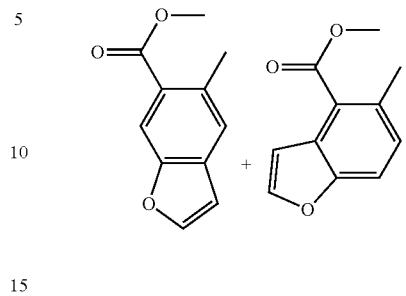

methyl 5-methyl-1-benzofuran-6-carboxylate and
methyl 5-methyl-1-benzofuran-4-carboxylate Into a 250-mL pressure tank reactor, were placed a mixture of 6-bromo-5-methyl-1-benzofuran and 4-bromo-5-methyl-1-benzofuran (3.5 g, 16.58 mmol, 1.00 equiv)(Example 151), Pd(dppf)Cl$_2$ (2.7 g, 3.69 mmol, 0.20 equiv), TEA (3.4 g, 33.60 mmol, 2.00 equiv) and methanol (100 mL). The resulted solution was purged with carbon monoxide and stirred overnight at 120° C. under an atmosphere of carbon monoxide. The resulted mixture was concentrated under vacuum. The residue was purified by silica gel column eluted with ethyl acetate/petroleum ether (1/10). This resulted in 2.0 g (63%) of methyl 5-methyl-1-benzofuran-6-carboxylate and methyl 5-methyl-1-benzofuran-4-carboxylate as off-white oil. GC-MS (ESI) m/z: calculated for C$_{11}$H$_{10}$O$_3$: 190 found: 190 [M]+.

Example 154, 155

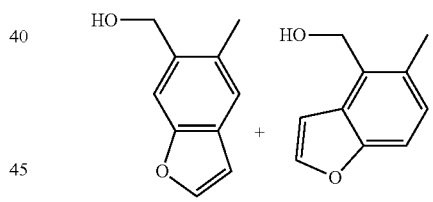

(5-methyl-1-benzofuran-6-yl)methanol and
(5-methyl-1-benzofuran-4-yl)methanol

Into a 250-mL 3-necked round-bottom flask, was placed a mixture of methyl 5-methyl-1-benzofuran-4-carboxylate and methyl 5-methyl-1-benzofuran-6-carboxylate (2.0 g, 10.52 mmol, 1.00 equiv)(Example 153) and tetrahydrofuran (40 mL) with stirring at 0° C., to which was added LAH (600 mg, 15.81 mmol, 1.50 equiv) in several batches. The resulted solution was stirred for additional 0.5 h at 25° C. The reaction was then quenched by the addition of 1.0 mL of water. The solids were filtered out. The resulted mixture was concentrated under vacuum. The residue was purified by silica gel column eluted with ethyl acetate/petroleum ether (1/5). This resulted in 1.4 g (82%) of (5-methyl-1-benzofuran-6-yl)methanol and (5-methyl-1-benzofuran-4-yl)methanol as off-white oil. LC-MS (ESI) m/z: calculated for C$_{10}$H$_{10}$O$_2$: 162 found: 145 [M+H]+.

Example 156, 157

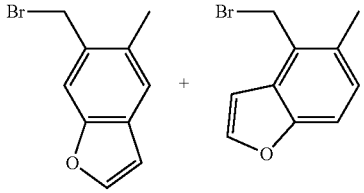

6-(bromomethyl)-5-methyl-1-benzofuran and
4-(bromomethyl)-5-methyl-1-benzofuran

Into an 100-mL round-bottom flask, was placed a mixture of (5-methyl-1-benzofuran-6-yl)methanol and (5-methyl-1-benzofuran-4-yl)methanol (1.0 g, 6.17 mmol, 1.00 equiv) (Example 155) and dichloromethane (40 mL). This was followed by the addition of $PBr_3$ (4.2 g, 15.52 mmol, 2.50 equiv) dropwise with stirring at 0° C. The resulting solution was stirred for 30 min at 25° C. The mixture was then concentrated under vacuum. This resulted in 1.50 g of 6-(bromomethyl)-5-methyl-1-benzofuran and 4-(bromomethyl)-5-methyl-1-benzofuran as red crude oil.

Example 158, 159

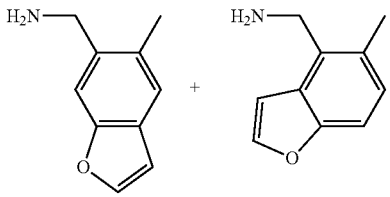

(5-methyl-1-benzofuran-6-yl)methanamine and (5-methyl-1-benzofuran-4-yl)methanamine Into a 500-mL round-bottom flask, was placed ammonia/dioxane=1/3(300 mL). This was followed by the addition of a solution of 6-(bromomethyl)-5-methyl-1-benzofuran and 4-(bromomethyl)-5-methyl-1-benzofuran in dioxane (10 mL)(Example 157) dropwise with stirring. The resulted solution was stirred for 30 min at 25° C. The resulted mixture was concentrated under vacuum. The crude product was purified by flash column chromatography eluted with PE/EA (1:1). This resulted in 700 mg (98%) of (5-methyl-1-benzofuran-6-yl)methanamine and (5-methyl-1-benzofuran-4-yl)methanamine as yellow solids. LC-MS (ESI) m/z: calculated for $C_{10}H_{11}NO$: 161 found: 145 [M+H]+.

Example 160 and Example 161

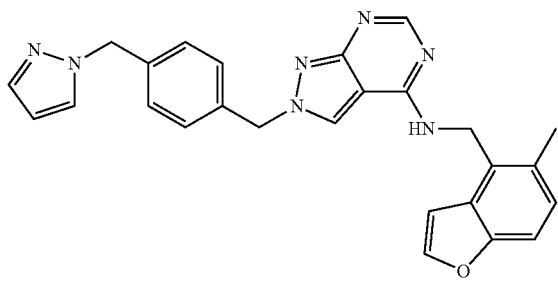

Example 160

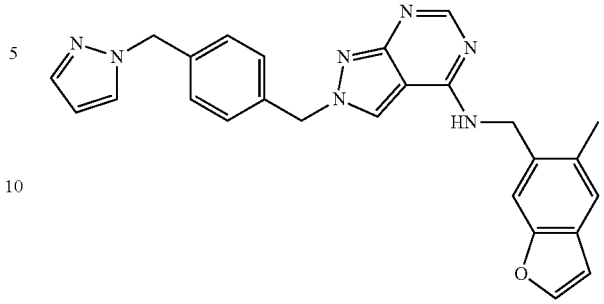

Example 161

N-[(5-methyl-1-benzofuran-4-yl)methyl]-2-[[4-(1H-pyrazol-1-ylmethyl)phenyl]methyl]-2H-pyrazolo[3,4-d]pyrimidin-4-amine and N-[(5-methyl-1-benzofuran-6-yl)methyl]-2-[[4-(1H-pyrazol-1-ylmethyl)phenyl]methyl]-2H-pyrazolo[3,4-d]pyrimidin-4-amine Into a 50-mL round-bottom flask, was placed a mixture of (5-methyl-1-benzofuran-4-yl)methanamine and (5-methyl-1-benzofuran-6-yl)methanamine (120 mg, 0.74 mmol, 1.00 equiv)(Example 159), DIEA (500 mg, 3.87 mmol, 5.00 equiv), N,N-dimethylformamide (5 mL) and 1-[4-(4-chloro-2H-pyrazolo[3,4-d]pyrimidin-2-ylmethyl)phenyl]methyl-1H-pyrazole (200 mg, 0.62 mmol, 0.80 equiv)(Example 23). The resulting solution was stirred for 2 h at 80° C. The mixture was diluted with water (10 mL) and extracted with EA(3×10 mL). Then the organic layer was concentrated under vacuum. The crude product (320 mg) was purified by Prep-HPLC with the following conditions. Column: Waters XBridge RP18 19*150 mm, 5 μm; mobile phase: $CH_3CN/H_2O$ (it contains 0.1% formic acid) with a gradient of 30% to 40% acetonitrile in 8 min; flow rate: 20 mL/min; detector UV wavelength: 254 nm. This resulted in 32.6 mg (10%) of N-[(5-methyl-1-benzofuran-4-yl)methyl]-2-[[4-(1H-pyrazol-1-ylmethyl)phenyl]methyl]-2H-pyrazolo[3,4-d]pyrimidin-4-amine as white solids and 15.7 mg (5%) of N-[(5-methyl-1-benzofuran-6-yl)methyl]-2-[[4-(1H-pyrazol-1-ylmethyl)phenyl]methyl]-2H-pyrazolo[3,4-d]pyrimidin-4-amine as light yellow solids.

N-[(5-methyl-1-benzofuran-4-yl)methyl]-2-[[4-(1H-pyrazol-1-ylmethyl)phenyl]methyl]-2H-pyrazolo[3,4-d]pyrimidin-4-amine $^1H$ NMR (300 MHz, DMSO-$d_6$): δ 9.68 (s, 1H), 8.61 (s, 1H), 8.54 (s, 1H), 7.96 (d, J=1.8 Hz, 1H), 7.80 (d, J=1.5 Hz, 1H), 7.51 (s, 1H), 7.44 (s, 1H), 7.33 (d, J=7.8 Hz, 2 H), 7.22 (d, J=7.8 Hz, 3H), 7.09 (d, J=1.2 Hz, 1H), 6.25 (s, 1H), 5.57 (s, 2H), 5.31 (s, 2H), 5.02 (d, J=4.8 Hz, 2H), 2.42 (s, 3H). LC-MS (ESI) m/z: calculated for $C_{26}H_{23}N_7O$: 449 found: 450 [M+H]+.

N-[(5-methyl-1-benzofuran-6-yl)methyl]-2-[[4-(1H-pyrazol-1-ylmethyl)phenyl]methyl]-2H-pyrazolo[3,4-d]pyrimidin-4-amine $^1H$ NMR (300 MHz, DMSO-d): δ 10.56 (s, 1H), 8.77 (s, 1H), 8.69 (s, 1H), 7.95 (s, 1H), 7.82 (s, 1H), 7.57 (s, 1H), 7.52 (s, 1H), 7.44 (s, 1H), 7.36 (d, J=7.8 Hz, 2H), 7.23 (d, J=7.5 Hz, 2H), 6.90 (s, 1H), 6.26 (s, 1H), 5.65 (s, 2H), 5.33 (s, 2H), 4.93 (d, J=4.5 Hz, 2H), 2.39 (s, 3H). LC-MS (ESI) m/z: calculated for $C_{26}H_{23}N_7O$: 449 found: 450 [M+H]+.

Example 162

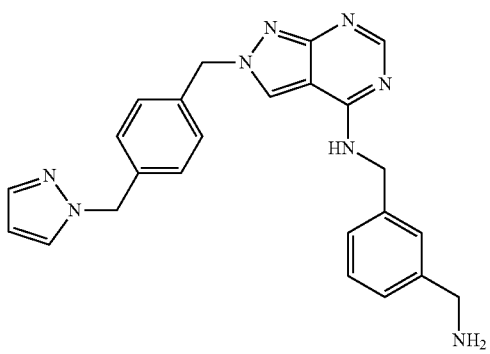 [SMILES: NCc1cccc(CNc2ncnc3nn(Cc4ccc(Cn5cccn5)cc4)cc23)c1]

2-(4-((1H-pyrazol-1-yl)methyl)benzyl)-N-(3-(aminomethyl)benzyl)-2H-pyrazolo[3,4-d]pyrimidin-4-amine 2-(4-((1H-pyrazol-1-yl)methyl)benzyl)-N-(3-(aminomethyl)benzyl)-2H-pyrazolo[3,4-d]pyrimidin-4-amine was prepared in a similar manner to Example 148. $^1$H NMR (400 MHz, DMSO-$d_6$) δ 10.42 (t, J=5.8 Hz, 1H), 8.69 (s, 1H), 8.58 (s, 1H), 8.24 (s, 3H), 7.80 (d, J=2.3 Hz, 1H), 7.45-7.31 (m, 6H), 7.21 (d, J=7.8 Hz, 2H), 6.24 (t, J=2.0 Hz, 1H), 5.61 (s, 2H), 5.31 (s, 2H), 4.85 (d, J=5.8 Hz, 2H), 3.99 (q, J=5.8 Hz, 2H). MS (M+H)+ found for $C_{24}H_{24}N_8$: 425.0.

Example 163

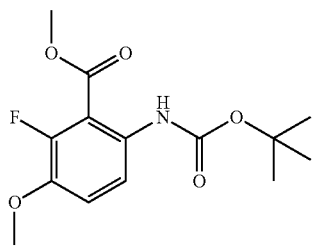 [SMILES: COC(=O)c1c(NC(=O)OC(C)(C)C)ccc(OC)c1F]

6-((tert-butoxycarbonyl)amino)-2-fluoro-3-methoxybenzoate

To a solution of methyl 6-bromo-2-fluoro-3-methoxybenzoate (2.20 g; 8.36 mmol; 1.00 eq.) in Dioxane (25 mL) was added tert-butyl carbamate (1.47 g; 12.54 mmol; 1.50 eq.), diacetoxypalladium (0.19 g; 0.84 mmol; 0.10 eq.), [5-(diphenylphosphanyl)-9,9-dimethyl-9H-xanthen-4-yl]diphenylphosphane (0.48 g; 0.84 mmol; 0.10 eq.) and Cesium carbonate (5.45 g; 16.73 mmol; 2.00 eq.). After heated at 100 degree for 15h, the mixture was cooled and diluted with EtOAc; solid was filtered off and the filtrate was concentrated to give crude product, which was purified by column chromatography to give methyl 6-((tert-butoxycarbonyl)amino)-2-fluoro-3-methoxybenzoate (1.80 g, 72%).

Example 164

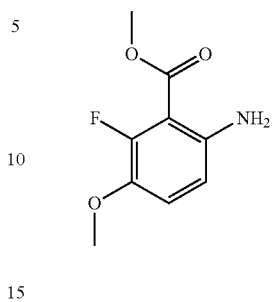

methyl 6-amino-2-fluoro-3-methoxybenzoate

To a solid sample of 6-((tert-butoxycarbonyl)amino)-2-fluoro-3-methoxybenzoate (1.80 g; 0.01 mol; 1.00 eq.)(Example 163) was added 4N HCl in dioxane, after reaction finished it was then concentrated to give amine HCl salt (1.20 g, 100%).

Example 165

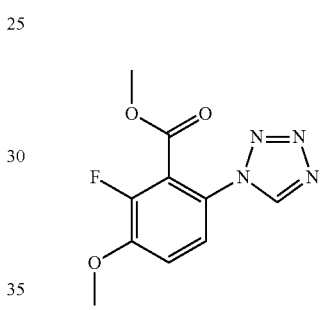

methyl 2-fluoro-3-methoxy-6-(1H-tetrazol-1-yl)benzoate

To a solution of methyl 6-amino-2-fluoro-3-methoxybenzoate (500.00 mg; 2.51 mmol; 1.00 eq.)(Example 164) in AcOH (2.0 mL) was added trimethoxymethane (0.82 ml; 7.53 mmol; 3.00 eq.) and sodium azide (489.58 mg; 7.53 mmol; 3.00 eq.), then it was stirred for 2h, and was then worked up to give crude product, which was purified by column chromatography to give methyl 2-fluoro-3-methoxy-6-(1H-tetrazol-1-yl)benzoate (190 mg, 30%).

Example 166

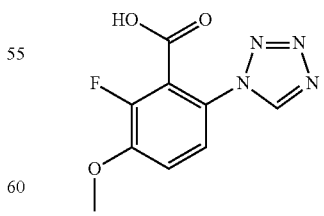

2-fluoro-3-methoxy-6-(1H-tetrazol-1-yl)benzoic acid

To a solution of methyl 2-fluoro-3-methoxy-6-(1H-1,2,3,4-tetrazol-1-yl)benzoate (190.00 mg; 0.75 mmol; 1.00 eq.)

(Example 165) in Dioxane (1 mL) was added MeOH (0.5 mL) and lithium hydroxide (36.08 mg; 1.51 mmol; 2.00 eq.) in water (0.5 mL), then it was stirred at room temperature until finished. The mixture was diluted with EtOAc and washed with a mixture of 1N HCl and Sat. NH4Cl, organic layer was separated and the organic layers were combined, dried and concentrated to give crude product, which was used for next step.

Example 167

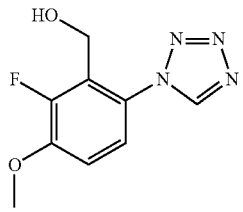 [SMILES: COc1ccc(-n2cnnn2)c(CO)c1F]

(2-fluoro-3-methoxy-6-(1H-tetrazol-1-yl)phenyl) methanol

To a solution of 2-fluoro-3-methoxy-6-(1H-1,2,3,4-tetrazol-1-yl)benzoic acid (180.00 mg; 0.76 mmol; 1.00 eq.) (Example 166) in THF (2 mL) at 0° C. was added triethylamine (0.16 ml; 1.13 mmol; 1.50 eq.) and isobutyl chloroformate (0.14 ml; 1.06 mmol; 1.40 eq.), after stirred for 30 min, it was added sodium borohydride (42.89 mg; 1.13 mmol; 1.50 eq.) in water (0.5 mL) and the mixture was stirred for additional 30 min and was then diluted with EtOAC and Sat. NH4Cl, aqueous layer was separated and was further extracted with EtOAc. The organic layers were combined and washed with sat. NaHCO3, concentrated to give (2-fluoro-3-methoxy-6-(1H-tetrazol-1-yl)phenyl) methanol as crude oil (110 mg, 65%).

Example 168

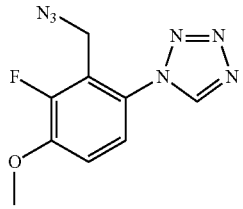 [SMILES: COc1ccc(-n2cnnn2)c(CN=[N+]=[N-])c1F]

1-(2-(azidomethyl)-3-fluoro-4-methoxyphenyl)-1H-tetrazole

To a solution of [2-fluoro-3-methoxy-6-(1H-1,2,3,4-tetrazol-1-yl)phenyl]methanol (110.00 mg; 0.49 mmol; 1.00 eq.) in DCM (2 mL) was added triethylamine (0.10 ml; 0.74 mmol; 1.50 eq.) and methanesulfonyl chloride (0.05 ml; 0.69 mmol; 1.40 eq.) after stirred for 1h, the mixture was diluted with EtOAc and brine, aqueous layer was separated and was extracted with EtOAc. Organic layers were combined, dried and concentrated to give desired crude mesylate. To the crude mesylate in DMF (2 mL) was added sodium azide (159.49 mg; 2.45 mmol; 5.00 eq.) and the mixture was heated at 80 degree for 1 h, HPLC checked the reaction is completed and the mixture was diluted with Ether and was washed with water and brine, dried and concentrated to give crude product, which was purified by column chromatography to give 1-(2-(azidomethyl)-3-fluoro-4-methoxyphenyl)-1H-tetrazole (80 mg, 65% over two steps).

Example 169

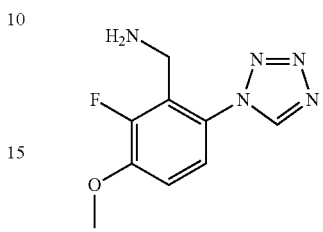

(2-fluoro-3-methoxy-6-(1H-tetrazol-1-yl)phenyl) methanamine

To a solution of 1-(2-(azidomethyl)-3-fluoro-4-methoxyphenyl)-1H-tetrazole (80.00 mg; 0.32 mmol; 1.00 eq.)(Example 168) in EtOH (1.5 mL) was added Pd(OH)₂/C and was charged with H₂ (1 atm), after stirred for 2h, the solid was filtered off and the filtrate was concentrated to give (2-fluoro-3-methoxy-6-(1H-tetrazol-1-yl)phenyl)methanamine (55 mg, 77%).

Example 170

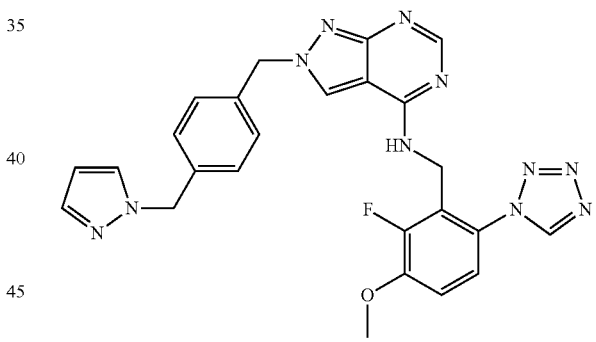

2-(4-((1H-pyrazol-1-yl)methyl)benzyl)-N-(2-fluoro-3-methoxy-6-(1H-tetrazol-1-yl)benzyl)-2H-pyrazolo[3,4-d]pyrimidin-4-amine To a solution of 1-{[4-({4-chloro-2H-pyrazolo[3,4-d]pyrimidin-2-yl}methyl)phenyl]methyl}-1H-pyrazole (36.38 mg; 0.11 mmol; 1.00 eq.)(Example 23) in DMF (1 mL) was added [2-fluoro-3-methoxy-6-(1H-1,2,3,4-tetrazol-1-yl)phenyl]methanamine (25.00 mg; 0.11 mmol; 1.00 eq.)(Example 169) and Hunig's base (0.03 ml; 0.17 mmol; 1.50 eq.), the mixture was heated at 90° C. for 1h and then it was cooled and diluted with water and AcCN, purified by preparative HPLC to give 2-(4-((1H-pyrazol-1-yl)methyl)benzyl)-N-(2-fluoro-3-methoxy-6-(1H-tetrazol-1-yl)benzyl)-2H-pyrazolo[3,4-d]pyrimidin-4-amine. $^1$H NMR (400 MHz, DMSO-$d_6$) δ 9.73 (d, J=1.5 Hz, 1H), 8.48 (t, J=5.3 Hz, 1H), 8.22 (s, 1H), 7.93 (s, 1H), 7.77 (s, 1H), 7.44-7.30 (m, 3H), 7.25 (d, J=7.8 Hz, 2H), 7.17 (d, J=7.9 Hz, 2H), 6.23 (d, J=2.1 Hz, 1H), 5.48 (s, 2H), 5.29 (s, 2H), 4.47 (d, J=5.1 Hz, 2H), 3.91 (s, 3H). MS (M+H)+ found for $C_{26}H_{22}FN_{11}O$: 512.3.

Example 171

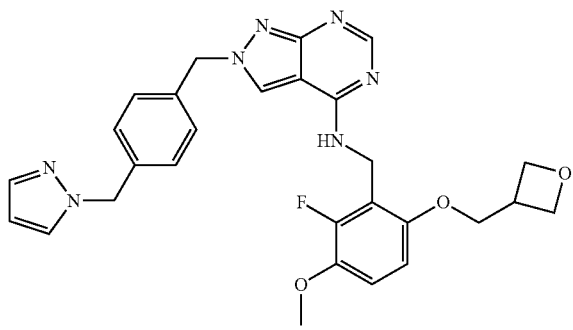 [SMILES: COc1ccc(OCC2COC2)c(CNc2ncnc3nn(Cc4ccc(Cn5cccn5)cc4)cc23)c1F]

2-(4-((1H-pyrazol-1-yl)methyl)benzyl)-N-(2-fluoro-3-methoxy-6-(oxetan-3-ylmethoxy)benzyl)-2H-pyrazolo[3,4-d]pyrimidin-4-amine Into an 8-mL vial, was placed a mixture of 1-[[4-([4-chloro-2H-pyrazolo[3,4-d]pyrimidin-2-yl]methyl)phenyl]methyl]-1H-pyrazole (150 mg, 0.46 mmol, 1.00 equiv) (Example 23), DMA (4 mL), [2-fluoro-3-methoxy-6-(oxetan-3-ylmethoxy)phenyl]methanamine (134 mg, 0.56 mmol, 1.20 equiv) and DIEA (237 mg, 1.83 mmol, 4.00 equiv). The resulted solution was stirred for 8 hr at 60° C. The crude product was purified by Prep-HPLC with the following conditions. Column: Waters X Bridge RP18 19*150 mm; mobile phase: $CH_3CN/H_2O$ (it contains 10 mM $NH_4HCO_3$+0.05% ammonia); gradient: 25% to 45% acetonitrile in 5 min; 45% to 80% acetonitrile in 5 min; flow rate: 15 mL/min; detector UV wavelength: 254 nm. This resulted in 51.0 mg (21%) of N-[[2-fluoro-3-methoxy-6-(oxetan-3-ylmethoxy)phenyl]methyl]-2-[[4-(1H-pyrazol-1-ylmethyl)phenyl]methyl]-2H-pyrazolo[3,4-d]pyrimidin-4-amine as a white solid. $^1$H NMR (300 MHz, DMSO-$d_6$): δ 8.26 (d, J=9.6 Hz, 2H), 8.12 (s, 1H), 7.79 (d, J=1.8 Hz, 1H), 7.44 (s, 1H), 7.31-7.17 (m, 4H), 7.09 (t, J=9.3 Hz, 1H), 6.84 (d, J=9.0 Hz, 1H), 6.25 (t, J=1.8 Hz, 1H), 5.50 (s, 2H), 5.30 (s, 2H), 4.67 (d, J=3.6 Hz, 2H), 4.51 (t, J=6.3 Hz, 2H), 4.28 (t, J=6.0 Hz, 2H), 4.14 (d, J=6.6 Hz, 2H), 3.79 (s, 3H), 3.25-3.16 (m, 1H). LC-MS (ESI) m/z: calculated for $C_{28}H_{28}FN_7O_3$: 529. found: 530 [M+H]+.

Example 172

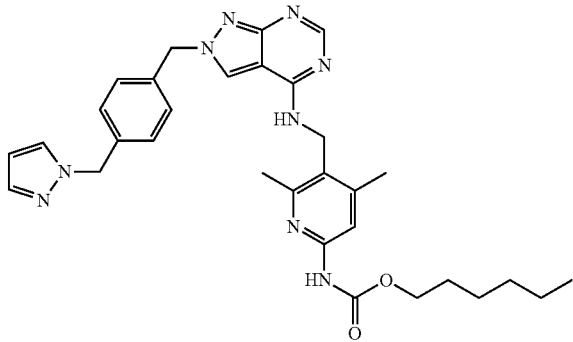 [SMILES: CCCCCCOC(=O)Nc1cc(C)c(CNc2ncnc3nn(Cc4ccc(Cn5cccn5)cc4)cc23)c(C)n1]

Hexyl 5-((2-(4-((1H-pyrazol-1-yl)methyl)benzyl)-2H-pyrazolo[3,4-d]pyrimidin-4-ylamino)methyl)-4,6-dimethylpyridin-2-ylcarbamate trifluoroacetate Into a 25-mL round-bottom flask, was placed a solution of 2-(4-((1H-pyrazol-1-yl)methyl)benzyl)-N-((6-amino-2,4-dimethylpyridin-3-yl)methyl)-2H-pyrazolo[3,4-d]pyrimidin-4-amine (400 mg, 0.78 mmol, 1.00 equiv)(Example 41) in pyridine (359 mg, 4.54 mmol, 5.00 equiv) and DMA (4 mL) with stirring at 0° C., to which was added chloro (hexyloxy)methanone (440 mg, 2.67 mmol, 3.00 equiv) dropwise. The resulted solution was stirred overnight at 50° C. in an oil bath. The solids were filtered out. The filtrate was concentrated under vacuum. The crude product was purified by Prep-HPLC with the following conditions. Column: Waters XBridge C18 19*150 mm, 5 μm; mobile phase: $CH_3CN$ and $H_2O$ (it is a buffer of 10 mM $NH_4HCO_3$+0.05% ammonia) with a gradient of 15% to 30% acetonitrile in 3 min then 30% to 75% acetonitrile in 8 min; flow rate: 20 mL/min; detector UV wavelength: 254 nm. This resulted in 110 mg (22%) of ethyl 4-[[[(6-[[(hexyloxy)carbonyl]amino]-2,4-dimethylpyridin-3-yl)methyl]amino]-2-[[4-(1H-pyrazol-1-ylmethyl)phenyl]methyl]-2H-pyrazolo[3,4-d]pyrimidine-6-carboxylate trifluoroacetate as a white solid $^1$H NMR (300 MHz, DMSO-$d_6$): δ 9.99 (s, 1H), 8.72 (s, 1H), 8.59 (s, 1H), 7.80 (d, J=1.5 Hz, 1H), 7.58 (s, 1H), 7.44 (d, J=1.8 Hz, 1H), 7.34 (d, J=8.4 Hz, 2H), 7.22 (d, J=8.1 Hz, 2H), 6.25 (t, J=2.1 Hz, 1H), 5.60 (s, 2H), 5.32 (s, 2H), 4.78 (s, 2H), 4.09 (t, J=7.2 Hz, 2H), 2.44 (s, 3H), 2.32 (s, 3H), 1.55-1.62 (m, 2H), 1.15-1.37 (m, 6H), 0.87 (t, J=6.6 Hz, 3H). LC-MS (ESI) m/z: calculated for C31H37N9O2: 567.31. found: 568 [M+H]+.

Example 173

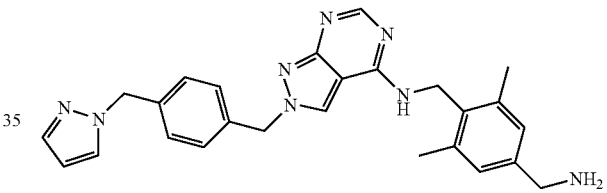

Example 174

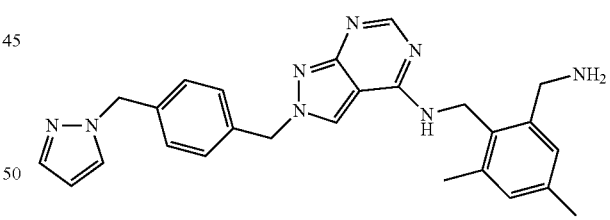

N-[[4-(aminomethyl)-2,6-dimethylphenyl]methyl]-2-[[4-(1H-pyrazol-1-ylmethyl)phenyl]methyl]-2H-pyrazolo[3,4-d]pyrimidin-4-amine And N-[[2-(aminomethyl)-4,6-dimethylphenyl]methyl]-2-[[4-(1H-pyrazol-1-ylmethyl)phenyl]methyl]-2H-pyrazolo[3,4-d]pyrimidin-4-amine Into a 8-mL vial, was placed a mixture of 1-[[4-([4-chloro-2H-pyrazolo[3,4-d]pyrimidin-2-yl]methyl)phenyl]methyl]-1H-pyrazole (200 mg, 0.62 mmol, 1.00 equiv) (Example 23), 2-[[4-(aminomethyl)-3,5-dimethylphenyl]methyl]-2,3-dihydro-1H-indene-1,3-dione and 2-[[2-(aminomethyl)-3,5-dimethylphenzyl]methyl]-2,3-dihydro- 1H-indene-1,3-dione (302 mg, 0.74 mmol, 1.20 equiv, TFA salt), DMA (2.0 mL), to which was followed by the addition of DIEA (398 mg, 3.08 mmol, 5.00 equiv) dropwise with stirring. The resulted mixture was stirred for 2 hours at 60° C. After the starting material was consumed completely, the reaction solution was directly poured into 40-mL vial, to which was added ethanol (10.0 mL). Then $NH_2NH_2 \cdot H_2O$ (1.0 mL) was added dropwise to the mixture with stirring. The resulted mixture was stirred for additional 1 hour at 70° C. The mixture was concentrated under vacuum, and the residue was purified directly by Prep-HPLC with the following conditions. Column: Waters X Bridge C18 19*150 mm; mobile phase, $CH_3CN$/water (10 mM $NH_4HCO_3$+ 0.05% ammonia) with a gradient of 15% to 45% acetonitrile in 5 min, flow rate: 20 mL/min; detector UV wavelength: 254 nm.

The HPLC fractions were concentrated under vacuum and lyophilized to afford 23.8 mg (2-steps yield: 8%) of N-[[4-(aminomethyl)-2,6-dimethylphenyl]methyl]-2-[[4-(1H-pyrazol-1-ylmethyl)phenyl]methyl]-2H-pyrazolo[3,4-d]pyrimidin-4-amine as a off-white solid.

$^1$H NMR (300 MHz, DMSO): ppm δ 8.31-8.26 (m, 2H), 8.03 (br, 1H), 7.79 (d, J=1.8 Hz, 1H), 7.43 (d, J=1.2 Hz, 1H)), 7.29 (d, J=8.1 Hz, 2H), 7.20 (d, J=8.1 Hz, 2H), 7.01 (s, 2H), 6.25 (t, J=1.8 Hz, 1H), 5.48 (s, 2H), 5.31 (s, 2H), 4.61 (d, J=4.2 Hz, 2H), 3.64 (s, 2H), 2.30 (s, 6H). MS (ESI) m/z 453 [M+H]$^+$.

The HPLC fractions were concentrated under vacuum and lyophilized to afford 84.9 mg (2-steps yield: 30%) of N-[[2-(aminomethyl)-4,6-dimethylphenyl]methyl]-2-[[4-(1H-pyrazol-1-ylmethyl)phenyl]methyl]-2H-pyrazolo[3,4-d]pyrimidin-4-amine as a pink solid.

$^1$H NMR (300 MHz, DMSO): ppm δ 8.34-8.21 (m, 3H), 7.79 (d, J=1.8 Hz, 1H), 7.43 (d, J=1.5 Hz, 1H)), 7.28 (d, J=8.1 Hz, 2H), 7.19 (d, J=8.1 Hz, 2H), 7.08-6.93 (m, 2H), 6.24 (t, J=1.8 Hz, 1H), 5.48 (s, 2H), 5.31 (s, 2H), 4.67 (s, 2H), 3.76 (s, 2H), 2.29 (s, 3H), 2.26 (s, 3H). MS (ESI) m/z 453 [M+H]$^+$.

Example 175

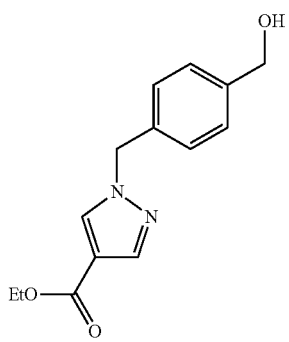 [SMILES: CCOC(=O)c1cnn(Cc2ccc(CO)cc2)c1]

Ethyl 1-(4-(hydroxymethyl)benzyl)-1H-pyrazole-4-carboxylate

Combined ethyl 1H-pyrazole-4-carboxylate (2.31 g; 16.48 mmol; 1.00 eq.), [4-(chloromethyl)phenyl]methanol (2.58 g; 16.48 mmol; 1.00 eq.), DMAP (0.04 g; 0.33 mmol; 0.02 eq.), and potassium carbonate (4.55 g; 32.97 mmol; 2.00 eq.) in acetonitrile (30.00 ml). Heated the reaction to 90° C. for 2 hours. Let the reaction cool to rt. Diluted reaction with water, extracted with ethyl acetate, combined organics, dried with MgSO$_4$, filtered, and concentrated. The residue was purified by silica gel column to give ethyl 1-(4-(hydroxymethyl)benzyl)-1H-pyrazole-4-carboxylate (3.7 g, 86%)$^1$H NMR (400 MHz, Chloroform-d) δ 7.93 (d, J=0.7 Hz, 1H), 7.84 (d, J=0.7 Hz, 1H), 7.40-7.34 (d, J=6.2 Hz, 2H), 7.24 (d, J=6.2 Hz, 2H), 5.29 (s, 2H), 4.70 (s, 2H), 4.27 (q, J=7.1 Hz, 2H), 1.36-1.29 (m, 3H).

Example 176

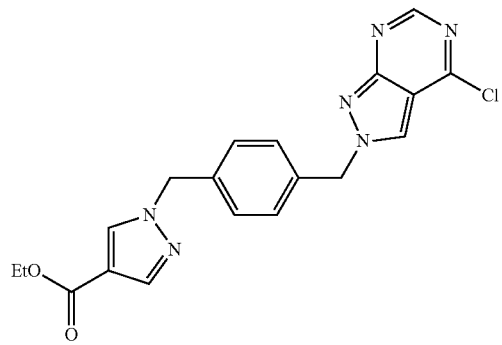 [SMILES: CCOC(=O)c1cnn(Cc2ccc(Cn3cc4c(Cl)ncnc4n3)cc2)c1]

Ethyl 1-(4-((4-chloro-2H-pyrazolo[3,4-d]pyrimidin-2-yl)methyl)benzyl)-1H-pyrazole-4-carboxylate Diisopropyl (E)-1,2-diazenedicarboxylate (0.62 g; 3.07 mmol; 1.00 eq.) was added dropwise to a precooled solution of ethyl 1-{[4-(hydroxymethyl)phenyl]methyl}-1H-pyrazole-4-carboxylate (0.80 g; 3.07 mmol; 1.00 eq.)(Example 175), 4-chloro-1H-pyrazolo[3,4-d]pyrimidine (0.48 g; 3.07 mmol; 1.00 eq.), and triphenylphosphane (0.81 g; 3.07 mmol; 1.00 eq.) in dichloromethane (20.00 ml) at 0° C. Let the reaction stir at 0° C. for 30 minutes. Concentrated and purified by silica gel column to give ethyl 1-(4-((4-chloro-2H-pyrazolo[3,4-d]pyrimidin-2-yl)methyl)benzyl)-1H-pyrazole-4-carboxylate (0.40 g; 33%).

Example 177

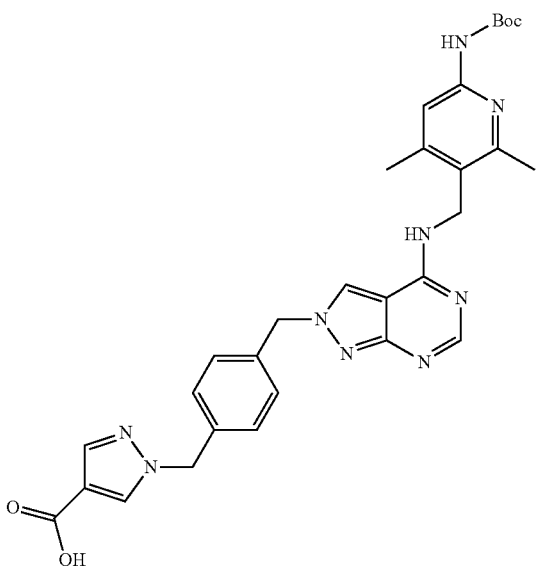 [SMILES: Cc1cc(NC(=O)OC(C)(C)C)nc(C)c1CNc1ncnc2nn(Cc3ccc(Cn4cc(C(=O)O)cn4)cc3)cc12]

1-(4-((4-(((6-((tert-butoxycarbonyl)amino)-2,4-dimethylpyridin-3-yl)methyl)amino)-2H-pyrazolo[3,4-d]pyrimidin-2-yl)methyl)benzyl)-1H-pyrazole-3-carboxylic acid Combined methyl 1-{[4-({4-chloro-2H-pyrazolo[3,4-d]pyrimidin-2-yl}methyl)phenyl]methyl}-1H-pyrazole-3-carboxylate (0.50 g; 1.31 mmol; 1.00 eq.)(Example 176), tert-butyl N-[5-(aminomethyl)-4,6-dimethylpyridin-2-yl]-N-[(tert-butoxy)carbonyl]carbamate (0.46 g; 1.31 mmol; 1.00 eq.), and Hunig's base (0.34 g; 2.61 mmol; 2.00 eq.) in N-Methyl-2-pyrrolidinone (10.00 ml) in a microwave vial. Heated the reaction in the microwave at 100° C. for 15 minutes. Diluted reaction with water, extracted with ethyl acetate, combined organics, dried, filtered and concentrated to afford the methyl ester of product. Treated resulting residue with 1 mL of 2M NaOH and heated to 60° C. for 30 minutes. Neutralized with cold 1M HCl and extracted aqueous layer with ethyl acetate, combined organics, dried with MgSO$_4$, filtered, and concentrated to give 1-(4-((4-(((6-((tert-butoxycarbonyl)amino)-2,4-dimethylpyridin-3-yl)methyl)amino)-2H-pyrazolo[3,4-d]pyrimidin-2-yl)methyl)benzyl)-1H-pyrazole-3-carboxylic acid (0.40 g; 52%) crude.

Example 178

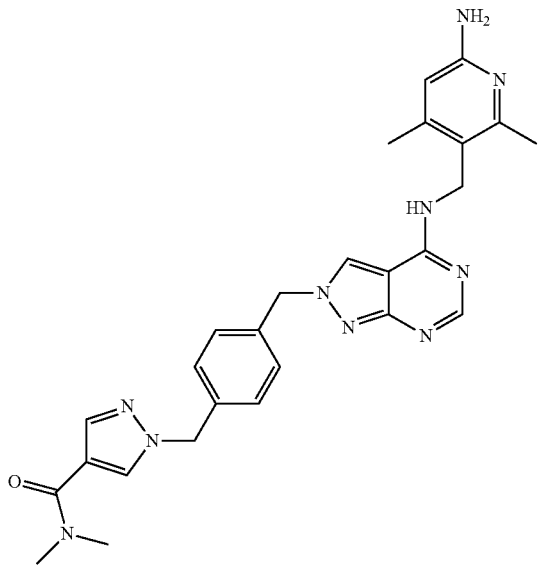 [SMILES: Cc1cc(N)nc(C)c1CNc1ncnc2nn(Cc3ccc(Cn4cc(C(=O)N(C)C)cn4)cc3)cc12]

Step 4. 1-(4-((4-(((6-amino-2,4-dimethylpyridin-3-yl)methyl)amino)-2H-pyrazolo[3,4-d]pyrimidin-2-yl)methyl)benzyl)-N,N-dimethyl-1H-pyrazole-4-carboxamide HATU (13.03 mg; 0.03 mmol; 1.00 eq.) was added to a solution containing 1-({4-[(4-{[(6-{[(tert-butoxy)carbonyl]amino}-2,4-dimethylpyridin-3-yl)methyl]amino}-2H-pyrazolo[3,4-d]pyrimidin-2-yl)methyl]phenyl}methyl)-1H-pyrazole-4-carboxylic acid (20.00 mg; 0.03 mmol; 1.00 eq.)(Example 177), N,N-dimethylamine in THF (0.07 ml; 1.00 mol/l; 0.07 mmol; 2.00 eq.) and Hunig's base (0.01 ml; 0.07 mmol; 2.00 eq.) in N,N-dimethylformamide (1.00 ml). Reaction was stirred for 30 minutes. Diluted reaction with water, extracted with ethyl acetate, combined organics, dried with MgSO$_4$, filtered and concentrated. Treated residue with 1 mL of 1M HCl and heated to 90° C. for 30 mins. Purified by prep HPLC to give 1-(4-((4-(((6-amino-2,4-dimethylpyridin-3-yl)methyl)amino)-2H-pyrazolo[3,4-d]pyrimidin-2-yl)methyl)benzyl)-N,N-dimethyl-1H-pyrazole-4-carboxamide (3.00 mg; 17%). $^1$H NMR (400 MHz, DMSO-d$_6$) δ 8.71 (s, 1H), 8.60 (s, 1H), 8.23 (d, J=0.8 Hz, 1H), 7.74-7.68 (m, 3H), 7.32 (d, J=8.0 Hz, 2H), 7.26 (d, J=8.2 Hz, 2H), 6.66 (s, 1H), 5.59 (s, 2H), 5.31 (s, 2H), 4.66 (d, J=4.7 Hz, 2H), 3.09 (s, 3H), 2.92 (s, 3H), 2.53 (s, 3H), 2.36 (s, 3H). MS (M+H)+ found for C$_{27}$H$_{30}$N$_{10}$O: 511.1.

Example 179

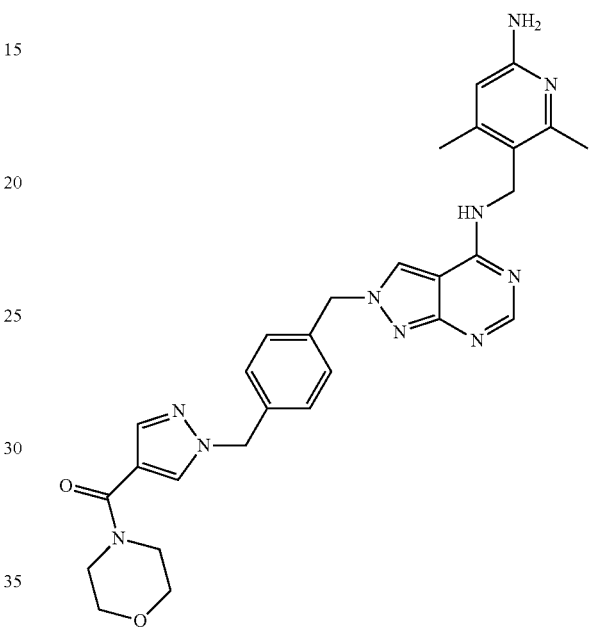

Preparation of (1-(4-((4-(((6-amino-2,4-dimethylpyridin-3-yl)methyl)amino)-2H-pyrazolo[3,4-d]pyrimidin-2-yl)methyl)benzyl)-1H-pyrazol-4-yl)(morpholino)methanone HATU (13.03 mg; 0.03 mmol; 1.00 eq.) was added to a solution containing 1-({4-[(4-{[(6-{[(tert-butoxy)carbonyl]amino}-2,4-dimethylpyridin-3-yl)methyl]amino}-2H-pyrazolo[3,4-d]pyrimidin-2-yl)methyl]phenyl}methyl)-1H-pyrazole-4-carboxylic acid (20.00 mg; 0.03 mmol; 1.00 eq.)(Example 177), morpholine (5.97 mg; 0.07 mmol; 2.00 eq.) and Hunig's base (0.01 ml; 0.07 mmol; 2.00 eq.) in N,N-dimethylformamide (1.00 ml). Reaction was stirred for 30 minutes. Diluted reaction with water. Extracted with ethyl acetate, combined organics, dried with MgSO$_4$, filtered and concentrated. Treated residue with 1M HCl and heated to 90° C. for 30 minutes. Purified by prep HPLC to give (1-(4-((4-(((6-amino-2,4-dimethylpyridin-3-yl)methyl)amino)-2H-pyrazolo[3,4-d]pyrimidin-2-yl)methyl)benzyl)-1H-pyrazol-4-yl)(morpholino)methanone (3 mgs, 16%). $^1$H NMR (400 MHz, DMSO-d$_6$) δ 8.49 (s, 1H), 8.41 (s, 1H), 8.21 (d, J=0.8 Hz, 1H), 7.67 (d, J=0.7 Hz, 1H), 7.60 (s, 2H), 7.35-7.22 (m, 4H), 6.65 (s, 1H), 5.55 (s, 2H), 5.31 (s, 2H), 4.59 (d, J=4.7 Hz, 2H), 3.56 (s, 8H), 2.52 (s, 3H), 2.36 (s, 3H). MS (M+H)+ found for C$_{29}$H$_{32}$N$_{10}$O$_2$: 552.9.

Example 180

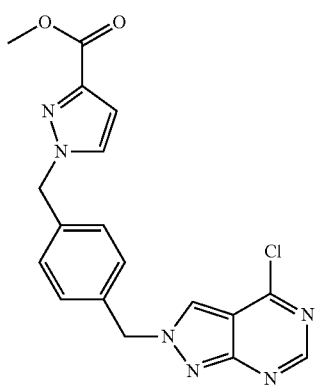 [SMILES: COC(=O)c1ccn(Cc2ccc(Cn3cc4c(Cl)ncnc4n3)cc2)n1]

Preparation of methyl 1-(4-((4-chloro-2H-pyrazolo[3,4-d]pyrimidin-2-yl)methyl)benzyl)-1H-pyrazole-3-carboxylate Methyl 1-(4-((4-chloro-2H-pyrazolo[3,4-d]pyrimidin-2-yl)methyl)benzyl)-1H-pyrazole-3-carboxylate was synthesized in a manner similar to ethyl 1-(4-((4-chloro-2H-pyrazolo[3,4-d]pyrimidin-2-yl)methyl)benzyl)-1H-pyrazole-4-carboxylate (Example 176) using methyl 1H-pyrazole-3-carboxylate to replace ethyl 1H-pyrazole-4-carboxylate. MS (M+H)+ found for $C_{18}H_{16}ClN_6O_2$: 382.9.

Example 181

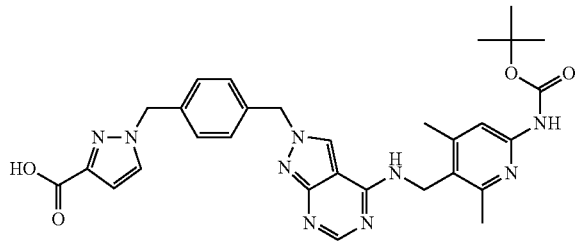 [SMILES: Cc1cc(NC(=O)OC(C)(C)C)nc(C)c1CNc1ncnc2nn(Cc3ccc(Cn4ccc(C(=O)O)n4)cc3)cc12]

1-(4-((4-(((6-((tert-butoxycarbonyl)amino)-2,4-dimethylpyridin-3-yl)methyl)amino)-2H-pyrazolo[3,4-d]pyrimidin-2-yl)methyl)benzyl)-1H-pyrazole-3-carboxylic acid Combined methyl 1-{[4-({4-chloro-2H-pyrazolo[3,4-d]pyrimidin-2-yl}methyl)phenyl]methyl}-1H-pyrazole-3-carboxylate (0.50 g; 1.31 mmol; 1.00 eq.) (Example 180), tert-butyl N-[5-(aminomethyl)-4,6-dimethylpyridin-2-yl]-N-[(tert-butoxy)carbonyl]carbamate (0.46 g; 1.31 mmol; 1.00 eq.)(Example 4, step 2), and Hunig's base (0.34 g; 2.61 mmol; 2.00 eq.) in N-Methyl-2-pyrrolidinone (10.00 ml) in a microwave vial. Heated the reaction in the microwave at 100° C. for 15 minutes. Diluted reaction with water, extracted with ethyl acetate, combined organics, dried, filtered and concentrated to give afford the methyl ester. Treated residue with 1 mL of 2M NaOH and heated to 60° C. for 30 minutes. Neutralized with 1M HCl and extracted with ethyl acetate, combined organics, dried with MgSO₄, filtered and concentrated to give 1-(4-((4-(((6-(((tert-butoxycarbonyl)amino)-2,4-dimethylpyridin-3-yl)methyl)amino)-2H-pyrazolo[3,4-d]pyrimidin-2-yl)methyl)benzyl)-1H-pyrazole-3-carboxylic acid (0.40 g; 52%) crude.

Example 182

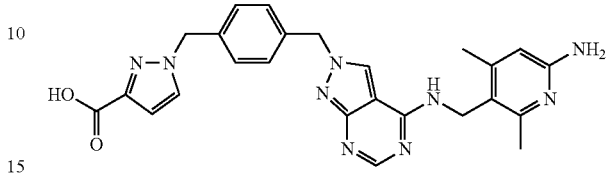

Step 9. 1-(4-((4-(((6-amino-2,4-dimethylpyridin-3-yl)methyl)amino)-2H-pyrazolo[3,4-d]pyrimidin-2-yl)methyl)benzyl)-1H-pyrazole-3-carboxylic acid 1-(4-((4-(((6-((tert-butoxycarbonyl)amino)-2,4-dimethylpyridin-3-yl)methyl)amino)-2H-pyrazolo[3,4-d]pyrimidin-2-yl)methyl)benzyl)-1H-pyrazole-3-carboxylic acid (20 mgs)(Example 181) was treated with 1 mL of 1M HCl and heated to 60° C. for 30 minutes. Purified by prep HPLC to give 1-(4-((4-(((6-amino-2,4-dimethylpyridin-3-yl)methyl)amino)-2H-pyrazolo[3,4-d]pyrimidin-2-yl)methyl)benzyl)-1H-pyrazole-3-carboxylic acid (1 mg). MS (M+H)+ found for $C_{25}H_{25}N_9O_2$: 484.4.

Example 183

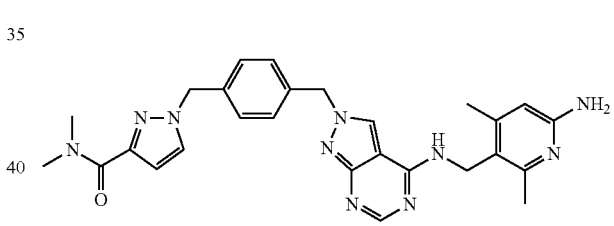

1-(4-((4-(((6-amino-2,4-dimethylpyridin-3-yl)methyl)amino)-2H-pyrazolo[3,4-d]pyrimidin-2-yl)methyl)benzyl)-N,N-dimethyl-1H-pyrazole-3-carboxamide HATU (32.57 mg; 0.09 mmol; 1.00 eq.) was added to a solution containing 1-({4-[(4-{[(6-{[(tert-butoxy)carbonyl]amino}-2,4-dimethylpyridin-3-yl)methyl]amino}-2H-pyrazolo[3,4-d]pyrimidin-2-yl)methyl]phenyl}methyl)-1H-pyrazole-3-carboxylic acid (Example 181) (50.00 mg; 0.09 mmol; 1.00 eq.), N,N-dimethylamine (13.80 mg; 0.17 mmol; 2.00 eq.), and Hunig's base (0.04 ml; 0.26 mmol; 3.00 eq.) in acetonitrile (1.00 ml). Stirred reaction for 15 minutes. Diluted reaction with water, extracted reaction with ethyl acetate, combined organics, dried, filtered, and concentrated. Treated residue with 1M HCl and heated to 60° C. for 30 minutes. Purified by prep HPLC to afford 1-(4-((4-(((6-amino-2,4-dimethylpyridin-3-yl)methyl)amino)-2H-pyrazolo[3,4-d]pyrimidin-2-yl)methyl)benzyl)-N,N-dimethyl-1H-pyrazole-3-carboxamide (12.00 mg; 27%). ¹H NMR (400 MHz, Methanol-d₄) δ 8.33 (s, 1H), 8.25 (s, 1H), 7.71 (d, J=2.4 Hz, 1H), 7.33 (d, J=8.2 Hz, 2H), 7.27 (d, J=8.3 Hz, 2H), 6.69 (s, 1H), 6.60 (d, J=2.3 Hz, 1H), 5.52 (s, 2H), 5.36 (s, 2H), 4.68 (s, 2H), 3.26 (s, 3H), 3.06 (s, 3H), 2.58 (s, 3H), 2.43 (s, 3H). MS (M+H)+ found for $C_{27}H_{30}N_{10}O$: 511.0.

Example 184

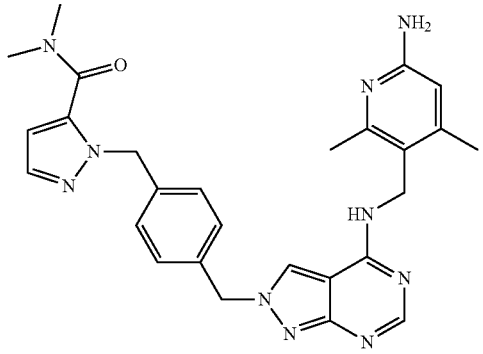

Preparation of 1-(4-((4-(((6-amino-2,4-dimethyl-pyridin-3-yl)methyl)amino)-2H-pyrazolo[3,4-d]py-rimidin-2-yl)methyl)benzyl)-N,N-dimethyl-1H-pyrazole-5-carboxamide 1-(4-((4-(((6-amino-2,4-dimethylpyridin-3-yl)methyl)amino)-2H-pyrazolo[3,4-d]pyrimidin-2-yl)methyl)benzyl)-N,N-dimethyl-1H-pyrazole-5-carboxamide was synthesized in a manner similar to Example 183 using methyl 1H-pyrazole-5-carboxylate to replace ethyl 1H-pyrazole-4-carboxylate in step 1. $^1$H NMR (400 MHz, Methanol-$d_4$) δ 8.31 (s, 1H), 8.27 (d, J=6.0 Hz, 1H), 7.51 (d, J=2.0 Hz, 1H), 7.34-7.27 (m, 2H), 7.20-7.11 (m, 3H), 6.65 (s, 1H), 6.48 (d, J=2.0 Hz, 1H), 5.50 (s, 2H), 5.40 (s, 2H), 4.67 (s, 2H), 2.89 (s, 3H), 2.72 (s, 3H), 2.56 (s, 3H), 2.42 (s, 3H). MS (M+H)+ found for $C_{27}H_{30}N_{10}O$: 511.2.

Example 185

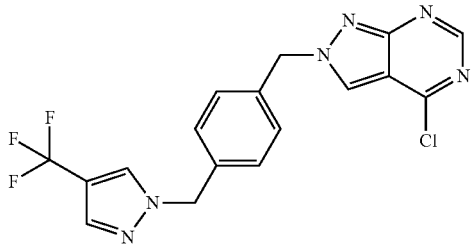 [SMILES: FC(F)(F)c1cnn(Cc2ccc(Cn3cc4c(Cl)ncnc4n3)cc2)c1]

Preparation of 4-chloro-2-(4-((4-(trifluoromethyl)-1H-pyrazol-1-yl)methyl)benzyl)-2H-pyrazolo[3,4-d]pyrimidine 4-Chloro-2-(4-((4-(trifluoromethyl)-1H-pyrazol-1-yl)methyl)benzyl)-2H-pyrazolo[3,4-d]pyrimidine was synthesized in a manner similar to ethyl 1-(4-((4-((4-chloro-2H-pyrazolo[3,4-d]pyrimidin-2-yl)methyl)benzyl)-1H-pyrazole-4-carboxylate (Example 23) using 4-(trifluoromethyl)-1H-pyrazole to replace replace ethyl 1H-pyrazole-4-carboxylate in step 1. MS (M+H)+ found for $C_{17}H_{12}ClF_3N_6$: 393.0.

Example 186

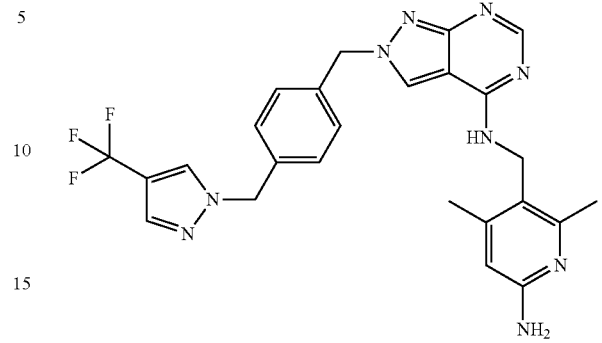

N-((6-amino-2,4-dimethylpyridin-3-yl)methyl)-2-(4-((4-(trifluoromethyl)-1H-pyrazol-1-yl)methyl)benzyl)-2H-pyrazolo[3,4-d]pyrimidin-4-amine 1-{[4-({4-chloro-2H-pyrazolo[3,4-d]pyrimidin-2-yl}methyl)phenyl]methyl}-4-(trifluoromethyl)-1H-pyrazole (400.00 mg; 1.02 mmol; 1.00 eq.)(Example 185), tert-butyl N-[5-(aminomethyl)-4,6-dimethylpyridin-2-yl]-N-[(tert-butoxy)carbonyl]carbamate (357.91 mg; 1.02 mmol; 1.00 eq.) (Example 4, Step 2), and Hunig's base (394.87 mg; 3.06 mmol; 3.00 eq.) in acetonitrile (10.00 ml) were stirred and heated to 90° C. for 1 hour. Let the reaction cool to rt. Diluted reaction with water, extracted with ethyl acetate, combined organics, and concentrated. Treated residue with 2 mL of 1M HCl and heated the solution to 60° C. for 30 minutes. Purified by prep HPLC to afford N-((6-amino-2,4-dimethylpyridin-3-yl)methyl)-2-(4-((4-(trifluoromethyl)-1H-pyrazol-1-yl)methyl)benzyl)-2H-pyrazolo[3,4-d]pyrimidin-4-amine (14.00 mg; 2%). $^1$H NMR (400 MHz, Methanol-$d_4$) δ 8.58 (s, 1H), 8.48 (s, 1H), 8.21-8.14 (m, 1H), 7.82-7.72 (m, 1H), 7.39 (d, J=8.0 Hz, 2H), 7.36-7.26 (m, 2H), 6.73 (s, 1H), 5.59 (s, 2H), 5.38 (s, 2H), 4.80 (s, 2H), 2.59 (s, 3H), 2.45 (s, 3H). MS (M+H)+ found for $C_{25}H_{24}F_3N_9$: 508.0.

Example 187

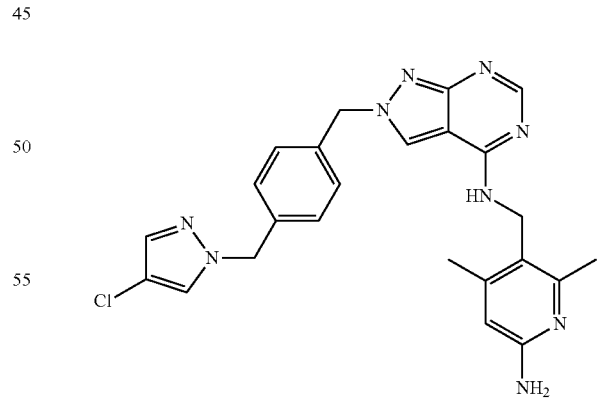

N-((6-amino-2,4-dimethylpyridin-3-yl)methyl)-2-(4-((4-chloro-1H-pyrazol-1-yl)methyl)benzyl)-2H-pyrazolo[3,4-d]pyrimidin-4-amine ( )

N-((6-amino-2,4-dimethylpyridin-3-yl)methyl)-2-(4-((4-chloro-1H-pyrazol-1-yl)methyl)benzyl)-2H-pyrazolo[3,4-d]

pyrimidin-4-amine was synthesized in a manner similar to Example 186 using 4-chloro-1H-pyrazole to replace 4-(trifluoromethyl)-1H-pyrazole. $^1$H NMR (400 MHz, Methanol-d$_4$) δ 8.33 (s, 1H), 8.31 (s, 1H), 7.75 (d, J=0.8 Hz, 1H), 7.44 (d, J=0.8 Hz, 1H), 7.36-7.29 (m, 2H), 7.27-7.19 (m, 2H), 6.60 (s, 1H), 5.51 (s, 2H), 5.27 (s, 2H), 4.66 (s, 2H), 2.53 (s, 3H), 2.39 (d, J=0.8 Hz, 3H). MS (M+H)+ found for $C_{24}H_{24}ClN_9$ : 474.0.

Example 188

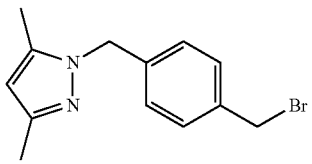 [SMILES: Cc1cc(C)n(Cc2ccc(CBr)cc2)n1]

1-(4-(bromomethyl)benzyl)-3,5-dimethyl-1H-pyrazole

Into a 100-mL 3-necked round-bottom flask purged and maintained with an inert atmosphere of nitrogen, were placed 3,5-dimethyl-1H-pyrazole (1 g, 10.40 mmol, 1.00 equiv), N,N-dimethylformamide (30 mL) and 1,4-bis(bromomethyl)benzene (5.28 g, 20.00 mmol, 2.00 equiv). This was followed by the addition of sodium hydride (480 mg, 20.00 mmol, 1.20 equiv; mineral oil suspension) in several batches at 0° C. The resulted solution was stirred for 2 h at room temperature. The reaction was then quenched by the addition of 20 mL of water/ice at 0° C. The mixture was extracted with ethyl acetate (20 mL×3). The organic phase was washed with 100 mL of brine, dried over anhydrous sodium sulfate and concentrated under vacuum. The residue was purified by silica gel column chromatography eluted with ethyl acetate/ petroleum ether (1:5). This resulted in 1.60 g (55%) of 1-(4-(bromomethyl)benzyl)-3,5-dimethyl-1H-pyrazole as a white solid. MS (ESI) m/z 279 [M+H]$^+$.

Example 189

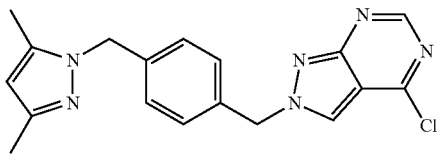 [SMILES: Cc1cc(C)n(Cc2ccc(Cn3cc4c(Cl)ncnc4n3)cc2)n1]

4-chloro-2-(4-((3,5-dimethyl-1H-pyrazol-1-yl) methyl)benzyl)-2H-pyrazolo[3,4-d]pyrimidine Into a 100-mL round-bottom flask purged and maintained with an inert atmosphere of nitrogen, were placed 1-(4-(bromomethyl)benzyl)-3,5-dimethyl-1H-pyrazole (800 mg, 2.87 mmol, 1.00 equiv)(Example 188), acetonitrile (20 mL), 4-chloro-2H-pyrazolo[3,4-d]pyrimidine (491 mg, 3.18 mmol, 1.10 equiv), potassium carboante (795 mg, 5.75 mmol, 2.00 equiv) and sodium iodide (432 mg, 2.87 mmol, 1.00 equiv). The resulted solution was stirred overnight at room temperature. The solids were filtered out. The filtrate was concentrated under vacuum. The crude product was purified by reverse phase column chromatography with the following conditions: column, C 18, 20-45 um, 100 A, 120 g; mobile phase, acetonitrile/ water (10 mM NH$_4$HCO$_3$) gradient from 45% to 70% in 15 min; flow rate: 60 mL/min; detector UV wave length: 254 nm. This resulted in 300 mg (30%) of 4-chloro-2-(4-((3,5-dimethyl-1H-pyrazol-1-yl) methyl)benzyl)-2H-pyrazolo[3,4-d]pyrimidine as a white solid. $^1$H NMR (300 MHz, DMSO): δ 9.08 (s, 1H), 8.79 (s, 1H), 7.37 (d, J=8.1 Hz, 2H), 7.09 (d, J=8.4 Hz, 2H), 5.82 (s, 1H), 5.69 (s, 2H), 5.16 (s, 2H), 2.13 (s, 3H), 2.07 (s, 3H). MS (ESI) m/z 353 [M+H]$^+$.

Example 190

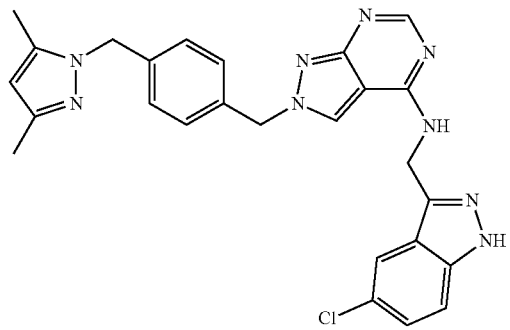 [SMILES: Cc1cc(C)n(Cc2ccc(Cn3cc4c(NCc5n[nH]c6ccc(Cl)cc56)ncnc4n3)cc2)n1]

N-((5-chloro-1H-indazol-3-yl)methyl)-2-(4-((3,5-dimethyl-1H-pyrazol-1-yl)methyl)benzyl)-2H-pyrazolo[3,4-d] pyrimidin-4-amine Into a 30-mL vial, was placed 1-[[4-([4-chloro-2H-pyrazolo[3,4-d]pyrimidin-2-yl]methyl)phenyl] methyl]-3,5-dimethyl-1H-pyrazole (130 mg, 0.37 mmol, 1.00 equiv)(Example 189), 1-ethoxy-2-(2-ethoxyethoxyl) ethane (6 mL), (5-chloro-1H-indazol-3-yl)methanamine (100 mg, 0.55 mmol, 1.50 equiv)(Example 2), dichlorozinc (502 mg, 3.68 mmol, 10 equiv), DIEA (953 mg, 7.37 mmol, 20.00 equiv). The resulting solution was stirred for 3 h at 120° C. The crude product was purified by Flash-Prep-HPLC with the following conditions (IntelFlash-1): Column, silica gel; mobile phase, DCM:EA:MeOH:NH4OH=4:4:1:0.2 increasing to DCM:EA:MeOH:NH4OH=4:4:1:0.2 within 25 min; Detector, UV 254 nm. The product was obtained and concentrated under vacuum. The crude product was purified by Prep-HPLC with the following conditions: Column, Bridge C18; mobile phase, ACN/water (0.05% NH4OH, 10 mM NH4HCO3) from 40% to 44% within 5 min, flow rate: 20 mL/min; Detector. The product was obtained and concentrated under vacuum. This resulted in 62.4 mg (34%) of N-[(5-chloro-1H-indazol-3-yl)methyl]-2-([4-[(3,5-dimethyl-1H-pyrazol-1-yl)methyl]phenyl] methyl)-2H-pyrazolo[3,4-d]pyrimidin-4-amine as a white solid. $^1$H NMR (300 MHz, DMSO-d$_6$): 13.08 (s, 1H), 8.70 (s, 1H), 8.35 (d, J=18.3 Hz, 2H), 7.86 (s, 1H), 7.54 (d, J=8.7 Hz, 1H), 7.49-7.34 (m, 3H), 7.09 (d, J=8.1 Hz, 2H), 5.82 (s, 2), 5.52 (s, 2H), 5.15 (s, 2H), 5.03 (d, J=5.7 Hz, 2H), 2.12 (3H, s), 2.07 (s, 3H). MS (ESI) m/z 498 [M+H]$^+$

Example 191

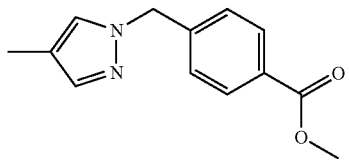

methyl 4-((4-methyl-1H-pyrazol-1-yl)methyl)benzoate

Into a 50-mL round-bottom flask purged and maintained with an inert atmosphere of nitrogen, was placed 4-methyl-1H-pyrazole (820 mg, 9.99 mmol, 1.00 equiv) in N,N-dimethylformamide (30 mL) with stirring at 0° C. This was followed by the addition of 60% sodium hydride in mineral oil (600 mg, 25.00 mmol, 1.50 equiv) in portions at 0° C. in 10 min. To this was added methyl 4-(bromomethyl)benzoate (2.29 g, 10.00 mmol, 1.00 equiv) in portions at 0° C. Then it was stirred for 2 h at 25° C. The mixture was diluted with 50 mL of water and extracted with ethyl acetate. The organic phase was washed with brine, dried over sodium sulfate and concentrated. This resulted in 2.10 g (91.1%) of methyl 4-[(4-methyl-1H-pyrazol-1-yl)methyl]benzoate as a yellow solid. MS (ESI) m/z 231 [M+1]$^+$

Example 192

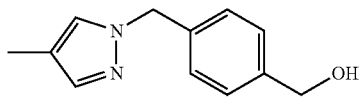

(4-((4-methyl-1H-pyrazol-1-yl)methyl)phenyl) methanol

Into a 50-mL 3-necked round-bottom flask, was placed methyl 4-[(4-methyl-1H-pyrazol-1-yl)methyl]benzoate (3.40 g, 14.77 mmol, 1.00 equiv)(Example 191) in THF (30 mL) with stirring at -10° C. This was followed by the addition of LiAlH$_4$ (674 mg, 19.87 mmol, 1.20 equiv) in portions at -10° C. in 10 min. The resulted solution was stirred for 2 h at -10° C. The reaction was then quenched by the addition of 1.5 mL of water. The solids were filtered out. The filtrate was dried over sodium sulfate and concentrated under vacuum. This resulted in 1.50 g (50%) of [4-[(4-methyl-1H-pyrazol-1-yl)methyl]phenyl]methanol as colorless oil. MS (ESI) m/z 203 [M+1]$^+$

Example 193

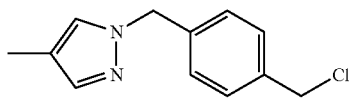

1-(4-(chloromethyl)benzyl)-4-methyl-1H-pyrazole

Into a 50-mL 3-necked round-bottom flask purged and maintained with an inert atmosphere of nitrogen, was placed [4-[(4-methyl-1H-pyrazol-1-yl)methyl]phenyl]methanol (1.50 g, 7.42 mmol, 1.00 equiv)(Example 192) in dichloromethane (20 mL) with stirring at 0° C. This was followed by the addition of thionyl dichloride (1.06 g, 8.91 mmol, 1.20 equiv) dropwise with stirring at 0° C. in 10 min. The resulted solution was stirred for 1.5 h at 0° C. in a water/ice bath. The mixture was concentrated under vacuum. This resulted in 1.30 g (79%) of 1-[[4-(chloromethyl)phenyl]methyl]-4-methyl-1H-pyrazole as a colorless oil. MS (ESI) m/z 221 [M+1]$^+$

Example 194

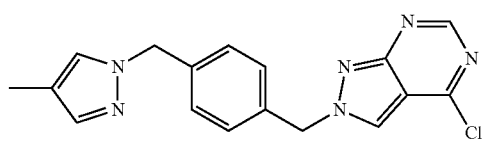 [SMILES: Cc1cnn(Cc2ccc(Cn3cc4c(Cl)ncnc4n3)cc2)c1]

4-chloro-2-(4-((4-methyl-1H-pyrazol-1-yl)methyl) benzyl)-2H-pyrazolo[3,4-d]pyrimidine Into a 100-mL round-bottom flask, were placed 1-[[4-(chloromethyl)phenyl]methyl]-4-methyl-1H-pyrazole (1.3 g, 5.89 mmol, 1.00 equiv)(Example 193), 4-chloro-2H-pyrazolo[3,4-d]pyrimidine (910 mg, 5.89 mmol, 1.00 equiv), KI (1.47 g, 1.50 equiv), K$_2$CO$_3$ (1.21 g, 8.75 mmol, 1.50 equiv) and CH$_3$CN (50 mL). The resulted solution was stirred for overnight at 25° C. The solids were filtered out. The filtrate was concentrated under vacuum. The crude product was purified by Prep-HPLC with the following conditions: column, waters sunfire C18 5 um, 19×150 mm, mobile phase: phase A: 0.05% NaHCO$_3$ in water; phase B: acetonitrile, detector UV wave length: 254 nm. This resulted in 0.1 g (5%) of 1-[[4-([4-chloro-2H-pyrazolo[3,4-d]pyrimidin-2-yl]methyl)phenyl]methyl]-4-methyl-1H-pyrazole as a white solid. MS (ESI) m/z 339 [M+1]+

Example 195

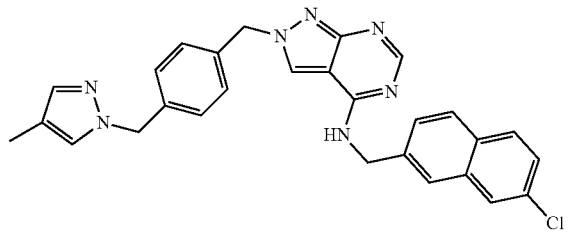 [SMILES: Cc1cnn(Cc2ccc(Cn3cc4c(NCc5ccc6ccc(Cl)cc6c5)ncnc4n3)cc2)c1]

N-((7-chloronaphthalen-2-yl)methyl)-2-(4-((4-methyl-1H-pyrazol-1-yl)methyl)benzyl)-2H-pyrazolo[3,4-d]pyrimidin-4-amine Into a 8-mL vial, were placed 1-[[4-([4-chloro-2H-pyrazolo[3,4-d]pyrimidin-2-yl]methyl)phenyl]methyl]-4-methyl-1H-pyrazole (100 mg, 0.30 mmol, 1.00 equiv)(Example 194), N,N-dimethylformamide (5 mL), (7-chloronaphthalen-2-yl)methanamine (85 mg, 0.44 mmol, 1.5 equiv) and DIEA (763 mg, 5.90 mmol, 20 equiv). The resulted solution was stirred overnight at room temperature.

The crude product was purified by flash column chromatography eluted with DCM/EA/MeOH/ concentrated ammonia aqueous solution (4:4:1:0.2). The crude product was further purified by Prep-HPLC with the following conditions: column, Waters XBridge RP18 19*150 mm; mobile phase, CH3CN/water (0.05% NH₄OH, 10 mM NH₄HCO₃) gradient from 50% to 55% with a 25-min run time, flow rate: 20 mL/min; detector UV wavelength: 254 nm. This resulted in 81.9 mg (56%) of N-[(7-chloronaphthalen-2-yl)methyl]-2-([4-[(4-methyl-1H-pyrazol-1-yl)methyl]phenyl]methyl)-2H-pyrazolo[3,4-d]pyrimidin-4-amine as white solid. ¹H NMR (300 MHz, CD₃OD-d): 8.27 (s, 2H), 7.88-7.83 (m, 3H), 7.71 (s, 1H), 7.54 (d, J=7.5 Hz, 1H), 7.43 (d, J=6.6 Hz, 2H), 7.36-7.30 (m, 3H), 5.54 (s, 2H), 5.30 (s, 2H), 4.95 (s, 2H), 2.06 (s, 3H). MS (ESI) m/z 494 [M+H]⁺

Example 196

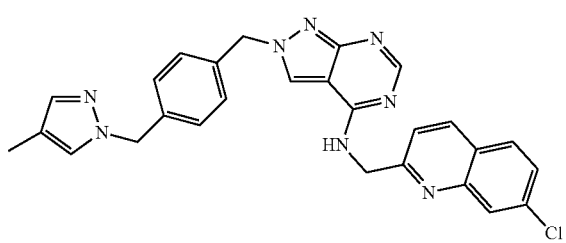 [SMILES: Cc1cnn(Cc2ccc(Cn3cc4c(NCc5ccc6ccc(Cl)cc6n5)ncnc4n3)cc2)c1]

N-((7-chloroquinolin-2-yl)methyl)-2-(4-((4-methyl-1H-pyrazol-1-yl)methyl)benzyl)-2H-pyrazolo[3,4-d]pyrimidin-4-amine N-((7-chloroquinolin-2-yl)methyl)-2-(4-((4-methyl-1H-pyrazol-1-yl)methyl)benzyl)-2H-pyrazolo[3,4-d]pyrimidin-4-amine was synthesized in a similar manner as Example 195. ¹H NMR (300 MHz, CD₃OD): δ 8.93 (s, 1H), 8.44 (s, 1H), 8.363 (d, J=14.5 Hz, 1H), 8.17 (s, 1H), 8.02 (d, J=8.7 Hz, 2H), 7.73-7.50 (m, 1H), 7.33 (d, J=8.1 Hz, 2H), 7.23 (d, J=10.2 Hz, 2H), 5.56 (s, 2H), 5.23 (s, 2H), 4.97 (d, J=6.0 Hz, 2H), 1.98 (s, 3H). MS (ESI) m/z 494 [M+H]⁺

Example 197

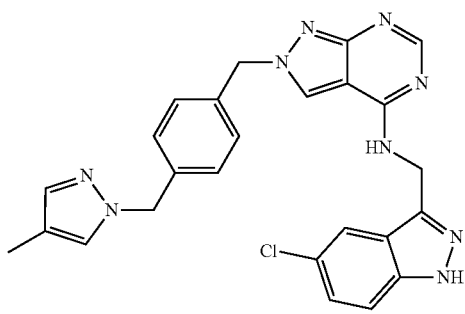 [SMILES: Cc1cnn(Cc2ccc(Cn3cc4c(NCc5n[nH]c6ccc(Cl)cc56)ncnc4n3)cc2)c1]

N-((5-chloro-1H-indazol-3-yl)methyl)-2-(4-((4-methyl-1H-pyrazol-1-yl)methyl)benzyl)-2H-pyrazolo[3,4-d]pyrimidin-4-amine N-((5-chloro-1H-indazol-3-yl)methyl)-2-(4-((4-methyl-1H-pyrazol-1-yl)methyl)benzyl)-2H-pyrazolo[3,4-d]pyrimidin-4-amine was prepared in a similar manner as Example 190. ¹H NMR (300 MHz, CD₃OD): δ 8.36 (s, 1H), 8.24 (s, 1H), 7.82 (s, 1H), 7.51 (d, J=8.7 Hz, 1H), 7.42 (s, 1H), 7.36-7.30 (m, 4H), 7.21 (d, J=8.1 Hz, 2H), 5.52 (s, 2H), 5.25 (s, 2H), 5.12 (s, 2H), 2.06 (s, 3H). MS (ESI) m/z 484 [M+H]⁺

Example 198

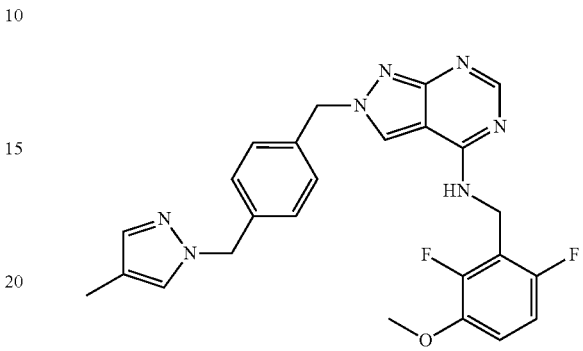

N-[(2,6-difluoro-3-methoxyphenyl)methyl]-2-({4-[(4-methyl-1H-pyrazol-1-yl)methyl]phenyl}methyl)-2H-pyrazolo[3,4-d]pyrimidin-4-amine N-[(2,6-difluoro-3-methoxyphenyl)methyl]-2-({4-[(4-methyl-1H-pyrazol-1-yl)methyl]phenyl}methyl)-2H-pyrazolo[3,4-d]pyrimidin-4-amine was prepared as described in Example 195. ¹H NMR (400 MHz, Methanol-d₄) δ 8.29 (s, 1H), 8.21 (s, 1H), 7.43-7.38 (m, 1H), 7.29 (m, 3H), 7.21-7.14 (m, 2H), 7.07 (m, 1H), 6.91 (m, 1H), 5.49 (s, 2H), 5.23 (s, 2H), 4.81 (m, 2H), 3.84 (s, 3H), 2.04 (s, 3H). MS (ES, m/z) found for C₂₅H₂₃F₂N₇O: 476.02 [M+H]⁺.

Example 199

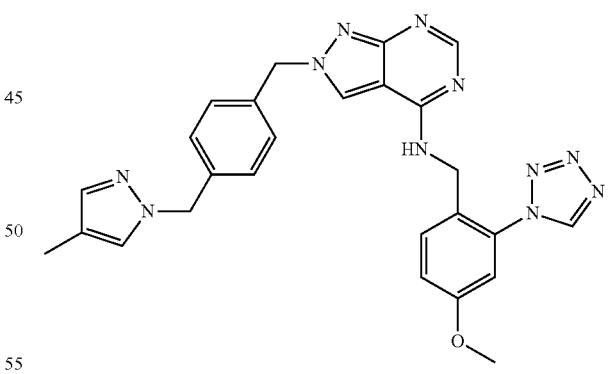

1-(4-((4-((5-methoxy-2-(1H-tetrazol-1-yl)benzyl)amino)-2H-pyrazolo[3,4-d]pyrimidin-2-yl)methyl)benzyl)pyridin-2(1H)-one 1-(4-((4-((5-methoxy-2-(1H-tetrazol-1-yl)benzyl)amino)-2H-pyrazolo[3,4-d]pyrimidin-2-yl)methyl)benzyl)pyridin-2(1H)-one was prepared in a similar manner to Example 111. ¹H NMR (400 MHz, DMSO-d₆) δ 9.83 (s, 1H), 8.49 (t, J=5.6 Hz, 1H), 8.27 (s, 1H), 8.06 (s, 1H), 7.52 (s, 1H), 7.51-7.47 (m, 1H), 7.30-7.13 (m, 7H), 5.50 (s, 2H), 5.20 (s, 2H), 4.44

(d, J=5.6 Hz, 2H), 3.78 (s, 3H), 1.96 (s, 3H). MS (M+H)+ found for C$_{26}$H$_{25}$N$_{11}$O: 508.2.

Example 200

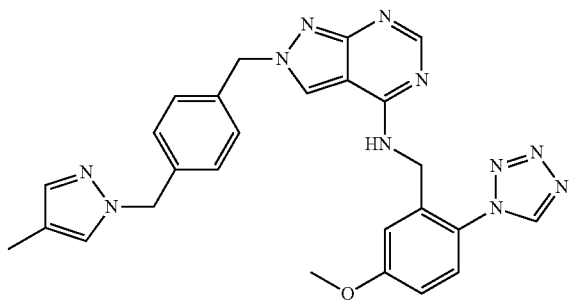 [SMILES: COc1ccc(-n2cnnn2)c(CNc2ncnc3nn(Cc4ccc(Cn5cc(C)cn5)cc4)cc23)c1]

N-(5-methoxy-2-(1H-tetrazol-1-yl)benzyl)-2-(4-((4-methyl-1H-pyrazol-1-yl)methyl)benzyl)-2H-pyrazolo[3,4-d]pyrimidin-4-amine N-(5-methoxy-2-(1H-tetrazol-1-yl)benzyl)-2-(4-((4-methyl-1H-pyrazol-1-yl)methyl)benzyl)-2H-pyrazolo[3,4-d]pyrimidin-4-amine was prepared in a similar manner to Example 111. $^1$H NMR (400 MHz, DMSO-d$_6$) δ 9.76 (s, 1H), 8.53 (t, J=5.6 Hz, 1H), 8.29 (s, 1H), 8.07 (s, 1H), 7.53-7.45 (m, 2H), 7.27 (d, J=7.9 Hz, 2H), 7.24-7.15 (m, 3H), 7.11 (d, J=2.8 Hz, 1H), 7.07 (dd, J=8.7, 2.9 Hz, 1H), 5.51 (s, 2H), 5.20 (s, 2H), 4.44 (d, J=5.6 Hz, 2H), 3.78 (s, 3H), 1.96 (s, 3H). MS (M+H)+ found for C$_{26}$H$_{25}$N$_{11}$O: 508.2.

Example 201

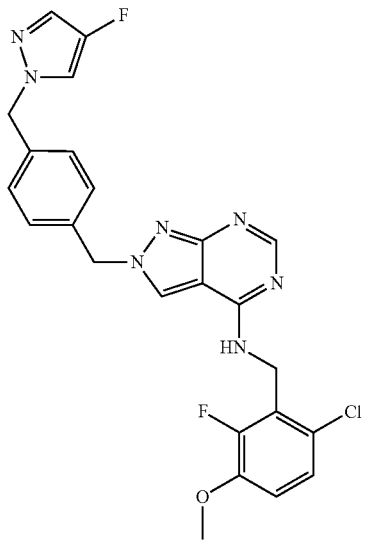 [SMILES: COc1ccc(Cl)c(CNc2ncnc3nn(Cc4ccc(Cn5cc(F)cn5)cc4)cc23)c1F]

N-(6-chloro-2-fluoro-3-methoxybenzyl)-2-(4-((4-fluoro-1H-pyrazol-1-yl)methyl)benzyl)-2H-pyrazolo[3,4-d]pyrimidin-4-amine N-(6-chloro-2-fluoro-3-methoxybenzyl)-2-(4-((4-fluoro-1H-pyrazol-1-yl)methyl)benzyl)-2H-pyrazolo[3,4-d]pyrimidin-4-amine was synthesized in a manner similar to Example 345 using 4-fluoro-1H-pyrazole to replace 5-chloro-1,2-dihydropyridin-2-one in step 12. $^1$H NMR (400 MHz, Methanol-d$_4$) δ 8.30 (s, 1H), 8.22 (s, 1H), 7.64 (d, J=4.5 Hz, 1H), 7.37 (d, J=4.1 Hz, 1H), 7.31 (d, J=7.9 Hz, 2H), 7.22 (dd, J=8.7, 2.3 Hz, 3H), 7.10 (t, J=8.9 Hz, 1H), 5.50 (s, 2H), 5.22 (s, 2H), 3.88 (s, 3H). MS (M+H)+ found for C$_{24}$H$_{20}$ClF$_2$N$_7$O: 496.1.

Example 202

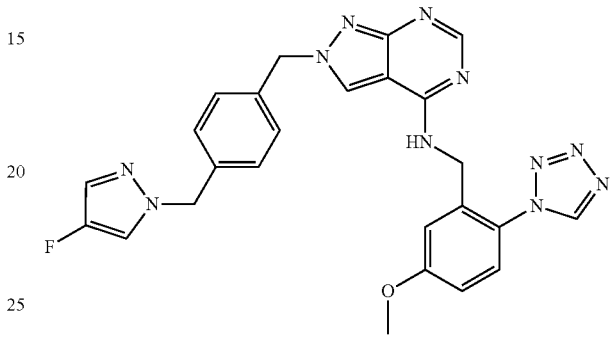

2-(4-((4-fluoro-1H-pyrazol-1-yl)methyl)benzyl)-N-(5-methoxy-2-(1H-tetrazol-1-yl)benzyl)-2H-pyrazolo[3,4-d]pyrimidin-4-amine 2-(4-((4-fluoro-1H-pyrazol-1-yl)methyl)benzyl)-N-(5-methoxy-2-(1H-tetrazol-1-yl)benzyl)-2H-pyrazolo[3,4-d]pyrimidin-4-amine was prepared similar to Example 111. $^1$H NMR (400 MHz, DMSO-d$_6$) δ 9.76 (s, 1H), 8.54 (t, J=5.6 Hz, 1H), 8.30 (s, 1H), 8.07 (s, 1H), 7.93 (dd, J=4.6, 0.8 Hz, 1H), 7.52-7.42 (m, 2H), 7.29 (d, J=8.0 Hz, 2H), 7.21 (d, J=8.2 Hz, 2H), 7.14-7.03 (m, 2H), 5.52 (s, 2H), 5.20 (s, 2H), 4.44 (d, J=5.6 Hz, 2H), 3.78 (s, 3H). MS (M+H)+ found for C$_{26}$H$_{22}$FN$_{11}$O: 512.2.

Example 203

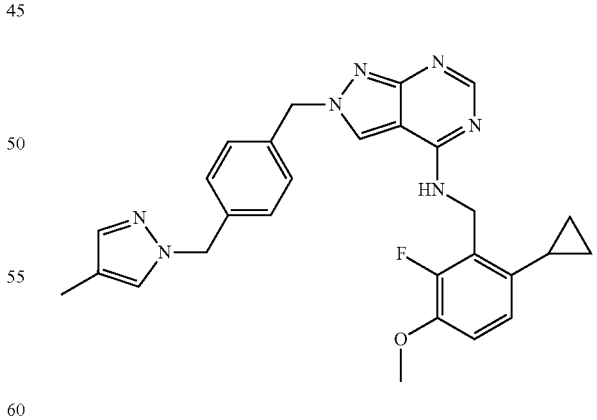

N-(6-cyclopropyl-2-fluoro-3-methoxybenzyl)-2-(4-((4-methyl-1H-pyrazol-1-yl)methyl)benzyl)-2H-pyrazolo[3,4-d]pyrimidin-4-amine N-(6-cyclopropyl-2-fluoro-3-methoxybenzyl)-2-(4-((4-methyl-1H-pyrazol-1-yl)methyl)benzyl)-2H-pyrazolo[3,4- d]pyrimidin-4-amine was prepared in a similar manner to Example 140. ¹H NMR (400 MHz, DMSO-d₆) δ 8.31-8.19 (m, 3H), 7.49 (s, 1H), 7.29-7.13 (m, 5H), 7.01 (t, J=8.7 Hz, 1H), 6.80 (d, J=8.6 Hz, 1H), 5.48 (s, 2H), 5.19 (s, 2H), 4.81 (dd, J=4.6, 2.1 Hz, 2H), 3.78 (s, 3H), 1.96 (s, 3H), 1.95 (m, 1H), 0.82-0.72 (m, 2H), 0.60-0.51 (m, 2H). MS (M+H)+ found for $C_{28}H_{28}FN_7O$: 498.2.

Example 204

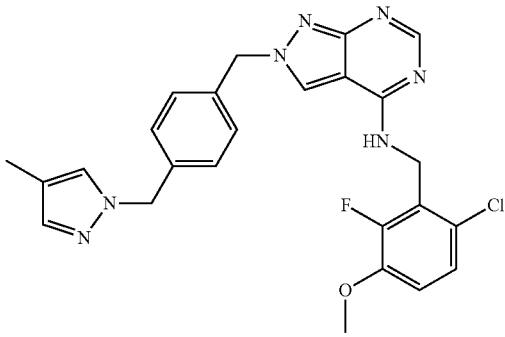 [SMILES: COc1ccc(Cl)c(CNc2ncnc3nn(Cc4ccc(Cn5cc(C)cn5)cc4)cc23)c1F]

N-(6-chloro-2-fluoro-3-methoxybenzyl)-2-(4-((4-methyl-1H-pyrazol-1-yl)methyl)benzyl)-2H-pyrazolo[3,4-d]pyrimidin-4-amine 2,2,2-trifluoroacetate N-(6-chloro-2-fluoro-3-methoxybenzyl)-2-(4-((4-methyl-1H-pyrazol-1-yl)methyl)benzyl)-2H-pyrazolo[3,4-d]pyrimidin-4-amine 2,2,2-trifluoroacetate Was prepared in a similar manner as Example 198. ¹H NMR (300 MHz, DMSO-d₆): δ 10.26 (s, 1H), δ 8.74 (s, 1H), δ 8.62 (s, 1H), δ 7.54 (s, 1H), 7.41-7.19 (m, 7H), δ 5.61 (s, 2H), δ 5.22 (s, 2H), 4.94 (m, 2H), δ 3.86 (s, 3H), δ 1.98 (s, 3H). LC-MS (ESI) m/z: calculated for $C_{23}H_{23}ClFN_7O$: 491. found: 492 [M+H]+. Rt: 2.019 min.

Example 205

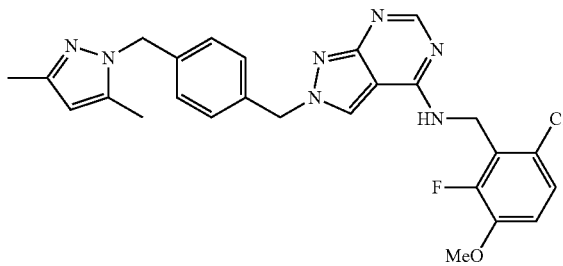

N-(6-chloro-2-fluoro-3-methoxybenzyl)-2-(4-((3,5-dimethyl-1H-pyrazol-1-yl)methyl)benzyl)-2H-pyrazolo[3,4-d]pyrimidin-4-amine N-(6-chloro-2-fluoro-3-methoxybenzyl)-2-(4-((3,5-dimethyl-1H-pyrazol-1-yl)methyl)benzyl)-2H-pyrazolo[3,4-d]pyrimidin-4-amine was prepared in a similar manner as Example 198. ¹H NMR (300 MHz, CDCl₃, ppm): 8.46 (s, 1H), 8.00 (s, 1H), 7.14-7.12 (m, 3H), 7.00 (d, J=7.5 Hz, 2H), 6.87 (t, J=9.0 Hz, 1H), 5.86 (s, 1H), 5.36 (s, 2H), 5.17 (s, 2H), 4.99 (s, 2H), 3.86 (s, 3H), 2.17 (d, J=8.1 Hz, 6H). LC-MS (ESI) m/z: calculated for $C_{26}H_{23}ClFN_7O$: 505.18. found: 506 [M+H]+.

Example 206

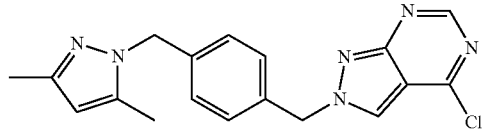 [SMILES: Cc1cc(C)n(Cc2ccc(Cn3cc4c(Cl)ncnc4n3)cc2)n1]

4-chloro-2-(4-((3,5-dimethyl-1H-pyrazol-1-yl) methyl)benzyl)-2H-pyrazolo[3,4-d]pyrimidine Into a 250-mL round-bottom flask, was placed a mixture of 1-[[4-(bromomethyl) phenyl]methyl]-3,5-dimethyl-1H-pyrazole (4.5 g, 16.12 mmol, 1.00 equiv), CH₃CN (100 mL), 4-chloro-2H-pyrazolo[3,4-d]pyrimidine (3.74 g, 24.20 mmol, 1.50 equiv) and Cs₂CO₃ (10.50 g, 32.23 mmol, 2.00 equiv). The resulted solution was stirred for 16 h at room temperature. The solids were filtered out. The filtrate was concentrated under vacuum. The residue was purified by silica gel column eluted with ethyl acetate/petroleum ether (1:1). This resulted in 450 mg (8%) of 4-chloro-2-(4-((3,5-dimethyl-1H-pyrazol-1-yl) methyl)benzyl)-2H-pyrazolo[3,4-d]pyrimidine as a white solid. LC-MS (ESI) m/z: calculated for C18H17ClN6: 352.12. found: 353[M+H]+.

Example 207

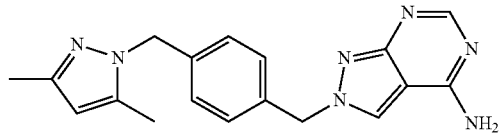 [SMILES: Cc1cc(C)n(Cc2ccc(Cn3cc4c(N)ncnc4n3)cc2)n1]

2-(4-((3,5-dimethyl-1H-pyrazol-1-yl)methyl)benzyl)-2H-pyrazolo[3,4-d]pyrimidin-4-amine Into a 50-mL round-bottom flask, was placed a solution of 1-[[4-([4-chloro-2H-pyrazolo[3,4-d]pyrimidin-2-yl]methyl)phenyl]methyl]-3,5-dimethyl-1H-pyrazole (450 mg, 1.28 mmol, 1.00 equiv)(Example 206), 1,4-dioxane (12 mL) and concentrated ammonia (4 mL). The resulting solution was stirred for 2 h at 60° C. and then concentrated under vacuum. This resulted in 400 mg (94%) of 2-(4-((3,5-dimethyl-1H-pyrazol-1-yl) methyl)benzyl)-2H-pyrazolo[3,4-d]pyrimidin-4-amine as a light yellow solid.

LC-MS (ESI) m/z: calculated for $C_{18}H_{13}N_7$: 333.17. found: 334 [M+H]+.

Example 208

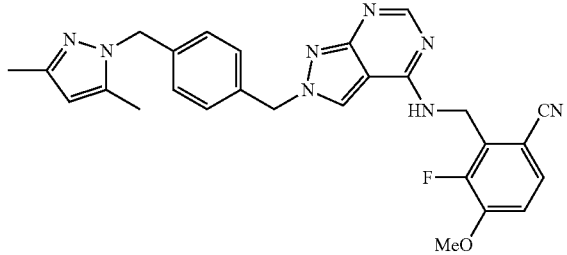 [SMILES: COc1ccc(C#N)c(CNc2ncnc3nn(Cc4ccc(Cn5nc(C)cc5C)cc4)cc23)c1F]

2-((2-(4-((3,5-dimethyl-1H-pyrazol-1-yl) methyl) benzyl)-2H-pyrazolo[3,4-d]pyrimidin-4-ylamino) methyl)-3-fluoro-4-methoxybenzonitrile Into a 50-mL round-bottom flask, was placed a solution of 2-([4-[(3,5-dimethyl-1H-pyrazol-1-yl)methyl]phenyl]

methyl)-2H-pyrazolo[3,4-d]pyrimidin-4-amine (400 mg, 1.20 mmol, 1.00 equiv)(Example 207), N,N-dimethylformamide (5.00 mL) and 2-(bromomethyl)-3-fluoro-4-methoxybenzonitrile (351 mg, 1.44 mmol, 1.20 equiv). The resulted solution was stirred for 16 h at 50° C. After filtration, the filtrate was purified by Prep-HPLC with the following conditions. Column: SunFire Prep C18, 19*150 mm, 5 μm; mobile phase: water (it contains 0.05% TFA) and acetonitrile with a gradient of 30% to 65% acetonitrile in 8 min; flow rate: 20 mL/min; detector UV wavelength: 254 nm. This resulted in 144.3 mg (24%) of 2-((2-(4-((3,5-dimethyl-1H-pyrazol-1-yl) methyl)benzyl)-2H-pyrazolo[3,4-d]pyrimidin-4-ylamino) methyl)-3-fluoro-4-methoxybenzonitrile trifluoroacetate as a light yellow solid. $^1$H NMR (300 MHz, CDCl$_3$, ppm): 11.17 (br, 3H), 10.77 (br, 1H), 9.12 (s, 1H), 8.47 (s, 1H), 7.52 (d, J=8.1 Hz, 2H), 7.40 (d, J=6.9 Hz, 2H), 7.15-7.13 (m, 3H), 6.09 (s, 1H), 5.61 (s, 2H), 5.46 (s, 4H), 3.95 (s, 3H), 2.39 (s, 3H), 2.29 (s, 3H). LC-MS (ESI) m/z: calculated for C29H26F4N8O3: 610.21. found: 497 [M-TFA+H]$^+$.

Example 209, 210

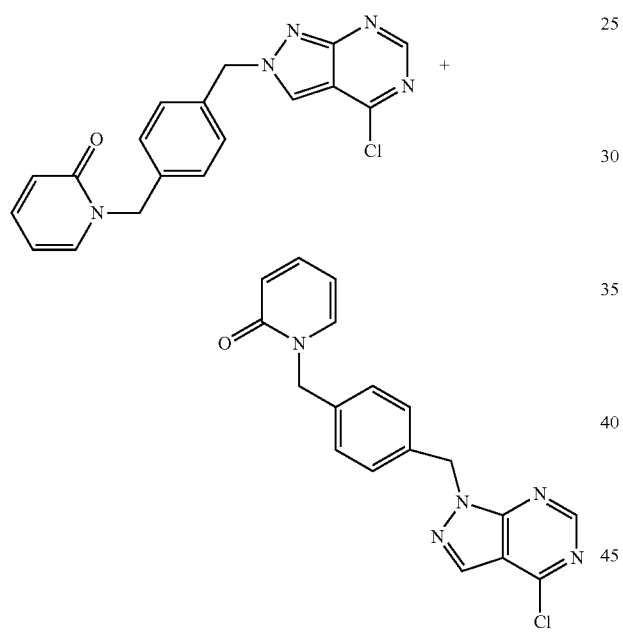

1-(4-((4-chloro-2H-pyrazolo[3,4-d]pyrimidin-2-yl) methyl)benzyl)pyridin-2(1H)-one and 1-(4-((4-chloro-1H-pyrazolo[3,4-d]pyrimidin-1-yl)methyl) benzyl)pyridin-2(1H)-one To a suspension of 4-chloro-1H-pyrazolo[3,4-d]pyrimidine (166.70 mg; 1.08 mmol; 1.00 eq.) and 1-(4-(bromomethyl)benzyl)pyridin-2(1H)-one (300.00 mg; 1.08 mmol; 1.00 eq.) in AcCN (3 mL) was added Potassium Carbonate (297.69 mg; 2.16 mmol; 2.00 eq.) and the mixture was stirred at ambient temperature for 2 h, then it was diluted with water and the aqueous layer was extracted with EtOAc, followed by DCM, the insoluble material was filtered off, the DCM layers were combined, washed with brine, dried and concentrated to give a mixture of 1-(4-((4-chloro-2H-pyrazolo[3,4-d]pyrimidin-2-yl)methyl)benzyl)pyridin-2(1H)-one and 1-(4-((4-chloro-1H-pyrazolo[3,4-d]pyrimidin-1-yl) methyl)benzyl)pyridin-2(1H)-one (220 mg).

Example 211, 212

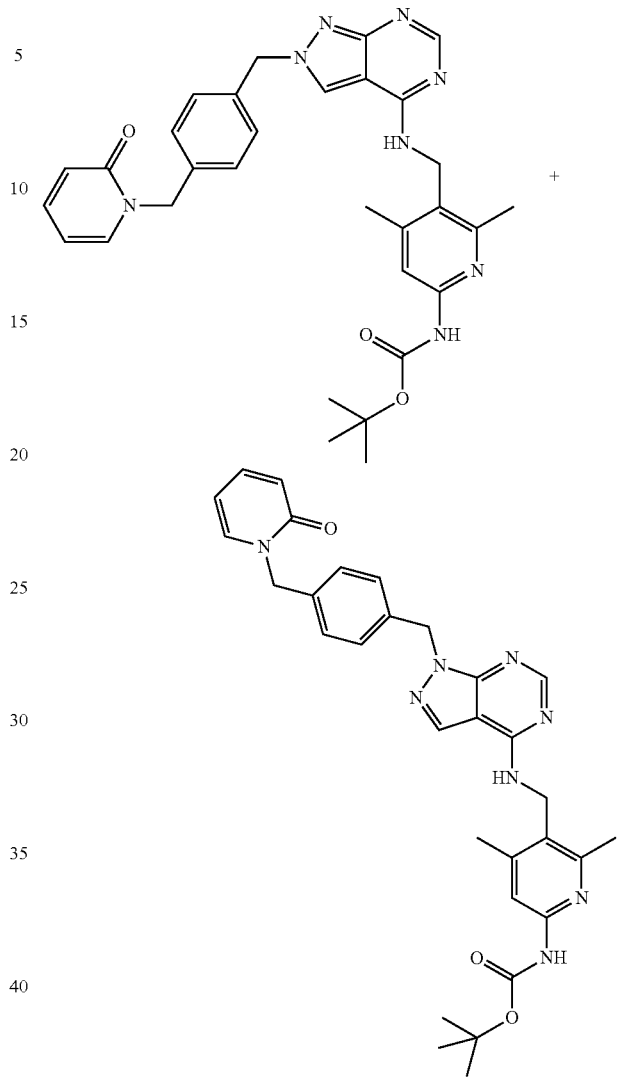

tert-butyl (4,6-dimethyl-5-(((2-(4-((2-oxopyridin-1 (2H)-yl)methyl)benzyl)-2H-pyrazolo[3,4-d]pyrimidin-4-yl)amino)methyl)pyridin-2-yl)carbamate and tert-butyl (4,6-dimethyl-5-(((1-(4-((2-oxopyridin-1 (2H)-yl)methyl)benzyl)-1H-pyrazolo[3,4-d]pyrimidin-4-yl)amino)methyl)pyridin-2-yl)carbamate To a solution of a mixture of isomers of 1-(4-((4-chloro-2H-pyrazolo[3,4-d]pyrimidin-2-yl)methyl)benzyl)pyridin-2 (1H)-one and 1-(4-((4-chloro-1H-pyrazolo[3,4-d]pyrimidin-1-yl)methyl)benzyl)pyridin-2(1H)-one (100.00 mg; 0.28 mmol; 1.00 eq.)(Example 209) in NMP (1 mL) was added tert-butyl N-[5-(aminomethyl)-4,6-dimethylpyridin-2-yl]-N-[(tert-butoxy)carbonyl]carbamate (119.88 mg; 0.34 mmol; 1.20 eq.)(Example 4, Step 2). The mixture was heated at 110° C. for 25 min in microwave synthesizer, and then it was cooled and purified by column chromatography to give tert-butyl (4,6-dimethyl-5-(((2-(4-((2-oxopyridin-1(2H)-yl) methyl)benzyl)-2H-pyrazolo[3,4-d]pyrimidin-4-yl)amino) methyl)pyridin-2-yl)carbamate and tert-butyl (4,6-dimethyl-5-(((1-(4-((2-oxopyridin-1(2H)-yl)methyl)benzyl)-1H-pyrazolo[3,4-d]pyrimidin-4-yl)amino)methyl)pyridin-2-yl) carbamate.

Example 213

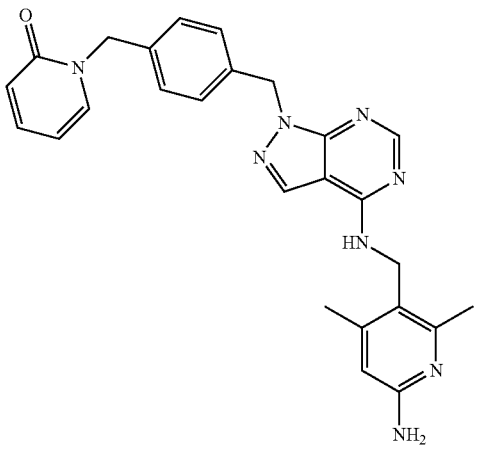 [SMILES: Cc1cc(N)nc(C)c1CNc1ncnc2c1cnn2Cc1ccc(Cn2ccccc2=O)cc1]

1-(4-((4-(((6-amino-2,4-dimethylpyridin-3-yl)methyl)amino)-1H-pyrazolo[3,4-d]pyrimidin-1-yl)methyl)benzyl)pyridin-2(1H)-one To a solution of tert-butyl (4,6-dimethyl-5-(((1-(4-((2-oxopyridin-1(2H)-yl)methyl)benzyl)-1H-pyrazolo[3,4-d]pyrimidin-4-yl)amino)methyl)pyridin-2-yl)carbamate (Example 212) in DCM (1 mL) was added TFA (2 mL) and the mixture was stirred for 2 h, then it was concentrated and purified by preparative HPLC to give 1-(4-((4-(((6-amino-2,4-dimethylpyridin-3-yl)methyl)amino)-1H-pyrazolo[3,4-d]pyrimidin-1-yl)methyl)benzyl)pyridin-2(1H)-one (9 mg). $^1$H NMR (400 MHz, DMSO-$d_6$) δ 8.30 (d, J=11.6 Hz, 2H), 8.08 (s, 1H), 7.72 (ddd, J=6.8, 2.1, 0.7 Hz, 1H), 7.53 (s, 2H), 7.38 (ddd, J=9.1, 6.6, 2.1 Hz, 1H), 7.23-7.13 (m, 4H), 6.65 (s, 1H), 6.36 (ddd, J=9.1, 1.4, 0.7 Hz, 1H), 6.19 (td, J=6.7, 1.4 Hz, 1H), 5.45 (s, 2H), 5.02 (s, 2H), 4.56 (d, J=4.7 Hz, 2H), 2.57 (s, 3H), 2.47 (s, 3H). MS (M+H)+ found for $C_{26}H_{26}N_8O$: 467.2.

Example 214

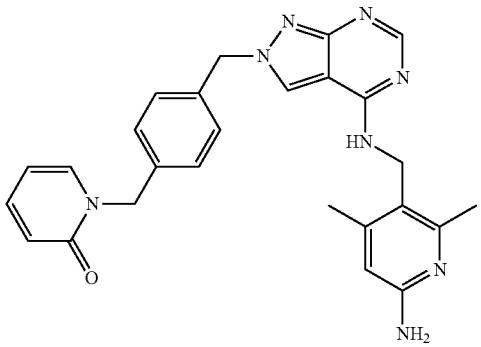 [SMILES: Cc1cc(N)nc(C)c1CNc1ncnc2nn(Cc3ccc(Cn4ccccc4=O)cc3)cc12]

1-(4-((4-(((6-amino-2,4-dimethylpyridin-3-yl)methyl)amino)-2H-pyrazolo[3,4-d]pyrimidin-2-yl)methyl)benzyl)pyridin-2(1H)-one To a solution of tert-butyl (4,6-dimethyl-5-(((2-(4-((2-oxopyridin-1(2H)-yl)methyl)benzyl)-2H-pyrazolo[3,4-d]pyrimidin-4-yl)amino)methyl)pyridin-2-yl)carbamate (Example 211) in DCM (1 mL) was added TFA (2 mL) and the mixture was stirred for 2 h, then it was concentrated and purified by preparative HPLC to give 1-(4-((4-(((6-amino-2,4-dimethylpyridin-3-yl)methyl)amino)-2H-pyrazolo[3,4-d]pyrimidin-2-yl)methyl)benzyl)pyridin-2(1H)-one (12 mg). $^1$H NMR (400 MHz, DMSO-$d_6$) δ 8.48 (s, 1H), 8.41 (s, 1H), 7.75 (ddd, J=6.8, 2.2, 0.7 Hz, 1H), 7.61 (s, 2H), 7.44-7.23 (m, 6H), 6.65 (s, 1H), 6.37 (ddd, J=9.1, 1.4, 0.7 Hz, 1H), 6.21 (td, J=6.7, 1.4 Hz, 1H), 5.56 (s, 2H), 5.06 (s, 2H), 4.61 (d, J=4.7 Hz, 2H), 2.57 (s, 3H), 2.36 (s, 3H). MS (M+H)+ found for $C_{26}H_{26}N_8O$: 467.2.

Example 215

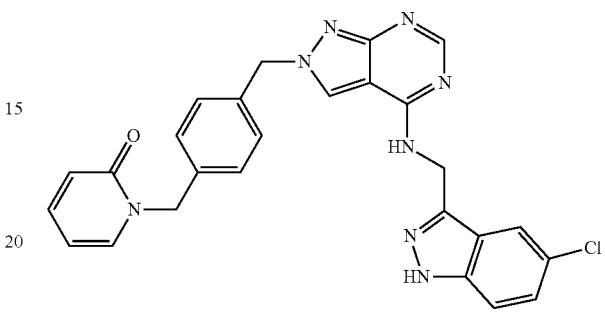

1-(4-((4-(((5-chloro-1H-indazol-3-yl)methyl)amino)-2H-pyrazolo[3,4-d]pyrimidin-2-yl)methyl)benzyl)pyridin-2(1H)-one To a solution of 1-(4-((4-chloro-2H-pyrazolo[3,4-d]pyrimidin-2-yl)methyl)benzyl)pyridin-2(1H)-one (50.00 mg; 0.14 mmol; 1.00 eq.)(Example 211) in NMP (0.5 mL) was added (5-chloro-1H-indazol-3-yl)methanamine (38.72 mg; 0.21 mmol; 1.50 eq.)(Example 2) and Hunig's base-ethylbis(propan-2-yl)amine (0.04 ml; 0.21 mmol; 1.50 eq.), then it was heated at 110° C. for 20 min, and it was cooled and purified by preparative HPLC to 1-(4-((4-(((5-chloro-1H-indazol-3-yl)methyl)amino)-2H-pyrazolo[3,4-d]pyrimidin-2-yl)methyl)benzyl)pyridin-2(1H)-one.). $^1$H NMR (400 MHz, DMSO-$d_6$) δ 13.07 (s, 1H), 8.68 (t, J=5.4 Hz, 1H), 8.33 (s, 1H), 8.26 (s, 1H), 7.84 (s, 1H), 7.72 (dd, J=6.7, 2.1 Hz, 1H), 7.50 (dd, J=1.9, 0.7 Hz, 1H), 7.43-7.21 (m, 6H), 6.37 (d, J=9.1 Hz, 1H), 6.23-6.15 (m, 1H), 5.50 (d, J=3.5 Hz, 2H), 5.05 (d, J=3.5 Hz, 2H), 4.99 (d, J=5.6 Hz, 2H). MS (M+H)+ found for $C_{26}H_{21}ClN_8O$: 497.1.

Example 216

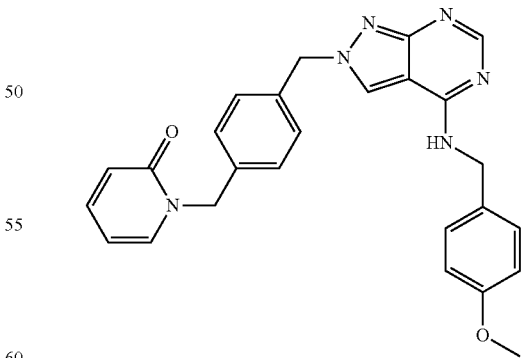

1-(4-((4-((4-methoxybenzyl)amino)-2H-pyrazolo[3,4-d]pyrimidin-2-yl)methyl)benzyl)pyridin-2(1H)-one 1-(4-((4-((4-methoxybenzyl)amino)-2H-pyrazolo[3,4-d]pyrimidin-2-yl)methyl)benzyl)pyridin-2(1H)-one was prepared similar to Example 215 using 4-methoxybenzyl amine to replace (5-chloro-1H-indazol-3-yl)methanamine. $^1$H NMR (400 MHz, DMSO-$d_6$) δ 8.59 (s, 1H), 8.33 (s, 1H), 8.19 (s, 1H), 7.73 (ddd, J=6.7, 2.1, 0.7 Hz, 1H), 7.39 (ddd, J=9.2, 6.6, 2.1 Hz, 1H), 7.32-7.20 (m, 6H), 6.92-6.82 (m, 2H), 6.38 (ddd, J=9.2, 1.4, 0.7 Hz, 1H), 6.20 (td, J=6.7, 1.4 Hz, 1H), 5.50 (s, 2H), 5.06 (s, 2H), 4.60 (d, J=5.7 Hz, 2H), 3.70 (d, J=4.1 Hz, 3H). MS (M+H)+ found for $C_{26}H_{24}N_6O_2$: 453.1.

Example 217

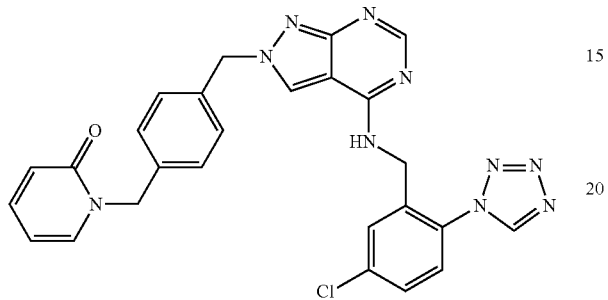

1-(4-((4-((5-chloro-2-(1H-tetrazol-1-yl)benzyl)amino)-2H-pyrazolo[3,4-d]pyrimidin-2-yl)methyl)benzyl)pyridin-2(1H)-one 1-(4-((4-((5-chloro-2-(1H-tetrazol-1-yl)benzyl)amino)-2H-pyrazolo[3,4-d]pyrimidin-2-yl)methyl)benzyl)pyridin-2(1H)-one was prepared similar to Example 215 using (5-chloro-2-(1H-tetrazol-1-yl)phenyl)methanamine to replace (5-chloro-1H-indazol-3-yl)methanamine. $^1$H NMR (400 MHz, DMSO-$d_6$) δ 9.85 (d, J=10.3 Hz, 1H), 8.59 (t, J=5.7 Hz, 1H), 8.30 (s, 1H), 8.07 (s, 1H), 7.74 (dd, J=6.9, 2.0 Hz, 1H), 7.63 (q, J=1.7 Hz, 3H), 7.39 (ddd, J=8.9, 6.6, 2.1 Hz, 1H), 7.33-7.22 (m, 4H), 6.38 (dd, J=9.2, 1.3 Hz, 1H), 6.20 (td, J=6.7, 1.4 Hz, 1H), 5.52 (s, 2H), 5.06 (s, 2H), 4.51 (d, J=5.7 Hz, 2H). MS (M+H)+ found for $C_{26}H_{21}ClN_{10}O$: 525.2, 527.2.

Example 218

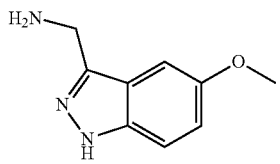

(5-methoxy-1H-indazol-3-yl)methanamine

Into a 250-mL round-bottom flask, were placed 5-methoxy-1H-indazole-3-carbonitrile (600 mg, 3.46 mmol, 1.00 equiv), methanol (100 mL), Raney Ni (200 mg) and concentrated ammonia aqueous solution (2 mL). The reaction solution was purged with hydrogen for three times. The reaction solution was stirred overnight at room temperature under an atmosphere of hydrogen (balloon). The reaction was filtered through celite and the filtrate was concentrated. The crude product was purified by medium pressure reverse phase chromatography with the following conditions (IntelFlash-1): silica gel column; mobile phase, dichloromethane/ethyl acetate/ methanol/ 20% ammonia aqueous solution (ratio 4:4:1:0.2) within 30 min; detector UV wavelength:

254 nm. This resulted in 240 mg (39%) of (5-methoxy-1H-indazol-3-yl)methanamine as a brown solid. MS (ESI) m/z 178 [M+H]$^+$ Example 219

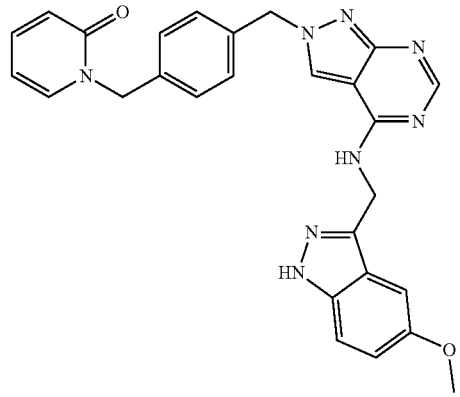 [SMILES: COc1ccc2[nH]nc(CNc3ncnc4nn(Cc5ccc(Cn6ccccc6=O)cc5)cc34)c2c1]

1-(4-((4-((5-methoxy-1H-indazol-3-yl)methylamino)-2H-pyrazolo[3,4-d]pyrimidin-2-yl)methyl)benzyl)pyridin-2(1H)-one 1-(4-((4-((5-methoxy-1H-indazol-3-yl)methylamino)-2H-pyrazolo[3,4-d]pyrimidin-2-yl)methyl)benzyl)pyridin-2(1H)-one was prepared in a similar manner as Example 215 using Example 218. $^1$H NMR (300 MHz, CD$_3$OD): 8.42 (s, 1H), 8.28 (s, 1H), 7.69 (d, J=6.9 Hz, 1H), 7.55-7.50 (m, 1H), 7.49-7.32 (m, 4H), 7.16 (s, 1H), 7.05-7.02 (d, J=9.3 Hz, 1H), 6.56 (d, J=2.1 Hz, 1H), 6.40-6.36 (m, 1H), 5.52 (s, 2H), 5.19 (d, J=20.1 Hz, 4H), 3.69 (s, 3H). MS (ESI) m/z 493 [M+H]$^+$.

Example 220

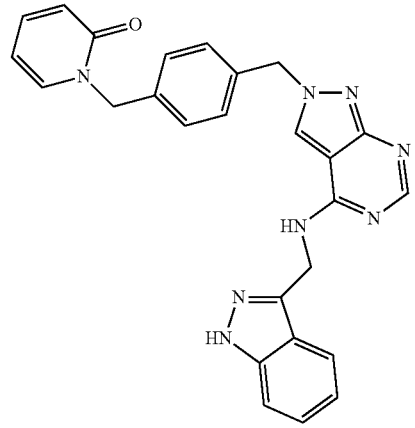 [SMILES: O=c1ccccn1Cc1ccc(Cn2cc3c(NCc4n[nH]c5ccccc45)ncnc3n2)cc1]

1-(4-((4-((1H-indazol-3-yl)methylamino)-2H-pyrazolo[3,4-d]pyrimidin-2-yl)methyl)benzyl)pyridin-2(1H)-one 1-(4-((4-((1H-indazol-3-yl)methylamino)-2H-pyrazolo[3,4-d]pyrimidin-2-yl)methyl)benzyl)pyridin-2(1H)-one was prepared in a similar manner as Example 215.
$^1$H NMR (300 MHz, CD$_3$OD): 8.45-8.20 (m, 2H), 7.78-7.64 (m, 2H), 7.59-7.49 (m, 2H), 7.40-7.35 (m, 1H), 7.32 (s, 4H), 7.13-7.08 (m, 1H), 6.58-6.36 (m, 2H), 5.51 (s, 2H), 5.18 (d, J=9.0 Hz, 2H). MS (ESI) m/z 463 [M+H]$^+$ Example 221

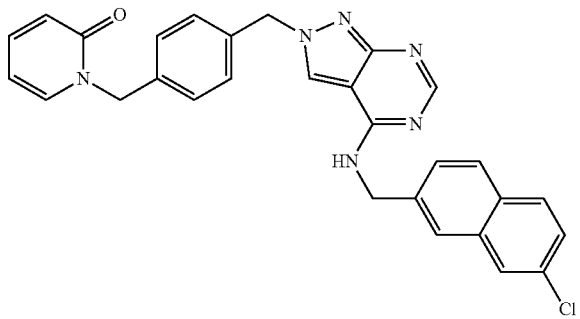

1-(4-((4-((7-chloronaphthalen-2-yl)methylamino)-2H-pyrazolo[3,4-d]pyrimidin-2-yl)methyl)benzyl)pyridin-2(1H)-one 1-(4-((4-((7-chloronaphthalen-2-yl)methylamino)-2H-pyrazolo[3,4-d]pyrimidin-2-yl)methyl)benzyl)pyridin-2(1H)-one was prepared in a similar manner as Example 215.
$^1$H NMR (300 MHz, CD$_3$OD): δ 8.28 (s, 2H), 7.88-7.84-(m, 3H), 7.79 (s, 1H), 7.706 (d, J=6.0 Hz, 1H), 7.56-7.51 (m, 2H), 7.45 (d, J=9.0 Hz, 1H), 7.36 (s, 4H), 6.59 (d, J=9.6 Hz, 1H), 6.44-6.36 (m, 1H), 5.55 (s, 2H), 5.20 (s, 2H), 4.95 (s, 2H). MS (ESI) m/z 507 [M+H]$^+$ Example 222

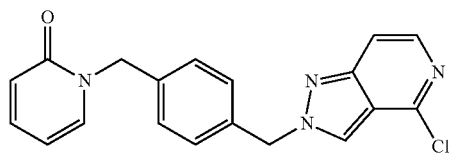 [SMILES: O=c1ccccn1Cc1ccc(Cn2cc3c(Cl)nccc3n2)cc1]

1-(4-((4-chloro-2H-pyrazolo[4,3-c]pyridin-2-yl)methyl)benzyl)pyridin-2(1H)-one

Into a 40-mL round-bottom flask, were placed a solution of 1-[[4-(bromomethyl)phenyl]methyl]-1,2-dihydropyridin-2-one (300 mg, 1.08 mmol, 1.00 equiv) in CH3CN (10 mL), 4-chloro-1H-pyrazolo[4,3-c]pyridine (337 mg, 2.19 mmol, 1.20 equiv), potassium carbonate (497 mg, 3.60 mmol, 2.00 equiv) and NaI (540 mg, 3.60 mmol, 2.00 equiv). The resulted solution was stirred for 1.5 days at room temperature. The reaction mixture was concentrated under vacuum. Then it was diluted with 30 mL of water and extracted with 3×30 mL of ethyl acetate. The organic phase was washed with 1×50 mL of water, 1×50 mL of brine and dried over anhydrous sodium sulfate. The solids were filtered out. The filtrate was concentrated under vacuum to give a residue. The crude product was further purified by Prep-HPLC with the following conditions. Column: Waters XBridge RP18 19*150 mm; mobile phase, CH3CN/water (0.05% NH$_4$OH, 10 mM NH$_4$HCO$_3$) with a gradient of acetonitrile from 26% to 31% in 5 min; flow rate: 20 mL/min; detector UV wavelength: 254 nm. This resulted in 85 mg (22%) of 1-[[4-[(4-chloro-2H-pyrazolo[4,3-c]pyridin-2-yl)methyl]phenyl]methyl]-1,2-dihydropyridin-2-one as light yellow solid. MS (ESI) m/z 351 [M+H]$^+$ Example 223

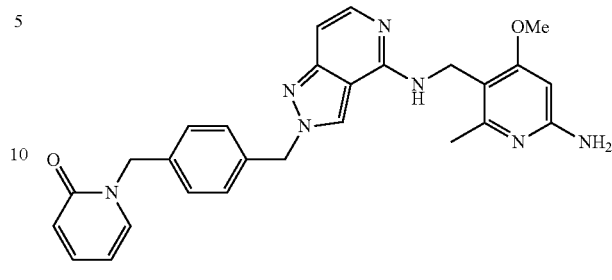

1-(4-((4-((6-amino-4-methoxy-2-methylpyridin-3-yl)methylamino)-2H-pyrazolo[4,3-c]pyridin-2-yl)methyl)benzyl)pyridin-2(1H)-one Into a 8-mL vial, were placed 1-[[4-([4-chloro-2H-pyrazolo[4,3-c]pyridin-2-yl]methyl)phenyl]methyl]-1,2-dihydropyridin-2-one (80 mg, 0.23 mmol, 1.00 equiv)(Example 222), 1-ethoxy-2-(2-ethoxyethoxy)ethane (6 mL), tert-butyl 5-(aminomethyl)-4-methoxy-6-methylpyridin-2-yl(tert-butoxycarboxyl)carbamate (126 mg, 0.34 mmol, 1.5 equiv) (Example 5) and zinc dichloride (311 mg, 2.28 mmol, 10.00 equiv). The resulted solution was stirred for 3 h at 120° C. The crude product was purified by flash column chromatography eluted with DCM/EA/MeOH/ concentrated ammonia aqueous solution (4:4:1:0.2). The crude product was further purified by Prep-HPLC with the following conditions. Column: Waters XBridge RP18 19*150 mm; mobile phase, CH$_3$CN/water (0.05% NH$_4$OH, 10 mM NH$_4$HCO$_3$) with a gradient of acetonitrile from 26% to 31% in 5 min; flow rate: 20 mL/min; detector UV wavelength: 254 nm. The product was obtained and concentrated under vacuum. This resulted in 41.9 mg (38%) of 1-([4-[(4-[[(6-amino-4-methoxy-2-methylpyridin-3-yl)methyl]amino]-2H-pyrazolo[4,3-c]pyridin-2-yl)methyl]phenyl]methyl)-1,2-dihydropyridin-2-one as white solid.
$^1$H NMR (300 MHz, CD$_3$OD): 8.36 (s, 1H), 7.72-7.32 (m, 2H), 7.55 (m, 1H), 7.30 (s, 4H), 6.72 (d, J=6.9 Hz, 1H), 6.58 (d, J=9.6 Hz, 1H), 6.40-6.37 (m, 1H), 6.08 (s, 1H), 5.75 (s, 2H), 5.50 (s, 2H), 4.50 (s, 2H), 3.81 (s, 3H), 2.34 (s, 3H). MS (ESI) m/z 482 [M+H]$^+$ Example 224

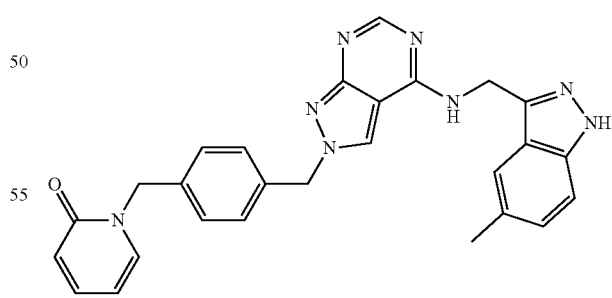

1-(4-((4-((5-methyl-1H-indazol-3-yl)methylamino)-2H-pyrazolo[3,4-d]pyrimidin-2-yl)methyl)benzyl)pyridin-2(1H)-one 1-(4-((4-((5-methyl-1H-indazol-3-yl)methylamino)-2H-pyrazolo[3,4-d]pyrimidin-2-yl)methyl)benzyl)pyridin-2(1H)-one was prepared in a similar manner as Example 215.

$^1$H NMR (300 MHz, CD$_3$OD): 8.35 (s, 1H), 8.25 (s, 1H), 7.70 (d, J=8.7 Hz, 1H), 7.55-7.50 (m, 2H), 7.41 (d, J=8.7 Hz, 1H), 7.33 (s, 4H), 7.25 (d, J=8.7 Hz, 1H), 6.58 (d, J=9.6 Hz, 1H), 6.40 (d, J=5.7 Hz, 1H), 5.52 (s, 2H), 5.21 (s, 2H), 5.19 (s, 2H), 2.39 (s, 3H). MS (ESI) m/z 476 [M+H]$^+$

Example 225

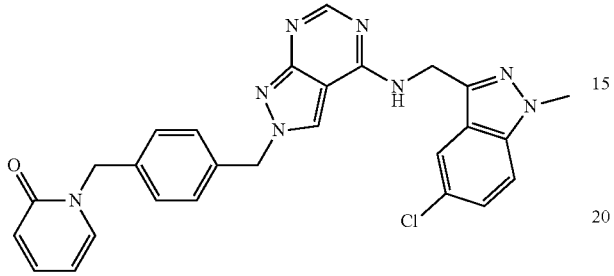

1-(4-((4-((5-chloro-1-methyl-1H-indazol-3-yl)methylamino)-2H-pyrazolo[3,4-d]pyrimidin-2-yl)methyl)benzyl)pyridin-2(1H)-one 2,2,2-trifluoroacetate 1-(4-((4-((5-chloro-1-methyl-1H-indazol-3-yl)methylamino)-2H-pyrazolo[3,4-d]pyrimidin-2-yl)methyl)benzyl)pyridin-2(1H)-one 2,2,2-trifluoroacetate was prepared in a similar manner as Example 215. $^1$H NMR (300 MHz, CD$_3$OD): δ 8.57 (s, 1H), 8.44 (1H, s), 7.83 (1H, s), 7.71 (d, J=6.6 Hz, 1H), 7.57-7.51 (m, 2H), 7.42-7.33 (m, 5H), 6.58 (d, J=9.0 Hz, 1H), 6.41-6.37 (m, 1H), 5.58 (s, 2H), 5.24 (d, J=12.0 Hz, 2H), 4.05 (s, 3H). MS (ESI) m/z 511 [M+H]$^+$ Example 226

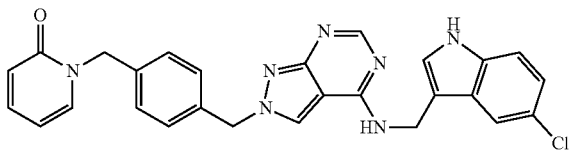 [SMILES: O=c1ccccn1Cc1ccc(Cn2cc3c(NCc4c[nH]c5ccc(Cl)cc45)ncnc3n2)cc1]

1-(4-((4-((5-chloro-1H-indol-3-yl)methylamino)-2H-pyrazolo[3,4-d]pyrimidin-2-yl)methyl)benzyl)pyridin-2(1H)-one 1-(4-((4-((5-chloro-1H-indol-3-yl)methylamino)-2H-pyrazolo[3,4-d]pyrimidin-2-yl)methyl)benzyl)pyridin-2(1H)-one was prepared in a similar manner as Example 215.

$^1$H NMR (300 MHz, CD$_3$OD): δ 8.33 (s, 1H), 8.21 (s, 1H), 7.69 (d, J=8.7 Hz, 1H), 7.58 (s, 1H), 7.55-7.49 (m, 1H), 7.36 (d, J=13.2 Hz, 6H), 7.10 (d, J=8.7 Hz, 1H), 6.58 (d, J=9 Hz, 1H), 6.41-6.36 (m, 1H), 5.50 (s, 2H), 5.19 (s, 2H), 4.88 (s, 2H). MS (ESI) m/z 460 [M+H]$^+$

Example 227

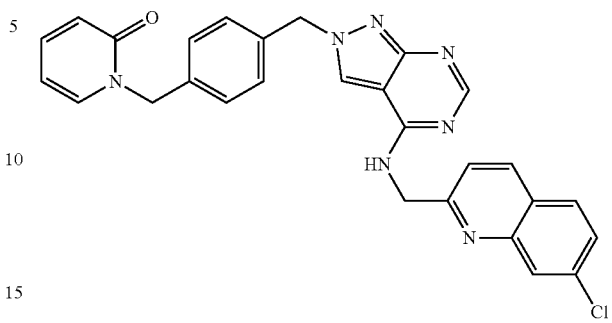

1-(4-((4-((6-chloroisoquinolin-3-yl)methylamino)-2H-pyrazolo[3,4-d]pyrimidin-2-yl)methyl)benzyl)pyridin-2(1H)-one 1-(4-((4-((6-chloroisoquinolin-3-yl)methylamino)-2H-pyrazolo[3,4-d]pyrimidin-2-yl)methyl)benzyl)pyridin-2(1H)-one was prepared in a similar manner as Example 215.

$^1$H NMR (300 MHz, DMSO-d): 8.93 (m, 1H), 8.44 (s, 1H), 8.36 (d, J=8.7 Hz, 1H), 8.17 (s, 1H), 8.02 (d, J=8.7 Hz, 2H), 7.77 (d, J=8.4 Hz, 1H), 7.63 (d, J=11.1 Hz, 1H), 7.55 (d, J=8.4 Hz, 1H), 7.44-7.28 (m, 5H), 6.41 (d, J=9.3 Hz, 1H), 6.24-6.19 (m, 1H), 5.56 (s, 2H), 5.03 (s, 2H), 4.97 (d, J=5.7 Hz, 2H). MS (ESI) m/z 508 [M+H]$^+$

Example 228

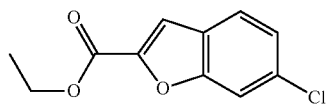

ethyl 6-chloro-1-benzofuran-2-carboxylate Into a 100-mL round-bottom flask purged and maintained with an inert atmosphere of nitrogen, was placed a solution of 4-chloro-2-hydroxybenzaldehyde (1.0 g, 6.39 mmol, 1.00 equiv) in 2-butanone (50 mL). This was followed by the addition of 1,3-diethyl 2-bromopropanedioate (3.04 g, 12.72 mmol, 2.00 equiv) and potassium carbonate (2.63 g, 19.03 mmol, 3.00 equiv). The resulting solution was refluxed for 5 h in an oil bath. The solids were filtered out. The filtrate was concentrated under vacuum. The residue was treated with 200 mL of EA, washed with 2×100 mL of water and 2×100 mL of brine. The organic phase was dried over sodium sulfate and concentrated under vacuum. The residue was purified by silica gel column chromatography eluted with EA: PE (1:20 to 1:15). This resulted in 500 mg (35%) of ethyl 6-chloro-1-benzofuran-2-carboxylate as white solid. MS (ESI) m/z 225 [M+H]$^+$.

Example 229

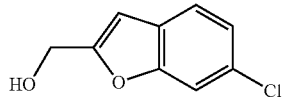

(6-chloro-1-benzofuran-2-yl)methanol

Into a 100-mL 3-necked round-bottom flask purged and maintained with an inert atmosphere of nitrogen, was placed a solution of ethyl 6-chloro-1-benzofuran-2-carboxylate (500 mg, 2.23 mmol, 1.00 equiv)(Example 228) in tetrahydrofuran (50 mL) at room temperature with stirring at 0° C., to which was added LiAlH$_4$ (101 mg, 2.66 mmol, 1.20 equiv) in several batches at 0° C. The resulting solution was stirred for 30 min at 0° C. The reaction solution was stirred for an additional 2 h at room temperature. The reaction was then quenched by the addition of 2 mL of water. The resulting solution was diluted with 100 mL of EA. The solids were filtered out. The filtrate was concentrated under vacuum. The residue was purified by silica gel column chromatography eluted with EA: PE (1:5 to 1:3). This resulted in 320 mg (79%) of (6-chloro-1-benzofuran-2-yl)methanol as white solid. MS (ESI) m/z 165 [M+H−H$_2$O]$^+$.

Example 230

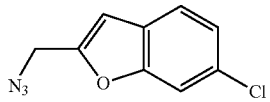 [SMILES: [N-]=[N+]=NCc1cc2ccc(Cl)cc2o1]

2-(azidomethyl)-6-chloro-1-benzofuran

Into a 100-mL round-bottom flask purged and maintained with an inert atmosphere of nitrogen, was placed a solution of (6-chloro-1-benzofuran-2-yl)methanol (320 mg, 1.75 mmol, 1.00 equiv)(Example 229) in tetrahydrofuran (50 mL) with stirring at 0° C., to which were added DPPA (1.2 g, 4.36 mmol, 2.50 equiv) and DBU (797 mg, 5.24 mmol, 3.00 equiv) at 0° C. The resulting solution was stirred overnight at room temperature. The reaction mixture was concentrated under vacuum. The residue was diluted with 200 mL of EA, washed with 2×100 mL of water and 2×100 mL of brine. The organic phase was dried over anhydrous sodium sulfate and concentrated under vacuum. The residue was purified by silica gel column chromatography eluted with EA: PE (1:10). This resulted in 200 mg (55%) of 2-(azidomethyl)-6-chloro-1-benzofuran as colorless oil. $^1$H NMR (300 MHz, DMSO-d$_6$): δ 7.80 (s, 1H), 7.68 (d, J=8.1 Hz, 1H), 7.32 (dd, J=8.1 Hz, 1.8 Hz, 1H), 7.01 (s, 1H), 4.68 (s, 2H).

Example 231

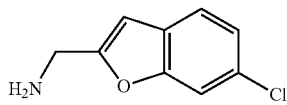 [SMILES: NCc1cc2ccc(Cl)cc2o1]

(6-chloro-1-benzofuran-2-yl)methanamine

Into a 50-mL round-bottom flask purged and maintained with an inert atmosphere of nitrogen, was placed a solution of 2-(azidomethyl)-6-chloro-1-benzofuran (200 mg, 0.96 mmol, 1.00 equiv)(Example 230) in tetrahydrofuran (20 mL). This was followed by the addition of water (2 mL), PPh$_3$ (302 mg, 1.15 mmol, 1.20 equiv). The resulting solution was stirred overnight at room temperature. The resulting mixture was concentrated under vacuum. The reaction solution was diluted with 100 mL of EA and washed with 2×50 mL of brine. The mixture was dried over anhydrous sodium sulfate and concentrated under vacuum. The residue was purified by silica gel column chromatography eluted with EA. This resulted in 120 mg (69%) of (6-chloro-1-benzofuran-2-yl)methanamine as yellow oil. MS (ESI) m/z 165 [M+H−NH$_3$]$^+$.

Example 232

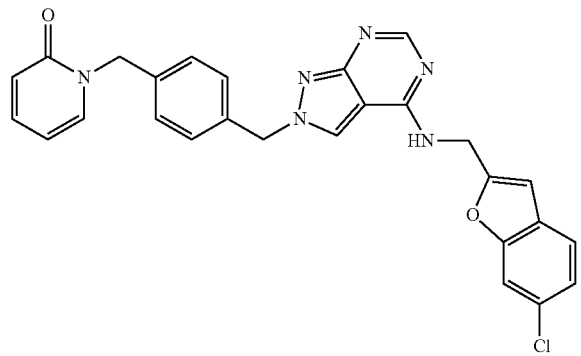 [SMILES: O=c1ccccn1Cc1ccc(Cn2cc3c(NCc4cc5ccc(Cl)cc5o4)ncnc3n2)cc1]

1-(4-((4-(((6-chlorobenzofuran-2-yl)methylamino)-2H-pyrazolo[3,4-d]pyrimidin-2-yl)methyl)benzyl)pyridin-2(1H)-one 1-(4-((4-(((6-chlorobenzofuran-2-yl)methylamino)-2H-pyrazolo[3,4-d]pyrimidin-2-yl)methyl)benzyl)pyridin-2(1H)-one was prepared in a similar manner as Example 215 using Example 231. $^1$H NMR (300 MHz, DMSO-d$_6$): δ 8.40 (s, 1H), 8.21 (s, 1H), 7.73-7.56 (m, 4H), 7.46-7.41 (m, 1H), 7.29-7.24 (m, 4H), 6.80 (s, 1H), 6.43 (d, J=9.0 Hz, 1H), 6.30-6.25 (m, 1H), 5.50 (s, 2H), 5.06 (s, 2H), 4.84 (s, 2H). MS (ESI) m/z 497 [M+H]$^+$.

Example 233

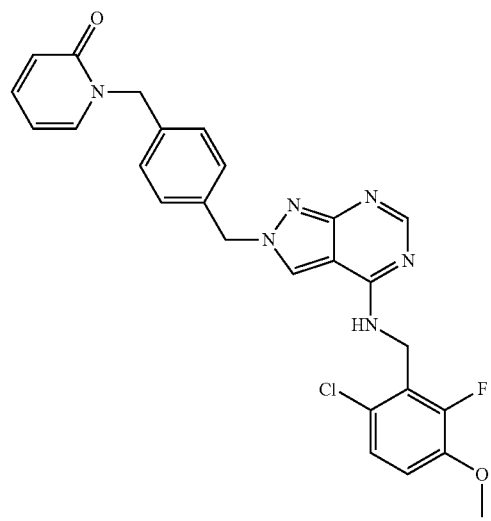 [SMILES: COc1ccc(Cl)c(CNc2ncnc3nn(Cc4ccc(Cn5ccccc5=O)cc4)cc23)c1F]

1-(4-((4-(((6-chloro-2-fluoro-3-methoxybenzyl)amino)-2H-pyrazolo[3,4-d]pyrimidin-2-yl)methyl)benzyl)pyridin-2(1H)-one 1-(4-((4-(((6-chloro-2-fluoro-3-methoxybenzyl)amino)-2H-pyrazolo[3,4-d]pyrimidin-2-yl)methyl)benzyl)pyridin-2

(1H)-one was synthesized in a manner similar to Example 215. ¹H NMR (400 MHz, Methanol-d₄) δ 8.31 (s, 1H), 8.22 (s, 1H), 7.70-7.62 (m, 1H), 7.51 (ddd, J=8.9, 6.7, 2.0 Hz, 1H), 7.37-7.26 (m, 4H), 7.21 (dd, J=9.0, 1.8 Hz, 1H), 7.10 (t, J=8.9 Hz, 1H), 6.55 (dd, J=9.1, 1.3 Hz, 1H), 6.37 (td, J=6.7, 1.4 Hz, 1H), 5.49 (s, 2H), 5.17 (s, 2H), 4.87 (d, J=2.1 Hz, 2H), 3.87 (s, 3H). MS (M+H)+ found for $C_{26}H_{22}ClFN_6O_2$: 505.0.

Example 234

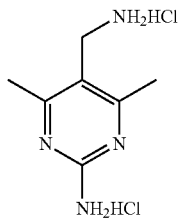

1-([4-[(4-[[(2-amino-4,6-dimethylpyrimidin-5-yl)methyl]amino]-2H-pyrazolo[3,4-d]pyrimidin-2-yl)methyl]phenyl]methyl)-1,2-dihydropyridin-2-one Into a 10-mL round-bottom flask, was placed a solution of tert-butyl N-[5-(aminomethyl)-4,6-dimethylpyrimidin-2-yl]-N-[(tert-butoxy)carbonyl]carbamate (100 mg, 0.28 mmol, 1.00 equiv) in methanol (5 mL) which was saturated with hydrogen chloride. The resulting solution was stirred for 2 h at room temperature. The reaction mixture was concentrated under vacuum. This resulted in 62.0 mg (crude) of 5-(aminomethyl)-4,6-dimethylpyrimidin-2-amine dihydrochloride as an off-white solid. The crude was used directly in the next step reaction without further purification.

Example 235

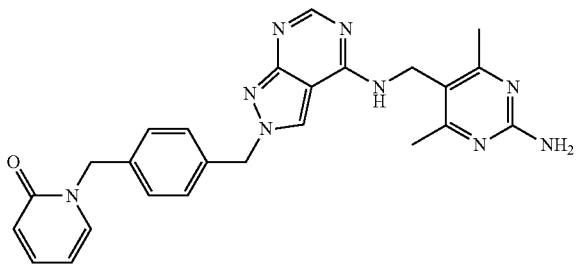 [SMILES: Cc1nc(N)nc(C)c1CNc1ncnc2nn(Cc3ccc(Cn4ccccc4=O)cc3)cc12]

1-([4-[(4-[[(2-amino-4,6-dimethylpyrimidin-5-yl)methyl]amino]-2H-pyrazolo[3,4-d]pyrimidin-2-yl)methyl]phenyl]methyl)-1,2-dihydropyridin-2-one 1-([4-[(4-[[(2-amino-4,6-dimethylpyrimidin-5-yl)methyl]amino]-2H-pyrazolo[3,4-d]pyrimidin-2-yl)methyl]phenyl]methyl)-1,2-dihydropyridin-2-one was prepared in a similar manner as Example 215 using Example 234. ¹H NMR (300 MHz, DMSO-d₆): δ 8.34 (s, 1H), 8.22 (s, 1H), 7.69 (m, 1H), 7.53 (m, 1H), 7.36 (d, J=10.2 Hz, 4H), 6.57 (d, J=9.3 Hz, 1H), 6.39 (m, 1H), 5.20 (s, 2H), 4.69 (s, 2H), 2.41 (s, 6H). MS (ESI) m/z: 468

Example 236

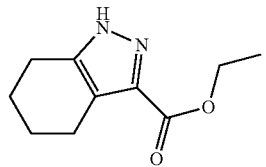

ethyl 4,5,6,7-tetrahydro-1H-indazole-3-carboxylate

To a solution of cyclohexanone (2.94 g, 29.96 mmol, 1.00 equiv) in DMSO (50.0 mL) were added ethyl 2-diazoacetate (6.84 g, 59.95 mmol, 2.00 equiv) and pyrrolidine (210 mg, 2.95 mmol, 0.10 equiv). The resulting solution was stirred at 80° C. overnight. The reaction mixture was diluted with 100 mL of H₂O. Then the mixture was extracted with 2×100 mL of ethyl acetate. The organic phase was washed with 1×100 mL of brine, dried over anhydrous sodium sulfate and concentrated under vacuum. The residue was purified by silica gel column chromatography eluted with ethyl acetate/petroleum ether=1/3. This resulted in 1.23 g (21%) of ethyl 4,5,6,7-tetrahydro-1H-indazole-3-carboxylate as a yellow solid. MS (ESI), m/z 195 [M+1]⁺

Example 237

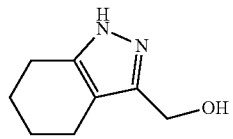 [SMILES: OCc1n[nH]c2c1CCCC2]

(4,5,6,7-tetrahydro-1H-indazol-3-yl)methanol

To a solution of LiAlH₄ (650 mg, 17.11 mmol, 3.00 equiv) in tetrahydrofuran (2.0 mL) with stirring at 0° C. was added dropwise a solution of ethyl 4,5,6,7-tetrahydro-1H-indazole-3-carboxylate (1.10 g, 5.66 mmol, 1.00 equiv)(Example 236) in tetrahydrofuran (10.0 mL). The resulting solution was stirred at room temperature overnight. The reaction mixture was then quenched by the sequential addition of 1.0 mL of methanol, 2.0 mL of NaOH (30%) and 0.2 mL H₂O. The mixture was dried over anhydrous magnesium sulfate. The resulting solution was diluted with 15 mL of dichloromethane and filtered. The filtrate was concentrated under vacuum. This resulted in 758 mg (88%) of 4,5,6,7-tetrahydro-1H-indazol-3-ylmethanol as a yellow solid. MS (ESI), m/z 153 [M+1]⁺

Example 238

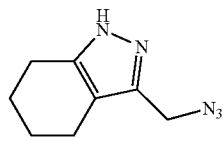 [SMILES: [N-]=[N+]=NCc1n[nH]c2c1CCCC2]

3-(azidomethyl)-4,5,6,7-tetrahydro-1H-indazole

To a solution of 4,5,6,7-tetrahydro-1H-indazol-3-ylmethanol (400 mg, 2.63 mmol, 1.00 equiv)(Example 237) in toluene (5.0 mL) were added DBU (600 mg, 3.94 mmol, 1.50 equiv) and DPPA (868.4 mg, 3.16 mmol, 1.20 equiv). The resulting solution was stirred at room temperature for 8 h. The resulting mixture was washed with 10.0 mL of H₂O. Then the separated toluene solution was collected for the next step directly. MS (ESI), m/z 178 [M+1]⁺

Example 239

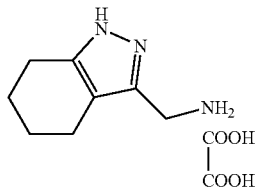

(4,5,6,7-tetrahydro-1H-indazol-3-yl)methanamine oxalate

To a solution of 3-(azidomethyl)-4,5,6,7-tetrahydro-1H-indazole (260 mg, 1.47 mmol, 1.00 equiv)(Example 238) in toluene (5.0 mL) were added triphenylphosphine (1.034 g, 3.94 mmol, 1.50 equiv) and H₂O (0.2 mL). The resulting solution was stirred at room temperature overnight. Then 1.0 M of oxalic acid ethanol solution was added into the above solution to precipitate the product. The solids were collected by filtration. The filter cake was washed with 3×10 mL of ethyl acetate. This resulted in 190 mg (54%) of 4,5,6,7-tetrahydro-1H-indazol-3-ylmethanamine oxalic acid as a white solid.

¹H NMR (300 MHz, DMSO-d₆): δ ppm 8.58-7.83 (brs, 2H), 3.89 (s, 2H), 2.72-2.54 (m, 2H), 2.49-2.40 (m, 2H), 1.68 (d, J=5.4 Hz, 4H). MS (ESI) m/z 152 [M+H]⁺

Example 240

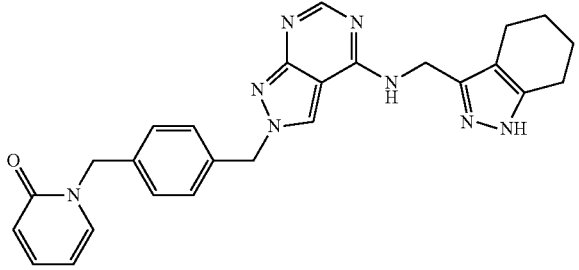 [SMILES: O=c1ccccn1Cc1ccc(Cn2cc3c(NCc4n[nH]c5c4CCCC5)ncnc3n2)cc1]

1-(4-((4-((4,5,6,7-tetrahydro-1H-indazol-3-yl)methylamino)-2H-pyrazolo[3,4-d]pyrimidin-2-yl)methyl)benzyl)pyridin-2(1H)-one 1-(4-((4-((4,5,6,7-tetrahydro-1H-indazol-3-yl)methylamino)-2H-pyrazolo[3,4-d]pyrimidin-2-yl)methyl)benzyl)pyridin-2(1H)-one was prepared in a similar manner as Example 215 using Example 239. ¹H NMR (300 MHz, DMSO-d₆): δ ppm 12.14 (brs, 1H), 8.37 (s, 1H), 8.22 (s, 1H), 7.42 (d, J=6.3 Hz, 1H), 7.38-7.29 (m, 5H), 6.40 (d, J=9.3 Hz, 1H), 6.22 (s, 1H), 5.51 (s, 2H), 5.08 (s, 2H), 4.58 (s, 2H), 4.05 (s, 1H), 2.33 (s, 4H), 1.65-1.63 (m, 4H). MS (ESI) m/z 467 [M+H]⁺

Example 241

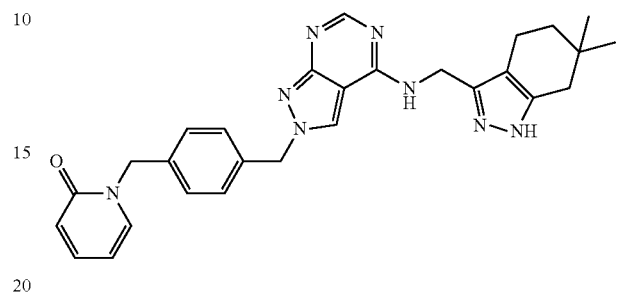

1-(4-((4-((6,6-dimethyl-4,5,6,7-tetrahydro-1H-indazol-3-yl)methylamino)-2H-pyrazolo[3,4-d]pyrimidin-2-yl)methyl)benzyl)pyridin-2(1H)-one 1-(4-((4-((6,6-dimethyl-4,5,6,7-tetrahydro-1H-indazol-3-yl)methylamino)-2H-pyrazolo[3,4-d]pyrimidin-2-yl) methyl)benzyl)pyridin-2(1H)-one was prepared in a similar manner to Example 215. ¹H NMR (300 MHz, DMSO-d₆): δ 8.46 (brs, 2H), 8.23 (brs, 1H), 7.80 (brs, 1H), 7.29 (s, 5H), 6.41 (d, 1H), 6.18 (brs, 1H), 5.51 (s, 2H), 5.08 (s, 2H), 4.60 (s, 2H), 2.30 (s, 4H), 1.39 (brs, 2H), 0.92 (s, 6H). MS (ESI) m/z 495 [M+H]⁺

Example 242

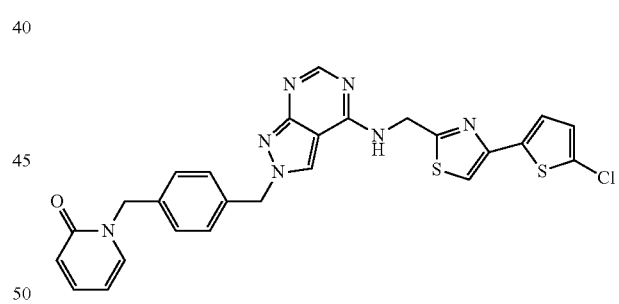

1-(4-((4-((4-(5-chlorothiophen-2-yl)thiazol-2-yl) methylamino)-2H-pyrazolo[3,4-d]pyrimidin-2-yl) methyl)benzyl)pyridin-2(1H)-one 1-(4-((4-((4-(5-chlorothiophen-2-yl)thiazol-2-yl)methylamino)-2H-pyrazolo[3,4-d]pyrimidin-2-yl)methyl)benzyl) pyridin-2(1H)-one was prepared in a similar manner as Example 215. ¹H NMR (300 MHz, CD₃OD): δ 9.10 (s, 1H), 8.41 (s, 1H), 8.26 (s, 1H), 7.89 (s, 1H), 7.76 (s, 1H), 7.44-7.41 (m, 2H), 7.32-7.30 (m, 4H), 7.14 (d, J=4.2 Hz, 1H), 6.41 (d, J=8.7 Hz, 1H), 6.22-6.21 (m, 1H), 5.57 (s, 2H), 5.08 (s, 2H), 4.99 (d, J=6 Hz, 2H). MS (ESI) m/z 456 [M+H]⁺

Example 243

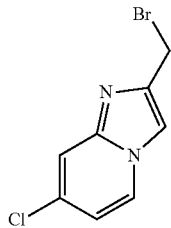 [SMILES: Clc1ccn2cc(CBr)nc2c1]

2-(bromomethyl)-7-chloroimidazo[1,2-a]pyridine

Into a 50-mL 3-necked round-bottom flask, was placed a solution of 4-chloropyridin-2-amine (1 g, 7.78 mmol, 1.00 equiv) and 1,3-dibromopropan-2-one (1.688 g, 7.82 mmol, 1.00 equiv) in ethylene glycol dimethyl ether (15 mL). The resulting solution was stirred for 1 h at 25° C. Then it was concentrated under vacuum. To the residue was added ethanol (20 mL) an the resulted solution was stirred for an additional 4 h at 90° C. The mixture was concentrated under vacuum. The pH value of the solution was adjusted to 7-8 with 3 N sodium bicarbonate aqueous solution. Then it was extracted with 3×50 mL of dichloromethane, washed with water and brine, dried over anhydrous sodium sulfate and concentrated under vacuum. The residue was purified by silica gel column chromatography eluted with petroleum /ethyl acetate (2:1). This resulted in 500 mg (26%) of 2-(bromomethyl)-7-chloroimidazo[1,2-a]pyridine as a white solid. MS (ESI) m/z: 247 [M+H]$^+$

Example 244

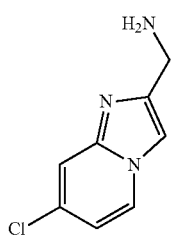 [SMILES: NCc1cn2ccc(Cl)cc2n1]

[6-chloroimidazo[1,2-a]pyridin-2-yl]methanamine

Into a 100-mL round-bottom flask, was placed 2-(bromomethyl)-6-chloroimidazo[1,2-a]pyridine (200 mg, 0.81 mmol, 1.00 equiv)(Example 243), 1,4-dioxane (13.3 mL), ammonia (6.7 mL). The resulting solution was stirred for 2 h at 25° C. The resulting mixture was concentrated under vacuum. The resulting mixture was washed with ×20 mL of H2O. The resulting solution was extracted with 3×20 mL of dichloromethane and the organic layers combined. The mixture was dried over anhydrous sodium sulfate and concentrated under vacuum. This resulted in 100 mg (67.6%) of [6-chloroimidazo[1,2-a]pyridin-2-yl]methanamine as a white solid. MS (ESI) m/z: 182 [M+H]$^+$

Example 245

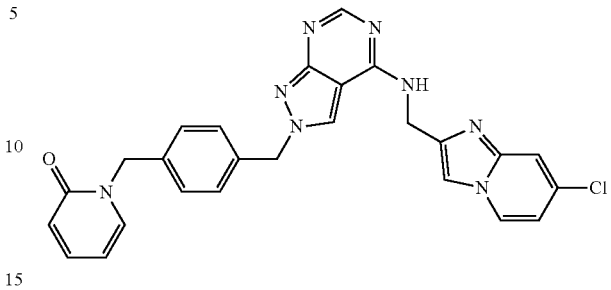

1-[[4-([4-[([7-chloroimidazo[1,2-a]pyridin-2-yl]methyl)amino]-2H-pyrazolo[3,4-d]pyrimidin-2-yl]methyl)phenyl]methyl]-1,2-dihydropyridin-2-one 1-[[4-([4-[([7-chloroimidazo[1,2-a]pyridin-2-yl]methyl)amino]-2H-pyrazolo[3,4-d]pyrimidin-2-yl]methyl)phenyl]methyl]-1,2-dihydropyridin-2-one was prepared in a similar manner as Example 215 using Example 244. $^1$H NMR (300 MHz, DMSO-d$_6$): δ 8.72 (s, 1H), 8.50 (d, J=7.2 Hz, 1H), 8.40 (s, 1H), 8.21 (s, 1H), 7.83 (s, 1H), 7.75 (d, J=5.4 Hz, 1H), 7.64 (s, 1H), 7.41 (t, J=7.05 Hz, 1H), 7.30 (s, 1H), 6.94 (m, 1H), 6.41 (d, J=9.0 Hz, 1H), 6.23 (t, J=6.45 Hz, 1H), 5.53 (s, 2H), 5.08 (s, 2H), 4.78 (d, J=5.1 Hz, 1H). MS (ESI) m/z: 497 [M+H]$^+$

Example 246

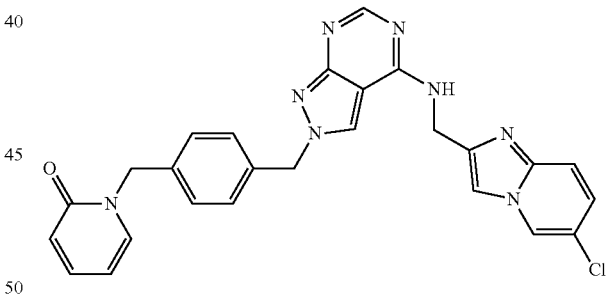

1-[[4-([4-[([6-chloroimidazo[1,2-a]pyridin-2-yl]methyl)amino]-2H-pyrazolo[3,4-d]pyrimidin-2-yl]methyl)phenyl]methyl]-1,2-dihydropyridin-2-one 1-[[4-([4-[([6-chloroimidazo[1,2-a]pyridin-2-yl]methyl)amino]-2H-pyrazolo[3,4-d]pyrimidin-2-yl]methyl)phenyl]methyl]-1,2-dihydropyridin-2-one was prepared in a similar manner as Example 245. $^1$H NMR (300 MHz, DMSO-d$_6$): δ 8.66 (m, 2H), 8.32 (s, 1H), 8.14 (s, 1H), 7.69 (m, 2H), 7.47 (d, J=9.6 Hz, 1H), 7.34 (m, 1H), 7.21 (m, 5H), 6.33 (d, J=9.0 Hz, 1H), 6.15 (m, 1H), 5.47 (s, 2H), 5.01 (s, 2H), 4.72 (d, J=5.7 Hz, 2H).

MS (ESI) m/z 497 [M+H]$^+$

Example 247

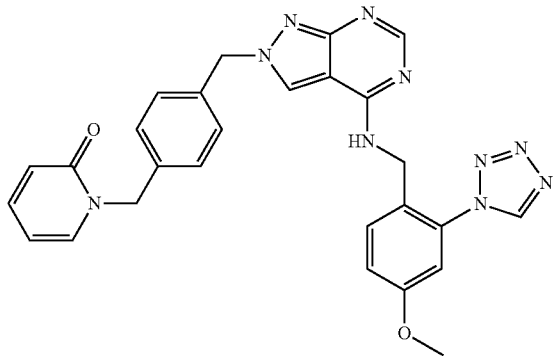 [SMILES: COc1ccc(CNc2ncnc3nn(Cc4ccc(Cn5ccccc5=O)cc4)cc23)c(-n2cnnn2)c1]

1-(4-((4-((4-methoxy-2-(1H-tetrazol-1-yl)benzyl)amino)-2H-pyrazolo[3,4-d]pyrimidin-2-yl)methyl)benzyl)pyridin-2(1H)-one 1-(4-((4-((4-methoxy-2-(1H-tetrazol-1-yl)benzyl)amino)-2H-pyrazolo[3,4-d]pyrimidin-2-yl)methyl)benzyl)pyridin-2(1H)-one was prepared in a similar manner as Example 111. $^1$H NMR (400 MHz, DMSO-d$_6$) δ 9.83 (s, 1H), 8.58 (d, J=5.7 Hz, 1H), 8.29 (s, 1H), 8.10 (d, J=15.5 Hz, 1H), 7.74 (dd, J=6.8, 2.0 Hz, 1H), 7.51 (d, J=8.4 Hz, 1H), 7.39 (ddd, J=8.9, 6.6, 2.1 Hz, 1H), 7.32-7.23 (m, 4H), 7.17 (d, J=8.7 Hz, 2H), 6.38 (dd, J=9.1, 1.3 Hz, 1H), 6.20 (td, J=6.7, 1.4 Hz, 1H), 5.51 (s, 2H), 5.06 (s, 2H), 4.45 (d, J=5.4 Hz, 2H), 3.78 (s, 3H). MS (M+H)+ found for C$_{27}$H$_{24}$N$_{10}$O$_2$: 521.1.

Example 248

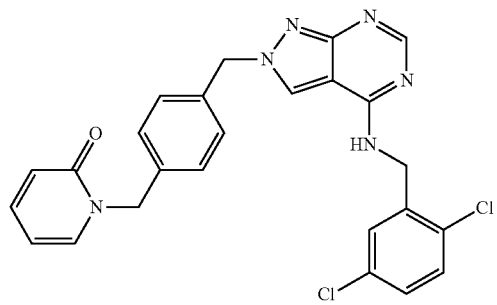 [SMILES: O=c1ccccn1Cc1ccc(Cn2cc3c(NCc4cc(Cl)ccc4Cl)ncnc3n2)cc1]

1-(4-((4-((2,5-dichlorobenzyl)amino)-2H-pyrazolo[3,4-d]pyrimidin-2-yl)methyl)benzyl)pyridin-2(1H)-one 1-(4-((4-((2,5-dichlorobenzyl)amino)-2H-pyrazolo[3,4-d]pyrimidin-2-yl)methyl)benzyl)pyridin-2(1H)-one was prepared similar to Example 215 using (2,5-dichlorophenyl)methanamine to replace (5-chloro-1H-indazol-3-yl)methanamine. $^1$H NMR (400 MHz, DMSO-d$_6$) δ 9.58 (s, 1H), 8.57 (s, 1H), 8.42 (s, 1H), 7.79-7.72 (m, 1H), 7.52 (d, J=8.5 Hz, 1H), 7.48-7.25 (m, 7H), 6.38 (d, J=9.1 Hz, 1H), 6.21 (dd, J=7.3, 6.0 Hz, 1H), 5.58 (s, 2H), 5.07 (s, 2H), 4.81 (d, J=5.5 Hz, 2H). MS (M+H)+ found for C$_{25}$H$_{20}$Cl2N$_6$O: 491.0, 493.0.

Example 249

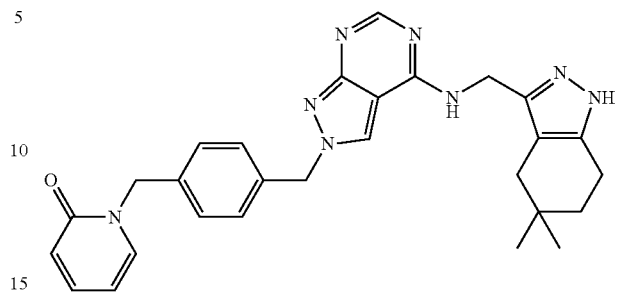

1-(4-((4-((5,5-dimethyl-4,5,6,7-tetrahydro-1H-indazol-3-yl)methylamino)-2H-pyrazolo[3,4-d]pyrimidin-2-yl)methyl)benzyl)pyridin-2(1H)-one 1-(4-((4-((5,5-dimethyl-4,5,6,7-tetrahydro-1H-indazol-3-yl)methylamino)-2H-pyrazolo[3,4-d]pyrimidin-2-yl)methyl)benzyl)pyridin-2(1H)-one was prepared in a similar manner to Example 215. $^1$H NMR (300 MHz, DMSO-d$_6$): 8.55 (brs, 1H), 8.40 (s, 1H), 8.26 (s, 1H), 7.76-7.73 (m, 1H), 7.44-7.37 (m, 1H), 7.28 (s, 4H), 6.40 (d, J=9.3 Hz, 1H), 6.24-6.19 (m, 1H), 5.52 (s, 2H), 5.07 (s, 2H), 4.57 (d, J=5.1 Hz, 2H); 2.50 (s, 2H), 2.15 (s, 2H), 1.48-1.44 (m, 2H), 0.89 (s, 6H). MS (ESI) m/z 495 [M+H]$^+$

Example 250

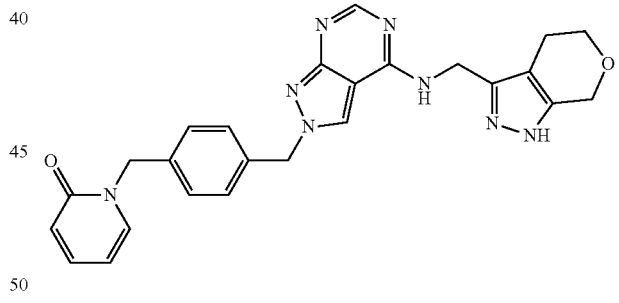

1-(4-((4-((1,4,5,7-tetrahydropyrano[3,4-c]pyrazol-3-yl)methylamino)-2H-pyrazolo[3,4-d]pyrimidin-2-yl)methyl)benzyl)pyridin-2(1H)-one 1-(4-((4-((1,4,5,7-tetrahydropyrano[3,4-c]pyrazol-3-yl)methylamino)-2H-pyrazolo[3,4-d]pyrimidin-2-yl)methyl)benzyl)pyridin-2(1H)-one was prepared in a similar manner to Example 215. $^1$H NMR (300 MHz, DMSO-d$_6$): δ 12.47 (br, 1H), 8.46 (br, 1H), 8.34 (s, 1H), 8.23 (s, 1H), 7.76 (d, J=6.6 Hz, 1H), 7.43-7.37 (m, 1H), 7.29 (s, 4H), 6.41 (d, J=9.0 Hz, 1H), 6.24-6.20 (m, 1H), 5.52 (s, 2H), 5.07 (s, 2H), 4.63-4.57 (m, 4H), 3.71 (br, 2H), 2.49 (br, 2H). MS (ESI) m/z: 469[M+H]$^+$

Example 251

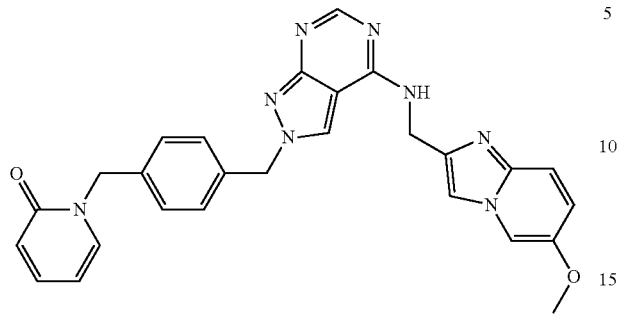

1-[[4-([4-[([6-methoxyimidazo[1,2-a]pyridin-2-yl]methyl)amino]-2H-pyrazolo[3,4-d]pyrimidin-2-yl]methyl)phenyl]methyl]-1,2-dihydropyridin-2-one 1-[[4-([4-[([6-methoxyimidazo[1,2-a]pyridin-2-yl]methyl)amino]-2H-pyrazolo[3,4-d]pyrimidin-2-yl]methyl)phenyl]methyl]-1,2-dihydropyridin-2-one was prepared in a similar manner to Example 215. $^1$H NMR (300 MHz, DMSO-$d_6$): δ 8.65 (br. s, 1H), δ 8.39 (s, 1H), 8.20 (m, 1H), 7.71 (m, 2H), 7.39 (m, 2H), 7.29 (m, 4H), 7.00 (m, 1H), 6.41 (m, 1H), 6.21 (s, 1H), 5.53 (s, 2H), 5.07 (s, 2H), 4.74 (d, J=5.7 Hz, 2H), 3.73 (s, 3H). MS (ESI) m/z: 493 [M+H]$^+$

Example 252

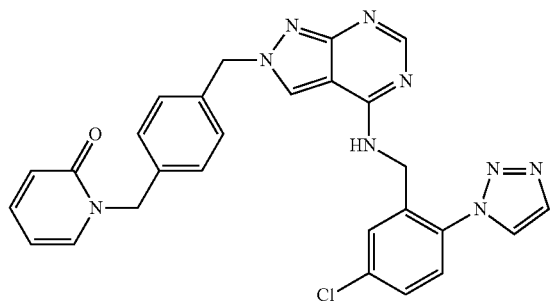 [SMILES: O=c1ccccn1Cc1ccc(Cn2cc3c(NCc4cc(Cl)ccc4-n4ccnn4)ncnc3n2)cc1]

1-(4-((4-((5-chloro-2-(1H-1,2,3-triazol-1-yl)benzyl)amino)-2H-pyrazolo[3,4-d]pyrimidin-2-yl)methyl)benzyl)pyridin-2(1H)-one 1-(4-((4-((5-chloro-2-(1H-1,2,3-triazol-1-yl)benzyl)amino)-2H-pyrazolo[3,4-d]pyrimidin-2-yl)methyl)benzyl)pyridin-2(1H)-one was prepared similar to Example 111. $^1$H NMR (400 MHz, DMSO-$d_6$) δ 8.59 (d, J=1.1 Hz, 2H), 8.33 (s, 1H), 8.11 (s, 1H), 7.96 (d, J=1.1 Hz, 1H), 7.74 (dd, J=6.8, 2.0 Hz, 1H), 7.60-7.47 (m, 3H), 7.44-7.22 (m, 5H), 6.38 (dd, J=9.0, 1.2 Hz, 1H), 6.20 (td, J=6.7, 1.4 Hz, 1H), 5.52 (s, 2H), 5.06 (s, 2H), 4.52 (d, J=5.6 Hz, 2H). MS (M+H)+ found for C$_{27}$H$_{22}$Cl2N$_9$O: 524.1, 526.0.

Example 253

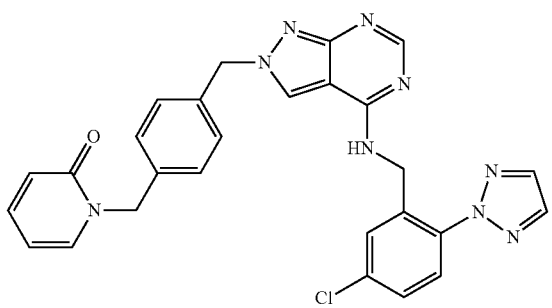 [SMILES: O=c1ccccn1Cc1ccc(Cn2cc3c(NCc4cc(Cl)ccc4-n4nccn4)ncnc3n2)cc1]

1-(4-((4-((5-chloro-2-(12H-1,2,3-triazol-1-yl)benzyl)amino)-2H-pyrazolo[3,4-d]pyrimidin-2-yl)methyl)benzyl)pyridin-2(1H)-one 1-(4-((4-((5-chloro-2-(12H-1,2,3-triazol-1-yl)benzyl)amino)-2H-pyrazolo[3,4-d]pyrimidin-2-yl)methyl)benzyl)pyridin-2(1H)-one was prepared similar to Example 111. $^1$H NMR (400 MHz, DMSO-$d_6$) δ 8.58 (t, J=5.8 Hz, 1H), 8.36 (s, 1H), 8.13 (d, J=11.0 Hz, 3H), 7.78-7.67 (m, 2H), 7.57-7.47 (m, 2H), 7.43-7.24 (m, 5H), 6.38 (dt, J=9.1, 0.9 Hz, 1H), 6.20 (td, J=6.7, 1.4 Hz, 1H), 5.53 (s, 2H), 5.06 (s, 2H), 4.82 (d, J=5.6 Hz, 2H). MS (M+H)+ found for C$_{27}$H$_{22}$Cl2N$_9$O: 524.1, 526.0.

Example 254

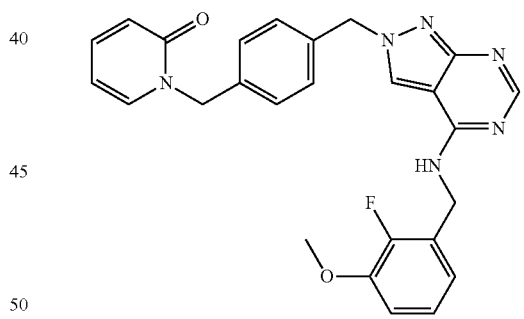

1-(4-((4-((2-fluoro-3-methoxybenzyl)amino)-2H-pyrazolo[3,4-d]pyrimidin-2-yl)methyl)benzyl)pyridin-2(1H)-one 1-(4-((4-((2-fluoro-3-methoxybenzyl)amino)-2H-pyrazolo[3,4-d]pyrimidin-2-yl)methyl)benzyl)pyridin-2(1H)-one was synthesized in a manner similar to Example 215. $^1$H NMR (400 MHz, Methanol-$d_4$) δ 8.26 (s, 2H), 7.67 (dd, J=6.9, 1.9 Hz, 1H), 7.51 (ddd, J=9.0, 6.7, 2.0 Hz, 1H), 7.32 (d, J=2.3 Hz, 4H), 7.08-6.89 (m, 3H), 6.55 (d, J=9.1 Hz, 1H), 6.37 (td, J=6.7, 1.4 Hz, 1H), 5.51 (s, 2H), 5.17 (s, 2H), 4.80 (s, 2H), 3.85 (s, 3H). MS (M+H)+ found for C$_{26}$H$_{23}$FN$_6$O$_2$: 471.1.

Example 255

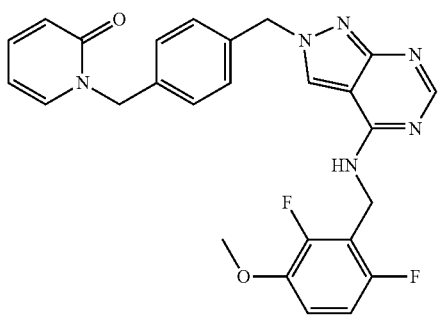 [SMILES: COc1ccc(F)c(CNc2ncnc3nn(Cc4ccc(Cn5ccccc5=O)cc4)cc23)c1F]

1-(4-((4-((2,6-difluoro-3-methoxybenzyl)amino)-2H-pyrazolo[3,4-d]pyrimidin-2-yl)methyl)benzyl)pyridin-2(1H)-one 1-(4-((4-((2,6-difluoro-3-methoxybenzyl)amino)-2H-pyrazolo[3,4-d]pyrimidin-2-yl)methyl)benzyl)pyridin-2(1H)-one was synthesized in a manner similar to Example 215. $^1$H NMR (400 MHz, Methanol-$d_4$) δ 8.30 (s, 1H), 8.23 (s, 1H), 7.65 (dd, J=6.8, 2.0 Hz, 1H), 7.50 (ddd, J=8.9, 6.7, 2.0 Hz, 1H), 7.28 (d, J=1.2 Hz, 4H), 7.06 (td, J=9.3, 5.2 Hz, 1H), 6.90 (td, J=9.1, 2.0 Hz, 1H), 6.54 (dd, J=9.3, 1.1 Hz, 1H), 6.36 (td, J=6.7, 1.4 Hz, 1H), 5.48 (s, 2H), 5.15 (s, 2H), 4.81 (s, 2H), 3.84 (s, 3H). MS (M+H)+ found for $C_{26}H_{22}F_2N_6O_2$: 488.7.

Example 256

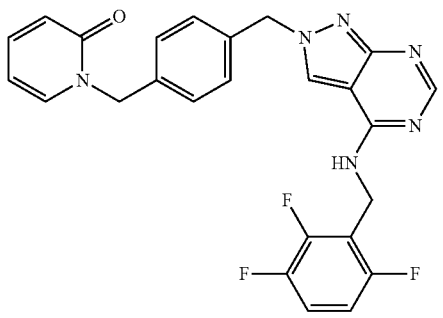 [SMILES: O=c1ccccn1Cc1ccc(Cn2cc3c(NCc4c(F)ccc(F)c4F)ncnc3n2)cc1]

1-(4-((4-((2,3,6-trifluorobenzyl)amino)-2H-pyrazolo[3,4-d]pyrimidin-2-yl)methyl)benzyl)pyridin-2(1H)-one 1-(4-((4-((2,3,6-trifluorobenzyl)amino)-2H-pyrazolo[3,4-d]pyrimidin-2-yl)methyl)benzyl)pyridin-2(1H)-one was synthesized in a manner similar to Example 215. $^1$H NMR (400 MHz, Methanol-$d_4$) δ 8.30 (s, 1H), 8.22 (s, 1H), 7.66 (dd, J=6.8, 2.0 Hz, 1H), 7.50 (ddd, J=9.0, 6.7, 2.0 Hz, 1H), 7.30 (s, 4H), 7.21 (td, J=8.5, 6.2 Hz, 1H), 6.94-6.83 (m, 1H), 6.59-6.48 (m, 1H), 6.36 (td, J=6.7, 1.4 Hz, 1H), 5.49 (s, 2H), 5.16 (s, 2H), 4.80 (s, 3H).

Example 257

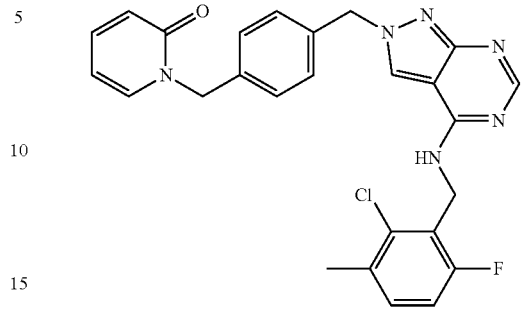

1-(4-((4-((2-chloro-6-fluoro-3-methylbenzyl)amino)-2H-pyrazolo[3,4-d]pyrimidin-2-yl)methyl)benzyl)pyridin-2(1H)-one 1-(4-((4-((2-chloro-6-fluoro-3-methylbenzyl)amino)-2H-pyrazolo[3,4-d]pyrimidin-2-yl)methyl)benzyl)pyridin-2(1H)-one was synthesized in a manner similar to Example 111. $^1$H NMR (400 MHz, Methanol-$d_4$) δ 8.31 (s, 1H), 8.20 (d, J=9.5 Hz, 1H), 7.65 (dd, J=6.9, 2.0 Hz, 1H), 7.50 (ddd, J=8.9, 6.7, 2.0 Hz, 1H), 7.35-7.24 (m, 5H), 7.04 (t, J=8.9 Hz, 1H), 6.54 (dd, J=9.3, 1.1 Hz, 1H), 6.36 (td, J=6.8, 1.4 Hz, 1H), 5.48 (s, 2H), 5.16 (s, 2H), 4.89 (d, J=2.0 Hz, 2H), 2.35 (s, 3H). MS (M+H)+ found for $C_{26}H_{22}ClFN_6O$: 489.1.

Example 258

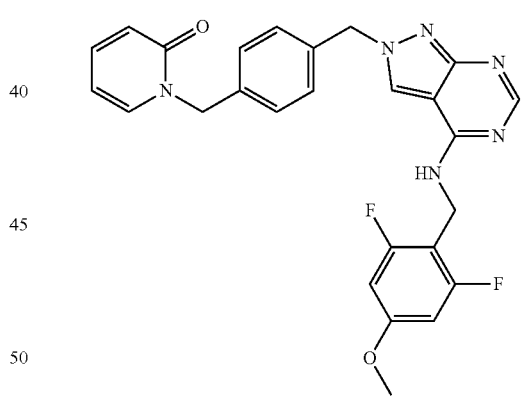

1-(4-((4-((2,6-difluoro-4-methoxybenzyl)amino)-2H-pyrazolo[3,4-d]pyrimidin-2-yl)methyl)benzyl)pyridin-2(1H)-one 1-(4-((4-((2-chloro-6-fluoro-3-methylbenzyl)amino)-2H-pyrazolo[3,4-d]pyrimidin-2-yl)methyl)benzyl)pyridin-2(1H)-one was synthesized in a manner similar to Example 215. $^1$H NMR (400 MHz, Methanol-$d_4$) δ 8.29 (s, 1H), 8.23 (s, 1H), 7.64 (dd, J=6.8, 2.0 Hz, 1H), 7.50 (ddd, J=8.9, 6.7, 2.0 Hz, 1H), 7.28 (d, J=1.4 Hz, 4H), 6.59 (d, J=9.5 Hz, 2H), 6.54 (dd, J=9.2, 1.3 Hz, 1H), 6.36 (td, J=6.7, 1.4 Hz, 1H), 5.47 (s, 2H), 5.15 (s, 2H), 4.72 (s, 2H), 3.78 (s, 3H). MS (M+H)+ found for $C_{26}H_{22}F_2N_6O_2$: 489.1.

Example 259

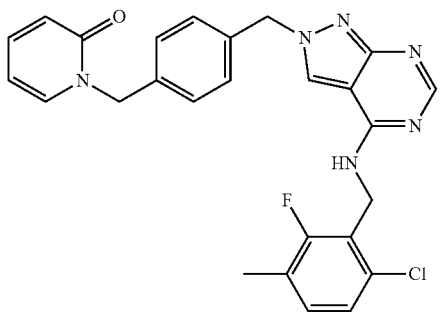 [SMILES: Cc1ccc(Cl)c(CNc2ncnc3nn(Cc4ccc(Cn5ccccc5=O)cc4)cc23)c1F]

1-(4-((4-((6-chloro-2-fluoro-3-methylbenzyl)amino)-2H-pyrazolo[3,4-d]pyrimidin-2-yl)methyl)benzyl)pyridin-2(1H)-one 1-(4-((4-((6-chloro-2-fluoro-3-methylbenzyl)amino)-2H-pyrazolo[3,4-d]pyrimidin-2-yl)methyl)benzyl)pyridin-2(1H)-one was synthesized in a manner similar to Example 15. $^{1}$H NMR (400 MHz, Methanol-d$_{4}$) δ 8.32 (s, 1H), 8.23 (s, 1H), 7.66 (dd, J=6.9, 2.0 Hz, 1H), 7.50 (ddd, J=9.0, 6.7, 2.0 Hz, 1H), 7.30 (d, J=1.4 Hz, 4H), 7.21 (dt, J=15.5, 8.2 Hz, 2H), 6.58-6.51 (m, 1H), 6.36 (td, J=6.8, 1.4 Hz, 1H), 5.49 (s, 2H), 5.16 (s, 2H), 4.88 (d, J=2.0 Hz, 2H), 2.26 (d, J=2.2 Hz, 3H). MS (M+H)+ found for C$_{26}$H$_{22}$ClFN$_{6}$O: 489.1.

Example 260

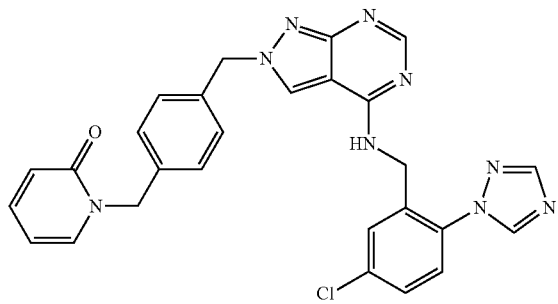 [SMILES: O=c1ccccn1Cc1ccc(Cn2cc3c(NCc4cc(Cl)ccc4-n4cncn4)ncnc3n2)cc1]

1-(4-((4-((5-chloro-2-(1H-1,2,4-triazol-1-yl)benzyl)amino)-2H-pyrazolo[3,4-d]pyrimidin-2-yl)methyl)benzyl)pyridin-2(1H)-one 1-(4-((4-((5-chloro-2-(1H-1,2,4-triazol-1-yl)benzyl)amino)-2H-pyrazolo[3,4-d]pyrimidin-2-yl)methyl)benzyl)pyridin-2(1H)-one was prepared similar to Example 111 using (5-chloro-2-(1H-1,2,4-triazol-1-yl)phenyl)methanamine to replace 4-methoxy-2-(1H-tetrazol-1-yl)phenyl)methanamine. $^{1}$H NMR (400 MHz, DMSO-d$_{6}$) δ 8.95 (s, 1H), 8.57 (t, J=5.7 Hz, 1H), 8.33 (s, 1H), 8.24 (s, 1H), 8.11 (s, 1H), 7.77-7.70 (m, 1H), 7.53 (d, J=4.6 Hz, 3H), 7.44-7.24 (m, 5H), 6.38 (d, J=9.1 Hz, 1H), 6.20 (t, J=6.6 Hz, 1H), 5.52 (s, 2H), 5.06 (s, 2H), 4.60 (d, J=5.6 Hz, 2H). MS (M+H)+ found for C$_{27}$H$_{22}$Cl2N$_{3}$O: 524.1, 526.0.

Example 261

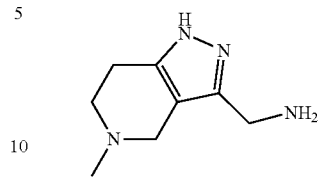

(5-methyl-4,5,6,7-tetrahydro-1H-pyrazolo[4,3-c]pyridin-3-yl)methanamine

Into a 100-mL 3-necked round-bottom flask purged and maintained with an inert atmosphere of nitrogen, was placed a mixture 3-(azidomethyl)-5-methyl-1H,4H,5H,6H,7H-pyrazolo[4,3-c]pyridine (250 mg, 1.30 mmol, 1.00 equiv), tetrahydrofuran (20 mL), water (4 mL) and PPh$_{3}$ (1.02 mg, 3.90 mmol, 3.00 equiv). The resulting solution was stirred overnight at room temperature. The reaction solution was diluted with 20 mL of EA and washed with 30 mL of brine. The organic phase was dried over anhydrous sodium sulfate and concentrated under vacuum. The crude product was purified by silica gel column chromatography eluted with ethyl acetate and petroleum ether (1:1). This resulted in 150 mg (69%) of (5-methyl-4,5,6,7-tetrahydro-1H-pyrazolo[4,3-c]pyridin-3-yl)methanamine as yellow solid. MS (ESI) m/z 167 [M+H]$^{+}$.

Example 262

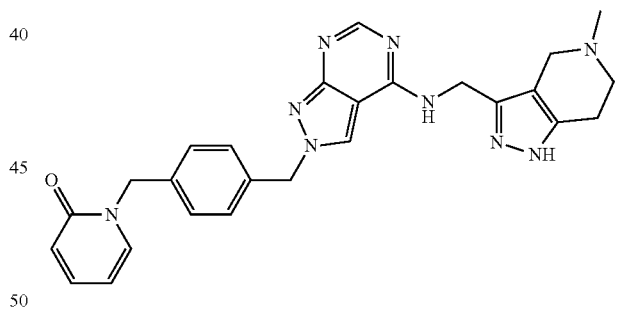

1-(4-((4-((5-methyl-4,5,6,7-tetrahydro-1H-pyrazolo[4,3-c]pyridin-3-yl)methylamino)-2H-pyrazolo[3,4-d]pyrimidin-2-yl)methyl)benzyl)pyridin-2(1H)-one 1-(4-((4-((5-methyl-4,5,6,7-tetrahydro-1H-pyrazolo[4,3-c]pyridin-3-yl)methylamino)-2H-pyrazolo[3,4-d]pyrimidin-2-yl)methyl)benzyl)pyridin-2(1H)-one was prepared in a similar manner as Example 215 using Example 261. $^{1}$H NMR (300 MHz, DMSO-d$_{6}$): δ 11.43 (br, 1H), 8.42 (br, 1H), 8.35 (s, 1H), 8.23 (s, 1H), 7.75 (dd, J=6.9, 1.5 Hz, 1H), 7.44-7.38 (m, 1H), 7.29 (s, 4H), 6.40 (d, J=8.7 Hz, 1H), 6.22 (td, J=6.6, 1.2 Hz, 1H), 5.52 (s, 2H), 5.07 (s, 2H), 4.52 (d, J=5.1 Hz, 2H), 2.86-2.83 (m, 2H), 2.68 (s, 3H), 2.41-2.35 (m, 2H), 1.88-1.77 (m, 2H). MS (ESI) m/z 482 [M+H]$^{+}$.

Example 263

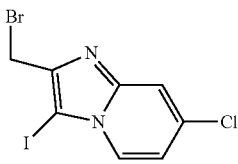

2-(bromomethyl)-7-chloro-3-iodoimidazo[1,2-a]pyridine

Into a 50-mL 3-necked round-bottom flask purged and maintained with an inert atmosphere of nitrogen, was placed a mixture of 2-(bromomethyl)-7-chloroimidazo[1,2-a]pyridine (1.00 g, 4.07 mmol, 1.00 equiv), acetic acid (1 mL) and dichloromethane (10 mL), to which was added NIS (775 mg, 3.44 mmol, 1.10 equiv) at 0° C. The resulted solution was stirred for 2 h at 25° C. The reaction solution was diluted with 20 mL of water and extracted with 3×20 mL of dichloromethane. The organic layers were combined and concentrated under vacuum. This resulted in 1.30 g (86%) of 2-(bromomethyl)-7-chloro-3-iodoimidazo[1,2-a]pyridine as white solid. MS (ESI) m/z 371 [M+H]$^+$

Example 264

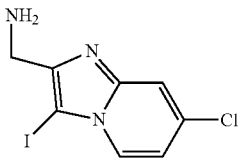 [SMILES: NCc1nc2cc(Cl)ccn2c1I]

[7-chloro-3-iodoimidazo[1,2-a]pyridin-2-yl]methanamine

Into a 100-mL round-bottom flask, was placed a mixture of 1,4-dioxane (10 mL) and concentrated ammonia (2 mL), to which was added 2-(bromomethyl)-7-chloro-3-iodoimidazo[1,2-a]pyridine (1.30 g, 3.50 mmol, 1.00 equiv)(Example 263) dropwise with stirring. The resulted solution was stirred for 2 h at 25° C. and then concentrated under vacuum. This resulted in 1.00 g (93%) of [7-chloro-3-iodoimidazo[1,2-a]pyridin-2-yl]methanamine as white solid. MS (ESI) m/z 308 [M+H]$^+$

Example 265

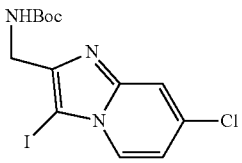 [SMILES: CC(C)(C)OC(=O)NCc1nc2cc(Cl)ccn2c1I]

tert-butyl N-([7-chloro-3-iodoimidazo[1,2-a]pyridin-2-yl]methyl)carbamate

Into a 100-mL 3-necked round-bottom flask, was placed a mixture of [7-chloro-3-iodoimidazo[1,2-a]pyridin-2-yl]methanamine (1.87 g, 6.08 mmol, 1.00 equiv)(Example 264), triethylamine (920 mg, 9.09 mmol, 1.50 equiv) and dichloromethane (20 mL), to which was added (Boc)$_2$O (1.59 g, 7.29 mmol, 1.20 equiv) at 0° C. The resulting solution was stirred for 2 h at 25° C. The resulting solution was diluted with 100 mL of water and extracted with 3×100 mL of dichloromethane. The organic layers were combined, dried over anhydrous sodium sulfate and concentrated under vacuum. The residue was purified by silica gel column chromatography eluted with ethyl acetate and petroleum ether (1:3). This resulted in 1.80 g (73%) of tert-butyl N-([7-chloro-3-iodoimidazo[1,2-a]pyridin-2-yl]methyl)carbamate as white solid. MS (ESI) m/z 408 [M+H]$^+$

Example 266

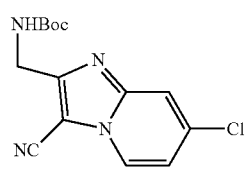 [SMILES: CC(C)(C)OC(=O)NCc1nc2cc(Cl)ccn2c1C#N]

tert-butyl N-([7-chloro-3-cyanoimidazo[1,2-a]pyridin-2-yl]methyl)carbamate

Into a 50-mL 3-necked round-bottom flask purged and maintained with an inert atmosphere of nitrogen, was placed a mixture of tert-butyl N-([7-chloro-3-iodoimidazo[1,2-a]pyridin-2-yl]methyl)carbamate (100 mg, 0.25 mmol, 1.00 equiv)(Example 265), Pd$_2$(dba)$_3$ (201 mg, 0.10 equiv), dppf (122 mg, 0.22 mmol, 0.10 equiv), DIEA (425.7 mg, 3.29 mmol, 1.50 equiv), Zn (14.3 mg, 0.22 mmol, 0.10 equiv), zinc cyanide (386 mg, 4.22 mmol, 1.50 equiv), water (0.1 mL) and N,N-dimethylformamide (10 mL). The resulted solution was stirred overnight at 25° C. The resulted mixture was concentrated under vacuum. The residue was purified by silica gel column chromatography eluted with ethyl acetate and petroleum ether (1:3 to 1:1). This resulted in 200 mg (crude) of tert-butyl N-([7-chloro-3-cyanoimidazo[1,2-a]pyridin-2-yl]methyl)carbamate as white solid. MS (ESI) m/z 307 [M+H]$^+$

Example 267

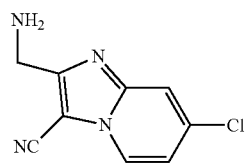 [SMILES: N#Cc1c(CN)nc2cc(Cl)ccn12]

2-(aminomethyl)-7-chloroimidazo[1,2-a]pyridine-3-carbonitrile

Into a 10-mL round-bottom flask, was placed a solution of tert-butyl N-([7-chloro-3-cyanoimidazo[1,2-a]pyridin-2-yl]methyl)carbamate (200 mg, 0.65 mmol, 1.00 equiv)(Example 266) in EA (5 mL). The resulting solution was bubbled with HCl (gas) and stirred for 1 h at 25° C. The resulting mixture was concentrated under vacuum. This resulted in 130 mg (96%) of 2-(aminomethyl)-7-chloroimidazo[1,2-a]pyridine-3-carbonitrile as white solid. MS (ESI) m/z 207 [M+H]⁺

Example 268

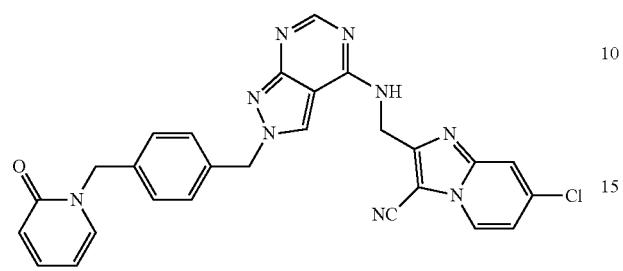

7-chloro-2-([[2-([4-[(2-oxo-1,2-dihydropyridin-1-yl)methyl]phenyl]methyl)-2H-pyrazolo[3,4-d]pyrimidin-4-yl]amino]methyl)imidazo[1,2-a]pyridine-3-carbonitrile Into a 10-mL round-bottom flask, was placed a mixture of 2-(aminomethyl)-7-chloro-2H,3H-imidazo[1,2-a]pyridine-3-carbonitrile hydrochloride (82.5 mg, 0.34 mmol, 1.20 equiv)(Example 267), DMA (5 mL), DIEA (183 mg, 1.42 mmol, 5.00 equiv) and 1-[[4-([4-chloro-2H-pyrazolo[3,4-d]pyrimidin-2-yl]methyl)phenyl]methyl]-1,2-dihydropyridin-2-one (100 mg, 0.28 mmol, 1.00 equiv)(Example 211). The resulted solution was stirred for 2 h at 80° C. The residue was purified by Prep-HPLC with the following conditions. Column: Waters X-bridge RP18 19×150 mm, 5 μm; mobile phase CH₃CN/H₂O (it contains 0.05% ammonia) with a gradient of acetonitrile from 35% to 40% in 5.5 min; flow rate: 20 mL/min; detector UV wavelength: 254 nm and 220 nm. This resulted in 34.2 mg (23%) of 7-chloro-2-([[2-([4-[(2-oxo-1,2-dihydropyridin-1-yl)methyl]phenyl]methyl)-2H-pyrazolo[3,4-d]pyrimidin-4-yl]amino]methyl)imidazo-[1,2-a]pyridine-3-carbonitrile as off-white solid. ¹H NMR (300 MHz, DMSO-d₆): δ 8.94 (br, 1H), 8.58 (d, J=7.8 Hz, 1H), 8.40 (s, 1H), 8.19 (s, 1H), 7.99 (s, 1H), 7.75 (dd, J=6.9 Hz, 1.5 Hz, 1H), 7.38-7.44 (m, 1H), 7.26-7.29 (m, 5H), 6.40 (d, J=9.0 Hz, 1H), 6.24 (t, J=6.9 Hz, 1H), 5.57 (s, 2H), 5.08 (s, 2H), 4.93 (d, J=5.7 Hz, 2H). MS (ESI) m/z 522 [M+H]⁺

Example 269

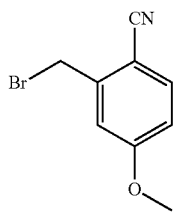

2-(bromomethyl)-4-methoxybenzonitrile

Into a 50-mL round-bottom flask, was placed a mixture of 4-methoxy-2-methylbenzonitrile (2 g, 13.59 mmol, 1.00 equiv), CCl₄ (30 mL), NBS (2.67 g, 15.00 mmol, 1.10 equiv) and BPO (100 mg, 0.39 mmol, 0.03 equiv). The resulted solution was stirred for 16 h at 80° C. After the reaction, it cooled to rt. The reaction mixture was washed with 3×20 mL of water. The organic phase was dried over anhydrous sodium sulfate and concentrated under vacuum. This resulted in 2.50 g (81%) of 2-(bromomethyl)-4-methoxybenzonitrile as a yellow solid. LC-MS (ESI) m/z: calculated for C9H8BrNO: 224. found: 395 [M+H]⁺. Rt: 1.44 min.

Example 270

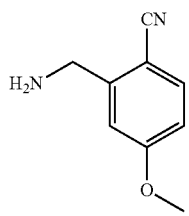

2-(aminomethyl)-4-methoxybenzonitrile

Into a 50-mL round-bottom flask, was placed a mixture of 2-(bromomethyl)-4-methoxybenzonitrile (2 g, 8.85 mmol, 1.00 equiv)(Example 269), methanol (20 mL) and concentrated ammonia aqueous solution (4 mL). The resulting solution was stirred for 2 h at 25° C. The resulting mixture was concentrated under vacuum. The residue was purified by a silica gel column eluted with ethyl acetate/petroleum ether (1:3). The crude product was purified by distillation. This resulted in 1.2 g (84%) of 2-(aminomethyl)-4-methoxybenzonitrile as a white solid. LC-MS (ESI) m/z: calculated for C9H10N2O: 162. found: 163 [M+H]⁺.

Example 271

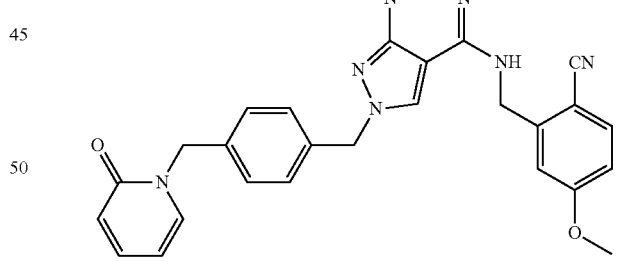

4-methoxy-2-((2-(4-((2-oxopyridin-1(2H)-yl)methyl)benzyl)-2H-pyrazolo[3,4-d]pyrimidin-4-ylamino)methyl)benzonitrile 4-methoxy-2-((2-(4-((2-oxopyridin-1(2H)-yl)methyl)benzyl)-2H-pyrazolo[3,4-d]pyrimidin-4-ylamino)methyl)benzonitrile was prepared in a similar manner as Example 215 using Example 270. ¹H NMR (300 MHz, DMSO-d₆): δ 8.56-9.11 (m, 1H), 8.21-8.46 (m, 1H), 7.75-7.81 (m, 2H), 7.30-7.50 (m, 7H), 7.00-7.11 (m, 2H), 6.37-6.42 (m, 1H), 6.22-6.23 (m, 1H), 5.63 (s, 1H), 5.55 (s, 1H), 5.34 (s, 1H), 5.08 (s, 2H), 4.80-4.82 (m, 1H), 3.78-3.87 (s, 3H). LC-MS (ESI) m/z: calculated for $C_{27}H_{23}N_7O_2$: 477. found: 478 $[M+H]^+$.

Example 272

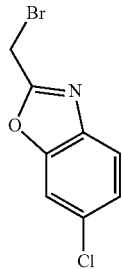 [SMILES: Clc1ccc2nc(CBr)oc2c1]

2-(bromomethyl)-6-chloro-1,3-benzoxazole

Into a 25-mL round-bottom flask purged and maintained with an inert atmosphere of nitrogen, were placed a mixture of 6-chloro-2-methyl-1,3-benzoxazole (600 mg, 3.58 mmol, 1.00 equiv), NBS (767 mg, 4.31 mmol, 1.20 equiv), BPO (92 mg, 0.36 mmol, 0.10 equiv) and $CCl_4$ (6 mL). The reaction mixture was stirred overnight at 80° C. The solids were filtered off. The filtrate was concentrated under vacuum. This resulted in 1.0 g (crude) of 2-(bromomethyl)-6-chloro-1,3-benzoxazole as a brown solid. MS (ESI) m/z 246 $[M+H]^+$ Example 273

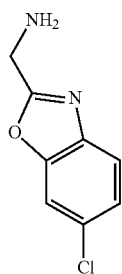 [SMILES: NCc1nc2ccc(Cl)cc2o1]

(6-chloro-1,3-benzoxazol-2-yl)methanamine

Into a 40-mL vial, was placed a mixture solution of $NH_3 \cdot H_2O$/dioxane (ratio: 1:2; 9 mL) to which was added a solution of 2-(bromomethyl)-6-chloro-1,3-benzoxazole (300 mg, 1.22 mmol, 1.00 equiv)(Example 272) in dioxane (0.5 mL) dropwise with stirring. The reaction mixture was stirred for 2 h at room temperature. The resulted mixture was concentrated under vacuum. The residue was diluted with 30 mL of $H_2O$ and washed with 3×30 mL of dichloromethane. The aqueous layer was concentrated under vacuum and dried. This resulted in 180 mg (81%) of (6-chloro-1,3-benzoxazol-2-yl)methanamine as a brown solid. MS (ESI) m/z 183 $[M+H]^+$ Example 274

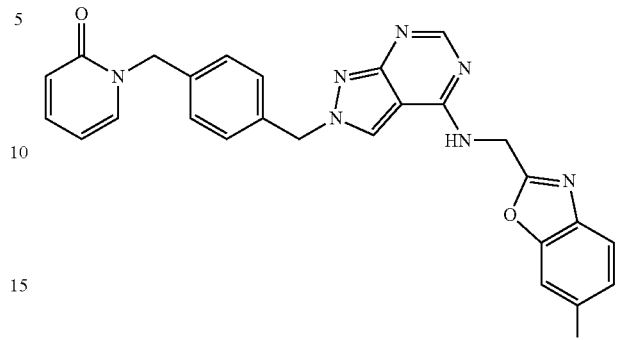

1-([4-[(4-[[(6-chloro-1,3-benzoxazol-2-yl)methyl] amino]-2H-pyrazolo[3,4-d]pyrimidin-2-yl)methyl] phenyl]methyl)-1,2-dihydropyridin-2-one 1-([4-[(4-[[(6-chloro-1,3-benzoxazol-2-yl)methyl] amino]-2H-pyrazolo[3,4-d]pyrimidin-2-yl)methyl]phenyl] methyl)-1,2-dihydropyridin-2-one was prepared in a similar manner as Example 215 using Example 273. $^1H$ NMR (300 MHz, $CD_3OD$): δ 8.99 (brs, 1H), 8.43 (s, 1H), 8.17 (s, 1H), 7.91 (d, J=2.4 Hz, 1H), 7.77-7.71 (m, 2H), 7.68-7.28 (m, 6H), 6.39 (d, J=9.3 Hz, 1H), 6.20-6.25 (m, 1H), 5.57 (s, 2H), 5.09 (s, 2H), 4.99 (d, J=5.7 Hz, 2H). MS (ESI) m/z 498 $[M+H]^+$.

Example 275

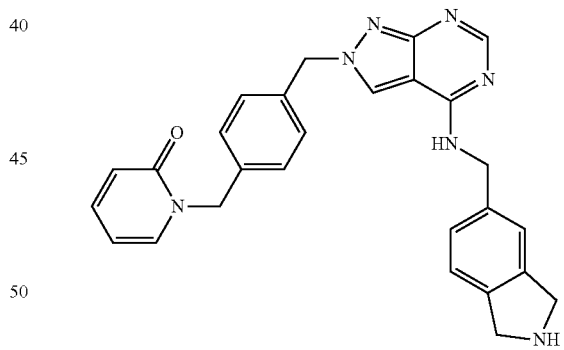

1-(4-((4-((isoindolin-5-ylmethyl)amino)-2H-pyrazolo[3,4-d]pyrimidin-2-yl)methyl)benzyl)pyridin-2(1H)-one 1-(4-((4-((isoindolin-5-ylmethyl)amino)-2H-pyrazolo[3,4-d]pyrimidin-2-yl)methyl)benzyl)pyridin-2(1H)-one was prepared in a similar manner as Example 215. $^1H$ NMR (400 MHz, DMSO-$d_6$) δ 10.27 (s, 1H), 9.49 (s, 2H), 8.64 (s, 1H), 8.55 (s, 1H), 7.76 (dd, J=6.8, 2.0 Hz, 1H), 7.45-7.25 (m, 7H), 6.41-6.34 (m, 1H), 6.22 (td, J=6.7, 1.4 Hz, 1H), 5.60 (s, 2H), 5.07 (s, 2H), 4.84 (d, J=5.8 Hz, 2H), 4.46 (q, J=5.8 Hz, 4H). MS (M+H)+ found for $C_{27}H_{26}N_7O$: 464.1.

Example 276

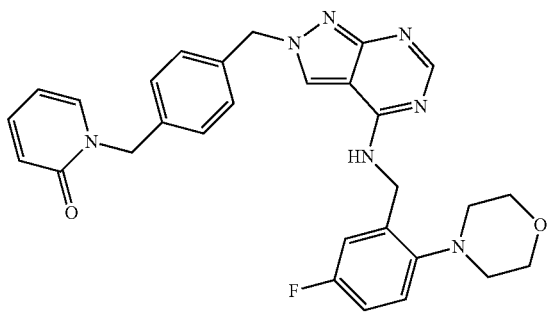 [SMILES: O=c1ccccn1Cc1ccc(Cn2cc3c(NCc4cc(F)ccc4N4CCOCC4)ncnc3n2)cc1]

1-(4-((4-((5-fluoro-2-morpholinobenzyl)amino)-2H-pyrazolo[3,4-d]pyrimidin-2-yl)methyl)benzyl)pyridin-2(1H)-one 1-(4-((4-((5-fluoro-2-morpholinobenzyl)amino)-2H-pyrazolo[3,4-d]pyrimidin-2-yl)methyl)benzyl)pyridin-2 (1H)-one was prepared in a similar manner as Example 215. $^1$H NMR (400 MHz, CD$_3$OD) δ 8.28 (s, 2H), 7.67 (s, 1H), 7.51 (s, 1H), 7.27 (d, J=38.5 Hz, 3H), 7.02 (t, J=10.9 Hz, 2H), 6.55 (d, J=9.0 Hz, 1H), 6.37 (s, 1H), 5.52 (s, 2H), 5.18 (s, 2H), 4.90 (s, 2H), 3.76 (s, 4H), 2.88 (s, 4H). MS (M+H)$^+$ found for C$_{23}$H$_{28}$FN$_7$O$_2$ 526.3.

Example 277

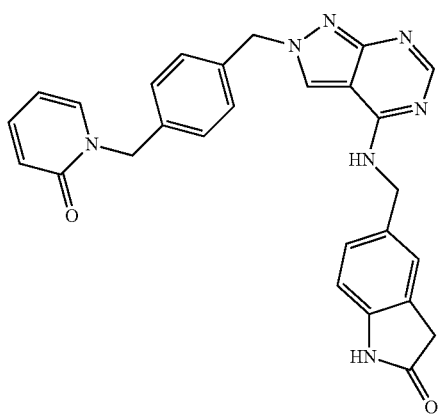 [SMILES: O=C1Cc2cc(CNc3ncnc4nn(Cc5ccc(Cn6ccccc6=O)cc5)cc34)ccc2N1]

5-(((2-(4-((2-oxopyridin-1(2H)-yl)methyl)benzyl)-2H-pyrazolo[3,4-d]pyrimidin-4-yl)amino)methyl)indolin-2-one 5-(((2-(4-((2-oxopyridin-1(2H)-yl)methyl)benzyl)-2H-pyrazolo[3,4-d]pyrimidin-4-yl)amino)methyl)indolin-2-one was prepared in a similar manner as Example 215. $^1$H NMR (400 MHz, CD$_3$OD) δ 8.57 (s, 1H), 8.51 (s, 1H), 7.71 (dd, J=6.6, 2.2 Hz, 1H), 7.53 (ddd, J=8.6, 6.6, 2.0 Hz, 1H), 7.42-7.21 (m, 6H), 6.88 (d, J=7.9 Hz, 1H), 6.56 (d, J=9.0 Hz, 1H), 6.40 (t, J=6.5 Hz, 1H), 5.58 (s, 2H), 5.19 (s, 2H), 4.89 (s, 2H), 3.50 (s, 2H). MS (M+H)$^+$ found for C$_{27}$H$_{23}$N$_7$O$_2$ 478.2.

Example 278

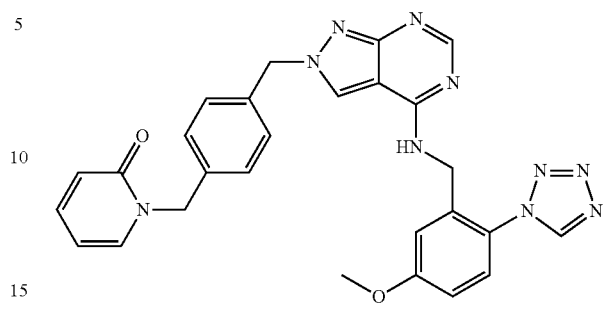

N-(4-methoxy-2-(1H-tetrazol-1-yl)benzyl)-2-(4-((4-methyl-1H-pyrazol-1-yl)methyl)benzyl)-2H-pyrazolo[3,4-d]pyrimidin-4-amine N-(4-methoxy-2-(1H-tetrazol-1-yl)benzyl)-2-(4-((4-methyl-1H-pyrazol-1-yl)methyl)benzyl)-2H-pyrazolo[3,4-d]pyrimidin-4-amine was prepared similar to Example 111. $^1$H NMR (400 MHz, DMSO-d$_6$) δ 9.75 (s, 1H), 8.54 (t, J=5.7 Hz, 1H), 8.29 (s, 1H), 8.07 (s, 1H), 7.73 (dd, J=6.8, 2.0 Hz, 1H), 7.48 (d, J=8.8 Hz, 1H), 7.39 (ddd, J=8.9, 6.6, 2.1 Hz, 1H), 7.32-7.16 (m, 4H), 7.11 (d, J=2.8 Hz, 1H), 7.06 (dd, J=8.7, 2.8 Hz, 1H), 6.42-6.34 (m, 1H), 6.20 (td, J=6.7, 1.4 Hz, 1H), 5.51 (s, 2H), 5.06 (s, 2H), 4.44 (d, J=5.5 Hz, 2H), 3.78 (s, 3H). MS (M+H)+ found for C$_{27}$H$_{24}$N$_{10}$O$_2$: 521.1.

Example 279

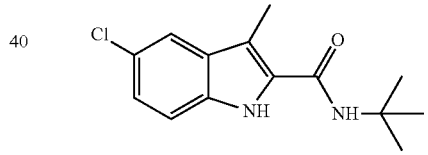

N-tert-butyl-5-chloro-3-methyl-1H-indole-2-carboxamide

Into a 25-mL 2-necked round-bottom flask purged and maintained with an inert atmosphere of nitrogen, was placed 5-chloro-3-methyl-1H-indole (2.0 g, 12.08 mmol, 1.00 equiv) in 10.0 mL dichloromethane with stirring at −10° C., to which was added sequentially 2-isocyanato-2-methylpropane (1.8 g, 18.16 mmol, 1.50 equiv) and BF$_3$.Et$_2$O (3.44 g, 24.23 mmol, 2.00 equiv). The resulted solution was stirred at −10° C. for additional 3.5 h. The pH value of the solution was adjusted to 8 with saturated sodium bicarbonate aqueous solution and the mixture was extracted with 3×50 mL of dichloromethane. The organic phase was washed with 1×10 mL of brine, dried over anhydrous sodium sulfate and concentrated under vacuum. The residue was purified by silica gel chromatography column eluted with ethyl acetate/petroleum ether=1/3. This resulted in 1.39 g (43%) of N-tert-butyl-5-chloro-3-methyl-1H-indole-2-carboxamide as a yellow solid. MS (ESI), m/z 265 [M+1]$^+$

Example 280

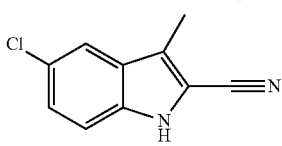

5-chloro-3-methyl-1H-indole-2-carbonitrile

Into a 20-mL round-bottom flask, was placed N-tert-butyl-5-chloro-3-methyl-1H-indole-2-carboxamide (440 mg, 1.66 mmol, 1.00 equiv)(Example 279) in toluene (7.0 mL). This was followed by the addition of phosphoroyl trichloride (688.5 mg, 4.49 mmol, 2.70 equiv). The resulted solution was stirred at 110° C. overnight. The reaction mixture was concentrated under vacuum and the crude was quenched by the addition of 2.0 mL of water. The pH value of the solution was adjusted to 8.0 with saturated sodium bicarbonate aqueous solution and the mixture was extracted with 3×30 mL of ethyl acetate. The combined organic layers were washed with 1×10 mL of brine, dried over anhydrous sodium sulfate and concentrated under vacuum. This resulted in 388 mg (crude) of 5-chloro-3-methyl-1H-indole-2-carbonitrile as a yellow solid.

Example 281

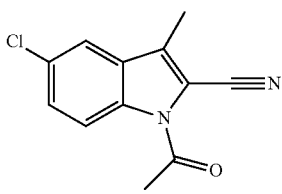 [SMILES: CC(=O)n1c(C#N)c(C)c2cc(Cl)ccc21]

1-acetyl-5-chloro-3-methyl-1H-indole-2-carbonitrile

Into a 50-mL round-bottom flask, was placed 5-chloro-3-methyl-1H-indole-2-carbonitrile (380 mg, 1.99 mmol, 1.00 equiv)(Example 280) in dichloromethane (5.0 mL), to which was added sequentially DIEA (516 mg, 3.99 mmol, 2.00 equiv), acetyl chloride (187.2 mg, 2.38 mmol, 1.20 equiv). The reaction solution was stirred at room temperature for 4 h. The resulted mixture was washed with 1×10 mL of H$_2$O and extracted with 3×30 mL of dichloromethane. The combined organic layers were washed with 1×5.0 mL of brine, dried over anhydrous sodium sulfate and concentrated under vacuum. This resulted in 430 mg (93%) of 1-acetyl-5-chloro-3-methyl-1H-indole-2-carbonitrile as a yellow solid.

$^1$H NMR (300 MHz, DMSO-d$_6$): 8.17 (d, J=9.0 Hz, 1H), 7.94 (d, J=2.1 Hz, 1H), 7.61 (t, J=2.1 Hz, 1H), 2.82 (s, 3H), 2.51-2.46 (m, 3H).

Example 282

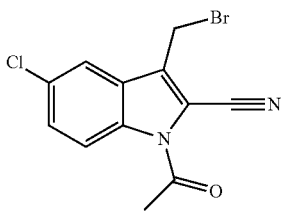 [SMILES: CC(=O)n1c(C#N)c(CBr)c2cc(Cl)ccc21]

1-acetyl-3-(bromomethyl)-5-chloro-1H-indole-2-carbonitrile

Into a 20-mL round-bottom flask, was placed chloro-3-methyl-1H-indole-2-carbonitrile (40 mg, 0.17 mmol, 1.00 equiv)(Example 281) in CCl$_4$ (1.5 mL) with stirring, to which was added sequentially 1-acetyl-5-AlBN (3 mg, 0.02 mmol, 0.10 equiv) and NBS (30.7 mg, 0.17 mmol, 1.00 equiv). The resulted solution was stirred at 80° C. for 4 h. Then the solids were filtered out and the filtrate was concentrated under vacuum. This resulted in 20.0 mg (crude) of 1-acetyl-3-(bromomethyl)-5-chloro-1H-indole-2-carbonitrile as a yellow solid.

Example 283

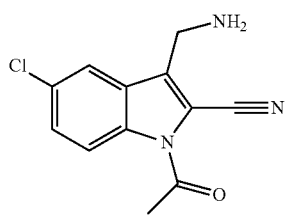 [SMILES: CC(=O)n1c(C#N)c(CN)c2cc(Cl)ccc21]

1-acetyl-3-(aminomethyl)-5-chloro-1H-indole-2-carbonitrile

Into a 25-mL 2-necked round-bottom flask, was placed a mixture of ammonia water (2.0 mL) and dioxane (4.0 mL). The solution of 1-acetyl-3-(bromomethyl)-5-chloro-1H-indole-2-carbonitrile (20 mg crude, 1.00 equiv)(Example 282) in dioxane (1.0 mL) was added into the flask with stirring. The resulted solution was stirred at room temperature for 3 h. The reaction mixture was concentrated under vacuum. The residue was purified by silica gel chromatography column eluted with dichloromethane/methanol=6/1. This resulted in 5 mg (12%) of 1-acetyl-3-(aminomethyl)-5-chloro-1H-indole-2-carbonitrile as a yellow solid.

Example 284

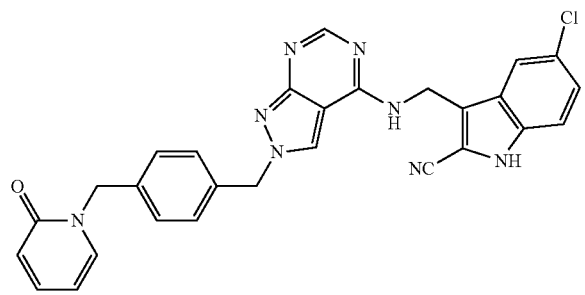 [SMILES: N#Cc1[nH]c2ccc(Cl)cc2c1CNc1ncnc2nn(Cc3ccc(Cn4ccccc4=O)cc3)cc12]

5-chloro-3-((2-(4-((2-oxopyridin-1(2H)-yl)methyl)benzyl)-2H-pyrazolo[3,4-d]pyrimidin-4-ylamino)methyl)-1H-indole-2-carbonitrile 5-chloro-3-((2-(4-((2-oxopyridin-1(2H)-yl)methyl)benzyl)-2H-pyrazolo[3,4-d]pyrimidin-4-ylamino)methyl)-1H-indole-2-carbonitrile was prepared in a similar manner as Example 215 using Example 283. $^1$H NMR (300 MHz, DMSO-d): 8.70-8.60 (m, 1H), 8.32-8.28 (m, 2H), 7.87 (d, J=1.8 Hz, 1H), 7.74 (dd, J=1.8 Hz, J=2.7 Hz, 1H), 7.46 (d, J=9.0 Hz, 1H), 7.43-7.37 (m, 1H), 7.32 (d, J=10.2 Hz, 1H), 7.28 (s, 4H), 6.39 (d, J=9.3 Hz, 1H), 6.23-6.19 (m, 1H), 5.52 (s, 2H), 5.07 (s, 2H), 4.93 (d, J=5.7 Hz, 2H). MS (ESI) m/z 521 [M+H]$^+$

Example 285

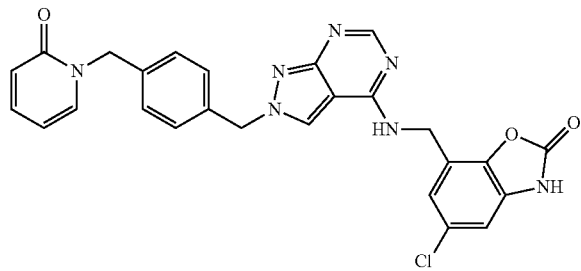 [SMILES: O=c1[nH]c2cc(Cl)cc(CNc3ncnc4nn(Cc5ccc(Cn6ccccc6=O)cc5)cc34)c2o1]

5-chloro-7-((2-(4-((2-oxopyridin-1(2H)-yl)methyl)
benzyl)-2H-pyrazolo[3,4-d]pyrimidin-4-ylamino)
methyl)benzo[d]oxazol-2(3H)-one 5-chloro-7-((2-(4-((2-oxopyridin-1(2H)-yl)methyl)benzyl)-2H-pyrazolo[3,4-d]pyrimidin-4-ylamino)methyl)benzo[d]oxazol-2(3H)-one was prepared in a manner similar to Example 97. $^1$H NMR (300 MHz, DMSO-d$_6$): δ 8.67 (br, 1H), 8.37 (s, 1H), 8.22 (s, 1H), 7.76 (d, J=6.3 Hz, 1H), 7.44-7.31 (m, 6H), 7.01 (s, 2H), 6.41 (d, J=8.7 Hz, 1H), 6.23 (t, J=6.3 Hz, 1H), 5.54 (s, 2H), 5.08 (s, 2H), 4.75 (d, J=5.1 Hz, 2H). MS (ESI) m/z 514 [M+H]$^+$.

Example 286

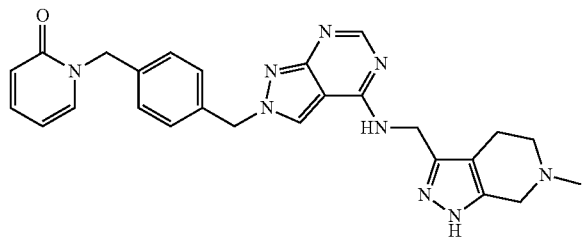 [SMILES: CN1CCc2c(CNc3ncnc4nn(Cc5ccc(Cn6ccccc6=O)cc5)cc34)n[nH]c2C1]

1-(4-((4-((6-methyl-4,5,6,7-tetrahydro-1H-pyrazolo
[3,4-c]pyridin-3-yl)methylamino)-2H-pyrazolo[3,4-
d]pyrimidin-2-yl)methyl)benzyl)pyridin-2(1H)-one 1-(4-((4-((6-methyl-4,5,6,7-tetrahydro-1H-pyrazolo[3,4-c]pyridin-3-yl)methylamino)-2H-pyrazolo[3,4-d]pyrimidin-2-yl)methyl)benzyl)pyridin-2(1H)-one was prepared in a similar manner as Example 215. $^1$H NMR (300 MHz, DMSO-d$_6$): δ 8.45 (br, 1H), 8.36 (s, 1H), 8.22 (s, 1H), 7.75 (d, J=6.9 Hz, 1H), 7.41 (t, J=6.9 Hz, 1H), 7.29 (s, 5H), 6.40 (d, J=9.6 Hz, 1H), 6.23 (t, J=6.6 Hz, 1H), 5.52 (s, 2H), 5.08 (s, 2H), 4.61 (d, J=4.8 Hz, 2H), 2.45 (m, 2H), 2.32 (s, 3H). MS (ESI) m/z 482 [M+H]$^+$.

Example 287

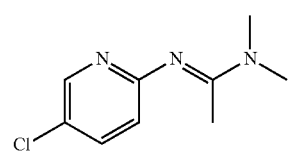

(E)-N'-(5-chloropyridin-2-yl)-N,N-dimethylacetimidamide

Into a 500-mL round-bottom flask, was placed a solution of 5-chloropyridin-2-amine (15.0 g, 116.68 mmol, 1.00 equiv) in methanol (250 mL), (1,1-dimethoxyethyl)dimethylamine (46.7 g, 350.63 mmol, 3.00 equiv) was added. The reaction mixture was stirred for 16 h at 80° C. in an oil bath. The resulting mixture was concentrated under vacuum. This resulted in 23.1 g (crude) of (E)-N'-(5-chloropyridin-2-yl)-N,N-dimethylacetimidamide as brown oil. The crude product was used for next step without further purification. MS (ESI) m/z 198 [M+H]$^+$

Example 288

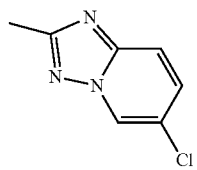

6-chloro-2-methyl-[1,2,4]triazolo[1,5-a]pyridine

Into a 500-mL round-bottom flask, was placed a solution of (E)-N'-(5-chloropyridin-2-yl)-N,N-dimethylacetimidamide (23.1 g, 116.86 mmol, 1.00 equiv)(Example 287) and pyridine (18.5 g, 233.88 mmol, 2.00 equiv) in methanol (250 mL). This was followed by the addition of (aminooxy)sulfonic acid (18.5 g, 163.58 mmol, 1.40 equiv) in portions at 0° C. The reaction mixture was stirred for 16 h at 20° C. The resulting mixture was concentrated under vacuum and the residue was diluted with 400 mL of Saturated NaHCO$_3$ solution. The solution was extracted with 3×500 mL of ethyl acetate and the organic layers combined. The resulting mixture was washed with 1×500 mL of H$_2$O, 1×1000 mL of brine. The mixture was dried over anhydrous sodium sulfate and concentrated under vacuum. The residue was applied onto a silica gel column with ethyl acetate/petroleum ether (1/2). This resulted in 9.5 g (49%) of 6-chloro-2-methyl-[1,2,4]triazolo[1,5-a]pyridine as a yellow solid. MS (ESI) m/z 168 [M+H]$^+$

Example 289

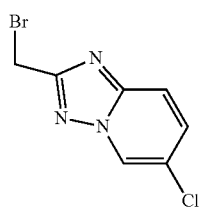 [SMILES: Clc1ccc2nc(CBr)nn2c1]

2-(bromomethyl)-6-chloro-[1,2,4]triazolo[1,5-a]pyridine

Into a 40-mL sealed tube, were placed 6-chloro-2-methyl-[1,2,4]triazolo[1,5-a]pyridine (200 mg, 1.19 mmol, 1.00 equiv)(Example 288), NBS (256 mg, 1.44 mmol, 1.20 equiv), AIBN (20 mg, 0.12 mmol, 0.10 equiv) and CCl$_4$ (4 mL). The reaction mixture was stirred for 2 h at 100° C. This reaction was conducted 10 batches (200 mg scale, total 2.0 g 6-chloro-2-methyl-[1,2,4]triazolo[1,5-a]pyridine used) in parallel. The resulting solutions were diluted with 100 mL of Cl$_2$Cl$_2$. The solids were filtered off. The filtrate was concentrated under vacuum. The crude product was purified by Flash-Prep-HPLC with the following conditions. C18 Column; mobile phase, CH₃CN/water (0.05% TFA) with a gradient of acetonitrile from 10% to 60% in 15 min flow rate: 80 mL/min; Detector, UV 254 nm. The product was concentrated under vacuum and lyophilized to afford 279 mg (9%) of 2-(bromomethyl)-6-chloro-[1,2,4]triazolo[1,5-a]pyridine as a brown solid. MS (ESI) m/z 246 [M+H]⁺

Example 290

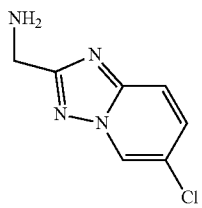 [SMILES: NCc1nc2ccc(Cl)cn2n1]

[6-chloro-[1,2,4]triazolo[1,5-a]pyridin-2-yl]methanamine

Into a 8-mL sealed tube, was placed a mixture solution of NH₃' H₂O/dioxane=1/2 (3 mL). This was followed by the addition of a solution of 2-(bromomethyl)-6-chloro-[1,2,4]triazolo[1,5-a]pyridine (150 mg, 0.61 mmol, 1.00 equiv) (Example 289) in dioxane (0.2 mL) dropwise with stirring. The reaction mixture was stirred for 2 h at room temperature. The resulted mixture was concentrated under vacuum. The residue was diluted with 20 mL of H₂O, washed with 3×20 mL of dichloromethane, the aqueous layer was concentrated under vacuum and dried. This resulted in 70 mg (63%) of [6-chloro-[1,2,4]triazolo[1,5-a]pyridin-2-yl]methanamine as a brown solid. MS (ESI) m/z 183 [M+H]⁺

Example 291

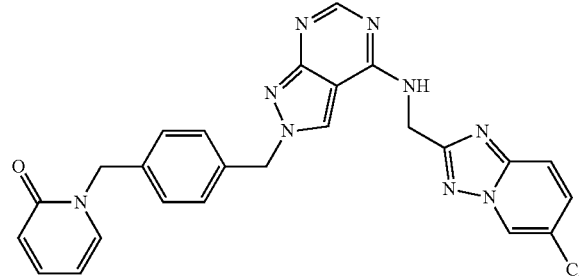

1-[[4-([4-[([6-chloro-[1,2,4]triazolo[1,5-a]pyridin-2-yl]methyl)amino]-2H-pyrazolo[3,4-d]pyrimidin-2-yl]methyl)phenyl]methyl]-1,2-dihydropyridin-2-one 1-[[4-([4-[([6-chloro-[1,2,4]triazolo[1,5-a]pyridin-2-yl]methyl)amino]-2H-pyrazolo[3,4-d]pyrimidin-2-yl]methyl)phenyl]methyl]-1,2-dihydropyridin-2-one was prepared in a similar manner as Example 215 using Example 290. ¹H-NMR (300 MHz, DMSO-d₆): δ 9.29 (s, 1H), 8.87 (brs, 1H), 8.41 (s, 1H), 8.17 (s, 1H), 7.82-7.71 (m, 3H) 7.44-7.38 (m, 1H), 7.31-7.31 (m, 4H), 6.41 (d, J=8.7 Hz, 1H), 6.25-6.20 (m, 1H), 5.55 (s, 2H), 5.08 (s, 2H), 4.94 (d, J=8.7 Hz, 2H). MS (ESI) m/z 498 [M+H]⁺.

Example 292

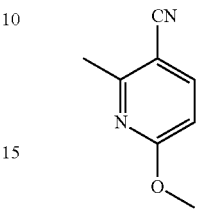

6-methoxy-2-methylpyridine-3-carbonitrile

Into a 100-mL round-bottom flask, was placed a solution of 6-chloro-2-methylpyridine-3-carbonitrile (2.00 g, 13.11 mmol, 1.00 equiv) in methanol (30 mL), to which was added methoxysodium (2.70 g, 49.98 mmol, 5.00 equiv) in portions. The reaction mixture was stirred for 2 h at 80° C. After cooled to 20° C., the solution was diluted with 20 mL of methanol. The solids were filtered out and the filtrate was concentrated under vacuum. The residue was dissolved in 50 mL of DCM. The solids were filtered out and the filtrate was concentrated under vacuum. This resulted in 1.80 g (93%) of 6-methoxy-2-methylpyridine-3-carbonitrile as a yellow solid. MS (ESI) m/z 149 [M+H]⁺

Example 293

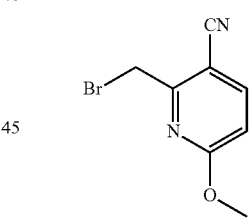

2-(bromomethyl)-6-methoxypyridine-3-carbonitrile

Into a 40-mL sealed tube, was placed a solution of 6-methoxy-2-methylpyridine-3-carbonitrile (1.10 g, 7.42 mmol, 1.00 equiv)(Example 292) in 1,2-dichloroethane (20 mL) and NBS (2.61 g, 14.66 mmol, 2.00 equiv) with stirring at rt, to which was added AIBN (121 mg, 0.74 mmol, 0.10 equiv). The reaction mixture was then stirred for 24 h at 100° C. in an oil bath. After cooled to 20° C., the solution was diluted with 20 mL of DCM. The solids were filtered out and the filtrate was concentrated under vacuum. The residue was purified by a silica gel column eluted with ethyl acetate/petroleum ether (1/10). This resulted in 700 mg (42%) of 2-(bromomethyl)-6-methoxypyridine-3-carbonitrile as a yellow solid. MS (ESI) m/z 227 [M+H]⁺

Example 294

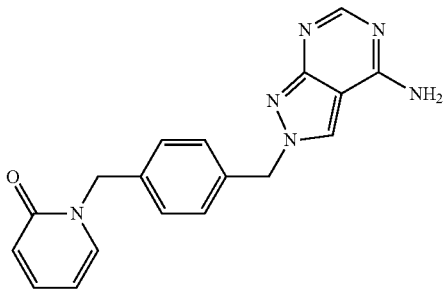 [SMILES: Nc1ncnc2nn(Cc3ccc(Cn4ccccc4=O)cc3)cc12]

1-[[4-([4-amino-2H-pyrazolo[3,4-d]pyrimidin-2-yl]methyl)phenyl]methyl]-1,2-dihydropyridin-2-one Into a 8-mL sealed tube, were placed a mixture of 1-[[4-([4-chloro-2H-pyrazolo[3,4-d]pyrimidin-2-yl]methyl)phenyl]methyl]-1,2-dihydropyridin-2-one (300 mg, 0.85 mmol, 1.00 equiv)(Example 209) and ammonia (4.0 mL). The reaction mixture was stirred for 2 h at 100° C. in an oil bath. The reaction mixture was then cooled to 20° C. The solids were collected by filtration, washed with H$_2$O (10 mL), dried under reduced pressure. This resulted in 203 mg (72%) of 1-[[4-([4-amino-2H-pyrazolo[3,4-d]pyrimidin-2-yl]methyl)phenyl]methyl]-1,2-dihydropyridin-2-one as a light yellow solid. MS (ESI) m/z 333 [M+H]$^+$

Example 295

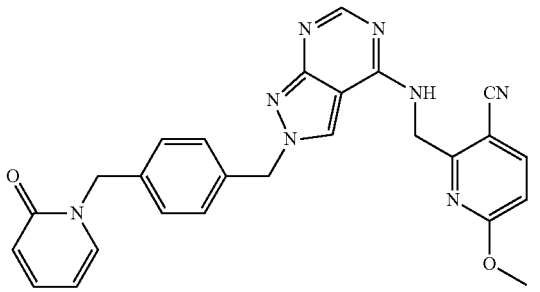 [SMILES: COc1ccc(C#N)c(CNc2ncnc3nn(Cc4ccc(Cn5ccccc5=O)cc4)cc23)n1]

6-methoxy-2-([[2-([4-[(2-oxo-1,2-dihydropyridin-1-yl)methyl]phenyl]methyl)-2H-pyrazolo[3,4-d]pyrimidin-4-yl]amino]methyl)pyridine-3-carbonitrile Into a 40-mL sealed tube, was placed a mixture of 2-(bromomethyl)-6-methoxypyridine-3-carbonitrile (102 mg, 0.45 mmol, 1.00 equiv)(Example 293), 1-[[4-([4-amino-2H-pyrazolo[3,4-d]pyrimidin-2-yl]methyl)phenyl]methyl]-1,2-dihydropyridin-2-one (150 mg, 0.45 mmol, 1.00 equiv) (Example 294), 4 Å MS (powder) (100 mg) and N,N-dimethylformamide (2.5 mL). The resulted solution was stirred for 2 h at 50° C. in an oil bath. The solids were filtered out. The crude product was purified by Prep-HPLC with the following conditions. Column: Waters XBridge RP18 19*150 mm 5 μm; mobile phase, CH$_3$CN/water (it contains 0.05% NH$_3$.H$_2$O) with a gradient of acetonitrile from 42% to 47% in 5 min; flow rate: 20 mL/min; detector UV wavelength: 254 nm. The product was concentrated under vacuum and lyophilized to afford 60.8 mg (28%) of 6-methoxy-2-([[2-([4-[(2-oxo-1,2-dihydropyridin-1-yl)methyl]phenyl]methyl)-2H-pyrazolo[3,4-d]pyrimidin-4-yl]amino]methyl)pyridine-3-carbonitrile as a yellow solid. $^1$H NMR (300 MHz, CD$_3$OD): 8.60-8.56 (m, 2H), 7.96 (d, J=8.7 Hz, 1H), 7.72-7.69 (m, 1H), 7.58-7.52 (m, 1H), 7.36-7.26 (m, 4H), 6.80 (d, J=8.4 Hz, 1H), 6.59 (d, J=9.0 Hz, 1H), 6.44-6.39 (m, 1H), 5.49 (s, 2H), 5.19 (s, 2H), 4.86 (s, 2H), 3.55 (s, 3H). MS (ESI) m/z 479 [M+H]$^+$

Example 296

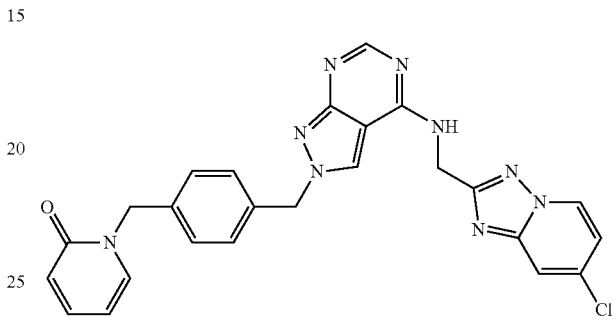

1-[[4-([4-[([7-chloro-[1,2,4]triazolo[1,5-a]pyridin-2-yl]methyl)amino]-2H-pyrazolo[3,4-d]pyrimidin-2-yl]methyl)phenyl]methyl]-1,2-dihydropyridin-2-one 1-[[4-([4-[([7-chloro-[1,2,4]triazolo[1,5-a]pyridin-2-yl]methyl)amino]-2H-pyrazolo[3,4-d]pyrimidin-2-yl]methyl)phenyl]methyl]-1,2-dihydropyridin-2-one was prepared in a similar manner as Example 291. $^1$H-NMR (300 MHz, CD$_3$OD): δ 8.78 (s, 1H), 8.72 (dd, J=7.2 Hz, 1.2 Hz, 1H), 8.56 (s, 1H), 7.80 (d, J=1.2 Hz, 1H), 7.73-7.69 (m, 1H), 7.57-7.51 (m, 1H), 7.35-7.25 (m, 5H), 6.58 (d, J=9.0 Hz, 1H), 6.43-6.38 (m, 1H), 5.82 (s, 2H), 5.54 (s, 2H), 5.17 (s, 2H). $^{19}$F NMR (300 MHz, CD$_3$OD): 77.11 ppm. MS (ESI) m/z 498 [M+H]$^+$.

Example 297

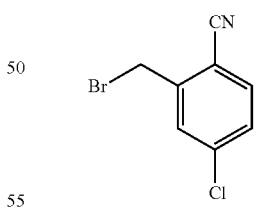

2-(bromomethyl)-4-chlorobenzonitrile

Into a 50-mL round-bottom flask, was placed a mixture of 4-chloro-2-methylbenzonitrile (1 g, 6.60 mmol, 1.00 equiv), CCl$_4$ (15 mL), NBS (1.29 g, 7.25 mmol, 1.10 equiv) and BPO (50 mg, 0.20 mmol, 0.03 equiv). The resulted solution was stirred for 16 h at 80° C. The reaction mixture was cooled to 25° C. Then it was washed with 3×15 mL of water. The organic phase was dried over anhydrous sodium sulfate and concentrated under vacuum. The residue was purified by a silica gel column and eluted with ethyl acetate/ hexane (1:50). This resulted in 0.45 g (30%) of 2-(bromomethyl)-4-chlorobenzonitrile as a light yellow solid. LC-MS (ESI) m/z: Calculated for $C_8H_5BrClN$: 228.9. found: 230 $[M+H]^+$.

Example 298

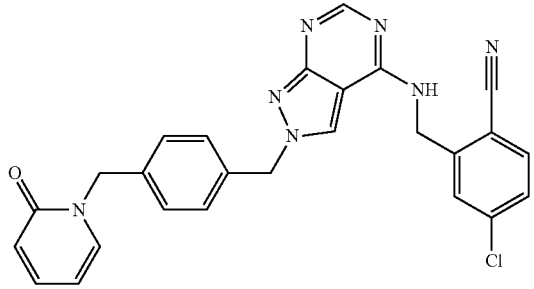 [SMILES: N#Cc1ccc(Cl)cc1CNc1ncnc2nn(Cc3ccc(Cn4ccccc4=O)cc3)cc12]

4-chloro-2-((2-(4-((2-oxopyridin-1(2H)-yl)methyl) benzyl)-2H-pyrazolo[3,4-d]pyrimidin-4-ylamino) methyl)benzonitrile 4-chloro-2-((2-(4-((2-oxopyridin-1(2H)-yl)methyl)benzyl)-2H-pyrazolo[3,4-d]pyrimidin-4-ylamino)methyl)benzonitrile was prepared in a similar manner as Example 295 using Example 297. $^1$H NMR (300 MHz, DMSO-$d_6$): δ 8.80 (m, 2H), 7.90 (d, J=8.4 Hz, 1H), 7.78-7.76 (m, 1H), 7.75 (s, 1H), 7.67-7.61 (m, 1H), 7.60-7.57 (m, 1H), 7.21 (s, 4H), 6.42 (d, J=9.0 Hz, 1H), 6.25 (t, J=6.1 Hz, 1H), 5.59 (s, 2H), 5.51 (s, 2H), 5.10 (s, 2H).

LC-MS (ESI) m/z: Calculated for $C_{24}H_{23}ClFN_7O$: 481. found: 482 $[M+H]^+$.

Example 299

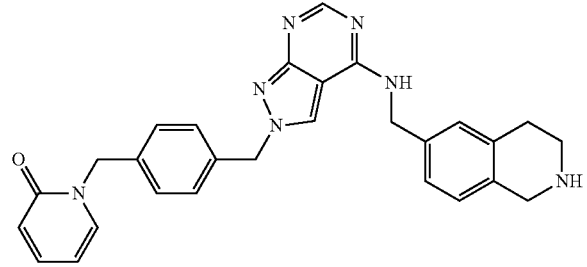 [SMILES: O=c1ccccn1Cc1ccc(Cn2cc3c(NCc4ccc5c(c4)CCNC5)ncnc3n2)cc1]

1-[[4-([4-[(1,2,3,4-tetrahydroisoquinolin-6-ylmethyl) amino]-2H-pyrazolo[3,4-d]pyrimidin-2-yl]methyl) phenyl]methyl]-1,2-dihydropyridin-2-one 1-[[4-([4-[(1,2,3,4-tetrahydroisoquinolin-6-ylmethyl) amino]-2H-pyrazolo[3,4-d]pyrimidin-2-yl]methyl)phenyl]methyl]-1,2-dihydropyridin-2-one was prepared in a similar manner to Example 215. $^1$H NMR (300 MHz, DMSO-$d_6$): δ 9.06 (br, 1H), 8.24 (s, 1H), 7.75 (dd, J=6.9 Hz, 1.5 Hz, 1H), 7.25-7.42 (m, 9H), 6.39 (d, J=9.0 Hz, 1H), 6.21 (t, J=6.6 Hz, 1H), 5.53 (s, 2H), 5.07 (s, 2H), 5.02 (s, 2H), 4.07 (br, 2H), 3.93 (s, 2H), 2.99 (br, 2H). MS (ESI) m/z 478 $[M+H]^+$ Example 300

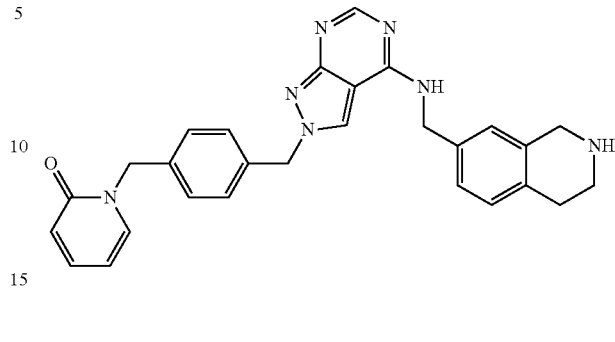

1-[[4-([4-[(1,2,3,4-tetrahydroisoquinolin-7-ylmethyl) amino]-2H-pyrazolo[3,4-d]pyrimidin-2-yl]methyl) phenyl]methyl]-1,2-dihydropyridin-2-one 1-[[4-([4-[(1,2,3,4-tetrahydroisoquinolin-7-ylmethyl) amino]-2H-pyrazolo[3,4-d]pyrimidin-2-yl]methyl)phenyl] methyl]-1,2-dihydropyridin-2-one was prepared in a similar manner to Example 215. $^1$H NMR (300 MHz, DMSO-$d_6$): δ 9.01 (br, 1H), 8.24 (s, 1H), 7.74 (dd, J=6.9 Hz, 1.8 Hz, 1H), 7.12-7.43 (m, 9H), 6.39 (d, J=9.3 Hz, 1H), 6.21 (t, J=6.6 Hz, 1H), 5.53 (s, 2H), 5.07 (s, 2H), 5.01 (s, 2H), 4.06 (br, 2H), 3.73 (s, 2H), 2.97 (br, 2H). MS (ESI) m/z 478 $[M+H]^+$ Example 301

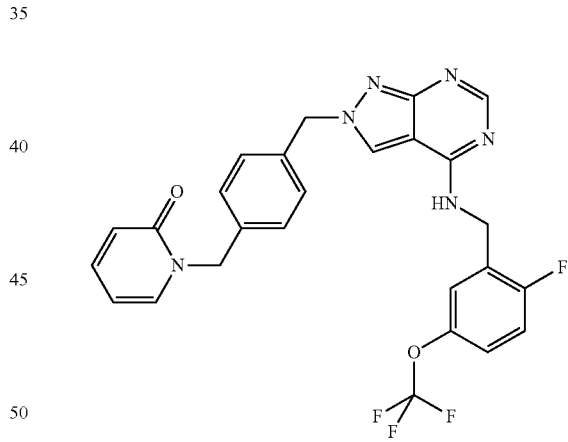

1-(4-((4-((2-fluoro-5-(trifluoromethoxy)benzyl) amino)-2H-pyrazolo[3,4-d]pyrimidin-2-yl)methyl) benzyl)pyridin-2(1H)-one 1-(4-((4-((2-fluoro-5-(trifluoromethoxy)benzyl)amino)-2H-pyrazolo[3,4-d]pyrimidin-2-yl)methyl)benzyl)pyridin-2 (1H)-one was prepared in a similar manner as Example 215. $^1$H NMR (400 MHz, DMSO-$d_6$) δ 8.66 (s, 1H), 8.35 (s, 1H), 8.19 (s, 1H), 7.74 (dd, J=7.0, 2.0 Hz, 1H), 7.40-7.17 (m, 8H), 6.45-6.32 (m, 1H), 6.20 (td, J=6.6, 1.4 Hz, 1H), 5.53 (s, 2H), 5.06 (s, 2H), 4.72 (d, J=5.6 Hz, 2H). MS $(M+H)^+$ found for $C_{26}H_{20}F_4N_6O_2$: 525.

Example 302

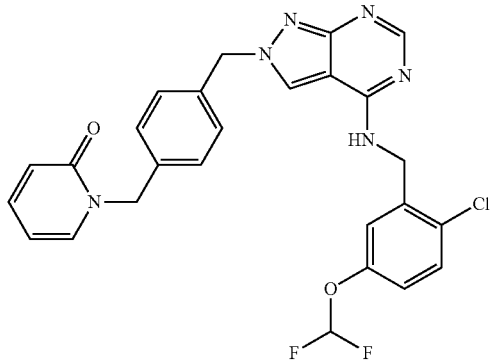 [SMILES: O=c1ccccn1Cc1ccc(Cn2cc3c(NCc4cc(OC(F)F)ccc4Cl)ncnc3n2)cc1]

1-(4-((4-((2-chloro-5-(difluoromethoxy)benzyl)
amino)-2H-pyrazolo[3,4-d]pyrimidin-2-yl)methyl)
benzyl)pyridin-2(1H)-one 1-(4-((4-((2-chloro-5-(difluoromethoxy)benzyl)amino)-2H-pyrazolo[3,4-d]pyrimidin-2-yl)methyl)benzyl)pyridin-2(1H)-one was prepared following the same synthetic path reported for Example 301 using 2-chloro-5-(difluoromethoxy)phenyl)methanamine instead of 6-chloro-2-fluoro-3-methoxyphenyl)methanamine. $^1$H NMR (400 MHz, DMSO-d$_6$) δ 8.64 (d, J=6.0 Hz, 1H), 8.38 (s, 1H), 8.18 (s, 1H), 7.74 (dd, J=6.7, 2.1 Hz, 1H), 7.52 (d, J=8.6 Hz, 1H), 7.44-7.22 (m, 5H), 7.20-7.05 (m, 3H), 6.47-6.31 (m, 1H), 6.20 (td, J=6.8, 1.3 Hz, 1H), 5.53 (s, 2H), 5.06 (s, 2H), 4.72 (d, J=5.6 Hz, 2H). MS (M+H)$^+$ found for C$_{26}$H$_{21}$ClF$_2$N$_6$O$_2$: 523.

Example 303

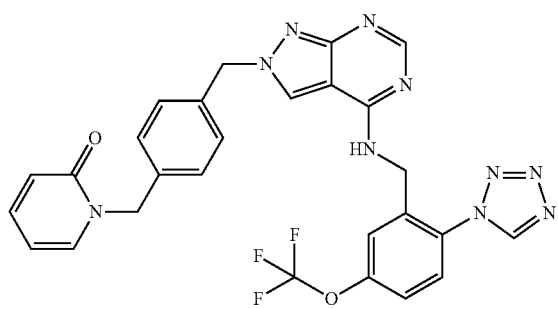 [SMILES: O=c1ccccn1Cc1ccc(Cn2cc3c(NCc4cc(OC(F)(F)F)ccc4-n4cnnn4)ncnc3n2)cc1]

1-(4-((4-((2-(1H-tetrazol-1-yl)-5-(trifluoromethoxy)
benzyl)amino)-2H-pyrazolo[3,4-d]pyrimidin-2-yl)
methyl)benzyl)pyridin-2(1H)-one 1-(4-((4-((2-(1H-tetrazol-1-yl)-5-(trifluoromethoxy)benzyl)amino)-2H-pyrazolo[3,4-d]pyrimidin-2-yl)methyl)benzyl)pyridin-2(1H)-one was prepared in am similar manner to Example 111. $^1$H NMR (400 MHz, DMSO-d$_6$) δ 9.89 (s, 1H), 8.62 (t, J=5.8 Hz, 1H), 8.30 (s, 1H), 8.07 (s, 1H), 7.79-7.70 (m, 2H), 7.56 (d, J=8.0 Hz, 2H), 7.39 (ddd, J=8.9, 6.6, 2.1 Hz, 1H), 7.33-7.23 (m, 4H), 6.42-6.34 (m, 1H), 6.20 (td, J=6.7, 1.4 Hz, 1H), 5.52 (s, 2H), 5.06 (s, 2H), 4.55 (d, J=5.5 Hz, 2H). MS (M+H)+ found for C$_{27}$H$_{21}$F$_3$N$_{10}$O$_2$: 575.1.

Example 304

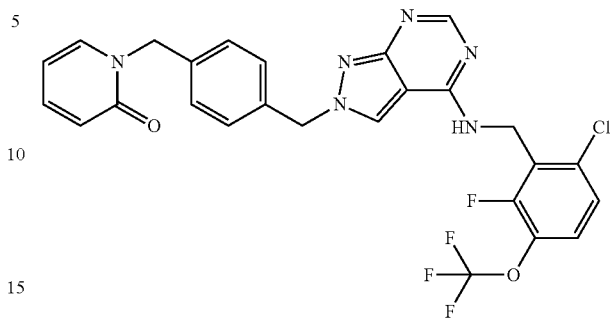

1-[(4-[[4-([[6-chloro-2-fluoro-3-(trifluoromethoxy)
phenyl]methyl]amino)-2H-pyrazolo[3,4-d]pyrimidin-2-yl]methyl]phenyl)methyl]-1,2-dihydropyridin-2-one 1-[(4-[[4-([[6-chloro-2-fluoro-3-(trifluoromethoxy)phenyl]methyl]amino)-2H-pyrazolo[3,4-d]pyrimidin-2-yl]methyl]phenyl)methyl]-1,2-dihydropyridin-2-one was prepared in a similar manner to Example 127. $^1$H NMR (300 MHz, DMSO-d$_6$): δ 8.43 (s, 1H), 8.29 (s, 1H), 8.25 (s, 1H), 7.75 (d, J=6.6 Hz, 1H), 7.64 (t, J=9.0 Hz, 1H), 7.51 (d, J=9.0 Hz, 1H), 7.43-7.38 (m, 1H), 7.33-7.26 (m, 4H), 6.41 (d, J=9.3 Hz, 1H), 6.22 (t, J=6.6 Hz, 1H), 5.52 (s, 2H), 5.08 (s, 2H), 4.81 (d, J=3.0 Hz, 1H). LC-MS (ESI) m/z: calculated for C$_{26}$H$_{13}$ClF$_4$N$_6$O$_2$: 558.12. found: 559 [M+H]$^+$.

Example 305

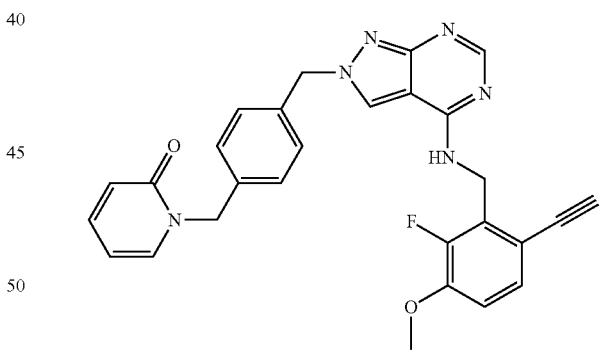

1-(4-((4-((6-ethynyl-2-fluoro-3-methoxybenzyl)
amino)-2H-pyrazolo[3,4-d]pyrimidin-2-yl)methyl)
benzyl)pyridin-2(1H)-one 1-(4-((4-((6-ethynyl-2-fluoro-3-methoxybenzyl)amino)-2H-pyrazolo[3,4-d]pyrimidin-2-yl)methyl)benzyl)pyridin-2(1H)-one was prepared in a similar manner as Example 215. $^1$H NMR (400 MHz, DMSO-d$_6$) δ 8.29-8.21 (m, 3H), 7.73 (dd, J=6.8, 2.1 Hz, 1H), 7.43-7.22 (m, 6H), 7.15 (t, J=8.6 Hz, 1H), 6.41-6.34 (m, 1H), 6.20 (td, J=6.6, 1.4 Hz, 1H), 5.48 (s, 2H), 5.05 (s, 2H), 4.79-4.72 (m, 2H), 4.21 (s, 1H), 3.85 (s, 3H). MS (M+H)+ found for C$_{28}$H$_{23}$FN$_6$O$_2$: 495.1.

Example 306

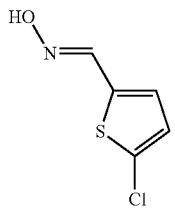

(E)-N-[(5-chlorothiophen-2-yl)methylidene]hydroxylamine

Into a 40-mL vial, was placed a mixture of 5-chlorothiophene-2-carbaldehyde (1.00 g, 6.82 mmol, 1.00 equiv), NH$_2$OH.HCl (1.43 g, 20.58 mmol, 3.00 equiv), Na$_2$CO$_3$ (1.09 g, 10.28 mmol, 1.50 equiv) and ethanol (10 mL). The resulted mixture was stirred for 2 hours at room temperature. After the starting material was consumed completely, the mixture was concentrated under vacuum. The residue was diluted with 50 mL of H$_2$O and extracted with 3×50 mL of ethyl acetate. The organic layers were washed with 1×80 mL of brine, dried over anhydrous sodium sulfate and concentrated under vacuum. The crude product was purified by silica gel column chromatography eluted with ethyl acetate/petroleum ether (1:10). This resulted in 640 mg (58%) of (E)-N-[(5-chlorothiophen-2-yl)methylidene]hydroxylamine as a light yellow solid. MS (ESI) m/z 162 [M+H]$^+$

Example 307

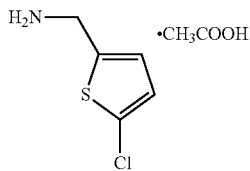

(5-chlorothiophen-2-yl)methanamine acetic acid salt

Into a 8-mL vial, was placed a mixture of (E)-N-[(5-chlorothiophen-2-yl)methylidene]hydroxylamine (100 mg, 0.62 mmol, 1.00 equiv), Zn (318 mg, 4.97 mmol, 8.00 equiv)(Example 306) and acetic acid (2.0 mL). The resulting mixture was stirred for 3 hours at 80° C. The solids were filtered and the filter cake was washed with 3×50 mL of acetonitrile. The filtrate was concentrated under vacuum. This resulted in 190 mg (crude) of (5-chlorothiophen-2-yl)methanamine (acetic acid salt) as a brown oil, which was used directly for next step without any purification. MS (ESI) m/z 148 [M+H]$^+$

Example 308

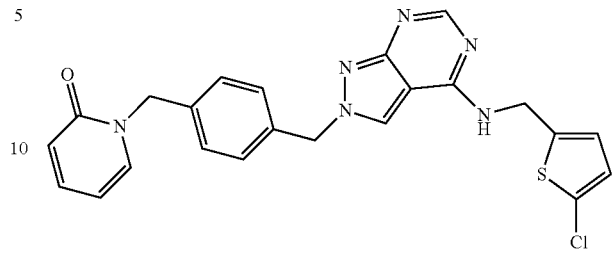

1-([4-[(4-[[(5-chlorothiophen-2-yl)methyl]amino]-2H-pyrazolo[3,4-d]pyrimidin-2-yl)methyl]phenyl]methyl)-1,2-dihydropyridin-2-one 1-([4-[(4-[[(5-chlorothiophen-2-yl)methyl]amino]-2H-pyrazolo[3,4-d]pyrimidin-2-yl)methyl]phenyl]methyl)-1,2-dihydropyridin-2-one was prepared in a similar manner as Example 215 using Example 307. $^1$H-NMR (300 MHz, DMSO): δ 8.80 (brs, 1H), 8.34 (s, 1H), 8.27 (s, 1H), 7.75 (d, J=6.9 Hz, 1H), 7.41 (t, J=7.2 Hz, 1H), 7.30 (s, 4H), 6.95 (s, 2H), 6.40 (d, J=9.3 Hz, 1H), 6.24-6.20 (m, 1H), 5.54 (s, 2H), 5.08 (s, 2H), 4.77 (d, J=5.7 Hz, 2H). MS (ESI) m/z 463 [M+H]$^+$.

Example 309

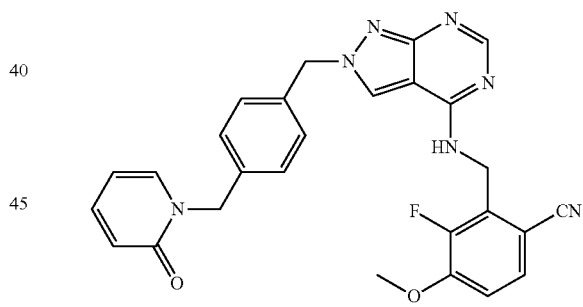

3-fluoro-4-methoxy-2-((2-(4-((2-oxopyridin-1(2H)-yl)methyl)benzyl)-2H-pyrazolo[3,4-d]pyrimidin-4-ylamino)methyl)benzonitrile 3-fluoro-4-methoxy-2-((2-(4-((2-oxopyridin-1(2H)-yl)methyl)benzyl)-2H-pyrazolo[3,4-d]pyrimidin-4-ylamino)methyl)benzonitrile was prepared in a similar manner to Example 295. $^1$H NMR (300 MHz, DMSO-d$_6$): δ 10.05 (s, 1H), 9.86 (s, 1H), 8.93 (s, 1H), 8.75 (d, J=3.3 Hz, 1H), 7.83-7.81 (m, 1H), 7.71-7.67 (m, 1H), 7.47-7.41 (m, 1H), 7.33-7.21 (m, 5H), 6.43 (d, J=8.7 Hz, 1H), 6.29-6.24 (m, 1H), 5.65 (s, 2H), 5.52 (s, 2H), 5.07 (s, 2H), 3.91 (s, 3H). LC-MS (ESI) m/z: calculated for C$_{27}$H$_{22}$FN$_7$O$_2$: 495.18. found: 496 [M+H]+.

Example 310

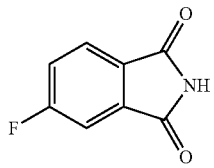 [SMILES: O=C1NC(=O)c2cc(F)ccc21]

5-fluoro-2,3-dihydro-1H-isoindole-1,3-dione

Into a 500-mL round-bottom flask, was placed a mixture of 5-fluoro-1,3-dihydro-2-benzofuran-1,3-dione (20.0 g, 120.41 mmol, 1.00 equiv), urea (14.4 g, 239.78 mmol, 2.00 equiv) and xylene (200 mL). The resulted solution was heated to reflux overnight. The solids were collected by filtration, washed with water and dried under vacuum. This resulted in 19.0 g (96%) of 5-fluoro-2,3-dihydro-1H-isoindole-1,3-dione as off-white solid. GC-MS (ESI) m/z: calculated for $C_{12}H_8FNO_2$: 165. found: 166 $[M+H]^+$.

Example 311

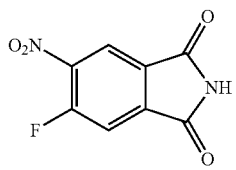

5-fluoro-6-nitro-2,3-dihydro-1H-isoindole-1,3-dione

Into an 100-mL round-bottom flask, was placed 20% oleum (50 mL). This was followed by the addition of fuming $HNO_3$ (5 mL) dropwise with stirring at 0° C., to which was added 5-fluoro-2,3-dihydro-1H-isoindole-1,3-dione (5.00 g, 30.28 mmol, 1.00 equiv)(Example 310) in several batches.

The resulting solution was stirred for 30 min at 80° C. The reaction was then quenched by the addition of 500 mL of icy water. The solids were collected by filtration, washed with water and dried under vacuum. This resulted in 2.30 g (36%) of 5-fluoro-6-nitro-2,3-dihydro-1H-isoindole-1,3-dione as off-white solid.

GC-MS (ESI) m/z: calculated for $C_8H_3FN_2O_4$: 210. found: 211 $[M+H]^+$. Rt: 8.18 min.

Example 312

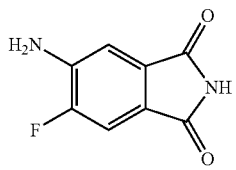 [SMILES: O=C1NC(=O)c2cc([N+](=O)[O-])c(F)cc21]

5-amino-6-fluoro-2,3-dihydro-1H-isoindole-1,3-dione
Into a 500-mL round-bottom flask, was placed a mixture of 5-fluoro-6-nitro-2,3-dihydro-1H-isoindole-1,3-dione (9.00 g, 42.83 mmol, 1.00 equiv)(Example 311), methanol (300 mL) and 10% palladium on carbon (900 mg) under nitrogen atmosphere. The mixture was purged with hydrogen for 3 times and stirred overnight at room temperature under hydrogen atmosphere. The mixture was filtered. The filter cake was washed with THF for 3 times. The combined filtrates were concentrated under vacuum. This resulted in 5.10 g (66%) of 5-amino-6-fluoro-2,3-dihydro-1H-isoindole-1,3-dione as dark green solids.

GC-MS (ESI) m/z: calculated for $C_8H_5FN_2O_2$: 180. found: 181 $[M]^+$.

Example 313

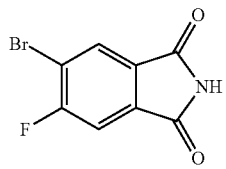 [SMILES: O=C1NC(=O)c2cc(Br)c(F)cc21]

5-bromo-6-fluoro-2,3-dihydro-1H-isoindole-1,3-dione

Into an 100-mL round-bottom flask, was placed a mixture of $CuBr_2$ (2.50 g, 1.00 equiv), 5-amino-6-fluoro-2,3-dihydro-1H-isoindole-1,3-dione (2.00 g, 11.10 mmol, 1.00 equiv)(Example 312) and $CH_3CN$ (20 mL) with stirring, to which was added $ONO^tBu$ (1.40 g, 1.20 equiv) dropwise at room temperature. The resulted solution was stirred for 3 h at 45° C. The mixture was then concentrated under vacuum. The residue was purified by silica gel column chromatography eluted with tetrahydrofuran/PE (1:5). This resulted in 1.80 g (66%) of 5-bromo-6-fluoro-2,3-dihydro-1H-isoindole-1,3-dione as off-white solid.

GC-MS (ESI) m/z: calculated for $C_{16}H_8BrF_2N_3O_4$: 243. found: 244 $[M+H]^+$.

Example 314

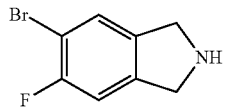

5-bromo-6-fluoroisoindoline

Into a 250-mL round-bottom flask, was placed a solution of 5-amino-6-fluoro-2,3-dihydro-1H-isoindole-1,3-dione (1.90 g, 10.55 mmol, 1.00 equiv)(Example 313) in tetrahydrofuran (80 mL) with stirring at −10° C., to which was added $NaBH_4$ (2.90 g, 76.66 mmol, 10.00 equiv). This was followed by the addition of $BF_3.Et_2O$ (13.00 g, 91.55 mmol, 11.00 equiv) dropwise at −10° C. The resulted mixture was stirred for 16 h at 70° C. The reaction was then quenched by the addition of icy water. The volatiles were removed under vacuum. The pH value of the solution was adjusted to 0 with concentrated hydrogen chloride aqueous solution. The resulted solution was extracted with of ethyl acetate to remove impurities. The aqueous phase was used to next step directly.

LC-MS (ESI) m/z: calculated for $C_8H_7BrFN$: 215. found: 216 [M+H]$^+$.

Example 315

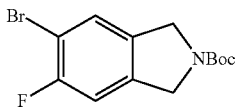

tert-butyl 5-bromo-6-fluoro-2,3-dihydro-1H-isoindole-2-carboxylate

Into an 100-mL round-bottom flask, was placed a solution of 5-bromo-6-fluoro-2,3-dihydro-1H-isoindole hydrochloride (Example 314) in water and ethanol (20 mL). The pH value of the solution was adjusted to 14 with 10% sodium hydroxide aqueous solution, to which was added (Boc)$_2$O (1.90 g, 8.71 mmol). The resulted solution was stirred for 1 h at room temperature. The volatiles were removed under vacuum. The mixture was extracted with 3×30 mL of ethyl acetate. The organic layers were combined and concentrated under vacuum. The residue was purified by silica gel column chromatography eluted with THF/PE (1:10). This resulted in 1.20 g (41%) of tert-butyl 5-bromo-6-fluoro-2,3-dihydro-1H-isoindole-2-carboxylate as off-white solid.

LC-MS (ESI) m/z: calculated for $C_{13}H_{18}BrFNO_2$: 315 found: 301 [M+H-56+41]$^+$.

Example 316

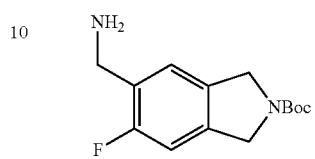

tert-butyl 5-cyano-6-fluoro-2,3-dihydro-1H-isoindole-2-carboxylate

Into a 40-mL vial purged and maintained with an inert atmosphere of nitrogen, was placed a mixture of tert-butyl 5-bromo-6-fluoro-2,3-dihydro-1H-isoindole-2-carboxylate (1.20 g, 3.80 mmol, 1.00 equiv)(Example 315), Pd(PPh$_3$)$_4$ (439 mg, 0.38 mmol, 0.10 equiv), Zn(CN)$_2$ (667 mg, 1.50 equiv) and N,N-dimethylformamide (10 mL). The resulting solution was stirred for 3 h at 110° C. The mixture was concentrated under vacuum. The crude was purified by silica gel column chromatography eluted with THF/PE (1:10). This resulted in 500 mg (50%) of tert-butyl 5-cyano-6-fluoro-2,3-dihydro-1H-isoindole-2-carboxylate as off-white solid. LC-MS (ESI) m/z: calculated for $C_{14}H_{15}FN_2O_2$: 262. found: 248 [M+H-56+41]$^+$.

Example 317

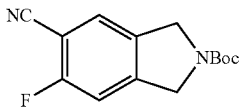

5-(aminomethyl)-6-fluoro-2,3-dihydro-1H-isoindole-2-carboxylate

Into a 10-mL round-bottom flask, was placed a mixture of tert-butyl 5-cyano-6-fluoro-2,3-dihydro-1H-isoindole-2-carboxylate (130 mg, 0.50 mmol, 1.00 equiv)(Example 216), methanol (2 mL), Raney Ni (20 mg) and concentrated ammonia (0.2 mL) under nitrogen atmosphere. The resulted mixture was purged with hydrogen for 3 times and stirred under hydrogen atmosphere for 2 h at room temperature. The solids were filtered out. The filtrate was concentrated under vacuum. This resulted in 130 mg (98.5%) of tert-butyl 5-(aminomethyl)-6-fluoro-2,3-dihydro-1H-isoindole-2-carboxylate as off-white crude solid. LC-MS (ESI) m/z: calculated for $C_{14}H_{19}FN_2O_2$: 266. found: 267 [M+H]$^+$.

Example 318

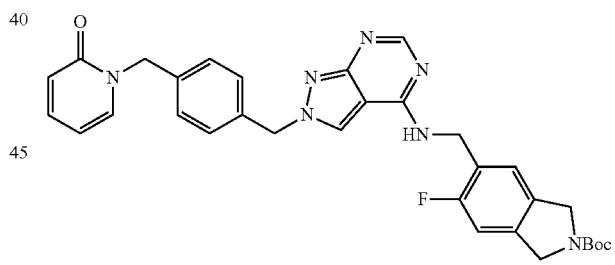

tert-butyl 5-fluoro-6-((2-(4-((2-oxopyridin-1(2H)-yl)methyl)benzyl)-2H-pyrazolo[3,4-d]pyrimidin-4-ylamino)methyl)isoindoline-2-carboxylate Into a 10-mL round-bottom flask, was placed a solution of tert-butyl 5-(aminomethyl)-6-fluoro-2,3-dihydro-1H-isoindole-2-carboxylate (100 mg, 0.38 mmol, 1.00 equiv)(Example 317), DMA (1 mL), DIEA (74 mg, 0.57 mmol, 1.50 equiv) and 1-[4-(4-chloro-2H-pyrazolo[3,4-d]pyrimidin-2-ylmethyl)phenyl]methyl-1,2-dihydropyridin-2-one (132 mg, 0.375 mmol, 1.00 equiv)(Example 209). The resulting solution was stirred for 2 h at 80° C. The solution was used to the next step directly. LC-MS (ESI) m/z: calculated for $C_{32}H_{32}FN_7O_3$: 581 found: 582 [M+H]$^+$. Rt: 1.244 min.

Example 319

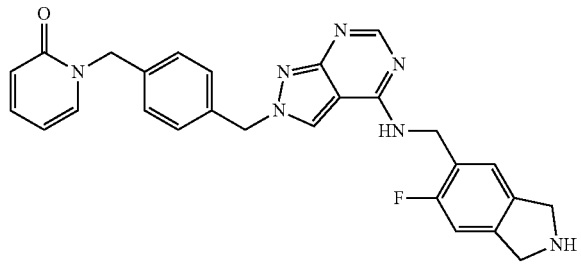 [SMILES: O=c1ccccn1Cc1ccc(Cn2cc3c(NCc4cc5c(cc4F)CNC5)ncnc3n2)cc1]

1-([4-[(4-[[(6-fluoro-2,3-dihydro-1H-isoindol-5-yl)
methyl]amino]-2H-pyrazolo[3,4-d]pyrimidin-2-yl)
methyl]phenyl]methyl)-1,2-dihydropyridin-2-one Into a 10-mL round-bottom flask, was placed a solution of tert-butyl 5-fluoro-6-((2-(4-((2-oxopyridin-1(2H)-yl)methyl)benzyl)-2H-pyrazolo[3,4-d]pyrimidin-4-ylamino)methyl)isoindoline-2-carboxylate in DMA (Example 318), to which was added concentrated hydrochloride aqueous solution (37%, 1 mL). The resulted solution was stirred for 2 h at room temperature. The mixture was purified by Prep-HPLC with the following conditions. Column: Waters XBridge RP18 19*150 mm, 5 μm; mobile phase: water (it is a buffer of 0.05% ammonia and 10 mM $NH_4HCO_3$) and acetonitrile with a gradient of 10% to 60% acetonitrile in 8 min; flow rate: 20 mL/min; detector UV wavelength: 254 nm. This resulted in 14.7 mg of 1-([4-[(4-[[(6-fluoro-2,3-dihydro-1H-isoindol-5-yl)methyl]amino]-2H-pyrazolo[3,4-d]pyrimidin-2-yl)methyl]phenyl]methyl)-1,2-dihydropyridin-2-one. $^1$H NMR (300 MHz, DMSO-$d_6$): δ 8.59 (br, 1H), 8.36 (s, 1H), 8.20 (s, 1H), 7.76 (dd, J=6.6 Hz, 2.1 Hz, 1H), 7.21-7.44 (m, 6H), 7.10 (d, J=10.2 Hz, 1H), 6.40 (d, J=9.0 Hz, 1H), 6.22-6.25 (m, 1H), 5.23 (s, 2H), 5.08 (s, 2H), 4.68 (d, J=6.0 Hz, 2H), 4.03 (s, 2H), 3.96 (s, 2H). LC-MS (ESI) m/z: calculated for $C_{28}H_{24}FN_7O_2$: 481. found: 482 [M+H]$^+$.

Example 320

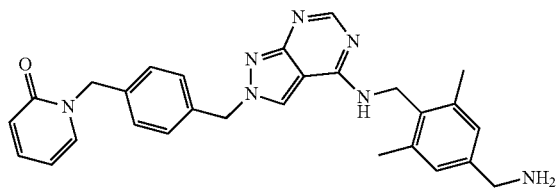 [SMILES: Cc1cc(CN)cc(C)c1CNc1ncnc2nn(Cc3ccc(Cn4ccccc4=O)cc3)cc12]

1-[(4-[[4-([[4-(aminomethyl)-2,6-dimethylphenyl]
methyl]amino)-2H-pyrazolo[3,4-d]pyrimidin-2-yl]
methyl]phenyl)methyl]-1,2-dihydropyridin-2-one 1-[(4-[[4-([[4-(aminomethyl)-2,6-dimethylphenyl]methyl]amino)-2H-pyrazolo[3,4-d]pyrimidin-2-yl]methyl]phenyl)methyl]-1,2-dihydropyridin-2-one was synthesized in a similar manner to Example 173. $^1$H NMR (300 MHz, DMSO): ppm δ 8.31 (s, 1H), 8.26 (s, 1H), 8.04 (br, 1H), 7.75 (dd, J=6.6 Hz, 1.8 Hz, 1H), 7.43-7.37 (m, 1H), 7.32-7.26 (m, 4H), 7.01-6.94 (m, 2H), 6.39 (d, J=9.3 Hz, 1H), 6.21 (td, J=6.6 Hz, 1.2 Hz, 1H), 5.48 (s, 2H), 5.07 (s, 2H), 4.06 (d, J=4.2 Hz, 2H), 3.63 (s, 2H), 2.30 (s, 6H). MS (ESI) m/z 480 [M+H]$^+$.

Example 321

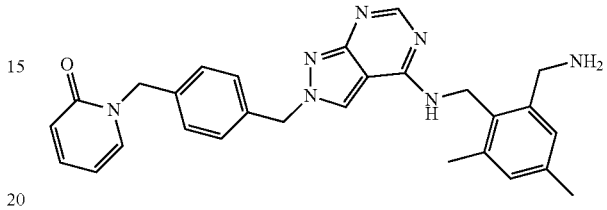

1-[(4-[[4-([[2-(aminomethyl)-4,6-dimethylphenyl]
methyl]amino)-2H-pyrazolo[3,4-d]pyrimidin-2-yl]
methyl]phenyl)methyl]-1,2-dihydropyridin-2-one 1-[(4-[[4-([[2-(aminomethyl)-4,6-dimethylphenyl]methyl]amino)-2H-pyrazolo[3,4-d]pyrimidin-2-yl]methyl]phenyl)methyl]-1,2-dihydropyridin-2-one was prepared in a similar manner to Example 174. $^1$H NMR (300 MHz, DMSO-$d_6$): δ 8.34-8.26 (m, 3H), 7.75 (dd, J=6.9 Hz, 1.8 Hz, 1H), 7.43-7.37 (m, 1H), 7.32-7.26 (m, 4H), 7.08 (s, 1H), 6.93 (s, 1H), 6.39 (d, J=8.7 Hz, 1H), 6.22 (t, J=6.6 Hz, 1H), 5.48 (s, 2H), 5.07 (s, 2H), 4.66 (s, 2H), 3.76 (s, 2H), 2.29 (s, 3H), 2.26 (s, 3H). MS (ESI) m/z 480 [M+H]$^+$.

Example 322

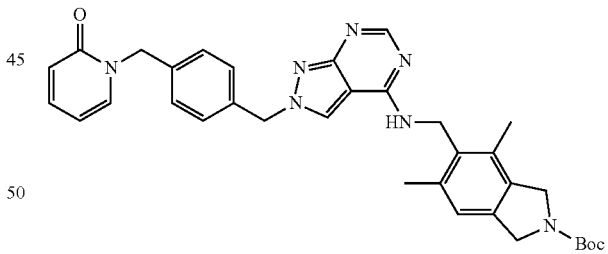

tert-butyl 4,6-dimethyl-5-([[2-([4-[(2-oxo-1,2-dihydropyridin-1-yl)methyl]phenyl]methyl)-2H-pyrazolo[3,4-d]pyrimidin-4-yl]amino]methyl)-2,3-dihydro-1H-isoindole-2-carboxylate tert-butyl 4,6-dimethyl-5-([[2-([4-[(2-oxo-1,2-dihydropyridin-1-yl)methyl]phenyl]methyl)-2H-pyrazolo[3,4-d]pyrimidin-4-yl]amino]methyl)-2,3-dihydro-1H-isoindole-2-carboxylate was prepared in a similar manner as Example 318. LC-MS (ESI) m/z: calculated for $C_{34}H_{37}N_7O_3$: 591.3. found: 592[M+H]$^+$.

Example 323

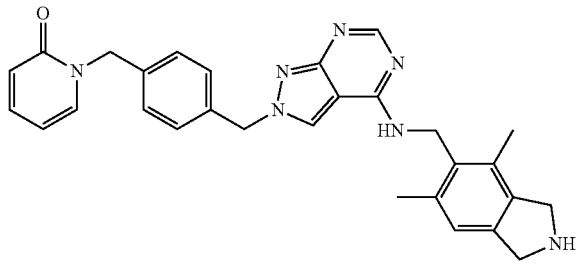 [SMILES: Cc1cc2c(c(C)c1CNc1ncnc3nn(Cc4ccc(Cn5ccccc5=O)cc4)cc13)CNC2]

1-([4-[(4-[[(4,6-dimethyl-2,3-dihydro-1H-isoindol-5-yl)methyl]amino]-2H-pyrazolo[3,4-d]pyrimidin-2-yl)methyl]phenyl]methyl)-1,2-dihydropyridin-2-one 1-([4-[(4-[[(4,6-dimethyl-2,3-dihydro-1H-isoindol-5-yl)methyl]amino]-2H-pyrazolo[3,4-d]pyrimidin-2-yl)methyl]phenyl]methyl)-1,2-dihydropyridin-2-one was prepared in a similar manner as Example 319. $^1$H NMR (300 MHz, DMSO-$d_6$): δ 8.31 (s, 1H), 8.27 (s, 1H), 8.02 (s, 1H), 7.75 (d, J=5.4 Hz, 1H), 7.40 (t, J=7.2 Hz, 1H), 7.29-7.26 (m, 4H), 7.00 (s, 1H), 6.39 (d, J=9.0 Hz, 1H), 6.22 (t, J=6.6 Hz, 1H), 5.48 (s, 2H), 5.07 (s, 2H), 4.63-4.53 (m, 3H), 4.08-4.05 (m, 3H), 2.30 (s, 3H), 2.18 (s, 3H).

Example 329

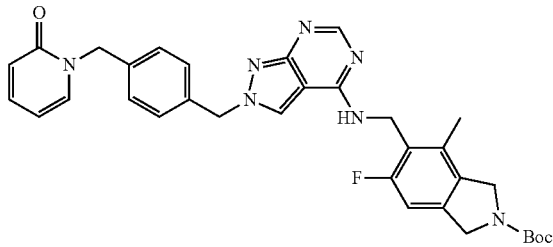

tert-butyl 6-fluoro-4-methyl-5-([[2-([4-[(2-oxo-1,2-dihydropyridin-1-yl)methyl]phenyl]methyl)-2H-pyrazolo[3,4-d]pyrimidin-4-yl]amino]methyl)-2,3-dihydro-1H-isoindole-2-carboxylate Into a 50-mL round-bottom flask, was placed a solution of tert-butyl 5-(aminomethyl)-6-fluoro-4-methyl-2,3-dihydro-1H-isoindole-2-carboxylate (200 mg, 0.71 mmol, 1.00 equiv)(Example 328) in N,N-dimethylformamide (5 mL), were added 1-[[4-([4-chloro-2H-pyrazolo[3,4-d]pyrimidin-2-yl]methyl)phenyl]methyl]-1,2-dihydro pyridin-2-one (251 mg, 0.71 mmol, 1.00 equiv) (Example 209) and DIEA (184 mg, 1.42 mmol, 2.00 equiv). The resulted solution was stirred for 4 h at 60° C. The crude product was diluted with 10 mL of H$_2$O and extracted with 3×20 mL of ethyl acetate. The combined organic layers were dried over anhydrous sodium sulfate and concentrated under vacuum. The residue was purified by silica gel column eluted with ethyl acetate/petroleum ether (1:1). This resulted in 220 mg (52%) of tert-butyl 6-fluoro-4-methyl-5-([[2-([4-[(2-oxo-1,2-dihydropyridin-1-yl)methyl]phenyl]methyl)-2H-pyrazolo[3,4-d]pyrimidin-4-yl]amino]methyl)-2,3-dihydro-1H-isoindole-2-carboxylate as a yellow solid. LC-MS (ESI) m/z: calculated for C33H34FN7O3: 595.27. found: 596 [M+H]$^+$.

Example 330

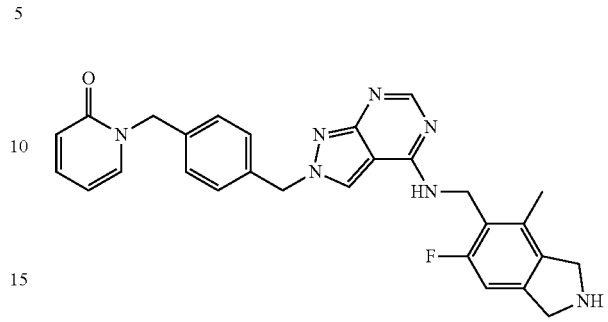

1-([4-[(4-[[(6-fluoro-4-methyl-2,3-dihydro-1H-isoindol-5-yl)methyl]amino]-2H-pyrazolo[3,4-d]pyrimidin-2-yl)methyl]phenyl]methyl)-1,2-dihydropyridin-2-one Into a 50-mL round-bottom flask, was placed a solution of tert-butyl 6-fluoro-4-methyl-5-([[2-([4-[(2-oxo-1,2-dihydropyridin-1-yl)methyl]phenyl]methyl)-2H-pyrazolo[3,4-d]pyrimidin-4-yl]amino]methyl)-2,3-dihydro-1H-isoindole-2-carboxylate (200 mg, 0.34 mmol, 1.00 equiv) (Example 329) in dioxane (3 mL), to which was added dioxane (3 mL) which was freshly saturated with hydrochloride (gas). The resulted solution was stirred for 1 h at room temperature. After concentration, the crude product was purified by Prep-HPLC with the following conditions. Column: Column: X Bridge C18 19*150 mm, 5 μm; mobile phase: CH$_3$CN and H$_2$O (it is a buffer of 10 mM NH$_4$HCO$_3$+0.05% ammonia) with a gradient of 28% to 40% acetonitrile in 8 min; flow rate: 20 mL/min; detector UV wavelength: 254 nm. This resulted in 91.6 mg (55%) of 1-([4-[(4-[[(6-fluoro-4-methyl-2,3-dihydro-1H-isoindol-5-yl)methyl]amino]-2H-pyrazolo[3,4-d]pyrimidin-2-yl)methyl]phenyl]methyl)-1,2-dihydropyridin-2-one as a white solid. $^1$H NMR (300 MHz, CD$_3$OD-$d_4$ ppm): δ 8.33 (br, 1H), 8.24 (s, 1H), 7.68 (d, J=5.1 Hz, 1H), 7.52 (t, J=6.9 Hz, 1H), 7.31 (s, 4H), 6.95 (d, J=9.3 Hz, 1H), 6.56 (d, J=9.3 Hz, 1H), 6.38 (t, J=6.9 Hz, 1H), 5.50 (s, 2H), 5.18 (s, 2H), 4.79 (s, 2H), 4.55-4.05 (m, 4H), 2.31 (s, 3H). LC-MS (ESI) m/z: calculated for C$_{28}$H$_{26}$FN$_7$O: 495.22. found: 496 [M+H]$^+$.

Example 331

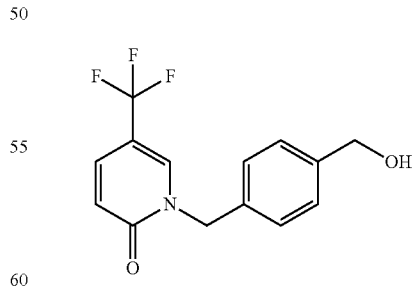

1-(4-(hydroxymethyl)benzyl)-5-(trifluoromethyl)pyridin-2(1H)-one

[4-(chloromethyl)phenyl]methanol (0.50 g; 3.19 mmol; 1.00 eq.) and 5-(trifluoromethyl)-2-pyridinol (0.57 g; 3.51 mmol; 1.10 eq.) were suspended in acetonitrile (9 ml). Potassium carbonate (1.32 g; 9.58 mmol; 3.00 eq.) was added and the reaction was stirred in a heat block at 40° C. After 16 h, the mixture was filtered, evaporated and purified by silica gel chromatography (ethyl acetate/DCM gradient) to give 1-(4-(hydroxymethyl)benzyl)-5-(trifluoromethyl) pyridin-2(1H)-one (0.82 g) as a yellow solid.

MS (M+H)$^+$ found for $C_{14}H_{12}F_3NO_2$: 284.1.

Example 332, 333

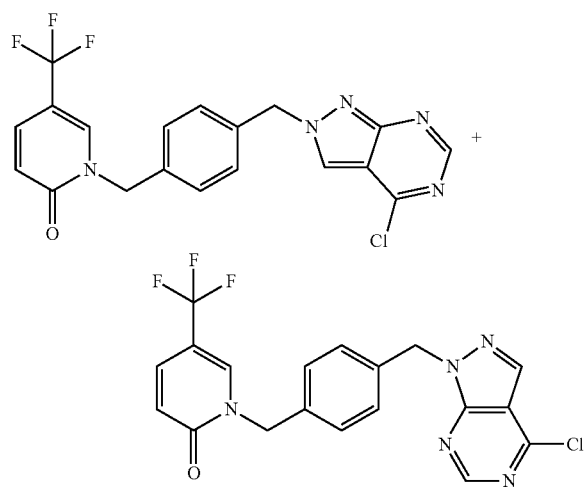

1-(4-((4-chloro-2H-pyrazolo[3,4-d]pyrimidin-2-yl) methyl)benzyl)-5-(trifluoromethyl)pyridin-2(1H)-one 1-{[4-(hydroxymethyl)phenyl]methyl}-5-(trifluoromethyl)-1,2-dihydropyridin-2-one (201.59 mg; 0.71 mmol; 1.10 eq.)(Example 331) and 4-chloro-1H-pyrazolo[3,4-d]pyrimidine (100.00 mg; 0.65 mmol; 1.00 eq.) were suspended in DCM (12 ml) and cooled in an salt/ice bath. Triphenylphosphine substituted polymer resin (322 mg, 3 mmol/g) was added followed by diisopropyl (E)-1,2-diazenedicarboxylate (0.32 ml; 1.62 mmol; 2.50 eq.) dropwise slowly. The mixture was stirred to 25° C. over 12 h and then more triphenylphosphine substituted polymer resin (100 mg, 3 mmol/g) was added followed by more diisopropyl (E)-1, 2-diazenedicarboxylate (0.1 ml; 0.51 mmol; 0.78 eq.) After 5 h, the reaction was filtered, evaporated and purified by silica gel chromatography (ethyl acetate/DCM gradient) to give 1-(4-((4-chloro-2H-pyrazolo[3,4-d]pyrimidin-2-yl) methyl)benzyl)-5-(trifluoromethyl)pyridin-2(1H)-one (59 mg) as a white solid. $^1$H NMR (400 MHz, CDCl$_3$) δ 8.85 (s, 1H), 8.07 (s, 1H), 7.66 (dd, J=2.9, 0.8 Hz, 1H), 7.45 (dd, J=9.6, 2.7 Hz, 1H), 7.43-7.33 (m, 4H), 6.67 (dd, J=9.5, 0.8 Hz, 1H), 5.62 (s, 2H), 5.15 (s, 2H). MS (M+H)$^+$ found for $C_{13}H_{13}ClF_3N_3O$: 420.1.

Example 334

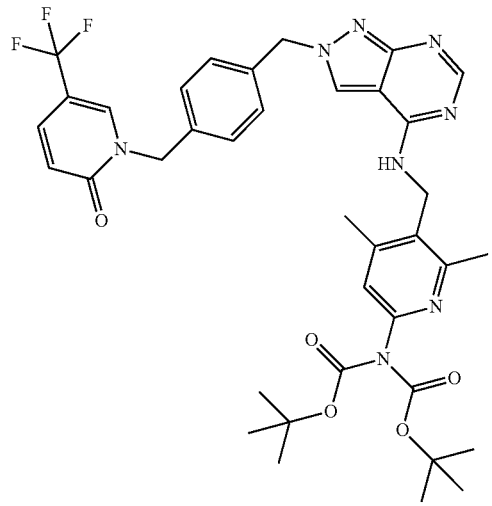 [SMILES: Cc1cc(N(C(=O)OC(C)(C)C)C(=O)OC(C)(C)C)nc(C)c1CNc1ncnc2nn(Cc3ccc(Cn4cc(C(F)(F)F)ccc4=O)cc3)cc12]

tert-butyl N-[(tert-butoxy)carbonyl]-N-{4,6-dimethyl-5-[({2-[(4-{[2-oxo-5-(trifluoromethyl)-1,2-dihydropyridin-1-yl]methyl}phenyl)methyl]-2H-pyrazolo[3,4-d]pyrimidin-4-yl}amino)methyl] pyridin-2-yl}carbamate 1-{[4-({4-chloro-2H-pyrazolo[3,4-d]pyrimidin-2-yl}methyl)phenyl]methyl}-5-(trifluoromethyl)-1,2-dihydropyridin-2-one (57.00 mg; 0.14 mmol; 1.00 eq.)(Example 332) was suspended in 1-butanol (3 ml). Tert-butyl N-[5-(aminomethyl)-4,6-dimethylpyridin-2-yl]-N-[(tert-butoxy) carbonyl]carbamate (71.58 mg; 0.20 mmol; 1.50 eq.)(Example 4, Step 2) was added and the reaction was heated in a microwave reactor to 110° C. for 60 m. The solvent was evaporated under vacuum and the resulting residue was used directly in the next step. MS (M+H)$^+$ found for $C_{37}H_{41}F_3N_8O_3$: 735.2.

Example 335

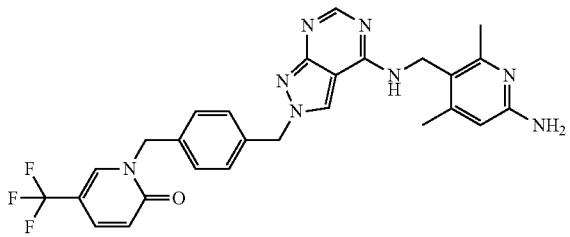 [SMILES: Cc1cc(N)nc(C)c1CNc1ncnc2nn(Cc3ccc(Cn4cc(C(F)(F)F)ccc4=O)cc3)cc12]

1-(4-((4-(((6-amino-2,4-dimethylpyridin-3-yl) methyl)amino)-2H-pyrazolo[3,4-d]pyrimidin-2-yl) methyl)benzyl)-5-(trifluoromethyl)pyridin-2(1H)-one Tert-butyl N-[(tert-butoxy)carbonyl]-N-{4,6-dimethyl-5-[({2-[(4-{[2-oxo-5-(trifluoromethyl)-1,2-dihydropyridin-1-yl]methyl}phenyl)methyl]-2H-pyrazolo[3,4-d]pyrimidin-4-yl}amino)methyl]pyridin-2-yl}carbamate (99.00 mg; 0.13 mmol; 1.00 eq.)(Example 335) was dissolved in DCM (1.5 ml) and cooled in an ice bath. Hydrochloric acid (3.37 ml; 4.00 mol/l; 13.47 mmol; 100.00 eq.; 4M dioxane soln.) was added slowly. The reaction was stirred at 25° C. for 4 h then evaporated and purified by reverse phase chromatography (acetonitrile gradient with 0.1% aqueous formic acid, Waters XSelect CSH column) to give 1-(4-((4-(((6-amino-2,4-dimethylpyridin-3-yl)methyl)amino)-2H-pyrazolo[3,4-d]pyrimidin-2-yl)methyl)benzyl)-5-(trifluoromethyl)pyridin-2(1H)-one (46 mg) as a white solid. $^1$H NMR (400 MHz, CD$_3$OD) δ 8.65 (d, J=9.1 Hz, 2H), 8.30 (s, 1H), 7.67 (dd, J=9.6, 2.7 Hz, 1H), 7.39 (q, J=8.0 Hz, 5H), 6.74 (s, 1H), 6.64 (d, J=9.6 Hz, 1H), 5.60 (s, 2H), 5.22 (s, 2H), 4.89 (s, 2H), 2.61 (s, 3H), 2.46 (s, 3H). MS (M+H)$^+$ found for C$_{27}$H$_{23}$F$_3$N$_8$O: 535.2.

Example 336

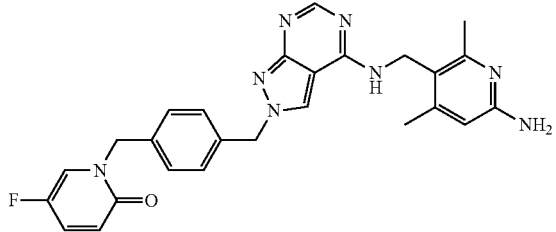 [SMILES: Cc1cc(N)nc(C)c1CNc1ncnc2nn(Cc3ccc(Cn4cc(F)ccc4=O)cc3)cc12]

1-(4-((4-(((6-amino-2,4-dimethylpyridin-3-yl)methyl)amino)-2H-pyrazolo[3,4-d]pyrimidin-2-yl)methyl)benzyl)-5-fluoropyridin-2(1H)-one 1-(4-((4-(((6-amino-2,4-dimethylpyridin-3-yl)methyl)amino)-2H-pyrazolo[3,4-d]pyrimidin-2-yl)methyl)benzyl)-5-fluoropyridin-2(1H)-one was prepared as in Example 335 except substituting 5-fluoropyridin-2-ol for 5-(trifluoromethyl)-2-pyridinol gave 1-(4-((4-(((6-amino-2,4-dimethylpyridin-3-yl)methyl)amino)-2H-pyrazolo[3,4-d]pyrimidin-2-yl)methyl)benzyl)-5-fluoropyridin-2(1H)-one as a white solid.
$^1$H NMR (400 MHz, CD$_3$OD) δ 8.65 (s, 1H), 8.60 (s, 1H), 7.79 (ddd, J=4.1, 3.3, 0.6 Hz, 1H), 7.55 (ddd, J=10.2, 7.1, 3.3 Hz, 1H), 7.44-7.33 (m, 4H), 6.77-6.72 (m, 1H), 6.56 (ddd, J=10.0, 5.2, 0.7 Hz, 1H), 5.61 (s, 2H), 5.15 (s, 2H), 4.89 (s, 2H), 2.60 (d, J=0.6 Hz, 3H), 2.46 (d, J=0.9 Hz, 3H). MS (M+H)$^+$ found for C$_{26}$H$_{25}$FN$_8$O: 485.2.

Example 337

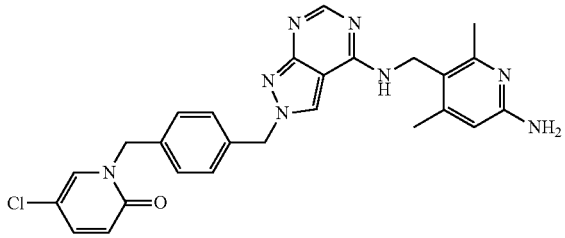 [SMILES: Cc1cc(N)nc(C)c1CNc1ncnc2nn(Cc3ccc(Cn4cc(Cl)ccc4=O)cc3)cc12]

1-(4-((4-(((6-amino-2,4-dimethylpyridin-3-yl)methyl)amino)-2H-pyrazolo[3,4-d]pyrimidin-2-yl)methyl)benzyl)-5-chloropyridin-2(1H)-one 1-(4-((4-(((6-amino-2,4-dimethylpyridin-3-yl)methyl)amino)-2H-pyrazolo[3,4-d]pyrimidin-2-yl)methyl)benzyl)-5-chloropyridin-2(1H)-one was prepared as in Example 335 except substituting 5-chloropyridin-2-ol for 5-(trifluoromethyl)-2-pyridinol gave 1-(4-((4-(((6-amino-2,4-dimethylpyridin-3-yl)methyl)amino)-2H-pyrazolo[3,4-d]pyrimidin-2-yl)methyl)benzyl)-5-chloropyridin-2(1H)-one as a white solid.
$^1$H NMR (400 MHz, CD$_3$OD) δ 8.65 (d, J=3.5 Hz, 2H), 7.88 (d, J=2.9 Hz, 1H), 7.51 (dd, J=9.7, 2.9 Hz, 1H), 7.44-7.32 (m, 4H), 6.74 (s, 1H), 6.55 (d, J=9.6 Hz, 1H), 5.60 (s, 2H), 5.15 (s, 2H), 4.89 (s, 2H), 2.61 (s, 3H), 2.46 (s, 3H). MS (M+H)$^+$ found for C$_{26}$H$_{25}$ClN$_8$O: 501.2.

Example 338

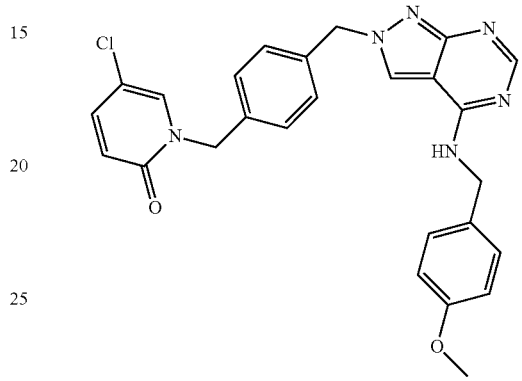

5-chloro-1-(4-((4-((4-methoxybenzyl)amino)-2H-pyrazolo[3,4-d]pyrimidin-2-yl)methyl)benzyl)pyridin-2(1H)-one 5-chloro-1-{[4-({4-chloro-2H-pyrazolo[3,4-d]pyrimidin-2-yl}methyl)phenyl]methyl}-1,2-dihydropyridin-2-one (60.00 mg; 0.16 mmol; 1.00 eq.) (Example 335) was suspended in 1-butanol (2 ml). (4-methoxyphenyl)methanamine (30.44 ul; 0.23 mmol; 1.50 eq.) was added and the reaction heated in a microwave reactor at 110° C. for 50 m. The solvent was evaporated, the resulting residue co-evaporated from acetonitrile (1×5 ml) and then purified by reverse phase chromatography (acetonitrile gradient with 0.1% aqueous formic acid, Waters XSelect CSH column) to give 5-chloro-1-(4-((4-((4-methoxybenzyl)amino)-2H-pyrazolo[3,4-d]pyrimidin-2-yl)methyl)benzyl)pyridin-2(1H)-one (51 mg) as a white solid. $^1$H NMR (400 MHz, CD$_3$OD) δ 8.28 (d, J=4.4 Hz, 2H), 7.85 (d, J=2.8 Hz, 1H), 7.49 (dd, J=9.7, 2.8 Hz, 1H), 7.39-7.23 (m, 6H), 6.92-6.83 (m, 2H), 6.54 (d, J=9.6 Hz, 1H), 5.52 (s, 2H), 5.14 (s, 2H), 4.70 (s, 2H), 3.76 (s, 3H). MS (M+H)$^+$ found for C$_{26}$H$_{23}$ClN$_6$O$_2$: 487.1.

Example 339

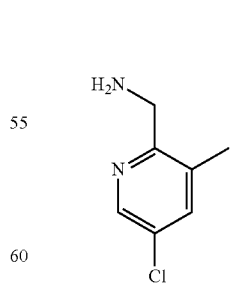

(5-chloro-3-methylpyridin-2-yl)methanamine 5-chloro-3-methylpyridine-2-carbonitrile (0.50 g; 3.28 mmol; 1.00 eq.) was dissolved in 7M ammonia/methanol (16 ml) and ethanol (16 ml) with Raney Ni which had been rinsed with ethanol 3×. The reaction was charged with H₂ and stirred vigorously. After 21 h, the reaction was filtered through Celite, evaporated to a reddish-blue residue of (5-chloro-3-methylpyridin-2-yl)methanamine which was carried on without further purification.

Example 340

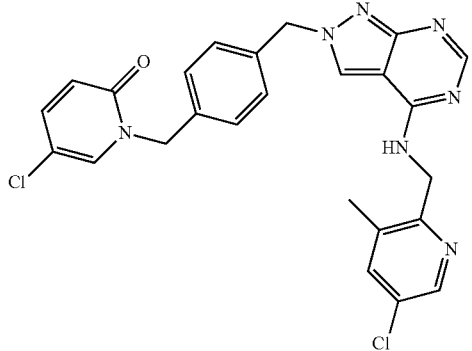 [SMILES: Cc1cc(Cl)cnc1CNc1ncnc2nn(Cc3ccc(Cn4cc(Cl)ccc4=O)cc3)cc12]

5-chloro-1-(4-((4-(((5-chloro-3-methylpyridin-2-yl)methyl)amino)-2H-pyrazolo[3,4-d]pyrimidin-2-yl)methyl)benzyl)pyridin-2(1H)-one 5-chloro-1-(4-((4-(((5-chloro-3-methylpyridin-2-yl)methyl)amino)-2H-pyrazolo[3,4-d]pyrimidin-2-yl)methyl)benzyl)pyridin-2(1H)-one was prepared in a similar manner as Example 335 using example 339. ¹H NMR (400 MHz, CD₃OD) δ 8.31 (t, J=20.6 Hz, 3H), 7.85 (d, J=2.9 Hz, 1H), 7.68 (s, 1H), 7.49 (dd, J=9.9, 2.9 Hz, 1H), 7.35 (s, 4H), 6.55 (d, J=9.6 Hz, 1H), 5.54 (s, 2H), 5.14 (s, 2H), 2.40 (s, 3H). MS (M+H)⁺ found for C₂₆H₂₁Cl₂N₇O: 506.1.

Example 341

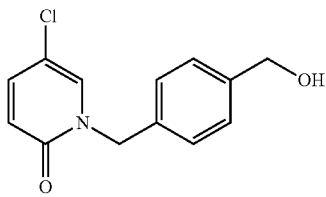 [SMILES: O=c1ccc(Cl)cn1Cc1ccc(CO)cc1]

5-chloro-1-(4-(hydroxymethyl)benzyl)pyridin-2(1H)-one

[4-(chloromethyl)phenyl]methanol (0.50 g; 3.19 mmol; 1.00 eq.) and 5-chloro-2-pyridinol (0.45 g; 3.51 mmol; 1.10 eq.) were suspended in acetonitrile (9 ml). Potassium Carbonate (1.32 g; 9.58 mmol; 3.00 eq.) was added and the mixture was stirred in a heat block at 40° C. After 16 h, the reaction was filtered, evaporated and purified by silica gel chromatography (ethyl acetate/DCM gradient) to give 5-chloro-1-(4-(hydroxymethyl)benzyl)pyridin-2(1H)-one (0.69 g) as a white solid. MS (M+H)⁺ found for C₁₃H₁₂ClNO₂: 250.

Example 342, 343

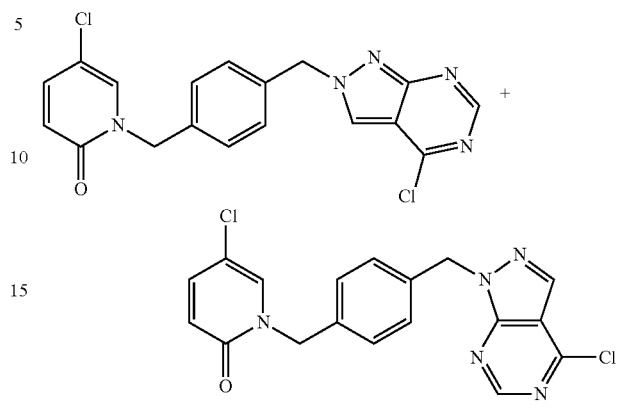

5-chloro-1-(4-((4-chloro-2H-pyrazolo[3,4-d]pyrimidin-2-yl)methyl)benzyl)pyridin-2(1H)-one 5-chloro-1-{[4-(hydroxymethyl)phenyl]methyl}-1,2-dihydropyridin-2-one (533.13 mg; 2.14 mmol; 1.10 eq.)(Example 341) was dissolved in, and 4-chloro-1H-pyrazolo[3,4-d]pyrimidine (300.00 mg; 1.94 mmol; 1.00 eq.) was suspended in DCM (40 ml). The mixture was cooled in an salt/ice bath. Triphenylphosphine substituted polymer resin (0.97 g, 3 mmol/g) was added followed by diisopropyl (E)-1,2-diazenedicarboxylate (0.95 ml; 4.85 mmol; 2.50 eq.) added dropwise slowly. The reaction was stirred to 25° C. over 5 h. The reaction was re-cooled and more triphenylphosphine substituted polymer resin (0.24 g, 3 mmol/g) was added followed by more diisopropyl (E)-1,2-diazenedicarboxylate (0.24 ml; 1.2 mmol; 0.62 eq.) After 14 h, the reaction was filtered, evaporated and purified by silica gel chromatography (ethyl acetate/DCM gradient) to give 5-chloro-1-(4-((4-chloro-2H-pyrazolo[3,4-d]pyrimidin-2-yl)methyl)benzyl)pyridin-2(1H)-one (0.2 g) as a white solid. MS (M+H)⁺ found for C₁₈H₁₃Cl₂N₅O: 386.1.

Example 344

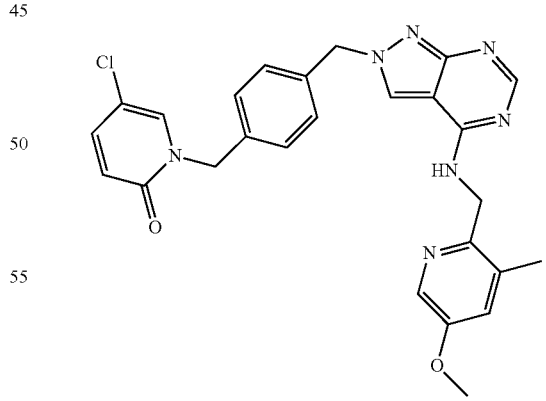

5-chloro-1-(4-((4-(((5-methoxy-3-methylpyridin-2-yl)methyl)amino)-2H-pyrazolo[3,4-d]pyrimidin-2-yl)methyl)benzyl)pyridin-2(1H)-one 5-chloro-1-{[4-({4-chloro-2H-pyrazolo[3,4-d]pyrimidin-2-yl}methyl)phenyl]methyl}-1,2-dihydropyridin-2-one (90.00 mg; 0.23 mmol; 1.00 eq.)(Example 342) was suspended in 1-butanol (4 ml) and Hunig's base (101.47 ul; 0.58 mmol; 2.50 eq.) (5-methoxy-3-methylpyridin-2-yl)methanamine (62.06 mg; 0.24 mmol; 1.05 eq.) was added and the reaction was heated in a microwave reactor at 110° C. for 30 m. More (5-methoxy-3-methylpyridin-2-yl)methanamine (30 mg; 0.12 mmol; 0.5 eq.) was added and the reaction reheated at 100° C. for 30 m. The mixture was cooled, evaporated, and the residue was taken up in acetonitrile and re-evaporated (2×5 ml). The residue was purified by reverse phase chromatography (acetonitrile gradient with 0.1% aqueous formic acid, Waters XSelect CSH column) to give 5-chloro-1-(4-((4-(((5-methoxy-3-methylpyridin-2-yl)methyl)amino)-2H-pyrazolo[3,4-d]pyrimidin-2-yl)methyl)benzyl)pyridin-2(1H)-one (13 mg) as a yellow solid. $^1$H NMR (400 MHz, CD$_3$OD) δ 8.65 (s, 1H), 8.57 (s, 1H), 8.18 (d, J=2.7 Hz, 1H), 7.88 (d, J=2.9 Hz, 1H), 7.69 (d, J=2.8 Hz, 1H), 7.51 (dd, J=9.7, 2.8 Hz, 1H), 7.46-7.32 (m, 4H), 6.55 (d, J=9.7 Hz, 1H), 5.63 (s, 2H), 5.16 (s, 2H), 5.08 (s, 2H), 3.94 (s, 3H), 2.51 (s, 3H). MS (M+H)$^+$ found for $C_{26}H_{24}ClN_7O_2$: 502.2.

Example 345

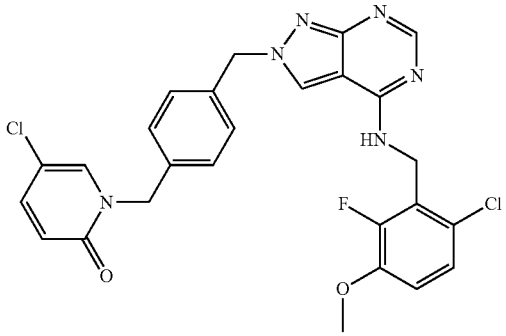 [SMILES: COc1ccc(Cl)c(CNc2ncnc3nn(Cc4ccc(Cn5cc(Cl)ccc5=O)cc4)cc23)c1F]

5-chloro-1-(4-((4-((6-chloro-2-fluoro-3-methoxybenzyl)amino)-2H-pyrazolo[3,4-d]pyrimidin-2-yl)methyl)benzyl)pyridin-2(1H)-one Combined 5-chloro-1-{[4-({4-chloro-2H-pyrazolo[3,4-d]pyrimidin-2-yl}methyl)phenyl]methyl}-1,2-dihydropyridin-2-one (203.69 mg; 0.53 mmol; 1.00 eq.), 6-chloro-2-fluoro-3-methoxybenzylamine (100.00 mg; 0.53 mmol; 1.00 eq.)(Example 342), and Hunig's base (0.18 ml; 1.05 mmol; 2.00 eq.) in N-Methyl-2-pyrrolidinone (2.00 ml) in a microwave vial. Heated the reaction in the microwave at 100° C. for 15 minutes. Purified by prep HPLC to afford 5-chloro-1-(4-((4-((6-chloro-2-fluoro-3-methoxybenzyl)amino)-2H-pyrazolo[3,4-d]pyrimidin-2-yl)methyl)benzyl)pyridin-2(1H)-one (71 mgs; 24%). $^1$H NMR (400 MHz, Methanol-d$_4$) δ 8.31 (s, 1H), 8.23 (s, 1H), 7.82 (d, J=2.8 Hz, 1H), 7.47 (dd, J=9.7, 2.8 Hz, 1H), 7.29 (s, 4H), 7.19 (dd, J=9.0, 1.8 Hz, 1H), 7.07 (t, J=8.9 Hz, 1H), 6.52 (d, J=9.7 Hz, 1H), 5.47 (s, 2H), 5.10 (s, 2H), 4.87 (s, 2H), 3.86 (s, 3H). MS (M+H)+ found for $C_{26}H_{21}Cl_2FN_6O_2$: 539.0.

Example 346

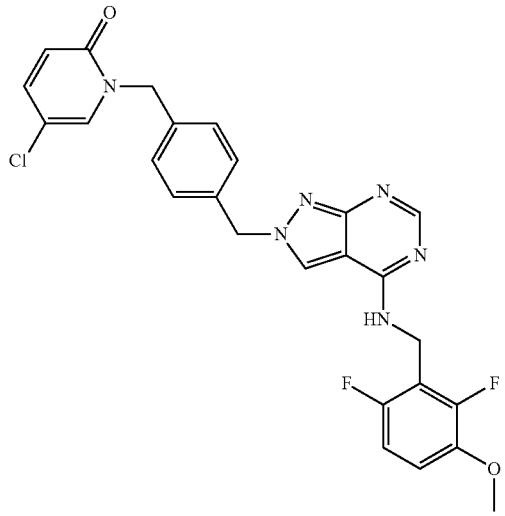 [SMILES: COc1ccc(F)c(CNc2ncnc3nn(Cc4ccc(Cn5cc(Cl)ccc5=O)cc4)cc23)c1F]

5-chloro-1-(4-((4-((2,6-difluoro-3-methoxybenzyl)amino)-2H-pyrazolo[3,4-d]pyrimidin-2-yl)methyl)benzyl)pyridin-2(1H)-one 5-chloro-1-(4-((4-((2,6-difluoro-3-methoxybenzyl)amino)-2H-pyrazolo[3,4-d]pyrimidin-2-yl)methyl)benzyl)pyrid in-2(1H)-one was synthesized in a similar manner to Example 345 using 2,6-difluoro-3-methoxybenzylamine to replace 6-chloro-2-fluoro-3-methoxybenzylamine in step 14. $^1$H NMR (400 MHz, Methanol-d$_4$) δ 8.30 (s, 1H), 8.21 (d, J=8.9 Hz, 1H), 7.84 (d, J=2.8 Hz, 1H), 7.49 (dd, J=9.7, 2.8 Hz, 1H), 7.32 (s, 4H), 7.07 (td, J=9.3, 5.2 Hz, 1H), 6.91 (td, J=9.1, 2.0 Hz, 1H), 6.54 (d, J=9.6 Hz, 1H), 5.51 (s, 2H), 5.13 (s, 2H), 4.81 (s, 2H), 3.85 (s, 3H). MS (M+H)+ found for $C_{26}H_{21}ClF_2N_6O_2$: 523.0.

Example 347

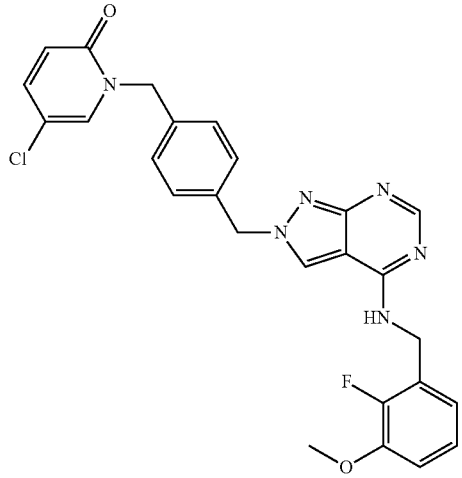 [SMILES: COc1cccc(CNc2ncnc3nn(Cc4ccc(Cn5cc(Cl)ccc5=O)cc4)cc23)c1F]

5-chloro-1-(4-((4-((2-fluoro-3-methoxybenzyl)amino)-2H-pyrazolo[3,4-d]pyrimidin-2-yl)methyl)benzyl)pyridin-2(1H)-one 5-chloro-1-(4-((4-((2-fluoro-3-methoxybenzyl)amino)-2H-pyrazolo[3,4-d]pyrimidin-2-yl)methyl)benzyl)pyridin-2

(1H)-one was synthesized in a similar manner to Example 345 using 2-fluoro-3-methoxybenzylamine to replace 6-chloro-2-fluoro-3-methoxybenzylamine in step 14. $^1$H NMR (400 MHz, Methanol-d$_4$) δ 8.27 (s, 1H), 8.26 (s, 1H), 7.84 (d, J=2.8 Hz, 1H), 7.49 (dd, J=9.7, 2.8 Hz, 1H), 7.33 (s, 4H), 7.01 (td, J=8.1, 7.1, 4.2 Hz, 2H), 6.93 (td, J=7.1, 6.5, 2.9 Hz, 1H), 6.54 (d, J=9.7 Hz, 1H), 5.52 (s, 2H), 5.13 (s, 2H), 4.79 (d, J=1.5 Hz, 2H), 3.85 (s, 3H). MS (M+H)+ found for C$_{26}$H$_{22}$ClF$_2$N$_6$O$_2$: 504.9.

Example 348

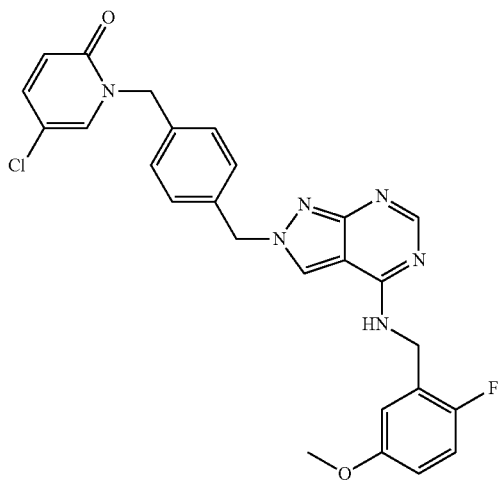 [SMILES: COc1ccc(F)c(CNc2ncnc3nn(Cc4ccc(Cn5cc(Cl)ccc5=O)cc4)cc23)c1]

5-chloro-1-(4-((4-((2-fluoro-5-methoxybenzyl)amino)-2H-pyrazolo[3,4-d]pyrimidin-2-yl)methyl)benzyl)pyridin-2(1H)-one 5-chloro-1-(4-((4-((2-fluoro-5-methoxybenzyl)amino)-2H-pyrazolo[3,4-d]pyrimidin-2-yl)methyl)benzyl)pyridin-2(1H)-one was synthesized in a similar manner to Example 345 using 2-fluoro-5-methoxybenzylamine to replace 6-chloro-2-fluoro-3-methoxybenzylamine in step 14. $^1$H NMR (400 MHz, Methanol-d$_4$) δ 8.25 (d, J=7.4 Hz, 2H), 7.85 (d, J=2.8 Hz, 1H), 7.49 (dd, J=9.7, 2.8 Hz, 1H), 7.33 (s, 3H), 7.01 (t, J=9.3 Hz, 1H), 6.93 (dd, J=6.0, 3.1 Hz, 1H), 6.82 (dt, J=8.9, 3.6 Hz, 1H), 6.54 (d, J=9.7 Hz, 1H), 5.52 (s, 2H), 5.14 (s, 2H), 4.76 (s, 2H), 3.71 (s, 2H). MS (M+H)+ found for C$_{26}$H$_{22}$ClF$_2$N$_6$O$_2$: 505.1

Example 349

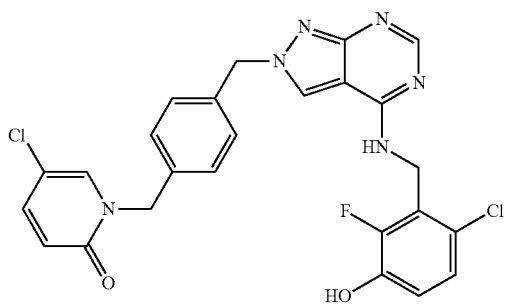 [SMILES: O=c1ccc(Cl)cn1Cc1ccc(Cn2cc3c(NCc4c(Cl)ccc(O)c4F)ncnc3n2)cc1]

5-chloro-1-({4-[(4-{[(6-chloro-2-fluoro-3-hydroxyphenyl)methyl]amino}-2H-pyrazolo[3,4-d]pyrimidin-2-yl)methyl]phenyl}methyl)-1,2-dihydropyridin-2-one To a flame dried vial under Ar was added 5-chloro-1-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one (Example 345) (10.00 mg; 0.02 mmol; 1.00 eq.) and dichloromethane (0.50 ml). This solution was cooled in a −78° C. bath. Boron tribromide (37.08 μl; 1.00 mol/l; 0.04 mmol; 2.00 eq.) was added dropwise. The resulting solution was stirred in −78° C. bath for 1 hour. It was then allowed to warm to room temperature and stir overnight. The reaction was quenched with the addition of methanol and water. The resulting solution was purified by reverse phase HPLC.

$^1$H NMR (400 MHz, Methanol-d$_4$) δ 8.39 (s, 1H), 8.31 (s, 1H), 7.85 (d, J=2.8 Hz, 1H), 7.49 (dd, J=9.7, 2.8 Hz, 1H), 7.33 (s, 4H), 7.09 (m, 1H), 6.91 (t, J=9.0 Hz, 1H), 6.54 (d, J=9.7 Hz, 1H), 5.52 (s, 2H), 5.13 (s, 2H), 4.91 (m, 2H). MS (ES, m/z) found for C$_{26}$H$_{19}$Cl$_2$FN$_6$O$_2$: 525.10 [M+H]$^+$.

Example 350

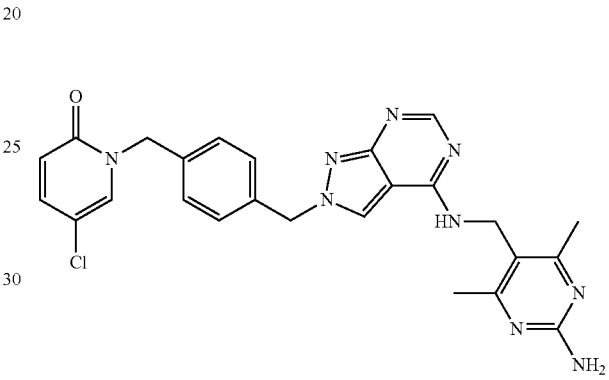

1-([4-[(4-[[(2-amino-4,6-dimethylpyrimidin-5-yl)methyl]amino]-2H-pyrazolo[3,4-d]pyrimidin-2-yl)methyl]phenyl]methyl)-5-chloro-1,2-dihydropyridin-2-one Into a 50-mL round-bottom flask purged and maintained with an inert atmosphere of nitrogen, was placed a solution of 5-chloro-1-[[4-([4-chloro-2H-pyrazolo[3,4-d]pyrimidin-2-yl]methyl)phenyl]methyl]-1,2-dihydropyridin-2-one (110 mg, 0.28 mmol, 1.00 equiv)(Example 342) and (5-(aminomethyl)-4,6-dimethylpyrimidin-2-amine dihydrochloride (65 mg, 0.29 mmol, 1.00 equiv) in N,N-dimethylformamide (6.0 mL). This was followed by the addition of DIEA (561 mg, 4.35 mmol, 15.00 equiv) dropwise with stirring in 5 min. The reaction mixture was stirred overnight at room temperature. The reaction was then diluted with 8 mL of H$_2$O and the precipitates were formed. The solids were collected by filtration. The crude product was further purified by prep-TLC eluted with dichloromethane/methanol (3:1). This resulted in 21 mg (15%) of 1-([4-[(4-[[(2-amino-4,6-dimethylpyrimidin-5-yl)methyl]amino]-2H-pyrazolo[3,4-d]pyrimidin-2-yl)methyl]phenyl]methyl)-5-chloro-1,2-dihydropyridin-2-one as a off-white solid.

$^1$H-NMR (300 MHz, CD$_3$OD): δ 8.32 (s, 1H), 8.21 (s, 1H), 7.87 (d, J=3.0 Hz, 1H), 7.53 (dd, J=9.6 Hz, 3.0 Hz, 1H), 7.36 (s, 4H), 6.56 (d, J=9.6 Hz, 1H), 5.53 (s, 2H), 5.15 (s, 2H), 4.67 (s, 2H), 2.40 (s, 6H). MS (ESI) m/z 502 [M+H]$^+$.

Example 351

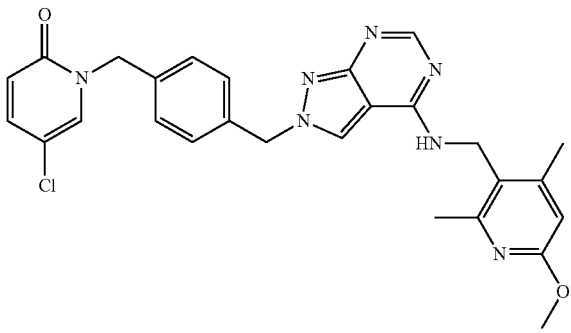 [SMILES: COc1cc(C)c(CNc2ncnc3nn(Cc4ccc(Cn5cc(Cl)ccc5=O)cc4)cc23)c(C)n1]

5-chloro-1-([4-[(4-[[(6-methoxy-2,4-dimethylpyridin-3-yl)methyl]amino]-2H-pyrazolo[3,4-d]pyrimidin-2-yl)methyl]phenyl]methyl)-1,2-dihydropyridin-2-one 5-chloro-1-([4-[(4-[[(6-methoxy-2,4-dimethylpyridin-3-yl)methyl]amino]-2H-pyrazolo[3,4-d]pyrimidin-2-yl)methyl]phenyl]methyl)-1,2-dihydropyridin-2-one was prepared in a similar manner to Example 77. $^1$H-NMR (300 MHz, CD$_3$OD): δ 8.36 (s, 1H), 8.26 (s, 1H), 7.86 (s, 1H), 7.51 (dd, J=9.6 Hz, 3.0 Hz, 1H), 7.35 (s, 4H), 6.57-6.54 (m, 2H), 5.53 (s, 2H), 5.15 (s, 2H), 4.75 (d, 2H), 3.88 (s, 3H), 2.50 (s, 3H), 2.35 (s, 3H).
MS (ESI) m/z 516 [M+H]$^+$.

Example 352

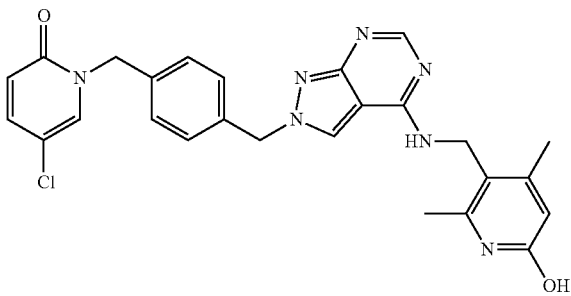 [SMILES: Cc1cc(O)nc(C)c1CNc1ncnc2nn(Cc3ccc(Cn4cc(Cl)ccc4=O)cc3)cc12]

5-chloro-1-([4-[(4-[[(6-hydroxy-2,4-dimethylpyridin-3-yl)methyl]amino]-2H-pyrazolo[3,4-d]pyrimidin-2-yl)methyl]phenyl]methyl)-1,2-dihydropyridin-2-one Into a 40-mL sealed tube, was placed a solution of 5-chloro-1-([4-[(4-[[(6-methoxy-2,4-dimethylpyridin-3-yl)methyl]amino]-2H-pyrazolo[3,4-d]pyrimidin-2-yl)methyl]phenyl]methyl)-1,2-dihydropyridin-2-one (180 mg, 0.35 mmol, 1.00 equiv)(Example 351) in dichloromethane (3 mL) with stirring, to which TMSI (217 mg, 1.08 mmol, 3.00 equiv) was then added. The reaction mixture was stirred for 6 h at 50° C. in an oil bath. The mixture was concentrated under vacuum and the residue was applied onto a silica gel column (eluent: dichloromethane/methanol=10/1). The product was further purified by Prep-HPLC with the following conditions. Column: Waters XBridge RP18 19*150 mm; mobile phase, CH$_3$CN/water (0.05% NH$_3$.H$_2$O) with a gradient of acetonitrile from 27% to 32% in 5 min; flow rate: 20 mL/min; detector UV wavelength: 254 nm. The product was concentrated and lyophilized to afford 55.7 mg (32%) of 5-chloro-1-([4-[(4-[[(6-hydroxy-2,4-dimethylpyridin-3-yl)methyl]amino]-2H-pyrazolo[3,4-d]pyrimidin-2-yl)methyl]phenyl]methyl)-1,2-dihydropyridin-2-one as a off-white solid. This resulted in 55.7 mg (32%) of 5-chloro-1-([4-[(4-[[(6-hydroxy-2,4-dimethylpyridin-3-yl)methyl]amino]-2H-pyrazolo[3,4-d]pyrimidin-2-yl)methyl]phenyl]methyl)-1,2-dihydropyridin-2-one as a off-white solid. $^1$H NMR (300 MHz, DMSO-d$_6$): δ 8.29-8.24 (m, 2H), 8.09 (d, J=3.0 Hz, 1H), 7.97 (brs, 1H), 7.47 (dd, J=9.6 Hz, 3.0 Hz, 1H), 7.31 (s, 4H), 6.44 (d, J=9.6 Hz, 1H), 6.04 (s, 1H), 5.51 (s, 2H), 5.05 (s, 2H), 4.39 (d, J=4.2 Hz, 2H), 2.25 (s, 3H), 2.13 (s, 3H). MS (ESI) m/z 502 [M+H]$^+$.

Example 353

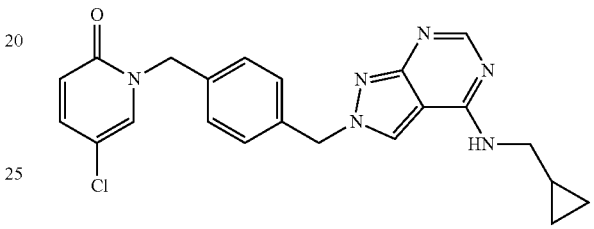

5-chloro-1-[[4-([4-[(cyclopropylmethyl)amino]-2H-pyrazolo[3,4-d]pyrimidin-2-yl]methyl)phenyl]methyl]-1,2-dihydropyridin-2-one 5-chloro-1-[[4-([4-[(cyclopropylmethyl)amino]-2H-pyrazolo[3,4-d]pyrimidin-2-yl]methyl)phenyl]methyl]-1,2-dihydropyridin-2-one was prepared in the same manner as Example 345. $^1$H NMR (300 MHz, DMSO-d): δ 8.35 (s, 1H), 8.25 (br, 1H), 8.16 (s, 1H), 8.10 (d, J=2.7 Hz, 1H), 7.48 (dd, J=9.9 Hz, 3.0 Hz, 1H), 7.30 (s, 4H), 6.45 (d, J=9.6 Hz, 1H), 5.52 (s, 2H), 5.05 (s, 2H), 3.35 (br, 2H), 1.03-1.11 (m, 1H), 0.43-0.49 (m, 2H), 0.19-0.24 (m, 2H). MS (ESI) m/z 422 [M+H]$^+$.

Example 354

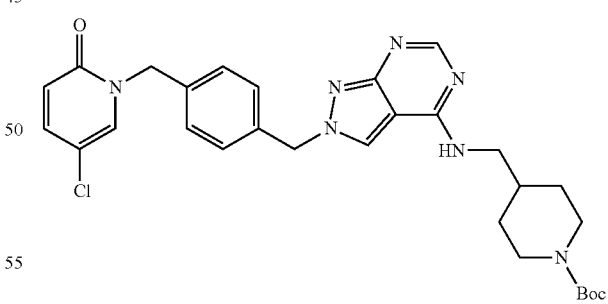

tert-butyl 4-([[2-([4-[(5-chloro-2-oxo-1,2-dihydropyridin-1-yl)methyl]phenyl]methyl)-2H-pyrazolo[3,4-d]pyrimidin-4-yl]amino]methyl)piperidine-1-carboxylate Into a 50-mL round-bottom flask purged and maintained with an inert atmosphere of nitrogen, was placed a mixture of 5-chloro-1-[[4-([4-chloro-2H-pyrazolo[3,4-d]pyrimidin-2-yl]methyl)phenyl]methyl]-1,2-dihydropyridin-2-one (60 mg, 0.16 mmol, 1.00 equiv)(Example 342) in N,N-dimethylformamide (10 mL), tert-butyl 4-(aminomethyl)piperidine-1-carboxylate (40 mg, 0.19 mmol, 1.20 equiv) and DIEA (206 mg, 1.59 mmol, 10.00 equiv). The resulted solution was stirred for 3 h at room temperature. The residue was purified by Prep-HPLC with the following conditions. Column: Waters X-bridge RP18, 19×150 mm, 5 μm; mobile phase: CH$_3$CN and H$_2$O (a buffer of 10 mM NH$_4$HCO$_3$+ 0.05% ammonia) with a gradient of 30% to 50% acetonitrile in 8 min; flow rate: 20 mL/min; detector UV wavelength: 254 nm and 220 nm. This resulted in 30 mg (34%) of tert-butyl 4-([[2-([4-[(5-chloro-2-oxo-1,2-dihydropyridin-1-yl)methyl]phenyl]methyl)-2H-pyrazolo[3,4-d]pyrimidin-4-yl]amino]methyl)-piperidine-1-carboxylate as white solid. MS (ESI) m/z 564 [M+H]$^+$.

Example 355

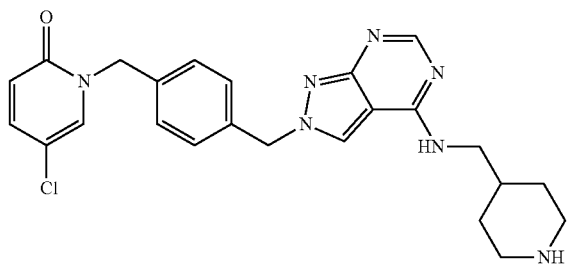 [SMILES: O=c1ccc(Cl)cn1Cc1ccc(Cn2cc3c(NCC4CCNCC4)ncnc3n2)cc1]

5-chloro-1-[[4-([4-[(piperidin-4-ylmethyl)amino]-2H-pyrazolo[3,4-d]pyrimidin-2-yl]methyl)phenyl]methyl]-1,2-dihydropyridin-2-one Into a 50-mL round-bottom flask, was placed a solution of tert-butyl 4-([[2-([4-[(5-chloro-2-oxo-1,2-dihydropyridin-1-yl)methyl]phenyl]methyl)-2H-pyrazolo[3,4-d]pyrimidin-4-yl]amino]methyl)piperidine-1-carboxylate (30 mg, 0.05 mmol, 1.00 equiv)(Example 354) in dichloromethane (5 mL) and trifluoroacetic acid (2 mL). The resulted solution was stirred for 1 h at room temperature. The resulted mixture was concentrated under vacuum. The residue was purified by Prep-HPLC with the following conditions. Column: Waters X-bridge RP18, 19×150 mm, 5 μm; mobile phase: CH$_3$CN and H$_2$O (a buffer of 10 mM NH4HCO3+0.05% ammonia) with a gradient of 30% to 45% in 8 min; flow rate: 20 mL/min; detector UV wavelength: 254 nm and 220 nm. This resulted in 22.4 mg (91%) of 5-chloro-1-[[4-([4-[(piperidin-4-ylmethyl)amino]-2H-pyrazolo[3,4-d]pyrimidin-2-yl]methyl)phenyl]methyl]-1,2-dihydropyridin-2-one as white solid. $^1$H NMR (300 MHz, DMSO-d$_6$): δ 8.32 (s, 1H), 8.10-8.14 (m, 3H), 7.48 (dd, J=9.9 Hz, 3.0 Hz, 1H), 7.32 (s, 4H), 6.45 (d, J=9.6 Hz, 1H), 5.52 (s, 2H), 5.05 (s, 2H), 2.92-2.96 (m, 2H), 2.49-2.51 (m, 2H), 1.61-1.65 (m, 3H), 1.03-1.14 (m, 2H). MS (ESI) m/z 464 [M+H]$^+$.

Example 356

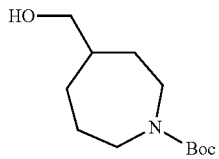

tert-butyl 4-(hydroxymethyl)azepane-1-carboxylate

Into a 50-mL 3-necked round-bottom flask purged and maintained with an inert atmosphere of nitrogen, was placed a mixture of 1-tert-butyl 4-ethyl azepane-1,4-dicarboxylate (1.00 g, 3.69 mmol, 1.00 equiv) and tetrahydrofuran (20 mL) with stirring at 0° C., to which was added LiAlH$_4$ (170 mg, 4.48 mmol, 1.20 equiv). The resulted solution was stirred for 2 h at room temperature. The reaction was then quenched by the addition of 10 mL of water/ice. The solids were filtered out. The filtrate was extracted with ethyl acetate (20 mL×3). The organic phase was washed with 1×50 mL of brine, dried over anhydrous sodium sulfate and concentrated under vacuum. The residue was purified by silica gel column chromatography eluted with ethyl acetate and petroleum ether (1:3). This resulted in 800 mg (95%) of tert-butyl 4-(hydroxymethyl)azepane-1-carboxylate as yellow oil. $^1$H NMR (300 MHz, DMSO-d$_6$): δ 4.49 (t, J=5.4 Hz, 1H), 3.33-3.44 (m, 2H), 3.12-3.23 (m, 4H), 1.72-1.81 (m, 3H), 1.39 (br, 11H), 1.16-1.20 (m, 1H), 0.91-1.08 (m, 1H).

Example 357

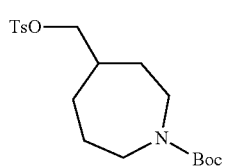

tert-butyl 4-([[(4-methylbenzene)sulfonyl]-oxy]methyl)azepane-1-carboxylate

Into a 100-mL round-bottom flask, was placed a mixture of tert-butyl 4-(hydroxymethyl)azepane-1-carboxylate (400 mg, 1.74 mmol, 1.00 equiv)(Example 356) and pyridine (10 mL) with stirring at 0° C., to which was added TsCl (332 mg, 1.74 mmol, 1.00 equiv). The resulted solution was stirred overnight at room temperature. The reaction mixture was diluted with 50 mL of water and extracted with 3×50 mL of dichloromethane. The organic layers were combined, dried over anhydrous sodium sulfate and concentrated under vacuum. This resulted in 390 mg (58%) of tert-butyl 4-([[(4-methylbenzene)sulfonyl]-oxy]methyl)azepane-1-carboxylate as yellow oil. MS (ESI) m/z 384 [M+H]$^+$.

Example 358

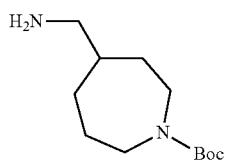

tert-butyl 4-(aminomethyl)azepane-1-carboxylate

Into a 100-mL sealed tube, was placed a solution of tert-butyl 4-([[(4-methylbenzene)sulfonyl]oxy]methyl)azepane-1-carboxylate (370 mg, 0.96 mmol, 1.00 equiv)(Example 357) in methanol (100 mL) with stirring, to which was bubbled ammonia (gas) while stirred for 48 h at room temperature. The resulted mixture was concentrated under vacuum. The resulted solution was diluted with 50 mL of water and extracted with 3×50 mL of dichloromethane, the

Example 359

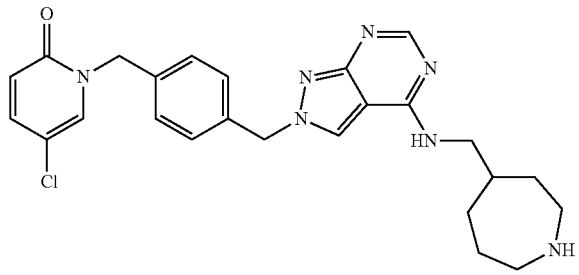 [SMILES: O=c1ccc(Cl)cn1Cc1ccc(Cn2cc3c(NCC4CCCNCC4)ncnc3n2)cc1]

1-[[4-([4-[(azepan-4-ylmethyl)amino]-2H-pyrazolo[3,4-d]pyrimidin-2-yl]methyl)phenyl]methyl]-5-chloro-1,2-dihydropyridin-2-one 1-[[4-([4-[(azepan-4-ylmethyl)amino]-2H-pyrazolo[3,4-d]pyrimidin-2-yl]methyl)phenyl]methyl]-5-chloro-1,2-dihydropyridin-2-one was prepared in a similar manner as Example 355. $^1$H NMR (300 MHz, DMSO-d): δ 8.34 (s, 1H), 8.09-8.17 (m, 3H), 7.46 (dd, J=9.9 Hz, 3.0 Hz, 1H), 7.30 (s, 4H), 6.45 (d, J=9.9 Hz, 1H), 5.52 (s, 2H), 5.06 (s, 2H), 3.33 (br, 2H), 2.62-2.83 (m, 4H), 1.70-1.88 (m, 4H), 1.41 (m, 1H), 1.24-1.30 (m, 2H). MS (ESI) m/z 478 [M+H]$^+$.

Example 360

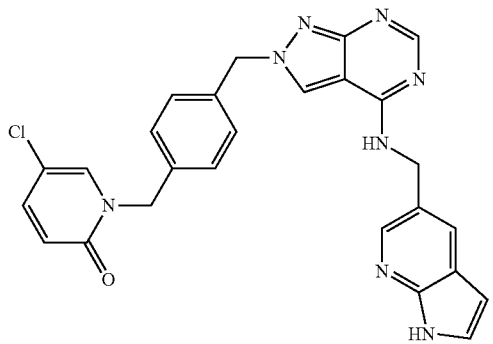 [SMILES: O=c1ccc(Cl)cn1Cc1ccc(Cn2cc3c(NCc4cnc5[nH]ccc5c4)ncnc3n2)cc1]

5-chloro-1-[[4-[[4-([1H-pyrrolo[2,3-b]pyridin-5-ylmethyl]amino)-2H-pyrazolo[3,4-d]pyrimidin-2-yl]methyl]phenyl)methyl]-1,2-dihydropyridin-2-one 5-chloro-1-[[4-[[4-([1H-pyrrolo[2,3-b]pyridin-5-ylmethyl]amino)-2H-pyrazolo[3,4-d]pyrimidin-2-yl]methyl]phenyl)methyl]-1,2-dihydropyridin-2-one was prepared in a similar manner as Example 345. $^1$H NMR (300 MHz, DMSO): δ 11.60 (brs, 1H), 8.62 (brs, 1H), 8.34 (s, 1H), 8.24 (s, 2H), 8.09 (d, J=2.7 Hz, 1H), 7.92 (s, 1H), 7.50-7.45 (m, 2H), 7.31 (s, 4H), 6.46-6.41 (m, 2H), 5.53 (s, 2H), 5.04 (s, 2H), 4.78 (d, J=5.4 Hz, 2H). MS (ESI) m/z 497 [M+H]$^+$.

Example 361

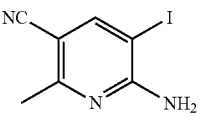

6-amino-5-iodo-2-methylpyridine-3-carbonitrile

Into a 100-mL round-bottom flask, was placed a mixture of 6-amino-2-methylpyridine-3-carbonitrile (2.00 g, 15.02 mmol, 1.00 equiv), NIS (6.77 g, 30.09 mmol, 2.00 equiv) and dry N,N-dimethylformamide (20 mL). The resulted mixture was stirred for 24 hours at 80° C. Then it was diluted with 200 mL of water, the resulted precipitates were collected by filtration and was dissolved in 200 mL of ethyl acetate, dried over anhydrous sodium sulfate and concentrated under vacuum. The residue was purified by flash chromatograph eluted with ethyl acetate/petroleum ether (1:2). This resulted in 3.04 g (78%) of 6-amino-5-iodo-2-methylpyridine-3-carbonitrile as a yellow solid. MS (ESI) m/z 260 [M+H]$^+$

Example 362

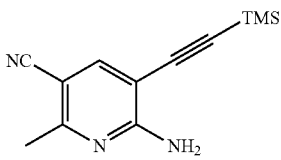

6-amino-2-methyl-5-[2-(trimethylsilyl)ethynyl]pyridine-3-carbonitrile

Into a 100-mL round-bottom flask purged and maintained with an inert atmosphere of nitrogen, was placed a mixture of 6-amino-5-iodo-2-methylpyridine-3-carbonitrile (3.00 g, 11.58 mmol, 1.00 equiv)(Example 361), TEA (2.34 g, 23.12 mmol, 2.00 equiv) and tetrahydrofuran/DCM (3/1, 40 mL). The resulted mixture was stirred for 1 minute at room temperature before Pd(PPh$_3$)$_2$Cl$_2$ (406 mg, 0.58 mmol, 0.05 equiv) and CuI (110 mg, 0.58 mmol, 0.05 equiv) were added sequentially. Then ethynyltrimethylsilane (1.70 g, 17.31 mmol, 1.50 equiv) was added dropwise with stirring. The resulted reaction was stirred for 1 hour at room temperature. After the starting material was consumed completely, the mixture was diluted with 100 mL of water, extracted with 3×100 mL of ethyl acetate. The organic phases were washed with 1×100 mL of brine, dried over anhydrous sodium sulfate and concentrated under vacuum. This resulted in 2.21 g (83%) of 6-amino-2-methyl-5-[2-(trimethylsilyl)ethynyl]pyridine-3-carbonitrile as a brown solid. MS (ESI) m/z 230 [M+H]$^+$

Example 363

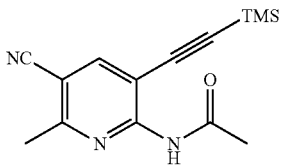 [SMILES: CC(=O)Nc1nc(C)c(C#N)cc1C#C[Si](C)(C)C]

N-[5-cyano-6-methyl-3-[2-(trimethylsilyl)ethynyl]pyridin-2-yl]acetamide

Into a 10-mL 2-necked round-bottom flask purged and maintained with an inert atmosphere of nitrogen, was placed a mixture of 6-amino-2-methyl-5-[2-(trimethylsilyl)ethynyl]pyridine-3-carbonitrile (500 mg, 2.18 mmol, 1.00 equiv) (Example 362), pyridine (431 mg, 5.45 mmol, 2.50 equiv) and dichloromethane (5.0 mL), to which was added acetyl chloride (428 mg, 5.45 mmol, 2.50 equiv) dropwise with stirring at 0° C. The resulted mixture was stirred for 16 hours at room temperature. Then it was concentrated under vacuum. This resulted in 709 mg (crude) of N-[5-cyano-6-methyl-3-[2-(trimethylsilyl)ethynyl]pyridin-2-yl]acetamide as a brown oil, which was used directly for next step without any purification. MS (ESI) m/z 272 [M+H]$^+$

Example 364

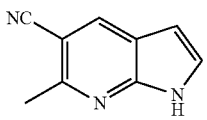

6-methyl-1H-pyrrolo[2,3-b]pyridine-5-carbonitrile

Into a 50-mL round-bottom flask purged and maintained with an inert atmosphere of nitrogen, was placed a mixture of N-[5-cyano-6-methyl-3-[2-(trimethylsilyl)ethynyl]pyridin-2-yl]acetamide (600 mg, 2.21 mmol, 1.00 equiv)(Example 363) and dry tetrahydrofuran (6.0 mL), to which was followed by the addition of TBAF (6.6 mL, 3.00 equiv, 1M/L in THF) dropwise with stirring. The resulted mixture was stirred for 1 hour at 70° C. Then it was diluted with 20 mL of H$_2$O and extracted with 3×20 mL of ethyl acetate. The organic phases were washed with 1×20 mL of brine, dried over anhydrous sodium sulfate and concentrated under vacuum. This resulted in 425 mg (crude) of 6-methyl-1H-pyrrolo[2,3-b]pyridine-5-carbonitrile as a brown solid, which was used directly for next step without further purification. MS (ESI) m/z 158 [M+H]$^+$

Example 365

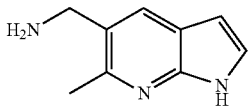

[6-methyl-1H-pyrrolo[2,3-b]pyridin-5-yl]methanamine

Into a 50-mL round-bottom flask purged with N$_2$, was placed a mixture of 6-methyl-1H-pyrrolo[2,3-b]pyridine-5-carbonitrile (100 mg, 0.64 mmol, 1.00 equiv)(Example 364), Raney Ni (50 mg) and ammonia/MeOH=1/10 (11 mL). The resulted mixture was degassed and purged with H$_2$ for four times and stirred 16 hours at room temperature maintained with an inert atmosphere of hydrogen. After the starting material was consumed completely, the solids were filtered out and the filtrate was concentrated under vacuum. This resulted in 83 mg (81%) of [6-methyl-1H-pyrrolo[2,3-b]pyridin-5-yl]methanamine as a yellow solid. MS (ESI) m/z 162 [M+H]$^+$

Example 366

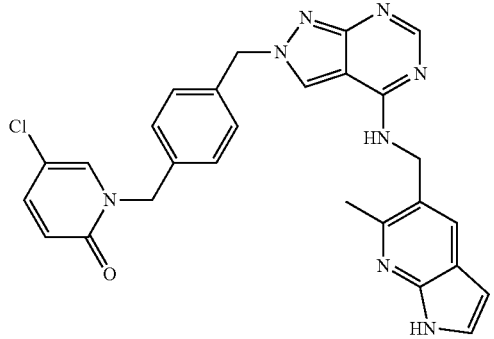 [SMILES: Cc1nc2[nH]ccc2cc1CNc1ncnc2nn(Cc3ccc(Cn4cc(Cl)ccc4=O)cc3)cc12]

5-chloro-1-[[4-([4-[([6-methyl-1H-pyrrolo[2,3-b]pyridin-5-yl]methyl)amino]-2H-pyrazolo[3,4-d]pyrimidin-2-yl]methyl)phenyl]methyl]-1,2-dihydropyridin-2-one 5-chloro-1-[[4-([4-[([6-methyl-1H-pyrrolo[2,3-b]pyridin-5-yl]methyl)amino]-2H-pyrazolo[3,4-d]pyrimidin-2-yl]methyl)phenyl]methyl]-1,2-dihydropyridin-2-one was prepared in a similar manner as Example 345 using Example 365. $^1$H NMR (300 MHz, DMSO): δ 11.46 (br, 1H), 9.08 (br, 1H), 8.48 (s, 1H), 8.38 (s, 1H), 8.11 (d, J=2.7 Hz, 1H), 7.84 (s, 1H), 7.49 (dd, J=9.6 Hz, 2.7 Hz, 1H), 7.35-7.33 (m, 5H), 6.45 (d, J=9.6 Hz, 1H), 6.36 (s, 1H), 5.56 (s, 2H), 5.05 (s, 2H), 4.80 (d, J=5.4 Hz, 2H), 2.54 (s, 3H). MS (ESI) m/z 511 [M+H]$^+$.

Example 367

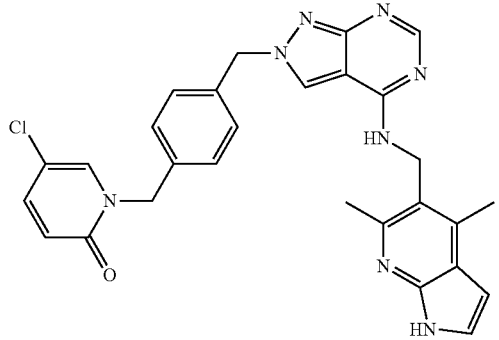 [SMILES: Cc1nc2[nH]ccc2c(C)c1CNc1ncnc2nn(Cc3ccc(Cn4cc(Cl)ccc4=O)cc3)cc12]

5-chloro-1-[[4-([4-[([4,6-dimethyl-1H-pyrrolo[2,3-b]pyridin-5-yl]methyl)amino]-2H-pyrazolo[3,4-d]pyrimidin-2-yl]methyl)phenyl]methyl]-1,2-dihydropyridin-2-one 5-chloro-1-[[4-([4-[([4,6-dimethyl-1H-pyrrolo[2,3-b]pyridin-5-yl]methyl)amino]-2H-pyrazolo[3,4-d]pyrimidin- 2-yl]methyl)phenyl]methyl]-1,2-dihydropyridin-2-one was synthesized in a similar manner as Example 366. $^1$H NMR (300 MHz, DMSO-d$_6$): δ 11.38 (br, 1H), 8.29-8.27 (m, 2H), 8.09-8.06 (m, 2H), 7.47 (dd, J=9.6 Hz, 2.7 Hz, 1H), 7.34-7.27 (m, 5H), 6.45-6.42 (m, 2H), 5.49 (s, 2H), 5.03 (s, 2H), 4.75 (d, J=3.6 Hz, 2H), 2.55 (s, 3H), 2.51 (s, 3H). MS (ESI) m/z 525 [M+H]$^+$. MS (ESI) m/z 225 [M+H]$^+$ Example 368, 369

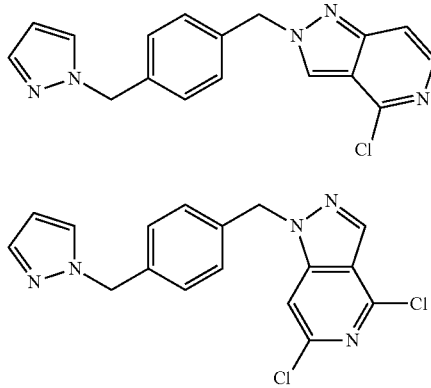

1-(4-((1H-pyrazol-1-yl)methyl)benzyl)-4,6-dichloro-1H-pyrazolo[4,3-c]pyridine and 2-(4-((1H-pyrazol-1-yl)methyl)benzyl)-4,6-dichloro-2H-pyrazolo[4,3-c]pyridine 4,6-dichloro-1H-pyrazolo[4,3-c]pyridine (0.20 g; 1.06 mmol; 1.00 eq.) and [4-(1H-pyrazol-1-ylmethyl)phenyl]methanol (0.25 g; 1.33 mmol; 1.25 eq.) were dissolved in THF (11 ml) and stirred in an ice bath. Triphenylphosphine substituted polymeric resin (1 g, 1.2 mmol/g) was added followed by dropwise addition of diisopropyl (E)-1,2-diazenedicarboxylate (0.52 ml; 2.66 mmol; 2.50 eq.) The mixture was then stirred to 25° C. over 18 h after which it was filtered. The solvent was evaporated to a yellow viscous oil and purified by silica gel chromatography (ethyl acetate/hexanes gradient) to give 1-(4-((1H-pyrazol-1-yl)methyl)benzyl)-4,6-dichloro-1H-pyrazolo[4,3-c]pyridine (0.2 g) and 2-(4-((1H-pyrazol-1-yl)methyl)benzyl)-4,6-dichloro-2H-pyrazolo[4,3-c]pyridine (0.15 g) as a white solid.

1-(4-((1H-pyrazol-1-yl)methyl)benzyl)-4,6-dichloro-1H-pyrazolo[4,3-c]pyridine $^1$H NMR (400 MHz, CDCl$_3$) δ 8.14 (d, J=1.0 Hz, 1H), 7.52 (dd, J=1.9, 0.7 Hz, 1H), 7.37 (dd, J=2.3, 0.7 Hz, 1H), 7.19-7.13 (m, 5H), 6.29-6.24 (m, 1H), 5.50 (s, 2H), 5.29 (s, 2H). MS (M+H)$^+$ found for C$_{17}$H$_{13}$Cl$_2$N$_5$: 358.0.

2-(4-((1H-pyrazol-1-yl)methyl)benzyl)-4,6-dichloro-2H-pyrazolo[4,3-c]pyridine $^1$H NMR (400 MHz, CDCl$_3$) δ 8.05 (s, 1H), 7.60-7.45 (m, 2H), 7.40 (d, J=2.2 Hz, 1H), 7.35-7.28 (m, 2H), 7.25-7.18 (m, 2H), 6.33-6.24 (m, 1H), 5.55 (s, 2H), 5.33 (s, 2H). MS (M+H)$^+$ found for C$_{17}$H$_{13}$Cl$_2$N$_5$: 358.0.

Example 370

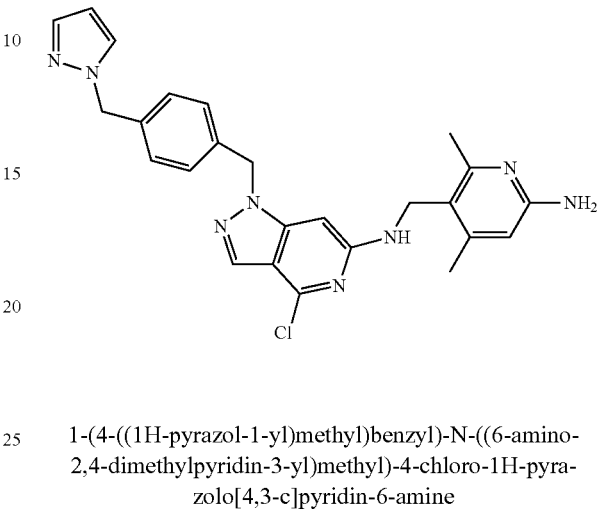

1-(4-((1H-pyrazol-1-yl)methyl)benzyl)-N-((6-amino-2,4-dimethylpyridin-3-yl)methyl)-4-chloro-1H-pyrazolo[4,3-c]pyridin-6-amine 1-{[4-({4,6-dichloro-1H-pyrazolo[4,3-c]pyridin-1-yl}methyl)phenyl]methyl}-1H-pyrazole (Example 369) (20.00 mg; 0.06 mmol; 1.00 eq.) was dissolved in 1-methylpyrrolidinone (dry, 0.5 ml). Ammonium 5-(aminomethyl)-4,6-dimethylpyridin-2-amine trifluoroacetate (14.18 mg; 0.05 mmol; 0.90 eq.)(Example 4) and Hunig's base (19.45 ul; 0.11 mmol; 2.00 eq.) were added and the reaction was sealed and heated in microwave reactor at 120° C. for 2 h More ammonium 5-(aminomethyl)-4,6-dimethylpyridin-2-amine trifluoroacetate (14.18 mg; 0.05 mmol; 0.90 eq.) and Hunig's base-ethylbis(propan-2-yl)amine (19.45 ul; 0.11 mmol; 2.00 eq.) were added and the reaction was heated to 150° C. for 1 h. More ammonium 5-(aminomethyl)-4,6-dimethylpyridin-2-amine trifluoroacetate (14.18 mg; 0.05 mmol; 0.90 eq.) was added and the reaction was stirred in a heat block at 100° C. for 20 h. The mixture was cooled and taken up in ethyl acetate (100 ml) and sodium bicarbonate solution (50 ml). The phases were separated, the aqueous phase was extracted with ethyl acetate (2×25 ml), the combined organic phases were washed with brine (20 ml) and dried over sodium sulfate. After evaporation, the residue was purified by reverse phase chromatography (acetonitrile gradient with 0.1% aqueous formic acid, Waters XSelect CSH column) to give 1-(4-((1H-pyrazol-1-yl)methyl)benzyl)-N-((6-amino-2,4-dimethylpyridin-3-yl)methyl)-4-chloro-1H-pyrazolo[4,3-c]pyridin-6-amine (3 mg) as a white solid. $^1$H NMR (400 MHz, CD$_3$OD) δ 8.09 (d, J=0.9 Hz, 1H), 7.65 (dd, J=2.3, 0.7 Hz, 1H), 7.49 (dd, J=2.0, 0.7 Hz, 1H), 7.18-7.12 (m, 4H), 6.72 (s, 1H), 6.70 (s, OH), 6.55 (s, 1H), 6.32-6.29 (m, 1H), 5.45 (s, 2H), 5.31 (s, 2H), 4.57 (s, 2H), 2.59 (s, 3H), 2.44 (d, J=0.8 Hz, 3H). MS (M+H)$^+$ found for C$_{25}$H$_{25}$ClN$_8$: 473.1.

Example 371

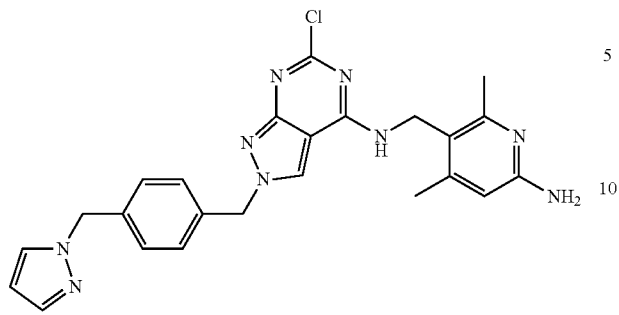

2-(4-((1H-pyrazol-1-yl)methyl)benzyl)-N-((6-amino-2,4-dimethylpyridin-3-yl)methyl)-6-chloro-2H-pyrazolo[3,4-d]pyrimidin-4-amine 2-(4-((1H-pyrazol-1-yl)methyl)benzyl)-N-((6-amino-2,4-dimethylpyridin-3-yl)methyl)-6-chloro-2H-pyrazolo[3,4-d]pyrimidin-4-amine was prepared in a similar manner to Example 335. $^1$H NMR (400 MHz, DMSO-$d_6$) δ 8.58 (t, J=4.3 Hz, 1H), 8.34 (s, 1H), 7.79 (d, J=2.2 Hz, 1H), 7.44 (d, J=1.8 Hz, 1H), 7.36-7.14 (m, 4H), 6.31-6.18 (m, 2H), 6.07 (s, 1H), 5.49 (s, 2H), 5.31 (s, 2H), 4.51-4.39 (m, 2H), 2.34 (s, 3H), 2.20 (s, 3H). MS (M+H)$^+$ found for $C_{24}H_{24}ClN_9$: 474.1.

Example 372

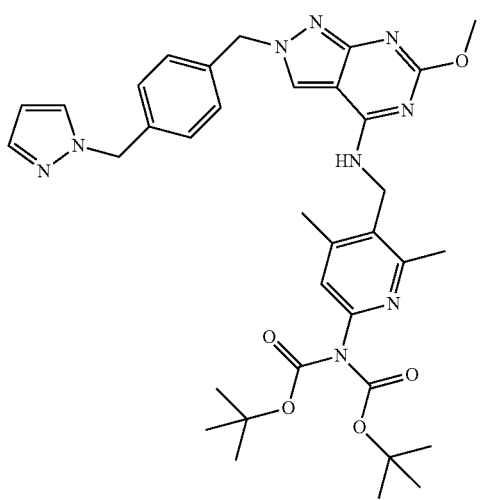 [SMILES: COc1nc(NCc2c(C)cc(N(C(=O)OC(C)(C)C)C(=O)OC(C)(C)C)nc2C)c2cn(Cc3ccc(Cn4cccn4)cc3)nc2n1]

2-(4-((1H-pyrazol-1-yl)methyl)benzyl)-N-((6-amino-2,4-dimethylpyridin-3-yl)methyl)-6-methoxy-2H-pyrazolo[3,4-d]pyrimidin-4-amine In a screw-cap reaction vial, tert-butyl N-[(tert-butoxy)carbonyl]-N-(5-{[(6-chloro-2-{[4-(1H-pyrazol-1-ylmethyl)phenyl]methyl}-2H-pyrazolo[3,4-d]pyrimidin-4-yl)amino]methyl}-4,6-dimethylpyridin-2-yl)carbamate (93.00 mg; 0.14 mmol; 1.00 eq.)(Example 389) was dissolved in methanol (dry, 2 ml). Sodium methanolate (37.26 mg; 0.69 mmol; 5.00 eq.) was added and the reaction was sealed and was heated in a microwave reactor at 110° C. for 1 h. More sodium methanolate (37.26 mg; 0.69 mmol; 5.00 eq.) was added and the reaction heated at 120° C. for 1 h. The resulting mixture was evaporated to a solid and carried directly into the next step.

Example 373

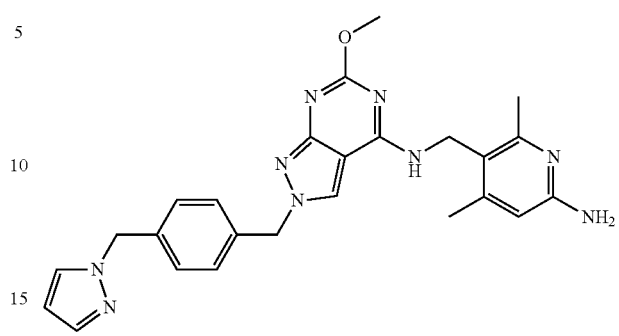

2-(4-((1H-pyrazol-1-yl)methyl)benzyl)-N-((6-amino-2,4-dimethylpyridin-3-yl)methyl)-6-methoxy-2H-pyrazolo[3,4-d]pyrimidin-4-amine A mixture containing tert-butyl (5-(((2-(4-((1H-pyrazol-1-yl)methyl)benzyl)-6-methoxy-2H-pyrazolo[3,4-d]pyrimidin-4-yl)amino)methyl)-4,6-dimethylpyridin-2-yl)carbamate (Example 372) was dissolved in 10% methanol/DCM (1.5 ml) and stirred in an ice bath. Hydrochloric acid (3.43 ml; 4.00 mol/l; 13.74 mmol; 100.00 eq.) (4M dioxane solution) was slowly added and the reaction was then stirred at 25° C. After 1.5 h, the solution was evaporated to leave a solid which was purified by reverse phase chromatography (acetonitrile gradient with 0.1% aqueous formic acid, Waters XSelect CSH column) to give 2-(4-((1H-pyrazol-1-yl)methyl)benzyl)-N-((6-amino-2,4-dimethylpyridin-3-yl)methyl)-6-methoxy-2H-pyrazolo[3,4-d]pyrimidin-4-amine (12 mg) as a white solid.

$^1$H NMR (400 MHz, DMSO-$d_6$) δ 8.20 (s, 1H), 8.06 (t, J=4.5 Hz, 1H), 7.79 (dd, J=2.3, 0.7 Hz, 1H), 7.43 (dd, J=1.8, 0.7 Hz, 1H), 7.30-7.24 (m, 2H), 7.23-7.16 (m, 2H), 6.27 (s, 1H), 6.25 (t, J=2.0 Hz, 1H), 6.23-6.05 (m, 2H), 5.39 (s, 2H), 5.31 (s, 2H), 4.44 (d, J=4.4 Hz, 2H), 3.79 (s, 3H), 2.35 (s, 3H), 2.20 (s, 3H). MS (M+H)$^+$ found for $C_{25}H_{27}N_9O$: 470.2.

Example 374

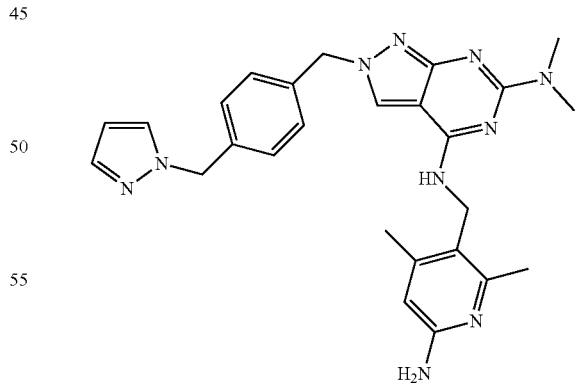

2-(4-((1H-pyrazol-1-yl)methyl)benzyl)-N4-((6-amino-2,4-dimethylpyridin-3-yl)methyl)-N6,N6-dimethyl-2H-pyrazolo[3,4-d]pyrimidine-4,6-diamine 5-{[(6-chloro-2-{[4-(1H-pyrazol-1-ylmethyl)phenyl]methyl}-2H-pyrazolo[3,4-d]pyrimidin-4-yl)amino]

methyl}-4,6-dimethylpyridin-2-amine (22.00 mg; 0.05 mmol; 1.00 eq.)(Example 389) was dissolved in DMF (dry, 1 ml). Sodium iminomethanide (13.65 mg; 0.28 mmol; 6.00 eq.) was added and the reaction was sealed and stirred in a heat block at 110° C. After 22 h, more sodium iminomethanide (25 mg; 0.5 mmol; 10 eq.) and stirred at 130° C. After 24 h, the solvent was evaporated and the residue was purified by reverse phase chromatography (acetonitrile gradient with 0.1% aqueous formic acid, Waters XSelect CSH column) to give 2-(4-((1H-pyrazol-1-yl)methyl)benzyl)-N4-((6-amino-2,4-dimethylpyridin-3-yl)methyl)-N6,N6-dimethyl-2H-pyrazolo[3,4-d]pyrimidine-4,6-diamine (13 mg) as a tan solid. $^1$H NMR (400 MHz, CD$_3$OD) δ 8.45 (s, 1H), 8.08 (s, 1H), 7.67 (d, J=2.3 Hz, 1H), 7.49 (d, J=1.8 Hz, 1H), 7.30 (d, J=7.8 Hz, 2H), 7.20 (d, J=7.8 Hz, 2H), 6.49 (s, 1H), 6.31 (t, J=2.2 Hz, 1H), 5.35 (d, J=15.5 Hz, 4H), 4.72 (s, 2H), 3.28 (s, 6H), 2.44 (s, 3H), 2.31 (s, 3H). MS (M+H)$^+$ found for C$_{26}$H$_{30}$N$_{10}$: 483.3.

Example 375

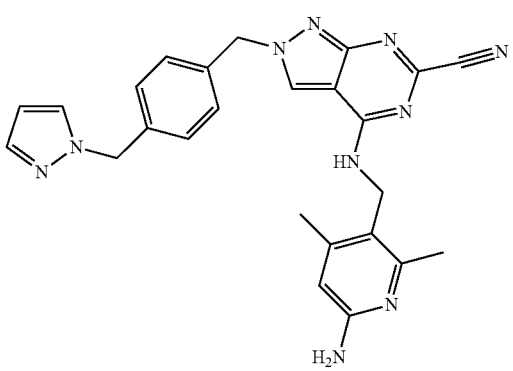 [SMILES: Cc1cc(N)nc(C)c1CNc1nc(C#N)nc2nn(Cc3ccc(Cn4cccn4)cc3)cc12]

2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carbonitrile Additional product obtained as described in Example 374—2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carbonitrile (2 mg) as a tan solid. $^1$H NMR (400 MHz, CD$_3$OD) δ 8.41 (s, 2H), 8.28 (s, 1H), 7.68 (td, J=2.5, 0.7 Hz, 1H), 7.50 (dd, J=1.9, 0.7 Hz, 1H), 7.36-7.29 (m, 2H), 7.24-7.18 (m, 2H), 6.54 (s, 1H), 6.31 (dd, J=2.6, 1.7 Hz, 1H), 5.55 (s, 2H), 5.39 (d, J=6.0 Hz, OH), 5.34 (d, J=4.1 Hz, 2H), 4.67 (s, 2H), 2.54 (s, 3H), 2.42-2.35 (m, 3H). MS (M+H)$^+$ found for C$_{23}$H$_{24}$N$_{10}$: 465.2.

Example 376, 377

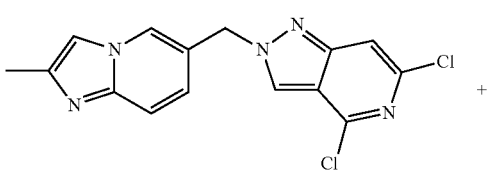

+

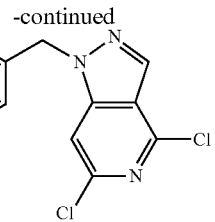

4,6-dichloro-2-((2-methylimidazo[1,2-a]pyridin-6-yl)methyl)-2H-pyrazolo[4,3-c]pyridine 4,6-dichloro-1H-pyrazolo[4,3-c]pyridine (0.60 g; 3.19 mmol; 1.00 eq.) and {2-methylimidazo[1,2-a]pyridin-6-yl}methanol (0.62 g; 3.83 mmol; 1.20 eq.) were suspended in THF (30 ml) and stirred in an ice bath. Triphenylphosphine substituted polymeric resin (3 g, 1.2 mmol/g) was added followed by addition of diisopropyl (E)-1,2-diazenedicarboxylate (1.57 ml; 7.98 mmol; 2.50 eq.) over 30 m (~30 m). The reaction was stirred to 25° C. over 23 h, then filtered and evaporated. The residue was purified by reverse phase chromatography (acetonitrile gradient with 0.1% aqueous formic acid, Waters XSelect CSH column) to give 4,6-dichloro-2-((2-methylimidazo[1,2-a]pyridin-6-yl)methyl)-2H-pyrazolo[4,3-c]pyridine (0.12 g).
MS (M+H)$^+$ found for C$_{13}$H$_{11}$Cl$_2$N$_3$: 332.0.

Example 378

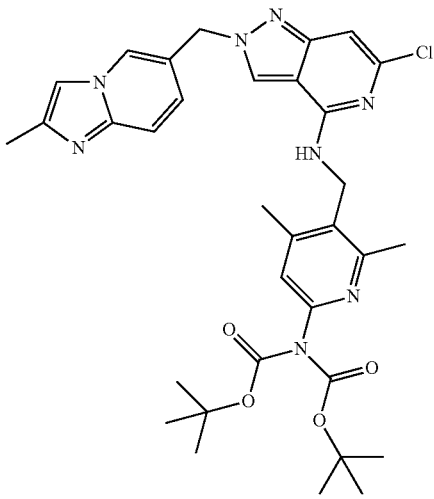 [SMILES: Cc1cn2cc(Cn3cc4c(NCc5c(C)cc(N(C(=O)OC(C)(C)C)C(=O)OC(C)(C)C)nc5C)nc(Cl)cc4n3)ccc2n1]

tert-butyl N-[(tert-butoxy)carbonyl]-N15-({[6-chloro-2-({2-methylimidazo[1,2-a]pyridin-6-yl}methyl)-2H-pyrazolo[4,3-c]pyridin-4-yl]amino}methyl)-4,6-dimethylpyridin-2-yl]carbamate 4,6-dichloro-2-({2-methylimidazo[1,2-a]pyridin-6-yl}methyl)-2H-pyrazolo[4,3-c]pyridine (119.00 mg; 0.36 mmol; 1.00 eq.)(Example 376) was suspended in toluene (5 ml) and the solution was purged with argon gas. Tert-butyl N-[5-(aminomethyl)-4,6-dimethylpyridin-2-yl]-N-[(tert-butoxy)carbonyl]carbamate (188.85 mg; 0.54 mmol; 1.50 eq.) (Example 4, Step 2), 2-(dicyclohexylphosphino)-2',4',6'-triisopropyl-1,1'-biphenyl (30.74 mg; 0.06 mmol; 0.18 eq.), Tris(dibenzylideneacetone)dipalladium(0) (29.52 mg; 0.03 mmol; 0.09 eq.) and then sodium 2-methyl-2-propanolate (68.85 mg; 0.72 mmol; 2.00 eq.) were added in sequence. The reaction was sealed and heated in a microwave reactor at 98° C. for 1 h. More reagents, tert-butyl N-[5-(aminomethyl)-4,6-dimethylpyridin-2-yl]-N-[(tert-butoxy)carbonyl] carbamate (126 mg; 0.36 mmol; 1 eq.), 2-(dicyclohexylphosphino)-2',4',6'-triisopropyl-1,1'-biphenyl (16 mg; 0.03 mmol; 0.09 eq.), Tris(dibenzylideneacetone)dipalladium(0) (15 mg; 0.015 mmol; 0.045 eq.) and then sodium 2-methyl-2-propanolate (35 mg; 0.36 mmol; 1 eq.) were added and the reaction was stirred in a heat block at 95° C. for 24 h. The reaction was then partitioned into ethyl acetate (50 ml) and sodium bicarbonate solution (25 ml) and then filtered to remove solids. The phases were separated, the aqueous phase was extracted with ethyl acetate (2×25 ml) and the combined organics phases were washed with brine (20 ml) and dried over sodium sulfate. After evaporation of solvent, the residue was purified by reverse phase chromatography (acetonitrile gradient with 0.1% aqueous formic acid, Waters XSelect CSH column) to give tert-butyl N-[(tert-butoxy)carbonyl]-N-[5-({[6-chloro-2-({2-methylimidazo[1,2-a]pyridin-6-yl}methyl)-2H-pyrazolo[4,3-c]pyridin-4-yl] amino}methyl)-4,6-dimethylpyridin-2-yl]carbamate (4 mg) as a solid. MS (M+H)$^+$ found for $C_{33}H_{33}ClN_8O_4$: 647.1.

Example 379

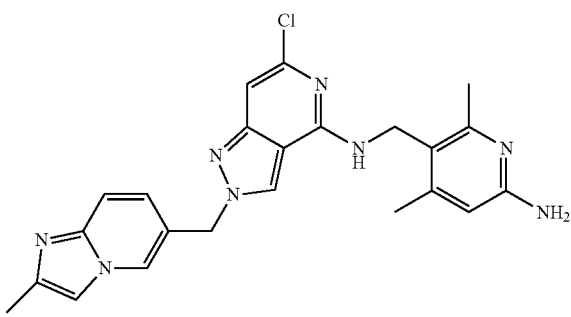 [SMILES: Cc1cn2cc(Cn3cc4c(NCc5c(C)cc(N)nc5C)nc(Cl)cc4n3)ccc2n1]

N-((6-amino-2,4-dimethylpyridin-3-yl)methyl)-6-chloro-2-((2-methylimidazo[1,2-a]pyridin-6-yl)methyl)-2H-pyrazolo[4,3-c]pyridin-4-amine Tert-butyl N-[(tert-butoxy)carbonyl]-N-[5-({[6-chloro-2-({2-methylimidazo[1,2-a]pyridin-6-yl}methyl)-2H-pyrazolo[4,3-c]pyridin-4-yl]amino}methyl)-4,6-dimethylpyridin-2-yl]carbamate (4.00 mg; 0.01 mmol; 1.00 eq.) (Example 378) was dissolved in DCM (1 ml) and stirred in an ice bath. Hydrochloric acid (1 ml; 4.00 mol/l; 4 mmol; 670.00 eq.) was added slowly and the reaction was stirred at 25° C. After 1.5 h, more hydrochloric acid (1 ml; 4.00 mol/l; 4 mmol; 670.00 eq.) was added and the reaction was stirred for 4 h more. The solvent was evaporated and the residue was purified by reverse phase chromatography (acetonitrile gradient with 0.1% aqueous formic acid, Waters XSelect CSH column) to give N-((6-amino-2,4-dimethylpyridin-3-yl)methyl)-6-chloro-2-((2-methylimidazo[1,2-a]pyridin-6-yl)methyl)-2H-pyrazolo[4,3-c]pyridin-4-amine (2.5 mg) as a solid. $^1$H NMR (400 MHz, CD$_3$OD) δ 8.74 (s, 1H), 8.58 (s, 1H), 7.94 (s, 1H), 7.86-7.75 (m, 2H), 6.70 (s, 1H), 6.67 (s, 1H), 5.71 (s, 2H), 4.59 (s, 2H), 2.70 (s, 3H), 2.57-2.50 (m, 6H). MS (M+H)$^+$ found for $C_{23}H_{23}ClN_8$: 447.1.

Example 380

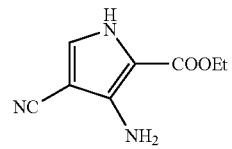

ethyl 3-amino-4-cyano-1H-pyrrole-2-carboxylate

Into a 500-mL 3-necked round-bottom flask purged and maintained with an inert atmosphere of nitrogen, was placed ethanol (100 mL) with stirring, to which was added Na (4.00 g, 174.00 mmol, 3.50 equiv) in several batches. After the sodium was dissolved in ethanol, to it was added a solution of 2-(ethoxymethylidene)propanedinitrile (6.00 g, 49.13 mmol, 1.00 equiv) and 1,3-diethyl 2-(aminomethyl)propanedioate hydrochloride (12.4 g, 54.95 mmol, 1.10 equiv) in ethanol (150 mL) dropwise with stirring. The resulting solution was stirred for 3 h at room temperature. The reaction was then quenched by the addition of 50 mL of AcOH and concentrated under vacuum. The residue was diluted with 200 mL of EA, washed with 3×200 mL of brine, dried over anhydrous sodium sulfate and concentrated under vacuum. The crude product was purified by re-crystallization from toluene. This resulted in 3.01 g (34%) of ethyl 3-amino-4-cyano-1H-pyrrole-2-carboxylate as a light yellow solid. MS (ESI) m/z 180 [M+H]$^+$.

Example 381

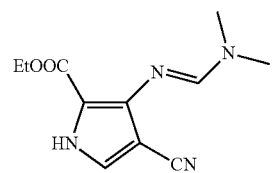 [SMILES: CCOC(=O)c1[nH]cc(C#N)c1/N=C/N(C)C]

ethyl 4-cyano-3-[(E)-[(dimethylamino)methylidene] amino]-1H-pyrrole-2-carboxylate Into a 100-mL round-bottom flask, was placed a solution of ethyl 3-amino-4-cyano-1H-pyrrole-2-carboxylate (1.00 g, 5.58 mmol, 1.00 equiv) (Example 380) in dichloromethane (50 mL) with stirring, to which was added DMF-DMA (3.22 g, 27.93 mmol, 5.00 equiv). The resulting solution was stirred 5 h at room temperature. The resulting mixture was concentrated under vacuum. The resulting solution was diluted with 50 mL of EA, washed with 3×50 mL of brine, dried over anhydrous sodium sulfate and concentrated under vacuum. This resulted in 0.99 g (76%) of ethyl 4-cyano-3-[(E)-[(dimethylamino)methylidene]amino]-1H-pyrrole-2-carboxylate as brown oil. MS (ESI) m/z 235 [M+H]$^+$.

Example 382

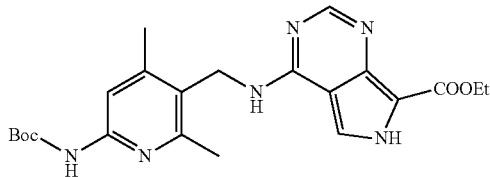 [SMILES: CCOC(=O)c1[nH]cc2c(NCc3c(C)cc(NC(=O)OC(C)(C)C)nc3C)ncnc12]

4-[[(6-[[(tert-butoxy)carbonyl]amino]-2,4-dimethyl-pyridin-3-yl)methyl]amino]-6H-pyrrolo[3,4-d]pyrimidine-7-carboxylate Into a 40-mL sealed tube, was placed a solution of ethyl 4-cyano-3-[(E)-[(dimethylamino)methylidene]amino]-1H-pyrrole-2-carboxylate (800 mg, 3.42 mmol, 1.00 equiv) (Example 381), toluene (20 ml), tert-butyl N-[5-(aminomethyl)-4,6-dimethylpyridin-2-yl]-N-[(tert-butoxy)carbonyl]carbamate (1.2 g, 3.41 mmol, 1.00 equiv) and TsOH (100 mg, 0.58 mmol, cat.) with stirring overnight at 100° C. The reaction mixture was cooled to room temperature. Then it was concentrated under vacuum. The residue was diluted with 50 mL of EA, washed with 3×50 mL of brine, dried over anhydrous sodium sulfate and concentrated under vacuum. This resulted in 400 mg (27%) of ethyl 4-[[(6-[[(tert-butoxy)carbonyl]amino]-2,4-dimethylpyridin-3-yl)methyl]amino]-6H-pyrrolo[3,4-d]pyrimidine-7-carboxylate as a brown solid. MS (ESI) m/z 441 [M+H]$^+$.

Example 383

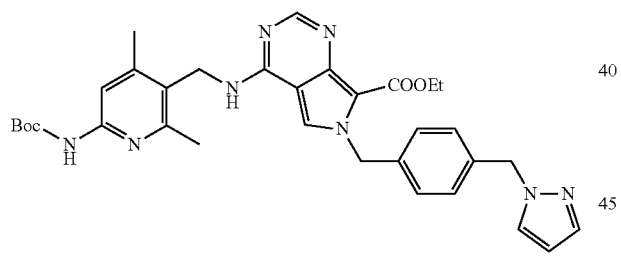

ethyl 4-[[(6-[[(tert-butoxy)carbonyl]amino]-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylate Into a 100-mL 3-necked round-bottom flask purged and maintained with an inert atmosphere of nitrogen, was placed a solution of ethyl 4-[[(6-[[(tert-butoxy)carbonyl]amino]-2,4-dimethylpyridin-3-yl)methyl]amino]-6H-pyrrolo[3,4-d]pyrimidine-7-carboxylate (300 mg, 0.68 mmol, 1.00 equiv)(Example 382), MeCN (50 mL), 1-[[4-(bromomethyl)phenyl]methyl]-1H-pyrazole (171 mg, 0.68 mmol, 1.00 equiv), NaI (20 mg, 0.13 mmol, 0.20 equiv) and K$_2$CO$_3$ (282 mg, 2.04 mmol, 3.00 equiv) with stirring overnight at room temperature. The reaction was then quenched by the addition of 20 mL of water. Then it was extracted with 3×50 mL of ethyl acetate and the organic layers were combined. The resulting mixture was washed with 3×50 mL of brine, dried over anhydrous sodium sulfate and concentrated under vacuum. The crude product was purified by Prep-HPLC with the following conditions. Column: Waters. X-Bridge C18; 19*150 mm, 5 μm; mobile phase: water (0.1% TFA) and CH$_3$CN with a gradient of 45% to 46% acetonitrile in 7 min, flow rate: 20 mL/min; detector UV wavelength: 254 nm. This resulted in 22 mg (5%) of ethyl 4-[[(6-[[(tert-butoxy)carbonyl]amino]-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylate as a white solid. MS (ESI) m/z 611 [M+H]+.

Example 384

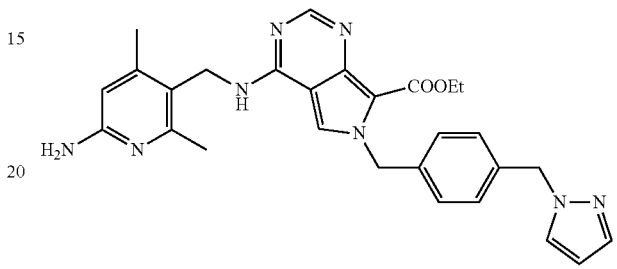 [SMILES: CCOC(=O)c1c2ncnc(NCc3c(C)cc(NC(=O)OC(C)(C)C)nc3C)c2cn1Cc1ccc(Cn2cccn2)cc1]

ethyl 4-[[(6-amino-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylate hydrochloride Into a 50-mL round-bottom flask, was placed ethyl 4-[[(6-[[(tert-butoxy)carbonyl]amino]-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylate (20 mg, 0.03 mmol, 1.00 equiv)(Example 383), dichloromethane (2 mL) and trifluoroacetic acid (0.5 mL). The resulting solution was stirred for 3 h at room temperature. The resulting mixture was concentrated under vacuum. The resulting solution was diluted with 1 mL of 2 N hydrogen chloride aqueous solution. The resulting mixture was concentrated under vacuum. This resulted in 10 mg (56%) of ethyl 4-[[(6-amino-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylate as a yellow solid. MS (ESI) m/z 511 [M+H]$^+$.

Example 385

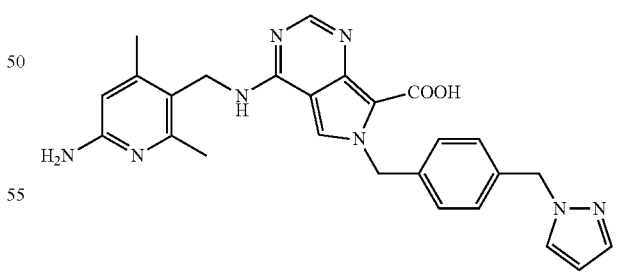

4-[[(6-amino-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylic acid Into a 50-mL round-bottom flask, was placed a solution of ethyl 4-[[(6-amino-2,4-dimethylpyridin-3-yl)methyl]

amino]-6-[[4-(1H-pyrazol-1-ylmethyl)phenyl]methyl]-6H-pyrrolo[3,4-d]pyrimidine-7-carboxylate hydrochloride (10 mg, 0.02 mmol, 1.00 equiv)(Example 384) in water (4 mL) with stirring, it was added of a solution of LiOH (0.9 mg, 0.04 mmol, 2.00 equiv) in water (1 mL) dropwise with stirred. The resulting solution was stirred for 14 h at room temperature. The pH value of the solution was adjusted to 2 with citric acid. The resulting mixture was concentrated under vacuum. The crude product (10 mg) was purified by Prep-HPLC with the following conditions. Column: Waters Sunfire C18 19*180, 51.1µm; mobile phase: water (0.05% TFA) and $CH_3CN$ with a gradient of 25%-30% acetonitrile in 5 min; flaw rate: 15 mL/ min; detector UV wavelength: 220 nm. This resulted in 2.8 mg (32%) of 4-[[(6-amino-2,4-dimethylpyridin-3-yl)methyl]amino]-6-[[4-(1H-pyrazol-1-ylmethyl)phenyl]methyl]-6H-pyrrolo[3,4-d]pyrimidine-7-carboxylic acid as a light yellow solid. $^1$H NMR (300 MHz, DMSO-$d_6$): δ 8.42 (s, 1H), 7.78 (br, 2H), 7.51 (br, 1H), 7.28 (br, 5H), 6.55-6.08 (m, 2H), 6.05-5.60 (m, 2H), 5.29 (br, 2H), 2.85 (br, 2H), 2.37 (br, 6H), 2.25 (br, 2H). MS (ESI) m/z 483 $[M+H]^+$.

Example 386

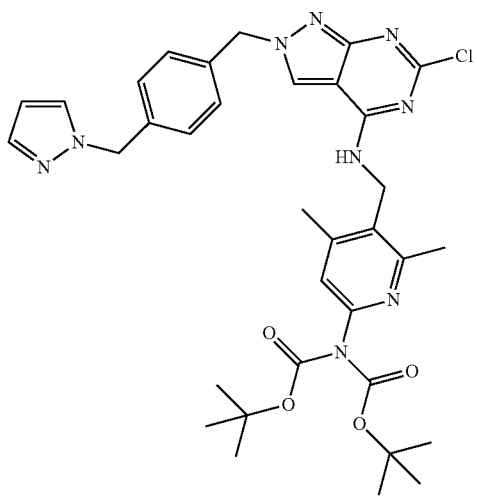 [SMILES: Cc1cc(N(C(=O)OC(C)(C)C)C(=O)OC(C)(C)C)nc(C)c1CNc1nc(Cl)nc2nn(Cc3ccc(Cn4cccn4)cc3)cc12]

tert-butyl N-[(tert-butoxy)carbonyl]-N-(5-{[(6-chloro-2-{[4-(1H-pyrazol-1-ylmethyl)phenyl]methyl}-2H-pyrazolo[3,4-d]pyrimidin-4-yl)amino]methyl}-4,6-dimethylpyridin-2-yl)carbamate 2-(4-((1H-pyrazol-1-yl)methyl)benzyl)-4-(((6-amino-2,4-dimethylpyridin-3-yl)methyl)amino)-N,N-dimethyl-2H-pyrazolo[3,4-d]pyrimidine-6-carboxamide was prepared as in Example 399 except substituting tert-butyl N-[5-(aminomethyl)-4,6-dimethylpyridin-2-yl]-N-[(tert-butoxy)carbonyl]carbamate for (6-chloro-2-fluoro-3-methoxyphenyl)methanamine gave tert-butyl N-[(tert-butoxy)carbonyl]-N-(5-{[(6-chloro-2-{[4-(1H-pyrazol-1-ylmethyl)phenyl]methyl}-2H-pyrazolo[3,4-d]pyrimidin-4-yl)amino]methyl}-4,6-dimethylpyridin-2-yl)carbamate. MS $(M+H)^+$ found for $C_{34}H_{40}ClN_9O_4$: 674.2.

Example 387

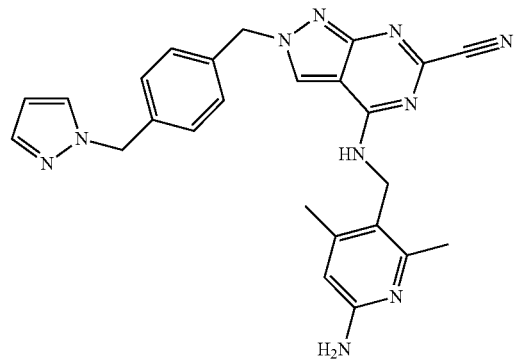 [SMILES: Cc1cc(N)nc(C)c1CNc1nc(C#N)nc2nn(Cc3ccc(Cn4cccn4)cc3)cc12]

2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carbonitrile Prepared as in Example 399 except substituting tert-butyl N-[(tert-butoxy)carbonyl]-N-(5-{[(6-chloro-2-{[4-(1H-pyrazol-1-ylmethyl)phenyl]methyl}-2H-pyrazolo[3,4-d]pyrimidin-4-yl)amino]methyl}-4,6-dimethylpyridin-2-yl)carbamate for 2-(4-((1H-pyrazol-1-yl)methyl)benzyl)-6-chloro-N-(6-chloro-2-fluoro-3-methoxybenzyl)-2H-pyrazolo[3,4-d]pyrimidin-4-amine gave 2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carbonitrile as an off-white solid. MS $(M+H)^+$ found for $C_{25}H_{24}N_{10}$: 465.

Example 388

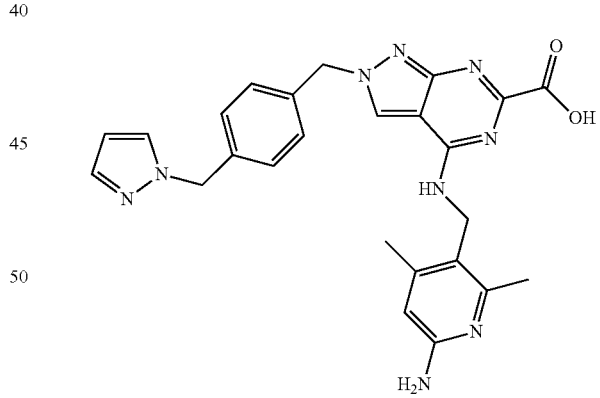

2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carboxylic acid 2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carboxylic acid was prepared as in Example 399 except substituting 2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carbonitrile for 4-{[(6- chloro-2-fluoro-3-methoxyphenyl)methyl]amino}-2-{[4-(1H-pyrazol-1-ylmethyl)phenyl]methyl}-2H-pyrazolo[3,4-d]pyrimidine-6-carbonitrile gave 2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carboxylic acid which was used directly in the next step. $^1$H NMR (400 MHz, DMSO-$d_6$) δ 13.63 (s, 1H), 8.71 (t, J=4.9 Hz, 1H), 8.43 (s, 1H), 7.80 (d, J=2.3 Hz, 1H), 7.57 (s, 2H), 7.44 (d, J=1.9 Hz, 1H), 7.31 (d, J=7.8 Hz, 2H), 7.21 (d, J=7.9 Hz, 2H), 6.64 (s, 1H), 6.25 (t, J=2.1 Hz, 1H), 5.58 (s, 2H), 5.32 (s, 2H), 4.57 (d, J=4.9 Hz, 2H), 2.61 (s, 3H), 2.43 (s, 3H). MS (M+H)$^+$ found for $C_{26}H_{26}N_3O_2$: 484.2. MS (M+H)$^+$ found for $C_{26}H_{26}N_3O_2$: 484.2.

Example 389

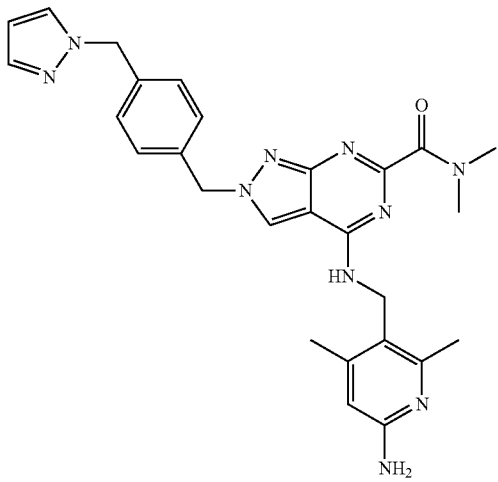 [SMILES: Cc1cc(N)nc(C)c1CNc1nc(C(=O)N(C)C)nc2nn(Cc3ccc(Cn4cccn4)cc3)cc12]

2-(4-((1H-pyrazol-1-yl)methyl)benzyl)-4-(((6-amino-2,4-dimethylpyridin-3-yl)methyl)amino)-N,N-dimethyl-2H-pyrazolo[3,4-d]pyrimidine-6-carboxamide 2-(4-((1H-pyrazol-1-yl)methyl)benzyl)-4-(((6-amino-2,4-dimethylpyridin-3-yl)methyl)amino)-N,N-dimethyl-2H-pyrazolo[3,4-d]pyrimidine-6-carboxamide was prepared as in Example 408 except substituting 2-(4-((1H-pyrazol-1-yl)methyl)benzyl)-4-(((6-amino-2,4-dimethylpyridin-3-yl)methyl)amino)-2H-pyrazolo[3,4-d]pyrimidine-6-carboxylic acid for 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidine-6-carboxylic acid, and substituting dimethylamine for azetidin-1-ium chloride gave 2-(4-((1H-pyrazol-1-yl)methyl)benzyl)-4-(((6-amino-2,4-dimethylpyridin-3-yl)methyl)amino)-N,N-dimethyl-2H-pyrazolo[3,4-d]pyrimidine-6-carboxamide as a white solid. $^1$H NMR (400 MHz, CD$_3$OD) δ 8.23 (s, 1H), 7.67 (d, J=2.4 Hz, 1H), 7.49 (d, J=2.0 Hz, 1H), 7.33 (d, J=7.8 Hz, 2H), 7.23-7.18 (m, 2H), 6.45 (s, 1H), 6.31 (t, J=2.1 Hz, 1H), 5.51 (s, 2H), 5.34 (s, 2H), 4.65 (s, 2H), 3.11 (s, 3H), 2.93 (s, 3H), 2.47 (s, 3H), 2.34 (s, 3H). MS (M+H)$^+$ found for $C_{27}H_{30}N_{10}O$: 511.3.

Example 390, 391

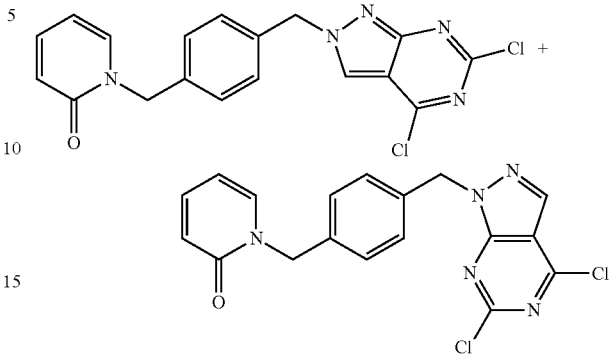

1-(4-((4,6-dichloro-2H-pyrazolo[3,4-d]pyrimidin-2-yl)methyl)benzyl)pyridin-2(1H)-one 1-{[4-(hydroxymethyl)phenyl]methyl}-1,2-dihydropyridin-2-one (610.09 mg; 2.83 mmol; 1.10 eq.) and 4,6-dichloro-1H-pyrazolo[3,4-d]pyrimidine (487.00 mg; 2.58 mmol; 1.00 eq.) were dissolved in DCM (14 ml) and the solution cooled in an salt/ice bath. Triphenylphosphine substituted polymer resin (1.29 g, 3 mmol/g) was added followed by diisopropyl (E)-1,2-diazenedicarboxylate (1.26 ml; 6.44 mmol; 2.50 eq.) added dropwise slowly. Stirred to 25° C. over 6 h. The reaction was then filtered, evaporated to a residue and purified by silica gel chromatography (ethyl acetate/DCM gradient) to give 1-(4-((4,6-dichloro-2H-pyrazolo[3,4-d]pyrimidin-2-yl)methyl)benzyl)pyridin-2(1H)-one (0.15 g) as a white solid. MS (M+H)$^+$ found for $C_{18}H_{13}Cl_2N_5O$: 386.1.

Example 392

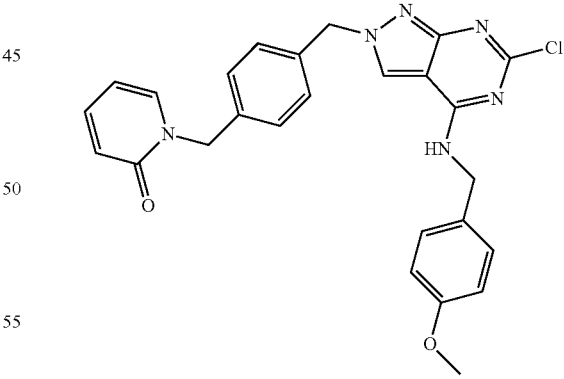

1-(4-((6-chloro-4-((4-methoxybenzyl)amino)-2H-pyrazolo[3,4-d]pyrimidin-2-yl)methyl)benzyl)pyridin-2(1H)-one 1-{[4-({4,6-dichloro-2H-pyrazolo[3,4-d]pyrimidin-2-yl}methyl)phenyl]methyl}-1,2-dihydropyridin-2-one (100.00 mg; 0.26 mmol; 1.00 eq.)(Example 390) was suspended in 1-butanol (1.5 ml). (4-methoxyphenyl)methanamine (50.74 ul; 0.39 mmol; 1.50 eq.) was added and the reaction was heated in a microwave reactor to 110° C. for 60 m. The solvent was evaporated and the residue was re-evaporated after addition of acetonitrile (10 ml). The crude residue was dried under vacuum and used directly in the next step.

Example 393

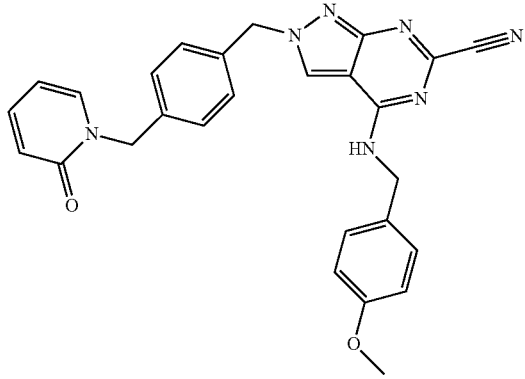 [SMILES: COc1ccc(CNc2nc(C#N)nc3nn(Cc4ccc(Cn5ccccc5=O)cc4)cc23)cc1]

4-((4-methoxybenzyl)amino)-2-(4-((2-oxopyridin-1 (2H)-yl)methyl)benzyl)-2H-pyrazolo[3,4-d]pyrimidine-6-carbonitrile 1-({4-[(6-chloro-4-{[(4-methoxyphenyl)methyl]amino)-2H-pyrazolo[3,4-d]pyrimidin-2-yl)methyl]phenyl}methyl)-1,2-dihydropyridin-2-one (126.00 mg; 0.19 mmol; 1.00 eq.) (Example 392) was dissolved in DMSO (3 ml). Potassium iodide (9.54 mg; 0.06 mmol; 0.30 eq.) and sodium iminomethanide (93.84 mg; 1.91 mmol; 10.00 eq.) were added and the reaction was heated in a microwave reactor at 160° C. for 1 h. More sodium iminomethanide (90 mg; 1.9 mmol; 10.00 eq.) was added and the mixture heated at 160° C. for 1 h, 3× more. The reaction was cooled to 25° C. and partitioned into ethyl acetate (50 ml) and brine (100 ml), the aqueous phase was separated and extracted with ethyl acetate (4×50 ml) and the combined organic phases were washed with brine (30 ml). After drying over sodium sulfate and evaporation, the resulting residue was purified by reverse phase chromatography (acetonitrile gradient with 0.1% aqueous formic acid, Waters XSelect CSH column) to give 4-((4-methoxybenzyl)amino)-2-(4-((2-oxopyridin-1 (2H)-yl)methyl)benzyl)-2H-pyrazolo[3,4-d]pyrimidine-6-carbonitrile (21 mg) as a tan solid. $^1$H NMR (400 MHz, CD$_3$OD) δ 8.28 (s, 1H), 7.67 (d, J=6.7 Hz, 1H), 7.51 (t, J=7.6 Hz, 1H), 7.36-7.24 (m, 6H), 6.88 (d, J=8.1 Hz, 2H), 6.55 (d, J=9.0 Hz, 1H), 6.42-6.33 (m, 1H), 5.54 (s, 2H), 5.17 (s, 2H), 4.69 (s, 2H), 3.77 (s, 3H). MS (M+H)$^+$ found for C$_{27}$H$_{23}$N$_7$O$_2$: 478.2.

Example 394, 395

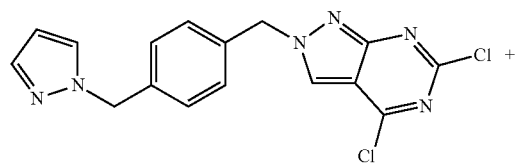

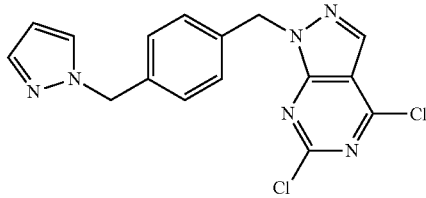

2-(4-((1H-pyrazol-1-yl)methyl)benzyl)-4,6-dichloro-2H-pyrazolo[3,4-d]pyrimidine

[4-(1H-pyrazol-1-ylmethyl)phenyl]methanol (438.19 mg; 2.33 mmol; 1.10 eq.) and 4,6-dichloro-1H-pyrazolo[3,4-d]pyrimidine (400.00 mg; 2.12 mmol; 1.00 eq.) were dissolved in DCM (42 ml) and cooled in a salt/ice bath. Triphenylphosphine substituted polymer resin (1.06 g, 3 mmol/g) was added followed by diisopropyl (E)-1,2-diazenedicarboxylate (1.04 ml; 5.29 mmol; 2.50 eq.) added dropwise slowly. The reaction was stirred to 25° C. over 3 h and then filtered. The solvent was evaporated and the residue was purified by silica gel chromatography (ethyl acetate/hexanes gradient) to give 2-(4-((1H-pyrazol-1-yl)methyl)benzyl)-4,6-dichloro-2H-pyrazolo[3,4-d]pyrimidine (0.2 g) as a lightly colored oil. MS (M+H)$^+$ found for C$_{16}$H$_{12}$Cl$_2$N$_6$: 359.1.

Example 396

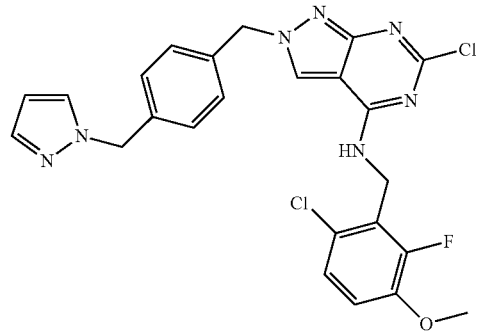 [SMILES: COc1ccc(Cl)c(CNc2nc(Cl)nc3nn(Cc4ccc(Cn5cccn5)cc4)cc23)c1F]

2-(4-((1H-pyrazol-1-yl)methyl)benzyl)-6-chloro-N-(6-chloro-2-fluoro-3-methoxybenzyl)-2H-pyrazolo[3,4-d]pyrimidin-4-amine 1-{[4-({4,6-dichloro-2H-pyrazolo[3,4-d]pyrimidin-2-yl}methyl)phenyl]methyl}-1H-pyrazole (200.00 mg; 0.56 mmol; 1.00 eq.)(Example 395) was suspended in 1-butanol (5 ml) and Hunig's base-ethylbis(propan-2-yl)amine (101.83 uL; 0.58 mmol; 1.05 eq.) (6-chloro-2-fluoro-3-methoxyphenyl)methanamine (110.85 mg; 0.58 mmol; 1.05 eq.) was added and the reaction heated in a microwave reactor at 110° C. for 30 m. The reaction was evaporated, coevaporated from an MeCN solution and dried under high vacuum to give 2-(4-((1H-pyrazol-1-yl)methyl)benzyl)-6-chloro-N-(6-chloro-2-fluoro-3-methoxybenzyl)-2H-pyrazolo[3,4-d]pyrimidin-4-amine. MS (M+H)$^+$ found for C$_{24}$H$_{20}$Cl$_2$FN$_7$O: 512.1.

Example 397

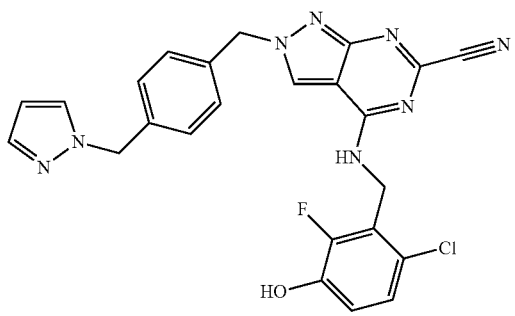 [SMILES: N#Cc1nc(NCc2c(Cl)ccc(O)c2F)c2cn(Cc3ccc(Cn4cccn4)cc3)nc2n1]

2-(4-((1H-pyrazol-1-yl)methyl)benzyl)-4-((6-chloro-2-fluoro-3-hydroxybenzyl)amino)-2H-pyrazolo[3,4-d]pyrimidine-6-carbonitrile 2-(4-((1H-pyrazol-1-yl)methyl)benzyl)-4-((6-chloro-2-fluoro-3-hydroxybenzyl)amino)-2H-pyrazolo[3,4-d]pyrimidine-6-carbonitrile was prepared as in Example 407 substituting 2-(4-((1H-pyrazol-1-yl)methyl)benzyl)-6-chloro-N-(6-chloro-2-fluoro-3-methoxybenzyl)-2H-pyrazolo[3,4-d]pyrimidin-4-amine for 6-chloro-N-[(6-chloro-2-fluoro-3-methoxyphenyl)methyl]-2-({4-[1-(1H-pyrazol-1-yl)ethyl]phenyl}methyl)-2H-pyrazolo[3,4-d]pyrimidin-4-amine to give 2-(4-((1H-pyrazol-1-yl)methyl)benzyl)-4-((6-chloro-2-fluoro-3-hydroxybenzyl)amino)-2H-pyrazolo[3,4-d]pyrimidine-6-carbonitrile as a light yellow solid (MS (M+H)$^+$ found for $C_{24}H_{18}ClFN_8O$: 489.1

Example 398

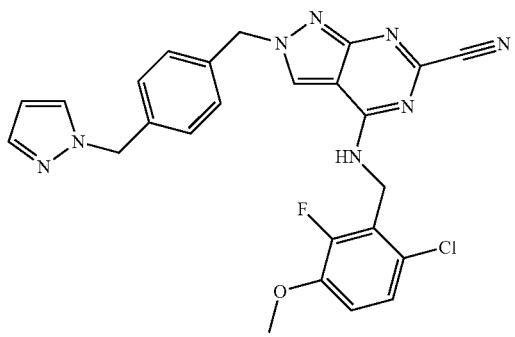 [SMILES: COc1ccc(Cl)c(CNc2nc(C#N)nc3nn(Cc4ccc(Cn5cccn5)cc4)cc23)c1F]

2-(4-((1H-pyrazol-1-yl)methyl)benzyl)-4-((6-chloro-2-fluoro-3-methoxybenzyl)amino)-2H-pyrazolo[3,4-d]pyrimidine-6-carbonitrile Prepared as in Example 407 substituting 2-(4-((1H-pyrazol-1-yl)methyl)benzyl)-4-((6-chloro-2-fluoro-3-hydroxybenzyl)amino)-2H-pyrazolo[3,4-d]pyrimidine-6-carbonitrile for 4-{[(6-chloro-2-fluoro-3-hydroxyphenyl)methyl]amino}-2-({4-[1-(1H-pyrazol-1-yl)ethyl]phenyl}methyl)-2H-pyrazolo[3,4-d]pyrimidine-6-carbonitrile to give 2-(4-((1H-pyrazol-1-yl)methyl)benzyl)-4-((6-chloro-2-fluoro-3-methoxybenzyl)amino)-2H-pyrazolo[3,4-d]pyrimidine-6-carbonitrile.

MS (M+H)$^+$ found for $C_{23}H_{20}ClFN_8O$: 503.2.

Example 399

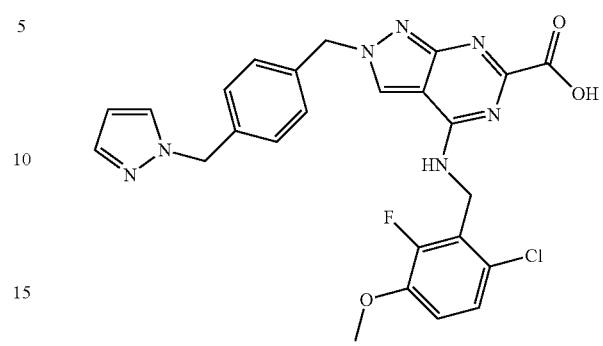

2-(4-((1H-pyrazol-1-yl)methyl)benzyl)-4-((6-chloro-2-fluoro-3-methoxybenzyl)amino)-2H-pyrazolo[3,4-d]pyrimidine-6-carboxylic acid 4-{[(6-chloro-2-fluoro-3-methoxyphenyl)methyl]amino}-2-{[4-(1H-pyrazol-1-ylmethyl)phenyl]methyl}-2H-pyrazolo[3,4-d]pyrimidine-6-carbonitrile (51.00 mg; 0.10 mmol; 1.00 eq.)(Example 398) was dissolved in ethanol (5 ml). 0.3 ml of 3 M NaOH solution was added and the reaction was heated in microwave reactor at 110° C. for 1 h. The reaction was acidified by addition of 1 M HCl solution to a pH 1 and then evaporated. The residue was purified by reverse phase chromatography (acetonitrile gradient with 0.1% aqueous formic acid, Waters XSelect CSH column) to give 2-(4-((1H-pyrazol-1-yl)methyl)benzyl)-4-((6-chloro-2-fluoro-3-methoxybenzyl)amino)-2H-pyrazolo[3,4-d]pyrimidine-6-carboxylic acid (28 mg) as an off-white solid. $^1$H NMR (400 MHz, CD$_3$OD) δ 8.33 (s, 1H), 7.67 (d, J=2.4 Hz, 1H), 7.52-7.46 (m, 1H), 7.33 (d, J=7.9 Hz, 2H), 7.24-7.16 (m, 3H), 7.10 (dd, J=8.9 Hz, 1H), 6.31 (dd, J=2.2 Hz, 1H), 5.54 (s, 2H), 5.33 (s, 2H), 5.08 (s, 2H), 3.87 (s, 3H). MS (M+H)$^+$ found for $C_{23}H_{21}ClFN_7O_3$: 522.2.

Example 400

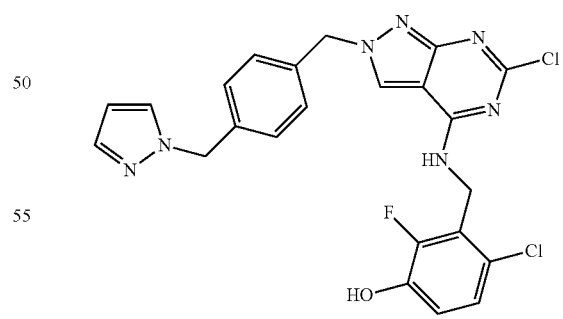

3-(((2-(4-((1H-pyrazol-1-yl)methyl)benzyl)-6-chloro-2H-pyrazolo[3,4-d]pyrimidin-4-yl)amino)methyl)-4-chloro-2-fluorophenol 3-(((2-(4-((1H-pyrazol-1-yl)methyl)benzyl)-6-chloro-2H-pyrazolo[3,4-d]pyrimidin-4-yl)amino)methyl)-4- chloro-2-fluorophenol was prepared in the same manner as Example 399. $^1$H NMR (400 MHz, CD$_3$OD) δ 8.19 (s, 1H), 7.67 (d, J=2.3 Hz, 1H), 7.50 (d, J=1.9 Hz, 1H), 7.30 (d, J=7.9 Hz, 1H), 7.20 (d, J=7.9 Hz, 1H), 7.09 (dd, J=8.8, 1.7 Hz, 1H), 6.91 (t, J=9.0 Hz, 1H), 6.31 (t, J=2.1 Hz, OH), 5.47 (s, 1H), 5.34 (s, 1H). MS (M+H)$^+$ found for C$_{23}$H$_{18}$Cl$_2$FN$_7$O: 498.1.

Example 401

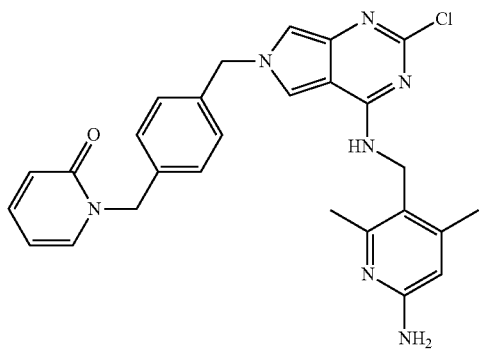 [SMILES: Cc1cc(N)nc(C)c1CNc1nc(Cl)nc2cn(Cc3ccc(Cn4ccccc4=O)cc3)cc12]

1-(4-((4-(((6-amino-2,4-dimethylpyridin-3-yl)methyl)amino)-2-chloro-6H-pyrrolo[3,4-d]pyrimidin-6-yl)methyl)benzyl)pyridin-2(1H)-one. This compound was a side product from the synthesis of Example 681. MS (M+H)$^+$ found for C$_{27}$H$_{26}$ClN$_7$O: 499/501.

Example 402

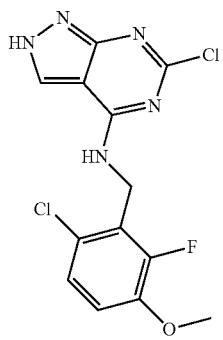 [SMILES: COc1ccc(Cl)c(CNc2nc(Cl)nc3n[nH]cc23)c1F]

6-chloro-N-(6-chloro-2-fluoro-3-methoxybenzyl)-2H-pyrazolo[3,4-d]pyrimidin-4-amine 4,6-dichloro-2H-pyrazolo[3,4-d]pyrimidine (750.00 mg; 3.97 mmol; 1.00 eq.) and (6-chloro-2-fluoro-3-methoxyphenyl)methanamine (752.43 mg; 3.97 mmol; 1.00 eq.) were suspended in 1-butanol (15 ml) and Hunig's base (0.73 ml; 4.17 mmol; 1.05 eq.) The mixture was heated in a microwave reactor at 100° C. for 40 m. The solution was evaporated and the resulting residue was purified by silica gel chromatography (ethyl acetate/dichloromethane gradient) to give 6-chloro-N-(6-chloro-2-fluoro-3-methoxybenzyl)-2H-pyrazolo[3,4-d]pyrimidin-4-amine (83%) as a yellow foam.

$^1$H NMR (400 MHz, CDCl$_3$) δ 10.65 (s, 1H), 7.91 (s, 1H), 7.21-7.15 (m, 1H), 6.92 (dd, J=9.0 Hz, 1H), 5.70 (s, 1H), 5.02 (d, J=5.4 Hz, 2H), 3.90 (s, 3H).

Example 403

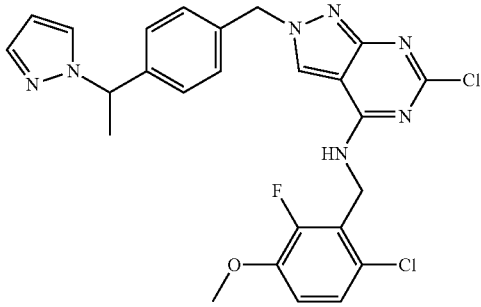 [SMILES: COc1ccc(Cl)c(CNc2nc(Cl)nc3nn(Cc4ccc(C(C)n5cccn5)cc4)cc23)c1F]

2-(4-(1-(1H-pyrazol-1-yl)ethyl)benzyl)-6-chloro-N-(6-chloro-2-fluoro-3-methoxybenzyl)-2H-pyrazolo[3,4-d]pyrimidin-4-amine 1-{1-[4-(bromomethyl)phenyl]ethyl}-1H-pyrazole (774.94 mg; 2.92 mmol; 1.00 eq.)(see Example 594) and 6-chloro-N-[(6-chloro-2-fluoro-3-methoxyphenyl)methyl]-1H-pyrazolo[3,4-d]pyrimidin-4-amine (1 000.00 mg; 2.92 mmol; 1.00 eq.)(Example 402) were suspended in acetonitrile (30 ml). Potassium Carbonate (806.65 mg; 5.85 mmol; 2.00 eq.) was added and the mixture was stirred at 25° C. for 8 h.

The reaction was filtered, the filtered solids rinsed with ethyl acetate and the filtrate evaporated to a residue which was purified by silica gel chromatography (ethyl acetate/dichloromethane gradient) to give 2-(4-(1-(1H-pyrazol-1-yl)ethyl)benzyl)-6-chloro-N-(6-chloro-2-fluoro-3-methoxybenzyl)-2H-pyrazolo[3,4-d]pyrimidin-4-amine (0.63 g) as a light yellow solid. MS (M+H)$^+$ found for C$_{25}$H$_{22}$Cl$_2$FN$_7$O: 526.1.

Example 404

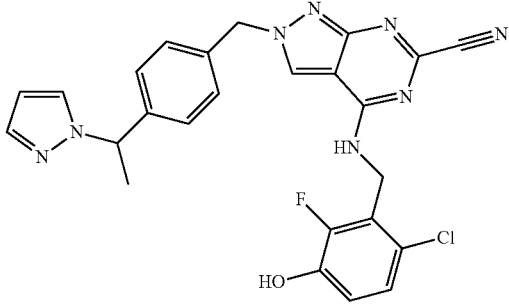 [SMILES: CC(c1ccc(Cn2cc3c(NCc4c(Cl)ccc(O)c4F)nc(C#N)nc3n2)cc1)n1cccn1]

2-(4-(1-(1H-pyrazol-1-yl)ethyl)benzyl)-4-((6-chloro-2-fluoro-3-hydroxybenzyl)amino)-2H-pyrazolo[3,4-d]pyrimidine-6-carbonitrile 6-chloro-N-[(6-chloro-2-fluoro-3-methoxyphenyl)methyl]-2-({4-[1-(1H-pyrazol-1-yl)ethyl]phenyl}methyl)-2H-pyrazolo[3,4-d]pyrimidin-4-amine (600.00 mg; 1.14 mmol; 1.00 eq.)(Example 403) was dissolved in DMSO (dry, 13 ml). Potassium iodide (28.38 mg; 0.17 mmol; 0.15 eq.) and sodium cyanide (586.53 mg; 11.97 mmol; 10.50 eq.) were added and the reaction was sealed and heated in a microwave reactor at 150° C. for 1 h. Two more cycles of adding more potassium iodide (28.38 mg; 0.17 mmol; 0.15 eq.) and sodium cyanide (280 mg; 5.7 mmol; 5 eq.) followed by heating for 1 h at 150° C. resulted in sufficient conversion to product. The reaction was cooled and partitioned into ethyl acetate (250 ml) and brine (150 ml). The phases were separated, the aqueous phase was extracted with more ethyl acetate (3×75 ml), the combined organic phases were washed with brine and dried over sodium sulfate. After evaporation, the residue was purified by silica gel chromatography (ethyl acetate/dichloromethane gradient) to give 2-(4-(1-(1H-pyrazol-1-yl)ethyl)benzyl)-4-((6-chloro-2-fluoro-3-hydroxybenzyl)amino)-2H-pyrazolo[3,4-d]pyrimidine-6-carbonitrile (0.26 g). MS (M+H)$^+$ found for $C_{25}H_{20}ClFN_8O$: 503.2.

Example 405

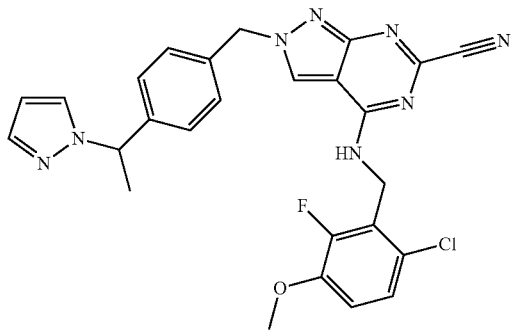 [SMILES: COc1ccc(Cl)c(CNc2nc(C#N)nc3nn(Cc4ccc(C(C)n5cccn5)cc4)cc23)c1F]

2-(4-(1-(1H-pyrazol-1-yl)ethyl)benzyl)-4-((6-chloro-2-fluoro-3-methoxybenzyl)amino)-2H-pyrazolo[3,4-d]pyrimidine-6-carbonitrile 4-{[(6-chloro-2-fluoro-3-hydroxyphenyl)methyl]amino}-2-({4-[1-(1H-pyrazol-1-yl)ethyl]phenyl}methyl)-2H-pyrazolo[3,4-d]pyrimidine-6-carbonitrile (260.00 mg; 0.52 mmol; 1.00 eq.)(Example 404) was dissolved in DMF (dry, 5 ml). The reaction was stirred in an ice bath and cesium carbonate (185.28 mg; 0.57 mmol; 1.10 eq.) and iodomethane (32.18 ul; 0.52 mmol; 1.00 eq.) were added. After 2.5 h, the reaction was partitioned into ethyl acetate (100 ml) and water (50 ml). The phases were separated and the aqueous phase was extracted with ethyl acetate (2×50 ml), the combined organic phases were washed with brine (50 ml) and dried over sodium sulfate. After evaporation, the residue was used directly in the next step. MS (M+H)$^+$ found for $C_{26}H_{22}ClFN_8O$: 517.2.

Example 406

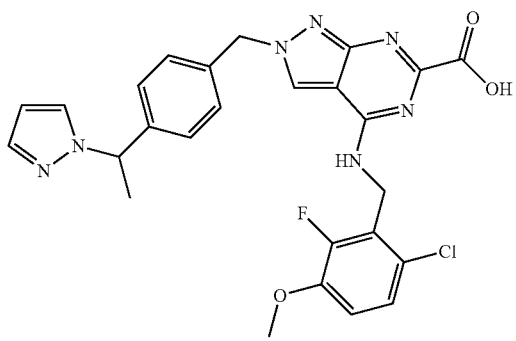 [SMILES: COc1ccc(Cl)c(CNc2nc(C(=O)O)nc3nn(Cc4ccc(C(C)n5cccn5)cc4)cc23)c1F]

2-(4-(1-(1H-pyrazol-1-yl)ethyl)benzyl)-4-((6-chloro-2-fluoro-3-methoxybenzyl)amino)-2H-pyrazolo[3,4-d]pyrimidine-6-carboxylic acid 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidine-6-carbonitrile (267.00 mg; 0.52 mmol; 1.00 eq.)(Example 405) was dissolved in ethanol (17 ml). A solution of 3 M NaOH solution (1.4 ml) was added and the solution was heated in microwave reactor at 110° C., 1 h. The reaction was neutralized by addition of 1 M HCl, evaporated, and taken up in ethyl acetate (100 ml) and brine (50 ml). The phases were separated and the aqueous phase was extracted with more ethyl acetate (2×50 ml). The combined organic phases were evaporated to an off-white solid which was carried directly into the next step. MS (M+H)$^+$ found for $C_{26}H_{23}ClFN_7O_3$: 536.2. $^1$H NMR (400 MHz, CD$_3$OD) δ 8.33 (s, 1H), 7.72 (d, J=2.4 Hz, 1H), 7.49 (d, J=1.8 Hz, 1H), 7.39-7.28 (m, 2H), 7.25-7.16 (m, 3H), 7.11 (dd, J=8.9, 7.4 Hz, 1H), 6.33-6.28 (m, 1H), 5.64-5.50 (m, 3H), 5.12-5.04 (m, 2H), 3.87 (s, 3H), 1.84 (d, J=7.0 Hz, 3H).

Example 407

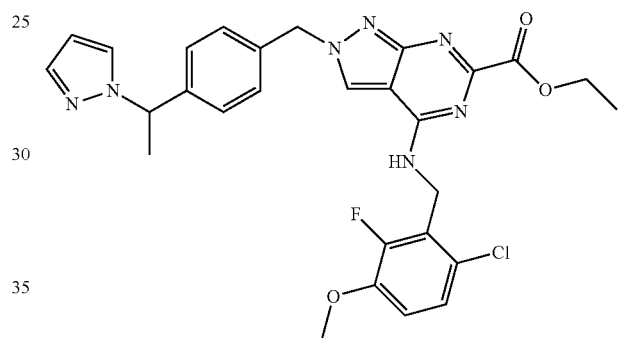

ethyl 2-(4-(1-(1H-pyrazol-1-yl)ethyl)benzyl)-4-((6-chloro-2-fluoro-3-methoxybenzyl)amino)-2H-pyrazolo[3,4-d]pyrimidine-6-carboxylate 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidine-6-carboxylic acid (138.00 mg; 0.26 mmol; 1.00 eq.)(Example 406) was added to a ice bath cooled solution of ethanol (9 ml) and acetyl chloride (1.83 ml; 25.75 mmol; 100.00 eq.) The reaction was sealed and stirred in a heat block to 75° C. for 2 h and then stirred at 25° C. for 16 h more. After evaporation the residue was purified by reverse phase chromatography (acetonitrile gradient with 0.1% aqueous formic acid, Waters XSelect CSH column) to give ethyl 2-(4-(1-(1H-pyrazol-1-yl)ethyl)benzyl)-4-((6-chloro-2-fluoro-3-methoxybenzyl)amino)-2H-pyrazolo[3,4-d]pyrimidine-6-carboxylate (54 mg) as a white solid. $^1$H NMR (400 MHz, CD$_3$OD) δ 8.25 (s, 1H), 7.69 (d, J=2.4 Hz, 1H), 7.48 (d, J=2.1 Hz, 1H), 7.31-7.25 (m, 2H), 7.18-7.11 (m, 3H), 7.03 (t, J=8.8 Hz, 1H), 6.32-6.27 (m, 1H), 5.56 (q, J=7.1 Hz, 1H), 5.49 (s, 2H), 4.95-4.89 (m, 2H), 4.41 (q, J=7.1 Hz, 2H), 3.84 (s, 3H), 1.82 (d, J=7.0 Hz, 3H), 1.41 (t, J=7.1 Hz, 3H). MS (M+H)$^+$ found for $C_{28}H_{27}ClFN_7O_3$: 564.2.

Example 408

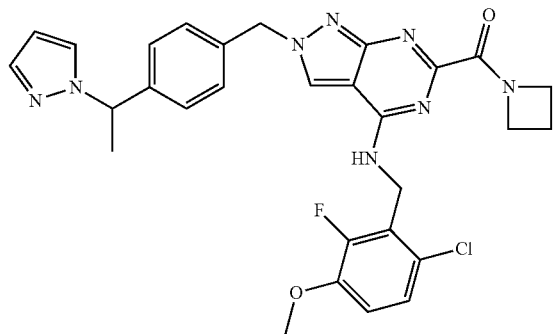 [SMILES: COc1ccc(Cl)c(CNc2nc(C(=O)N3CCC3)nc3nn(Cc4ccc(C(C)n5cccn5)cc4)cc23)c1F]

Example 409

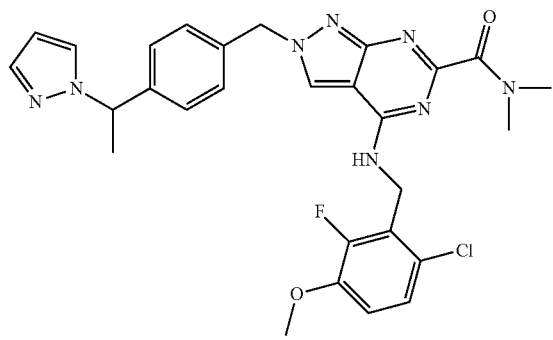 [SMILES: COc1ccc(Cl)c(CNc2nc(C(=O)N(C)C)nc3nn(Cc4ccc(C(C)n5cccn5)cc4)cc23)c1F]

2-(4-(1-(1H-pyrazol-1-yl)ethyl)benzyl)-4-((6-chloro-2-fluoro-3-methoxybenzyl)amino)-2H-pyrazolo[3,4-d]pyrimidin-6-yl)(azetidin-1-yl)methanone and 2-(4-(1-(1H-pyrazol-1-yl)ethyl)benzyl)-4-((6-chloro-2-fluoro-3-methoxybenzyl)amino)-N,N-dimethyl-2H-pyrazolo[3,4-d]pyrimidine-6-carboxamide 4-{[(6-chloro-2-fluoro-3-methoxyphenyl)methyl]amino}-2-({4-[1-(1H-pyrazol-1-yl)ethyl]phenyl}methyl)-2H-pyrazolo[3,4-d]pyrimidine-6-carboxylic acid (138.00 mg; 0.26 mmol; 1.00 eq.)(Example 406) was suspended in DMF (3 ml). HATU (196 mg; 0.51 mmol; 2.00 eq.), then Hunig's base-ethylbis(propan-2-yl)amine (0.18 ml; 1.03 mmol; 4.00 eq.), and then azetidin-1-ium chloride (48.18 mg; 0.51 mmol; 2.00 eq.) were added in sequence. The reaction was stirred for 2 h and then partitioned into ethyl acetate (50 ml) and water (30 ml). The phases were separated, the aqueous phase was extracted with more ethyl acetate (50 ml) and the combined organic phases were washed with water (20 ml) and brine (20 ml). After drying over sodium sulfate, the solvent was evaporated and the residue was purified by reverse phase chromatography (acetonitrile gradient with 0.1% aqueous formic acid, Waters XSelect CSH column) to give (2-(4-(1-(1H-pyrazol-1-yl)ethyl)benzyl)-4-((6-chloro-2-fluoro-3-methoxybenzyl)amino)-2H-pyrazolo[3,4-d]pyrimidin-6-yl)(azetidin-1-yl) methanone (24 mg) as an off-white solid and 2-(4-(1-(1H-pyrazol-1-yl)ethyl)benzyl)-4-((6-chloro-2-fluoro-3-methoxybenzyl)amino)-N,N-dimethyl-2H-pyrazolo[3,4-d]pyrimidine-6-carboxamide (18 mg) as a white solid.

2-(4-(1-(1H-pyrazol-1-yl)ethyl)benzyl)-4-((6-chloro-2-fluoro-3-methoxybenzyl)amino)-2H-pyrazolo[3,4-d]pyrimidin-6-yl)(azetidin-1-yl)methanone $^1$H NMR (400 MHz, CD$_3$OD) δ 8.24 (s, 1H), 7.70 (d, J=2.4 Hz, 1H), 7.50-7.46 (m, 1H), 7.28 (d, J=7.9 Hz, 2H), 7.23-7.14 (m, 3H), 7.08 (dd, J=8.9 Hz, 1H), 6.30 (t, J=2.1 Hz, 1H), 5.58 (q, J=7.1 Hz, 1H), 5.49 (s, 2H), 4.95-4.91 (m, 2H), 4.62 (t, J=7.7 Hz, 2H), 4.21 (t, J=7.8 Hz, 2H), 3.87 (s, 3H), 2.37 (p, J=7.7 Hz, 2H), 1.83 (d, J=7.1 Hz, 3H). MS (M+H)$^+$ found for C$_{23}$H$_{28}$ClFN$_8$O$_2$: 575.2.

2-(4-(1-(1H-pyrazol-1-yl)ethyl)benzyl)-4-((6-chloro-2-fluoro-3-methoxybenzyl)amino)-N,N-dimethyl-2H-pyrazolo[3,4-d]pyrimidine-6-carboxamide $^1$H NMR (400 MHz, CD$_3$OD) δ 8.23 (s, 1H), 7.71 (d, J=2.4 Hz, 1H), 7.49 (d, J=2.0 Hz, 1H), 7.34-7.27 (m, 2H), 7.22-7.16 (m, 3H), 7.07 (t, J=8.8 Hz, 1H), 6.31 (t, J=2.1 Hz, 1H), 5.59 (q, J=7.1 Hz, 1H), 5.50 (s, 2H), 4.88 (d, J=2.0 Hz, 2H), 3.87 (s, 3H), 3.10 (s, 3H), 2.90 (s, 3H), 1.84 (d, J=7.1 Hz, 3H). MS (M+H)$^+$ found for C$_{28}$H$_{28}$ClFN$_8$O$_2$: 563.2.

Example 410

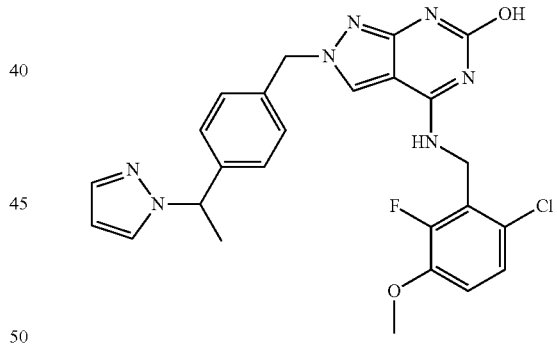

2-(4-(1-(1H-pyrazol-1-yl)ethyl)benzyl)-4-((6-chloro-2-fluoro-3-methoxybenzyl)amino)-2H-pyrazolo[3,4-d]pyrimidin-6-ol 2-(4-(1-(1H-pyrazol-1-yl)ethyl)benzyl)-4-((6-chloro-2-fluoro-3-methoxybenzyl)amino)-2H-pyrazolo[3,4-d]pyrimidin-6-ol was prepared in a similar manner as Example 403. $^1$H NMR (400 MHz, DMSO-d$_6$) δ 10.7 (s, 1H), 8.29 (s, 1H), 8.06 (s, 1H), 7.80 (d, J=2.4 Hz, 1H), 7.42 (d, J=1.8 Hz, 1H), 7.29 (dd, J=9.0, 1.6 Hz, 1H), 7.24-7.14 (m, 5H), 6.23 (t, J=2.0 Hz, 1H), 5.58 (q, J=7.1 Hz, 1H), 5.25 (s, 2H), 4.64 (s, 2H), 3.84 (s, 3H), 1.75 (d, J=7.1 Hz, 3H). MS (M+H)+ found for C$_{26}$H$_{23}$ClFN$_7$O$_2$: 508.1, 510.1.

Example 411

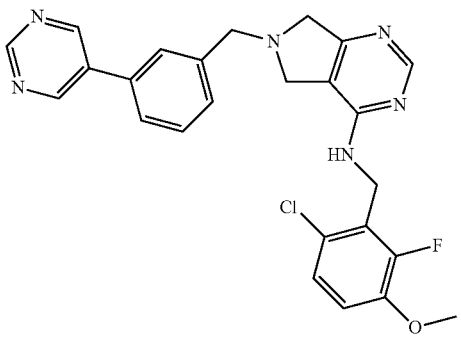 [SMILES: COc1ccc(Cl)c(CNc2ncnc3c2CN(Cc2cccc(-c4cncnc4)c2)C3)c1F]

N-(6-chloro-2-fluoro-3-methoxybenzyl)-6-(3-(py-rimidin-5-yl)benzyl)-6,7-dihydro-5H-pyrrolo[3,4-d]pyrimidin-4-amine and N-(6-chloro-2-fluoro-3-methoxybenzyl)-6-(3-(pyrimidin-5-yl)benzyl)-6H-pyrrolo[3,4-d]pyrimidin-4-amine N-(6-chloro-2-fluoro-3-methoxybenzyl)-6-(3-(pyrimidin-5-yl)benzyl)-6,7-dihydro-5H-pyrrolo[3,4-d]pyrimidin-4-amine and N-(6-chloro-2-fluoro-3-methoxybenzyl)-6-(3-(pyrimidin-5-yl)benzyl)-6H-pyrrolo[3,4-d]pyrimidin-4-amine were prepared in a similar manner as Examples 418 and 419.

N-(6-chloro-2-fluoro-3-methoxybenzyl)-6-(3-(py-rimidin-5-yl)benzyl)-6,7-dihydro-5H-pyrrolo[3,4-d]pyrimidin-4-amine $^1$H NMR (400 MHz, CD$_3$OD) δ 9.13 (s, 1H), 9.08 (s, 2H), 8.38 (s, 1H), 7.76 (s, 1H), 7.66 (ddd, J=5.6, 3.7, 2.0 Hz, 1H), 7.54 (dd, J=3.9, 1.6 Hz, 2H), 7.16 (dd, J=9.0, 1.8 Hz, 1H), 7.04 (t, J=8.9 Hz, 1H), 4.76 (d, J=2.0 Hz, 2H), 4.03 (s, 2H), 3.91 (t, J=2.2 Hz, 2H), 3.85 (d, J=3.9 Hz, 5H). MS (M+H)$^+$ found for C$_{23}$H$_{22}$ClFN$_6$O: 477.4.

Example 412

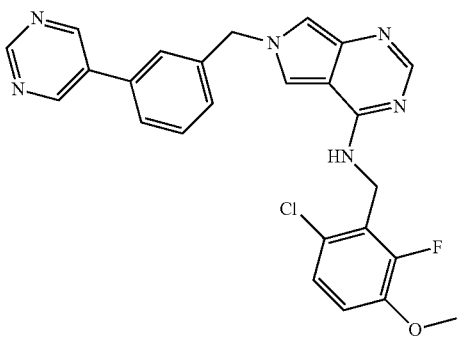 [SMILES: COc1ccc(Cl)c(CNc2ncnc3cn(Cc4cccc(-c5cncnc5)c4)cc23)c1F]

N-(6-chloro-2-fluoro-3-methoxybenzyl)-6-(3-(py-rimidin-5-yl)benzyl)-6H-pyrrolo[3,4-d]pyrimidin-4-amine $^1$H NMR (400 MHz, CD$_3$OD) δ 9.14 (s, 1H), 9.04 (s, 2H), 8.25 (s, 1H), 7.74-7.68 (m, 2H), 7.64 (s, 1H), 7.56 (dd, J=7.7 Hz, 1H), 7.42-7.36 (m, 1H), 7.32 (d, J=2.2 Hz, 1H), 7.23 (dd, J=9.0, 1.8 Hz, 1H), 7.11 (dd, J=8.9 Hz, 1H), 5.50 (s, 2H), 4.95 (d, J=2.2 Hz, 2H), 3.88 (s, 3H). MS (M+H)$^+$ found for C$_{23}$H$_{20}$ClFN$_6$O: 475.1

Example 413

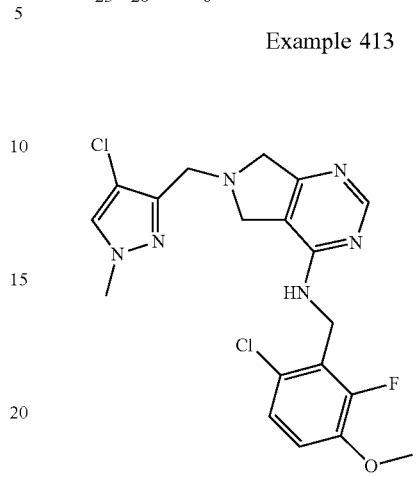

6-((4-chloro-1-methyl-1H-pyrazol-3-yl)methyl)-N-(6-chloro-2-fluoro-3-methoxybenzyl)-6,7-dihydro-5H-pyrrolo[3,4-d]pyrimidin-4-amine 6-((4-chloro-1-methyl-1H-pyrazol-3-yl)methyl)-N-(6-chloro-2-fluoro-3-methoxybenzyl)-6,7-dihydro-5H-pyrrolo[3,4-d]pyrimidin-4-amine was prepared in the same manner as Example 418. $^1$H NMR (400 MHz, CD$_3$OD) δ 8.37 (s, 1H), 8.19 (s, 1H), 7.66 (s, 1H), 7.18 (dd, J=8.9, 1.9 Hz, 1H), 7.06 (t, J=8.9 Hz, 1H), 4.78 (d, J=2.0 Hz, 2H), 3.99 (t, J=2.1 Hz, 2H), 3.97-3.94 (m, 4H), 3.87 (s, 3H), 3.84 (s, 3H). MS (M+H)$^+$ found for C$_{13}$H$_{13}$Cl$_2$FN$_6$O: 437.1.

Example 414

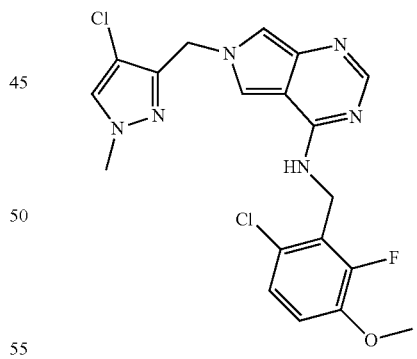

6-((4-chloro-1-methyl-1H-pyrazol-3-yl)methyl)-N-(6-chloro-2-fluoro-3-methoxybenzyl)-6H-pyrrolo[3,4-d]pyrimidin-4-amine 6-((4-chloro-1-methyl-1H-pyrazol-3-yl)methyl)-N-(6-chloro-2-fluoro-3-methoxybenzyl)-6H-pyrrolo[3,4-d]py-rimidin-4-amine was prepared in a similar manner as Example 419. $^1$H NMR (400 MHz, CD$_3$OD) δ 8.46 (s, 2H), 8.29 (s, 1H), 8.22 (s, OH), 7.67 (d, J=27.6 Hz, 1H), 7.58 (d, J=21.5 Hz, 1H), 7.27-7.21 (m, 1H), 7.12 (dd, J=8.9, 4.1 Hz, 1H), 5.34 (s, 1H), 5.01 (d, J=2.1 Hz, 1H), 4.94 (d, J=2.1 Hz, 1H), 4.24 (s, 1H), 3.89 (d, J=0.9 Hz, 3H), 3.85 (s, 1H), 3.80 (s, 2H). (M+H)+ found for C$_{13}$H$_{17}$Cl$_2$FN$_6$O: 435.0.

Example 415

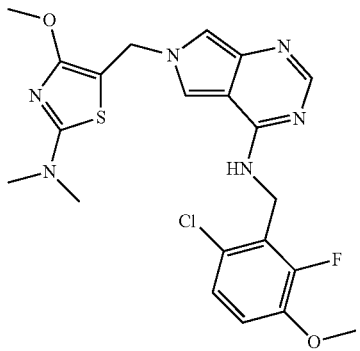

5-((4-((6-chloro-2-fluoro-3-methoxybenzyl)amino)-6H-pyrrolo[3,4-d]pyrimidin-6-yl)methyl)-4-methoxy-N,N-dimethylthiazol-2-amine 5-((4-((6-chloro-2-fluoro-3-methoxybenzyl)amino)-6H-pyrrolo[3,4-d]pyrimidin-6-yl)methyl)-4-methoxy-N,N-dimethylthiazol-2-amine was prepared in a similar manner as Example 418. $^1$H NMR (400 MHz, CD$_3$OD) δ 8.59-8.41 (m, 4H), 7.22 (dd, J=6.7, 1.9 Hz, 1H), 7.10 (dd, J=8.9, 6.6 Hz, 1H), 5.03 (s, 2H), 4.97 (d, J=4.3 Hz, 2H), 4.23 (s, 3H), 3.88 (d, J=1.7 Hz, 3H), 3.47 (d, J=4.9 Hz, 3H), 3.25 (s, 2H). MS (M+H)+ found for C$_{21}$H$_{22}$ClFN$_6$O$_2$S: 477.2.

Example 416

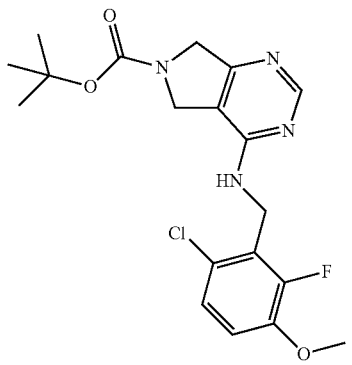 [SMILES: COc1ccc(Cl)c(CNc2ncnc3c2CN(C(=O)OC(C)(C)C)C3)c1F]

tert-butyl 4-((6-chloro-2-fluoro-3-methoxybenzyl)amino)-5,7-dihydro-6H-pyrrolo[3,4-d]pyrimidine-6-carboxylate Tert-butyl 4-chloro-5H,6H,7H-pyrrolo[3,4-d]pyrimidine-6-carboxylate (1.50 g; 5.87 mmol; 1.00 eq.) and (6-chloro-2-fluoro-3-methoxyphenyl)methanamine (1 112.32 mg; 5.87 mmol; 1.00 eq.) were dissolved in DMF (19 ml). Hunig's base-ethylbis(propan-2-yl)amine (1.53 ml; 8.80 mmol; 1.50 eq.) was added and the reaction was heated in metal sand bath at 45° C. for 14 h. The reaction temperature was then increased to 60° C. for 8 h more before cooling to 25° C. The reaction mixture was partitioned into water (200 ml) and ethyl acetate (100 ml), the phases were separated and the aqueous phase was extracted with more ethyl acetate (2×50 ml). An insoluble solid was filtered from the liquid phases. The combined organic phases were washed with water (100 ml) and brine (50 ml), dried over sodium sulfate and evaporated to a solid. The insoluble solid was extracted with 1:1 ethyl acetate:DCM (100 ml) to leave a white solid of tert-butyl 4-((6-chloro-2-fluoro-3-methoxybenzyl)amino)-5,7-dihydro-6H-pyrrolo[3,4-d]pyrimidine-6-carboxylate (0.63 g). The extraction solvent and crude solid from evaporation were combined and purified by silica gel chromatography (ethyl acetate/hexanes gradient then ethyl acetate/DCM gradient) to give more tert-butyl 4-((6-chloro-2-fluoro-3-methoxybenzyl)amino)-5,7-dihydro-6H-pyrrolo[3,4-d]pyrimidine-6-carboxylate (1.38 g) as a white solid. $^1$H NMR (400 MHz, DMSO-d$_6$) δ 8.43 (s, 1H), 7.65-7.56 (m, 1H), 7.31-7.24 (m, 1H), 7.18 (d, J=9.0, 3.4 Hz, 1H), 4.70-4.63 (m, 2H), 4.41-4.29 (m, 4H), 3.85 (s, 3H), 1.44 (s, 9H).

Example 417

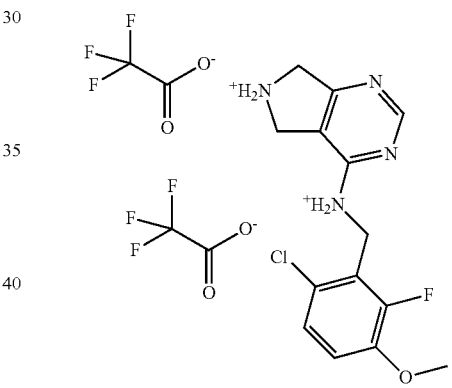

4-((6-chloro-2-fluoro-3-methoxybenzyl)ammonio)-6,7-dihydro-5H-pyrrolo[3,4-d]pyrimidin-6-ium 2,2,2-trifluoroacetate Tert-butyl 4-{[(6-chloro-2-fluoro-3-methoxyphenyl)methyl]amino}-5H,6H,7H-pyrrolo[3,4-d]pyrimidine-6-carboxylate (2.01 g; 4.92 mmol; 1.00 eq.)(Example 416) was suspended in dichloromethane (15 ml). The reaction was stirred in an ice bath and trifluoroacetic acid (9.41 ml; 122.90 mmol; 25.00 eq.) was added slowly. The reaction was then stirred at 25° C. After 2 h, the reaction was evaporated to a syrup, triturated with toluene and evaporated (3×50 ml) to give 4-((6-chloro-2-fluoro-3-methoxybenzyl)ammonio)-6,7-dihydro-5H-pyrrolo[3,4-d]pyrimidin-6-ium 2,2,2-trifluoroacetate (3.2 g) as a white solid. $^1$H NMR (400 MHz, DMSO-d$_6$) δ 9.41 (s, 2H), 8.53 (s, 1H), 7.88-7.79 (m, 1H), 7.30 (dd, J=9.0, 1.7 Hz, 1H), 7.20 (dd, J=8.9 Hz, 1H), 4.75-4.67 (m, 2H), 4.40-4.24 (m, 4H), 3.85 (s, 3H). MS (M+H)+ found for C$_{14}$H$_{16}$ClF: 309.0.

Example 418

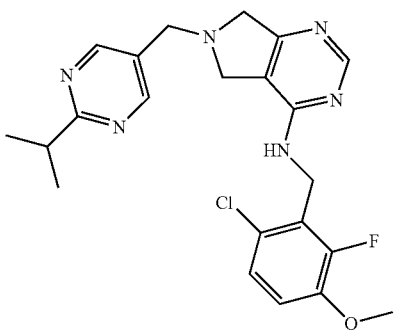 [SMILES: COc1ccc(Cl)c(CNc2ncnc3c2CN(Cc2cnc(C(C)C)nc2)C3)c1F]

Example 419

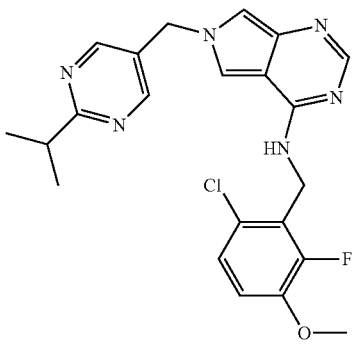 [SMILES: COc1ccc(Cl)c(CNc2ncnc3cn(Cc4cnc(C(C)C)nc4)cc23)c1F]

N-(6-chloro-2-fluoro-3-methoxybenzyl)-6-((2-isopropylpyrimidin-5-yl)methyl)-6,7-dihydro-5H-pyrrolo[3,4-d]pyrimidin-4-amine and N-(6-chloro-2-fluoro-3-methoxybenzyl)-6-((2-isopropylpyrimidin-5-yl)methyl)-6H-pyrrolo[3,4-d]pyrimidin-4-amine 2-Isopropyl-5-pyrimidinecarbaldehyde (30.04 mg; 0.20 mmol; 1.10 eq.) was dissolved in 1,2-dichloroethane (3 ml). 4-{[[(6-chloro-2-fluoro-3-methoxyphenyl)methyl]azaniumyl}-5H,6H,7H-pyrrolo[3,4-d]pyrimidin-6-ium ditrifluoroacetate (119.02 mg; 0.18 mmol; 1.00 eq.)(Example 417) and 3 Å molecular sieves (45 mg) were added and the reaction was stirred for 50 m. Na(OAc)₃BH (96.34 mg; 0.45 mmol; 2.50 eq.) was then added and the reaction was stirred for 16 h. Sodium bicarbonate solution (5 ml) was added and the reaction was partitioned into ethyl acetate (50 ml) and more dilute sodium bicarbonate solution (20 ml). The phases were separated and the aqueous phase was extracted with ethyl acetate (2×25 ml). The combined organic phases were washed with brine and dried over sodium sulfate. After evaporation the residue was purified by reverse phase chromatography (acetonitrile gradient with 0.1% aqueous formic acid, Waters XSelect CSH column) to give N-(6-chloro-2-fluoro-3-methoxybenzyl)-6-((2-isopropylpyrimidin-5-yl)methyl)-6,7-dihydro-5H-pyrrolo[3,4-d]pyrimidin-4-amine (42 mg) as a white solid, and N-(6-chloro-2-fluoro-3-methoxybenzyl)-6-((2-isopropylpyrimidin-5-yl)methyl)-6H-pyrrolo[3,4-d]pyrimidin-4-amine (8 mg) as a white solid.

N-(6-chloro-2-fluoro-3-methoxybenzyl)-6-((2-isopropylpyrimidin-5-yl)methyl)-6,7-dihydro-5H-pyrrolo[3,4-d]pyrimidin-4-amine ¹H NMR (400 MHz, CD₃OD) δ 8.73 (s, 2H), 8.38 (s, 1H), 7.17 (dd, J=8.9, 1.9 Hz, 1H), 7.05 (dd, J=8.8 Hz, 1H), 4.77 (d, J=2.0 Hz, 2H), 3.95 (s, 2H), 3.91-3.88 (m, 2H), 3.86 (s, 3H), 3.81-3.76 (m, 2H), 3.20 (dq, J=13.8, 6.9 Hz, 1H), 1.32 (d, J=6.9 Hz, 6H). MS (M+H)⁺ found for C₂₂H₂₄ClFN₆O: 443.2.

N-(6-chloro-2-fluoro-3-methoxybenzyl)-6-((2-isopropylpyrimidin-5-yl)methyl)-6H-pyrrolo[3,4-d]pyrimidin-4-amine ¹H NMR (400 MHz, CD₃OD) δ 8.63 (s, 2H), 8.48 (s, 1H), 8.17 (s, 1H), 7.55 (s, 1H), 7.29 (d, J=2.2 Hz, 1H), 7.23 (dd, J=9.0, 1.8 Hz, 1H), 7.11 (dd, J=8.9 Hz, 1H), 7.07 (s, OH), 5.45 (s, 2H), 4.90 (d, J=2.2 Hz, 2H), 3.87 (d, J=9.3 Hz, 4H), 3.18 (hept, J=7.0 Hz, 1H), 1.34-1.26 (m, 6H). MS (M+H)⁺ found for C₂₂H₂₂ClFN₆O: 441.1.

Example 420

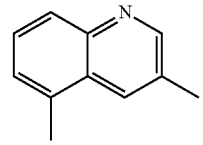

3,5-dimethylquinoline

Into a 100-mL 3-necked round-bottom flask purged and maintained with an inert atmosphere of nitrogen, was placed a mixture of 5-bromo-3-methylquinoline (2.50 g, 11.26 mmol, 1.00 equiv), dioxane (50 mL), Pd(PPh₃)₄ (1.30 g, 1.12 mmol, 0.10 equiv), potassium carbonate (4.00 g, 28.94 mmol, 2.50 equiv) and trimethyl-1,3,5,2,4,6-trioxatriborinane (2.10 g, 16.73 mmol, 1.50 equiv). The resulted solution was stirred overnight at 110° C. The resulted mixture was concentrated under vacuum. The residue was purified by silica gel column chromatography eluted with ethyl acetate and petroleum ether (1:10). This resulted in 1.65 g (93%) of 3,5-dimethylquinoline as yellow solid. MS (ESI) m/z 158 [M+H]⁺.

Example 421, 422

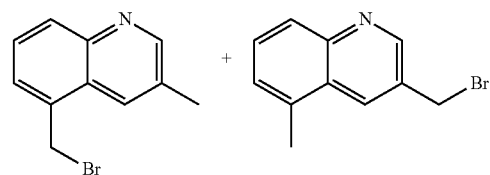

7-(bromomethyl)-1-methylnaphthalene and 1-(bromomethyl)-7-methylnaphthalene Into a 100-mL round-bottom flask purged and maintained with an inert atmosphere of nitrogen, was placed a mixture of 3,5-dimethylquinoline (1.6 g, 10.18 mmol, 1.00 equiv)(Example 420), NBS (2.0 g, 11.24 mmol, 1.10 equiv), AIBN (164 mg, 1.00 mmol, 0.10 equiv) and CCl₄ (30 mL). The resulted solution was stirred for 5 h at 80° C. The resulted mixture was concentrated under vacuum. The residue was purified by silica gel column chromatography eluted with ethyl acetate and petroleum ether (1:10). This resulted in 350 mg (a mixture of two isomers) of 7-(bromomethyl)-1-methylnaphthalene and 1-(bromomethyl)-7-methylnaphthalene as yellow solid. MS (ESI) m/z 236 [M+H]⁺.

3. Synthesis of 6-chloro-N-[(6-chloro-2-fluoro-3-methoxyphenyl)methyl]-2-[(3-methylquinolin-5-yl)methyl]-2H-pyrazolo[3,4-d]pyrimidin-4-amine and 6-chloro-N-[(6-chloro-2-fluoro-3-methoxyphenyl)methyl]-2-[(5-methylquinolin-3-yl)methyl]-2H-pyrazolo[3,4-d]pyrimidin-4-amine Example 423, 424

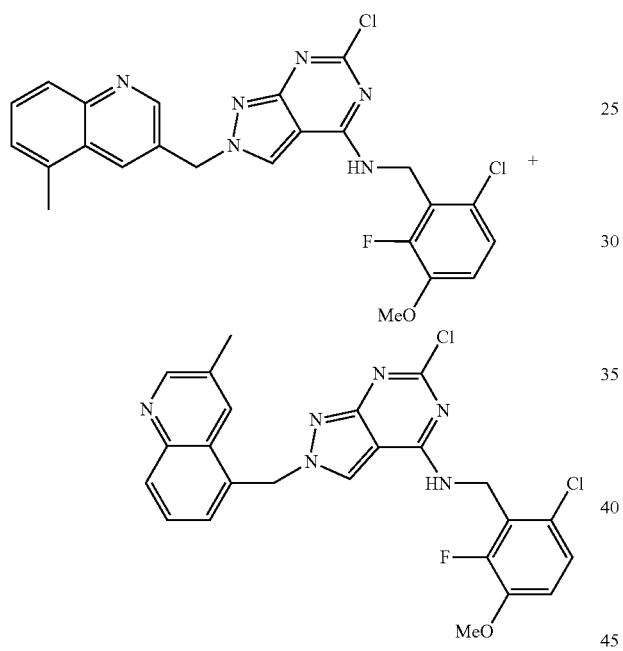

6-chloro-N-[(6-chloro-2-fluoro-3-methoxyphenyl)methyl]-2-[(3-methylquinolin-5-yl)methyl]-2H-pyrazolo[3,4-d]pyrimidin-4-amine and 6-chloro-N-[(6-chloro-2-fluoro-3-methoxyphenyl)methyl]-2-[(5-methylquinolin-3-yl)methyl]-2H-pyrazolo[3,4-d]pyrimidin-4-amine Into a 100-mL round-bottom flask purged and maintained with an inert atmosphere of nitrogen, was placed a mixture of 5-(bromomethyl)-3-methylquinoline and 3-(bromomethyl)-5-methylquinoline (two isomers, 350 mg, 1.48 mmol, 1.00 equiv)(Example 421, 422), CH₃CN (30 mL), 6-chloro-N-[(6-chloro-2-fluoro-3-methoxyphenyl)methyl]-2H-pyrazolo[3,4-d]pyrimidin-4-amine (507 mg, 1.48 mmol, 1.00 equiv), Cs₂CO₃ (965 mg, 2.96 mmol, 2.00 equiv) and KI (246 mg, 1.00 equiv). The resulted solution was stirred for 2 h at room temperature. The solids were filtered out. The filtrate was concentrated under vacuum. The residue was purified by Prep-HPLC with the following conditions. Column: Waters X-bridge RP18, 19×150 mm, 5 μm; mobile phase: CH₃CN and H₂O (it contains 10 mM NH₄HCO₃) with a gradient of 40% to 60% acetonitrile in 6 min; flow rate: 20 mL/min; detector UV wavelength: 254 nm and 220 nm. This resulted in 90 mg (two isomers) of 6-chloro-N-[(6-chloro-2-fluoro-3-methoxyphenyl)methyl]-2-[(3-methylquinolin-5-yl)methyl]-2H-pyrazolo[3,4-d]pyrimidin-4-amine and 6-chloro-N-[(6-chloro-2-fluoro-3-methoxyphenyl)methyl]-2-[(5-methylquinolin-3-yl)methyl]-2H-pyrazolo[3,4-d]pyrimidin-4-amine as white solid. MS (ESI) m/z 497 [M+H]⁺.

Example 425, 426

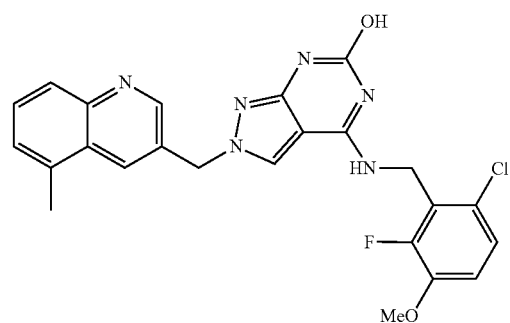

Example 425

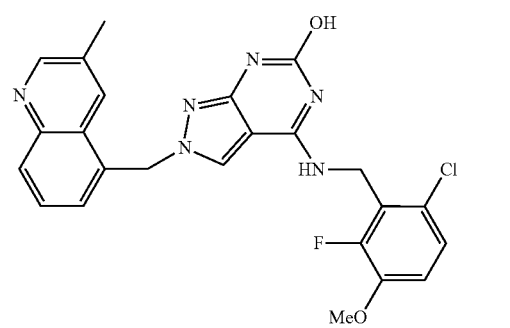

Example 426

4-[[(6-chloro-2-fluoro-3-methoxyphenyl)methyl]amino]-2-[(5-methylquinolin-3-yl)methyl]-2H-pyrazolo[3,4-d]pyrimidin-6-ol and 4-[[(6-chloro-2-fluoro-3-methoxyphenyl)methyl]amino]-2-[(3-methylquinolin-5-yl)methyl]-2H-pyrazolo[3,4-d]pyrimidin-6-ol Into a 50-mL round-bottom flask, was placed 6-chloro-N-[(6-chloro-2-fluoro-3-methoxyphenyl)methyl]-2-[(5-methylquinolin-3-yl)methyl]-2H-pyrazolo[3,4-d]pyrimidin-4-amine and 6-chloro-N-[(6-chloro-2-fluoro-3-methoxyphenyl)methyl]-2-[(3-methylquinolin-5-yl)methyl]-2H-pyrazolo[3,4-d]pyrimidin-4-amine (two isomers, 88 mg, 0.18 mmol, 1.00 equiv)(Example 423, 424) and concentrated HCl aqueous solution (10 mL). The resulted solution was stirred for 1 h at 90° C. The reaction mixture was concentrated under vacuum. The residue was purified by Prep-HPLC with the following conditions. Column: Sunfire C18, 19×150 mm, 5 μm; mobile phase: CH₃CN and H₂O (it contains 0.05% of ammonia) with a gradient of 15% to 30% CH₃CN in 6 min; flow rate: 20 mL/min; detector UV wavelength: 254 nm and 220 nm. This resulted in 2.3 mg (3%) of 4-[[(6-chloro-2-fluoro-3-methoxyphenyl)methyl]amino]-2-[(5-methylquinolin-3-yl)methyl]-2H-pyrazolo[3,4-d]pyrimidin-6-ol and 26.7 mg (32%) of 4-[[(6-chloro-2-fluoro-3-methoxyphenyl)methyl]amino]-2-[(3-methylquinolin-5-yl)methyl]-2H-pyrazolo[3,4-d]pyrimidin-6-ol as white solids.

$^1$H NMR (300 MHz, DMSO-$d_6$): δ 10.71 (br, 1H), 8.86 (s, 1H), 8.48 (s, 1H), 8.39 (br, 1H), 8.24 (br, 1H), 8.14 (s, 1H), 7.87 (d, J=8.4 Hz, 1H), 7.66 (t, J=7.5 Hz, 1H), 7.48 (d, J=7.5 Hz, 1H), 7.29-7.32 (m, 1H), 7.20-7.23 (m, 1H), 5.58 (s, 2H), 4.65 (br, 2H), 3.85 (s, 3H), 2.65 (s, 3H). MS (ESI) m/z 479 [M+H]$^+$.

$^1$H NMR (300 MHz, DMSO-$d_6$): δ 12.37 (s, 1H), 10.64 (br, 1H), 8.93 (s, 1H), 8.55 (s, 2H), 8.09 (d, J=8.1 Hz, 1H), 7.78 (t, J=7.8 Hz, 1H), 7.59 (d, J=6.9 Hz, 1H), 7.27-7.40 (m, 2H), 5.99 (s, 2H), 4.86 (br, 2H), 3.87 (s, 3H), 2.54 (s, 3H). MS (ESI) m/z 479 [M+H]$^+$.

Example 427

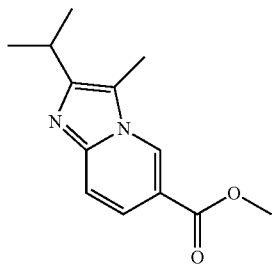 [SMILES: COC(=O)c1ccc2nc(C(C)C)c(C)n2c1]

methyl 3-methyl-2-(propan-2-yl)imidazo[1,2-a]pyridine-6-carboxylate

Into a 250-mL 3-necked round-bottom flask purged and maintained with an inert atmosphere of nitrogen, was placed a solution of 2-methylpentan-3-one (6.00 g, 59.90 mmol, 1.00 equiv) in tetrahydrofuran (60 mL), to which was added LiHMDS (63 mL, 1.05 equiv, 1M) dropwise with stirring at −78° C., to which was added Br$_2$ (9.60 g, 60.07 mmol, 1.00 equiv) at −78° C. The resulted solution was stirred for 30 min at −78° C. The reaction was then quenched by the addition of 120 mL of saturated NaHCO$_3$ aqueous solution. The resulted solution was extracted with 3×100 mL of ethyl acetate and the organic layers were combined, washed with 1×100 mL of Na$_2$S$_2$O$_3$ aqueous solution and concentrated under vacuum. This resulted in 10.60 g (crude) of 2-bromo-4-methylpentan-3-one as brown solid.

Into a 100-mL round-bottom flask, was placed a mixture of methyl 6-aminopyridine-3-carboxylate (3 g, 19.72 mmol, 1.00 equiv), ethanol (60 mL), 2-bromo-4-methylpentan-3-one (7 g, crude) and DIEA (3.8 g, 29.40 mmol, 1.50 equiv). The resulted solution was refluxed overnight. The mixture was then concentrated under vacuum. The residue was purified by silica gel column chromatography eluted with ethyl acetate and petroleum ether (1:3). This resulted in 1.05 g (23%) of methyl 3-methyl-2-(propan-2-yl)imidazo[1,2-a]pyridine-6-carboxylate as yellow solid. MS (ESI) m/z 233 [M+H]$^+$.

Example 428

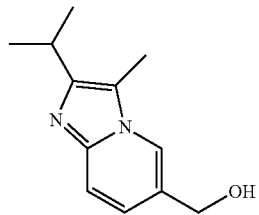

[3-methyl-2-(propan-2-yl)imidazo[1,2-a]pyridin-6-yl]methanol

Into a 100-mL 3-necked round-bottom flask purged and maintained with an inert atmosphere of nitrogen, was placed a mixture of methyl 3-methyl-2-(propan-2-yl)imidazo[1,2-a]pyridine-6-carboxylate (1.05 g, 4.52 mmol, 1.00 equiv) (Example 427) in tetrahydrofuran (30 mL), to which was added LiAlH$_4$ (342 mg, 9.01 mmol, 2.00 equiv) in several batches at 0° C. The resulted solution was stirred for 2 h at room temperature. The reaction was then quenched by the addition of 20 mL of water/ice. The solids were filtered out. The filtrate was extracted with ethyl acetate (50 mL×3), washed with 100 mL of brine, dried over anhydrous sodium sulfate and concentrated under vacuum. The residue was purified by silica gel column chromatography eluted with ethyl acetate and petroleum ether (1:1). This resulted in 400 mg (43%) of [3-methyl-2-(propan-2-yl)imidazo[1,2-a]pyridin-6-yl]methanol as yellow solid. MS (ESI) m/z 205 [M+H]+.

Example 429

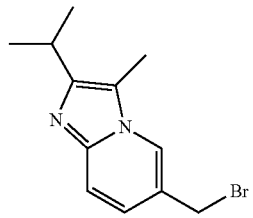

6-(bromomethyl)-3-methyl-2-(propan-2-yl)imidazo[1,2-a]pyridine

Into a 50-mL 3-necked round-bottom flask purged and maintained with an inert atmosphere of nitrogen, was placed a mixture of [3-methyl-2-(propan-2-yl)imidazo[1,2-a]pyridin-6-yl]methanol (150 mg, 0.73 mmol, 1.00 equiv)(Example 428) in dichloromethane (10 mL), to which was added PBr$_3$ (200 mg, 0.74 mmol, 1.00 equiv) with stirring at 0° C. The resulted solution was stirred for 1 h at room temperature. The reaction was then quenched by the addition of saturated NaHCO$_3$ aqueous solution (50 mL) at 0° C. Then it was extracted with 3×20 mL of CH$_2$Cl$_2$, dried over anhydrous sodium sulfate and concentrated under vacuum. This resulted in 160 mg (82%) of 6-(bromomethyl)-3-methyl-2-(propan-2-yl)imidazo[1,2-a]pyridine as yellow solids. MS (ESI) m/z 267 [M+H]$^+$.

Example 430

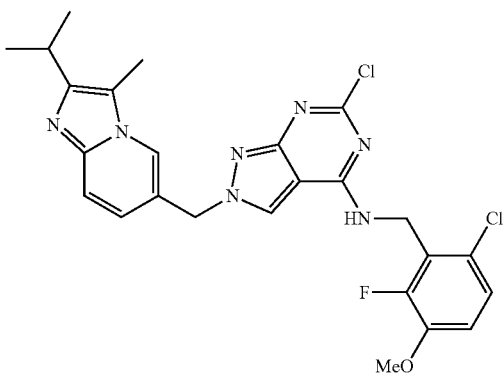 [SMILES: COc1ccc(Cl)c(CNc2nc(Cl)nc3nn(Cc4ccc5nc(C(C)C)c(C)n5c4)cc23)c1F]

6-chloro-N-[(6-chloro-2-fluoro-3-methoxyphenyl)methyl]-2-[[3-methyl-2-(propan-2-yl)imidazo[1,2-a]pyridin-6-yl]methyl]-2H-pyrazolo[3,4-d]pyrimidin-4-amine Into a 100-mL round-bottom flask purged and maintained with an inert atmosphere of nitrogen, was placed a mixture of 6-(bromomethyl)-3-methyl-2-(propan-2-yl)imidazo[1,2-a]pyridine (220 mg, 0.82 mmol, 1.00 equiv), $CH_3CN$ (30 mL), 6-chloro-N-[(6-chloro-2-fluoro-3-methoxyphenyl)methyl]-2H-pyrazolo[3,4-d]pyrimidin-4-amine (280 mg, 0.82 mmol, 1.00 equiv)(Example 429), $Cs_2CO_3$ (535 mg, 1.64 mmol, 2.00 equiv) and KI (136 mg, 1.00 equiv). The resulted solution was stirred for 3 h at room temperature. The solids were filtered out. The filtrate was concentrated under vacuum. The residue was purified by Prep-HPLC with the following conditions. Column: Waters X-bridge RP18, 19×150 mm, 5 μm; mobile phase: $CH_3CN$ and $H_2O$ (it contains 10 mM $NH_4HCO_3$+0.05% ammonia) with a gradient of 55% to 75% acetonitrile in 8 min; flow rate: 20 mL/min; detector UV wavelength: 254 nm and 220 nm. This resulted in 43 mg (10%) of 6-chloro-N-[(6-chloro-2-fluoro-3-methoxyphenyl)methyl]-2-[[3-methyl-2-(propan-2-yl)imidazo[1,2-a]pyridin-6-yl]methyl]-2H-pyrazolo[3,4-d]pyrimidin-4-amine as yellow solid. MS (ESI) m/z 528 $[M+H]^+$.

Example 431

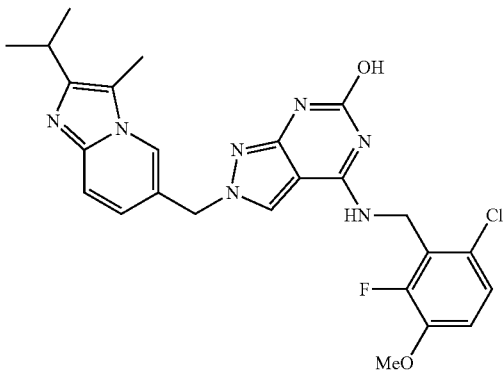 [SMILES: COc1ccc(Cl)c(CNc2nc(O)nc3nn(Cc4ccc5nc(C(C)C)c(C)n5c4)cc23)c1F]

4-[[(6-chloro-2-fluoro-3-methoxyphenyl)methyl]amino]-2-[[3-methyl-2-(propan-2-yl)imidazo[1,2-a]pyridin-6-yl]methyl]-2H-pyrazolo[3,4-d]pyrimidin-6-ol Into a 8-mL vial, was placed a mixture of 6-chloro-N-[(6-chloro-2-fluoro-3-methoxyphenyl)methyl]-2-[[3-methyl-2-(propan-2-yl)imidazo[1,2-a]pyridin-6-yl]methyl]-2H-pyrazolo[3,4-d]pyrimidin-4-amine (41 mg, 0.08 mmol, 1.00 equiv)(Example 430) and concentrated HCl aqueous solution (5 mL). The resulted solution was stirred for 1 h at 90° C. The resulted mixture was concentrated under vacuum. The residue was purified by Prep-HPLC with the following conditions. Column: Sunfire C18, 19×150 mm, 5 μm; mobile phase: $CH_3CN$ and $H_2O$ (it contains 0.05% ammonia) with a gradient of 40% to 50% $CH_3CN$ in 8 min; flow rate: 20 mL/min; detector UV wavelength: 254 nm and 220 nm. This resulted in 1.5 mg (4%) of 4-[[(6-chloro-2-fluoro-3-methoxyphenyl)methyl]amino]-2-[[3-methyl-2-(propan-2-yl)imidazo[1,2-a]pyridin-6-yl]methyl]-2H-pyrazolo[3,4-d]pyrimidin-6-ol as white solid. $^1$H NMR (300 MHz, DMSO-$d_6$): δ 10.70 (br, 1H), 8.39 (s, 1H), 8.16-8.18 (m, 1H), 8.02 (s, 1H), 7.46 (d, J=8.7 Hz, 1H), 7.29-7.32 (m, 1H), 7.20-7.23 (m, 1H), 7.06-7.09 (m, 1H), 5.32 (s, 2H), 4.63 (br, 2H), 3.85 (s, 3H), 2.28 (s, 3H), 1.23 (d, J=6.6 Hz, 6H). MS (ESI) m/z 510 $[M+H]^+$.

Example 432

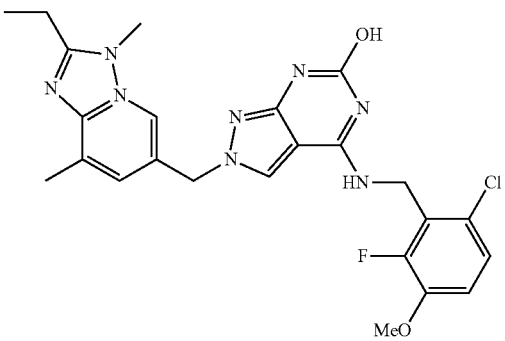

4-[[(6-chloro-2-fluoro-3-methoxyphenyl)methyl]amino]-2-[(2-ethyl-1,4-dimethyl-1H-1,3-benzodiazol-6-yl)methyl]-2H-pyrazolo[3,4-d]pyrimidin-6-ol 4-[[(6-chloro-2-fluoro-3-methoxyphenyl)methyl]amino]-2-[(2-ethyl-1,4-dimethyl-1H-1,3-benzodiazol-6-yl)methyl]-2H-pyrazolo[3,4-d]pyrimidin-6-ol was prepared in a similar manner as Example 431. $^1$H NMR (300 MHz, DMSO-d): δ 10.67 (br, 1H), 8.15 (br, 1H), 7.95 (br, 1H), 7.28-7.31 (m, 2H), 7.16-7.22 (m, 1H), 6.94 (br, 1H), 5.32 (br, 2H), 4.63 (br, 2H), 3.84 (s, 3H), 3.69 (s, 3H), 2.86 (q, J=7.2 Hz, 2H), 1.29 (t, J=7.5 Hz, 3H).
MS (ESI) m/z 510 $[M+H]^+$

Example 433

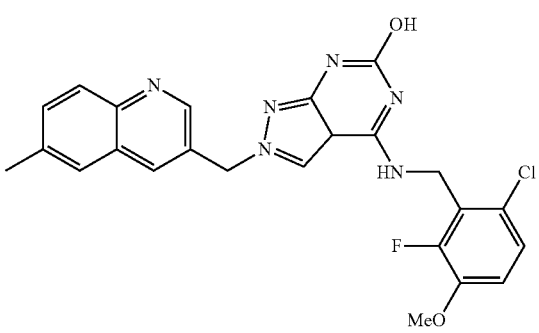

4-[[(6-chloro-2-fluoro-3-methoxyphenyl)methyl]amino]-2-[(6-methylquinolin-3-yl)methyl]-2H-pyrazolo[3,4-d]pyrimidin-6-ol 4-[[(6-chloro-2-fluoro-3-methoxyphenyl)methyl]amino]-2-[(6-methylquinolin-3-yl)methyl]-2H-pyrazolo[3,4-d]pyrimidin-6-ol was prepared in a similar manner as Example 431. ¹H NMR (300 MHz, DMSO-d₆): δ 10.71 (br, 1H), 8.80 (s, 1H), 8.25 (br, 1H), 8.14-8.17 (m, 2H), 7.92 (d, J=8.7 Hz, 1H), 7.75 (br, 1H), 7.60-7.62 (m, 1H), 7.31 (d, J=8.7 Hz, 1H), 7.18-7.24 (m, 1H), 5.55 (s, 2H), 4.66 (br, 2H), 3.86 (s, 3H).
MS (ESI) m/z 480 [M+H]⁺.

Example 434

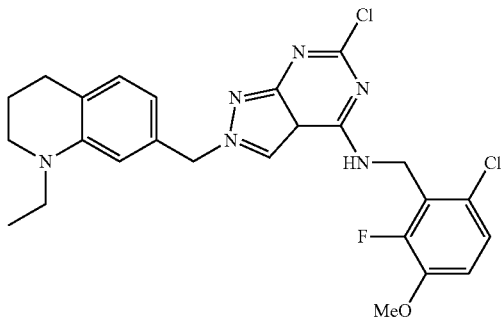

6-chloro-N-[(6-chloro-2-fluoro-3-methoxyphenyl)methyl]-2-[(1-ethyl-1,2,3,4-tetrahydroquinolin-7-yl)methyl]-2H-pyrazolo[3,4-d]pyrimidin-4-amine 6-chloro-N-[(6-chloro-2-fluoro-3-methoxyphenyl)methyl]-2-[(1-ethyl-1,2,3,4-tetrahydroquinolin-7-yl)methyl]-2H-pyrazolo[3,4-d]pyrimidin-4-amine was prepared in a similar manner as Example 430. ¹H NMR (300 MHz, DMSO-d₆): δ 8.80 (br, 1H), 8.24 (s, 1H), 7.20-7.32 (m, 2H), 6.84 (d, J=7.5 Hz, 1H), 6.60 (s, 1H), 6.41 (br, 1H), 5.35 (s, 2H), 4.71 (s, 2H), 3.85 (s, 3H), 3.19 (br, 3H), 2.62 (br, 2H), 1.82 (br, 2H), 1.23 (br, 1H), 1.00 (br, 3H). MS (ESI) m/z 515 [M+H]⁺.

Example 435

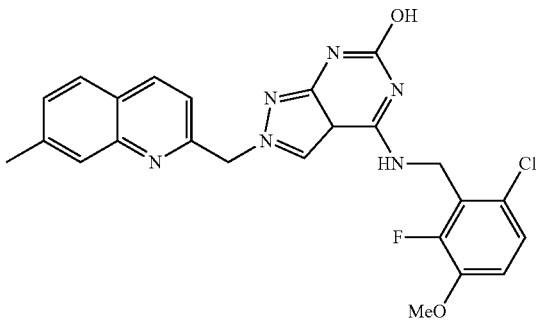

4-[[(6-chloro-2-fluoro-3-methoxyphenyl)methyl]amino]-2-[(7-methylquinolin-2-yl)methyl]-2H-pyrazolo[3,4-d]pyrimidin-6-ol 4-[[(6-chloro-2-fluoro-3-methoxyphenyl)methyl]amino]-2-[(7-methylquinolin-2-yl)methyl]-2H-pyrazolo[3,4-d]pyrimidin-6-ol was prepared in a similar manner as Example 431. ¹H NMR (300 MHz, DMSO-d): δ 10.72 (br, 1H), 8.21-8.24 (m, 1H), 8.16 (br, 1H), 7.89-7.98 (m, 1H), 7.77 (s, 1H), 7.40-7.47 (m, 2H), 7.30-7.33 (m, 1H), 7.18-7.24 (m, 1H), 5.81 (s, 0.5H), 5.53 (s, 1.5H), 4.66 (br, 1.5H), 4.62 (br, 1.5H), 3.85 (s, 3H), 2.64 (s, 3H). MS (ESI) m/z 479 [M+H]⁺.

Example 436

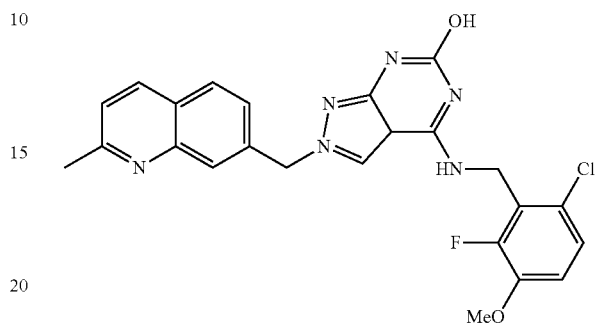

4-[[(6-chloro-2-fluoro-3-methoxyphenyl)methyl]amino]-2-[(2-methylquinolin-7-yl)methyl]-2H-pyrazolo[3,4-d]pyrimidin-6-ol 4-[[(6-chloro-2-fluoro-3-methoxyphenyl)methyl]amino]-2-[(2-methylquinolin-7-yl)methyl]-2H-pyrazolo[3,4-d]pyrimidin-6-ol was prepared in a similar manner as Example 431. ¹H NMR (300 MHz, DMSO-d₆): δ 10.72 (br, 1H), 8.22-8.24 (m, 2H), 8.16 (s, 1H), 7.90 (d, J=8.1 Hz, 1H), 7.77 (s, 1H), 7.40-7.42 (m, 2H), 7.30-7.32 (m, 1H), 7.21-7.23 (m, 1H), 5.53 (s, 2H), 4.66 (br, 2H), 3.85 (s, 3H), 2.64 (s, 3H). MS (ESI) m/z 479 [M+H]⁺.

Example 437

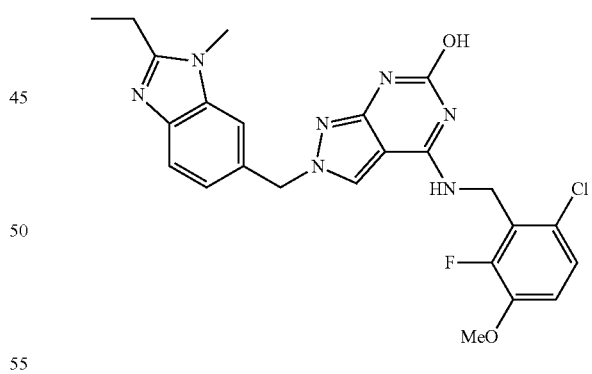

4-[[(6-chloro-2-fluoro-3-methoxyphenyl)methyl]amino]-2-[(2-ethyl-1-methyl-1H-1,3-benzodiazol-6-yl)methyl]-2H-pyrazolo[3,4-d]pyrimidin-6-ol 4-[[(6-chloro-2-fluoro-3-methoxyphenyl)methyl]amino]-2-[(2-ethyl-1-methyl-1H-1,3-benzodiazol-6-yl)methyl]-2H-pyrazolo[3,4-d]pyrimidin-6-ol was prepared in a similar manner as Example 431. ¹H-NMR (300 MHz, DMSO-d₆): δ 8.17-8.14 (m, 1H), 7.97 (s, 1H), 7.54-7.49 (m, 2H), 7.31-7.10 (m, 3H), 5.37 (s, 1H), 4.64-4.60 (m, 2H), 3.84 (s, 3H), 3.70 (s, 3H), 2.90-2.82 (m, 2H), 1.29 (t, J=7.2 Hz, 3H). LC-MS (ESI) m/z: calculated for C22H19ClFN7O2: 495. found: 496 [M+H]+.

Example 438

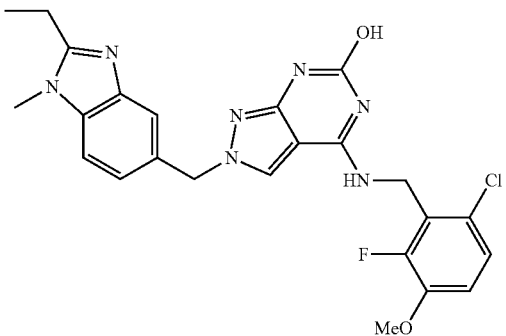 [SMILES: CCc1nc2cc(Cn3cc4c(NCc5c(Cl)ccc(OC)c5F)nc(O)nc4n3)ccc2n1C]

4-[[(6-chloro-2-fluoro-3-methoxyphenyl)methyl]amino]-2-[(2-ethyl-1-methyl-1H-1,3-benzodiazol-5-yl)methyl]-2H-pyrazolo[3,4-d]pyrimidin-6-ol 4-[[(6-chloro-2-fluoro-3-methoxyphenyl)methyl]amino]-2-[(2-ethyl-1-methyl-1H-1,3-benzodiazol-5-yl)methyl]-2H-pyrazolo[3,4-d]pyrimidin-6-ol was prepared in a similar manner as Example 431. ¹H-NMR (300 MHz, DMSO-d₆): δ 8.16-8.14 (m, 1H), 7.98-7.97 (m, 1H), 7.60-7.45 (m, 2H), 7.31-7.10 (m, 3H), 5.40-5.31 (m, 2H), 4.66-4.59 (m, 2H), 3.70 (s, 3H), 3.51 (s, 3H), 2.91-2.80 (m, 2H), 1.28 (t, J=7.5 Hz, 3H). LC-MS (ESI) m/z: calculated for C22H19ClFN7O2: 495. found: 496 [M+H]+. Rt: 1.007 min.

Example 439

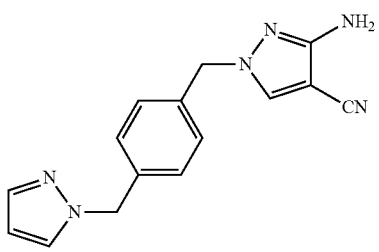 [SMILES: N#Cc1cn(Cc2ccc(Cn3cccn3)cc2)nc1N]

1-(4-((1H-pyrazol-1-yl)methyl)benzyl)-3-amino-1H-pyrazole-4-carbonitrile

Into an 100-mL round-bottom flask, was placed 60% sodium hydride (1.16 g, 29.00 mmol, 1.30 equiv, in oil) in tetrahydrofuran (50 mL) with stirring at 0° C., to which was added a solution of 3-amino-1H-pyrazole-4-carbonitrile (2.54 g, 23.50 mmol, 1.05 equiv) in THF (20 mL) dropwise during 10 min. The reaction was stirred for half an hour at 0° C., then a solution of 1-{[4-(bromomethyl)phenyl]methyl}-1H-pyrazole (5.60 g, 22.30 mmol, 1.00 equiv) in tetrahydrofuran (20 mL) was added dropwise during 10 min. The resulted solution was stirred for an additional 2 h at 60° C. The reaction was then quenched by the addition of 20 mL of water. The resulted solution was extracted with 2×50 of ethyl acetate. The organic phase was washed with 3×20 mL of brine, dried over anhydrous sodium sulfate and concentrated under vacuum. The residue was purified by silica gel column eluted with ethyl acetate/petroleum ether (4:1). This resulted in 3.00 g (48%) of 3-amino-1-[[4-(1H-pyrazol-1-ylmethyl)phenyl]methyl]-1H-pyrazole-4-carbonitrile as a light yellow solid. LC-MS (ESI) m/z: calculated for C11H14N2O2: 278.11. found: 279 [M+H]+.

Example 440

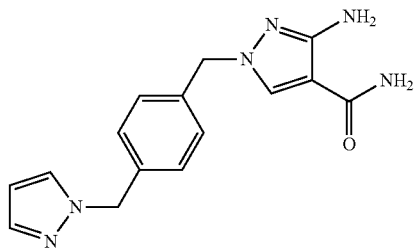 [SMILES: NC(=O)c1cn(Cc2ccc(Cn3cccn3)cc2)nc1N]

1-(4-((1H-pyrazol-1-yl)methyl)benzyl)-3-amino-1H-pyrazole-4-carboxamide

Into an 100-mL round-bottom flask, was placed a mixture of 3-amino-1-[[4-(1H-pyrazol-1-ylmethyl)phenyl]methyl]-1H-pyrazole-4-carbonitrile (3.00 g, 10.78 mmol, 1.00 equiv) (Example 439), potassium carbonate (744 mg, 5.34 mmol, 0.50 equiv), 60% hydrogen peroxide (1.83 g, 53.80 mmol, 1.50 equiv) and DMSO (30 mL). The resulted solution was stirred for 1 h at room temperature, then diluted with 90 mL of EA and washed with 2×30 mL of brine. The organic phase was dried over anhydrous sodium sulfate and concentrated under vacuum. This resulted in 2.30 g (72%) crude of 3-amino-1-[[4-(1H-pyrazol-1-ylmethyl)phenyl]methyl]-1H-pyrazole-4-carboxamide as a light yellow solid.

Example 441

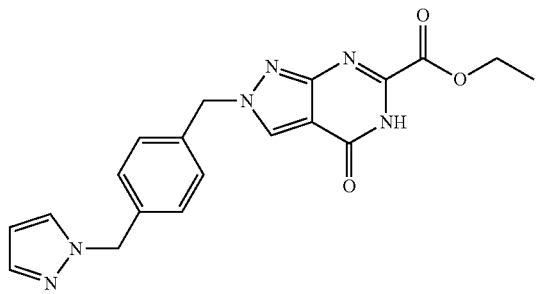 [SMILES: CCOC(=O)c1nc2nn(Cc3ccc(Cn4cccn4)cc3)cc2c(=O)[nH]1]

4-chloro-2-((6-(pyrrolidin-1-yl)pyridin-3-yl)methyl)-2H-pyrazolo[3,4-d]pyrimidine Into a 50-mL round-bottom flask, was placed a mixture of 3-amino-1-[[4-(1H-pyrazol-1-ylmethyl)phenyl]methyl]-1H-pyrazole-4-carboxamide (2.3 g, 7.76 mmol, 1.00 equiv) (Example 440), ethanol (23 mL), diethyl oxalate (1.19 g, 8.14 mmol, 1.05 equiv) and NaOEt (555 mg, 8.16 mmol, 1.05 equiv). The resulted solution was stirred for 5 h at 100° C. in an oil bath. The pH value of the solution was adjusted to 6.0 with 1 N hydrochloride aqueous solution. The resulted solution was extracted with 3×30 mL of ethyl acetate. The organic phase was washed with 2×50 mL of brine, dried over anhydrous sodium sulfate and concentrated under vacuum. This resulted in 2.60 g (crude) of ethyl 4-oxo-2-[[4-(1H-pyrazol-1-ylmethyl)phenyl]methyl]-2H,4H,5H-pyrazolo[3,4-d]pyrimidine-6-carboxylate as a yellow solid.

Example 442

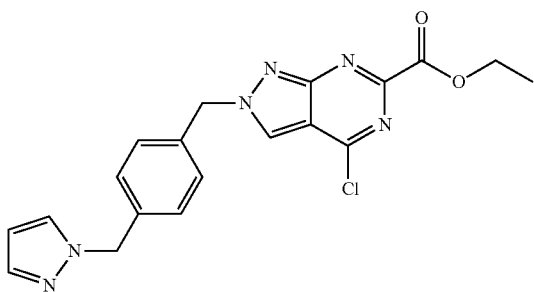 [SMILES: CCOC(=O)c1nc(Cl)c2cn(Cc3ccc(Cn4cccn4)cc3)nc2n1]

ethyl 2-(4-((1H-pyrazol-1-yl)methyl)benzyl)-4-chloro-2H-pyrazolo[3,4-d]pyrimidine-6-carboxylate Into a 50-mL round-bottom flask, was placed a mixture of ethyl 4-oxo-2-[[4-(1H-pyrazol-1-ylmethyl)phenyl]methyl]-2H,4H,5H-pyrazolo[3,4-d]pyrimidine-6-carboxylate (2.40 g, 4.44 mmol, 1.00 equiv, 70%)(Example 441), POCl3 (24 mL) and N,N-dimethylformamide (23 mg, 0.222 mmol, 0.05 equiv) with stirring. The resulted solution was reflux for 3 h. The mixture was diluted with 24 mL of DCM, quenched by the addition of 24 mL of water at 0° C. The resulted solution was extracted with 2×24 mL of dichloromethane. The organic phase was washed with 3×24 mL of brine, dried over anhydrous sodium sulfate and concentrated under vacuum. The residue was purified by silica gel column eluted with ethyl acetate/petroleum ether (4:1). This resulted in 800 mg (45%) of ethyl 4-chloro-2-[[4-(1H-pyrazol-1-ylmethyl)phenyl]methyl]-2H-pyrazolo[3,4-d]pyrimidine-6-carboxylate as a yellow solid.

Example 443

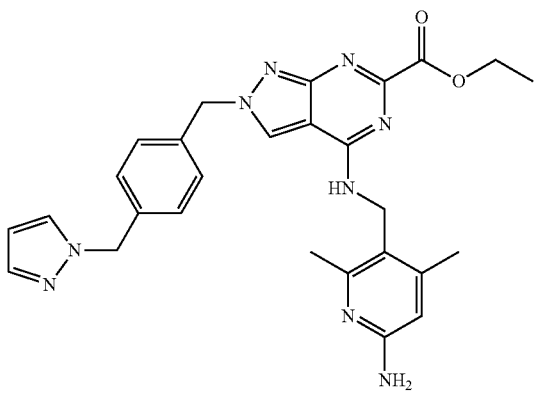 [SMILES: CCOC(=O)c1nc(NCc2c(C)cc(N)nc2C)c2cn(Cc3ccc(Cn4cccn4)cc3)nc2n1]

ethyl 2-(4-((1H-pyrazol-1-yl)methyl)benzyl)-4-((6-amino-2,4-dimethylpyridin-3-yl)methylamino)-2H-pyrazolo[3,4-d]pyrimidine-6-carboxylate Into a 25-mL round-bottom flask, was placed a mixture of ethyl 4-chloro-2-[[4-(1H-pyrazol-1-ylmethyl)phenyl]methyl]-2H-pyrazolo[3,4-d]pyrimidine-6-carboxylate (800 mg, 2.02 mmol, 1.00 equiv), 5-(aminomethyl)-4,6-dimethylpyridin-2-amine (319 mg, 2.11 mmol, 1.05 equiv)(Example 442), DIEA (520 mg, 4.02 mmol, 2.00 equiv) and DMA (8 mL). The resulted solution was stirred for 1 h at 60° C. in an oil bath. The resulted solution was diluted with 16 mL of DCM and washed with 3×8 mL of brine. The organic phase was dried over anhydrous sodium sulfate and concentrated under vacuum. This resulted in 600 mg (58%) of ethyl 4-[[(6-amino-2,4-dimethylpyridin-3-yl)methyl]amino]-2-[[4-(1H-pyrazol-1-ylmethyl)phenyl]methyl]-2H-pyrazolo[3,4-d]pyrimidine-6-carboxylate as a light yellow solid. LC-MS (ESI) m/z: calculated for $C_{27}H_{29}N_9O_2$: 511.24. found: 512 [M+H]+.

Example 444

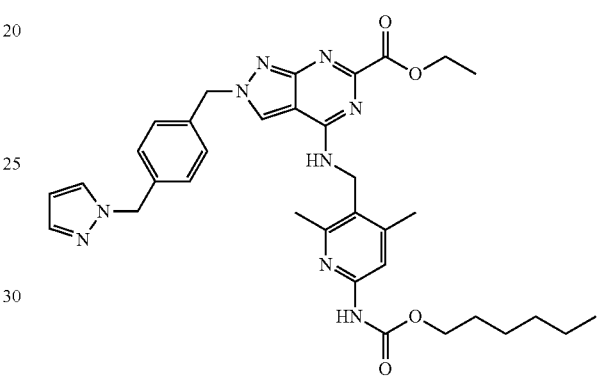

ethyl 2-(4-((1H-pyrazol-1-yl)methyl)benzyl)-4-((6-(hexyloxycarbonylamino)-2,4-dimethylpyridin-3-yl)methylamino)-2H-pyrazolo[3,4-d]pyrimidine-6-carboxylate Into a 40-mL round-bottom flask, was placed a mixture of ethyl 4-[[(6-amino-2,4-dimethylpyridin-3-yl)methyl]amino]-2-[[4-(1H-pyrazol-1-ylmethyl)phenyl]methyl]-2H-pyrazolo[3,4-d]pyrimidine-6-carboxylate (600 mg, 1.17 mmol, 1.00 equiv)(Example 442), chloro(hexyloxy)methanone (580 mg, 3.52 mmol, 3.00 equiv), pyridine (463 mg, 5.85 mmol, 5.00 equiv) and DMA (12 mL). The resulted solution was stirred for 5 h at 50° C. in an oil bath. The solids were filtered out. The filtrate was purified by Prep-HPLC with the following conditions. Column: Waters XBridge C18 19*150 mm, 5 µm; mobile phase: H2O (it is a buffer of 10 mM NH4HCO3+0.05% ammonia) and water with a gradient of 15% to 30% acetonitrile in 3 min followed by 30% to 75% acetonitrile in 8 min; flow rate: 20 mL/min; detector UV wavelength: 254 nm. This resulted in 319.2 mg (43%) of ethyl 4-[[(6-[[(hexyloxy)carbonyl]amino]-2,4-dimethylpyridin-3-yl)methyl]amino]-2-[[4-(1H-pyrazol-1-ylmethyl)phenyl]methyl]-2H-pyrazolo[3,4-d]pyrimidine-6-carboxylate as a off-white solid. $^1$H NMR (300 MHz, DMSO-$d_6$, ppm): δ 10.01 (s, 1H), 8.71 (t, J=4.5 Hz, 1H), 8.22 (s, 1H), 7.77 (d, J=2.1 Hz, 1H), 7.53 (s, 1H), 7.41 (d, J=1.2 Hz, 1H), 7.14-7.18 (m, 4H), 6.25 (t, J=2.1 Hz, 1H), 5.50 (s, 2H), 5.27-5.30 (m, 2H), 4.69 (d, J=4.5 Hz, 2H), 4.09 (q, J=7.2 Hz, 2H), 4.09 (t, J=6.6 Hz, 1H), 2.59 (s, 3H), 2.46 (s, 3H), 1.55-1.62 (m, 2H), 1.27-1.35 (m, 9H), 0.88 (t, J=6.3 Hz, 3H). LC-MS (ESI) m/z: calculated for $C_{34}H_{41}N_9O_4$: 639.33. found: 640 [M+H]+.

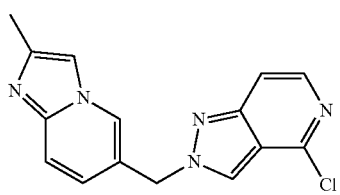 [SMILES: Cc1cn2cc(Cn3cc4c(Cl)nccc4n3)ccc2n1]

4-chloro-2-((2-methylimidazo[1,2-a]pyridin-6-yl)methyl)-2H-pyrazolo[4,3-c]pyridine Into a 50-mL 3-necked round-bottom flask purged and maintained with an inert atmosphere of nitrogen, were placed (2-methyl-2H-1,3-benzodiazol-5-yl)methanol (500 mg, 3.08 mmol, 1.00 equiv), tetrahydrofuran (10 mL), 4-chloro-2H-pyrazolo[4,3-c]pyridine (475 mg, 3.09 mmol, 1.00 equiv) and triphenyl phosphine (970 mg, 3.70 mmol, 1.20 equiv) with stirring at 0° C. This was followed by the addition of a solution of DTAD (852 mg, 3.70 mmol, 1.20 equiv) in tetrahydrofuran (5 mL) dropwise with stirring at 0° C. in 5 min. The resulting solution was stirred overnight at room temperature. The resulting mixture was concentrated under vacuum. The crude product was purified by Prep-HPLC with the following conditions: column: Waters Atlantis T3, 19×150 mm, 5 um. Mobile phase: solvent A: acetonitrile, solvent B: water contains 0.05% TFA. Gradient: solvent A from 25% to 30%. Run time: 7 min. Flow rate: 20 mL/min. UV detector wavelength: 254 nm. The PH value of the solution was adjusted to 8 with aqueous sodium bicarbonate (1 mol/L). The resulting solution was extracted with 3×100 mL of ethyl acetate and washed with 3×300 mL of brine. The organic phase was dried over anhydrous sodium sulfate and concentrated under vacuum. This resulted in 150 mg (16%) of 5-([4-chloro-2H-pyrazolo[4,3-c]pyridin-2-yl]methyl)-2-methyl-2H-1,3-benzodiazole as a light yellow solid. MS (ESI) m/z 298 [M+H]$^+$.

Example 446

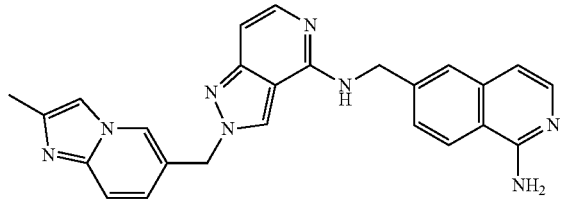 [SMILES: Cc1cn2cc(Cn3cc4c(NCc5ccc6c(N)nccc6c5)nccc4n3)ccc2n1]

6-((2-((2-methylimidazo[1,2-a]pyridin-6-yl)methyl)-2H-pyrazolo[4,3-c]pyridin-4-ylamino)methyl)isoquinolin-1-amine Into a 20-mL vial, were placed 6-([4-chloro-2H-pyrazolo[4,3-c]pyridin-2-yl]methyl)-2-methylimidazo[1,2-a]pyridine (100 mg, 0.34 mmol, 1.00 equiv)(Example 445), 2-Ethoxyethyl ether (10 mL), tert-butyl N-[6-(aminomethyl)isoquinolin-1-yl]-N-[(tert-butoxy)carbonyl]carbamate (188 mg, 0.50 mmol, 1.50 equiv) and zinc chloride (458 mg, 3.36 mmol). The resulting solution was stirred for 1 h at 180° C. in microwave reactor. The reaction mixture was cooled to room temperature. The resulting solution was diluted with 10 mL of DMSO. The crude product (300 mg) was purified by Combi-Flash with the following conditions: column C18, 20-45 um, 100A, 120 g. Mobile phase: solvent A: water contains 0.05% TFA, solvent B: CH$_3$CN. Gradient: 8-40%. Run time: 20 min. Flow rate: 80 mL/min. This resulted in 100 mg (crude) product. The product (100 mg) was purified by Prep-HPLC with the following conditions: Column: Waters Atlantis T3, 19 X 150 mm, 5 um; Mobile phase: CH$_3$CN/water (0.05% TFA) from 9% to 19% in 6 mins; Flow rate: 20 ml/min; UV detector wavelength: 254 nm. The fractions were concentrated under vacuum and dried by lyophilization. This resulted in 32.4 mg (18%) of 6-((2-((2-methylimidazo[1,2-a]pyridin-6-yl)methyl)-2H-pyrazolo[4,3-c]pyridin-4-ylamino)methyl)isoquinolin-1-amine 2,2,2-trifluoroacetate as a white solid. $^1$H NMR (300 MHz, CD$_3$OD): δ 9.07 (s, 1H), 8.89 (s, 1H), 8.49 (d, J=8.1 Hz, 1H), 7.94-7.99 (m, 3H), 7.83 (d, J=9.9 Hz, 2H), 7.58 (d, J=7.2 Hz, 1H), 7.41 (d, J=7.5 Hz, 1H), 7.20 (d, J=7.5 Hz, 1H), 7.08 (d, J=7.5 Hz, 1H), 5.87 (s, 2H), 5.07 (s, 2H), 2.56 (s, 3H).

MS (ESI) m/z 435 [M+H-TFA]$^+$.

Example 447

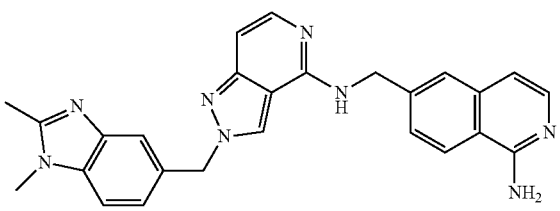 [SMILES: Cc1nc2cc(Cn3cc4c(NCc5ccc6c(N)nccc6c5)nccc4n3)ccc2n1C]

6-((2-((1,2-dimethyl-1H-benzo[d]imidazol-5-yl)methyl)-2H-pyrazolo[4,3-c]pyridin-4-ylamino)methyl)isoquinolin-1-amine 6-((2-((1,2-dimethyl-1H-benzo[d]imidazol-5-yl)methyl)-2H-pyrazolo[4,3-c]pyridin-4-ylamino)methyl)isoquinolin-1-amine was prepared in a similar manner as Example 446. $^1$H NMR (300 MHz, CD$_3$OD): δ 8.94 (s, 1H), 8.48 (d, J=8.7 Hz, 1H), 7.96 (s, 1H), 7.79-7.85 (m, 3H), 7.58-7.63 (m, 2H), 7.39 (d, J=7.5 Hz, 1H), 7.20 (d, J=7.2 Hz, 1H), 7.09 (d, J=6.9 Hz, 1H), 5.87 (s, 2H), 5.05 (s, 2H), 3.96 (s, 3H), 2.82 (s, 3H). MS (ESI) m/z 449 [M+H]$^+$.

Example 448

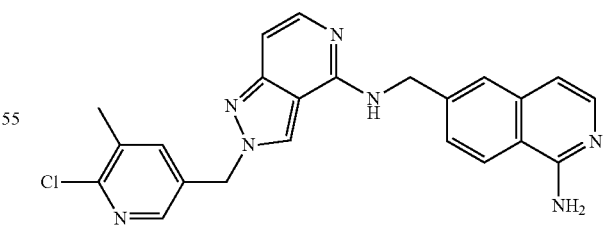

6-((2-((6-chloro-5-methylpyridin-3-yl)methyl)-2H-pyrazolo[4,3-c]pyridin-4-ylamino)methyl)isoquinolin-1-amine 6-((2-((6-chloro-5-methylpyridin-3-yl)methyl)-2H-pyrazolo[4,3-c]pyridin-4-ylamino)methyl)isoquinolin-1-amine was prepared in a similar manner as Example 446. ¹H NMR (300 MHz, CD₃OD): δ 8.85 (s, 1H), 8.48 (d, J=9.0 Hz, 1H), 8.27 (s, 1H), 7.96 (s, 1H), 7.82-7.85 (m, 2H), 7.58 (d, J=7.2 Hz, 1H), 7.40 (d, J=7.2 Hz, 1H), 7.21 (d, J=6.9 Hz, 1H), 7.10 (J=7.8 Hz, 1H), 5.72 (s, 2H), 5.05 (s, 2H), 2.40 (s, 3H). MS (ESI) m/z 430 [M+H]⁺.

Example 449

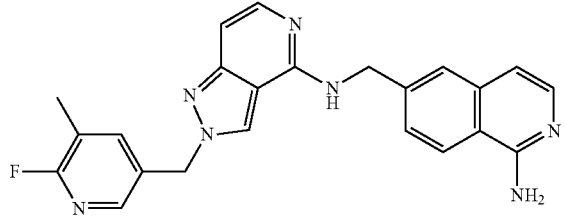 [SMILES: Cc1cc(Cn2cc3c(NCc4ccc5c(N)nccc5c4)nccc3n2)cnc1F]

6-((2-((6-fluoro-5-methylpyridin-3-yl)methyl)-2H-pyrazolo[4,3-c]pyridin-4-ylamino)methyl)isoquinolin-1-amine 6-((2-((6-fluoro-5-methylpyridin-3-yl)methyl)-2H-pyrazolo[4,3-c]pyridin-4-ylamino)methyl)isoquinolin-1-amine was prepared in a similar manner as Example 446. ¹H NMR (300 MHz, CD₃OD): δ 8.84 (s, 1H), 8.48 (d, J=8.7 Hz, 1H), 8.11 (s, 1H), 7.95 (s, 1H), 7.82-7.90 (m, 2H), 7.58 (d, J=6.9 Hz), 7.40 (d, J=7.2 Hz, 1H), 7.21 (d, J=6.3 Hz, 1H), 7.10 (d, J=7.5 Hz, 1H), 5.70 (s, 2H), 5.05 (s, 2H), 2.29 (s, 3H). MS (ESI) m/z 414 [M+H]⁺.

Example 450

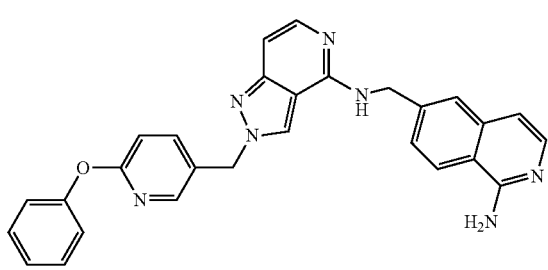 [SMILES: Nc1nccc2cc(CNc3nccc4nn(Cc5ccc(Oc6ccccc6)nc5)cc34)ccc12]

6-((2-((6-phenoxypyridin-3-yl)methyl)-2H-pyrazolo[4,3-c]pyridin-4-ylamino)methyl)isoquinolin-1-amine 6-((2-((6-phenoxypyridin-3-yl)methyl)-2H-pyrazolo[4,3-c]pyridin-4-ylamino)methyl)isoquinolin-1-amine was prepared in a similar manner as Example 446. ¹H NMR (300 MHz, CD₃OD): δ8.84 (s, 1H), 8.49-8.46 (d, 1H, J=8.7 Hz), 8.24 (d, 1H, J=2.4 Hz), 7.95-7.94 (m, 2H), 7.81 (d, 1H, J=1.8 Hz), 7.59 (d, 1H, J=6.9 Hz), 7.46-7.40 (m, 3H), 7.27-7.20 (m, 2H), 7.12-7.10 (m, 3H), 6.97 (d, 1H, J=8.4 Hz), 5.69 (s, 2H), 5.04 (s, 2H).

MS (ESI) m/z 474 [M+H]⁺.

Example 451

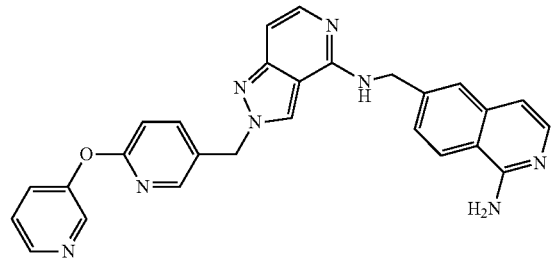 [SMILES: Nc1nccc2cc(CNc3nccc4nn(Cc5ccc(Oc6cccnc6)nc5)cc34)ccc12]

6-((2-((6-(pyridin-3-yloxy)pyridin-3-yl)methyl)-2H-pyrazolo[4,3-c]pyridin-4-ylamino)methyl)isoquinolin-1-amine 2,2,2-trifluoroacetate 6-((2-((6-(pyridin-3-yloxy)pyridin-3-yl)methyl)-2H-pyrazolo[4,3-c]pyridin-4-ylamino)methyl)isoquinolin-1-amine 2,2,2-trifluoroacetate was prepared in a similar manner as Example 446. ¹H NMR (300 MHz, CD₃OD): δ8.89 (s, 1H), 8.52-8.49 (m, 3H), 8.25 (s, 1H), 8.01-7.97 (m, 2H), 7.86-7.78 (m, 2H), 7.63-7.59 (m, 2H), 7.41 (d, 1H, J=7.2 Hz), 7.24-7.11 (m, 3H), 5.72 (s, 2H), 5.02 (s, 2H). MS (ESI) m/z 475 [M+H-TFA]⁺.

Example 452

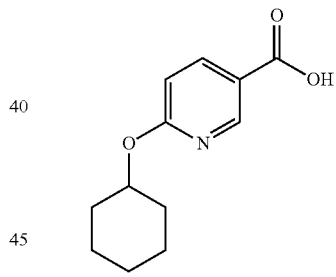

6-(cyclohexyloxy)pyridine-3-carboxylic acid

Into a 100-mL 3-necked round-bottom flask purged and maintained with an inert atmosphere of nitrogen, were placed N,N-dimethylformamide (30 mL), 6-chloropyridine-3-carboxylic acid (3 g, 19.04 mmol, 1.00 equiv) and cyclohexanol (2.44 g, 24.36 mmol, 1.50 equiv) with stirring at 0° C. This was followed by the addition of sodium hydride (60% oil suspension) (1.9 g, 79.17 mmol, 2.50 equiv). The resulting solution was stirred overnight at 130° C. The reaction mixture was cooled to room temperature and quenched with icy water. The reaction was then quenched by the addition of 300 mL of water/ice. The pH value of the solution was adjusted to 5 with acetic acid. The solids were collected by filtration. This resulted in 3.2 g (76%) of 6-(cyclohexyloxy)pyridine-3-carboxylic acid as a yellow solid. MS(ESI) m/z 222 [M+H]⁺

Example 453

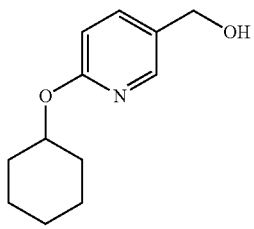 [SMILES: OCc1ccc(OC2CCCCC2)nc1]

[6-(cyclohexyloxy)pyridin-3-yl]methanol

Into a 100-mL 3-necked round-bottom flask purged and maintained with an inert atmosphere of nitrogen, was placed tetrahydrofuran (30 mL), 6-(cyclohexyloxy)pyridine-3-carboxylic acid (3 g, 13.56 mmol, 1.00 equiv)(Example 452). This was followed by the addition of LiAlH$_4$ (0.52 g, 13.56 mmol, 1.00 equiv) dropwise with stirring in several batches at 0° C. The resulting solution was stirred for 2 h at room temperature. The reaction mixture was cooled to 0° C. with a water/ice bath. The reaction was then quenched by the sequential addition of 0.5 mL of water, 1.5 mL of 15% aqueous sodium hydroxide solution and 0.5 mL of water. The mixture was filtered and washed with 2×30 mL of DCM. The filtrate was collected and extracted with 2×30 mL of dichloromethane. The organic phase was washed with 1×30 mL of water and 1×30 mL of brine. After dried over anhydrous sodium sulfate, it was concentrated under vacuum and resulted in 2.0 g (71%) of [6-(cyclohexyloxy)pyridin-3-yl]methanol as yellow oil. MS(ESI) m/z 208 [M+H]$^+$

Example 454

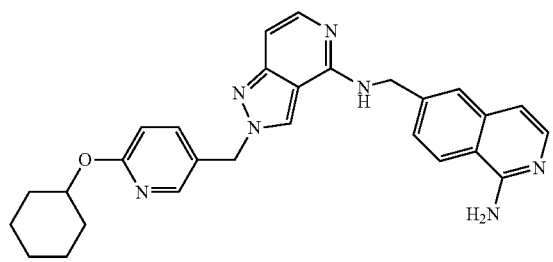 [SMILES: Nc1nccc2cc(CNc3nccc4nn(Cc5ccc(OC6CCCCC6)nc5)cc34)ccc12]

6-((2-((6-(cyclohexyloxy)pyridin-3-yl)methyl)-2H-pyrazolo[4,3-c]pyridin-4-ylamino)methyl)isoquinolin-1-amine 6-((2-((6-(cyclohexyloxy)pyridin-3-yl)methyl)-2H-pyrazolo[4,3-c]pyridin-4-ylamino)methyl)isoquinolin-1-amine was prepared using Example 453 in a similar manner as Example 446. $^1$H NMR (300 MHz, CD$_3$OD): δ8.83 (s, 1H), 8.50 (d, 1H, J=5.7 Hz), 8.25 (s, 1H), 7.96 (s, 1H), 7.85 (d, 1H, J=1.5 Hz), 7.82 (d, 1H, J=1.8 Hz), 7.76 (d, 1H, J=6.6 Hz), 7.59 (d, 1H, J=6.9 Hz), 7.40 (d, 1H, J=7.5 Hz), 7.22 (d, 1H, J=7.2 Hz), 7.12 (d, 1H, J=7.2 Hz), 6.77 (d, 1H, J=8.7 Hz), 5.632 (s, 1H), 5.05-4.99 (m, 3H), 2.01-1.79 (m, 4H), 1.64-1.32 (m, 6H). MS (ESI) m/z 480 [M+H-TFA]$^+$.

Example 455

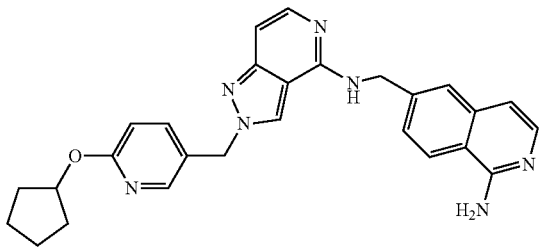 [SMILES: Nc1nccc2cc(CNc3nccc4nn(Cc5ccc(OC6CCCC6)nc5)cc34)ccc12]

6-((2-((6-(cyclopentyloxy)pyridin-3-yl)methyl)-2H-pyrazolo[4,3-c]pyridin-4-ylamino)methyl)isoquinolin-1-amine 6-((2-((6-(cyclopentyloxy)pyridin-3-yl)methyl)-2H-pyrazolo[4,3-c]pyridin-4-ylamino)methyl)isoquinolin-1-amine was prepared in a similar manner as Example 466. $^1$H NMR (300 MHz, CD$_3$OD): δ8.45 (s, 1H), 8.20 (d, 1H, J=2.1 Hz), 8.11 (d, 1H, J=8.4 Hz), 7.70-7.65 (m, 3H), 7.57 (d, 2H, J=6.6 Hz), 6.96 (d, 1H, J=6.6 Hz), 6.80-6.74 (m, 2H), 5.54 (s, 1H), 5.36-5.32 (m, 1H), 4.89 (s, 2H), 1.98-1.64 (m, 10H). MS (ESI) m/z 466 [M+H]$^+$.

Example 456

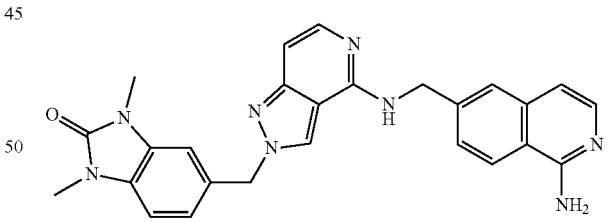

5-((4-((1-aminoisoquinolin-6-yl)methylamino)-2H-pyrazolo[4,3-c]pyridin-2-yl)methyl)-1,3-dimethyl-1H-benzo[d]imidazol-2(3H)-one 5-((4-((1-aminoisoquinolin-6-yl)methylamino)-2H-pyrazolo[4,3-c]pyridin-2-yl)methyl)-1,3-dimethyl-1H-benzo[d]imidazol-2(3H)-one was prepared in a similar manner as Example 446. $^1$H NMR (300 MHz, CD$_3$OD): δ 8.42 (s, 1H), 8.05 (d, J=9 Hz, 1H), 7.8-8.0 (m, 1H), 7.69 (d, J=9.0 Hz, 1H), 7.52-7.57 (m, 2H), 7.38 (d, J=8.9 Hz, 1H), 7.23 (s, 1H), 7.15 (s, 1H), 6.77-6.83 (m, 3H), 6.60 (d, J=8.7 Hz, 1H), 5.85 (s, 2H), 4.76 (d, J=5.1 Hz, 2H). MS (ESI) m/z 465 [M+H-TFA]$^+$.

Example 457

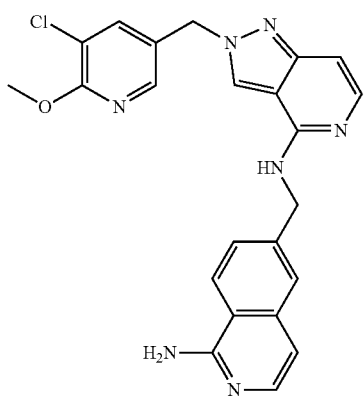 [SMILES: COc1ncc(Cn2cc3c(NCc4ccc5c(N)nccc5c4)nccc3n2)cc1Cl]

6-((2-((5-chloro-6-methoxypyridin-3-yl)methyl)-2H-pyrazolo[4,3-c]pyridin-4-ylamino)methyl)isoquinolin-1-amine 6-((2-((5-chloro-6-methoxypyridin-3-yl)methyl)-2H-pyrazolo[4,3-c]pyridin-4-ylamino)methyl)isoquinolin-1-amine was prepared in a similar manner as Example 446. $^1$H NMR (300 MHz, CD$_3$OD): δ 8.85 (s, 1H), 8.47 (d, J=8.7 Hz, 1H), 8.22 (s, 1H), 7.81-7.95 (m, 3H), 7.57 (d, J=6.9 Hz, 1H), 7.39 (d, J=7.2 Hz, 1H), 7.20 (d, J=6.9 Hz, 1H), 7.10 (d, J=7.5 Hz, 1H), 5.64 (s, 2H), 5.05 (s, 2H), 4.00 (s, 3H). MS (ESI) m/z 446 [M+H-TFA]$^+$.

Example 458

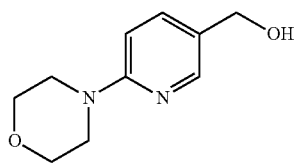 [SMILES: OCc1ccc(N2CCOCC2)nc1]

[6-(morpholin-4-yl)pyridin-3-yl]methanol

[6-(morpholin-4-yl)pyridin-3-yl]methanol was prepared in a similar manner as Example 453. MS(ESI) m/z 195 [M+H]$^+$

Example 459

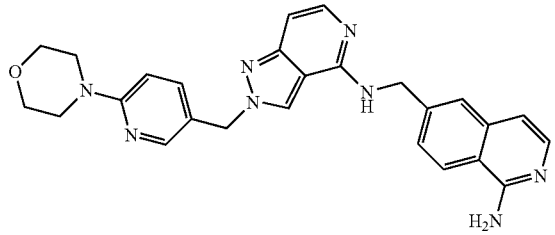 [SMILES: Nc1nccc2cc(CNc3nccc4nn(Cc5ccc(N6CCOCC6)nc5)cc34)ccc12]

6-((2-((6-morpholinopyridin-3-yl)methyl)-2H-pyrazolo[4,3-c]pyridin-4-ylamino)methyl)isoquinolin-1-amine 6-((2-((6-morpholinopyridin-3-yl)methyl)-2H-pyrazolo[4,3-c]pyridin-4-ylamino)methyl)isoquinolin-1-amine was prepared in a similar manner as Example 446. $^1$H NMR (300 MHz, CD$_3$OD): δ 8.19 (d, 1H, J=0.9 Hz), 8.11 (d, 1H, J=8.7 Hz), 7.75-7.64 (m, 4H), 7.51-7.51 (d, 1H, J=1.5 Hz), 7.15-7.12 (m, 1H), 6.78-6.76 (m, 1H), 6.37 (d, 1H, J=8.7 Hz), 3.91 (s, 2H), 3.79-3.75 (m, 4H). MS (ESI) m/z 467 [M+H]$^+$.

Example 460

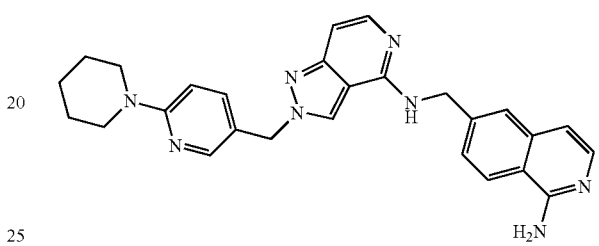

6-((2-((6-(piperidin-1-yl)pyridin-3-yl)methyl)-2H-pyrazolo[4,3-c]pyridin-4-ylamino)methyl)isoquinolin-1-amine 6-((2-((6-(piperidin-1-yl)pyridin-3-yl)methyl)-2H-pyrazolo[4,3-c]pyridin-4-ylamino)methyl)isoquinolin-1-amine was synthesized in a similar manner as as Example 446. $^1$H NMR (300 MHz, CD$_3$OD): δ8.20 (s, 1H), 8.10 (d, 1H, J=8.4 Hz), 7.76 (s, 1H), 7.72 (d, 1H, J=1.8 Hz), 7.67-7.64 (m, 2H), 7.52 (d, 1H, J=6.9 Hz), 7.11-7.07 (m, 1H), 6.78-6.75 (m, 1H), 6.37 (d, 1H, J=8.7 Hz), 3.95 (d, 2H, J=7.5 Hz), 3.39-3.37 (m, 4H), 1.63-1.49 (m, 6H). MS (ESI) m/z 465 [M+H]$^+$.

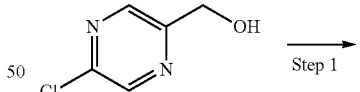

Step 1

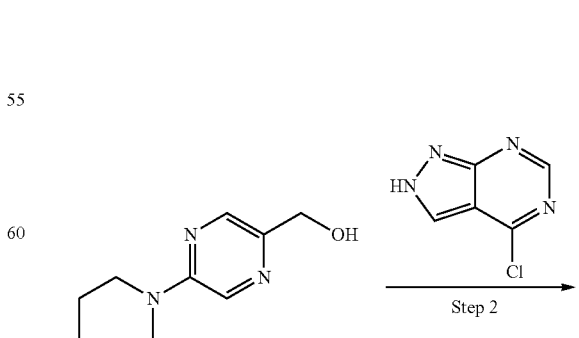

Step 2

Example 461

315
-continued

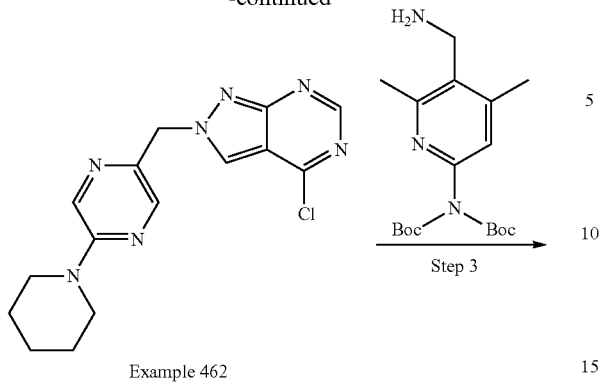

Example 462

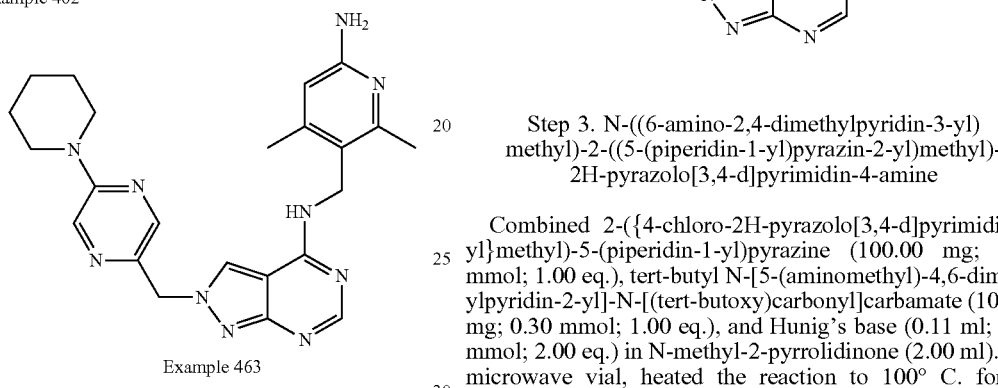

Example 463

Example 461

Step 1. (5-(piperidin-1-yl)pyrazin-2-yl)methanol

Combined (5-chloropyrazin-2-yl)methanol (500.00 mg; 3.46 mmol; 1.00 eq.), potassium carbonate (954.63 mg; 0.01 mol; 2.00 eq.) and piperidine (589.02 mg; 6.92 mmol; 2.00 eq.) in N,N-dimethylformamide (10.00 ml). Heated the reaction to 90° C. for overnight. Let the reaction cool to rt. Diluted reaction with water, extracted with ethyl acetate, combined organics, dried with MgSO$_4$, filtered, and concentrated to give (5-(piperidin-1-yl)pyrazin-2-yl)methanol (0.67 g; 100% crude). MS (M+H)+ found for $C_{10}H_{15}N_3O$: 193.6.

Example 462

Step 2. 4-chloro-2-((5-(piperidin-1-yl)pyrazin-2-yl)methyl)-2H-pyrazolo[3,4-d]pyrimidine Diisopropyl (E)-1,2-diazenedicarboxylate (732.46 mg; 3.62 mmol; 1.00 eq.) was added dropwise to a precooled solution of [5-(piperidin-1-yl)pyrazin-2-yl]methanol (700.00 mg; 3.62 mmol; 1.00 eq.), 4-chloro-2H-pyrazolo[3,4-d]pyrimidine (559.86 mg; 3.62 mmol; 1.00 eq.) and triphenylphosphine (950.09 mg; 3.62 mmol; 1.00 eq.) in dichloromethane (10.00 ml) at 0° C. The reaction was stirred for 30 minutes. Diluted reaction with water, extracted with ethyl acetate, combined organics, dried with MgSO$_4$, filtered and concentrated. Purified by silica gel column using 70% ethyl acetate in hexanes to give 4-chloro-2-((5-(piperidin-1-yl)pyrazin-2-yl)methyl)-2H-pyrazolo[3,4-d]pyrimidine (402.00 mg; 33%). MS (M+H)+ found for $C_{15}H_{16}N_7Cl$: 330.3.

316

Example 463

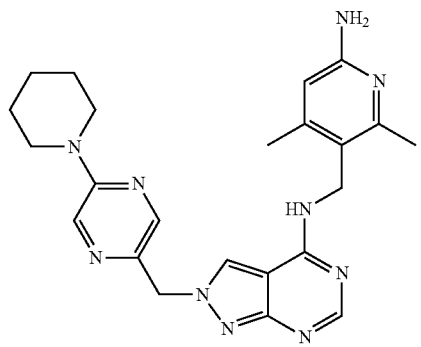 [SMILES: Cc1cc(N)nc(C)c1CNc1ncnc2nn(Cc3cnc(N4CCCCC4)cn3)cc12]

Step 3. N-((6-amino-2,4-dimethylpyridin-3-yl)methyl)-2-((5-(piperidin-1-yl)pyrazin-2-yl)methyl)-2H-pyrazolo[3,4-d]pyrimidin-4-amine Combined 2-({4-chloro-2H-pyrazolo[3,4-d]pyrimidin-2-yl}methyl)-5-(piperidin-1-yl)pyrazine (100.00 mg; 0.30 mmol; 1.00 eq.), tert-butyl N-[5-(aminomethyl)-4,6-dimethylpyridin-2-yl]-N-[(tert-butoxy)carbonyl]carbamate (106.57 mg; 0.30 mmol; 1.00 eq.), and Hunig's base (0.11 ml; 0.61 mmol; 2.00 eq.) in N-methyl-2-pyrrolidinone (2.00 ml). In a microwave vial, heated the reaction to 100° C. for 15 minutes. Diluted reaction with water, extracted with ethyl acetate, combined organics, dried with MgsO$_4$, filtered, and concentrated. Treated residue with 1M HCl and heated to 90° C. for 30 minutes. Purified by prep HPLC to give N-((6-amino-2,4-dimethylpyridin-3-yl)methyl)-2-((5-(piperidin-1-yl)pyrazin-2-yl)methyl)-2H-pyrazolo[3,4-d]pyrimidin-4-amine (34.00 mg; 25%). $^1$H NMR (400 MHz, Methanol-d$_4$) δ 8.30 (s, 2H), 8.15 (d, J=1.4 Hz, 1H), 8.11 (d, J=1.5 Hz, 1H), 6.60 (s, 1H), 5.46 (s, 2H), 4.67 (s, 2H), 3.64-3.56 (m, 4H), 2.54 (s, 3H), 2.40 (d, J=0.8 Hz, 3H), 1.74-1.55 (m, 6H). MS (M+H)+ found for $C_{23}H_{28}N_{10}$: 445.0.

Example 464

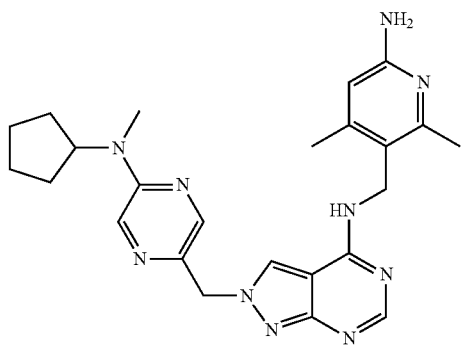 [SMILES: Cc1cc(N)nc(C)c1CNc1ncnc2nn(Cc3cnc(N(C)C4CCCC4)cn3)cc12]

N-((6-amino-2,4-dimethylpyridin-3-yl)methyl)-2-((5-(cyclopentyl(methyl)amino)pyrazin-2-yl)methyl)-2H-pyrazolo[3,4-d]pyrimidin-4-amine N-((6-amino-2,4-dimethylpyridin-3-yl)methyl)-2-((5-(cyclopentyl(methyl)amino)pyrazin-2-yl)methyl)-2H-pyrazolo[3,4-d]pyrimidin-4-amine was synthesized in a manner similar to Example 463 using N-methylcyclopentanamine to replace piperidine in step 5. ¹H NMR (400 MHz, Methanol-d₄) δ 8.31 (s, 2H), 8.16 (d, J=1.4 Hz, 1H), 8.02 (d, J=1.4 Hz, 1H), 6.68 (s, 1H), 5.47 (s, 2H), 4.69 (s, 2H), 2.94 (s, 3H), 2.81 (dt, J=5.7, 0.9 Hz, 1H), 2.59 (s, 3H), 2.45 (s, 3H), 1.93-1.57 (m, 8H). MS (M+H)+ found for C₂₄H₃₀N₁₀ : 459.2.

Example 465

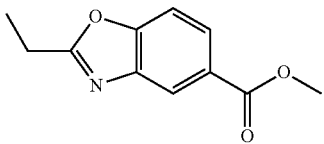

2-ethyl-1,3-benzoxazole-5-carboxylate

Into a 100-mL round-bottom flask purged and maintained with an inert atmosphere of nitrogen, was placed methyl 3-amino-4-hydroxybenzoate (3 g, 17.95 mmol, 1.00 equiv), 1,1,1-triethoxypropane (37 mL), trifluoroacetic acid (2.2 mL). The resulting solution was stirred for 1.5 h at 25° C. The reaction solution was diluted with 50 mL of DCM. The mixture was washed with 2×20 mL of saturated aqueous NaHCO₃ and 1×50 mL of brine. Then it was dried over anhydrous sodium sulfate and concentrated under vacuum. This resulted in 3.8 g of methyl 2-ethyl-1,3-benzoxazole-5-carboxylate as a red brown oil.

Example 466

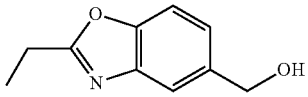

(2-ethyl-1,3-benzoxazol-5-yl)methanol

Into a 100-mL 3-necked round-bottom flask purged and maintained with an inert atmosphere of nitrogen, was placed methyl 2-ethyl-1,3-benzoxazole-5-carboxylate (3.8 g, 18.52 mmol, 1.00 equiv) (Example 465), THF (40 mL) with stirring at −20° C., to which was added LiAlH₄ (700 mg, 20.63 mmol, 1.00 equiv) in portions. The resulting solution was stirred for 40 min at −20° C. The reaction was then quenched by the addition of 0.7 mL of water at −20° C. The resulting solution was diluted with 2.1 mL of aqueous NaOH (15%) and 0.7 mL EA at room temperature. The solids were filtered out. The resulting mixture was concentrated under vacuum. The residue was purified by silica column with eluent ethyl acetate/petroleum ether (1:10-1:1). This resulted in 2.7 g (82%) of (2-ethyl-1,3-benzoxazol-5-yl)methanol as red brown oil.

Example 467

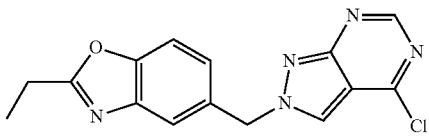 [SMILES: CCc1nc2cc(Cn3cc4c(Cl)ncnc4n3)ccc2o1]

5-([4-chloro-2H-pyrazolo[3,4-d]pyrimidin-2-yl]methyl)-2-ethyl-1,3-benzoxazole

Into a 100-mL 3-necked round-bottom flask purged and maintained with an inert atmosphere of nitrogen, was placed (2-ethyl-1,3-benzoxazol-5-yl)methanol (1 g, 5.64 mmol, 1.00 equiv)(Example 466), PPh₃ (1.78 g, 6.79 mmol, 1.20 equiv) and 4-chloro-2H-pyrazolo[3,4-d]pyrimidine (870 mg, 5.63 mmol, 1.00 equiv) in tetrahydrofuran (40 mL) with stirring at 0° C., to which was added DEAD (1.17 g, 6.72 mmol, 1.20 equiv) dropwise. The resulting solution was stirred overnight at 25° C. The mixture was concentrated under vacuum. The crude product was purified by silica gel column chromatography eluted with DCM/MeOH(1:0 to 9:1). This resulted in 350 mg (20%) of 5-([4-chloro-2H-pyrazolo[3,4-d]pyrimidin-2-yl]methyl)-2-ethyl-1,3-benzoxazole as a light yellow solid. ¹H NMR (300 MHz, CDCL3-d): δ ppm 8.80 (s, 1H), 8.18 (s, 1H), 7.68 (s, 1H), 7.34-7.45 (m, 2H), 5.76 (s, 2H), 2.88-2.99 (m, 2H); 1.45-1.50 (m, 3H). MS (ESI) m/z: 314[M+H]⁺

Example 468

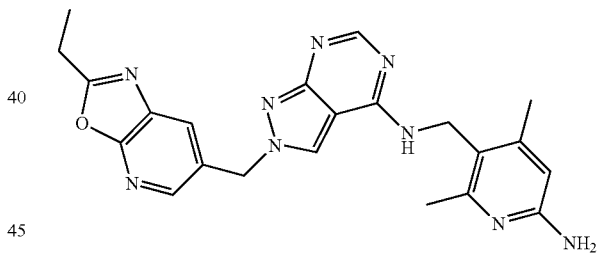

5-[([2-[(2-ethyl-1,3-benzoxazol-5-yl)methyl]-2H-pyrazolo[3,4-d]pyrimidin-4-yl]amino)methyl]-4,6-dimethylpyridin-2-amine Into a 50-mL round-bottom flask, was placed 5-([4-chloro-2H-pyrazolo[3,4-d]pyrimidin-2-yl]methyl)-2-ethyl-1,3-benzoxazole (100 mg, 0.32 mmol, 1.00 equiv)(Example 467), zinc dichloride (428 mg, 3.14 mmol, 10.00 equiv) and tert-butyl N-[5-(aminomethyl)-4,6-dimethylpyridin-2-yl]-N-[(tert-butoxy)carbonyl]carbamate (224 mg, 0.64 mmol, 2.00 equiv) (Example 4, Step 2) in 1-ethoxy-2-(2-ethoxyethoxy)ethane (5 mL). The resulting solution was stirred for 2 h at 120° C. The reaction mixture was cooled with a water/ice bath. The resulting mixture was diluted with 2 mL of DMSO. The crude product was purified by silica gel column chromatography eluted with DCM/MeOH (1:0 to 3:1). This resulted in 41 mg (30%) of 5-[([2-[(2-ethyl-1,3-benzoxazol-5-yl)methyl]-2H-pyrazolo[3,4-d]pyrimidin-4-yl]amino)methyl]-4,6-dimethylpyridin-2-amine as a light yellow solid. ¹H NMR (300 MHz, DMSO-d₆): 8.33 (s, 1H), 8.26 (s, 1H), 8.12-8.04 (m, 2H), 7.71-7.68 (m, 2H), 7.65-7.34 (m, 2H), 6.38 (s, 1H); 5.64 (s, 2H), 4.52-4.50 (d, J=4.2 Hz, 2H), 2.98-2.96 (m, 2H), 2.40 (s, 3H), 2.28 (s, 3H), 1.37-1.29 (m, 3H). MS (ESI) m/z: 429[M+H]⁺

Example 469

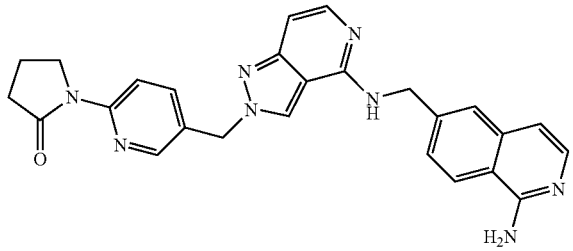 [SMILES: Nc1nccc2cc(CNc3nccc4nn(Cc5ccc(N6CCCC6=O)nc5)cc34)ccc12]

1-(5-((4-((1-aminoisoquinolin-6-yl)methylamino)-2H-pyrazolo[4,3-c]pyridin-2-yl)methyl)pyridin-2-yl)pyrrolidin-2-one 1-(5-((4-((1-aminoisoquinolin-6-yl)methylamino)-2H-pyrazolo[4,3-c]pyridin-2-yl)methyl)pyridin-2-yl)pyrrolidin-2-one was prepared in a similar manner as Example 446. ¹H NMR (300 MHz, DMSO-d₆): δ8.49 (s, 1H), 8.45 (d, 1H, J=1.8 Hz), 8.29 (d, 1H, J=8.1 Hz), 8.11 (d, 1H, J=8.4 Hz), 7.88-7.79 (m, 2H), 7.73 (d, 1H, J=6.0 Hz), 7.57-7.530 (m, 2H), 7.42 (d, 1H, J=8.1 Hz), 6.82 (d, 1H, J=6.0 Hz), 6.68 (s, 2H), 6.63 (d, 1H, J=6.6 Hz), 5.60 (s, 2H), 4.78 (d, 2H, J=5.4 Hz), 4.00-3.95 (m, 2H), 2.60-2.54 (m, 2H), 2.06-2.01 (m, 2H). MS (ESI) m/z 465 [M+H]⁺.

Example 470

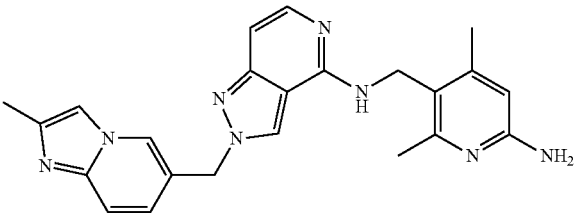 [SMILES: Cc1cn2cc(Cn3cc4c(NCc5c(C)cc(N)nc5C)nccc4n3)ccc2n1]

N-((6-amino-2,4-dimethylpyridin-3-yl)methyl)-2-((2-methylimidazo[1,2-a]pyridin-6-yl)methyl)-2H-pyrazolo[4,3-c]pyridin-4-amine N-((6-amino-2,4-dimethylpyridin-3-yl)methyl)-2-((2-methylimidazo[1,2-a]pyridin-6-yl)methyl)-2H-pyrazolo[4,3-c]pyridin-4-amine was prepared in a similar manner to Example 468. ¹H NMR (300 MHz, DMSO-d₆): δ 8.56 (s, 1H), 8.46 (s, 1H), 7.71 (s, 1H), 7.61 (d, 1H, J=6.3 Hz), 7.41 (d, 1H, J=8.1 Hz), 7.11-6.99 (m, 2H), 6.62 (d, 1H, J=4.8 Hz), 6.13 (s, 1H), 5.64 (s, 2H), 5.51 (s, 2H), 4.41 (d, 2H, J=4.2 Hz), 2.31 (s, 3H), 2.281 ((s, 3H), 2.144 (s, 3H). MS (ESI) m/z 413 [M+H]⁺

Example 471

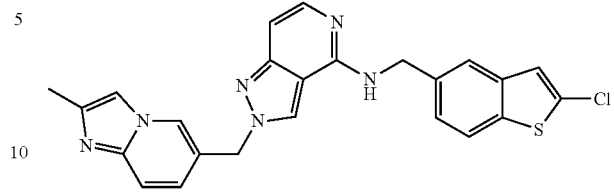

N-((2-chlorobenzo[b]thiophen-5-yl)methyl)-2-((2-methylimidazo[1,2-a]pyridin-6-yl)methyl)-2H-pyrazolo[4,3-c]pyridin-4-amine N-((2-chlorobenzo[b]thiophen-5-yl)methyl)-2-((2-methylimidazo[1,2-a]pyridin-6-yl)methyl)-2H-pyrazolo[4,3-c]pyridin-4-amine was prepared in a similar manner as Example 468. ¹H NMR (300 MHz, CD₃OD): δ9.03 (s, 1H), 8.84 (s, 1H), 7.81-8.02 (m, 5H), 7.40-7.51 (m, 2H), 7.31 (s, 1H), 7.03 (d, 1H, J=7.5 Hz,), 5.84 (s, 2H), 2.55 (s, 3H). MS (ESI) m/z 459 [M+H+TFA]⁺.

Example 472

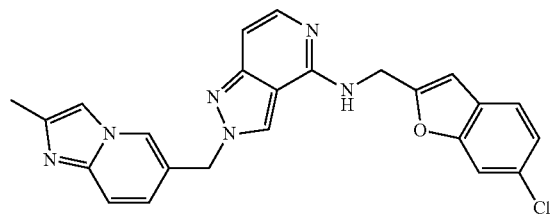 [SMILES: Cc1cn2cc(Cn3cc4c(NCc5cc6ccc(Cl)cc6o5)nccc4n3)ccc2n1]

N-((6-chlorobenzofuran-2-yl)methyl)-2-((2-methylimidazo[1,2-a]pyridin-6-yl)methyl)-2H-pyrazolo[4,3-c]pyridin-4-amine N-((6-chlorobenzofuran-2-yl)methyl)-2-((2-methylimidazo[1,2-a]pyridin-6-yl)methyl)-2H-pyrazolo[4,3-c]pyridin-4-amine was prepared in a similar manner as Example 468. ¹H NMR (300 MHz, DMSO-d₆): δ 8.58 (s, 1H), 8.48 (s, 1H), 7.85 (t, 1H, J=6.0 Hz), 7.69 (d, 2H, J=9.9 Hz), 7.54-7.58 (m, 2H), 7.41 (d, 1H, J=9 Hz), 7.24 (dd, 1H, J=1.8 Hz, J=8.1 Hz), 7.13 (dd, 1H, J=1.8 Hz, J=8.1 Hz), 6.74 (s, 1H), 6.66 (d, 1H, J=6 Hz), 5.57 (s, 2H), 4.78 (d, 2H, J=5.7 Hz), 2.31 (s, 3H). MS (ESI) m/z 443 [M+H]⁺.

Example 473

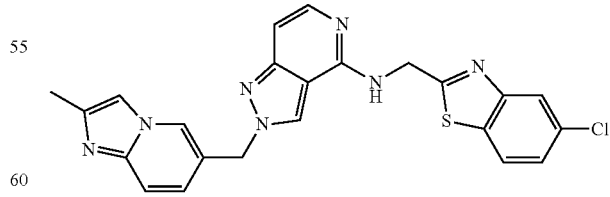

N-((5-chlorobenzo[d]thiazol-2-yl)methyl)-2-((2-methylimidazo[1,2-a]pyridin-6-yl)methyl)-2H-pyrazolo[4,3-c]pyridin-4-amine N-((5-chlorobenzo[d]thiazol-2-yl)methyl)-2-((2-methylimidazo[1,2-a]pyridin-6-yl)methyl)-2H-pyrazolo[4,3-c]

pyridin-4-amine was prepared in a similar manner as Example 468. ¹H NMR (300 MHz, DMSO-d₆): δ 8.61 (s, 1H), 8.52 (s, 1H), 8.30-8.40 (m, 1H), 7.80-8.03 (m, 2H), 7.74 (s, 1H), 7.57 (d, 1H, J=6.3 Hz), 7.41-7.46 (m, 2H), 7.17 (d, 1H, J=9.3 Hz), 6.72 (d, 1H, J=6.0 Hz), 5.61 (s, 2H), 5.02 (d, 2H, J=6.0 Hz), 2.33 (s, 3H). MS (ESI) m/z 460[M+H]⁺.

Example 474

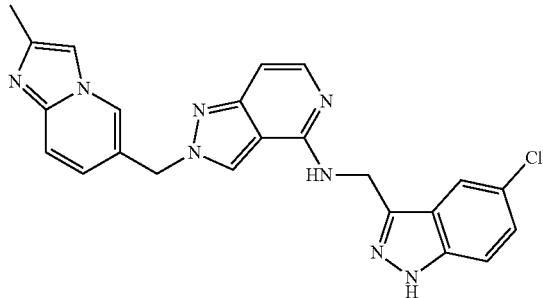 [SMILES: Cc1cn2cc(Cn3cc4c(NCc5n[nH]c6ccc(Cl)cc56)nccc4n3)ccc2n1]

N-((5-chloro-1H-indazol-3-yl)methyl)-2-((2-methyl-imidazo[1,2-a]pyridin-6-yl)methyl)-2H-pyrazolo[4,3-c]pyridin-4-amine N-((5-chloro-1H-indazol-3-yl)methyl)-2-((2-methylimidazo[1,2-a]pyridin-6-yl)methyl)-2H-pyrazolo[4,3-c]pyridin-4-amine was prepared in a similar manner as Example 468. ¹H NMR (300 MHz, CD₃OD): δ 8.47 (s, 1H), 8.42 (s, 1H), 7.77 (d, 1H, J=1.8 Hz), 7.68 (d, 1H, J=6.6 Hz), 7.60 (s, 1H), 7.48 (d, 1H, J=9.0 Hz), 7.42 (d, 1H, J=9.0 Hz), 7.34 (d, 1H, J=1.8 Hz), 7.33 (d, 1H, J=1.8 Hz), 7.22 (d, 1H, J=9.3 Hz), 6.80 (d, 1H, J=6.6 Hz), 5.57 (s, 2H), 5.02 (d, 2H, J=8.4 Hz), 2.40 (s, 3H). MS (ESI) m/z 443 [M+H]⁺.

Example 475

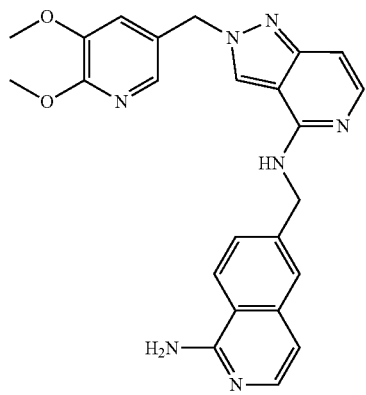 [SMILES: COc1cc(Cn2cc3c(NCc4ccc5c(N)nccc5c4)nccc3n2)cnc1OC]

6-((2-((5,6-dimethoxypyridin-3-yl)methyl)-2H-pyrazolo[4,3-c]pyridin-4-ylamino)methyl)isoquinolin-1-amine 6-((2-((5,6-dimethoxypyridin-3-yl)methyl)-2H-pyrazolo[4,3-c]pyridin-4-ylamino)methyl)isoquinolin-1-amine was prepared in the same manner as Example 446. ¹H NMR (300 MHz, CD₃OD): δ 8.78 (s, 1H), 8.47 (d, J=9.0 Hz, 1H), 7.91 (d, J=8.4 Hz, 1H), 7.81 (d, J=9.0 Hz, 2H), 7.59 (d, J=9.0 Hz, 1H), 7.40 (d, J=7.5 Hz, 1H), 7.33 (s, 1H), 7.19 (d, J=6.9 Hz, 1H), 7.11 (d, J=7.5 Hz, 1H), 5.59 (d, J=9.0 Hz, 2H), 5.04 (s, 2H), 3.95 (s, 3H), 3.82 (s, 3H). MS (ESI) m/z 442 [M+H-TFA]⁺.

Example 476

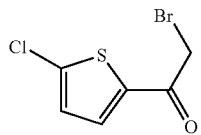

2-bromo-1-(5-chlorothiophen-2-yl)ethanone

Into a 250-mL 3-necked round-bottom flask purged and maintained with an inert atmosphere of nitrogen, were placed a solution of 1-(5-chlorothiophen-2-yl)ethan-1-one (6.4 g, 39.85 mmol, 1.00 equiv) in chloroform (64 mL), hydrogen bromide (0.2 mL), acetic acid (0.2 mL). This was followed by the addition of a solution of dibromane (7.04 g, 44.05 mmol, 1.10 equiv) in chloroform (64 mL) dropwise with stirring at 45° C. in 90 min. The resulted solution was stirred for 60 min at 45° C. in a Hg-lamp light bath. The resulted solution was diluted with 500 mL of DCM, washed with 1×500 mL of saturated aqueous sodium bicarbonate and 2×500 mL of brine. The organic phase was dried over anhydrous sodium sulfate and concentrated under vacuum. The residue was purified by a silica gel column eluted with ethyl acetate/petroleum ether (1:50-1:30). This resulted in 3.50 g (37%) of 2-bromo-1-(5-chlorothiophen-2-yl)ethan-1-one as light yellow solid.

Example 477

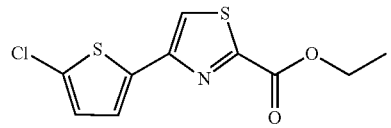 [SMILES: CCOC(=O)c1nc(-c2ccc(Cl)s2)cs1]

ethyl 4-(5-chlorothiophen-2-yl)thiazole-2-carboxylate

Into a 100-mL 3-necked round-bottom flask purged and maintained with an inert atmosphere of nitrogen, were placed a solution of 2-bromo-1-(5-chlorothiophen-2-yl)ethan-1-one (3.40 g, 14.20 mmol, 1.00 equiv)(Example 476) in ethanol (40 mL) and ethyl carbamothioylformate (2.09 g, 15.69 mmol, 1.10 equiv). The resulted solution was stirred for 1 h at 80° C. in an oil bath. The mixture was concentrated under vacuum. The residue was diluted with 500 mL of ethyl acetate, washed with 3×500 mL of brine and dried over anhydrous sodium sulfate. The organic phase was concentrated under vacuum. The residue was purified by silica gel column chromatography eluted with ethyl acetate/petroleum ether (1:30). This resulted in 2.5 g (64%) of ethyl 4-(5-chlorothiophen-2-yl)-1,3-thiazole-2-carboxylate as light yellow solid. MS (ESI) m/z 274 [M+H]⁺

Example 478

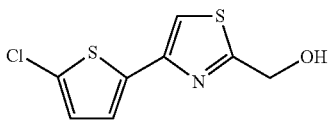 [SMILES: OCc1nc(-c2ccc(Cl)s2)cs1]

(4-(5-chlorothiophen-2-yl)thiazol-2-yl)methanol

Into a 100-mL 3-necked round-bottom flask purged and maintained with an inert atmosphere of nitrogen, was placed a solution of ethyl 4-(5-chlorothiophen-2-yl)-1,3-thiazole-2-carboxylate (2 g, 7.31 mmol, 1.00 equiv)(Example 477) in ethanol (40 mL). This was followed by the addition of NaBH$_4$ (835 mg, 21.97 mmol, 3.00 equiv), in portions at 0° C. The resulted solution was stirred for 24 h at room temperature. The mixture was concentrated under vacuum. The residue was diluted with 500 mL of ethyl acetate, washed with 3×500 mL of brine and dried over anhydrous sodium sulfate. The organic phase was concentrated under vacuum. This resulted in 1.4 g (crude) of [4-(5-chlorothiophen-2-yl)-1,3-thiazol-2-yl]methanol as light yellow solid. MS (ESI) m/z 232 [M+H]$^+$

Example 479

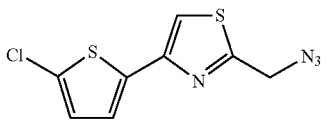 [SMILES: [N-]=[N+]=NCc1nc(-c2ccc(Cl)s2)cs1]

2-(azidomethyl)-4-(5-chlorothiophen-2-yl)thiazole

Into a 250-mL 3-necked round-bottom flask purged and maintained with an inert atmosphere of nitrogen, were placed [4-(5-chlorothiophen-3-yl)-1,3-thiazol-2-yl]methanol (1.35 g, 5.83 mmol, 1.00 equiv)(Example 478) and tetrahydrofuran (100 mL) stirred at 0° C. This was followed by the addition of DPPA (4.02 g, 14.61 mmol, 2.50 equiv) dropwise with stirring, followed by the addition of DBU (2.67 g, 10.60 mmol, 3.00 equiv) at 0° C. The resulted solution was stirred for overnight at 25° C. The solution was diluted with 500 mL of ethyl acetate, washed with 3×500 mL of brine and dried over anhydrous sodium sulfate and concentrated under vacuum. The residue was purified by silica gel column chromatography eluted with ethyl acetate/petroleum ether (1:50). This resulted in 1.1 g (74%) of 2-(azidomethyl)-4-(5-chlorothiophen-3-yl)-1,3-thiazole as yellow solid. MS (ESI) m/z 257 [M+H]$^+$

Example 480

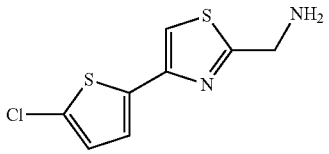 [SMILES: NCc1nc(-c2ccc(Cl)s2)cs1]

(4-(5-chlorothiophen-2-yl)thiazol-2-yl)methanamine

Into a 100-mL 3-necked round-bottom flask and maintained with an inert atmosphere of nitrogen, were placed 2-(azidomethyl)-4-(5-chlorothiophen-2-yl)-1,3-thiazole (800 mg, 3.12 mmol, 1.00 equiv)(Example 479), tetrahydrofuran (16 mL) and triphenylphosphane (2456 mg, 9.36 mmol, 3.00 equiv). This was followed by the addition of water (1.6 mL) dropwise with stirring. The resulted solution was stirred overnight at room temperature. The mixture was concentrated under vacuum. The residue was purified by silica column chromatography eluted with ethyl acetate/petroleum ether (1:5-1:1). This resulted in 300 mg (42%) of [4-(5-chlorothiophen-2-yl)-1,3-thiazol-2-yl]methanamine as white solid.
MS (ESI) m/z 231 [M+H]$^+$

Example 481

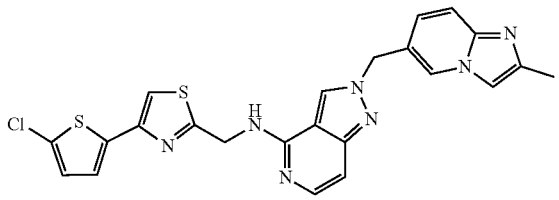 [SMILES: Cc1cn2cc(Cn3cc4c(NCc5nc(-c6ccc(Cl)s6)cs5)nccc4n3)ccc2n1]

N-((4-(5-chlorothiophen-2-yl)thiazol-2-yl)methyl)-2-((2-methylimidazo[1,2-a]pyridin-6-yl)methyl)-2H-pyrazolo[4,3-c]pyridin-4-amine Into a 8-mL vial, were placed [4-(5-chlorothiophen-2-yl)-1,3-thiazol-2-yl]methanamine-oxalic acid (50 mg, 0.16 mmol, 1.50 equiv), 6-(4-chloro-2H-pyrazolo[4,3-c]pyridin-2-ylmethyl)-2-methylimidazo[1,2-a]pyridine (30.9 mg, 0.10 mmol, 1.00 equiv)(Example 445), 1-ethoxy-2-(2-ethoxyethoxy)ethane (6 mL) and zinc dichloride (139.6 mg, 1.02 mmol, 10.00 equiv). The resulted solution was stirred for 3 h at 120° C. The crude product was purified by flash column chromatography eluted with DCM/methanol//concentrated ammonia aqueous solution (4:1:0.1). The crude product was further purified by Prep-HPLC with the following conditions: column, Waters X-Bridge RP18 19 X 150 mm, 5 um; mobile phase, CH3CN/water (0.05% NH$_4$OH, 10 mM NH$_4$HCO$_3$) from 50% to 54% with a 4-min run time; flow rate: 20 mL/min; detector UV wavelength: 254 nm. This resulted in 7.1 mg (13%) of N-[[4-(5-chlorothiophen-2-yl)-1,3-thiazol-2-yl]methyl]-2-([2-methylimidazo[1,2-a]pyridin-6-yl]methyl)-2H-pyrazolo[4,3-c]pyridin-4-amine as white solid. $^1$H NMR (300 MHz, CD$_3$OD): 8.48 (s, 2H), 7.65 (d, J=8.4 Hz, 2H), 7.56 (s, 1H), 7.47 (d, J=9.2 Hz, 1H), 7.30-7.25 (m, 2H), 6.97 (d, J=4 Hz, 1H), 6.83 (d, J=7.2 Hz, 1H), 5.63 (s, 2H), 5.01 (s, 2H), 2.42 (s, 3H). MS (ESI) m/z 492 [M+H]$^+$

Example 482

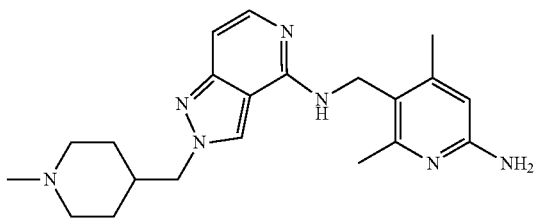 [SMILES: Cc1cc(N)nc(C)c1CNc1nccc2nn(CC3CCN(C)CC3)cc12]

N-((6-amino-2,4-dimethylpyridin-3-yl)methyl)-2-((1-methylpiperidin-4-yl)methyl)-2H-pyrazolo[4,3-c]pyridin-4-amine N-((6-amino-2,4-dimethylpyridin-3-yl)methyl)-2-((1-methylpiperidin-4-yl)methyl)-2H-pyrazolo[4,3-c]pyridin-4- amine was prepared in a similar manner as Example 468. ¹H NMR (300 MHz, CD₃OD): δ 8.34 (s, 1H), 7.65 (d, J=6.6 Hz, 1H), 6.74 (d, J=6.3 Hz, 1H), 6.36 (s, 1H), 4.54 (s, 2H), 4.23 (d, J=6.9 Hz, 2H), 2.86 (d, J=11.7 Hz, 2H), 2.41 (s, 3H), 2.27-2.28 (m, 6H), 1.98-2.05 (m, 3H), 1.48-1.58 (m, 2H), 1.33-1.41 (m, 2H)

MS (ESI) m/z 380 [M+H]⁺. Example 483

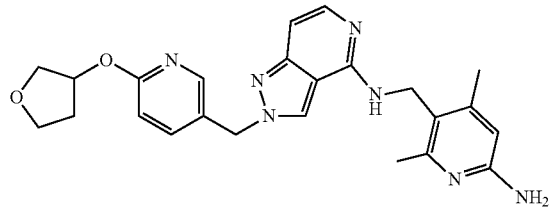 [SMILES: Cc1cc(N)nc(C)c1CNc1nccc2nn(Cc3ccc(OC4CCOC4)nc3)cc12]

N-((6-amino-2,4-dimethylpyridin-3-yl)methyl)-2-((6-(tetrahydrofuran-3-yloxy)pyridin-3-yl)methyl)-2H-pyrazolo[4,3-c]pyridin-4-amine N-((6-amino-2,4-dimethylpyridin-3-yl)methyl)-2-((6-(tetrahydrofuran-3-yloxy)pyridin-3-yl)methyl)-2H-pyrazolo[4,3-c]pyridin-4-amine was prepared in the same manner as Example 468. ¹H NMR (300 MHz, CD₃OD): δ 8.41 (s, 1H), 8.18 (s, 1H), 7.66-7.64 (m, 2H), 6.80-6.74 (m, 2H), 6.34 (d, 1H, J=6.9 Hz), 5.52-5.48 (m, 3H), 4.53 (s, 2H), 3.99-3.85 (m, 4H), 2.40 (s, 3H), 2.27-2.05 (m, 5H). MS (ESI) m/z 446 [M+H]⁺.

Example 484

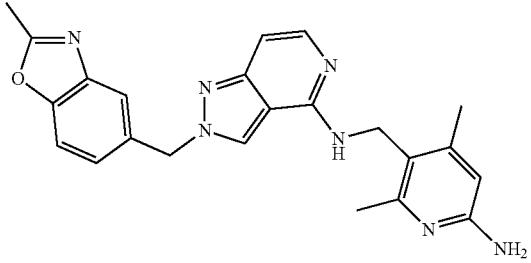

N-((6-amino-2,4-dimethylpyridin-3-yl)methyl)-2-((2-methylbenzo[d]oxazol-5-yl)methyl)-2H-pyrazolo[4,3-c]pyridin-4-amine N-((6-amino-2,4-dimethylpyridin-3-yl)methyl)-2-((2-methylbenzo[d]oxazol-5-yl)methyl)-2H-pyrazolo[4,3-c]pyridin-4-amine was prepared in a manner as described in Example 468. ¹H NMR (300 MHz, CD₃OD): δ 8.44 (s, 1H), 7.55-7.65 (m, 3H), 7.34-7.37 (m, 1H), 6.76 (d, J=6.6 Hz, 1H), 6.35 (s, 1H), 5.65 (s, 2H), 4.52 (s, 2H), 2.63 (s, 3H), 2.39 (s, 3H), 2.26 (s, 3H). MS (ESI) m/z 414 [M+H]⁺.

Example 485

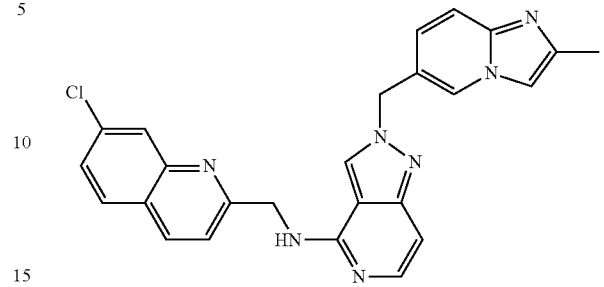

N-((7-chloroquinolin-2-yl)methyl)-2-((2-methylimidazo[1,2-a]pyridin-6-yl)methyl)-2H-pyrazolo[4,3-c]pyridin-4-amine N-((7-chloroquinolin-2-yl)methyl)-2-((2-methylimidazo[1,2-a]pyridin-6-yl)methyl)-2H-pyrazolo[4,3-c]pyridin-4-amine was prepared in a similar manner as Example 481. ¹H NMR (300 MHz, CD₃OD-d): 8.69 (s, 1H), 8.51 (s, 1H), 8.35 (d, J=6.3 Hz, 1H), 8.21-8.20 (1H, m), 8.04 (s, 1H), 7.96 (d, J=6.6 Hz, 1H), 7.64-7.55 (m, 4H), 7.47 (d, J=6.9 Hz, 1H), 7.30 (d, J=8.1 Hz, 1H), 6.89 (d, J=5.1 Hz, 1H), 5.66 (s, 2H), 5.04 (s, 2H), 2.42 (s, 3H). MS (ESI) m/z 454 [M+H]⁺

Example 486

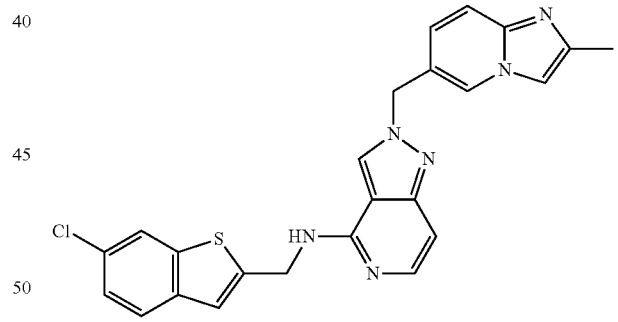

N-((6-chlorobenzo[b]thiophen-2-yl)methyl)-2-((2-methylimidazo[1,2-a]pyridin-6-yl)methyl)-2H-pyrazolo[4,3-c]pyridin-4-amine N-((6-chlorobenzo[b]thiophen-2-yl)methyl)-2-((2-methylimidazo[1,2-a]pyridin-6-yl)methyl)-2H-pyrazolo[4,3-c]pyridin-4-amine was prepared in a similar manner as Example 481. ¹H NMR (300 MHz, CD₃OD): δ 8.99 (s, 1H), 8.84 (s, 1H), 7.96-7.75 (m, 5H), 7.47-7.37 (m, 3H), 7.11 (d, J=7.2 Hz, 1H), 5.85 (s, 2H), 5.10 (s, 2H), 2.56 (s, 3H), 1.40-1.31 (2H, m). MS (ESI) m/z 459 [M+H]⁺

Example 487

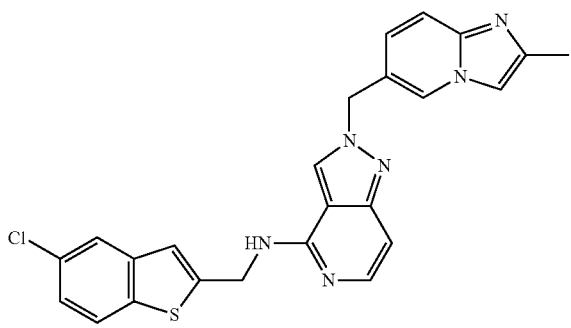 [SMILES: Cc1cn2cc(Cn3cc4c(NCc5cc6cc(Cl)ccc6s5)nccc4n3)ccc2n1]

N-((5-chlorobenzo[b]thiophen-2-yl)methyl)-2-((2-methylimidazo[1,2-a]pyridin-6-yl)methyl)-2H-pyrazolo[4,3-c]pyridin-4-amine N-((5-chlorobenzo[b]thiophen-2-yl)methyl)-2-((2-methylimidazo[1,2-a]pyridin-6-yl)methyl)-2H-pyrazolo[4,3-c]pyridin-4-amine was prepared in a similar manner as Example 481. $^1$H NMR (300 MHz, CD$_3$OD-d): 9.04 (s, 1H), 8.87 (s, 1H), 7.98-7.81 (m, 5H), 7.50-7.40 (m, 2H), 7.40 (d, J=21.9 Hz, 1H), 5.87 (s, 2H), 5.19 (s, 2H), 2.56 (s, 3H). MS (ESI) m/z 459 [M+H]$^+$

Example 488

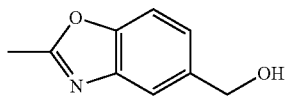

(2-methyl-1,3-benzoxazol-5-yl)methanol

Into a 250-mL round-bottom flask purged and maintained with an inert atmosphere of nitrogen, was placed methyl 3-amino-4-hydroxybenzoate (7.00 g, 41.88 mmol, 1.00 equiv), 1,1,1-trimethoxyethane (50 mL), trifluoroacetic acid (5.2 mL). The resulting solution was stirred for 1.5 h at 25° C. The resulting solution was diluted with 100 mL of DCM. The organic phase was washed with 2×50 mL of saturated sodium bicarbonate aqueous solution and 1×100 mL of brine, dried over anhydrous sodium sulfate and concentrated under vacuum. This resulted in 7.60 g (crude) of methyl 2-methyl-1,3-benzoxazole-5-carboxylate as light brown solids. Into a 100-mL 3-necked round-bottom flask purged and maintained with an inert atmosphere of nitrogen, was placed methyl 2-methyl-1,3-benzoxazole-5-carboxylate (6.00 g, 31.38 mmol, 1.00 equiv), oxolane (50 mL) with stirring at −20° C., to which was added LiAlH$_4$ (1.19 g, 35.08 mmol, 1.00 equiv) in small portions. The resulting solution was stirred for 1 h at −20° C. The reaction was then quenched by the addition of 1.2 mL of water at -20° C. The resulting solution was diluted with 3.6 mL of aqueous NaOH solution (15%) and 1.2 mL of EA at room temperature. The solids were filtered out. The resulting mixture was concentrated under vacuum. The residue was purified by silica column eluted with ethyl acetate/petroleum ether (1:10-1:1). This resulted in 3.65 g (71%) of (2-methyl-1,3-benzoxazol-5-yl)methanol as a brown solid. MS (ESI) m/z: 164[M+H]$^+$

Example 489

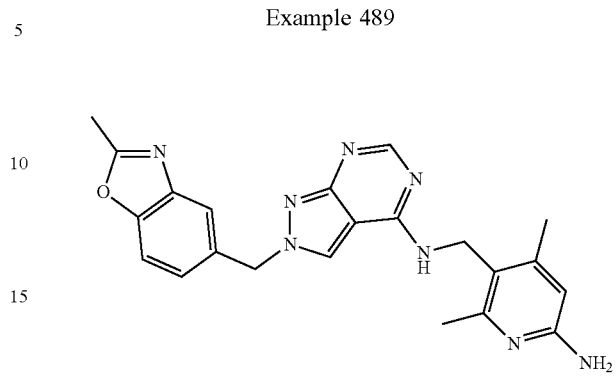

4,6-dimethyl-5-[([2-[(2-methyl-1,3-benzoxazol-5-yl)methyl]-2H-pyrazolo[3,4-d]pyrimidin-4-yl]amino)methyl]pyridin-2-amine Into a 100-mL 3-necked round-bottom flask purged and maintained with an inert atmosphere of nitrogen, was placed a mixture of (2-methyl-1,3-benzoxazol-5-yl)methanol (1.00 g, 6.13 mmol, 1.00 equiv)(Example 488), PPh$_3$ (1.9 g, 7.24 mmol, 1.20 equiv) and 4-chloro-2H-pyrazolo[3,4-d]pyrimidine (950 mg, 6.13 mmol, 1.00 equiv), tetrahydrofuran (40 mL) with stirring at 0° C. for 5 min, to which was added DEAD (1.3 g, 7.46 mmol, 1.20 equiv) dropwise. The resulting solution was stirred overnight at 25° C. The reaction mixture was concentrated under vacuum. The crude product was purified by silica gel column chromatography, eluted with EA/PE (1:10 to 1:1). This resulted in 700 mg (crude) of 5-([4-chloro-2H-pyrazolo[3,4-d]pyrimidin-2-yl]methyl)-2-methyl-1,3-benzoxazole as an off-white solid, which was used in the next step. Into a 50-mL round-bottom flask, was placed 5-([4-chloro-2H-pyrazolo[3,4-d]pyrimidin-2-yl]methyl)-2-methyl-1,3-benzoxazole (200 mg, 0.33 mmol, 1.00 equiv), dichlorozinc (448 mg, 0.33 mmol, 10.00 equiv) and tert-butyl N-[5-(aminomethyl)-4,6-dimethylpyridin-2-yl]-N-[(tert-butoxy)carbonyl]carbamate (235 mg, 0.66 mmol, 2.00 equiv)(Example 4, Step 2) in 1-ethoxy-2-(2-ethoxyethoxy)ethane (7 mL). The resulting solution was stirred for 2 h at 120° C. The reaction mixture was cooled with a water/ice bath and diluted with 2 mL of DMSO. The crude product was purified by Flash-Prep-HPLC with silica gel column chromatography eluted with DCM/MeOH (1:0 to 3:1) to give a residue. The crude product was further purified by Prep-HPLC with the following conditions. Column: Waters, Prep X-bridge RP18, 19*150 mm, 5 μm; mobile phase: acetonitrile and water (a buffer of 10 mM ammonium bicarbonate+0.05% ammonia) with a gradient of 35% to 38% acetonitrile in 5 min; flow rate: 20 mL/min; detector UV wavelength: 254 nm. This resulted in 34 mg (25%) of 4,6-dimethyl-5-[([2-[(2-methyl-1,3-benzoxazol-5-yl)methyl]-2H-pyrazolo[3,4-d]pyrimidin-4-yl]amino)methyl]pyridin-2-amine as a white solid.

$^1$H NMR (300 MHz, DMSO-d$_6$): ppm δ 8.25 (s, 1H), 8.18 (s, 1H), 7.88 (s, 1H), 7.63-7.75 (m, 2H), 7.30 (d, J=8.1 Hz, 1H), 6.07 (s, 1H), 5.62 (s, 2H), 5.55 (s, 2H), 4.43 (d, J=4.2 Hz, 2H), 2.53 (s, 3H), 2.21 (s, 3H), 2.07 (s, 3H). MS (ESI) m/z: 415[M+H]$^+$.

Example 490

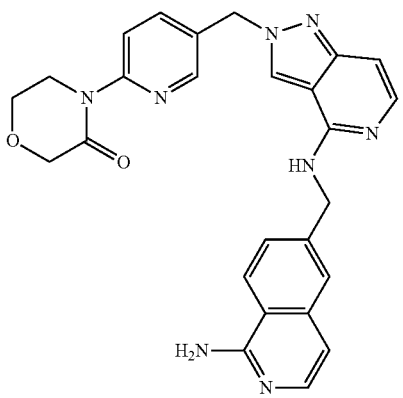 [SMILES: Nc1nccc2cc(CNc3nccc4nn(Cc5ccc(N6CCOCC6=O)nc5)cc34)ccc12]

4-(5-((4-((1-aminoisoquinolin-6-yl)methylamino)-2H-pyrazolo[4,3-c]pyridin-2-yl)methyl)pyridin-2-yl)morpholin-3-one 4-(5-((4-((1-aminoisoquinolin-6-yl)methylamino)-2H-pyrazolo[4,3-c]pyridin-2-yl)methyl)pyridin-2-yl)morpholin-3-one was prepared in a similar manner as Example 446. $^1$H NMR (300 MHz, CD$_3$OD): δ 8.51 (d, 2H, J=2.7 Hz), 8.27 (d, 1H, J=8.4 Hz), 7.99-7.94 (m, 1H), 7.88-7.79 (m, 1H), 7.70-7.66 (m, 2H), 7.57 (d, 2H, J=9.6 Hz), 6.97 (d, 1H, J=5.7 Hz), 6.78 (d, 1H, J=6.6 Hz), 5.66 (d, 2H, J=6.9 Hz), 4.31 (s, 2H), 4.04 (m, 4H). MS (ESI) m/z 481 [M+H-TFA]$^+$.

Example 491

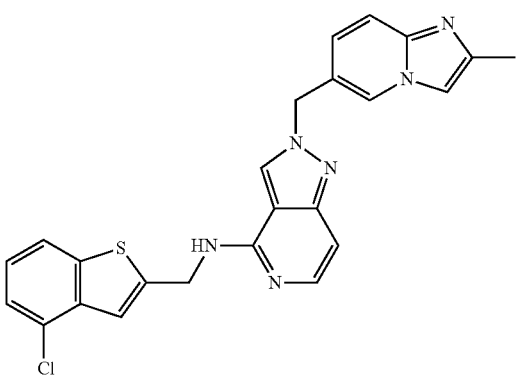 [SMILES: Cc1cn2cc(Cn3cc4c(NCc5cc6c(Cl)cccc6s5)nccc4n3)ccc2n1]

N-((4-chlorobenzo[b]thiophen-2-yl)methyl)-2-((2-methylimidazo[1,2-a]pyridin-6-yl)methyl)-2H-pyrazolo[4,3-c]pyridin-4-amine N-((4-chlorobenzo[b]thiophen-2-yl)methyl)-2-((2-methylimidazo[1,2-a]pyridin-6-yl)methyl)-2H-pyrazolo[4,3-c]pyridin-4-amine was prepared in a similar manner to Example 481. $^1$H NMR (300 MHz, CD$_3$OD): 8.46 (s, 2H), 7.73-7.61 (3H, m), 7.45-7.42 (m, 2H), 7.35 (d, J=6.9 Hz, 1H), 7.22-7.27 (m, 2H), 6.80 (d, J=5.7 Hz, 2H), 5.60 (s, 2H), 5.10 (s, 2H), 2.41 (s, 3H). MS (ESI) m/z 459 [M+H]$^+$

Example 492

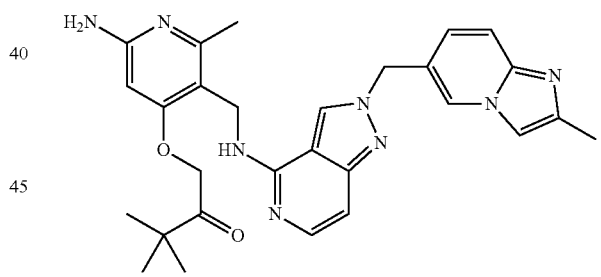

N-((2-(5-chlorothiophen-2-yl)thiazol-5-yl)methyl)-2-((2-methylimidazo[1,2-a]pyridin-6-yl)methyl)-2H-pyrazolo[4,3-c]pyridin-4-amine N-((2-(5-chlorothiophen-2-yl)thiazol-5-yl)methyl)-2-((2-methylimidazo[1,2-a]pyridin-6-yl)methyl)-2H-pyrazolo[4,3-c]pyridin-4-amine was prepared in a similar manner as Example 481. $^1$H NMR (300 MHz, CD$_3$OD): 8.47 (s, 2H), 7.68 (d, J=4.8 Hz, 2H), 7.63 (s, 1H), 7.46 (d, J=7.2 Hz, 1H), 7.35 (s, 1H), 7.27 (d, J=8.1 Hz, 1H), 7.01 (s, 1H), 6.85 (d, J=5.1 Hz, 1H), 5.61 (s, 2H), 4.94 (s, 2H), 2.41 (s, 3H). MS (ESI) m/z 492 [M+H]$^+$

Example 493

1-(6-amino-2-methyl-3-((2-((2-methylimidazo[1,2-a]pyridin-6-yl)methyl)-2H-pyrazolo[4,3-c]pyridin-4-ylamino)methyl)pyridin-4-yloxy)-3,3-dimethylbutan-2-one 1-(6-amino-2-methyl-3-((2-((2-methylimidazo[1,2-a]pyridin-6-yl)methyl)-2H-pyrazolo[4,3-c]pyridin-4-ylamino)methyl)pyridin-4-yloxy)-3,3-dimethylbutan-2-one was prepared in a similar manner as Example 481. $^1$H NMR (300 MHz, CD$_3$OD-d): 8.55 (s, 1H), 8.45 (s, 1H), 7.71 (s, 1H), 7.61 (d, J=6.4 Hz, 1H), 7.41 (d, J=9.2 Hz, 1H), 7.103 (d, J=10.8 Hz, 1H), 6.97 (s, 1H), 6.612 (d, J=6.4 Hz, 1H), 5.71 (d, J=6.8 Hz, 3H), 5.51 (s, 2H), 5.07 (s, 1H), 4.45 (s, 2H), 2.40 (s, 6H), 2.31 (s, 3H), 1.12 (s, 9H). MS (ESI) m/z 513 [M+H]$^+$

Example 494

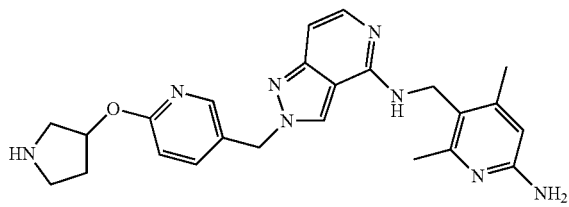 [SMILES: Cc1cc(N)nc(C)c1CNc1nccc2nn(Cc3ccc(OC4CCNC4)nc3)cc12]

N-((6-amino-2,4-dimethylpyridin-3-yl)methyl)-2-((6-(pyrrolidin-3-yloxy)pyridin-3-yl)methyl)-2H-pyrazolo[4,3-c]pyridin-4-amine N-((6-amino-2,4-dimethylpyridin-3-yl)methyl)-2-((6-(pyrrolidin-3-yloxy)pyridin-3-yl)methyl)-2H-pyrazolo[4,3-c]pyridin-4-amine was prepared in the same way as Example 446. $^1$H NMR (300 MHz, DMSO-$d_6$): δ 8.4 (s, 1H), 8.20-8.23 (m, 1H), 7.59-7.66 (m, 2H), 6.99 (s, 1H), 6.74-6.83 (m, 1H), 6.60 (d, J=6.6 Hz, 1H), 6.13 (s, 1H), 5.62 (s, 2H), 5.46 (s, 2H), 5.31-5.35 (m, 1H), 4.41 (d, J=4.2 Hz, 2H), 3.01-3.50 (m, 2H), 2.72-2.90 (m, 2H), 2.28 (s, 3H), 2.15 (s, 3H), 1.65-2.05 (m, 2H). MS (ESI) m/z 445 [M+H]$^+$.

Example 495

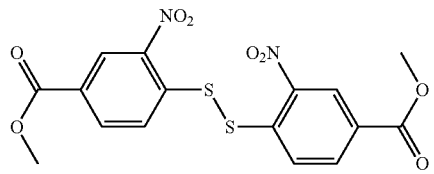 [SMILES: COC(=O)c1ccc(SSc2ccc(C(=O)OC)cc2[N+](=O)[O-])c([N+](=O)[O-])c1]

methyl 4-[[4-(methoxycarbonyl)-2-nitrophenyl]disulfanyl]-3-nitrobenzoate

Into a 100-mL round-bottom flask purged and maintained with an inert atmosphere of nitrogen, was placed a solution of methyl 4-bromo-3-nitrobenzoate (6.0 g, 23.07 mmol, 1.00 equiv) in methanol (50 mL), sulfur (0.43 g, 13.00 mmol, 0.58 equiv), a solution of sodium sulfide hydrate (Na$_2$S.9H$_2$O, 2.2 g, 13.00 mmol, 0.58 equiv) in water (30 mL). The resulting solution was stirred for 3 h at 85° C. The reaction mixture was cooled to room temperature. The solids were collected by filtration. The filtrate was diluted with 150 mL of ethanol and stirred overnight at room temperature. The solids were collected by filtration. The solids were washed with 3x 30 mL of ethanol. This resulted in 3.06 g (62%) of methyl 4-[[4-(methoxycarbonyl)-2-nitrophenyl]disulfanyl]-3-nitrobenzoate as a yellow solid. MS (ESI) m/z 425 [M+H]$^+$.

Example 496

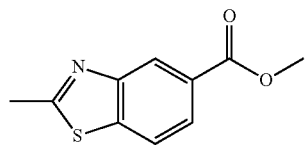

methyl 2-methyl-1,3-benzothiazole-5-carboxylate

Into a 100-mL round-bottom flask, was placed methyl 4-[[4-(methoxycarbonyl)-2-nitrophenyl]disulfanyl]-3-nitrobenzoate (1.5 g, 3.53 mmol, 1.00 equiv)(Example 495) in acetic acid (30 mL). To the stirred solution was added zinc powder (3.0 g, 46.66 mmol, 14.00 equiv) portion by portion with stirring. The resulted mixture was stirred 3 h at 80° C. To it was added another batch of zinc powder (1.5 g, 23.34 mmol, 7.0 equiv). The resulted mixture was stirred for additional 0.5 h at 80° C. To the mixture was added acetic anhydride (1 mL). The resulting solution was allowed to react with stirring for an additional 2 hr at 80° C. The reaction mixture was then cooled to room temperature. The resulted solution was diluted with 50 mL of ethyl acetate. The solids were filtered out. The filter cake was washed with 2×50 mL of ethyl acetate. The filtrate was concentrated under vacuum to give 800 mg (55%) of methyl 2-methyl-1,3-benzothiazole-5-carboxylate as a light yellow solid. MS (ESI) m/z 208 [M+H]$^+$

Example 497

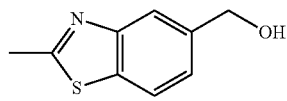

(2-methyl-1,3-benzothiazol-5-yl)methanol

Into a 100-mL 3-necked round-bottom flask, was placed a solution of methyl 2-methyl-1,3-benzothiazole-5-carboxylate (800 mg, 3.86 mmol, 1.00 equiv)(Example 496) in tetrahydrofuran (30 mL) stirred at 0° C. for 5 minutes. To it was added lithium aluminum hydride (180 mg, 4.74 mmol, 1.20 equiv) in several batches at 0° C. The resulted solution was stirred for 15 min at room temperature.

The reaction was then quenched by the addition of 0.18 mL of water at 0° C. To the solution was added with 0.18 mL of aqueous of NaOH (15%) and 0.54 mL of H$_2$O. The mixture was diluted with 50 mL of H$_2$O and 50 ml of ethyl acetate. The solids were filtered out. The filter cake was washed with 3×20 mL of ethyl acetate. The filtrate was washed with 1×80 mL of water and 1×50 mL of brine. The organic layer was dried over anhydrous sodium sulfate and concentrated under vacuum. This resulted in 600 mg (87%) of (2-methyl-1,3-benzothiazol-5-yl)methanol as a yellow oil. MS (ESI) m/z 178 [M+H]$^+$.

Example 498

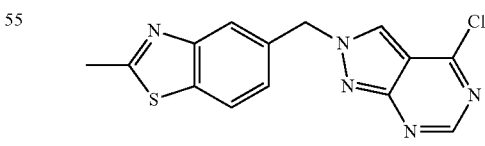

5-([4-chloro-2H-pyrazolo[3,4-d]pyrimidin-2-yl]methyl)-2-methyl-1,3-benzothiazole Into a 100-mL 3-necked round-bottom flask purged and maintained with an inert atmosphere of nitrogen, were placed (2-methyl-1,3-benzothiazol-5-yl)methanol (500 mg, 2.79 mmol, 1.00 equiv)(Example 497), 4-chloro-1H-pyrazolo[3,4-d]pyrimidine (462 mg, 2.99 mmol, 1.07 equiv), triphenyl phosphine (954 mg, 3.64 mmol, 1.30 equiv) and tetrahydrofuran (30 mL) with stirring at 0° C. This was followed by the addition of DEAD (633 mg, 3.63 mmol, 1.30 equiv) dropwise with stirring at 0° C. The resulted solution was stirred overnight at room temperature. The mixture was concentrated under vacuum. The residue was diluted with 100 mL of water and extracted with 3×50 mL of ethyl acetate. The organic phase was washed with 2×100 mL of water and 1×100 mL of brine and dried over anhydrous sodium sulfate. The crude was purified by silica gel column with ethyl acetate/petroleum ether (1:4-1:1). This resulted in 220 mg (25%) of 5-([4-chloro-2H-pyrazolo[3,4-d]pyrimidin-2-yl]methyl)-2-methyl-1,3-benzothiazole as a off-white solid. MS (ESI) m/z 316 [M+H]+.

Example 499

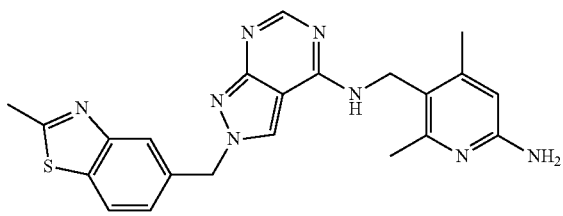 [SMILES: Cc1nc2cc(Cn3cc4c(NCc5c(C)cc(N)nc5C)ncnc4n3)ccc2s1]

4,6-dimethyl-5-[([2-[(2-methyl-1,3-benzothiazol-5-yl)methyl]-2H-pyrazolo[3,4-d]pyrimidin-4-yl]amino)methyl]pyridin-2-amine Into a 30-mL bottle, were placed 5-([4-chloro-2H-pyrazolo[3,4-d]pyrimidin-2-yl]methyl)-2-methyl-1,3-benzothiazole (110 mg, 0.35 mmol, 1.00 equiv)(Example 498), tert-butyl N-[5-(aminomethyl)-4,6-dimethylpyridin-2-yl]-N-[(tert-butoxy)carbonyl]carbamate (184 mg, 0.52 mmol, 1.50 equiv)(Example 4, Step 2), 1-ethoxy-2-(2-ethoxyethoxyl)ethane (10 mL) and dichlorozinc (468 mg, 3.43 mmol, 10.00 equiv). The resulted solution was stirred 3 h at 120° C. The crude product was purified by reverse phase medium pressure column chromatography with the following conditions: column, silica gel; mobile phase, methanol/0.05% ammonia aqueous solution (ratio: 4:1) within 12 min; detector UV wavelength: 254 nm. The crude product was further purified by Prep-HPLC with the following conditions: column, Bridge C18; mobile phase, acetonitrile/water (0.05% NH4OH, 10 mM NH4HCO3) gradient from 18% to 36% within 6 min, flow rate: 20 mL/min; detector UV wavelength: 254 nm. This resulted in 60.9 mg (41%) of 4,6-dimethyl-5-[([2-[(2-methyl-1,3-benzothiazol-5-yl)methyl]-2H-pyrazolo[3,4-d]pyrimidin-4-yl]amino)methyl]pyridin-2-amine as a white solid. 1H NMR (300 MHz, CD3OD): 8.33 (s, 2H), 7.95 (d, J=8.4 Hz, 1H), 7.85 (s, 1H), 6.34 (s, 1H), 5.68 (s, 2H), 4.68 (s, 2H), 2.82 (s, 3H), 2.39 (s, 3H), 2.26 (s, 3H). MS (ESI) m/z 431 [M+H]+.

Example 500

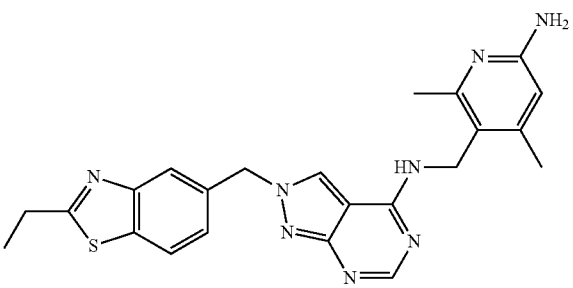 [SMILES: CCc1nc2cc(Cn3cc4c(NCc5c(C)cc(N)nc5C)ncnc4n3)ccc2s1]

5-[([2-[(2-ethyl-1,3-benzothiazol-5-yl)methyl]-2H-pyrazolo[3,4-d]pyrimidin-4-yl]amino)methyl]-4,6-dimethylpyridin-2-amine 5-[([2-[(2-ethyl-1,3-benzothiazol-5-yl)methyl]-2H-pyrazolo[3,4-d]pyrimidin-4-yl]amino)methyl]-4,6-dimethylpyridin-2-amine was prepared in a similar manner as Example 499. 1H NMR (300 MHz, CD3OD): 8.32 (s, 2H), 7.96-7.85 (m, 2H), 7.42 (d, J=8.4 Hz, 1H), 6.33 (s, 1H), 5.68 (s, 1H), 4.65 (s, 1H), 3.18-3.09 (m, 2H), 2.39 (s, 3H), 2.26 (s, 3H), 1.47-1.42 (m, 3H). MS (ESI) m/z 445 [M+H]+.

Example 501

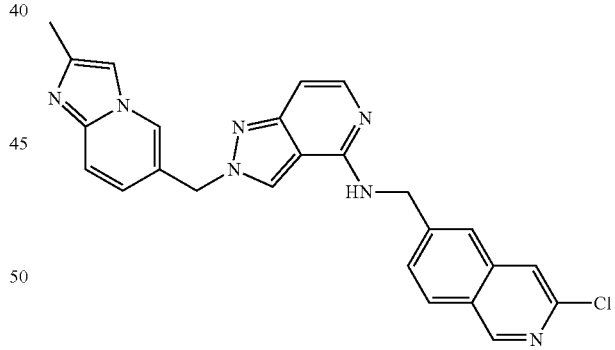

N-((3-chloroisoquinolin-6-yl)methyl)-2-((2-methylimidazo[1,2-a]pyridin-6-yl)methyl)-2H-pyrazolo[4,3-c]pyridin-4-amine N-((3-chloroisoquinolin-6-yl)methyl)-2-((2-methylimidazo[1,2-a]pyridin-6-yl)methyl)-2H-pyrazolo[4,3-c]pyridin-4-amine was prepared in a similar manner as Example 481. 1H NMR (300 MHz, CD3OD-d): 9.05 (s, 1H), 8.49 (d, J=6.3, 2H), 8.09 (d, J=8.7 Hz, 1H), 7.83 (s, 2H), 7.72 (d, J=8.4 Hz, 1H), 7.62-7.57 (m, 2H), 7.47 (d, J=9.3 Hz, 1H), 7.28 (d, J=14.4 Hz, 1H), 6.79 (d, J=7.2 Hz, 1H), 5.61 (s, 2H), 4.93 (s, 2H), 2.41 (s, 3H). MS (ESI) m/z 454 [M+H]⁺.

Example 502

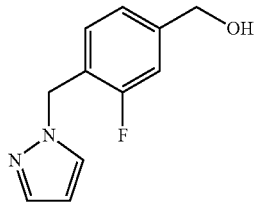 [SMILES: OCc1ccc(Cn2cccn2)c(F)c1]

(4-((1H-pyrazol-1-yl)methyl)-3-fluorophenyl)methanol

To a solution of methyl 4-((1H-pyrazol-1-yl)methyl)-3-fluorobenzoate (250.00 mg; 1.07 mmol; 1.00 eq.) in THF (4 mL) was added lithium aluminum hydride (1.60 ml; 1.00 mol/l; 1.60 mmol; 1.50 eq.) at 0° C. and the mixture was stirred until finished, then it was quenched with water and extracted with EtOAc, organic layer was combined and concentrated to give crude product, which was purified by column chromatography to give (4-((1H-pyrazol-1-yl)methyl)-3-fluorophenyl)methanol (170 mg).

Example 503

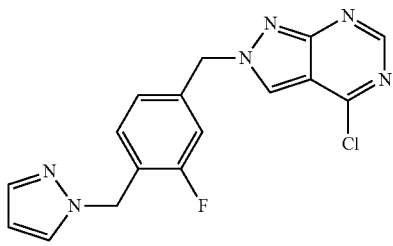 [SMILES: Fc1cc(Cn2cc3c(Cl)ncnc3n2)ccc1Cn1cccn1]

2-(4-((1H-pyrazol-1-yl)methyl)-3-fluorobenzyl)-4-chloro-2H-pyrazolo[3,4-d]pyrimidine To a solution of (4-((1H-pyrazol-1-yl)methyl)-3-fluorophenyl)methanol (170.00 mg; 0.82 mmol; 1.00 eq.)(Example 502) and 4-chloro-1H-pyrazolo[3,4-d]pyrimidine (140.15 mg; 0.91 mmol; 1.10 eq.) in THF (6 mL) was added polymer supported PPh3 and diisopropyl (E)-1,2-diazenedicarboxylate (0.21 ml; 1.07 mmol; 1.30 eq.), at 0° C., after stirred further for 2 h, the mixture was filtered and the filtrate was concentrated to give crude product, which was purified by column chromatography to give 2-(4-((1H-pyrazol-1-yl)methyl)-3-fluorobenzyl)-4-chloro-2H-pyrazolo[3,4-d]pyrimidine (40 mg).

Example 504

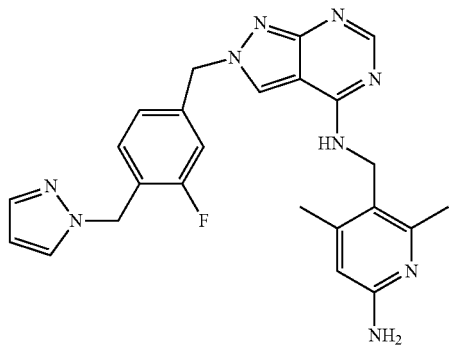 [SMILES: Cc1cc(N)nc(C)c1CNc1ncnc2nn(Cc3ccc(Cn4cccn4)c(F)c3)cc12]

2-(4-((1H-pyrazol-1-yl)methyl)-3-fluorobenzyl)-N-((6-amino-2,4-dimethylpyridin-3-yl)methyl)-2H-pyrazolo[3,4-d]pyrimidin-4-amine To a solution of 2-(4-((1H-pyrazol-1-yl)methyl)-3-fluorobenzyl)-4-chloro-2H-pyrazolo[3,4-d]pyrimidine (40.00 mg; 0.12 mmol; 1.00 eq.)(Example 503) and tert-butyl N-[5-(aminomethyl)-4,6-dimethylpyridin-2-yl]-N-[(tert-butoxy)carbonyl]carbamate (51.27 mg; 0.15 mmol; 1.25 eq.) (Example 4, Step 2) in NMP (0.5 mL) was added Hunig's base (0.03 ml; 0.15 mmol; 1.25 eq.) and the mixture was heated in microwave synthesizer for 25 min at 110° C., then it was cooled and diluted with EtOAc, washed with brine, dried and concentrated to give crude oil, which was diluted with DCM (1 mL) and was treated with TFA (1 mL), after stirred for 2 hr at room temperature, it was concentrated and purified by preparative HPLC to give 2-(4-((1H-pyrazol-1-yl)methyl)-3-fluorobenzyl)-N-((6-amino-2,4-dimethylpyridin-3-yl)methyl)-2H-pyrazolo[3,4-d]pyrimidin-4-amine (37 mg). $^1$H NMR (400 MHz, DMSO-$d_6$) δ 8.51 (d, J=13.7 Hz, 2H), 7.78 (dd, J=2.2, 0.6 Hz, 1H), 7.68 (s, 2H), 7.42 (dd, J=1.8, 0.7 Hz, 1H), 7.21 (d, J=10.8 Hz, 1H), 7.14 (d, J=4.5 Hz, 2H), 6.66 (s, 1H), 6.24 (dd, J=2.3, 1.8 Hz, 1H), 5.60 (s, 2H), 5.35 (s, 2H), 4.63 (d, J=4.7 Hz, 2H), 2.51 (s, 3H), 2.43 (p, J=2.0 Hz, 1H), 2.37 (s, 3H).MS (M+H)+ found for $C_{24}H_{24}FN_9$: 458.2.

Example 505

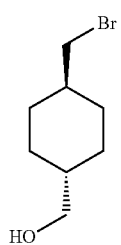

4-(bromomethyl)cyclohexylmethanol

To a solution of cyclohexane-1,4-diyldimethanol (1.44 g; 10.00 mmol; 2.00 eq.) in DMF (20 mL) was added dibromo(triphenyl)phosphorane (2.11 g; 5.00 mmol; 1.00 eq.) and the mixture was stirred for 3 hr at room temperature, then it was diluted with water and was extracted with hexane, organic layer was combined and concentrated to give crude product, which was purified by column chromatography to give ((1R,4R)-4-(bromomethyl)cyclohexyl)methanol (350 mg).

Example 506

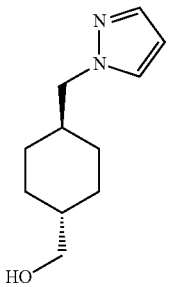

4-((1H-pyrazol-1-yl)methyl)cyclohexyl)methanol

To a solution of ((1R,4R)-4-(bromomethyl)cyclohexyl)methanol (318.00 mg; 1.54 mmol; 1.00 eq.)(Example 505) and 1H-pyrazole (156.79 mg; 2.30 mmol; 1.50 eq.) AcCN (6 mL) was added Potassium Carbonate (423.78 mg; 3.07 mmol; 2.00 eq.) and the suspension was heated at reflux for 15 h, then it was concentrated and diluted with water and EtOAc, organic layer was separated and washed with brine, dried and concentrated to give crude product, which was purified by column to give 4-((1H-pyrazol-1-yl)methyl)cyclohexyl)methanol.

Example 507

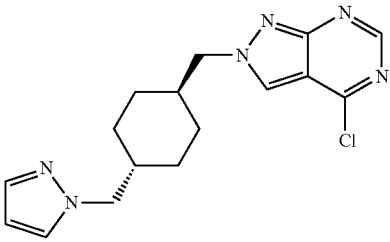 [SMILES: Clc1ncnc2nn(C[C@H]3CC[C@H](Cn4cccn4)CC3)cc12]

2-((-4-((1H-pyrazol-1-yl)methyl)cyclohexyl)methyl)-4-chloro-2H-pyrazolo[3,4-d]pyrimidine To a solution of (4-((1H-pyrazol-1-yl)methyl)cyclohexyl-methanol (110.00 mg; 0.57 mmol; 1.00 eq.)(Example 506) and 4-chloro-1H-pyrazolo[3,4-d]pyrimidine (96.26 mg; 0.62 mmol; 1.10 eq.) in THF (4 mL) was added polymer supported PPh3 and diisopropyl (E)-1,2-diazenedicarboxylate (0.13 ml; 0.68 mmol; 1.20 eq.) at 0° C., then it was stirred for 1 h, and insoluble material was filter off, the filtrate was concentrated and purified by column chromatography to give 2-((-4-((1H-pyrazol-1-yl)methyl)cyclohexyl)methyl)-4-chloro-2H-pyrazolo[3,4-d]pyrimidine (10 mg).

Example 508

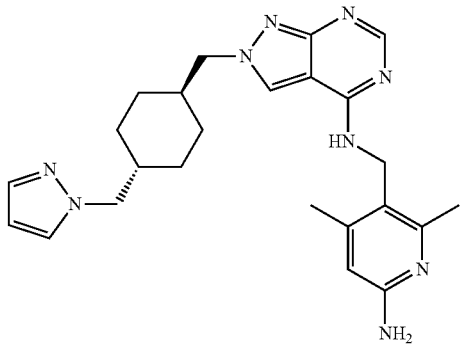 [SMILES: Cc1cc(N)nc(C)c1CNc1ncnc2nn(C[C@H]3CC[C@H](Cn4cccn4)CC3)cc12]

2-((4-((1H-pyrazol-1-yl)methyl)cyclohexyl)methyl)-N-((6-amino-2,4-dimethylpyridin-3-yl)methyl)-2H-pyrazolo[3,4-d]pyrimidin-4-amine To a solution of 2-((4-((1H-pyrazol-1-yl)methyl)cyclohexyl)methyl)-4-chloro-2H-pyrazolo[3,4-d]pyrimidine (10.00 mg; 0.03 mmol; 1.00 eq.)(Example 507) in NMP (0.5 mL) was added Hunig's base (0.01 ml; 0.03 mmol; 1.10 eq.) and tert-butyl N-[5-(aminomethyl)-4,6-dimethylpyridin-2-yl]-N-[(tert-butoxy)carbonyl]carbamate (11.69 mg; 0.03 mmol; 1.10 eq.)(Example 4, Step 2) and heated at 110° C. for 20 min in microwave, then it was worked up with EtOAc and water and the organic layer was concentrated to give crude product, which was diluted with DCM (1 mL) and TFA (1 mL) and stirred at room temperature for 2 h, the solution was concentrated and the crude oil was purified by preparative HPLC to give 2-((4-((1H-pyrazol-1-yl)methyl)cyclohexyl)methyl)-N-((6-amino-2,4-dimethylpyridin-3-yl)methyl)-2H-pyrazolo[3,4-d]pyrimidin-4-amine (11 mg). $^1$H NMR (400 MHz, DMSO-$d_6$) δ 8.64 (d, J=17.9 Hz, 1H), 8.46 (s, 1H), 7.73 (s, 2H), 7.62 (dd, J=2.2, 0.8 Hz, 1H), 7.38 (dd, J=1.9, 0.7 Hz, 1H), 6.67 (s, 1H), 6.18 (t, J=2.0 Hz, 1H), 4.68 (d, J=4.8 Hz, 2H), 4.23 (d, J=6.9 Hz, 2H), 3.91 (d, J=7.0 Hz, 2H), 2.64 (s, 3H), 2.47 (s, 3H), 1.81 (s, 1H), 1.72 (s, 1H), 1.49 (d, J=12.1 Hz, 4H), 0.93 (q, J=12.7 Hz, 4H). MS (M+H)+ found for $C_{24}H_{31}N_9$: 446.2.

Example 509

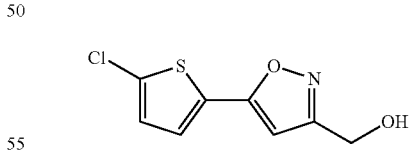

(5-(5-chlorothiophen-2-yl)isoxazol-3-yl)methanol

Into a 50-mL 3-necked round-bottom flask purged and maintained with an inert atmosphere of nitrogen, was placed 5-(5-chlorothiophen-2-yl)-1,2-oxazole-3-carboxylic acid (300 mg, 1.31 mmol, 1.00 equiv) in anhydrous tetrahydrofuran (10 mL) stirred at 0° C. To the solution was added borane-tetrahydrofuran solution (6 mL, 1 M) dropwise at 0° C. The resulting solution was stirred for 1 h at room temperature. The reaction was then quenched by the addition of methanol (10 mL) at 0° C. The resulting mixture was concentrated under vacuum. The crude product was purified by silica gel column chromatography eluted with ethyl acetate and petroleum ether (1:2). This resulted in 60 mg (20%) of (5-(5-chlorothiophen-2-yl)isoxazol-3-yl)methanol as yellow solid. MS (ESI) m/z 216 [M+H]+.

Example 510

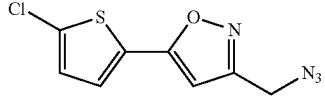 [SMILES: [N-]=[N+]=NCc1cc(-c2ccc(Cl)s2)on1]

3-(azidomethyl)-5-(5-chlorothiophen-2-yl)isoxazole

Into a 50-mL 3-necked round-bottom flask purged and maintained with an inert atmosphere of nitrogen, were placed (5-(5-chlorothiophen-2-yl)isoxazol-3-yl)methanol (60 mg, 0.28 mmol, 1.00 equiv)(Example 509) in tetrahydrofuran (10 mL) and DPPA (193 mg, 0.70 mmol, 2.50 equiv). This was followed by the addition of DBU (128 mg, 0.84 mmol, 3.00 equiv) in several batches at 0° C. The resulting solution was stirred overnight at room temperature. The resulting solution was diluted with 20 mL of ethyl acetate. The resulting mixture was washed with 1×20 mL of brine and dried over anhydrous sodium sulfate and concentrated under vacuum. The crude product was purified by silica gel column chromatography eluted with ethyl acetate and petroleum ether (1:3). This resulted in 50 mg (75%) of 3-(azidomethyl)-5-(5-chlorothiophen-2-yl)isoxazole as a yellow solid. MS (ESI) m/z 241 [M+H]+.

Example 511

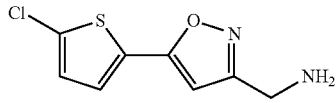 [SMILES: NCc1cc(-c2ccc(Cl)s2)on1]

(5-(5-chlorothiophen-2-yl)isoxazol-3-yl)methanamine

Into a 50-mL 3-necked round-bottom flask purged and maintained with an inert atmosphere of nitrogen, were placed 3-(azidomethyl)-5-(5-chlorothiophen-2-yl)isoxazole (50 mg, 0.21 mmol, 1.00 equiv)(Example 510), (10 mL), water (2 mL), triphenyl phosphine (165 mg, 0.63 mmol, 3.00 equiv). The resulting solution was stirred overnight at room temperature. The solution was extracted with 20 mL of ethyl acetate and washed with 1×20 mL of brine. The organic phase was dried over anhydrous sodium sulfate and concentrated under vacuum. The crude product was purified by silica gel column chromatography eluted with ethyl acetate and petroleum ether (1:3). This resulted in 40 mg (90%) of (5-(5-chlorothiophen-2-yl)isoxazol-3-yl)methanamine as yellow solid. MS (ESI) m/z 215 [M+H]+.

Example 512

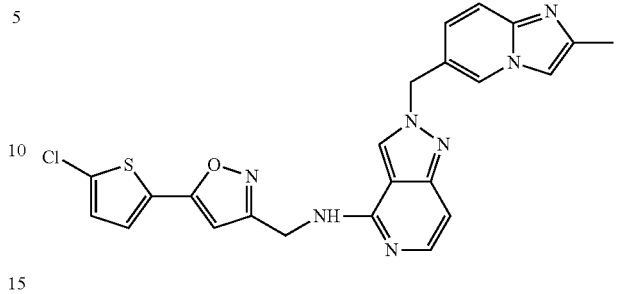

N-((5-(5-chlorothiophen-2-yl)isoxazol-3-yl)methyl)-2-((2-methylimidazo[1,2-a]pyridin-6-yl)methyl)-2H-pyrazolo[4,3-c]pyridin-4-amine Into a 8-mL vial, were placed 6-([4-chloro-2H-pyrazolo[4,3-c]pyridin-2-yl]methyl)-2-methylimidazo[1,2-a]pyridine (37 mg, 0.12 mmol, 1.00 equiv)(Example 445), [5-(5-chlorothiophen-2-yl)-1,2-oxazol-3-yl]methanamine (40 mg, 0.19 mmol, 1.50 equiv)(Example 511), 1-ethoxy-2-(2-ethoxyethoxy)ethane (6 mL), dichlorozinc (169.5 mg, 1.24 mmol, 10.00 equiv) and DIEA (322.5 mg, 2.50 mmol, 20.00 equiv). The resulting solution was stirred 3 h at 120° C. The crude product was purified by reverse phase column chromatography with the following conditions: silica gel column; mobile phase: dichloromethane /ethyl acetate/ methanol/ concentrated ammonia aqueous solution (ratio: 4:4:1: 0.2) within 30 min; detector UV wavelength: 254 nm. The crude product was purified by Prep-HPLC with the following conditions: column, Bridge C18; mobile phase: acetonitrile/water (0.05% NH4OH, 10 mM NH4HCO3) gradient from 45% to 51% within 5 min, flow rate: 20 mL/min; detector UV wavelength: 254 nm. This resulted in 7.1 mg (12%) of N-[[5-(5-chlorothiophen-2-yl)-1,2-oxazol-3-yl]methyl]-2-([2-methylimidazo[1,2-a]pyridin-6-yl]methyl)-2H-pyrazolo[4,3-c]pyridin-4-amine as a white solid. 1H NMR (300 MHz, CD3OD-d): 8.45 (s, 2H), 7.66-7.61 (m, 2H), 7.49-7.37 (m, 2H), 7.28 (d, J=18.6 MHz, 1H), 7.09 (d, J=9.3 MHz, 1H), 6.80 (d, J=6.6 MHz, 1H), 5.60 (s, 2H), 4.85 (2H, s), 2.40 (s, 3H). MS (ESI) m/z 476 [M+H]+

Example 513

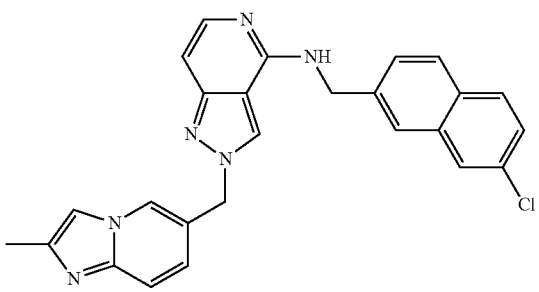 [SMILES: Cc1cn2cc(Cn3cc4c(NCc5ccc6ccc(Cl)cc6c5)nccc4n3)ccc2n1]

N-((7-chloronaphthalen-2-yl)methyl)-2-((2-methylimidazo[1,2-a]pyridin-6-yl)methyl)-2H-pyrazolo[4, 3-c]pyridin-4-amine N-((7-chloronaphthalen-2-yl)methyl)-2-((2-methylimidazo[1,2-a]pyridin-6-yl)methyl)-2H-pyrazolo[4,3-c]pyridin-4-amine was prepared in a similar manner as Example 446. ¹H NMR (300 MHz, CD₃OD-d): 8.84 (s, 1H), 8.53 (s, 1H), 7.82-7.75 (m, 4H), 7.60 (s, 1H), 7.49-7.42 (m, 2H), 7.37 (d, J=10.8 Hz, 1H), 7.31 (d, J=7.2 Hz, 1H), 6.93 (d, J=7.6 Hz, 1H), 5.60 (s, 2H), 4.84 (s, 2H), 2.34 (s, 3H). MS (ESI) M/Z: 453 [M+H]⁺

Example 514

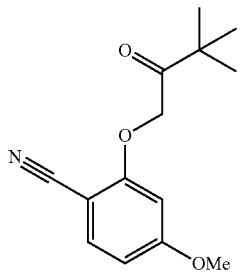 [SMILES: COc1ccc(C#N)c(OCC(=O)C(C)(C)C)c1]

2-(3,3-dimethyl-2-oxobutoxy)-4-methoxybenzonitrile

Into a 250-mL 3-necked round-bottom flask purged and maintained with an inert atmosphere of nitrogen, was placed a mixture of 2-hydroxy-4-methoxybenzonitrile (2 g, 13.41 mmol, 1.00 equiv), acetone (80 mL), 1-bromo-3,3-dimethylbutan-2-one (2.63 g, 14.69 mmol, 1.10 equiv), K₂CO₃ (3.59 g, 25.97 mmol, 2.00 equiv). The reaction solution was stirred overnight at 56° C. The mixture was cooled to room temperature. The solids were filtered out. The filtrate was concentrated under vacuum. The residue was dissolved with 100 mL of EA and washed with 100 mL of brine. The organic phase was dried over anhydrous sodium sulfate and concentrated under vacuum. This resulted in 2.60 g (78%) of 2-(3,3-dimethyl-2-oxobutoxy)-4-methoxybenzonitrile as brown solid.

¹H NMR (300 MHz, DMSO-d): δ 7.64 (d, J=8.7 Hz, 1H), 6.66 (dd, J=6.3 Hz, 2.1 Hz, 1H), 6.52 (d, J=2.4 Hz, 1H), 5.38 (s, 2H), 3.80 (s, 3H), 1.18 (s, 9H).

Example 515

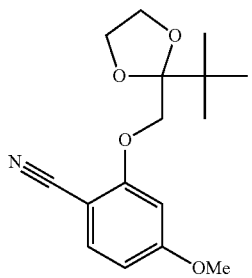 [SMILES: COc1ccc(C#N)c(OCC2(C(C)(C)C)OCCO2)c1]

2-((2-tert-butyl-1,3-dioxolan-2-yl)methoxy)-4-methoxybenzonitrile

Into a 100-mL 3-necked round-bottom flask purged and maintained with an inert atmosphere of nitrogen, was placed a mixture of 2-(3,3-dimethyl-2-oxobutoxy)-4-methoxybenzonitrile (1 g, 4.04 mmol, 1.00 equiv)(Example 514), ethane-1,2-diol (20 mL) and BF₃-Et₂O (10 mL). The resulting solution was stirred for 3 h at 60° C. The reaction mixture was then cooled at 0° C., to which was added 20 mL of water. The resulting mixture was extracted with EA (20 mL×3). The organic phase was dried over anhydrous sodium sulfate and concentrated under vacuum. This resulted in 900 mg (76%) of 2-((2-tert-butyl-1,3-dioxolan-2-yl)methoxy)-4-methoxybenzonitrile as brown solid.

¹H NMR (300 MHz, DMSO-d): δ 7.47 (d, J=8.4 Hz, 1H), 6.51 (dd, J=8.7 Hz, 2.4 Hz, 1H), 6.43 (d, J=2.1 Hz, 1H), 4.47-4.42 (m, 2H), 4.21 (s, 2H), 4.07-4.02 (m, 2H), 3.85 (s, 3H), 1.05 (s, 9H).

Example 516

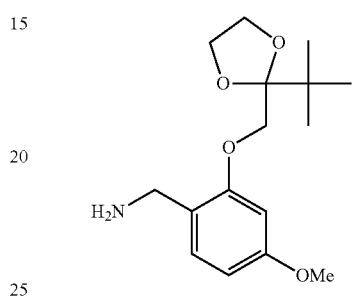

(2-((2-tert-butyl-1,3-dioxolan-2-yl)methoxy)-4-methoxyphenyl)methanamine

Into a 100-mL 3-necked round-bottom flask purged and maintained with an inert atmosphere of nitrogen, was placed 2-((2-tert-butyl-1,3-dioxolan-2-yl)methoxy)-4-methoxybenzonitrile (350 mg, 1.20 mmol, 1.00 equiv)(Example 515) in tetrahydrofuran (10 mL) with stirring at 0° C., to which wad added 2M BH₃-Me₂S in tetrahydrofuran solution (2.40 mL, 4.00 equiv) dropwise. The resulting solution was refluxed for 1 h. The reaction was then quenched by the addition of 10 mL of methanol at 0° C. The resulting mixture was stirred for 1 h at room temperature. The mixture was concentrated under vacuum. The crude product was purified by Combi-Flash with the following conditions. Column: C18, 20-45 um, 100 Å, 120 g; mobile phase: water (it contains 0.05% ammonia and 10 mM NH₄HCO₃) and acetonitrile with a gradient of 30% to 65% acetonitrile in 10 min; flow rate: 60 mL/min; detector UV wavelength: 254 nm and 220 nm. This resulted in 100 mg (28%) of (2-((2-tert-butyl-1,3-dioxolan-2-yl)methoxy)-4-methoxyphenyl)methanamine as yellow solid. ES (ESI) m/z 296 [M+H]⁺.

Example 517

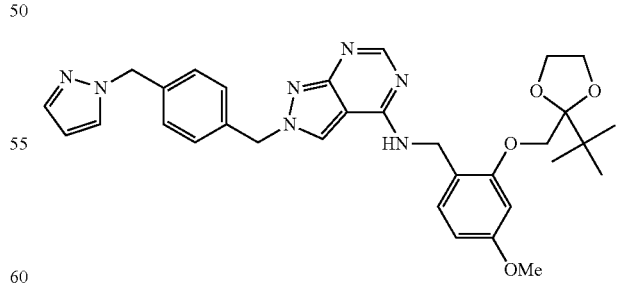

2-(4-((1H-pyrazol-1-yl)methyl)benzyl)-N-(2-((2-tert-butyl-1,3-dioxolan-2-yl)methoxy)-4-methoxybenzyl)-2H-pyrazolo[3,4-d]pyrimidin-4-amine Into a 50-mL round-bottom flask purged and maintained with an inert atmosphere of nitrogen, was placed a mixture of 2-(4-((1H-pyrazol-1-yl)methyl)benzyl)-4-chloro-2H-pyrazolo[3,4-d]pyrimidine (91 mg, 0.28 mmol, 1.00 equiv) (Example 23), N,N-dimethylformamide (10 mL), (2-((2-tert-butyl-1,3-dioxolan-2-yl)methoxy)-4-methoxyphenyl)methanamine (100 mg, 0.34 mmol, 1.20 equiv)(Example 516) and DIEA (361 mg, 2.79 mmol, 10.00 equiv). The resulting solution was stirred overnight at room temperature. The solids were filtered out and the filtrate was purified by Prep-HPLC with the following conditions. Column: Waters X-bridge RP18, 19×150 mm, 5 um; mobile phase: water (it contains 0.05% ammonia and 10 mM $NH_4HCO_3$) and acetonitrile with a gradient of 48% to 53% acetontrile in 5.5 min; flow rate: 20 mL/min; detector UV wavelength: 254 nm and 220 nm. This resulted in 70 mg (43%) of 2-(4-((1H-pyrazol-1-yl)methyl)benzyl)-N-(2-((2-tert-butyl-1,3-dioxolan-2-yl)methoxy)-4-methoxybenzyl)-2H-pyrazolo[3,4-d]pyrimidin-4-amine as white solid. MS (ESI) m/z 584 $[M+H]^+$.

Example 518

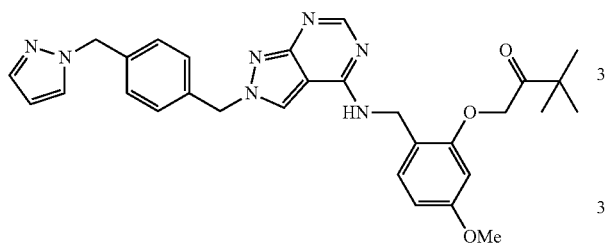

1-(2-((2-(4-((1H-pyrazol-1-yl)methyl)benzyl)-2H-pyrazolo[3,4-d]pyrimidin-4-ylamino)methyl)-5-methoxyphenoxy)-3,3-dimethylbutan-2-one Into a 8-mL vial, was placed a solution of 2-(4-((1H-pyrazol-1-yl)methyl)benzyl)-N-(2-((2-tert-butyl-1,3-dioxolan-2-yl)methoxy)-4-methoxybenzyl)-2H-pyrazolo[3,4-d]pyrimidin-4-amine (70 mg, 0.12 mmol, 1.00 equiv) (Example 517) in tetrahydrofuran (2 mL) and HCl aqueous solution (2 mL, 6 M). The resulting solution was stirred overnight at room temperature. The resulting mixture was concentrated under vacuum. The PH value of the solution was adjusted to 8-9 with concentrate ammonia. The crude product was purified by Prep-HPLC with the following conditions. Column: Waters X-bridge RP18, 19×150 mm, 5 um; mobile phase: water (0.05% ammonia) and acetonitrile with a gradient of 45% to 50% acetonitrile in 5 min; flow rate: 20 mL/min; detector UV wavelength: 254 nm and 220 nm. This resulted in 22.2 mg (34%) of 1-(2-((2-(4-((1H-pyrazol-1-yl)methyl)benzyl)-2H-pyrazolo[3,4-d]pyrimidin-4-ylamino)methyl)-5-methoxyphenoxy)-3,3-dimethylbutan-2-one as white solid. $^1$H NMR (300 MHz, DMSO-$d_6$): δ 8.38 (s, 1H), 8.18 (s, 1H), 7.78 (s, 1H), 7.44 (s, 1H), 7.28-7.11 (m, 5H), 6.44 (m, 2H), 6.25 (s, 1H), 5.50 (s, 2H), 5.30 (s, 2H), 5.19 (s, 2H), 4.63 (s, 2H), 3.69 (s, 3H), 1.15 (s, 9H). MS (ESI) m/z 540 $[M+H]^+$.

Example 519

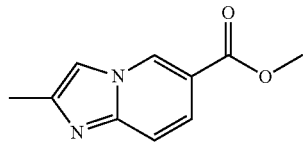

N-((6-amino-2,4-dimethylpyridin-3-yl)methyl)-2-((2-methylimidazo[1,2-a]pyridin-6-yl)methyl)-2H-pyrazolo[3,4-d]pyrimidin-4-amine Into a 2000-mL 4-necked round-bottom flask, were placed methyl 6-aminopyridine-3-carboxylate (80 g, 525.79 mmol, 1.00 equiv), ethanol (240 mL) and 1-bromopropan-2-one (215 g, 1.57 mol, 3.00 equiv). The resulted solution was stirred overnight at 80° C. in an oil bath. The mixture was diluted with 1500 mL of DCM, washed with 3×500 mL of brine, dried over anhydrous sodium sulfate and concentrated under vacuum. The residue was purified by a silica gel column eluted with dichloromethane/ethyl acetate (8:1-4:1). This resulted in 40 g (40%) of methyl 2-methylimidazo[1,2-a]pyridine-6-carboxylate as brown solid. MS (ESI) m/z $[M+H]^+$: 191.

Example 520

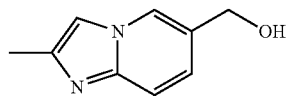

(2-methylimidazo[1,2-a]pyridin-6-yl)methanol

Into a 1-L 4-necked round-bottom flask purged and maintained with inert atmosphere of nitrogen, were placed methyl 2-methylimidazo[1,2-a]pyridine-6-carboxylate (32 g, 168.25 mmol, 1.00 equiv)(Example 519) in tetrahydrofuran (400 mL) stirred at −50° C. This was followed by the addition of LiAlH$_4$ (7.68 g, 226.40 mmol, 1.20 equiv) in several batches at −50° C. The reaction solution was stirred for 30 min at −40° C. The reaction was then quenched by the addition of 7.7 mL of water, 23 mL aqueous of NaOH (15%) and 7.7 mL of water. The solids were filtered out and washed with 400 mL of mixed solvent of DCM:THF=1:1 and the filtrate was collected. The resulted mixture was concentrated under vacuum. The residue was purified by silica gel column eluted with dichloromethane/methanol (40:1-30:1). This resulted in 10 g (37%) of (2-methylimidazo[1,2-a]pyridin-6-yl)methanol as yellow solid. MS (ESI) m/z $[M+H]^+$: 163.

Example 521

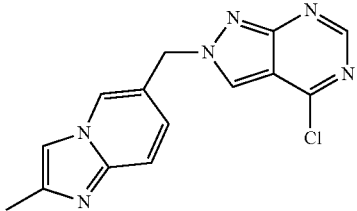 [SMILES: Cc1cn2cc(Cn3cc4c(Cl)ncnc4n3)ccc2n1]

6-([4-chloro-2H-pyrazolo[4,3-c]pyridin-2-yl]methyl)-2-methylimidazo[1,2-a]pyrimidine Into a 1-L 4-necked round-bottom flask purged and maintained with inert atmosphere of nitrogen, were placed [2-methylimidazo[1,2-a]pyridin-6-yl]methanol (6.3 g, 38.84 mmol, 1.00 equiv)(Example 520), 4-chloro-2H-pyrazolo[4,3-c]pyrimidine (5.95 g, 38.74 mmol, 1.00 equiv), PPh$_3$ (12.2 g, 46.56 mmol, 1.20 equiv) and THF (300 mL). This was followed by the addition of a solution of (E)-N-[(tert-butoxy)carbonyl]imino(tert-butoxy)formamide (10.73 g, 46.60 mmol, 1.20 equiv) in tetrahydrofuran (100 mL) dropwise with stirring at 0° C. The resulted solution was stirred for 4 h at room temperature. The reaction mixture was extracted with 1000 mL of DCM and washed with 3×300 mL of brine. The mixture was dried over anhydrous sodium sulfate and concentrated under vacuum. The residue was purified by silica gel column eluted with DCM/THF (1:1). This resulted in 3.70 g (32%) of 6-([4-chloro-2H-pyrazolo[4,3-c]pyridin-2-yl]methyl)-2-methylimidazo[1,2-a]pyrimidine as brown solid. MS (ESI) m/z [M+H]$^+$:298

Example 522

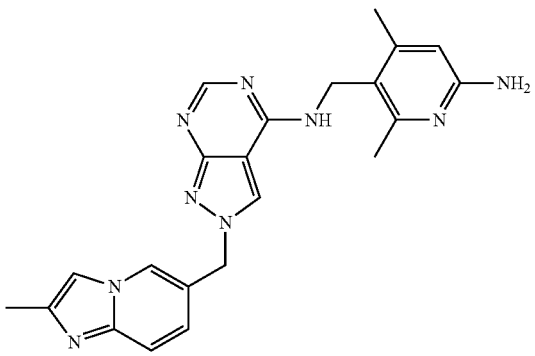 [SMILES: Cc1cn2cc(Cn3cc4c(NCc5c(C)cc(N)nc5C)ncnc4n3)ccc2n1]

N-((6-amino-2,4-dimethylpyridin-3-yl)methyl)-2-((2-methylimidazo[1,2-a]pyridin-6-yl)methyl)-2H-pyrazolo[3,4-d]pyrimidin-4-amine Into a 30-mL bottle, were placed 4-chloro-2-([2-methylimidazo[1,2-a]pyridin-6-yl]methyl)-2H-pyrazolo[3,4-d]pyrimidine (100 mg, 0.33 mmol, 1.00 equiv)(Example 521), tert-butyl N-[5-(aminomethyl)-4,6-dimethylpyridin-2-yl]-N-[(tert-butoxy)carbonyl]carbamate (176.7 mg, 0.50 mmol, 1.5 equiv)(Example 4, Step 2), 1-ethoxy-2-(2-ethoxyethoxy)ethane (10 mL) and zinc dichloride (450 mg, 3.30 mmol, 10.00 equiv). The resulted solution was stirred for 3 h at 120° C. The crude product was purified by silica gel column chromatography with the following conditions (IntelFlash-1): column, silica gel; mobile phase: DCM/EA/MeOH/concentrated ammonia aqueous solution (ratio: 4:4:1:0.2). The crude product was further purified by Prep-HPLC with the following conditions: Waters XBridge RP18 19*150 mm; mobile phase: acetonitrile / water (0.05% NH$_4$OH, 10 mM NH$_4$HCO$_3$); gradient from 18% to 23% with a 7-min run time, flow rate: 20 mL/min; detector UV wavelength: 254 nm. This resulted in 50.7 mg (37%) of 4,6-dimethyl-5-([[2-([2-methylimidazo[1,2-a]pyridin-6-yl]methyl)-2H-pyrazolo[3,4-d]pyrimidin-4-yl]amino]methyl)pyridin-2-amine as white solid. $^1$H NMR (300 MHz, CD$_3$OD): 8.45 (s, 1H), 8.34 (d, J=5.4 Hz, 2H), 7.59 (s, 1H), 7.44 (d, J=9.3 Hz, 1H), 7.256 (d, J=9.3 Hz, 1H), 6.34 (s, 1H), 5.54 (s, 2H), 4.65 (s, 2H), 2.39 (s, 6H), 2.26 (s, 3H). MS (ESI) m/z, [M+H]$^+$:414

Example 523

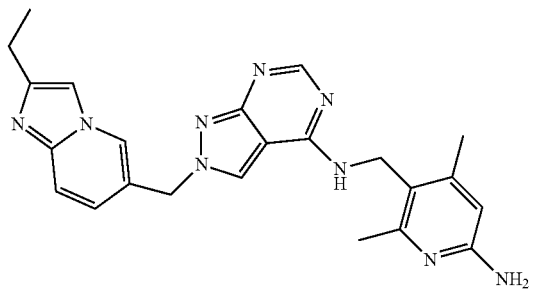 [SMILES: CCc1cn2cc(Cn3cc4c(NCc5c(C)cc(N)nc5C)ncnc4n3)ccc2n1]

N-((6-amino-2,4-dimethylpyridin-3-yl)methyl)-2-((2-ethylimidazo[1,2-a]pyridin-6-yl)methyl)-2H-pyrazolo[3,4-d]pyrimidin-4-amine N-((6-amino-2,4-dimethylpyridin-3-yl)methyl)-2-((2-ethylimidazo[1,2-a]pyridin-6-yl)methyl)-2H-pyrazolo[3,4-d]pyrimidin-4-amine was synthesized in the same manner as Example 522. $^1$H NMR (300 MHz, CD$_3$OD): 8.47 (s, 1H), 8.34 (s, 2H), 7.62 (s, 1H), 7.46 (d, J=9.3 Hz, 1H), 7.27 (d, J=8.1 Hz, 1H), 6.36 (s, 1H), 5.55 (s, 2H), 4.66 (s, 2H), 2.79-2.72 (m, 2H), 2.41 (s, 3H), 2.27 (3H, s), 1.35-1.28 (m, 3H). MS (ESI) m/z 428 [M+H]$^+$

Example 524

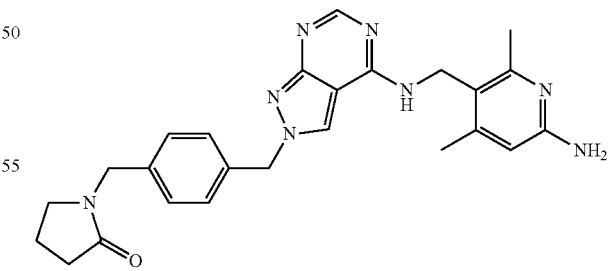

1-(4-((4-(((6-amino-2,4-dimethylpyridin-3-yl)methyl)amino)-2H-pyrazolo[3,4-d]pyrimidin-2-yl)methyl)benzyl)pyrrolidin-2-one 1-(4-((4-(((6-amino-2,4-dimethylpyridin-3-yl)methyl)amino)-2H-pyrazolo[3,4-d]pyrimidin-2-yl)methyl)benzyl)

pyrrolidin-2-one was prepared in a similar manner as Example 335. ¹H NMR (400 MHz, CD₃OD) δ 8.67 (d, J=2.7 Hz, 2H), 7.44-7.38 (m, 2H), 7.32-7.26 (m, 2H), 6.74 (s, 1H), 5.61 (s, 2H), 4.90 (s, 3H), 4.45 (s, 2H), 3.35 (d, J=1.5 Hz, 2H), 2.61 (s, 3H), 2.47-2.40 (m, 6H), 2.07-1.97 (m, 2H). MS (M+H)⁺ found for $C_{25}H_{28}N_8O$: 457.2.

Example 525

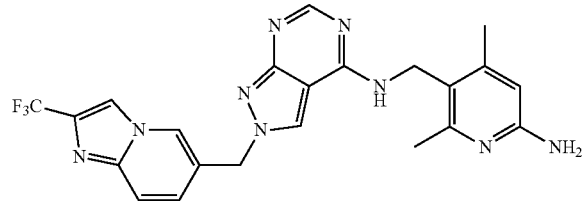 [SMILES: Cc1cc(N)nc(C)c1CNc1ncnc2nn(Cc3ccc4nc(C(F)(F)F)cn4c3)cc12]

N-((6-amino-2,4-dimethylpyridin-3-yl)methyl)-2-((2-(trifluoromethyl)imidazo[1,2-a]pyridin-6-yl)methyl)-2H-pyrazolo[3,4-d]pyrimidin-4-amine N-((6-amino-2,4-dimethylpyridin-3-yl)methyl)-2-((2-(trifluoromethyl)imidazo[1,2-a]pyridin-6-yl)methyl)-2H-pyrazolo[3,4-d]pyrimidin-4-amine was synthesized in a similar manner as Example 522. ¹H NMR (300 MHz, CD₃OD): 8.58 (s, 1H), 8.39 (3H, d, J=17.7 Hz), 7.64 (d, J=1.5 Hz, 1H), 7.47 (d, J=8.1 Hz, 1H), 6.37 (s, 1H), 5.61 (2H, s), 4.66 (s, 2H), 2.40 (s, 3H), 2.27 (s, 3H). MS (ESI) m/z 498 [M+H]⁺

Example 526

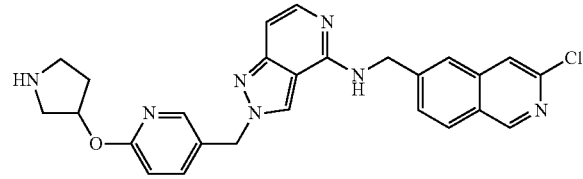 [SMILES: Clc1cc2cc(CNc3nccc4nn(Cc5ccc(OC6CCNC6)nc5)cc34)ccc2cn1]

N-((3-chloroisoquinolin-6-yl)methyl)-2-((6-(pyrrolidin-3-yloxy)pyridin-3-yl)methyl)-2H-pyrazolo[4,3-c]pyridin-4-amine N-((3-chloroisoquinolin-6-yl)methyl)-2-((6-(pyrrolidin-3-yloxy)pyridin-3-yl)methyl)-2H-pyrazolo[4,3-c]pyridin-4-amine was synthesized in a similar manner as Example 446. ¹H NMR (300 MHz, CD30D-d): 9.13 (s, 1H), 8.89 (s, 1H), 8.30-8.18 (m, 2H), 7.80-7.73 (m, 4H), 7.42 (d, J=7.5 Hz, 1H), 7.09 (d, J=7.5 Hz, 1H), 6.88 (d, J=9.9 Hz, 1H), 5.71 (d, J=17.7 Hz, 3H), 5.033 (s, 2H), 3.63-3.46 (m, 4H), 2.45 (2H, s). MS (ESI) m/z 486 [M+H]⁺

Example 527

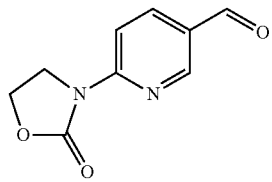 [SMILES: O=Cc1ccc(N2CCOC2=O)nc1]

6-(2-oxo-1,3-oxazolidin-3-yl)pyridine-3-carbaldehyde

Into a 100-mL 3-necked round-bottom flask purged and maintained with an inert atmosphere of nitrogen, was placed a mixture of 6-fluoropyridine-3-carbaldehyde (2 g, 15.99 mmol, 1.00 equiv), DMSO (50 mL), 1,3-oxazolidin-2-one (1.53 g, 17.57 mmol, 1.10 equiv) and NaHCO₃ (8.06 g, 95.94 mmol, 6.00 equiv). The resulting solution was stirred overnight at 110° C. The reaction mixture was cooled to room temperature. The solids were filtered out. The crude product was purified by Prep-HPLC with the following conditions. Column: Waters Atlantis T3, 19×150 mm, 5 μm; mobile phase: CH₃CN/H₂O (0.05% TFA) with a gradient of 5% to 10% acetontirle in 7 min; flow rate: 20 mL/min; detector UV wavelength: 254 nm and 220 nm. This resulted in 200 mg (6%) of 6-(2-oxo-1,3-oxazolidin-3-yl)pyridine-3-carbaldehyde as yellow solids. MS (ESI) m/z 193 [M+H]⁺.

Example 528

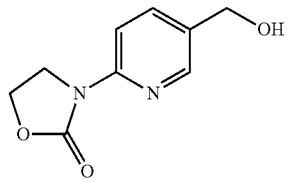 [SMILES: O=C1OCCN1c1ccc(CO)cn1]

3-(5-(hydroxymethyl)pyridin-2-yl)oxazolidin-2-one

Into a 100-mL 3-necked round-bottom flask purged and maintained with an inert atmosphere of nitrogen, was placed a mixture of 6-(2-oxo-1,3-oxazolidin-3-yl)pyridine-3-carbaldehyde (200 mg, 1.04 mmol, 1.00 equiv)(Example 527) and tetrahydrofuran (10 mL) with stirring at 0° C., to which was added NaBH₄ (40 mg, 1.06 mmol, 1.00 equiv) in several batches at 0° C. The resulting solution was stirred for 2 h at room temperature. The reaction was then quenched by the addition of water at 0° C. The resulting solution was extracted with 3×20 mL of EA and the organic layers were combined. The organic phase was washed with 1×50 mL of brine, dried over anhydrous sodium sulfate and concentrated under vacuum. This resulted in 140 mg (70%) of 3-(5-(hydroxymethyl)pyridin-2-yl)oxazolidin-2-one as yellow solid. MS (ESI) m/z 195 [M+H]⁺.

Example 529

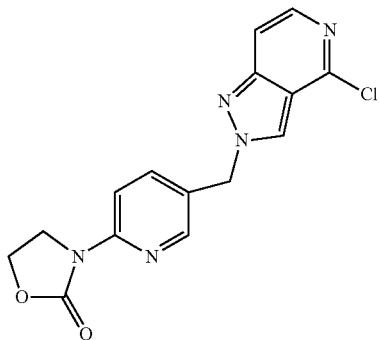 [SMILES: O=C1OCCN1c1ccc(Cn2cc3c(Cl)nccc3n2)cn1]

3-(5-((4-chloro-2H-pyrazolo[4,3-c]pyridin-2-yl)methyl)pyridin-2-yl)oxazolidin-2-one Into a 100-mL 3-necked round-bottom flask purged and maintained with an inert atmosphere of nitrogen, was placed a mixture of 3-(5-(hydroxymethyl)pyridin-2-yl)oxazolidin-2-one (140 mg, 0.72 mmol, 1.00 equiv)(Example 528), 4-chloro-1H-pyrazolo[4,3-c]pyridine (110 mg, 0.72 mmol, 1.00 equiv), tetrahydrofuran (15 mL) and PPh$_3$ (225 mg, 0.86 mmol, 1.20 equiv) with stirring at 0° C., to which was added a solution of DBAD (198 mg, 0.85 mmol, 1.20 equiv) in THF (5 mL) dropwise with stirring at 0° C. The resulting solution was stirred overnight at room temperature. The reaction solution was extracted with 50 mL of EA and washed with 1×50 mL of brine. The organic phase was dried over anhydrous sodium sulfate and concentrated under vacuum. The crude product was purified by Prep-HPLC with the following conditions: Column: Waters XBridge RP18, 5 μm, 19×150 mm; mobile phase: CH$_3$CN/H$_2$O (0.05% NH$_3$.H$_2$O) with a gradient of 32% to 37% acetonitrile in 5 min; flow rate: 20 mL/min; detector UV wavelength: 254 nm and 220 nm. This resulted in 80 mg (16%) of 3-(5-((4-chloro-2H-pyrazolo[4,3-c]pyridin-2-yl)methyl)pyridin-2-yl)oxazolidin-2-one as white solid. $^1$H NMR (300 MHz, DMSO-d): δ 8.98 (s, 1H), 8.49 (s, 1H), 8.07 (d, J=8.7 Hz, 1H), 7.99 (d, J=6.3 Hz, 1H), 7.87 (d, J=8.7 Hz, 1H), 7.56 (d, J=6.3 Hz, 1H), 5.72 (s, 2H), 4.45 (t, J=8.4 Hz, 2H), 4.15 (t, J=8.4 Hz, 2H). MS (ESI) m/z 330 [M+H]$^+$.

Example 530

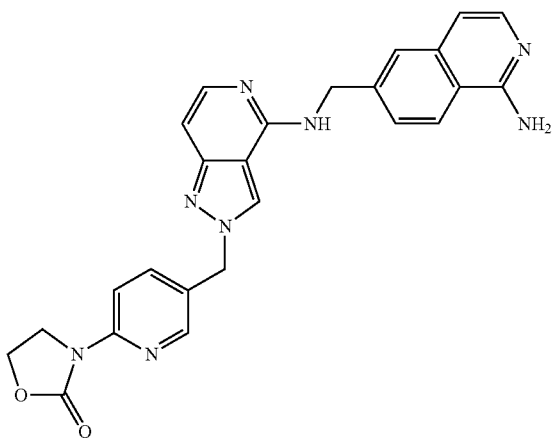 [SMILES: Nc1nccc2cc(CNc3nccc4nn(Cc5ccc(N6CCOC6=O)nc5)cc34)ccc12]

3-(5-((4-((1-aminoisoquinolin-6-yl)methylamino)-2H-pyrazolo[4,3-c]pyridin-2-yl)methyl)pyridin-2-yl)oxazolidin-2-one 3-(5-((4-((1-aminoisoquinolin-6-yl)methylamino)-2H-pyrazolo[4,3-c]pyridin-2-yl)methyl)pyridin-2-yl)oxazolidin-2-one was synthesized in a similar manner as Example 446 using Example 529. $^1$H NMR (300 MHz, CD$_3$OD): δ 8.40-8.45 (2H, d, J=18.6 MHz), 8.15 (1H, d, J=9.0 Hz), 8.06 (1H, d, J=8.7 Hz), 7.74-7.82 (1H, m), 7.67-7.71 (2H, m), 7.52-7.61 (2H, m), 6.93 (1H, d, J=6.3 Hz), 6.76 (1H, d, J=7.2 Hz), 5.60 (H, s), 4.49-4.54 (2H, m), 4.24-4.29 (2H, m), 1.30 (3H, s). MS (ESI) m/z 467 [M+H]$^+$

Example 531

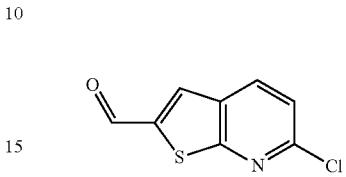

6-chlorothieno[2,3-b]pyridine-2-carbaldehyde

Into a 100-mL 3-necked round-bottom flask purged and maintained with an inert atmosphere of nitrogen, was placed a solution of 2-bromo-6-chlorothieno[2,3-b]pyridine (1.0 g, 4.02 mmol, 1.00 equiv) in tetrahydrofuran (20 mL). This was followed by the addition of n-butyl lithium (1.8 mL, 4.4 mmol, 1.10 equiv, 2.5 M) at −78° C. The resulting solution was stirred for 0.5 h at −78° C. To this was added N,N-dimethylformamide (0.3 mL) at −78° C. The resulting solution was allowed to warm to room temperature with stirring for an additional 0.5 h. The reaction was then quenched by the addition of 5 mL of water. The resulting mixture was stirred for 5 minutes. The resulting solution was diluted with 50 mL of water and extracted with 2×50 mL of ethyl acetate. The organic phase was washed with 1×100 mL of water and 1×100 mL of brine. The mixture was then dried over anhydrous sodium sulfate and concentrated under vacuum. The residue was purified by silica gel column chromatography eluted with ethyl acetate/petroleum ether (1:10). This resulted in 355 mg (45%) of 6-chlorothieno[2,3-b]pyridine-2-carbaldehyde as a off-white solid. MS (ESI) m/z 198 [M+H]$^+$.

Example 532

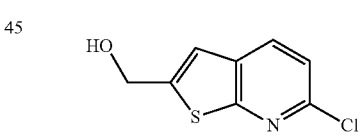

[6-chlorothieno[2,3-b]pyridin-2-yl]methanol

Into a 100-mL 3-necked round-bottom flask, was placed a solution of 6-chlorothieno[2,3-b]pyridine-2-carbaldehyde (355 mg, 1.80 mmol, 1.00 equiv)(Example 531) in methanol (30 mL). This was followed by the addition of sodium borohydride (76 mg, 1.93 mmol, 1.10 equiv) in several batches at 0° C. The resulting solution was stirred for 0.5 h at room temperature. The mixture was then concentrated under vacuum. The residue was diluted with 50 mL of H$_2$O and extracted with 2×50 mL of ethyl acetate. The organic phase was washed with 1×100 mL of water and 1×100 mL of brine and dried over anhydrous sodium sulfate. The concentration resulted in 350 mg (98%) of [6-chlorothieno[2,3-b]pyridin-2-yl]methanol as a white solid. MS (ESI) m/z 200 [M+H]$^+$.

Example 533

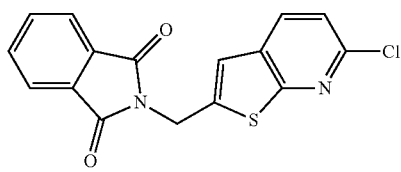 [SMILES: O=C1c2ccccc2C(=O)N1Cc1cc2ccc(Cl)nc2s1]

2-([6-chlorothieno[2,3-b]pyridin-2-yl]methyl)-2,3-dihydro-1H-isoindole-1,3-dione Into a 100-mL 3-necked round-bottom flask, was placed a solution of [6-chlorothieno[2,3-b]pyridin-2-yl]methanol (250 mg, 1.25 mmol, 1.00 equiv)(Example 532) in tetrahydrofuran (30 mL), to which were added 2,3-dihydro-1H-isoindole-1,3-dione (203 mg, 1.38 mmol, 1.10 equiv), triphenylphosphine (430 mg, 1.64 mmol, 1.30 equiv) sequentially. This was followed by the addition of DEAD (285 mg, 1.64 mmol, 1.30 equiv) dropwise with stirring at 0° C. The resulting solution was stirred for 15 min at room temperature. The mixture was then concentrated under vacuum. The residue was diluted with 50 mL of H$_2$O and extracted with 3×50 mL of ethyl acetate. The organic phase was washed with 1×100 mL of water and 1×100 mL of brine. After dried over anhydrous sodium sulfate and concentrated under vacuum, the residue was purified by a silica gel column chromatography eluted with ethyl acetate/petroleum ether (1:10-1:3). This resulted in 320 mg (78%) of 2-([6-chlorothieno[2,3-b]pyridin-2-yl]methyl)-2,3-dihydro-1H-isoindole-1,3-dione as a white solid. MS (ESI) m/z 329 [M+H]$^+$.

Example 534

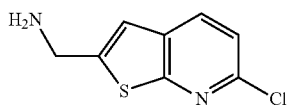

[6-chlorothieno[2,3-b]pyridin-2-yl]methanamine

Into a 100-mL round-bottom flask, was placed 2-([6-chlorothieno[2,3-b]pyridin-2-yl]methyl)-2,3-dihydro-1H-isoindole-1,3-dione (300 mg, 0.91 mmol, 1.00 equiv) in ethanol (20 mL), to which was added NH$_2$NH$_2$—H$_2$O (2 mL). The resulting solution was stirred for 0.5 h at 68° C. The resulting mixture was concentrated under vacuum. The residue was diluted with 30 mL of H$_2$O and extracted with 3×30 mL of ethyl ether. The organic phase was washed with 2×50 mL of water and 1×50 mL of brine. Then it was dried over anhydrous sodium sulfate and concentrated under vacuum to give 180 mg (99%) of [6-chlorothieno[2,3-b]pyridin-2-yl]methanamine as a light yellow solid. MS (ESI) m/z 199 [M+H]$^+$.

Example 535

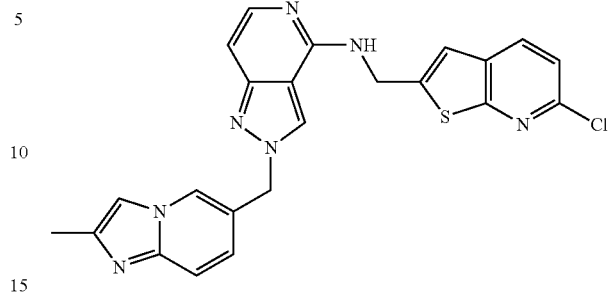

N-([6-chlorothieno[2,3-b]pyridin-2-yl]methyl)-2-([2-methylimidazo[1,2-a]pyridin-6-yl]methyl)-2H-pyrazolo[4,3-c]pyridin-4-amine N-([6-chlorothieno[2,3-b]pyridin-2-yl]methyl)-2-([2-methylimidazo[1,2-a]pyridin-6-yl]methyl)-2H-pyrazolo[4,3-c]pyridin-4-amine was prepared in a similar manner as Example 446 using Example 534. $^1$H NMR (300 MHz, CD$_3$OD-d): 8.44 (s, 2H), 8.12 (d, J=20.4 MHz, 1H), 7.66-7.61 (m, 2H), 7.46-7.35 (m, 2H), 7.29-7.22 (m, 2H), 6.79 (d, J=7.5 MHz, 1H), 5.60 (s, 2H), 4.98 (s, 2H), 2.41 (s, 3H). MS (ESI) m/z 460 [M+H]$^+$.

Example 536

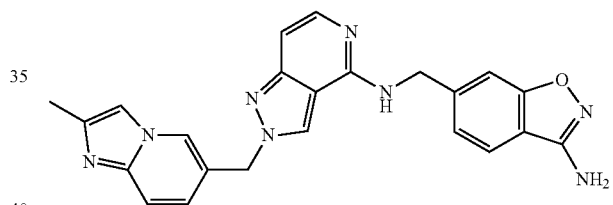

6-((2-((2-methylimidazo[1,2-a]pyridin-6-yl)methyl)-2H-pyrazolo[4,3-c]pyridin-4-ylamino)methyl)benzo[d]isoxazol-3-amine 6-((2-((2-methylimidazo[1,2-a]pyridin-6-yl)methyl)-2H-pyrazolo[4,3-c]pyridin-4-ylamino)methyl)benzo[d]isoxazol-3-amine was synthesized in a similar manner as Example 446. $^1$H NMR (300 MHz, CD$_3$OD-d): 8.47 (d, J=6.6 Hz, 2H), 7.70 (d, J=8.1 Hz, 1H), 7.61 (d, J=8.4 Hz, 2H), 7.46-7.37 (2H, m), 7.30-7.22 (2H, m), 6.70 (d, J=7.2 Hz, 1H), 5.60 (s, 2H), 4.85 (s, 2H), 2.41 (s, 3H). MS (ESI) m/z 425 [M+H]$^+$ Example 537

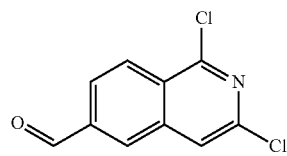 [SMILES: O=Cc1ccc2c(Cl)nc(Cl)cc2c1]

1,3-dichloroisoquinoline-6-carbaldehyde

Into a 100-mL 3-necked round-bottom flask purged and maintained with an inert atmosphere of nitrogen, was placed a solution of 6-bromo-1,3-dichloroisoquinoline (500 mg, 1.81 mmol, 1.00 equiv) in tetrahydrofuran (20 mL) with stirring at −78° C. To it was added n-butyl lithium (0.9 mL, 1.20 equiv, 2.5 M) dropwise. The resulted solution was stirred for 0.5 h at −78° C. To this was added N,N-dimethylformamide (0.5 mL) dropwise with stirring at −78° C. The temperature was increased to room temperature naturally. The reaction was then quenched by the addition of 20 mL of saturated aqueous ammonium chloride. The resulting solution was diluted with 100 mL of water and extracted with 3×50 mL of ethyl acetate. The organic phase was washed with 100 mL of water and 100 mL of brine. The crude was purified by silica gel column chromatography eluted with ethyl acetate/petroleum ether (1:10). This resulted in 310 mg (76%) of 1,3-dichloroisoquinoline-6-carbaldehyde as a yellow solid. MS (ESI) m/z 226 [M+H]$^+$.

Example 538

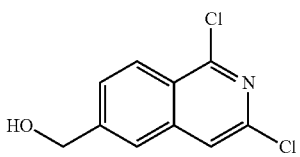 [SMILES: OCc1ccc2c(Cl)nc(Cl)cc2c1]

(1,3-dichloroisoquinoline-6-yl)methanol

Into a 100-mL 3-necked round-bottom flask purged and maintained with an inert atmosphere of nitrogen, was placed a solution of 1,3-dichloroisoquinoline-6-carbaldehyde (310 mg, 1.37 mmol, 1.00 equiv)(Example 537) in methanol (30 mL) stirred at 0° C. To it was added sodium borohydride (63 mg, 1.67 mmol, 1.20 equiv) portion by portion at 0° C. The resulted solution was stirred for 15 min at room temperature. The mixture was concentrated under vacuum. The residue was diluted with 50 mL of water and extracted with 3× 30 mL of ethyl acetate. The organic phase was washed with 50 mL of water and 50 mL of brine and dried over anhydrous sodium sulfate. After concentration under vacuum, it resulted in 300 mg (96%) of (1,3-dichloroisoquinolin-6-yl)methanol as a white solid. MS (ESI) m/z 228 [M+H]$^+$.

Example 539

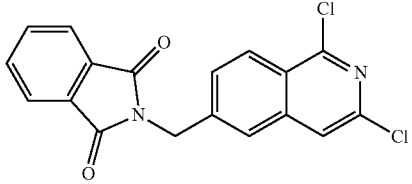 [SMILES: O=C1c2ccccc2C(=O)N1Cc1ccc2c(Cl)nc(Cl)cc2c1]

2-[(1,3-dichloroisoquinolin-6-yl)methyl]-2,3-dihydro-1H-isoindole-1,3-dione

Into a 100-mL round-bottom flask, were placed (1,3-dichloroisoquinolin-6-yl)methanol (250 mg, 1.10 mmol, 1.00 equiv)(Example 538), 2,3-dihydro-1H-isoindole-1,3-dione (194 mg, 1.32 mmol, 1.20 equiv), triphenyl phosphine (366 mg, 1.40 mmol, 1.30 equiv) and tetrahydrofuran (50 mL) with stirring at 0° C., to which was added DEAD (244 mg, 1.40 mmol, 1.30 equiv) dropwise. The resulted solution was stirred for 15 min at room temperature. The mixture was concentrated under vacuum. The residue was diluted with 50 mL of water and extracted with 3×50 mL of ethyl acetate. The organic phase was washed with 50 mL of brine and dried over anhydrous sodium sulfate and concentrated under vacuum. The residue was purified by silica gel column chromatography eluted with ethyl acetate/petroleum ether (1:3-1:1). This resulted in 320 mg (82%) of 2-[(1,3-dichloroisoquinolin-6-yl)methyl]-2,3-dihydro-1H-isoindole-1,3-dione as a white solid. MS (ESI) m/z 357 [M+H]$^+$.

Example 540

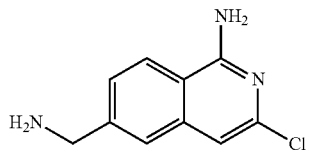 [SMILES: NCc1ccc2c(N)nc(Cl)cc2c1]

6-(aminomethyl)-3-chloroisoquinolin-1-amine

Into a 50-mL vial, was placed 2-[(1,3-dichloroisoquinolin-6-yl)methyl]-2,3-dihydro-1H-isoindole-1,3-dione (300 mg, 0.84 mmol, 1.00 equiv)(Example 539), concentrated ammonia aqueous solution (20 mL). The resulting solution was stirred 6 h at 120° C. The reaction mixture was cooled to room temperature. The solution was extracted with 5×30 mL of ethyl ether. The organic phase was washed with 2×100 mL of water and 100 mL of brine, dried over anhydrous sodium sulfate and concentrated under vacuum. This resulted in 150 mg (86%) of 6-(aminomethyl)-3-chloroisoquinolin-1-amine as a light yellow solid. MS (ESI) m/z 208 [M+H]$^+$.

Example 541

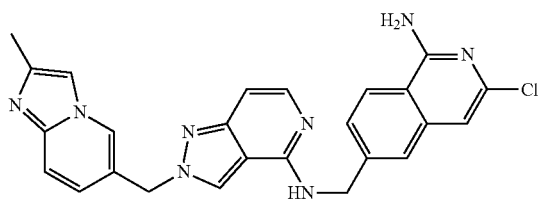 [SMILES: Cc1cn2cc(Cn3cc4c(NCc5ccc6c(N)nc(Cl)cc6c5)nccc4n3)ccc2n1]

3-chloro-6-([[2-([2-methylimidazo[1,2-a]pyridin-6-yl]methyl)-2H-pyrazolo[4,3-c]pyridin-4-yl]amino] methyl)isoquinolin-1-amine 3-chloro-6-([[2-([2-methylimidazo[1,2-a]pyridin-6-yl] methyl)-2H-pyrazolo[4,3-c]pyridin-4-yl]amino]methyl)isoquinolin-1-amine was prepared in a similar manner as Example 446 using Example 540. $^1$H NMR (300 MHz, CD$_3$OD): 8.48 (d, J=8.7 Hz, 2H), 8.05 (d, J=8.7 Hz, 1H), 7.61 (d, J=6.9 Hz, 3H), 7.51-7.43 (m, 2H), 7.26 (d, J=11.1 Hz, 1H), 6.92 (s, 1H), 6.77 (d, J=7.5 Hz, 1H), 5.60 (s, 2H), 4.86 (s, 2H), 2.41 (s, 3H). MS (ESI) m/z 469 [M+H]$^+$.

Example 542

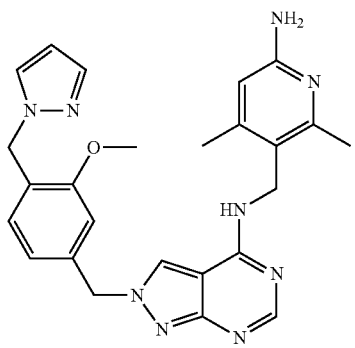 [SMILES: COc1cc(Cn2cc3c(NCc4c(C)cc(N)nc4C)ncnc3n2)ccc1Cn1cccn1]

Preparation of 2-(4-((1H-pyrazol-1-yl)methyl)-3-methoxybenzyl)-N-((6-amino-2,4-dimethylpyridin-3-yl)methyl)-2H-pyrazolo[3,4-d]pyrimidin-4-amine 2-(4-((1H-pyrazol-1-yl)methyl)-3-methoxybenzyl)-N-((6-amino-2,4-dimethylpyridin-3-yl)methyl)-2H-pyrazolo[3,4-d]pyrimidin-4-amine was synthesized in a manner similar to Example 186. $^1$H NMR (400 MHz, Methanol-d$_4$) δ 8.65 (d, J=1.5 Hz, 2H), 7.65 (dd, J=2.4, 0.7 Hz, 1H), 7.48 (dd, J=2.0, 0.7 Hz, 1H), 7.12 (d, J=1.4 Hz, 1H), 6.97-6.91 (m, 2H), 6.76-6.70 (m, 1H), 6.29 (t, J=2.2 Hz, 1H), 5.59 (s, 2H), 5.32 (s, 2H), 4.89 (s, 2H), 3.86 (s, 3H), 2.60 (d, J=0.6 Hz, 3H), 2.45 (d, J=0.9 Hz, 3H). MS (M+H)+ found for C$_{23}$H$_{27}$N$_3$O: 470.0.

Example 543

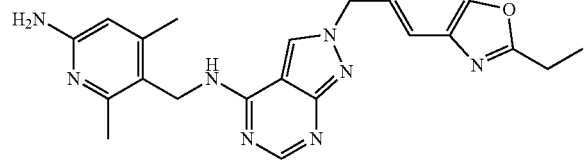

5-[([2-[(2-ethyl-7-methyl-1,3-benzoxazol-5-yl)methyl]-2H-pyrazolo[3,4-d]pyrimidin-4-yl]amino)methyl]-4,6-dimethylpyridin-2-amine 5-[([2-[(2-ethyl-7-methyl-1,3-benzoxazol-5-yl)methyl]-2H-pyrazolo[3,4-d]pyrimidin-4-yl]amino)methyl]-4,6-dimethylpyridin-2-amine was prepared in a similar manner as Example 468. $^1$H NMR (300 MHz, CD$_3$OD): δ 8.30 (2H, d, J=13.8 Hz), 7.46 (1H, s), 7.22 (1H, s), 6.34 (1H, s), 5.59 (2H, s), 4.64 (2H, s), 2.94-3.03 (2H, m), 2.49 (3H, s), 2.39 (3H, s), 2.26 (3H, s), 1.40-1.45 (3H, m). MS (ESI) m/z 443 [M+H]$^+$.

Example 544

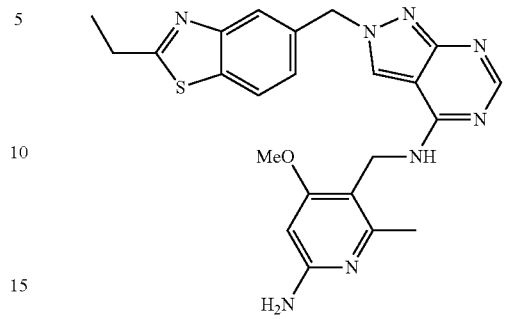

N-((6-amino-4-methoxy-2-methylpyridin-3-yl)methyl)-2-((2-ethylbenzo[d]thiazol-5-yl)methyl)-2H-pyrazolo[3,4-d]pyrimidin-4-amine N-((6-amino-4-methoxy-2-methylpyridin-3-yl)methyl)-2-((2-ethylbenzo[d]thiazol-5-yl)methyl)-2H-pyrazolo[3,4-d]pyrimidin-4-amine was prepared in a similar manner as Example 468. $^1$H NMR (300 MHz, CD$_3$OD): 8.32 (d, J=7.5 Hz, 2H), 7.96 (d, J=8.4 Hz, 1H), 7.85 (s, 1H), 7.42 (d, J=8.1 Hz, 1H), 6.08 (s, 1H), 5.68 (s, 2H), 4.62 (s, 2H), 3.85 (s, 2H), 3.19-3.09 (2H, m), 2.40 (3H, s), 1.47-1.42 (3H, m). MS (ESI) m/z 461 [M+H]$^+$

Example 545

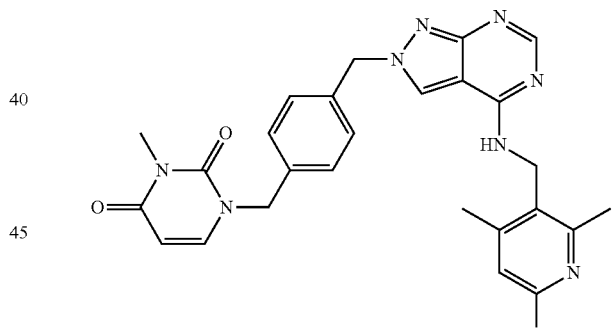

1-(4-((4-(((6-amino-2,4-dimethylpyridin-3-yl)methyl)amino)-2H-pyrazolo[3,4-d]pyrimidin-2-yl)methyl)benzyl)-3-methylpyrimidine-2,4(1H,3H)-dione 1-(4-((4-(((6-amino-2,4-dimethylpyridin-3-yl)methyl)amino)-2H-pyrazolo[3,4-d]pyrimidin-2-yl)methyl)benzyl)-3-methylpyrimidine-2,4(1H,3H)-dione was synthesized in a manner similar to Example 186 using 3-methyl uracil to replace 4-(trifluoromethyl)-1H-pyrazole. $^1$H NMR (400 MHz, Methanol-d$_4$) δ 8.30 (s, 1H), 8.24 (s, 1H), 7.62 (d, J=7.9 Hz, 1H), 7.34 (s, 4H), 6.61 (s, 1H), 5.72 (d, J=7.9 Hz, 1H), 5.52 (s, 2H), 4.95 (s, 2H), 4.67 (s, 2H), 3.26 (s, 3H), 2.54 (s, 3H), 2.40 (s, 3H). MS (M+H)+ found for C$_{26}$H$_{27}$N$_9$O$_2$: 480.1.

Example 546

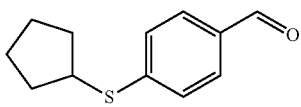 [SMILES: O=Cc1ccc(SC2CCCC2)cc1]

4-(cyclopentylsulfanyl)benzaldehyde

Into a 500-mL 3-necked round-bottom flask, was placed a solution of 4-fluorobenzaldehyde (10.00 g, 80.57 mmol, 1.00 equiv) in DMSO (100 mL), cyclopentanethiol (8.20 g, 80.57 mmol, 1.00 equiv) and $K_2CO_3$ (16.7 g, 120.83 mmol, 1.50 equiv). The resulting solution was stirred for 14 h at 100° C. in an oil bath. The reaction was then quenched by the addition of 200 mL of water/ice. The resulting solution was extracted with 2×200 mL of ethyl acetate and the organic layers were combined. Then it was washed with 1×100 mL of brine, dried over sodium sulfate and concentrated under vacuum. The residue was purified by a silica gel column eluted with ethyl acetate/petroleum ether (1:5). This resulted in 15.00 g (90%) of 4-(cyclopentylsulfanyl)benzaldehyde as yellow oil.

Example 547

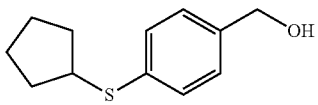 [SMILES: OCc1ccc(SC2CCCC2)cc1]

[4-(cyclopentylsulfanyl)phenyl]methanol

Into a 250-mL 3-necked round-bottom flask, was placed a solution of 4-(cyclopentylsulfanyl)benzaldehyde (6.00 g, 29.08 mmol, 1.00 equiv)(Example 546) in methanol (50 mL). This was followed by the addition of $NaBH_4$ (1.70 g, 44.94 mmol, 1.50 equiv) in portions at 0° C. The resulting solution was stirred for 1 h at room temperature. The reaction was then quenched by the addition of 50 mL of aqueous NH4Cl at 10° C. The resulting solution was extracted with 2×200 mL of ethyl acetate, the organic layers were combined and concentrated under vacuum. The residue was purified by a silica gel column eluted with ethyl acetate/petroleum ether (1:2). This resulted in 4.00 g (66%) of [4-(cyclopentylsulfanyl)phenyl]methanol as yellow oil.

Example 548

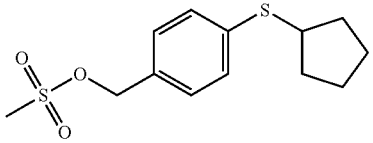 [SMILES: CS(=O)(=O)OCc1ccc(SC2CCCC2)cc1]

[4-(cyclopentylsulfanyl)phenyl]methyl methanesulfonate

Into a 100-mL 3-necked round-bottom flask purged and maintained with an inert atmosphere of nitrogen, was placed a solution of [4-(cyclopentylsulfanyl)phenyl]methanol (2.50 g, 12.00 mmol, 1.00 equiv)(Example 547) in dichloromethane (20 mL) and TEA (3.6 g, 35.58 mmol, 3.00 equiv) with stirring at 0° C., to which was added methanesulfonyl chloride (1.6 g, 13.97 mmol, 1.20 equiv) dropwise. The resulting solution was stirred for 14 h at room temperature. The reaction was then quenched by the addition of 20 mL of water/ice. The reaction solution was extracted with 2×50 mL of dichloromethane, the organic layers combined and concentrated under vacuum. The residue was purified by a silica gel column eluted with ethyl acetate/petroleum ether (1:10). This resulted in 2.00 g (58%) of [4-(cyclopentylsulfanyl)phenyl]methyl methanesulfonate as yellow oil.

Example 549

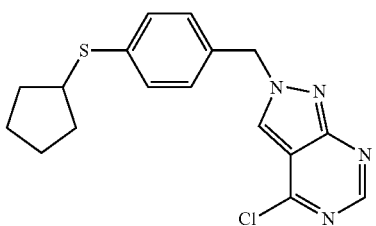 [SMILES: Clc1ncnc2nn(Cc3ccc(SC4CCCC4)cc3)cc12]

4-chloro-2-[[4-(cyclopentylsulfanyl)phenyl]methyl]-2H-pyrazolo[3,4-d]pyrimidine

Into a 100-mL 3-necked round-bottom flask, was placed a solution of [4-(cyclopentylsulfanyl)phenyl]methyl methanesulfonate (1.00 g, 3.49 mmol, 1.00 equiv) in $CH_3CN$ (20 mL), 4-chloro-2H-pyrazolo[3,4-d]pyrimidine (647 mg, 4.19 mmol, 1.20 equiv)(Example 548), NaI (1 g, 6.67 mmol, 2.00 equiv) and $K_2CO_3$ (965 mg, 6.67 mmol, 2.00 equiv). The resulting solution was stirred for 14 h at room temperature. The resulting mixture was concentrated under vacuum. The residue was purified by silica gel column chromatography eluted with ethyl acetate/petroleum ether (1:3). This resulted in 460 mg (38%) of 4-chloro-2-[[4-(cyclopentylsulfanyl) phenyl]methyl]-2H-pyrazolo[3,4-d]pyrimidine as brown oil. MS (ESI) m/z 345, 347[M+H]$^+$.

Example 550

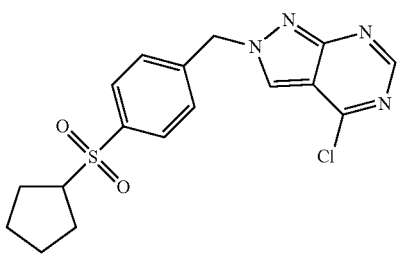 [SMILES: O=S(=O)(c1ccc(Cn2cc3c(Cl)ncnc3n2)cc1)C1CCCC1]

4-chloro-2-[[4-(cyclopentanesulfonyl)phenyl] methyl]-2H-pyrazolo[3,4-d]pyrimidine Into a 50-mL round-bottom flask, was placed 4-chloro-2-[[4-(cyclopentylsulfanyl)phenyl]methyl]-2H-pyrazolo[3,4-d]pyrimidine (400 mg, 1.16 mmol, 1.00 equiv)(Example 549), dichloromethane (20 mL) and m-CPBA (498 mg, 2.89 mmol, 2.50 equiv). The reaction solution was stirred for 18 h at room temperature. The reaction was then quenched by the addition of 20 mL of Na$_2$SO$_3$ aqueous solution and 20 mL of aqueous NaHCO$_3$. The resulting solution was extracted with 2×20 mL of dichloromethane. The organic layers were combined and concentrated under vacuum. The residue was purified by a silica gel column chromatography eluted with PE/EA/DCM (1:1:1). This resulted in 130 mg (30%) of 4-chloro-2-[[4-(cyclopentanesulfonyl)phenyl] methyl]-2H-pyrazolo[3,4-d]pyrimidine as a off-yellow solid. ES (ESI) m/z 377, 379[M+H]$^+$.

Example 551

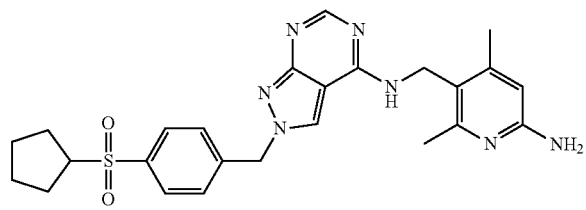 [SMILES: Cc1cc(N)nc(C)c1CNc1ncnc2nn(Cc3ccc(S(=O)(=O)C4CCCC4)cc3)cc12]

N-((6-amino-2,4-dimethylpyridin-3-yl)methyl)-2-(4-(cyclopentylsulfonyl)benzyl)-2H-pyrazolo[3,4-d]pyrimidin-4-amine N-((6-amino-2,4-dimethylpyridin-3-yl)methyl)-2-(4-(cyclopentylsulfonyl)benzyl)-2H-pyrazolo[3,4-d]pyrimidin-4-amine was synthesized in a similar manner as Example 468 using Example 550. $^1$H NMR (300 MHz, DMSO-d$_6$): δ 8.45 (s, 1H), 8.27 (s, 1H), 8.09 (s, 1H), 7.88 (d, J=8.4 Hz, 2H), 7.50 (d, J=8.1 Hz, 2H), 6.20 (s, 1H), 5.85 (s, 2H), 5.70 (s, 2H), 4.52 (d, J=3.9 Hz, 2H), 3.75-3.60 (m, 1H), 2.32 (s, 3H), 2.18 (s, 3H), 1.90-1.70 (m, 4H), 1.61-1.53 (m, 4H). MS (ESI) m/z: 492 [M+H]$^+$.

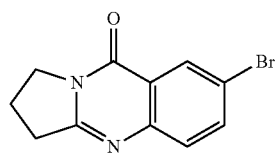 [SMILES: O=c1c2cc(Br)ccc2nc2n1CCC2]

7-bromo-1H,2H,3H,9H-pyrrolo[2,1-b]quinazolin-9-one

Into a 1000-mL 3-necked round-bottom flask purged and maintained with an inert atmosphere of nitrogen, were placed 2-amino-5-bromobenzoic acid (10 g, 46.29 mmol, 1.00 equiv), 4-aminobutanoic acid (7.2 g, 69.82 mmol, 1.50 equiv), m-xylene (500 mL) and phosphophosphonic acid (33 g, 229.23 mmol, 5.00 equiv). The mixture was stirred for 3 h at 145° C. The reaction mixture was cooled to 25° C. with a water/ice bath. The solids were collected by filtration. The filtrate was diluted with 1000 mL of water. The pH value of the solution was adjusted to 7-8 with aqueous Na$_2$CO$_3$ (1 mol/L) solution. Then it was extracted with 3×500 mL of ethyl acetate and washed with 1×300 mL of brine. The organic phase was concentrated under vacuum. The crude product was purified by flash silica gel column chromatography eluted with ethyl acetate/ petroleum ether (1:10-1:0). This resulted in 5.00 g (41%) of 7-bromo-1H,2H,3H,9H-pyrrolo[2,1-b]quinazolin-9-one as a yellow solid.

MS (ESI) m/z: 267[M+H]$^+$

Example 553

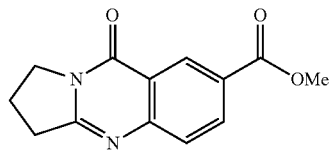 [SMILES: COC(=O)c1ccc2nc3n(c(=O)c2c1)CCC3]

9-oxo-1H,2H,3H,9H-pyrrolo[2,1-b]quinazoline-7-carboxylate Into a 250-mL pressure tank reactor (10 atm), were placed 7-bromo-1H,2H,3H,9H-pyrrolo[2,1-b]quinazolin-9-one (5.0 g, 18.86 mmol, 1.00 equiv)(Example 552), Pd(dppf)Cl$_2$ (1.5 g, 2.05 mmol, 0.10 equiv), triethylamine (3.8 g, 37.55 mmol, 2.00 equiv) and methanol (130 mL). To reaction solution was purged with carbon monoxide and was stirred for 15 h at 80° C. in an atmosphere of carbon monoxide. The resulted mixture was concentrated under vacuum. The crude product was purified by flash column chromatography eluted with ethyl acetate/ petroleum ether (1:10-1:0). This resulted in 2.60 g (56%) of methyl 9-oxo-1H,2H,3H,9H-pyrrolo[2,1-b]quinazoline-7-carboxylate as a pink solid. MS (ESI) m/z: 245[M+H]$^+$ Example 554

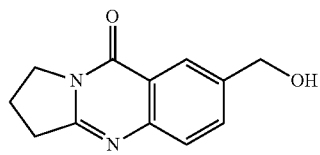 [SMILES: O=c1c2cc(CO)ccc2nc2n1CCC2]

7-(hydroxymethyl)-1H,2H,3H,9H-pyrrolo[2,1-b] quinazolin-9-one

Into a 250-mL 3-necked round-bottom flask purged and maintained with an inert atmosphere of nitrogen, was placed methyl 9-oxo-1H,2H,3H,9H-pyrrolo[2,1-b]quinazoline-7-carboxylate (1.1 g, 4.50 mmol, 1.00 equiv)(Example 553) in tetrahydrofuran (100 mL) with stirring at −25° C. This was followed by the addition of aluminum lithium hydride (250 mg, 6.58 mmol, 1.50 equiv) in portions at −25° C. in 10 min. The resulted solution was stirred for 20 min at −25° C. The reaction was then quenched by the addition of 0.25 mL of water at −25° C., followed by the addition of 0.75 mL of aqueous NaOH solution (15%) and 0.25 mL of water sequentially. After filtration over Celite, the filtrate was concentrated under vacuum. The residue was purified by silica gel column eluted with ethyl acetate/petroleum ether/ methanol (1:1:0 to 1:1:6). This resulted in 525 mg (54%) of 7-(hydroxymethyl)-1H,2H,3H,9H-pyrrolo[2,1-b]quinazolin-9-one as white solid. MS (ESI) m/z: 217[M+H]$^+$ Example 555

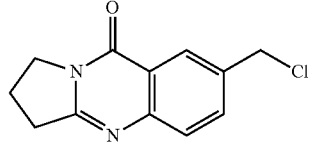 [SMILES: O=c1c2cc(CCl)ccc2nc2n1CCC2]

7-(chloromethyl)-1H,2H,3H,9H-pyrrolo[2,1-b]quinazolin-9-one Into a 100-mL round-bottom flask purged and maintained with an inert atmosphere of nitrogen, were placed 7-(hydroxymethyl)-1H,2H,3H,9H-pyrrolo[2,1-b]quinazolin-9-one (500 mg, 2.31 mmol, 1.00 equiv)(Example 554), dichloromethane (60 mL), N,N-dimethylformamide (0.1 mL) and thionyl dichloride (819 mg, 6.88 mmol, 3.00 equiv). The resulted solution was stirred for 2 h at 25° C. The mixture was concentrated under vacuum. This resulted in 500 mg (92%) of 7-(chloromethyl)-1H,2H,3H,9H-pyrrolo[2,1-b]quinazolin-9-one as light yellow oil. MS (ESI) m/z: 235[M+H]$^+$

Example 556

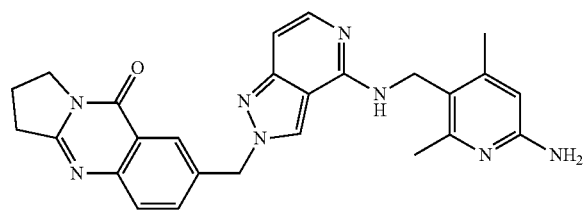 [SMILES: Cc1cc(N)nc(C)c1CNc1nccc2nn(Cc3ccc4nc5n(c(=O)c4c3)CCC5)cc12]

7-((4-(((6-amino-2,4-dimethylpyridin-3-yl)methyl-amino)-2H-pyrazolo[4,3-c]pyridin-2-yl)methyl)-2,3-dihydropyrrolo[2,1-b]quinazolin-9(1H)-one 7-((4-(((6-amino-2,4-dimethylpyridin-3-yl)methylamino)-2H-pyrazolo[4,3-c]pyridin-2-yl)methyl)-2,3-dihydropyrrolo[2,1-b]quinazolin-9(1H)-one was prepared in a similar manner as Example 468 using Example 555. $^1$H NMR (300 MHz, CD$_3$OD): 8.48 (s, 1H), 8.12 (s, 1H), 7.77 (d, J=10.5 Hz, 1H), 7.68-7.62 (m, 2H), 6.77 (d, J=6.6 Hz, 1H), 6.34 (s, 1H), 5.69 (s, 2H), 4.53 (s, 2H), 4.20-4.15 (m, 2H), 3.23-3.16 (m, 2H), 2.40 (s, 3H), 2.35-2.25 (m, 5H). MS (ESI) m/z 467 [M+H]$^+$

Example 557

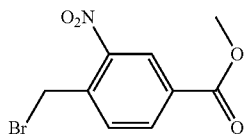

methyl 4-(bromomethyl)-3-nitrobenzoate

Into a 1000-mL round-bottom flask purged and maintained with an inert atmosphere of nitrogen, were placed methyl 4-methyl-3-nitrobenzoate (10 g, 51.24 mmol, 1.00 equiv), NBS (9.13 g, 51.29 mmol, 1.00 equiv), BPO (1.24 g, 5.12 mmol, 0.10 equiv) and tetrachloromethane (400 mL). The resulted solution was stirred for 15 h at 100° C. The crude product was purified by silica gel column chromatography eluted with ethyl acetate/ petroleum ether (0:1-1:9). This resulted in 11.1 g (79%) of methyl 4-(bromomethyl)-3-nitrobenzoate as yellow oil. The crude product was used in the next step without further purification.

Example 558

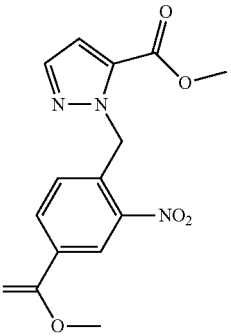

1-[[4-(methoxycarbonyl)-2-nitrophenyl]methyl]-1H-pyrazole-5-carboxylate

Into a 500-mL 3-necked round-bottom flask purged and maintained with an inert atmosphere of nitrogen, were placed potassium carbonate (11.2 g, 80.45 mmol, 2.00 equiv), methyl 1H-pyrazole-5-carboxylate (5.08 g, 40.28 mmol, 1.00 equiv)(Example 557) and acetonitrile (100 mL) with stirring at 0° C. This was followed by the addition of a solution of methyl 4-(bromomethyl)-3-nitrobenzoate (11 g, 40.14 mmol, 1.00 equiv) in acetonitrile (100 mL) dropwise with stirring at 0° C. in 5 min. The resulted solution was stirred overnight at 25° C. The mixture was concentrated under vacuum. The crude product was purified by flash column chromatography eluted with ethyl acetate/petroleum ether (1:10-1:0). This resulted in 3.00 g (23%) of methyl 1-[[4-(methoxycarbonyl)-2-nitrophenyl]methyl]-1H-pyrazole-5-carboxylate as white solid. The crude product was used in the next step without further purification.

Example 559

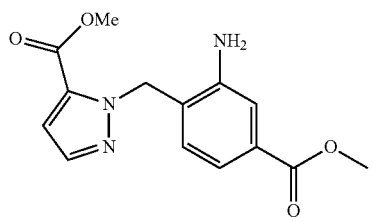 [SMILES: COC(=O)c1ccc(Cn2nccc2C(=O)OC)c(N)c1]

methyl 1-[[2-amino-4-(methoxycarbonyl)phenyl]methyl]-1H-pyrazole-5-carboxylate Into a 250-mL round-bottom flask, were placed methyl 1-[[4-(methoxycarbonyl)-2-nitrophenyl]methyl]-1H-pyrazole-5-carboxylate (3.20 g, 10.02 mmol, 1.00 equiv)(Example 558), Raney Ni (2 g) in methanol (80 mL). The reaction solution was purged with hydrogen for 3 times and stirred overnight at 25° C. in an atmosphere of hydrogen (at 4 atm of pressure). The solids were filtered out. The filtrate was concentrated under vacuum. This resulted in 2.70 g (93%) of methyl 1-[[2-amino-4-(methoxycarbonyl)phenyl]methyl]-1H-pyrazole-5-carboxylate as white solid. MS (ESI) m/z: 290[M+H]$^+$

Example 560

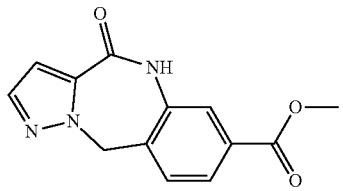 [SMILES: COC(=O)c1ccc2c(c1)NC(=O)c1ccnn1C2]

methyl 4-oxo-5,10-dihydro-4H-benzo[e]pyrazolo[1,5-a][1,4]diazepine-7-carboxylate Into a 100-mL round-bottom flask purged and maintained with an inert atmosphere of nitrogen, was placed methyl 1-[[2-amino-4-(methoxycarbonyl)phenyl]methyl]-1H-pyrazole-5-carboxylate (2.70 g, 9.33 mmol, 1.00 equiv)(Example 559) in AcOH (60 mL). The resulted solution was stirred overnight at 100° C. The reaction mixture was cooled to 25° C. and diluted with 300 mL of ether. The solids were collected by filtration. This resulted in 2.01 g (83%) of methyl 4-oxo-5,10-dihydro-4H-benzo[e]pyrazolo[1,5-a][1,4]diazepine-7-carboxylate as white solid. MS (ESI) m/z: 258[M+H]$^+$

Example 561

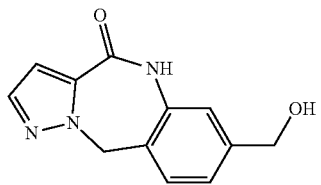 [SMILES: O=C1Nc2cc(CO)ccc2Cn2nccc21]

7-(hydroxymethyl)-5,10-dihydro-4H-benzo[e]pyrazolo[1,5-a][1,4]diazepin-4-one

Into a 250-mL 3-necked round-bottom flask purged and maintained with an inert atmosphere of nitrogen, was placed methyl 4-oxo-5,10-dihydro-4H-benzo[e]pyrazolo[1,5-a][1,4]diazepine-7-carboxylate (1.0 g, 3.89 mmol, 1.00 equiv) (Example 560) in tetrahydrofuran (80 mL). This was followed by the addition of alumane lithium (220 mg, 5.79 mmol, 1.50 equiv) in portions at 0° C. in 5 min. The resulted solution was stirred for 30 min at 0° C. The reaction was then quenched by the addition of 0.2 mL of water, 0.6 mL of aqueous NaOH (15%) and 0.2 mL of water at 0° C. sequentially. The resulted mixture was then concentrated under vacuum. The crude product was purified by silica gel column chromatography eluted with ethyl acetate and petroleum ether (1:10-1:0). This resulted in 700 mg (79%) of 7-(hydroxymethyl)-5,10-dihydro-4H-benzo[e]pyrazolo[1,5-a][1,4]diazepin-4-one as white solid. MS (ESI) m/z: 230 [M+H]$^+$

Example 562

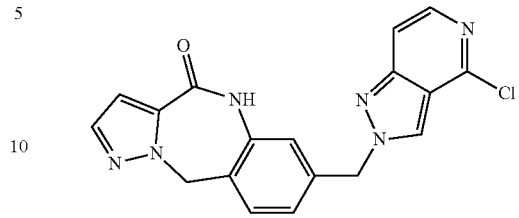

12-([4-chloro-2H-pyrazolo[4,3-c]pyridin-2-yl]methyl)-3,4,9-triazatricyclo[8.4.0.0^[3,7]]tetradeca-1(10),4,6,11,13-pentaen-8-one Into a 250-mL 3-necked round-bottom flask purged and maintained with an inert atmosphere of nitrogen, were placed 7-(hydroxymethyl)-5,10-dihydro-4H-benzo[e]pyrazolo[1,5-a][1,4]diazepin-4-one (700 mg, 3.05 mmol, 1.00 equiv)(Example 561), dichloromethane (100 mL) and triethylamine (618 mg, 6.11 mmol, 2.00 equiv) with stirring at 0° C. This was followed by the addition of methanesulfonyl chloride (383 mg, 3.34 mmol, 1.10 equiv) dropwise. The reaction solution was stirred for 2 h at 25° C. Then it was diluted with 100 mL of water. The organic phase was washed with 2×50 mL of brine, dried over anhydrous sodium sulfate and concentrated under vacuum. This resulted in 700 mg (crude) of [8-oxo-3,4,9-triazatricyclo[8.4.0.0^[3,7]]tetradeca-1(10),4,6,11,13-pentaen-12-yl]methyl methanesulfonate as yellow oil. The crude product was used in the next step without further purification.

Into a 250-mL round-bottom flask purged and maintained with an inert atmosphere of nitrogen, were placed [8-oxo-3,4,9-triazatricyclo[8.4.0.0^[3,7]]tetradeca-1(10),4,6,11,13-pentaen-12-yl]methyl methanesulfonate (700 mg, 2.28 mmol, 1.00 equiv), CH$_3$CN (150 mL), K$_2$CO$_3$ (629 mg, 4.52 mmol, 2.00 equiv), Bu4NI (1683 mg, 4.52 mmol, 2.00 equiv) and 4-chloro-2H-pyrazolo[4,3-c]pyridine (523 mg, 3.41 mmol, 1.50 equiv). The resulted solution was stirred for 3 h at 25° C. The reaction mixture was concentrated under vacuum. The residue was purified by a silica gel column eluted with ethyl acetate/petroleum ether (1:10-1:0). This resulted in 80 mg (10%) of 12-([4-chloro-2H-pyrazolo[4,3-c]pyridin-2-yl]methyl)-3,4,9-triazatricyclo[8.4.0.0$^3$[3,7]]tetradeca-1(10),4,6,11,13-pentaen-8-one as white solid. MS (ESI) m/z: 365[M+H]$^+$

Example 563

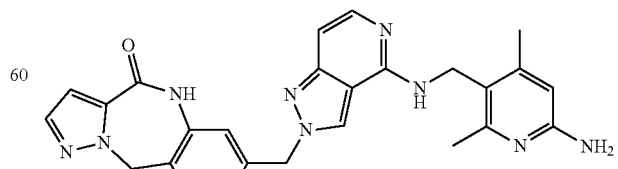

12-[(4-{[(6-amino-2,4-dimethylpyridin-3-yl)methyl]amino}-2H-pyrazolo[4,3-c]pyridin-2-yl)methyl]-3,4,9-triazatricyclo[8.4.0.0³,7]tetradeca-1(10),4,6,11,13-pentaen-8-one Into a 8-mL vial, were placed 12-([4-chloro-2H-pyrazolo[4,3-c]pyridin-2-yl]methyl)-3,4,9-triazatricyclo[8.4.0.0^[3,7]]tetradeca-1(10),4,6,11,13-pentaen-8-one (50 mg, 0.14 mmol, 1.00 equiv)(Example 562), 1-ethoxy-2-(2-ethoxyethoxy)ethane (5 mL), tert-butyl N-[5-(aminomethyl)-4,6-dimethylpyridin-2-yl]-N-[(tert-butoxy)carbonyl]carbamate (72.3 mg, 0.21 mmol, 1.5 equiv)(Example 4, Step 2), zinc dichloride (187 mg, 1.37 mmol, 10 equiv) and DIEA (355 mg, 2.75 mmol, 20.00 equiv). The crude product was purified by flash column chromatography eluted with DCM/EA/MeOH/concentrated ammonia aqueous solution (4:4:1:0.2). The crude product was further purified by Prep-HPLC with the following conditions: column, Waters XBridge RP18 19*150 mm; mobile phase, CH3CN/water (0.05% NH₄OH, 10 mM NH₄HCO₃) gradient from 25% to 30% with a 25-min run time, flow rate: 20 mL/min; detector UV wavelength: 254 nm. The product was obtained and concentrated under vacuum. This resulted in 11.8 mg (18%) of 12-[(4-[[(6-amino-2,4-dimethylpyridin-3-yl)methyl]amino]-2H-pyrazolo[4,3-c]pyridin-2-yl)methyl]-3,4,9-triazatricyclo[8.4.0.0^[3,7]]tetradeca-1(10),4,6,11,13-pentaen-8-one as white solid. $^1$H NMR (300 MHz, CD3OD-d): 8.40 (s, 1H), 7.68 (d, J=6.6 Hz, 1H), 7.47 (d, J=5.1 Hz, 2H), 7.18-7.09 (m, 2H), 6.86 (s, 1H), 7.76 (d, J=6.3 Hz, 1H), 6.34 (s, 1H), 5.56 (s, 2H), 5.41 (s, 2H), 4.52 (s, 2H), 2.39 (s, 3H), 2.26 (s, 3H). MS (ESI) m/z 480 [M+H]$^+$ Example 564

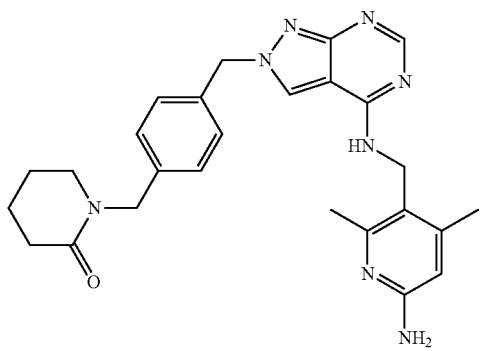 [SMILES: Cc1cc(N)nc(C)c1CNc1ncnc2nn(Cc3ccc(CN4CCCCC4=O)cc3)cc12]

1-({4-[(4-{[(6-amino-2,4-dimethylpyridin-3-yl)methyl]amino}-2H-pyrazolo[3,4-d]pyrimidin-2-yl)methyl]phenyl}methyl)piperidin-2-one 1-({4-[(4-{[(6-amino-2,4-dimethylpyridin-3-yl)methyl]amino}-2H-pyrazolo[3,4-d]pyrimidin-2-yl)methyl]phenyl}methyl)piperidin-2-one was prepared in a similar manner as Example 335. $^1$H NMR (400 MHz, Methanol-d₄) δ 8.45 (s, 1H), 8.30 (s, 1H), 8.23 (s, 1H), 7.37-7.13 (m, 4H), 6.55 (s, 1H), 5.50 (s, 2H), 4.65 (s, 2H), 4.55 (s, 2H), 3.28-3.18 (m, 2H), 2.50 (s, 3H), 2.38 (m, 5H), 1.77 (m, 4H). MS (ES, m/z) found for C₂₆H₃₀N₈O: 471.22 [M+H]$^+$.

Example 565

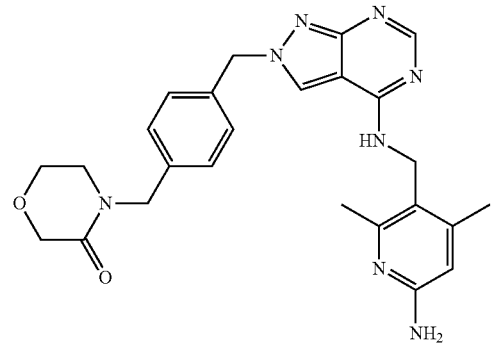 [SMILES: Cc1cc(N)nc(C)c1CNc1ncnc2nn(Cc3ccc(CN4CCOCC4=O)cc3)cc12]

4-({4-[(4-{[(6-amino-2,4-dimethylpyridin-3-yl)methyl]amino}-2H-pyrazolo[3,4-d]pyrimidin-2-yl)methyl]phenyl}methyl)morpholin-3-one 4-({4-[(4-{[(6-amino-2,4-dimethylpyridin-3-yl)methyl]amino}-2H-pyrazolo[3,4-d]pyrimidin-2-yl)methyl]phenyl}methyl)morpholin-3-one was prepared as described in Example 335. $^1$H NMR (400 MHz, Methanol-d4) δ 8.30 (s, 1H), 8.25 (s, 1H), 7.31 (m, 4H), 7.22 (m, 1H), 7.10 (m, 1H), 5.51 (s, 2H), 4.87 (m, 2H), 4.60 (s, 2H), 4.17 (s, 2H), 3.88 (s, 3H), 3.82 (m, 2H). MS (ES, m/z) for C₂₅H₂₈N₈O₂: 473.22 [M+H]$^+$ Example 566

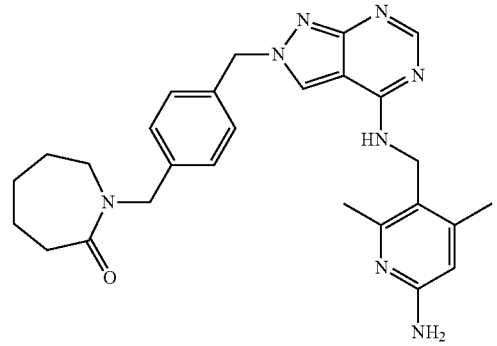 [SMILES: Cc1cc(N)nc(C)c1CNc1ncnc2nn(Cc3ccc(CN4CCCCCC4=O)cc3)cc12]

1-({4-[(4-{[(6-amino-2,4-dimethylpyridin-3-yl)methyl]amino}-2H-pyrazolo[3,4-d]pyrimidin-2-yl)methyl]phenyl}methyl)azepan-2-one 1-({4-[(4-{[(6-amino-2,4-dimethylpyridin-3-yl)methyl]amino}-2H-pyrazolo[3,4-d]pyrimidin-2-yl)methyl]phenyl}methyl)azepan-2-one was prepared as described in Example 335. $^1$H NMR (400 MHz, Methanol-d₄) δ 8.39 (s, 1H), 8.31 (s, 1H), 8.22 (s, 1H), 7.29 (m, 4H), 6.57 (s, 1H), 5.51 (s, 2H), 4.66 (s, 2H), 4.55 (s, 2H), 3.41-3.33 (m, 2H), 2.63-2.56 (m, 2H), 2.52 (s, 3H), 2.38 (s, 3H), 1.77-1.60 (m, 4H), 1.48 (m, 2H). MS (ES, m/z) for C₂₇H₃₂N₈O: 485.31 [M+H]$^+$

Example 567

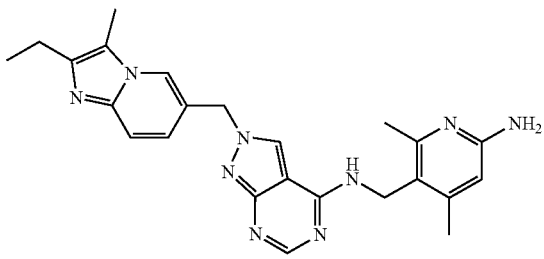 [SMILES: CCc1nc2ccc(Cn3cc4c(NCc5c(C)cc(N)nc5C)ncnc4n3)cn2c1C]

5-([[2-([2-ethyl-3-methylimidazo[1,2-a]pyridin-6-yl]methyl)-2H-pyrazolo[3,4-d]pyrimidin-4-yl]amino]methyl)-4,6-dimethylpyridin-2-amine 5-([[2-([2-ethyl-3-methylimidazo[1,2-a]pyridin-6-yl]methyl)-2H-pyrazolo[3,4-d]pyrimidin-4-yl]amino]methyl)-4,6-dimethylpyridin-2-amine was prepared in a similar manner as Example 468. $^1$H NMR (300 MHz, CD$_3$OD): δ 8.32-8.35 (3H, m), 7.44 (1H, d, J=9.9 Hz), 7.23 (2H, d, J=7.8 Hz), 6.34 (1H, s), 5.59 (2H, s), 4.65 (2H, s), 2.72-2.80 (2H, m), 2.47 (3H, s), 2.39 (3H, s), 2.26 (3H, s), 1.25-1.37 (3H, m). MS (ESI) m/z 442 [M+H]$^+$.

Example 568

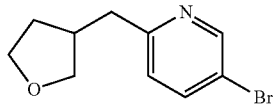 [SMILES: Brc1ccc(CC2CCOC2)nc1]

5-bromo-2-(oxolan-3-ylmethyl)pyridine

Into a 250-mL 3-necked round-bottom flask purged and maintained with an inert atmosphere of nitrogen, was placed a mixture of magnesium (690 mg, 28.75 mmol, 2.40 equiv) and tetrahydrofuran (10 mL), to which was added 3-(bromomethyl)oxolane (4.00 g, 24.24 mmol, 2.00 equiv) in tetrahydrofuran (20 mL) dropwise with stirring. The freshly prepared Grignard reagent was added dropwise to a solution of ZnCl$_2$ (3.92 g, 28.82 mmol, 2.40 equiv) in 20 mL of anhydrous THF at 0° C. The reaction mixture was stirred for 1 h at room temperature. Into a 250-mL 3-necked round-bottom flask purged and maintained with an inert atmosphere of nitrogen, was placed 2,5-dibromopyridine (2.84 g, 11.99 mmol, 1.00 equiv), Pd(PPh$_3$)$_4$ (139 mg, 0.12 mmol, 0.01 equiv) and 30 mL of THF. The freshly prepared zinc chloride complex solution was added dropwise to the reaction mixture. The reaction mixture was then stirred for 3 h at room temperature. The mixture was concentrated under vacuum and was added 100 mL of water. The solids were filtered out. The filtrate was extracted with EA (50 mL×3). The organic phase was washed with 1×100 mL of brine, dried over anhydrous sodium sulfate and concentrated under vacuum. The residue was purified by silica gel column chromatography eluted with ethyl acetate and petroleum ether (1:5). This resulted in 1.90 g (65%) of 5-bromo-2-(oxolan-3-ylmethyl)pyridine as yellow oil. MS (ESI) m/z 242 [M+H]$^+$.

Example 569

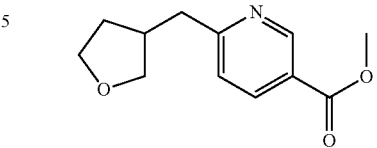

methyl 6-(oxolan-3-ylmethyl)pyridine-3-carboxylate

Into a 100-mL pressure tank reactor, was placed a mixture of 5-bromo-2-(oxolan-3-ylmethyl)pyridine (1 g, 4.13 mmol, 1.00 equiv)(Example 568), methanol (50 mL), TEA (1.2 g, 11.86 mmol, 3.00 equiv) and Pd(dppf)Cl$_2$ (146 mg, 0.20 mmol, 0.05 equiv). The resulting solution was purged with carbon monoxide (gas) and stirred for 3 h at 80° C. The reaction mixture was cooled to room temperature. The solids were filtered out. The filtrate was concentrated under vacuum. The residue was purified by silica gel column chromatography eluted with EA:PE (1:5). This resulted in 650 mg (71%) of methyl 6-(oxolan-3-ylmethyl)pyridine-3-carboxylate as brown solid. MS (ESI) m/z 222 [M+H]$^+$.

Example 570

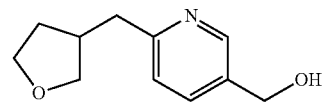 [SMILES: OCc1ccc(CC2CCOC2)nc1]

(6-((tetrahydrofuran-3-yl)methyl)pyridin-3-yl)methanol

Into a 100-mL 3-necked round-bottom flask purged and maintained with an inert atmosphere of nitrogen, was placed a mixture of methyl 6-(oxolan-3-ylmethyl)pyridine-3-carboxylate (650 mg, 2.94 mmol, 1.00 equiv)(Example 569) in tetrahydrofuran (20 mL). This was followed by the addition of LiAlH$_4$ (223 mg, 5.88 mmol, 2.00 equiv) in several batches at 0° C. The resulting solution was stirred for 2 h at room temperature. The reaction was then quenched by the addition of 15 mL of water/ice.

The solids were filtered out. The filtrate was extracted with EA (20 mL×3). The organic phase was washed with 1×50 mL of brine, dried over anhydrous sodium sulfate and concentrated under vacuum. The residue was purified by silica gel column chromatography eluted with EA:PE (1:1). This resulted in 350 mg (62%) of (6-((tetrahydrofuran-3-yl)methyl)pyridin-3-yl)methanol as yellow oil. MS (ESI) m/z 194 [M+H]$^+$.

Example 571

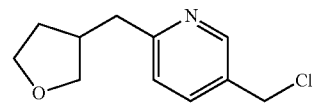 [SMILES: ClCc1ccc(CC2CCOC2)nc1]

5-(chloromethyl)-2-(oxolan-3-ylmethyl)pyridine

Into a 50-mL round-bottom flask purged and maintained with an inert atmosphere of nitrogen, was placed (6-((tetrahydrofuran-3-yl)methyl)pyridin-3-yl)methanol (350 mg, 1.81 mmol, 1.00 equiv)(Example 570) in dichloromethane (10 mL) with stirring at 0° C., to which was added thionyl chloride (646 mg, 3.00 equiv). The resulting solution was stirred for 2 h at room temperature. The resulting mixture was concentrated under vacuum. This resulted in 320 mg (83%) of 5-(chloromethyl)-2-(oxolan-3-ylmethyl)pyridine as yellow oil. MS (ESI) m/z 212 [M+H]$^+$.

Example 572

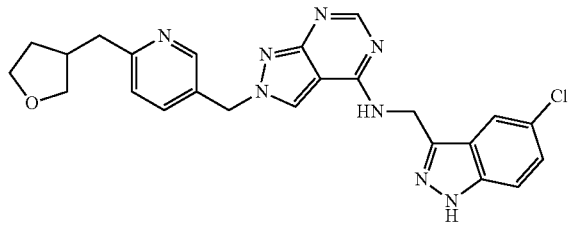 [SMILES: Clc1ccc2[nH]nc(CNc3ncnc4nn(Cc5ccc(CC6CCOC6)nc5)cc34)c2c1]

N-((5-chloro-1H-indazol-3-yl)methyl)-2-((6-((tetra-hydrofuran-3-yl)methyl)pyridin-3-yl)methyl)-2H-pyrazolo[3,4-d]pyrimidin-4-amine N-((5-chloro-1H-indazol-3-yl)methyl)-2-((6-((tetrahydrofuran-3-yl)methyl)pyridin-3-yl)methyl)-2H-pyrazolo[3,4-d]pyrimidin-4-amine was prepared in a similar manner as Example 335 using Example 571 and Example 2. $^1$H NMR (300 MHz, DMSO-d): δ 8.76 (s, 1H), 8.52 (s, 1H), 8.42 (s, 1H), 8.29 (s, 1H), 7.87 (s, 1H), 7.65-7.52 (m, 2H), 7.34-7.26 (m, 2H), 5.57 (s, 2H), 5.04 (s, 2H), 3.71 (m, 4H), 2.79-2.76 (m, 2H), 2.51 (m, 1H), 1.90-1.88 (m, 1H), 1.56-1.50 (m, 1H). MS (ESI) m/z 475 [M+H]$^+$.

Example 573

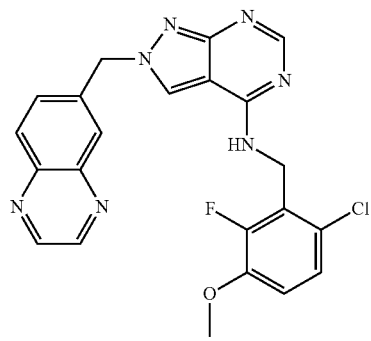 [SMILES: COc1ccc(Cl)c(CNc2ncnc3nn(Cc4ccc5nccnc5c4)cc23)c1F]

N-(6-chloro-2-fluoro-3-methoxybenzyl)-2-(quinoxa-lin-6-ylmethyl)-2H-pyrazolo[3,4-d]pyrimidin-4-amine N-(6-chloro-2-fluoro-3-methoxybenzyl)-2-(quinoxalin-6-ylmethyl)-2H-pyrazolo[3,4-d]pyrimidin-4-amine was prepared in a similar manner as Example 345. $^1$H NMR (400 MHz, DMSO-d$_6$) δ 8.94 (s, 2H), 8.42 (s, 1H), 8.34 (d, J=4.7 Hz, 1H), 8.26 (s, 1H), 8.09 (d, J=8.7 Hz, 1H), 8.02 (s, 1H), 7.76 (d, J=8.8 Hz, 1H), 7.31-7.25 (m, 1H), 7.18 (t, J=9.0 Hz, 1H), 5.84 (s, 2H), 4.75 (d, J=3.8 Hz, 2H), 3.83 (s, 3H). MS (M+H)$^+$ found for C$_{22}$H$_{17}$ClFN$_7$O: 450.

Example 574

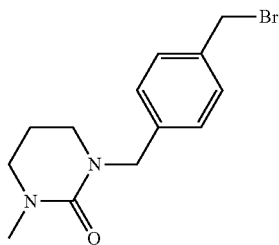 [SMILES: CN1CCCN(Cc2ccc(CBr)cc2)C1=O]

1-(4-(bromomethyl)benzyl)-3-methyltetrahydropy-rimidin-2(1H)-one

To a flame dried flask was added sodium hydride (192.72 mg; 4.82 mmol; 1.10 eq.). The flask was cooled in an ice bath before the addition of DMF (4 mL). After stirring this suspension for 10 minutes, a solution of 1-methyl-1,3-diazinan-2-one (500.00 mg; 4.38 mmol; 1.00 eq.) in N,N-dimethylformamide (5 mL) was added dropwise. This reaction solution was stirred for 25 minutes before 1,4-bis (bromomethyl)benzene (1.27 g; 4.82 mmol; 1.10 eq.) was added in one portion. The reaction mixture was stirred for 2 hours and then warmed to room temperature. The reaction was quenched with water and diluted with EtOAc. The organic layer was washed with water and brine and then dried (MgSO$_4$). The solvent was removed in vacuo and the residue was purified via automated column chromatography. The colorless oil was used directly in the next step. MS (ES, m/z) for C$_{13}$H$_{17}$BrN$_2$O: 298.66[M+H]$^+$ Example 575

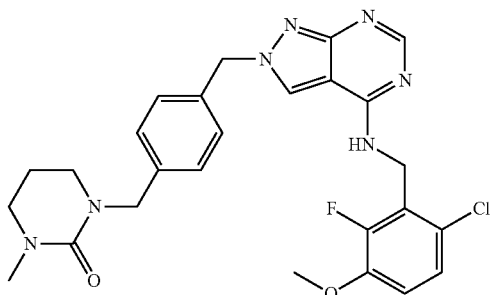

1-({4-[(4-{[(6-chloro-2-fluoro-3-methoxyphenyl) methyl]amino}-2H-pyrazolo[3,4-d]pyrimidin-2-yl) methyl]phenyl}methyl)-3-methyl-1,3-diazinan-2-one 1-({4-[(4-{[(6-chloro-2-fluoro-3-methoxyphenyl)methyl] amino}-2H-pyrazolo[3,4-d]pyrimidin-2-yl)methyl] phenyl}methyl)-3-methyl-1,3-diazinan-2-one was prepared in a similar manner to Example 345 using Example 574. $^1$H NMR (400 MHz, Methanol-d$_4$) δ 8.30 (s, 1H), 8.22 (s, 1H), 7.30 (m, 2H), 7.28-7.19 (m, 3H), 7.09 (t, J=8.9 Hz, 1H), 5.49

(s, 2H), 4.86 (m, 2H), 4.49 (s, 2H), 3.87 (s, 3H), 3.28 (m, 2H), 3.19 (t, J=5.9 Hz, 2H), 2.92 (s, 3H), 1.97-1.85 (m, 2H). MS (ES, m/z) for $C_{26}H_{27}ClFN_7O_2$: 524.10 [M+H]$^+$ Example 576

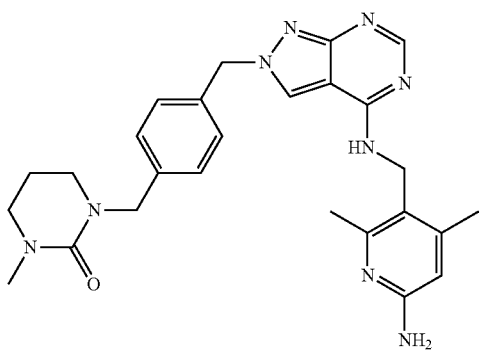 [SMILES: Cc1cc(N)nc(C)c1CNc1ncnc2nn(Cc3ccc(CN4CCCN(C)C4=O)cc3)cc12]

1-({4-[(4-{[(6-amino-2,4-dimethylpyridin-3-yl)methyl]amino}-2H-pyrazolo[3,4-d]pyrimidin-2-yl)methyl]phenyl}methyl)-3-methyl-1,3-diazinan-2-one 1-({4-[(4-{[(6-amino-2,4-dimethylpyridin-3-yl)methyl]amino}-2H-pyrazolo[3,4-d]pyrimidin-2-yl)methyl]phenyl}methyl)-3-methyl-1,3-diazinan-2-one was prepared in a similar manner to Example 468 using Example 574. $^1$H NMR (400 MHz, Methanol-$d_4$) δ 8.31 (s, 1H), 8.21 (s, 1H), 7.31 (m, 2H), 7.25 (m, 2H), 6.46 (s, 1H), 5.49 (s, 2H), 4.65 (s, 2H), 4.49 (s, 2H), 3.20 (t, J=5.9 Hz, 2H), 2.92 (s, 3H), 2.45 (s, 3H), 2.32 (s, 3H), 1.92 (p, J=6.0 Hz, 2H). MS (ES, m/z) for $C_{26}H_{31}N_9O$: 486.31 [M+H]$^+$ Example 577

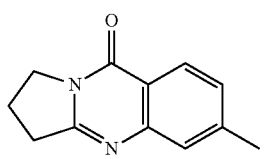

6-methyl-1H,2H,3H,9H-pyrrolo[2,1-b]quinazolin-9-one

Into a 50-mL round-bottom flask, was placed a mixture of 2-amino-4-methylbenzoic acid (1.00 g, 6.62 mmol, 1.00 equiv), N,N-dimethylformamide (10 mL) and 5-methoxy-3,4-dihydro-2H-pyrrole (660 mg, 6.66 mmol, 1.10 equiv). The resulted solution was stirred overnight at 90° C. The reaction solution was diluted with 50 mL of water and extracted with 3×30 mL of ethyl acetate. The organic layers were combined and concentrated under vacuum. The residue was purified by silica gel column chromatography eluted with ethyl acetate and petroleum ether (1:5). This resulted in 1.00 g (75%) of 6-methyl-1H,2H,3H,9H-pyrrolo[2,1-b]quinazolin-9-one as off-white solid. MS (ESI) m/z 201 [M+H]$^+$ Example 578

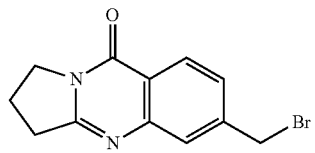 [SMILES: O=c1c2ccc(CBr)cc2nc2n1CCC2]

6-(bromomethyl)-1H,2H,3H,9H-pyrrolo[2,1-b]quinazolin-9-one

Into a 100-mL round-bottom flask, was placed a mixture of 6-methyl-1H,2H,3H,9H-pyrrolo[2,1-b]quinazolin-9-one (1.50 g, 7.49 mmol, 1.00 equiv)(Example 577), NBS (1.60 g, 8.99 mmol, 1.20 equiv) and BPO (73 mg, 0.28 mmol, 0.10 equiv) in CCl$_4$ (30 mL). The resulted solution was stirred for 2 h at 80° C. The resulted mixture was concentrated under vacuum. The residue was purified by silica gel column chromatography eluted with petroleum and ethyl acetate (5:1). This resulted in 400 mg (crude) of 6-(bromomethyl)-1H,2H,3H,9H-pyrrolo[2,1-b]quinazolin-9-one as yellow solid. MS (ESI) m/z 279 [M+H]$^+$ Example 579

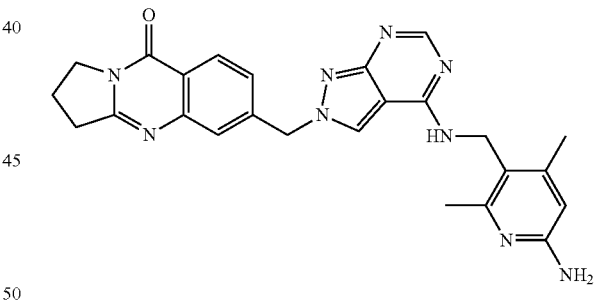

6-[(4-[[(6-amino-2,4-dimethylpyridin-3-yl)methyl]amino]-2H-pyrazolo[3,4-d]pyrimidin-2-yl)methyl]-1H,2H,3H,9H-pyrrolo[2,1-b]quinazolin-9-one 6-[(4-[[(6-amino-2,4-dimethylpyridin-3-yl)methyl]amino]-2H-pyrazolo[3,4-d]pyrimidin-2-yl)methyl]-1H,2H,3H,9H-pyrrolo[2,1-b]quinazolin-9-one was prepared as described in Example 563 using Example 578. $^1$H NMR (300 MHz, DMSO-$d_6$): δ 8.44 (s, 1H), 8.26 (s, 1H), 8.05-8.10 (m, 2H), 7.46 (s, 1H), 7.35 (d, J=8.1 Hz, 1H), 6.16 (s, 1H), 5.69 (d, J=10.2 Hz, 3H), 4.51 (d, J=3.9 Hz, 2H), 4.05 (t, J=7.2 Hz, 2H), 3.06 (t, J=7.8 Hz, 2H), 2.29 (s, 3H), 2.11-2.21 (m, 4H), 2.07 (s, 4H). MS (ESI) m/z 468 [M+H]$^+$ Example 580

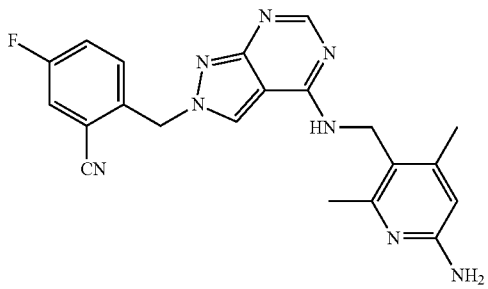 [SMILES: Cc1cc(N)nc(C)c1CNc1ncnc2nn(Cc3ccc(F)cc3C#N)cc12]

2-((4-(((6-amino-2,4-dimethylpyridin-3-yl)methyl-amino)-2H-pyrazolo[3,4-d]pyrimidin-2-yl)methyl)-5-fluorobenzonitrile 2-((4-(((6-amino-2,4-dimethylpyridin-3-yl)methylamino)-2H-pyrazolo[3,4-d]pyrimidin-2-yl)methyl)-5-fluorobenzonitrile was prepared in a similar manner as Example 335. $^1$H NMR (300 MHz, DMSO-$d_6$): 8.38 (s, 1H), 8.19 (s, 1H), 8.03 (br, 1H), 7.86 (dd, $J_1$=2.4 Hz, $J_2$=2.7 Hz, 1H), 7.56-7.48 (m, 2H), 6.09 (s, 1H), 5.64 (s, 4H), 4.45 (d, J=3.9 Hz, 2H), 2.23 (s, 3H), 2.09 (s, 3H). MS (ESI) m/z 403 [M+H]$^+$ Example 581

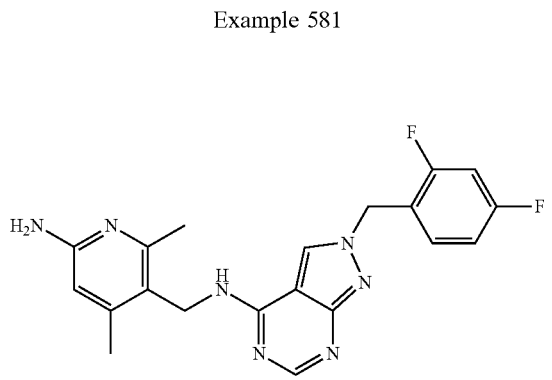

N-((6-amino-2,4-dimethylpyridin-3-yl)methyl)-2-(2,4-difluorobenzyl)-2H-pyrazolo[3,4-d]pyrimidin-4-amine N-((6-amino-2,4-dimethylpyridin-3-yl)methyl)-2-(2,4-difluorobenzyl)-2H-pyrazolo[3,4-d]pyrimidin-4-amine was prepared in a similar manner as Example 335. $^1$H NMR (300 MHz, DMSO-$d_6$): δ 8.36 (s, 1H), 8.25 (s, 1H), 7.99 (s, 1H), 7.49 (br, 1H), 7.32 (br, 1H), 7.14 (br, 1H), 6.15 (s, 1H), 5.70 (s, 2H), 5.56 (s, 2H), 4.50 (d, J=3.9 Hz, 2H), 2.29 (s, 3H), 2.15 (s, 3H). MS (ESI) m/z 396 [M+H]$^+$ Example 582

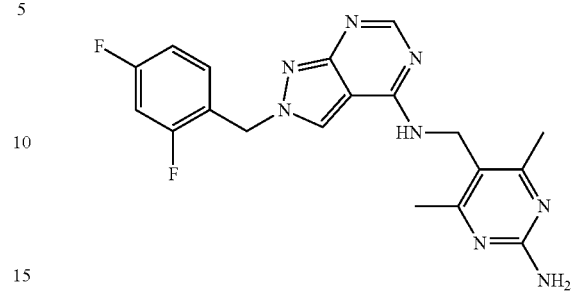

5-[([2-[(2,4-difluorophenyl)methyl]-2H-pyrazolo[3,4-d]pyrimidin-4-yl]amino)methyl]-4,6-dimethylpyrimidin-2-amine 5-[([2-[(2,4-difluorophenyl)methyl]-2H-pyrazolo[3,4-d]pyrimidin-4-yl]amino)methyl]-4,6-dimethylpyrimidin-2-amine was prepared in a similar manner as Example 335. $^1$H NMR (300 MHz, DMSO-$d_6$): δ 8.33 (s, 1H), 8.26 (s, 1H), 8.05 (br, 1H), 7.78 (s, 1H), 7.45-7.53 (m, 1H), 7.28-7.35 (m, 1H), 7.13-7.16 (m, 1H), 6.38 (s, 2H), 5.57 (s, 2H), 4.52 (d, J=4.2 Hz, 2H), 2.28 (s, 6H). MS (ESI) m/z 397 [M+H]$^+$ Example 583

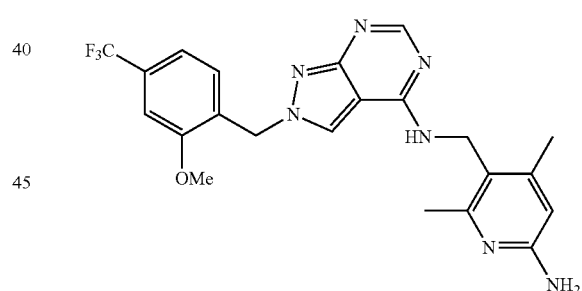

5-[[(2-[[2-methoxy-4-(trifluoromethyl)phenyl]methyl]-2H-pyrazolo[3,4-d]pyrimidin-4-yl)amino]methyl]-4,6-dimethylpyridin-2-amine 5-[[(2-[[2-methoxy-4-(trifluoromethyl)phenyl]methyl]-2H-pyrazolo[3,4-d]pyrimidin-4-yl)amino]methyl]-4,6-dimethylpyridin-2-amine was prepared in a similar manner as Example 335. $^1$H NMR (300 MHz, CD$_3$OD-d): 8.31 (s, 1H), 8.25 (s, 1H), 8.00 (s, 1H), 7.31-7.30 (m, 3H), 6.15 (s, 1H), 5.69 (s, 2H), 5.54 (s, 2H), 4.51 (d, J=6.0 Hz, 2H), 3.89 (s, 3H), 2.29 (s, 3H), 2.15 (s, 3H). MS (ESI) m/z 458 [M+1]$^+$: (ES, m/z):

Example 584

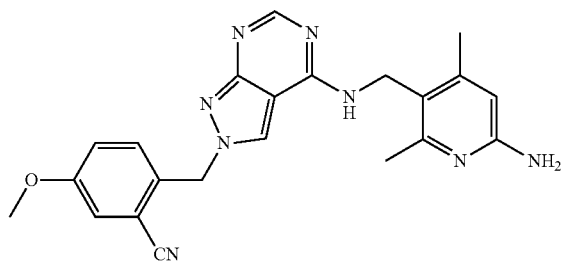 [SMILES: COc1ccc(Cn2cc3c(NCc4c(C)cc(N)nc4C)ncnc3n2)c(C#N)c1]

2-((4-(((6-amino-2,4-dimethylpyridin-3-yl)methyl-amino)-2H-pyrazolo[3,4-d]pyrimidin-2-yl)methyl)-5-methoxybenzonitrile 2-((4-(((6-amino-2,4-dimethylpyridin-3-yl)methylamino)-2H-pyrazolo[3,4-d]pyrimidin-2-yl)methyl)-5-methoxybenzonitrile was prepared in a similar manner as Example 335. $^1$H NMR (300 MHz, CDCl$_3$): δ 8.87 (s, 3H), 8.46 (s, 1H), 7.14-7.26 (m, 2H), 6.91-7.04 (m, 1H), 6.52 (s, 1H), 5.72 (s, 2H), 4.70 (s, 2H), 3.80 (s, 3H), 2.57 (s, 3H), 2.37 (s, 3H).

LC-MS (ESI) m/z: calculated for C$_{22}$H$_{22}$N$_8$O: 414. found: 415 [M+H]$^+$.

Example 585

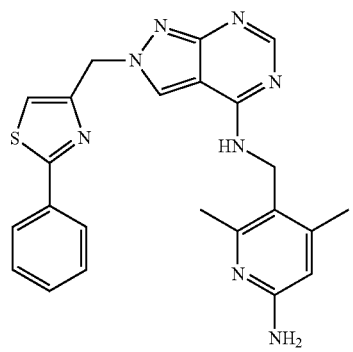 [SMILES: Cc1cc(N)nc(C)c1CNc1ncnc2nn(Cc3csc(-c4ccccc4)n3)cc12]

N-((6-amino-2,4-dimethylpyridin-3-yl)methyl)-2-((2-phenylthiazol-4-yl)methyl)-2H-pyrazolo[3,4-d]pyrimidin-4-amine N-((6-amino-2,4-dimethylpyridin-3-yl)methyl)-2-((2-phenylthiazol-4-yl)methyl)-2H-pyrazolo[3,4-d]pyrimidin-4-amine was prepared in a similar manner as Example 335. $^1$H NMR (300 MHz, DMSO-d$_6$): δ 8.43-8.38 (m, 2H), 8.27 (s, 1H), 7.99-7.76 (m, 2H), 7.74 (s, 1H), 7.49 (br, 3H), 7.33-7.20 (m, 2H), 5.70 (s, 2H), 4.79-4.65 (m, 2H), 3.85 (s, 3H). MS (ESI) m/z 481 [M+H]$^+$.

Example 586

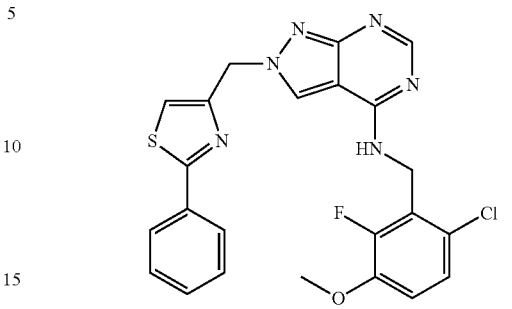

N-(6-chloro-2-fluoro-3-methoxybenzyl)-2-((2-phenylthiazol-4-yl)methyl)-2H-pyrazolo[3,4-d]pyrimidin-4-amine N-(6-chloro-2-fluoro-3-methoxybenzyl)-2-((2-phenylthiazol-4-yl)methyl)-2H-pyrazolo[3,4-d]pyrimidin-4-amine was prepared in a similar manner as Example 335. $^1$H NMR (300 MHz, DMSO-d$_6$): δ 8.43-8.38 (m, 2H), 8.27 (s, 1H), 7.99-7.76 (m, 2H), 7.74 (s, 1H), 7.49 (br, 3H), 7.33-7.20 (m, 2H), 5.70 (s, 2H), 4.79-4.65 (m, 2H), 3.85 (s, 3H). MS (ESI) m/z 481 [M+H]$^+$.

Example 587

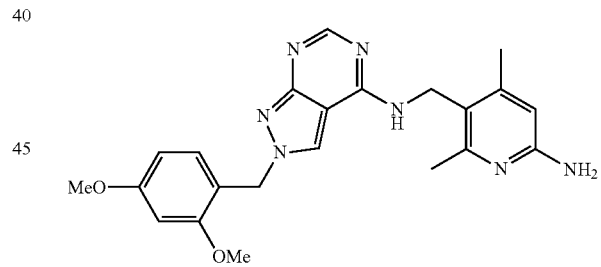

N-((6-amino-2,4-dimethylpyridin-3-yl)methyl)-2-(2,4-dimethoxybenzyl)-2H-pyrazolo[3,4-d]pyrimidin-4-amine N-((6-amino-2,4-dimethylpyridin-3-yl)methyl)-2-(2,4-dimethoxybenzyl)-2H-pyrazolo[3,4-d]pyrimidin-4-amine was prepared in a similar manner as Example 335. $^1$H NMR (300 MHz, DMSO-d$_6$): 8.23 (s, 1H), 8.14 (s, 1H), 7.88 (br, 1H), 7.23 (d, J=8.4 Hz, 1H), 6.61 (d, J=2.4 Hz, 1H), 6.57-6.53 (m, 1H), 6.14 (s, 1H), 5.68 (s, 2H), 5.34 (s, 2H), 4.48 (d, J=4.2 Hz, 2H), 3.76 (s, 6H), 2.27 (s, 3H), 2.13 (s, 3H). MS (ESI) m/z 420 [M+H]$^+$

Example 588

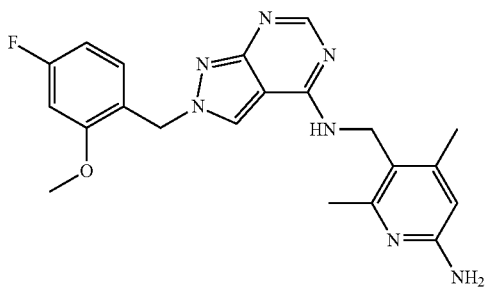 [SMILES: COc1cc(F)ccc1Cn1cc2c(NCc3c(C)cc(N)nc3C)ncnc2n1]

5-[([2-[(4-fluoro-2-methoxyphenyl)methyl]-2H-pyrazolo[3,4-d]pyrimidin-4-yl]amino)methyl]-4,6-dimethylpyridin-2-amine 5-[([2-[(4-fluoro-2-methoxyphenyl)methyl]-2H-pyrazolo[3,4-d]pyrimidin-4-yl]amino)methyl]-4,6-dimethylpyridin-2-amine was prepared in a similar manner as Example 335. $^1$H NMR (300 MHz, DMSO-d): δ 8.23 (d, J=6.9 Hz, 2H), 7.92 (br, 1H), 7.28 (t, J=6.6 Hz, 1H), 6.99 (d, J=9.0 Hz, 1H), 6.80 (t, J=7.2 Hz, 1H), 6.14 (s, 1H), 5.69 (s, 2H), 5.41 (s, 2H), 4.50 (d, J=5.7 Hz, 2H), 3.80 (s, 3H), 2.28 (s, 3H), 2.14 (s, 3H). MS (ESI) m/z 408 [M+H]$^+$

Example 589

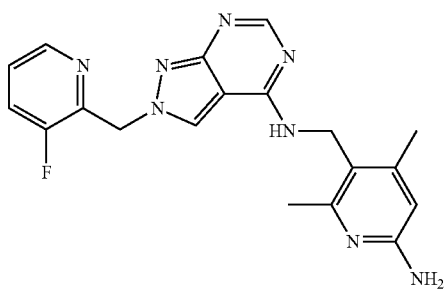 [SMILES: Cc1cc(N)nc(C)c1CNc1ncnc2nn(Cc3ncccc3F)cc12]

5-[([2-[(3-fluoropyridin-2-yl)methyl]-2H-pyrazolo[3,4-d]pyrimidin-4-yl]amino)methyl]-4,6-dimethyl-pyridin-2-amine 5-[([2-[(3-fluoropyridin-2-yl)methyl]-2H-pyrazolo[3,4-d]pyrimidin-4-yl]amino)methyl]-4,6-dimethylpyridin-2-amine was prepared in a similar manner as Example 335. $^1$H NMR (300 MHz, DMSO): δ 8.49 (s, 1H), 8.39 (dd, J=3.3 Hz, 1.5 Hz, 1H), 8.25 (s, 1H), 8.04 (brs, 1H), 7.84-7.77 (m, 1H), 7.53-7.47 (m, 1H), 6.17 (s, 1H), 5.71 (s, 4H), 4.53 (d, J=4.2 Hz, 2H), 2.31 (s, 3H), 2.17 (s, 3H). MS (ESI) m/z 379 [M+H]$^+$.

Example 590

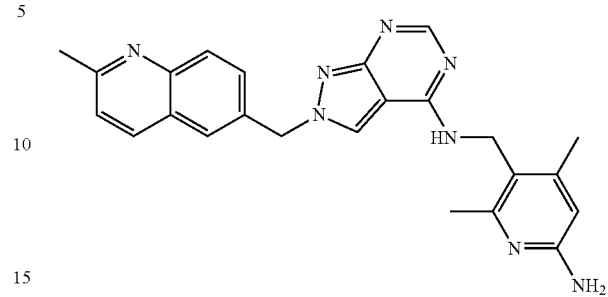

N-((6-amino-2,4-dimethylpyridin-3-yl)methyl)-2-((2-methylquinolin-6-yl)methyl)-2H-pyrazolo[3,4-d]pyrimidin-4-amine N-((6-amino-2,4-dimethylpyridin-3-yl)methyl)-2-((2-methylquinolin-6-yl)methyl)-2H-pyrazolo[3,4-d]pyrimidin-4-amine was prepared as described for Example 468. $^1$H NMR (300 MHz, DMSO-d): δ 8.39 (s, 1H), 8.26-8.23 (m, 2H), 7.99 (m, 1H), 7.93-7.87 (m, 2H), 7.64 (d, J=8.4 Hz, 1H), 7.43 (d, J=8.4 Hz, 1H), 6.14 (s, 1H), 5.71 (s, 2H), 5.68 (s, 2H), 4.50 (d, J=3.6 Hz, 2H), 2.64 (s, 3H), 2.28 (s, 3H), 2.14 (s, 3H). MS (ESI) m/z 425 [M+H]$^+$.

Example 591

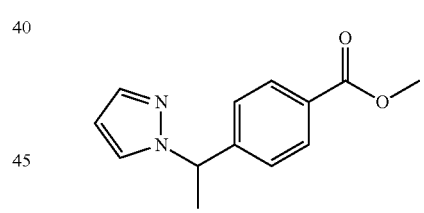

4-(1-(1H-pyrazol-1-yl)ethyl)benzoate

To a solution of 1H-pyrazole (0.44 g; 6.52 mmol; 1.10 eq.) in DMF (6 mL) was added Sodium hydride (0.25 g; 6.22 mmol; 1.05 eq.) at 0° C. and the mixture was warmed to room temperature. After stirred for 30 min, it was added methyl 4-(1-bromoethyl)benzoate (1.44 g; 5.92 mmol; 1.00 eq.) in DMF (2 mL) and the mixture was further stirred for 2 hr at room temperature, the solution was then quenched with water, the aqueous layer was extracted with EtOAc, organic layers were combined, washed with brine, dried and concentrated to give crude product, which was purified by column chromatography to give methyl 4-(1-(1H-pyrazol-1-yl)ethyl)benzoate (1.06 g, 78%).

Example 592

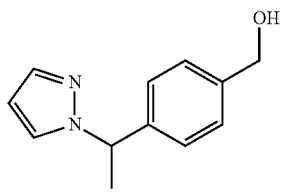

(4-(1-(1H-pyrazol-1-yl)ethyl)phenyl)methanol

To a solution of 4-(1-(1H-pyrazol-1-yl)ethyl)benzoate (1.06 g; 4.60 mmol; 1.00 eq.) in THF (5 mL) was added lithium tetrahydridoaluminate(1-) (4.60 ml; 1.00 mol/l; 4.60 mmol; 1.00 eq.)(Example 591) at 0° C. and the mixture was stirred for 2 h, then it was quenched with Sat. Na HCO3 and extracted with EtOAc, organic layers were combined, washed with brine, dried and concentrated to give crude product, which was purified by column chromatography to give (4-(1-(1H-pyrazol-1-yl)ethyl)phenyl)methanol (716 mg, 77%).

Example 593

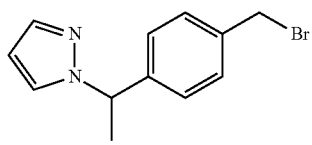

1-(1-(4-(bromomethyl)phenyl)ethyl)-1H-pyrazole

To a solution of (4-(1-(1H-pyrazol-1-yl)ethyl)phenyl)methanol (716.00 mg; 3.54 mmol; 1.00 eq.)(Example 592) in DCM (3 mL) was added phosphorous tribromide (0.67 ml; 7.08 mmol; 2.00 eq.) at 0° C. and the mixture was further stirred for 1h, then it was quenched with ice water and Sat. NaHCO3, the aqueous layer was extracted with DCM, organic layers were combined and concentrated and purified by column to give 1-(1-(4-(bromomethyl)phenyl)ethyl)-1H-pyrazole (700 mg, 74%).

Example 594

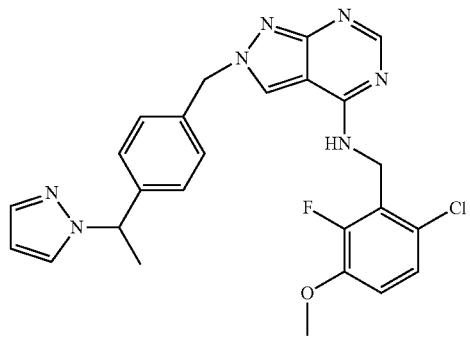 [SMILES: COc1ccc(Cl)c(CNc2ncnc3nn(Cc4ccc(C(C)n5cccn5)cc4)cc23)c1F]

2-(4-(1-(1H-pyrazol-1-yl)ethyl)benzyl)-N-(6-chloro-2-fluoro-3-methoxybenzyl)-2H-pyrazolo[3,4-d]pyrimidin-4-amine 2-(4-(1-(1H-pyrazol-1-yl)ethyl)benzyl)-N-(6-chloro-2-fluoro-3-methoxybenzyl)-2H-pyrazolo[3,4-d]pyrimidin-4-amine was prepared using Example 593 above in a similar manner as Example 345. ¹H NMR (400 MHz, DMSO-d$_6$) δ 8.33-8.21 (m, 3H), 7.84-7.77 (m, 1H), 7.45-7.39 (m, 1H), 7.32-7.13 (m, 6H), 6.22 (t, J=2.0 Hz, 1H), 5.58 (q, J=7.1 Hz, 1H), 5.48 (s, 2H), 4.73 (dd, J=4.7, 2.1 Hz, 2H), 3.83 (s, 3H), 1.74 (d, J=7.0 Hz, 3H). MS (M+H)+ found for $C_{25}H_{23}ClFN_7O$: 492.1, 494.1.

Example 595

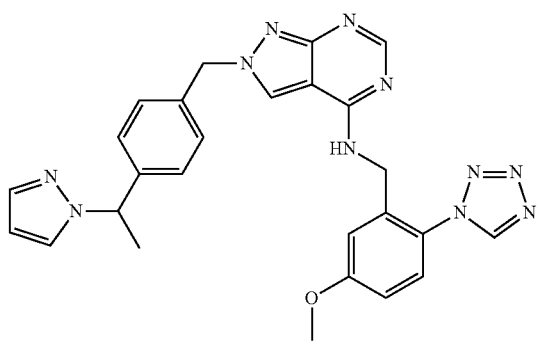 [SMILES: COc1ccc(-n2cnnn2)c(CNc2ncnc3nn(Cc4ccc(C(C)n5cccn5)cc4)cc23)c1]

2-(4-(1-(1H-pyrazol-1-yl)ethyl)benzyl)-N-(5-methoxy-2-(1H-tetrazol-1-yl)benzyl)-2H-pyrazolo[3,4-d]pyrimidin-4-amine 2-(4-(1-(1H-pyrazol-1-yl)ethyl)benzyl)-N-(5-methoxy-2-(1H-tetrazol-1-yl)benzyl)-2H-pyrazolo[3,4-d]pyrimidin-4-amine was prepared similar to Example 594 using (5-methoxy-2-(1H-tetrazol-1-yl)phenyl)methanamine to replace (6-chloro-2-fluoro-3-methoxyphenyl)methanamine. ¹H NMR (400 MHz, DMSO-d$_6$) δ 9.76 (s, 1H), 8.54 (t, J=5.7 Hz, 1H), 8.30 (s, 1H), 8.07 (s, 1H), 7.83-7.77 (m, 1H), 7.48 (d, J=8.7 Hz, 1H), 7.42 (dd, J=1.7, 0.7 Hz, 1H), 7.26 (d, J=8.1 Hz, 2H), 7.23-7.03 (m, 4H), 6.23 (t, J=2.0 Hz, 1H), 5.59 (q, J=7.1 Hz, 1H), 5.50 (s, 2H), 4.44 (d, J=5.6 Hz, 2H), 3.78 (s, 3H), 1.75 (d, J=7.1 Hz, 3H). MS (M+H)+ found for $C_{26}H_{25}N_{11}O$: 508.2.

Example 596

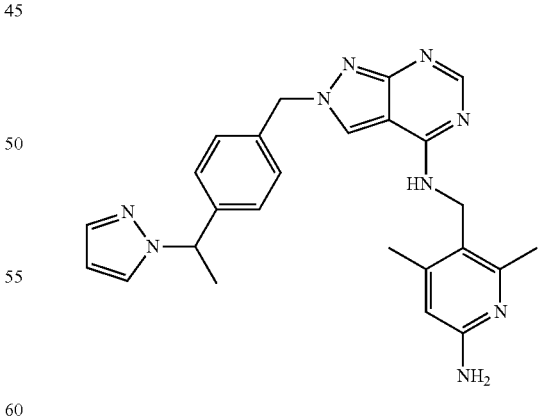

2-(4-(1-(1H-pyrazol-1-yl)ethyl)benzyl)-N-((6-amino-2,4-dimethylpyridin-3-yl)methyl)-2H-pyrazolo[3,4-d]pyrimidin-4-amine 2-(4-(1-(1H-pyrazol-1-yl)ethyl)benzyl)-N-((6-amino-2,4-dimethylpyridin-3-yl)methyl)-2H-pyrazolo[3,4-d]pyrimidin-4-amine was prepared similar to Example 594 using tert-butyl N-[5-(aminomethyl)-4,6-dimethylpyridin-2-yl]-N-[(tert-butoxy)carbonyl]carbamate to replace (6-chloro-2-fluoro-3-methoxyphenyl)methanamine. $^1$H NMR (400 MHz, DMSO-d$_6$) δ 9.20 (s, 1H), 8.48 (d, J=17.9 Hz, 2H), 7.84-7.79 (m, 3H), 7.45-7.39 (m, 1H), 7.29 (d, J=7.9 Hz, 2H), 7.20 (d, J=7.9 Hz, 2H), 6.65 (s, 1H), 6.23 (t, J=2.1 Hz, 1H), 5.64-5.52 (m, 3H), 4.62 (d, J=5.1 Hz, 2H), 2.49 (s, 3H), 2.36 (s, 3H), 1.75 (d, J=7.1 Hz, 3H). MS (M+H)+ found for C$_{25}$H$_{27}$N$_9$: 454.2.

Example 597

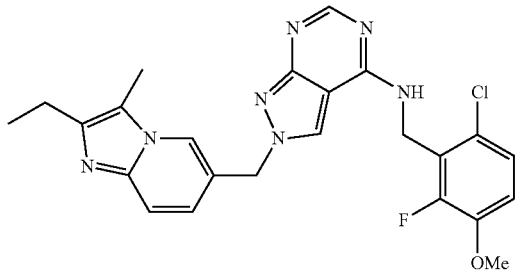 [SMILES: CCc1nc2ccc(Cn3cc4c(NCc5c(Cl)ccc(OC)c5F)ncnc4n3)cn2c1C]

N-(6-chloro-2-fluoro-3-methoxybenzyl)-2-((2-ethyl-3-methylimidazo[1,2-a]pyridin-6-yl)methyl)-2H-pyrazolo[

3,4-d]pyrimidin-4-amine N-(6-chloro-2-fluoro-3-methoxybenzyl)-2-((2-ethyl-3-methylimidazo[1,2-a]pyridin-6-yl)methyl)-2H-pyrazolo[3,4-d]pyrimidin-4-amine was prepared in a similar manner to Example 567. $^1$H NMR (300 MHz, CD$_3$OD): δ 8.34-8.30 (m, 3H), 7.46-7.43 (m, 1H), 7.25-7.21 (m, 2H), 7.14-7.08 (m, 1H), 5.62 (s, 2H), 3.91 (s, 3H), 2.79 (q, J=7.0 Hz, 2H), 2.49 (3, 3H), 1.30 (t, J=7.0 Hz, 3H). LC-MS (ESI) m/z: 480[M+H]$^+$ Example 598

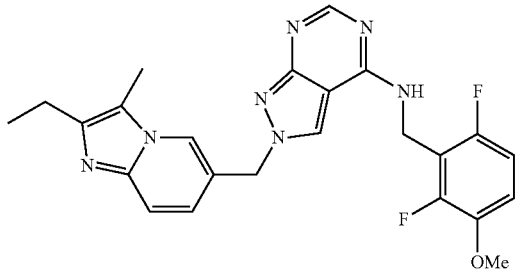 [SMILES: CCc1nc2ccc(Cn3cc4c(NCc5c(F)ccc(OC)c5F)ncnc4n3)cn2c1C]

N-(2,6-difluoro-3-methoxybenzyl)-2-((2-ethyl-3-methylimidazo[1,2-a]pyridin-6-yl)methyl)-2H-pyrazolo[3,4-d]pyrimidin-4-amine N-(2,6-difluoro-3-methoxybenzyl)-2-((2-ethyl-3-methylimidazo[1,2-a]pyridin-6-yl)methyl)-2H-pyrazolo[3,4-d]pyrimidin-4-amine was prepared in a similar manner as Example 567. $^1$H NMR (300 MHz, CD$_3$OD): δ 8.41 (s, 1H), 8.23 (s, 1H), 8.15-8.05 (m, 1H), 7.38 (d, J=9.0 Hz, 1H), 7.25-7.17 (m, 1H), 7.17-7.04 (m, 1H), 6.97-6.89 (m, 1H), 5.59 (s, 2H), 3.85 (s, 3H), 2.78 (q, J=7.8 Hz, 2H), 2.46 (s, 3H), 1.29 (t, J=7.8 Hz, 3H). LC-MS (ESI) m/z: 464[M+H]$^+$ Example 599

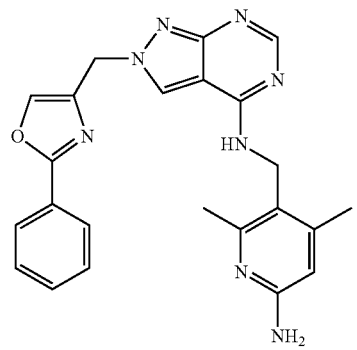 [SMILES: Cc1cc(N)nc(C)c1CNc1ncnc2nn(Cc3coc(-c4ccccc4)n3)cc12]

4,6-dimethyl-5-[([2-[(2-phenyl-1,3-oxazol-4-yl)methyl]-2H-pyrazolo[3,4-d]pyrimidin-4-yl]amino)methyl]pyridin-2-amine 4,6-dimethyl-5-[([2-[(2-phenyl-1,3-oxazol-4-yl)methyl]-2H-pyrazolo[3,4-d]pyrimidin-4-yl]amino)methyl]pyridin-2-amine was prepared in a similar manner as Example 335. $^1$H NMR (300 MHz, CD$_3$OD): δ 8.42 (s, 1H), 8.32 (s, 1H), 8.10 (s, 1H), 8.02-7.99 (m, 2H), 7.54-7.49 (m, 3H), 6.35 (s, 1H), 5.53 (s, 2H), 4.66 (s, 2H), 2.40 (s, 3H), 2.25 (s, 3H). MS (ESI), m/z 427[M+1]$^+$ Example 600

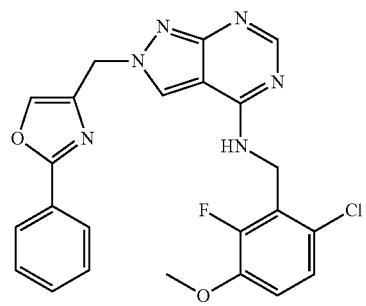 [SMILES: COc1ccc(Cl)c(CNc2ncnc3nn(Cc4coc(-c5ccccc5)n4)cc23)c1F]

N-[(6-chloro-2-fluoro-3-methoxyphenyl)methyl]-2-[(2-phenyl-1,3-oxazol-4-yl)methyl]-2H-pyrazolo[3,4-d]pyrimidin-4-amine N-[(6-chloro-2-fluoro-3-methoxyphenyl)methyl]-2-[(2-phenyl-1,3-oxazol-4-yl)methyl]-2H-pyrazolo[3,4-d]pyrimidin-4-amine was prepared in a similar manner as Example 335. 1H-NMR (CD$_3$OD): δ 8.42 (s, 1H), 8.33 (s, 1H), 8.10 (s, 1H), 8.02 (d, J=8.5 Hz, 2H), 7.54-7.47 (m, 3H), 7.25-7.22 (m, 1H), 7.14-7.08 (m, 1H), 5.54 (s, 2H), 4.89 (s, 2H), 3.89 (s, 3H). MS (ESI): m/z 465[M+1]$^+$

Example 601

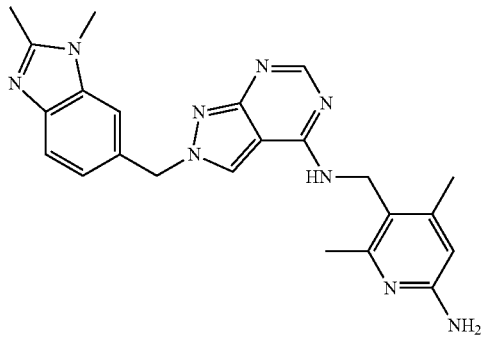 [SMILES: Cc1cc(N)nc(C)c1CNc1ncnc2nn(Cc3ccc4nc(C)n(C)c4c3)cc12]

N-((6-amino-2,4-dimethylpyridin-3-yl)methyl)-2-((2,3-dimethyl-3H-benzo[d]imidazol-5-yl)methyl)-2H-pyrazolo[3,4-d]pyrimidin-4-amine N-((6-amino-2,4-dimethylpyridin-3-yl)methyl)-2-((2,3-dimethyl-3H-benzo[d]imidazol-5-yl)methyl)-2H-pyrazolo[3,4-d]pyrimidin-4-amine was prepared in a similar manner as Example 468. $^1$H NMR (300 MHz, MeOD): δ 8.32 (s, 1H), 8.24 (s, 1H), 7.56 (d, J=8.2 Hz, 2H), 7.27 (d, J=8.2 Hz, 1H), 6.33 (s, 1H), 5.65 (s, 2H), 4.64 (s, 2H), 3.78 (s, 3H), 2.59 (s, 3H), 2.35 (s, 3H), 2.25 (s, 3H) ppm. MS (ESI) m/z: 428 [M+H]$^+$

Example 602

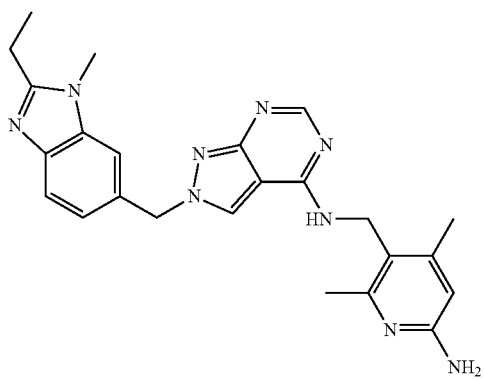 [SMILES: CCc1nc2ccc(Cn3cc4c(NCc5c(C)cc(N)nc5C)ncnc4n3)cc2n1C]

5-[([2-[(2-ethyl-1-methyl-1H-1,3-benzodiazol-6-yl)methyl]-2H-pyrazolo[3,4-d]pyrimidin-4-yl]amino)methyl]-4,6-dimethylpyridin-2-amine 5-[([2-[(2-ethyl-1-methyl-1H-1,3-benzodiazol-6-yl)methyl]-2H-pyrazolo[3,4-d]pyrimidin-4-yl]amino) methyl]-4,6-dimethylpyridin-2-amine was prepared in a similar manner as Example 468. $^1$H NMR (300 MHz, CD$_3$OD): δ 8.32 (s, 1H), 8.23 (s, 1H), 7.59-7.55 (m, 2H), 7.27 (d, J=8.4 Hz, 1H), 6.35 (s, 1H), 5.65 (s, 2H), 4.64 (s, 2H), 3.78 (s, 3H), 2.96 (q, J=7.5 Hz, 2H), 2.39 (s, 3H), 2.26 (s, 3H), 1.40 (t, J=7.5 Hz, 3H). LC-MS (ESI) m/z: calculated for C$_{24}$H$_{27}$N$_9$: 441.24. found: 442 [M+H]$^+$.

Example 603

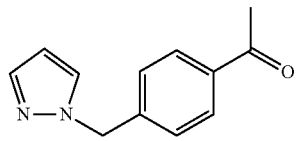

1-(4-((1H-pyrazol-1-yl)methyl)phenyl)ethan-1-one

1-[4-(bromomethyl)phenyl]ethan-1-one (482.00 mg; 2.26 mmol; 1.00 eq.) was dissolved in acetonitrile (7 ml). 1H-pyrazole (200.20 mg; 2.94 mmol; 1.30 eq.) and potassium carbonate (0.94 g; 6.79 mmol; 3.00 eq.) were added and the mixture was stirred in a heat block at 50° C. After 7 h the reaction was stirred at 25° C. for 15 h more. The mixture was then filtered, concentrated and a portion of the residue purified by silica gel chromatography (ethyl acetate/hexanes gradient) to give 1-(4-((1H-pyrazol-1-yl)methyl)phenyl)ethan-1-one (0.27 g). MS (M+H)$^+$ found for C$_{12}$H$_{12}$N$_2$O: 201.0.

Example 604

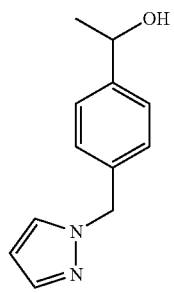

1-(4-((1H-pyrazol-1-yl)methyl)phenyl)ethan-1-ol

1-[4-(1H-pyrazol-1-ylmethyl)phenyl]ethan-1-one (0.27 g; 1.35 mmol; 1.00 eq.)(Example 603) was dissolved in THF (10 ml). The solution was stirred in an ice bath and sodium borohydride (51.01 mg; 1.35 mmol; 1.00 eq.) was added followed by dry methanol (2 ml) slowly. After 1.5 h of stirring at 25° C., the reaction was diluted with ethyl acetate (100 ml), washed with water (3×30 ml) and washed with brine (20 ml). The solution was dried over sodium sulfate, evaporated to give 1-(4-((1H-pyrazol-1-yl)methyl)phenyl)ethan-1-ol (0.25 g) as an oily residue which was used directly in the next step. MS (M+H)$^+$ found for C$_{12}$H$_{14}$N$_2$O: 203.1.

Example 605

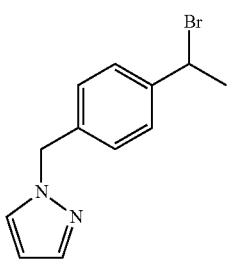

1-(4-(1-bromoethyl)benzyl)-1H-pyrazole

1-[4-(1H-pyrazol-1-ylmethyl)phenyl]ethan-1-ol (0.25 g; 1.24 mmol; 1.00 eq.)(Example 604) was dissolved in DCM (5 ml) and the reaction was stirred in an ice bath. Phosphorous tribromide (0.12 ml; 1.24 mmol; 1.00 eq.) was added dropwise and the mixture was stirred at 20° C. for 6 h. More phosphorous tribromide (0.1 ml; 1.03 mmol; 0.83 eq.) and DCM (3 ml) were added. The reaction was stirred for 18 h more at which point it was diluted with sodium bicarbonate solution (20 ml) and more DCM (100 ml). The phases were separated, the aqueous phase was extracted with DCM (50 ml), and the combined organic phases were dried over sodium sulfate. After evaporation, an oily residue containing 1-(4-(1-bromoethyl)benzyl)-1H-pyrazole (0.31 g) was obtained and used directly in the next step. MS (M+H)+ found for $C_{12}H_{13}BrN_2$: 196.9, 198.8.

Example 606

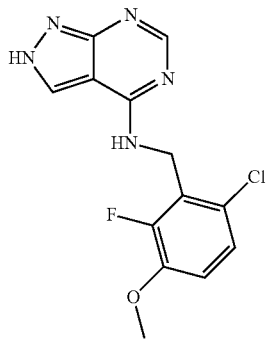 [SMILES: COc1ccc(Cl)c(CNc2ncnc3n[nH]cc23)c1F]

N-(6-chloro-2-fluoro-3-methoxybenzyl)-2H-pyrazolo[3,4-d]pyrimidin-4-amine 4-chloro-2H-pyrazolo[3,4-d]pyrimidine (500.00 mg; 3.24 mmol; 1.00 eq.)(Example 605) was suspended in 1-butanol (15 ml) and Hunig's base-ethylbis(propan-2-yl)amine (0.59 ml; 3.40 mmol; 1.05 eq.) (6-chloro-2-fluoro-3-methoxyphenyl)methanamine (644.08 mg; 3.40 mmol; 1.05 eq.) was then added and the mixture was heated in a microwave reactor at 100° C. for 40 m. The reaction was evaporated and partly dissolved in dichloromethane (90 ml) and methanol (10 ml). Solids were filtered, the solution was evaporated and purified by silica gel chromatography (ethyl acetate/hexanes gradient) to give, after combining with the solid above, N-(6-chloro-2-fluoro-3-methoxybenzyl)-2H-pyrazolo[3,4-d]pyrimidin-4-amine (0.77 g) as a white solid. MS (M+H)+ found for $C_{13}H_{11}ClFN_5O$: 308.1.

Example 607

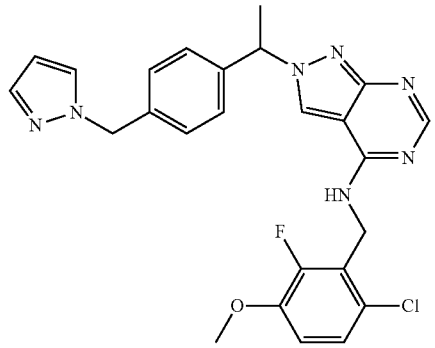 [SMILES: COc1ccc(Cl)c(CNc2ncnc3nn(C(C)c4ccc(Cn5cccn5)cc4)cc23)c1F]

Example 608

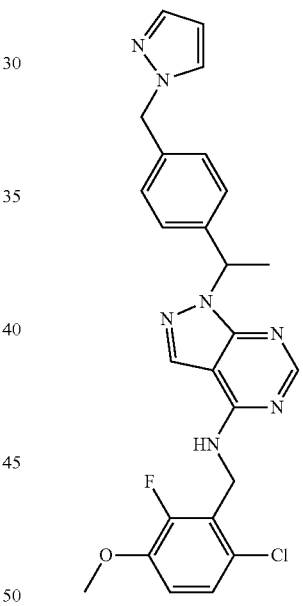

2-(1-(4-((1H-pyrazol-1-yl)methyl)phenyl)ethyl)-N-(6-chloro-2-fluoro-3-methoxybenzyl)-2H-pyrazolo[3,4-d]pyrimidin-4-amine and 1-(1-(4-((1H-pyrazol-1-yl)methyl)phenyl)ethyl)-N-(6-chloro-2-fluoro-3-methoxybenzyl)-1H-pyrazolo[3,4-d]pyrimidin-4-amine 1-{[4-(1-bromoethyl)phenyl]methyl}-1H-pyrazole (236.96 mg; 0.54 mmol; 1.10 eq.) and N-[(6-chloro-2-fluoro-3-methoxyphenyl)methyl]-1H-pyrazolo[3,4-d]pyrimidin-4-amine (150.00 mg; 0.49 mmol; 1.00 eq.)(Example 606) were combined in acetonitrile (1.5 ml). Potassium carbonate (134.54 mg; 0.97 mmol; 2.00 eq.) was added and the mixture stirred at 60° C. for 17 h. The reaction mixture Example 607 was filtered and the solid was washed with ethyl acetate. The solvent was evaporated and the residue purified by reverse phase chromatography (acetonitrile gradient with 0.1% aqueous formic acid, Waters XSelect CSH column) to give 2-(1-(4-((1H-pyrazol-1-yl)methyl)phenyl)ethyl)-N-(6-chloro-2-fluoro-3-methoxybenzyl)-2H-pyrazolo[3,4-d]pyrimidin-4-amine (16 mg) as a white solid and 1-(1-(4-((1H-pyrazol-1-yl)methyl)phenyl)ethyl)-N-(6-chloro-2-fluoro-3-methoxybenzyl)-1H-pyrazolo[3,4-d]pyrimidin-4-amine (71 mg) as a white solid.

Example 607

$^1$H NMR (400 MHz, CD$_3$OD) δ 8.39-8.19 (m, 2H), 7.66 (d, J=2.3 Hz, 1H), 7.49 (d, J=2.0 Hz, 1H), 7.30 (d, J=7.9 Hz, 2H), 7.24-7.15 (m, 3H), 7.10 (t, J=8.9 Hz, 1H), 6.30 (t, J=2.1 Hz, 1H), 5.74 (q, J=7.0 Hz, 1H), 5.32 (s, 2H), 3.88 (s, 3H), 1.93 (d, J=7.0 Hz, 3H). MS (M+H)$^+$ found for C$_{25}$H$_{23}$ClFN$_7$O: 492.2.

Example 608

$^1$H NMR (400 MHz, CD$_3$OD) δ 8.29 (s, 1H), 8.08 (s, 1H), 7.64-7.59 (m, 1H), 7.47 (d, J=2.0 Hz, 1H), 7.31-7.24 (m, 2H), 7.23-7.18 (m, 1H), 7.15-7.03 (m, 3H), 6.31-6.25 (m, 1H), 6.06 (q, J=7.1 Hz, 1H), 5.28 (s, 2H), 4.92-4.87 (m, 2H), 3.86 (s, 3H), 1.90 (d, J=7.1 Hz, 3H). MS (M+H)$^+$ found for C$_{25}$H$_{23}$ClFN$_7$O: 492.2.

Example 609

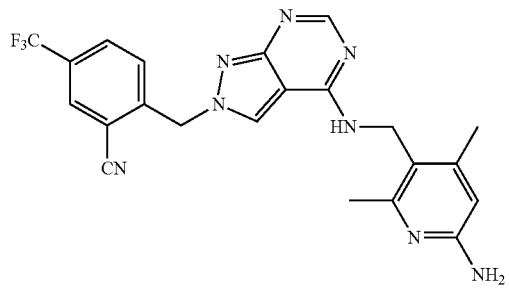 [SMILES: Cc1cc(N)nc(C)c1CNc1ncnc2nn(Cc3ccc(C(F)(F)F)cc3C#N)cc12]

2-[(4-[[(6-amino-2,4-dimethylpyridin-3-yl)methyl]amino]-2H-pyrazolo[3,4-d]pyrimidin-2-yl)methyl]-5-(trifluoromethyl)benzonitrile 2-[(4-[[(6-amino-2,4-dimethylpyridin-3-yl)methyl]amino]-2H-pyrazolo[3,4-d]pyrimidin-2-yl)methyl]-5-(trifluoromethyl)benzonitrile was prepared in a similar manner as Example 468. $^1$H NMR (300 MHz, DMSO-d$_6$): δ 8.52 (s, 1H), 8.43 (s, 1H), 8.28 (s, 1H), 8.16 (br, 1H), 8.10 (d, J=8.1 Hz, 2H), 7.58 (d, J=8.1 Hz, 1H), 6.20 (s, 1H), 5.84 (br, 4H), 4.53 (d, J=4.2 Hz, 2H), 2.33 (s, 3H), 2.19 (s, 3H). MS (ESI) m/z 453 [M+H]$^+$ Example 610

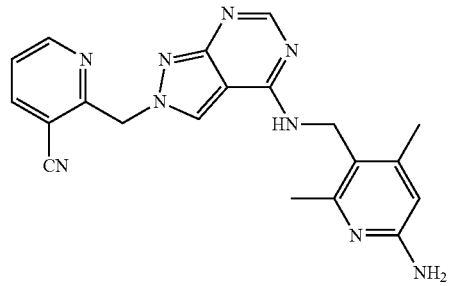 [SMILES: Cc1cc(N)nc(C)c1CNc1ncnc2nn(Cc3ncccc3C#N)cc12]

2-[(4-[[(6-amino-2,4-dimethylpyridin-3-yl)methyl]amino]-2H-pyrazolo[3,4-d]pyrimidin-2-yl)methyl]pyridine-3-carbonitrile 2-[(4-[[(6-amino-2,4-dimethylpyridin-3-yl)methyl]amino]-2H-pyrazolo[3,4-d]pyrimidin-2-yl)methyl]pyridine-3-carbonitrile was prepared in a similar manner as Example 468. $^1$H NMR (300 MHz, DMSO): δ 8.78 (dd, J=4.8 Hz, 1.5 Hz, 1H), 8.55 (s, 1H), 8.41 (dd, J=7.8 Hz, 1.5 Hz, 1H), 8.26 (s, 1H), 8.10 (br, 1H), 7.60 (dd, J=7.8 Hz, 4.8 Hz, 1H), 6.17 (s, 1H), 5.85 (s, 2H), 5.71 (s, 2H), 4.54 (d, J=4.2 Hz, 2H), 2.32 (s, 3H), 2.18 (s, 3H). MS (ESI) m/z 386 [M+H]$^+$.

Example 611

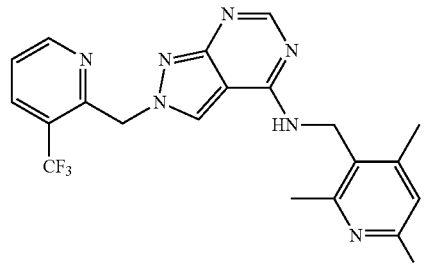

4,6-dimethyl-5-[[(2-[[3-(trifluoromethyl)pyridin-2-yl]methyl]-2H-pyrazolo[3,4-d]pyrimidin-4-yl)amino]methyl]pyridin-2-amine 4,6-dimethyl-5-[[(2-[[3-(trifluoromethyl)pyridin-2-yl]methyl]-2H-pyrazolo[3,4-d]pyrimidin-4-yl)amino]methyl]pyridin-2-amine was prepared in a similar manner as Example 468. $^1$H NMR (300 MHz, CD$_3$OD): δ 8.70 (d, J=4.8 Hz, 1H), 8.42 (s, 1H), 8.32 (s, 1H), 8.21 (d, J=7.8 Hz, 1H), 7.55 (dd, J=7.8 Hz, 4.8 Hz, 1H), 6.37 (s, 1H), 5.87 (s, 2H), 4.69 (s, 2H), 2.43 (s, 3H), 2.30 (s, 3H). MS (ESI) m/z 429 [M+H]$^+$.

Example 612

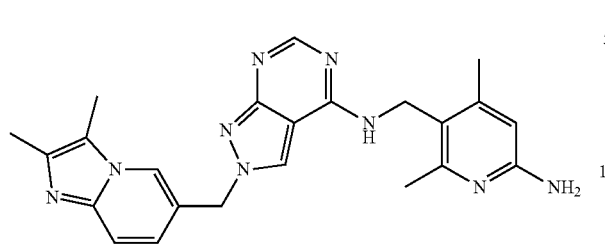

5-([[2-([2,3-dimethylimidazo[1,2-a]pyridin-6-yl]
methyl)-2H-pyrazolo[3,4-d]pyrimidin-4-yl]amino]
methyl)-4,6-dimethylpyridin-2-amine 5-([[2-([2,3-dimethylimidazo[1,2-a]pyridin-6-yl]methyl)-2H-pyrazolo[3,4-d]pyrimidin-4-yl]amino]methyl)-4,6-dimethylpyridin-2-amine was prepared in a similar manner as Example 431. $^1$H NMR (300 MHz, CD$_3$OD): δ 8.40-8.34 (m, 3H), 7.43 (d, J=9.3 Hz, 1H), 7.24 (d, J=9.3 Hz, 1H), 6.35 (s, 1H), 5.59 (s, 2H), 4.66 (s, 2H), 2.47 (s, 3H), 2.39 (s, 6H), 2.27 (s, 3H). LC-MS (ESI) m/z: calculated for C$_{23}$H$_{25}$N$_9$: 427.22. found: 428 [M+H]$^+$.

Example 613

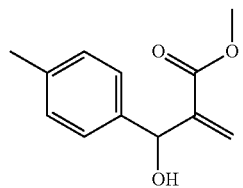

2-(hydroxy(p-tolyl)methyl)acrylate

Into a 100-mL 3-necked round-bottom flask purged and maintained with an inert atmosphere of nitrogen, was placed a mixture of 4-methylbenzaldehyde (6.00 g, 49.94 mmol, 1.00 equiv), methyl prop-2-enoate (12.90 g, 149.84 mmol, 1.50 equiv) and DABCO (1.12 g, 10 mmol, 0.20 equiv). The resulted solution was stirred for 5 d at room temperature. The resulted solution was diluted with 200 mL of EA and washed with 2×200 mL of brine. The organic phase was dried over anhydrous sodium sulfate and concentrated under vacuum. The residue was purified by silica gel column chromatography eluted with ethyl acetate and petroleum ether (1:3). This resulted in 7.01 g (68%) of methyl 2-(hydroxy(p-tolyl)methyl)acrylate as white solid. $^1$H NMR (300 MHz, CDCl$_3$): δ 7.25 (d, J=7.8 Hz, 2H), 7.14 (d, J=7.8 Hz, 2H), 6.32 (s, 1H), 5.85 (s, 1H), 5.53 (s, 1H), 3.71 (s, 3H), 2.33 (s, 3H).

Example 614

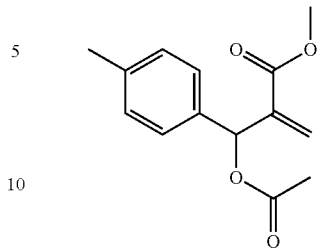

methyl 2-(acetoxy(p-tolyl)methyl)acrylate

Into a 250-mL 3-necked round-bottom flask purged and maintained with an inert atmosphere of nitrogen, was placed a mixture of methyl 2-(hydroxy(p-tolyl)methyl)acrylate (6.00 g, 29.09 mmol, 1.00 equiv)(Example 613) in dichloromethane (50 mL) and pyridine (6.87 g, 86.85 mmol, 3.00 equiv) with stirring at 0° C., to which was added a solution of acetyl chloride (4.50 g, 57.33 mmol, 2.00 equiv) in dichloromethane (50 mL) dropwise. The resulted solution was stirred for 3 h at room temperature. The reaction solution was added 1M HCl aqueous solution at 0° C. It was extracted with 3×50 mL of EA, washed with 2×100 mL of saturated NaHCO$_3$ aqueous solution. The resulted mixture was dried over anhydrous sodium sulfate and concentrated under vacuum. This resulted in 4.50 g (62%) of methyl 2-(acetoxy(p-tolyl)methyl)acrylate as yellow oil. $^1$H NMR (300 MHz, DMSO-d$_6$): δ 7.16-7.24 (m, 4H), 6.48 (s, 1H), 6.32 (s, 1H), 5.89 (s, 1H), 3.66 (s, 3H), 2.29 (s, 3H), 2.08 (s, 3H).

Example 615

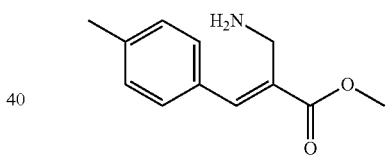

(E)-methyl 2-(aminomethyl)-3-p-tolylacrylate Into a 250-mL pressure tank reactor was placed a mixture of 7 M NH$_3$ methanol solution (150 mL) and methyl 2-(acetoxy(p-tolyl)methyl)acrylate (1.5 g, 6.04 mmol, 1.00 equiv)(Example 614). To the above mixture was bubbled ammonia (gas) while stirred for 1 h at room temperature. The reaction mixture was concentrated under vacuum. The reaction protocol was repeated for 4 times. This resulted in 5.00 g (crude) of (E)-methyl 2-(aminomethyl)-3-p-tolylacrylate as yellow oil. MS (ESI) m/z 206 [M+H]$^+$.

Example 616

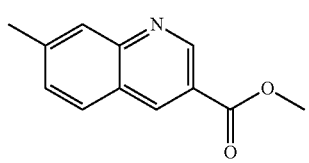

methyl 7-methylquinoline-3-carboxylate

Into a 500-mL 3-necked round-bottom flask purged and maintained with an inert atmosphere of nitrogen, was placed a mixture of (E)-methyl 2-(aminomethyl)-3-p-tolylacrylate (5 g, 24.36 mmol, 1.00 equiv)(Example 615), chloroform (300 mL) and I$_2$ (19.05 g, 3.00 equiv). The resulted solution was stirred for 10 min at room temperature. Potassium carbonate (10.35 g, 74.89 mmol, 3.00 equiv) was added to the reaction mixture. The reaction solution was stirred overnight at room temperature. The reaction was then quenched by the addition of saturated Na$_2$S$_2$O$_3$ aqueous solution (200 mL). Then it was extracted with 3×50 mL of CHCl$_3$, washed with 1×200 mL of brine, dried over anhydrous sodium sulfate and concentrated under vacuum. The residue was purified by silica gel column chromatography eluted with ethyl acetate and petroleum ether (1:3). This resulted in 600 mg (12%) of methyl 7-methylquinoline-3-carboxylate as yellow solid. MS (ESI) m/z 202 [M+H]$^+$.

Example 617

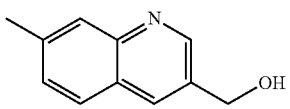

(7-methylquinolin-3-yl)methanol

Into a 100-mL 3-necked round-bottom flask purged and maintained with an inert atmosphere of nitrogen, was placed a mixture of methyl 7-methylquinoline-3-carboxylate (600 mg, 2.98 mmol, 1.00 equiv)(Example 616) in tetrahydrofuran (15 mL) with stirring at 0° C., to which was added LiAlH$_4$ (228 mg, 6.01 mmol, 2.00 equiv) in several batches at 0° C. The resulted solution was stirred for 2 h at room temperature. The reaction was then quenched by the addition of 15 mL of water/ice. The solids were filtered out. The filtrate was extracted with EA (20 mL×3), washed with 1×50 mL of brine, dried over anhydrous sodium sulfate and concentrated under vacuum. The residue was purified by silica gel column chromatography eluted with ethyl acetate and petroleum ether (1:1). This resulted in 200 mg (39%) of (7-methylquinolin-3-yl)methanol as yellow solid. MS (ESI) m/z 174 [M+H]$^+$.

Example 618

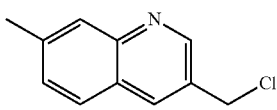

3-(chloromethyl)-7-methylquinoline

Into a 50-mL round-bottom flask purged and maintained with an inert atmosphere of nitrogen, was placed a mixture of (7-methylquinolin-3-yl)methanol (200 mg, 1.15 mmol, 1.00 equiv)(Example 617) in dichloromethane (15 mL) with stirring at 0° C., to which was added thionyl chloride (415 mg, 3.00 equiv). The resulted solution was stirred for 2 h at room temperature. The resulted mixture was concentrated under vacuum. This resulted in 180 mg (81%) of 3-(chloromethyl)-7-methylquinoline as yellow solid. MS (ESI) m/z 192 [M+H]$^+$.

Example 619

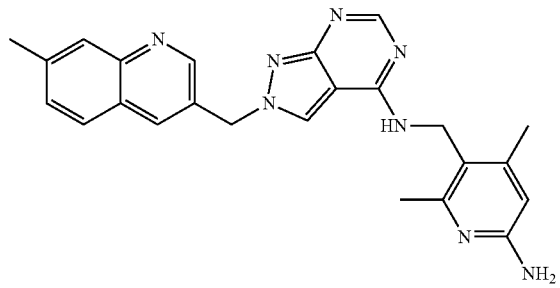

N-((6-amino-2,4-dimethylpyridin-3-yl)methyl)-2-((7-methylquinolin-3-yl)methyl)-2H-pyrazolo[3,4-d]pyrimidin-4-amine N-((6-amino-2,4-dimethylpyridin-3-yl)methyl)-2-((7-methylquinolin-3-yl)methyl)-2H-pyrazolo[3,4-d]pyrimidin-4-amine was prepared in a similar manner as Example 468 using Example 618. $^1$H NMR (300 MHz, DMSO-d): δ 8.88 (br, 1H), 8.42 (s, 1H), 8.26 (br, 2H), 8.00 (br, 1H), 7.89 (d, J=8.4 Hz, 1H), 7.83 (s, 1H), 7.47 (d, J=7.8 Hz, 1H), 6.14 (s, 1H), 5.75 (s, 2H), 5.69 (s, 2H), 4.50 (br, 2H), 2.29 (s, 3H), 2.15 (s, 3H). MS (ESI) m/z 425 [M+H]$^+$.

Example 620

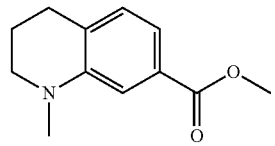

methyl 1-methyl-1,2,3,4-tetrahydroquinoline-7-carboxylate

Into a 100-mL 3-necked round-bottom flask purged and maintained with an inert atmosphere of nitrogen, was placed a mixture of methyl 1,2,3,4-tetrahydroquinoline-7-carboxylate (700 mg, 3.66 mmol, 1.00 equiv) in tetrahydrofuran (30 mL) with stirring in at −20° C., to which was added 1 M LiHMDS tetrahydrofuran solution (5.5 mL, 5.49 mmol, 1.50 equiv) dropwise. Then, CH$_3$I (1.04 g, 7.33 mmol, 2.00 equiv) was then added to the reaction mixture. The resulted solution was stirred for 1 h at room temperature. The reaction was quenched with 20 mL of icy water. The resulted mixture was extracted with EA (30 mL×3). The organic phase was washed with 100 mL of brine, dried over anhydrous sodium sulfate and concentrated under vacuum. The residue was purified by silica gel column chromatography eluted with ethyl acetate and petroleum ether (1:3). This resulted in 500 mg (67%) of methyl 1-methyl-1,2,3,4-tetrahydroquinoline-7-carboxylate as yellow oil. MS (ESI) m/z 202 [M+H]$^+$.

Example 621

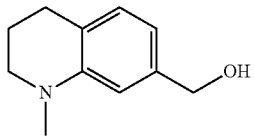

(1-methyl-1,2,3,4-tetrahydroquinolin-7-yl)methanol

Into a 100-mL 3-necked round-bottom flask purged and maintained with an inert atmosphere of nitrogen, was placed methyl 1-methyl-1,2,3,4-tetrahydroquinoline-7-carboxylate (620 mg, 3.02 mmol, 1.00 equiv) in tetrahydrofuran (10 mL) with stirring at 0° C., to which was added LiAlH$_4$ (230 mg, 6.06 mmol, 2.00 equiv) in several batches. The resulted solution was stirred for 2 h at room temperature. The reaction was then quenched with 10 mL of icy water. The solids were filtered out. The filtrate was extracted with EA (20 mL×3). The organic phase was washed with 1×50 mL of brine, dried over anhydrous sodium sulfate and concentrated under vacuum. The residue was purified by silica gel column chromatography eluted with ethyl acetate and petroleum ether (1:1). This resulted in 400 mg (75%) of (1-methyl-1,2,3,4-tetrahydroquinolin-7-yl)methanol as yellow solid. MS (ESI) m/z 178 [M+H]$^+$.

Example 622

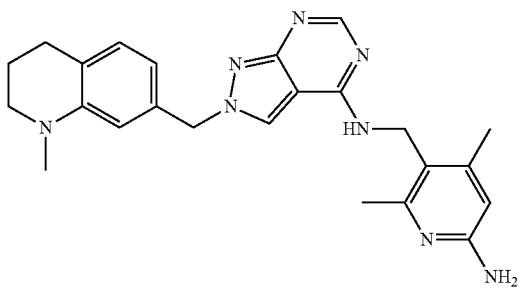 [SMILES: Cc1cc(N)nc(C)c1CNc1ncnc2nn(Cc3ccc4c(c3)N(C)CCC4)cc12]

N-((6-amino-2,4-dimethylpyridin-3-yl)methyl)-2-((1-methyl-1,2,3,4-tetrahydroquinolin-7-yl)methyl)-2H-pyrazolo[3,4-d]pyrimidin-4-amine N-((6-amino-2,4-dimethylpyridin-3-yl)methyl)-2-((1-methyl-1,2,3,4-tetrahydroquinolin-7-yl)methyl)-2H-pyrazolo[3,4-d]pyrimidin-4-amine was prepared in the same manner as Example 468 using Example 621. $^1$H NMR (300 MHz, DMSO-d): δ 8.25 (s, 2H), 7.94 (br, 1H), 6.86 (d, J=7.5 Hz, 1H), 6.60 (s, 1H), 6.48 (d, J=7.5 Hz, 1H), 6.15 (s, 1H), 5.69 (s, 2H), 5.35 (s, 2H), 4.50 (d, J=3.9 Hz, 2H), 3.17 (t, J=6.3 Hz, 2H), 2.80 (s, 3H), 2.65 (t, J=6.3 Hz, 2H), 2.28 (s, 3H), 2.14 (s, 3H), 1.93-1.73 (m, 2H). MS (ESI) m/z 429 [M+H]$^+$.

Example 623

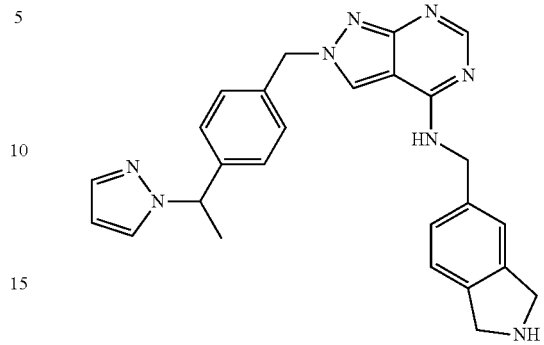

2-(4-(1-(1H-pyrazol-1-yl)ethyl)benzyl)-N-(isoindolin-5-ylmethyl)-2H-pyrazolo[3,4-d]pyrimidin-4-amine 2-(4-(1-(1H-pyrazol-1-yl)ethyl)benzyl)-N-(isoindolin-5-ylmethyl)-2H-pyrazolo[3,4-d]pyrimidin-4-amine was prepared similar to Example 275. $^1$H NMR (400 MHz, DMSO-d$_6$) δ 10.08 (s, 1H), 9.53 (s, 2H), 8.61 (s, 1H), 8.50 (s, 1H), 7.82 (d, J=2.2 Hz, 1H), 7.42 (d, J=1.8 Hz, 1H), 7.40-7.28 (m, 4H), 7.21 (d, J=8.1 Hz, 2H), 6.24 (t, J=2.0 Hz, 1H), 5.60 (d, J=11.5 Hz, 3H), 4.82 (d, J=5.9 Hz, 2H), 4.50-4.43 (m, 4H), 1.76 (d, J=7.1 Hz, 3H). MS (M+H)+ found for C$_{26}$H$_{26}$N$_8$: 451.2.

Example 624

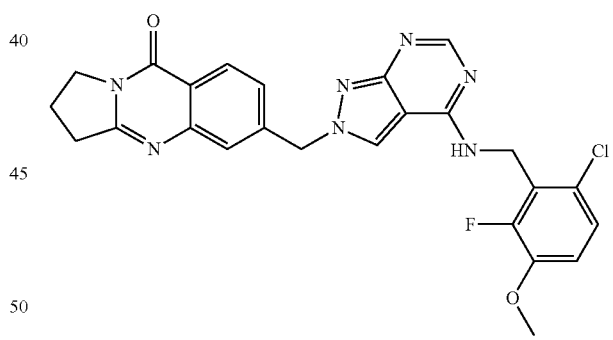

6-[(4-[[(6-chloro-2-fluoro-3-methoxyphenyl)methyl]amino]-2H-pyrazolo[3,4-d]pyrimidin-2-yl)methyl]-1H,2H,3H,9H-pyrrolo[2,1-b]quinazolin-9-one 6-[(4-[[(6-chloro-2-fluoro-3-methoxyphenyl)methyl]amino]-2H-pyrazolo[3,4-d]pyrimidin-2-yl)methyl]-1H,2H,3H,9H-pyrrolo[2,1-b]quinazolin-9-one was prepared in a similar manner as Example 563. $^1$H NMR (300 MHz, DMSO-d$_6$): δ 8.43 (s, 1H), 8.37 (br, 1H), 8.28 (s, 1H), 8.10 (d, J=8.4 Hz, 1H), 7.47 (s, 1H), 7.29-7.36 (m, 2H), 7.21 (t, J=9.0 Hz, 1H), 5.74 (s, 2H), 4.78 (br, 2H), 4.05 (t, J=8.4 Hz, 2H), 3.86 (s, 3H), 3.07 (t, J=8.4 Hz, 2H), 2.11-2.21 (m, 2H). MS (ESI) m/z 506 [M+H]$^+$

Example 625

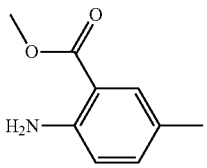

methyl 2-amino-5-methylbenzoate

Into a 250-mL 3-necked round-bottom flask, was placed a mixture of 2-amino-5-methylbenzoic acid (5.00 g, 33.08 mmol, 1.00 equiv) and methanol (50 mL) with stirring at 0° C., to which was added sulfurous dichloride (39.00 g, 327.81 mmol, 10.00 equiv) dropwise. The resulted solution was stirred overnight at 70° C. The cooled reaction solution was extracted with 3×50 mL of dichloromethane. The organic layers were combined and concentrated under vacuum. This resulted in 5.00 g (crude) of methyl 2-amino-5-methylbenzoate as off-white solid. MS (ESI) m/z 166 [M+H]$^+$

Example 626

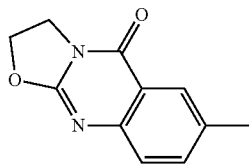

7-methyl-2H,3H,5H-[1,3]oxazolo[3,2-b]isoquinolin-5-one

Into a 100-mL round-bottom flask, was placed a mixture of methyl 2-amino-5-methylbenzoate (4.00 g, 24.21 mmol, 1.00 equiv)(Example 625), ClCH$_2$CH$_2$Cl (30 mL) and 1-chloro-2-isocyanatoethane (3.82 g, 36.20 mmol, 1.50 equiv), to which was added triethylamine (3.67 g, 36.27 mmol, 1.50 equiv) with stirring. The resulted solution was stirred overnight at 100° C. The cooled reaction mixture was concentrated under vacuum and diluted with 50 mL of H$_2$O. The resulted solution was extracted with 3×50 mL of dichloromethane. The organic layers were combined and concentrated under vacuum. The residue was purified by silica gel column chromatography eluted with dichloromethane and tetrahydrofuran (10:1). This resulted in 2.50 g (51%) of 7-methyl-2H,3H,5H-[1,3]oxazolo[3,2-b]isoquinolin-5-one as off-white solid. MS (ESI) m/z 203 [M+H]$^+$

Example 627

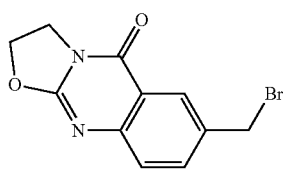 [SMILES: O=c1c2cc(CBr)ccc2nc2n1CCO2]

7-(bromomethyl)-2H,3H,5H-[1,3]oxazolo[2,3-b]quinazolin-5-one

Into a 100-mL round-bottom flask, was placed a mixture of 7-methyl-2H,3H,5H-[1,3]oxazolo[2,3-b]quinazolin-5-one (2.0 g, 9.89 mmol, 1.00 equiv)(Example 626), NBS (2.11 g, 11.86 mmol, 1.20 equiv), AlBN (325 mg, 1.98 mmol, 0.20 equiv) and CCl$_4$ (20 mL). The resulted solution was stirred for 4 h at 80° C. The reaction mixture was concentrated under vacuum. The residue was purified by silica gel column chromatography eluted with dichloromethane and ethyl acetate (20:1). This resulted in 408 mg (15%) of 7-(bromomethyl)-2H,3H,5H-[1,3]oxazolo[2,3-b]quinazolin-5-one as light yellow solid. MS (ESI) m/z 281 [M+H]$^+$

Example 628

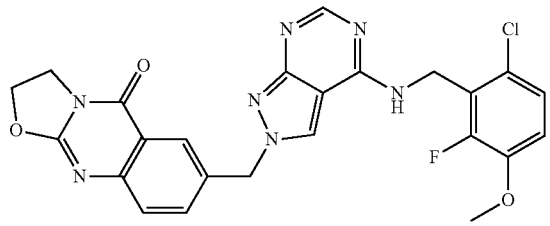 [SMILES: COc1ccc(Cl)c(CNc2ncnc3nn(Cc4ccc5nc6n(c(=O)c5c4)CCO6)cc23)c1F]

7-[(4-[[(6-chloro-2-fluoro-3-methoxyphenyl)methyl]amino]-2H-pyrazolo[3,4-d]pyrimidin-2-yl)methyl]-2H,3H,5H-[1,3]oxazolo[2,3-b]quinazolin-5-one 7-[(4-[[(6-chloro-2-fluoro-3-methoxyphenyl)methyl]amino]-2H-pyrazolo[3,4-d]pyrimidin-2-yl)methyl]-2H,3H,5H-[1,3]oxazolo[2,3-b]quinazolin-5-one was prepared in a similar manner as Example 563 using Example 627. $^1$H NMR (300 MHz, DMSO-d): δ 8.38 (br, 2H), 8.27 (s, 1H), 8.04 (s, 1H), 7.68 (d, J=8.1 Hz, 1H), 7.44 (d, J=8.1 Hz, 1H), 7.31 (d, J=9.3 Hz, 1H), 7.21 (br, 1H), 5.67 (s, 2H), 4.72-4.77 (m, 4H), 4.25 (br, 2H), 3.86 (s, 3H). MS (ESI) m/z 508 [M+H]$^+$

Example 629

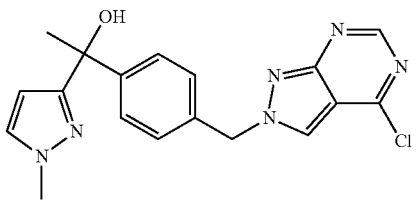 [SMILES: Cn1ccc(C(C)(O)c2ccc(Cn3cc4c(Cl)ncnc4n3)cc2)n1]

1-[4-([4-chloro-2H-pyrazolo[3,4-d]pyrimidin-2-yl]methyl)phenyl]-1-(1-methyl-1H-pyrazol-3-yl) ethan-1-ol Into a 20-mL 2-necked round-bottom flask purged and maintained with an inert atmosphere of nitrogen, was placed a solution of 3-bromo-1-methyl-1H-pyrazole (168 mg, 1.04 mmol, 3.00 equiv) in ether (5 mL) and then stirred −100° C., to which was added t-BuLi (0.65 mL, 1.6 M in hexane, 3.00 equiv) dropwise with stirring at −100° C. After the addition, the reaction solution was stirred for additional 0.5 h at −100° C. Thereafter to the reaction mixture was added a solution of 1-[4-([4-chloro-2H-pyrazolo[3,4-d]pyrimidin-2-yl]methyl)phenyl]ethan-1-one (100 mg, 0.35 mmol, 1.00 equiv) in ether (1 mL) dropwise with stirring at −100° C. The resulted solution was allowed to react with stirring for 2 h −100° C. The reaction mixture was then quenched by the addition of 2 mL of water. After warmed to room temperature, the solution was extracted with 50 mL of ethyl acetate, washed with 15 mL of brine, dried over anhydrous sodium sulfate and concentrated under vacuum to give a residue. The crude was purified by silica gel column eluted with ethyl acetate/petroleum ether=1/2.

This resulted in 44 mg (34%) of 1-[4-([4-chloro-2H-pyrazolo[3,4-d]pyrimidin-2-yl]methyl)phenyl]-1-(1-methyl-1H-pyrazol-3-yl)ethan-1-ol as colorless oil. LC-MS (ESI) m/z: calculated for $C_{18}H_{17}ClN_6O$: 368.12. found: 369 $[M+H]^+$.

Example 630

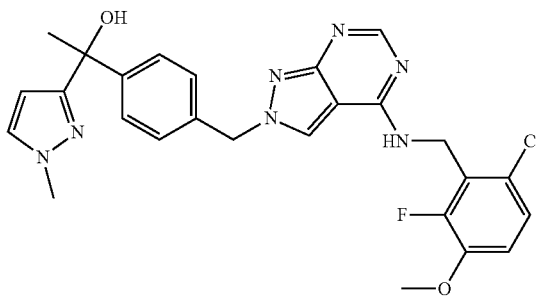 [SMILES: COc1ccc(Cl)c(CNc2ncnc3nn(Cc4ccc(C(C)(O)c5ccn(C)n5)cc4)cc23)c1F]

1-[4-[(4-[[(6-chloro-2-fluoro-3-methoxyphenyl)methyl]amino]-2H-pyrazolo[3,4-d]pyrimidin-2-yl)methyl]phenyl]-1-(1-methyl-1H-pyrazol-3-yl)ethan-1-ol 1-[4-[(4-[[(6-chloro-2-fluoro-3-methoxyphenyl)methyl]amino]-2H-pyrazolo[3,4-d]pyrimidin-2-yl)methyl]phenyl]-1-(1-methyl-1H-pyrazol-3-yl)ethan-1-ol was prepared in a similar manner as Example 594 using Example 629. $^1$H NMR (300 MHz, CDCl$_3$): δ 8.46 (s, 1H), 8.01 (s, 1H), 7.44 (d, J=8.1 Hz, 2H), 7.30-7.26 (m, 4H), 7.19 (dd, J=8.7 Hz, J=1.8 Hz, 1H), 6.92 (t, J=8.7, 1H), 6.09 (d, J=2.1 Hz, 1H), 5.56 (s, 2H), 5.03 (s, 2H), 3.90 (s, 3H), 3.86 (s, 3H), 3.13 (s, 1H), 1.86 (s, 3H). LC-MS (ESI) m/z: calculated for $C_{26}H_{25}ClFN_7O_2$: 521.17. found: 522 $[M+H]^+$.

Example 631

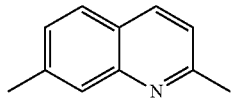

2,7-dimethylquinoline

Into a 500-mL pressure tank reactor purged and maintained with an inert atmosphere of nitrogen, was placed a mixture of 3-methylaniline (5.00 g, 46.66 mmol, 1.00 equiv), CH$_3$CN (200 mL), ethoxyethene (10.10 g, 140.07 mmol, 3.00 equiv), PdCl$_2$ (832 mg, 0.10 equiv) and 10% palladium on carbon (1.00 g). The resulted solution was stirred for 24 h at 80° C. The reaction was cooled to room temperature and the solids were filtered out. The filtrate was concentrated under vacuum. The residue was purified by silica gel column chromatography eluted with ethyl acetate and petroleum ether (1:10). This resulted in 3.20 g (44%) of 2,7-dimethylquinoline as yellow solid. MS (ESI) m/z 158 $[M+H]^+$.

Example 631, 632

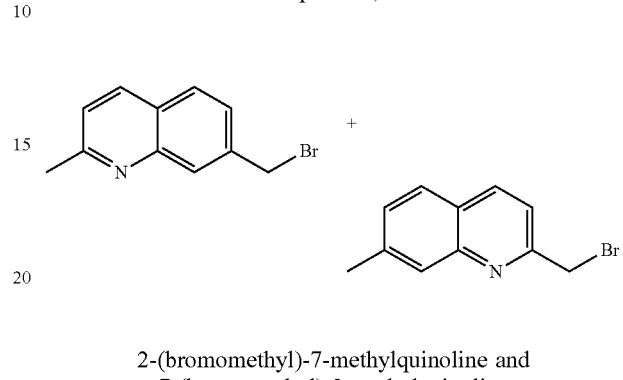

2-(bromomethyl)-7-methylquinoline and 7-(bromomethyl)-2-methylquinoline

Into a 100-mL 3-necked round-bottom flask purged and maintained with an inert atmosphere of nitrogen, was placed a mixture of 2,7-dimethylquinoline (1.10 g, 7.00 mmol, 1.00 equiv)(Example 630), CCl$_4$ (20 mL), NBS (1.50 g, 8.43 mmol, 1.20 equiv) and AlBN (230 mg, 1.40 mmol, 0.20 equiv). The resulted solution was stirred for 5 h at 80° C. The reaction was cooled to room temperature and the solids were filtered out. The filtrate was concentrated under vacuum. The residue was purified by silica gel column chromatography eluted with ethyl acetate and petroleum ether (1:5). This resulted in 500 mg (a mixture of two isomers) of 2-(bromomethyl)-7-methylquinoline and 7-(bromomethyl)-2-methylquinoline as yellow solids. MS (ESI) m/z 236 $[M+H]^+$.

Example 633

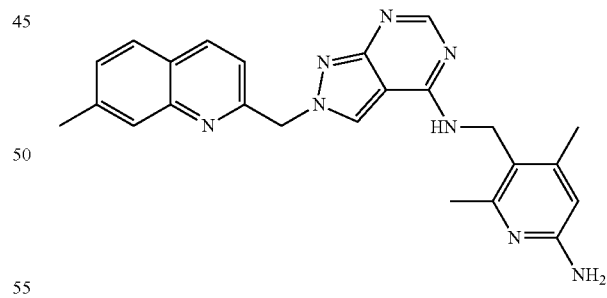

N-((6-amino-2,4-dimethylpyridin-3-yl)methyl)-2-((7-methylquinolin-2-yl)methyl)-2H-pyrazolo[3,4-d]pyrimidin-4-amine N-((6-amino-2,4-dimethylpyridin-3-yl)methyl)-2-((7-methylquinolin-2-yl)methyl)-2H-pyrazolo[3,4-d]pyrimidin-4-amine was prepared in a similar manner as Example 468 using example Example 632. $^1$H NMR (300 MHz, DMSO-d): δ 8.43 (d, J=8.7 Hz, 1H), 8.24 (d, J=9.0 Hz, 2H), 7.90-7.96 (m, 2H), 7.73 (t, J=8.7 Hz, 1H), 7.54 (d, J=6.9 Hz, 1H), 7.46 (d, J=8.4 Hz, 1H), 6.12 (s, 1H), 6.02 (s, 2H), 5.68 (s, 2H), 4.46 (d, J=3.6 Hz, 2H), 2.64 (s, 3H), 2.25 (s, 3H), 2.11 (s, 3H). MS (ESI) m/z 425 [M+H]⁺.

Example 634

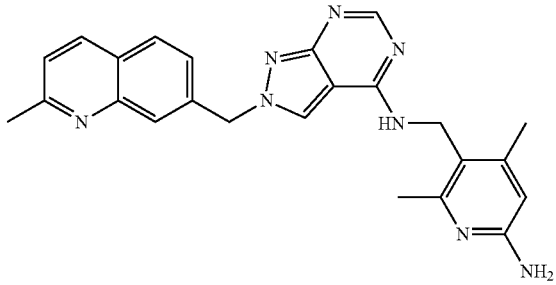 [SMILES: Cc1ccc2ccc(Cn3cc4c(NCc5c(C)cc(N)nc5C)ncnc4n3)cc2n1]

4,6-dimethyl-5-[([2-[(2-methylquinolin-7-yl)methyl]-2H-pyrazolo[3,4-d]pyrimidin-4-yl]amino)methyl]pyridin-2-amine 4,6-dimethyl-5-[([2-[(2-methylquinolin-7-yl)methyl]-2H-pyrazolo[3,4-d]pyrimidin-4-yl]amino)methyl]pyridin-2-amine was prepared in a similar manner as Example 633. ¹H NMR (300 MHz, DMSO-d₆): δ 8.41 (s, 1H), 8.22-8.27 (m, 2H), 8.00 (m, 1H), 7.92 (d, J=8.4 Hz, 1H), 7.80 (s, 1H), 7.43 (t, J=8.4 Hz, 2H), 6.14 (s, 1H), 5.75 (s, 2H), 5.69 (s, 2H), 4.50 (d, J=3.9 Hz, 2H), 2.63 (s, 3H), 2.28 (s, 3H), 2.14 (s, 3H). MS (ESI) m/z 425 [M+H]⁺.

Example 635

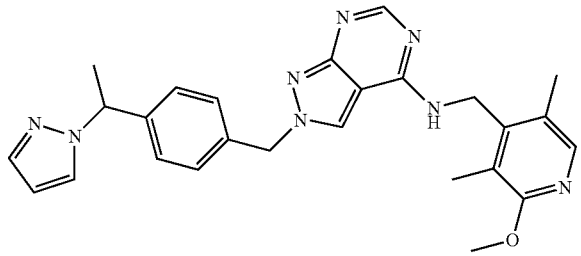 [SMILES: COc1ncc(C)c(CNc2ncnc3nn(Cc4ccc(C(C)n5cccn5)cc4)cc23)c1C]

N-[(2-methoxy-3,5-dimethylpyridin-4-yl)methyl]-2-([4-[1-(1H-pyrazol-1-yl)ethyl]phenyl]methyl)-2H-pyrazolo[3,4-d]pyrimidin-4-amine N-[(2-methoxy-3,5-dimethylpyridin-4-yl)methyl]-2-([4-[1-(1H-pyrazol-1-yl)ethyl]phenyl]methyl)-2H-pyrazolo[3,4-d]pyrimidin-4-amine was prepared in a similar way as Example 120. ¹H NMR (300 MHz, CD₃OD): δ 8.34 (s, 1H), 8.21 (s, 1H), 7.83 (s, 1H), 7.74 (s, 1H), 7.52 (s, 1H), 7.32 (d, J=8.0 Hz, 2H), 7.21 (d, J=8.0 Hz, 2H), 6.32 (s, 1H), 5.65-5.58 (m, 1H), 5.51 (s, 2H), 4.76 (s, 2H), 3.92 (s, 3H), 2.29 (s, 3H), 2.24 (s, 3H), 1.86 (d, J=7.2 Hz, 3H). MS (ESI) m/z 469 [M+H]⁺

Example 636

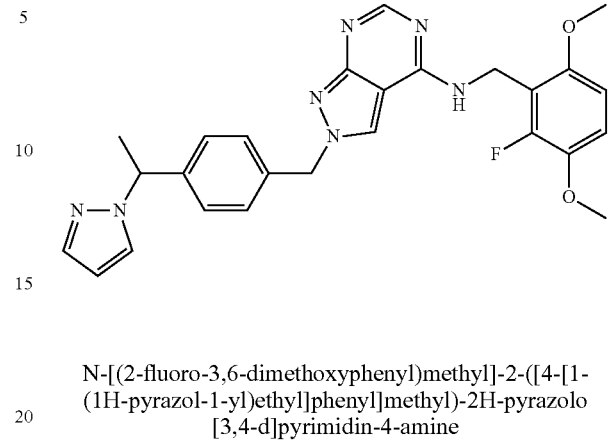

N-[(2-fluoro-3,6-dimethoxyphenyl)methyl]-2-([4-[1-(1H-pyrazol-1-yl)ethyl]phenyl]methyl)-2H-pyrazolo[3,4-d]pyrimidin-4-amine N-[(2-fluoro-3,6-dimethoxyphenyl)methyl]-2-([4-[1-(1H-pyrazol-1-yl)ethyl]phenyl]methyl)-2H-pyrazolo[3,4-d]pyrimidin-4-amine was prepared in a similar manner as Example 594. ¹H NMR (300 MHz, DMSO-d): δ 8.31 (s, 1H), 8.22 (s, 1H), 8.16 (t, J=3.6 Hz, 1H), 7.80 (d, J=1.8 Hz, 1H), 7.43 (d, J=1.5 Hz, 1H), 7.25 (d, J=8.1 Hz, 2H), 7.19 (d, J=8.1 Hz, 2H), 7.09 (t, J=9.3 Hz, 1H), 6.79 (dd, J=9.3 Hz, 1.8 Hz, 1H), 6.24 (t, J=1.8 Hz, 1H), 5.59 (q, J=6.9 Hz, 1H), 5.47 (s, 2H), 4.61 (d, J=3.3 Hz, 2H), 3.77 (s, 3H), 3.75 (s, 3H), 1.75 (d, J=7.2 Hz, 3H). MS (ESI) m/z 488 [M+H]⁺.

Example 637

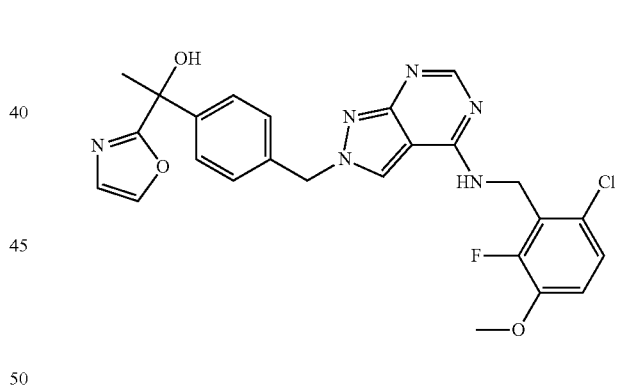

1-[4-[(4-[[(6-chloro-2-fluoro-3-methoxyphenyl)methyl]amino]-2H-pyrazolo[3,4-d]pyrimidin-2-yl)methyl]phenyl]-1-(1,3-oxazol-2-yl)ethan-1-ol 1-[4-[(4-[[(6-chloro-2-fluoro-3-methoxyphenyl)methyl]amino]-2H-pyrazolo[3,4-d]pyrimidin-2-yl)methyl]phenyl]-1-(1,3-oxazol-2-yl)ethan-1-ol Was prepared in a similar manner as Example 630. ¹H NMR (300 MHz, CDCl₃): δ 8.47 (s, 1H), 7.92 (s, 1H), 7.60 (s, 1H), 7.39 (d, J=8.4 Hz, 2H), 7.31 (d, J=8.4 Hz, 2H), 7.18 (dd, J=9.0 Hz, J=1.8 Hz, 1H), 7.07 (s, 1H), 6.91 (t, J=8.7 Hz, 1H), 5.57 (s, 2H), 5.03 (s, 2H), 3.90 (s, 3H), 3.45 (br, 1H), 1.93 (s, 3H). LC-MS (ESI) m/z: calculated for C₂₅H₂₂ClFN₆O₃: 508.14. found: 509 [M+H]⁺.

Example 638

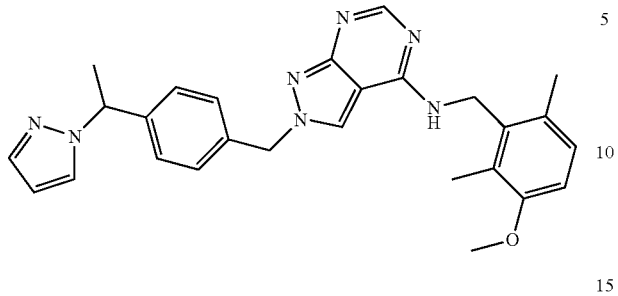

N-[(3-methoxy-2,6-dimethylphenyl)methyl]-2-([4-[1-(1H-pyrazol-1-yl)ethyl]phenyl]methyl)-2H-pyrazolo[3,4-d]pyrimidin-4-amine N-[(3-methoxy-2,6-dimethylphenyl)methyl]-2-([4-[1-(1H-pyrazol-1-yl)ethyl]phenyl]methyl)-2H-pyrazolo[3,4-d]pyrimidin-4-amine was prepared in a similar manner as Example 121. $^1$H NMR (300 MHz, DMSO): δ 8.32 (s, 1H), 8.27 (s, 1H), 8.04 (brs, 1H), 7.81 (d, J=2.1 Hz, 1H), 7.44 (s, 1H), 7.27 (d, J=8.1 Hz, 2H), 7.20 (d, J=8.1 Hz, 2H), 7.04 (d, J=8.4 Hz, 1H), 6.85 (d, J=8.1 Hz, 1H), 6.24 (d, J=1.8 Hz, 1H), 5.61-5.59 (m, 1H), 5.47 (s, 2H), 4.62 (d, J=4.2 Hz, 2H), 3.76 (s, 3H), 2.26 (s, 3H), 2.15 (s, 3H), 1.76 (d, J=7.2 Hz, 3H). MS (ESI) m/z 468 [M+H]$^+$

Example 639

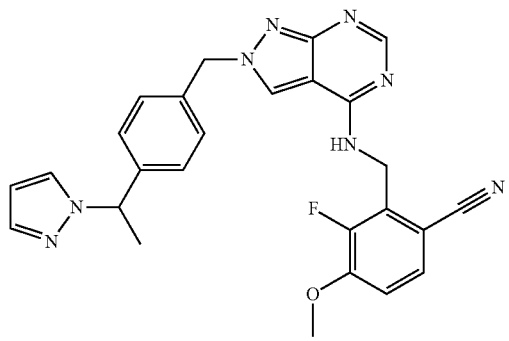

2-(((2-(4-(1-(1H-pyrazol-1-yl)ethyl)benzyl)-2H-pyrazolo[3,4-d]pyrimidin-4-yl)amino)methyl)-3-fluoro-4-methoxybenzonitrile 2-(4-(1-(1H-pyrazol-1-yl)ethyl)benzyl)-N-(6-chloro-2-fluoro-3-methoxybenzyl)-2H-pyrazolo[3,4-d]pyrimidin-4-amine (Example 594) (40.00 mg; 0.08 mmol; 1.00 eq.), Pd2(dba)3 (1.49 mg; 0.00 mmol; 0.02 eq.), 2-(dicyclohexylphosphino)-2',6'-dimethoxy-1,1'-biphenyl (1.34 mg; 0.00 mmol; 0.04 eq.), and zinc dicarbonitrile (5.73 mg; 0.05 mmol; 0.60 eq.) in N-Methyl-2-pyrrolidinone (2.00 ml) were placed in a microwave vial. Heated the reaction to 150° C. for 2 hours. Filtered thru a plug of Celite and purified by prep HPLC to afford 2-(((2-(4-(1-(1H-pyrazol-1-yl)ethyl)benzyl)-2H-pyrazolo[3,4-d]pyrimidin-4-yl)amino)methyl)-3-fluoro-4-methoxybenzonitrile (3 mgs; 7%). $^1$H NMR (400 MHz, DMSO-d$_6$) δ 8.55 (s, 1H), 8.25 (s, 1H), 7.80 (d, J=2.2 Hz, 1H), 7.41 (d, J=1.7 Hz, 1H), 7.35 (dt, J=7.8, 3.7 Hz, 3H), 7.22-7.15 (m, 3H), 6.22 (t, J=2.0 Hz, 1H), 5.62 (s, 2H), 5.57 (q, J=7.1 Hz, 1H), 5.41 (s, 2H), 3.94 (s, 3H), 1.75 (d, J=7.1 Hz, 3H). MS (M+H)+ found for C$_{26}$H$_{23}$FN$_8$O: 483.1.

Example 640

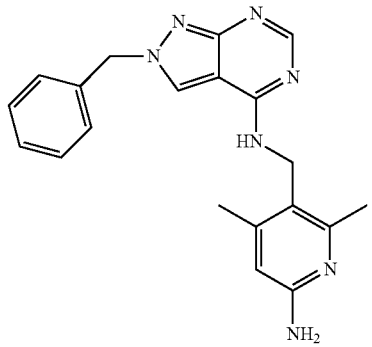 [SMILES: Cc1cc(N)nc(C)c1CNc1ncnc2nn(Cc3ccccc3)cc12]

N-((6-amino-2,4-dimethylpyridin-3-yl)methyl)-2-benzyl-2H-pyrazolo[3,4-d]pyrimidin-4-amine N-((6-amino-2,4-dimethylpyridin-3-yl)methyl)-2-benzyl-2H-pyrazolo[3,4-d]pyrimidin-4-amine was prepared in a similar manner as Example 468. $^1$H NMR (400 MHz, DMSO-d6) δ 8.32 (s, 1H), 8.23 (s, 1H), 8.21 (s, 1H), 7.96 (s, 1H), 7.39-7.27 (m, 5H), 6.12 (s, 1H), 5.67 (s, 2H), 5.50 (s, 2H), 4.48 (d, J=4.2 Hz, 2H), 2.27 (s, 4H), 2.13 (s, 3H). MS (M+H)$^+$ found for C$_{20}$H$_{21}$N$_7$: 360.

Example 641

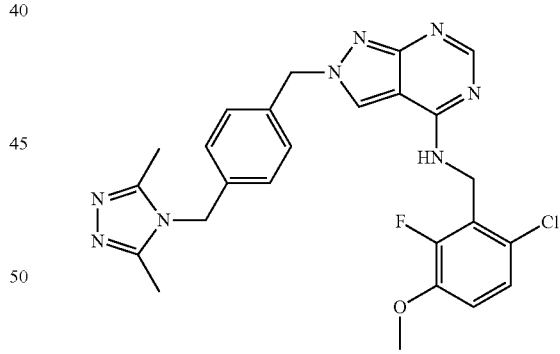

N-(6-chloro-2-fluoro-3-methoxybenzyl)-2-(4-((3,5-dimethyl-4H-1,2,4-triazol-4-yl)methyl)benzyl)-2H-pyrazolo[3,4-d]pyrimidin-4-amine N-(6-chloro-2-fluoro-3-methoxybenzyl)-2-(4-((3,5-dimethyl-4H-1,2,4-triazol-4-yl)methyl)benzyl)-2H-pyrazolo[3,4-d]pyrimidin-4-amine was prepared in a similar manner as Example 468. $^1$H NMR (400 MHz, DMSO-d6) δ 8.29 (s, 2H), 7.28 (dd, J=7.7, 1.9 Hz, 3H), 7.18 (dd, J=9.8, 8.4 Hz, 3H), 5.50 (s, 2H), 5.21 (s, 2H), 4.78-4.68 (m, 2H), 3.84 (s, 3H), 2.30 (s, 3H), 2.12 (s, 3H). MS (M+H)$^+$ found for C$_{25}$H$_{24}$ClFN$_8$O: 507/509.

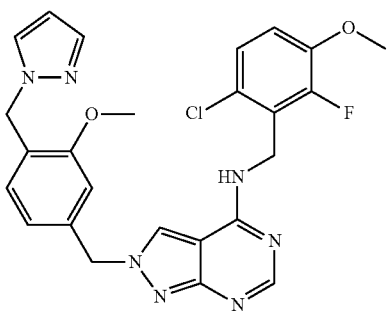 [SMILES: COc1cc(Cn2cc3c(NCc4c(Cl)ccc(OC)c4F)ncnc3n2)ccc1Cn1cccn1]

Preparation of 2-(4-((1H-pyrazol-1-yl)methyl)-3-methoxybenzyl)-N-(6-chloro-2-fluoro-3-methoxybenzyl)-2H-pyrazolo[3,4-d]pyrimidin-4-amine 2-(4-((1H-pyrazol-1-yl)methyl)-3-methoxybenzyl)-N-(6-chloro-2-fluoro-3-methoxybenzyl)-2H-pyrazolo[3,4-d]pyrimidin-4-amine was prepared in a similar manner as Example 504. $^1$H NMR (400 MHz, DMSO-d$_6$) δ 8.26 (d, J=14.6 Hz, 2H), 7.68 (d, J=2.2 Hz, 1H), 7.41 (dd, J=1.8, 0.7 Hz, 1H), 7.28 (dd, J=9.0, 1.6 Hz, 1H), 7.18 (t, J=8.9 Hz, 1H), 7.07 (d, J=1.2 Hz, 1H), 6.87-6.75 (m, 2H), 6.22 (t, J=2.1 Hz, 1H), 5.48 (s, 2H), 5.24 (s, 2H), 4.73 (dd, J=4.4, 2.2 Hz, 2H), 3.83 (s, 3H), 3.78 (s, 3H). MS (M+H)+ found for C$_{25}$H$_{23}$ClFN$_7$O$_2$: 507.6.

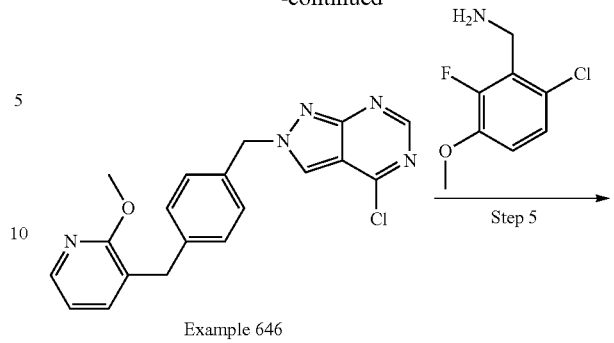

Example 646

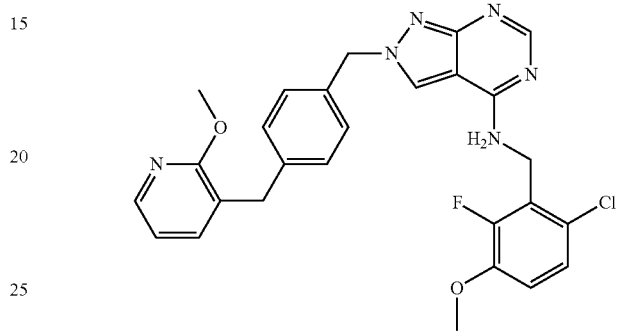

Example 647

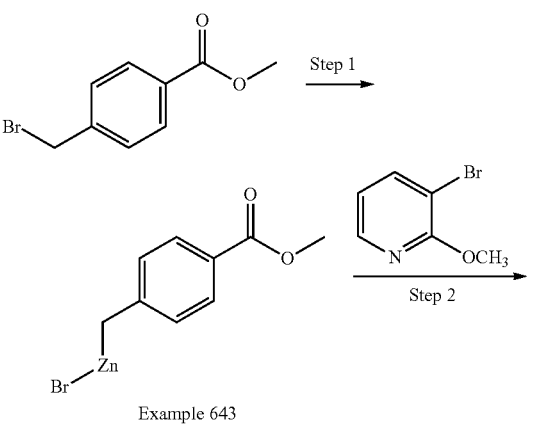

Example 643

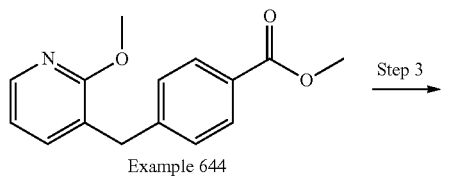

Example 644

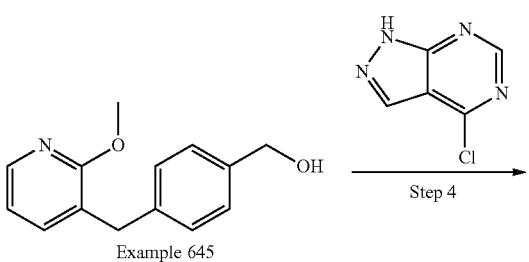

Example 645

Step 1. (4-(methoxycarbonyl)benzyl)zinc(II) bromide. Zn dust was activated by stirring it 5 min with 1N HCl followed by washing successively with water, acetone and diethyl ether. The activated zinc (1.37 g; 20.95 mmol; 1.20 eq.) was suspended in 2.3 ml of THF and dibromomethane (0.05 ml; 0.70 mmol; 0.04 eq.) was added to the mix. The system was flushed with nitrogen and heated to 70° C. for 7 min. After the mix was cooled to 0° C. under a nitrogen atmosphere, a solution of methyl 4-(bromomethyl)benzoate (4.00 g; 17.46 mmol; 1.00 eq.) in 2 ml of THF was added drop wise and the reaction mix was stirred at 0° C. for 30 min after which the ice bath was removed and the reaction mix was left stirring at RT. After 2h there was no starting material left by TLC. The solution was filtered through a polypropylene cartridge and the crude (4-(methoxycarbonyl)benzyl)zinc(II) bromide was used as is in the next step.

Step 2. methyl 4-((2-methoxypyridin-3-yl)methyl)benzoate. To a microwave vial containing a solution of 3-bromo-2-methoxypyridine (1.034 g; 5.50 mmol; 0.90 eq.), in N-methyl-2-pyrrolidinone (9.00 ml) were added Pd$_2$(dba)$_3$ (111.96 mg; 0.12 mmol; 0.02 eq.) and tri(tert-butyl)phosphonium tetrafluoroborate (141.89 mg; 0.49 mmol; 0.08 eq.) and the system was flushed with nitrogen for 5 minutes. Half of the solution of zincate 4-(methoxycarbonyl)benzyl)zinc (II) bromide (1.80 g; 6.11 mmol; 1.00 eq.) was added to it and the system was flushed with nitrogen once again. The vial was capped and heated in a microwave reactor at 145° C. for 10 minutes. The reaction mix was partitioned in EtOAc/water. The organic layer was isolated and the aqueous layer was back extracted twice with EtOAc. The combined organics were washed with brine, dried over Na$_2$SO$_4$, filtered and concentrated. The crude was purified on a silica gel column using 0-20% EtOAc in hexanes. The isolated product was contaminated with a byproduct and was subjected to a second purification using 0-5% MeOH in DCM as eluent to give the desired methyl 4-((2-methoxypyridin-3-yl)methyl)benzoate (1.080 g). $^1$H NMR (400 MHz, DMSO-d6) δ 8.03 (dd, J=5.0, 1.9 Hz, 1H), 7.93-7.77 (m, 2H), 7.52 (dd, J=7.2, 1.9 Hz, 1H), 7.36-7.26 (m, 2H), 6.92 (dd, J=7.2, 5.0 Hz, 1H), 3.94 (s, 2H), 3.82 (d, J=8.2 Hz, 6H). MS (M+H)+ found for $C_{15}H_{15}NO_3$: 257.

Step 3. (4-((2-methoxypyridin-3-yl)methyl)phenyl)methanol. Lithium aluminum hydride (2.68 ml; 2.00 mol/l; 5.36 mmol; 2.00 eq.) 1M solution in THF was added drop wise to a solution of methyl 4-((2-methoxypyridin-3-yl)methyl)benzoate (690.00 mg; 2.68 mmol; 1.00 eq.) in tetrahydrofuran (6.90 ml) at 0° C. and the reaction was kept at 0° C. for 45 minutes. The reaction mix was diluted with THF and a small scoop of celite was added to it. It was then quenched by drop wise addition of 150 µl of water, 150 µl of 15% NaOH and 450 µl of water. The resulting suspension was stirred for 15 minutes. The celite and the salts were removed by filtration and the remaining cake was suspended in EtOAc and stirred for 15 minutes before filtering it. The organic cake wash was combined with the first filtrate and the solvent was removed under vacuum to give crude (4-((2-methoxypyridin-3-yl)methyl)phenyl)methanol (580 mg) which was used as is in the next step. $^1$H NMR (400 MHz, DMSO-d6) δ 8.00 (dd, J=5.0, 1.9 Hz, 1H), 7.44 (dd, J=7.2, 1.9 Hz, 1H), 7.26-7.07 (m, 4H), 6.89 (dd, J=7.2, 5.0 Hz, 1H), 5.07 (t, J=5.7 Hz, 1H), 4.42 (d, J=5.7 Hz, 2H), 3.83 (m, 5H). MS (M+H)+ found for $C_{14}H_{15}NO_2$: 229.

Step 4. 4-chloro-2-(4-((2-methoxypyridin-3-yl)methyl)benzyl)-2H-pyrazolo[3,4-d]pyrimidine. {4-[(2-Methoxypyridin-3-yl)methyl]phenyl}methanol (308.00 mg; 1.34 mmol; 1.00 eq.) and 4-chloro-1H-pyrazolo[3,4-d]pyrimidine (207.63 mg; 1.34 mmol; 1.00 eq.) were dissolved in dichloromethane (4.62 ml) and the resulting suspension was cooled in an salt/ice bath. Triphenylphosphine (671.68 mg; 2.02 mmol; 1.50 eq.) resin (Aldrich) was added followed by drop wise addition of diisopropyl (E)-1,2-diazenedicarboxylate (0.66 ml; 3.36 mmol; 2.50 eq.) (Aldrich). The resulting mix was left to reach RT slowly. The resulting mix was left to reach RT slowly. After 3h, additional 0.5 eq of triphenylphosphine and 0.8 eq of the diazodicarboxylate were added and the reaction mix was left stirring overnight at RT. The resin was removed by filtration, rinsed with DCM and the combine filtrates concentrated. The crude was purified on a silica gel column using 0-100% EtOAc in hexanes. The two isomers were isolated and the most polar one was the desired 4-chloro-2-(4-((2-methoxypyridin-3-yl)methyl)benzyl)-2H-pyrazolo[3,4-d]pyrimidine (152 mg). $^1$H NMR (400 MHz, DMSO-d6) δ 9.06 (s, 1H), 8.77 (s, 1H), 8.00 (dd, J=5.0, 1.9 Hz, 1H), 7.45 (dd, J=7.2, 1.9 Hz, 1H), 7.32 (d, J=8.1 Hz, 2H), 7.26-7.11 (m, 3H), 6.89 (dd, J=7.2, 5.0 Hz, 1H), 5.65 (s, 2H), 3.83 (d, J=6.1 Hz, 5H). MS (M+H)+ found for $C_{19}H_{16}ClN_5O$: 366/368.

Step 5. N-(6-chloro-2-fluoro-3-methoxybenzyl)-2-(4-((2-methoxypyridin-3-yl)methyl)benzyl)-2H-pyrazolo[3,4-d]pyrimidin-4-amine. Hunig's base (0.03 ml; 0.17 mmol; 1.50 eq.) was added to a solution of 4-chloro-2-(4-((2-methoxypyridin-3-yl)methyl)benzyl)-2H-pyrazolo[3,4-d]pyrimidine (41.00 mg; 0.11 mmol; 1.00 eq.) and (6-chloro-2-fluoro-3-methoxyphenyl)methanamine (21.25 mg; 0.11 mmol; 1.00 eq.) in N,N-dimethylformamide (1.00 ml) and the reaction mix was heated at 70° C. for 90 minutes. Heating was stopped and the reaction mix was left to reach RT overnight. The reaction flask was cooled in an ice bath and treated by drop wise addition of water. A precipitate appeared which was removed by filtration. The recovered solid was dissolved in DCM, loaded onto a silica gel column and eluted with 0-5% MeOH in DCM. The fractions containing the product were concentrated to dryness. The residue was taken in acetonitrile/water, freeze and lyophilized to give the desired N-(6-chloro-2-fluoro-3-methoxybenzyl)-2-(4-((2-methoxypyridin-3-yl)methyl)benzyl)-2H-pyrazolo[3,4-d]pyrimidin-4-amine (40 mg). $^1$H NMR (400 MHz, DMSO-d6) δ 8.25 (d, J=15.2 Hz, 3H), 8.00 (dd, J=5.0, 1.8 Hz, 1H), 7.44 (dd, J=7.1, 1.9 Hz, 1H), 7.28 (dd, J=9.0, 1.7 Hz, 1H), 7.19 (td, J=8.9, 4.9 Hz, 5H), 6.88 (dd, J=7.2, 5.0 Hz, 1H), 5.47 (s, 2H), 4.79-4.64 (m, 2H), 3.83 (d, J=4.4 Hz, 8H). MS (M+H)+ found for $C_{27}H_{24}ClFN_6O_2$: 519/521.

Example 648

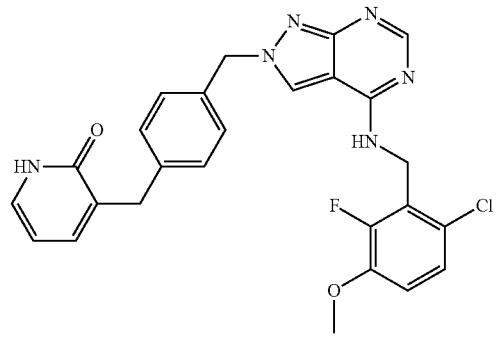 [SMILES: COc1ccc(Cl)c(CNc2ncnc3nn(Cc4ccc(Cc5ccc[nH]c5=O)cc4)cc23)c1F]

Procedure for 3-(4-((4-((6-chloro-2-fluoro-3-methoxybenzyl)amino)-2H-pyrazolo[3,4-d]pyrimidin-2-yl)methyl)benzyl)pyridin-2(1H)-one. N-(6-chloro-2-fluoro-3-methoxybenzyl)-2-(4-((2-methoxypyridin-3-yl)methyl)benzyl)-2H-pyrazolo[3,4-d]pyrimidin-4-amine (60.00 mg; 0.12 mmol; 1.00 eq.)(Example 647) was placed in a microwave vial and suspended in a 4N solution of hydrochloric acid (4.80 ml; 4.00 mol/l; 19.20 mmol; 80.00 V) in dioxane and 0.5 ml of water. The vial was capped and heated in a microwave reactor at 110° C. for 20 minutes. LCMS showed clean reaction with some starting material. The vial was placed in the microwave for additional 15 min at 110° C. The reaction mix was transferred to a round bottom flask and concentrated to almost dryness. The residue was diluted in 0.5 ml of water and neutralized with NaHCO3 solution. The aqueous layer was extracted three times with EtOAc and the combined organics were dried over $Na_2SO_4$, filtered and concentrated. The crude was purified on a silica gel column using 0-5% MeOH in DCM to give the desired 3-(4-((4-((6-chloro-2-fluoro-3-methoxybenzyl)amino)-2H-pyrazolo[3,4-d]pyrimidin-2-yl)methyl)benzyl)pyridin-2(1H)-one (43 mg). $^1$H NMR (400 MHz, DMSO-d6) δ 11.50 (s, 1H), 8.27 (dd, J=15.5, 5.8 Hz, 3H), 7.46-6.98 (m, 8H), 6.06 (t, J=6.6 Hz, 1H), 5.46 (s, 2H), 4.73 (d, J=3.9 Hz, 2H), 3.83 (s, 3H), 3.66 (s, 2H). MS (M+H)+ found for $C_{26}H_{22}ClFN_6O_2$: 504/506.

Example 649

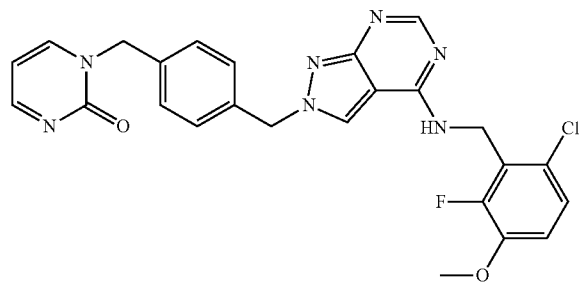 [SMILES: COc1ccc(Cl)c(CNc2ncnc3nn(Cc4ccc(Cn5cccnc5=O)cc4)cc23)c1F]

1-([4-[(4-[[(6-chloro-2-fluoro-3-methoxyphenyl)methyl]amino]-2H-pyrazolo[3,4-d]pyrimidin-2-yl)methyl]phenyl]methyl)-1,2-dihydropyrimidin-2-one 1-([4-[(4-[[(6-chloro-2-fluoro-3-methoxyphenyl)methyl]amino]-2H-pyrazolo[3,4-d]pyrimidin-2-yl)methyl]phenyl]

methyl)-1,2-dihydropyrimidin-2-one was prepared in a similar manner as Example 468. $^1$H NMR (300 MHz, DMSO-d$_6$): δ 8.56-8.53 (m, 1H), 8.33-8.25 (m, 4H), 7.32-7.29 (m, 5H), 7.20 (t, J=9.0 Hz, 1H), 6.44 (dd, J=6.6 Hz, J=4.2 Hz, 1H), 5.52 (s, 2H), 5.03 (s, 2H), 4.75 (d, J=2.1 Hz, 2H), 3.85 (s, 3H). LC-MS (ESI) m/z: calculated for C$_{25}$H$_{21}$ClFN$_7$O$_2$: 505.14. found: 506 [M+H]$^+$.

Example 650

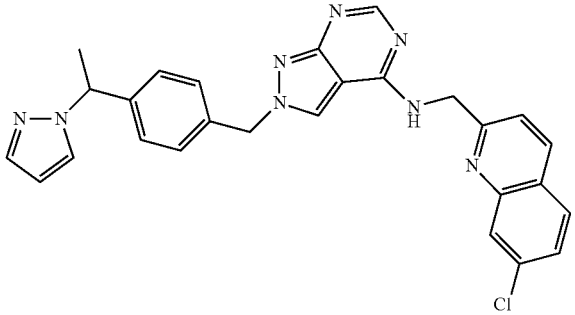 [SMILES: CC(c1ccc(Cn2cc3c(NCc4ccc5ccc(Cl)cc5n4)ncnc3n2)cc1)n1cccn1]

N-[(7-chloroquinolin-2-yl)methyl]-2-([4-[1-(1H-pyrazol-1-yl)ethyl]phenyl]methyl)-2H-pyrazolo[3,4-d]pyrimidin-4-amine N-[(7-chloroquinolin-2-yl)methyl]-2-([4-[1-(1H-pyrazol-1-yl)ethyl]phenyl]methyl)-2H-pyrazolo[3,4-d]pyrimidin-4-amine was prepared in a similar manner as Example 594. $^1$H-NMR (300 MHz, DMSO): δ 8.95 (brs, 1H), 8.50 (s, 1H), 8.44 (d, J=8.7 Hz, 1H), 8.18 (s, 1H), 8.01 (d, J=8.7 Hz, 2H), 7.83 (s, 1H), 7.62 (d, J=9.0 Hz, 1H), 7.54 (d, J=8.4 Hz, 1H), 7.45 (s, 1H), 7.32 (d, J=8.1 Hz, 2H), 7.22 (d, J=7.5 Hz, 2H), 6.25 (s, 1H), 5.65-5.56 (m, 3H), 4.97 (d, J=6.0 Hz, 2H), 1.78 (d, J=7.2 Hz, 3H). MS (ESI) m/z 495 [M+H]$^+$.

Example 651

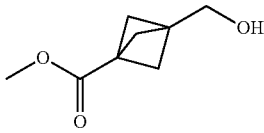

methyl 3-(hydroxymethyl)bicyclo[1.1.1]pentane-1-carboxylate 3-(methoxycarbonyl)bicyclo[1.1.1]pentane-1-carboxylic acid (547.00 mg; 3.21 mmol; 1.00 eq.) was dissolved in THF (16 ml). 4-methylmorpholine (0.44 ml; 4.02 mmol; 1.25 eq.) was added and the solution was stirred in an ice bath, followed by slow addition of isobutyl chloroformate (0.52 ml; 4.02 mmol; 1.25 eq.) After 1.5 h the mixture was filtered under N$_2$ pressure and the solid was rinsed with THF (15 ml).

The solution was then added slowly to a solution of sodium borohydride (243.23 mg; 6.43 mmol; 2.00 eq.) in water (13 ml). The reaction was maintained at approximately 10° C. for 20 h and then acidified with 1 M aqueous HCl to pH<3. The mixture was then extracted with ethyl acetate (5×50 ml), the extracts were washed with brine (25 ml) and dried over sodium sulfate. After evaporation, the residue was purified by silica gel chromatography (ethyl acetate/hexanes gradient) to give methyl 3-(hydroxymethyl) bicyclo[1.1.1]pentane-1-carboxylate as a colorless liquid (0.5 g).

$^1$H NMR (400 MHz, CDCl$_3$) δ 3.68 (s, 3H), 3.64 (s, 2H), 2.02-1.93 (m, 6H).

Example 652

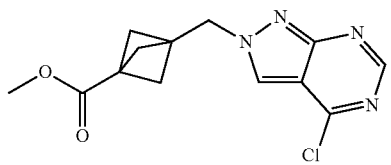 [SMILES: COC(=O)C12CC(Cn3cc4c(Cl)ncnc4n3)(C1)C2]

methyl 3-((4-chloro-2H-pyrazolo[3,4-d]pyrimidin-2-yl)methyl)bicyclo[1.1.1]pentane-1-carboxylate 4-chloro-1H-pyrazolo[3,4-d]pyrimidine (240.00 mg; 1.55 mmol; 1.00 eq.)(Example 651) was suspended in DCM (15 ml) containing methyl 3-(hydroxymethyl)bicyclo[1.1.1]pentane-1-carboxylate (363.78 mg; 2.33 mmol; 1.50 eq.) The mixture was cooled in an ice bath and triphenylphosphine resin (1.04 g; 3 mmol/g; 3.11 mmol; 2 eq.) was added followed by slow addition of diisopropyl -1,2-diazenedicarboxylate (914.54 ul; 4.66 mmol; 3.00 eq.) After 14 h, the mixture was filtered, the resin rinsed w/ DCM and the solution evaporated. The residue was purified by silica gel chromatography (ethyl acetate/hexanes gradient) to give methyl 3-((4-chloro-2H-pyrazolo[3,4-d]pyrimidin-2-yl)methyl)bicyclo[1.1.1]pentane-1-carboxylate as a white solid (90 mg). MS (M+H)$^+$ found for C$_{13}$H$_{13}$ClN$_4$O$_2$: 293.1.

Example 653

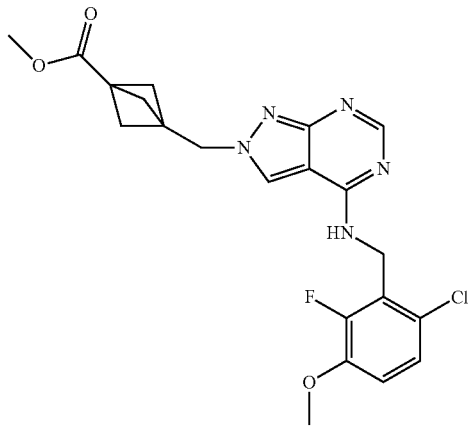 [SMILES: COC(=O)C12CC(Cn3cc4c(NCc5c(Cl)ccc(OC)c5F)ncnc4n3)(C1)C2]

methyl 3-((4-((6-chloro-2-fluoro-3-methoxybenzyl) amino)-2H-pyrazolo[3,4-d]pyrimidin-2-yl)methyl) bicyclo[1.1.1]pentane-1-carboxylate Methyl 3-({4-chloro-2H-pyrazolo[3,4-d]pyrimidin-2-yl}methyl)bicyclo[1.1.1]pentane-1-carboxylate (90.00 mg; 0.31 mmol; 1.00 eq.)(Example 652) was partly dissolved in 1-butanol (3.5 ml). (6-chloro-2-fluoro-3-methoxyphenyl) methanamine (64.13 mg; 0.34 mmol; 1.10 eq.) and Hunig's base-ethylbis(propan-2-yl)amine (58.91 ul; 0.34 mmol; 1.10 eq.) were added and the resulting solution was heated in a microwave reactor at 110° C. for 40 m. The reaction was evaporated and purified by silica gel chromatography (methanol/DCM gradient) to give methyl 3-((4-((6-chloro-2-fluoro-3-methoxybenzyl)amino)-2H-pyrazolo[3,4-d]pyrimidin-2-yl)methyl)bicyclo[1.1.1]pentane-1-carboxylate as a white solid (73 mg). MS (M+H)$^+$ found for C$_{21}$H$_{21}$ClFN$_5$O$_3$: 446.1.

Example 654

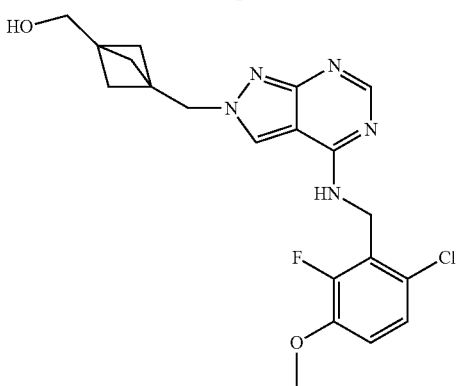 [SMILES: COc1ccc(Cl)c(CNc2ncnc3nn(CC45CC(CO)(C4)C5)cc23)c1F]

(3-((4-((6-chloro-2-fluoro-3-methoxybenzyl)amino)-2H-pyrazolo[3,4-d]pyrimidin-2-yl)methyl)bicyclo[1.1.1]pentan-1-yl)methanol Methyl 3-[(4-{[(6-chloro-2-fluoro-3-methoxyphenyl)methyl]amino}-2H-pyrazolo[3,4-d]pyrimidin-2-yl)methyl]bicyclo[1.1.1]pentane-1-carboxylate (73.60 mg; 0.17 mmol; 1.00 eq.)(Example 653) was dissolved in THF (2.5 ml) and then cooled in an ice bath. Lithium aluminum hydride (0.17 ml; 1.00 mol/l in THF; 0.17 mmol; 1.05 eq.) was added slowly. The reaction was stirred in the ice bath. After 2.75 h, ~7 ul of water, ~7 ul 15% NaOH soln., ~20 ul water were added carefully in sequence. The solid was filtered, rinsed with THF (10 ml) and evaporated. The residue was carried into the next step directly. MS (M+H)$^+$ found for $C_{20}H_{21}ClFN_5O_2$: 418.1.

Example 655

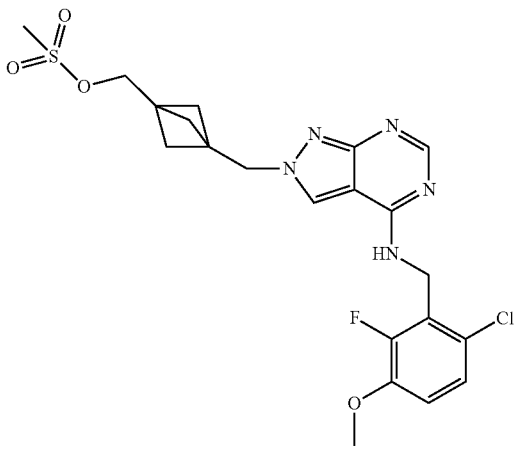 [SMILES: COc1ccc(Cl)c(CNc2ncnc3nn(CC45CC(COS(C)(=O)=O)(C4)C5)cc23)c1F]

{3-[(4-{[(6-chloro-2-fluoro-3-methoxyphenyl)methyl]amino}-2H-pyrazolo[3,4-d]pyrimidin-2-yl)methyl]bicyclo[1.1.1]pentan-1-yl}methyl methanesulfonate {3-[(4-{[(6-chloro-2-fluoro-3-methoxyphenyl)methyl]amino}-2H-pyrazolo[3,4-d]pyrimidin-2-yl)methyl]bicyclo[1.1.1]pentan-1-yl}methanol (69.00 mg; 0.17 mmol; 1.00 eq.)(Example 654) was partly dissolved in THF (2 ml). The mixture was cooled in an ice bath, and triethylamine (46.03 ul; 0.33 mmol; 2.00 eq.) and then methanesulfonyl chloride (14.06 ul; 0.18 mmol; 1.10 eq.) were added slowly. The reaction was stirred at 25° C. for 4 h. It was then re-cooled and more methanesulfonyl chloride (7 ul; 0.09 mmol; 0.5 eq.) was added. After another 1.5 h, the reaction was worked up by addition of DCM (25 ml) and water (20 ml). The phases were separated and the aqueous phase was extracted with more DCM (2×25 ml). The combined organic phases were then washed with brine (10 ml) and dried over sodium sulfate. The solution was evaporated and brought into the next step directly. MS (M+H)$^+$ found for $C_{21}H_{23}ClFN_5O_4S$: 496.1.

Example 656

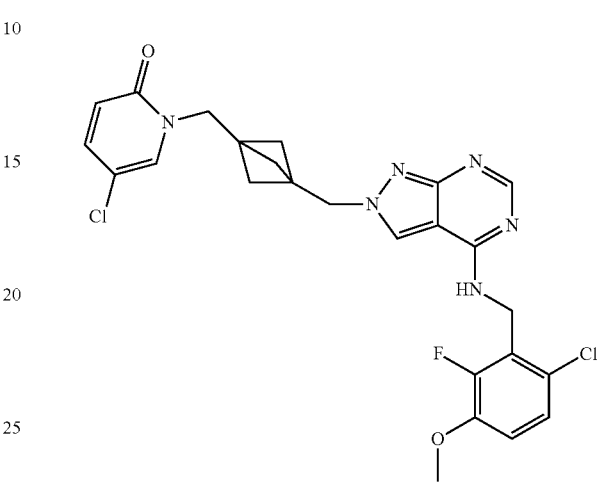

5-chloro-1-((3-((4-((6-chloro-2-fluoro-3-methoxybenzyl)amino)-2H-pyrazolo[3,4-d]pyrimidin-2-yl)methyl)bicyclo[1.1.1]pentan-1-yl)methyl)pyridin-2(1H)-one 5-chloro-1-((3-((4-((6-chloro-2-fluoro-3-methoxybenzyl)amino)-2H-pyrazolo[3,4-d]pyrimidin-2-yl)methyl)bicyclo[1.1.1]pentan-1-yl)methyl)pyridin-2(1H)-one was prepared in a similar manner as Example 594 using Example 655. $^1$H NMR (400 MHz, CD$_3$OD) δ 8.33 (s, 1H), 8.20 (s, 1H), 7.66 (d, J=2.8 Hz, 1H), 7.47 (dd, J=9.7, 2.8 Hz, 1H), 7.24 (dd, J=8.9, 1.8 Hz, 1H), 7.11 (dd, J=8.9 Hz, 1H), 6.50 (d, J=9.7 Hz, 1H), 4.88 (d, J=2.2 Hz, 2H), 4.41 (s, 2H), 4.05 (s, 2H), 3.89 (s, 3H), 1.62 (s, 6H). MS (M+H)$^+$ found for $C_{25}H_{23}Cl_2FN_6O_2$: 529.2, 531.1.

Example 657

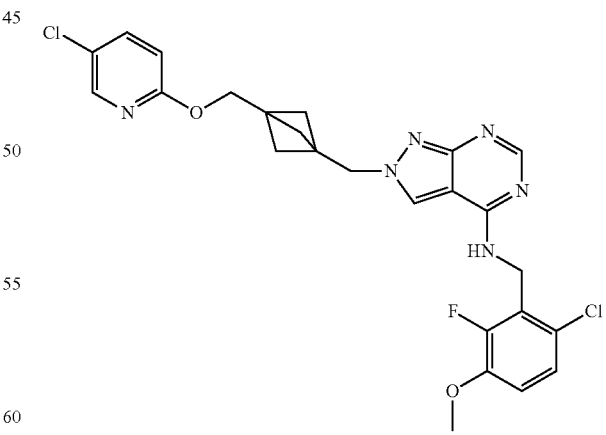

N-(6-chloro-2-fluoro-3-methoxybenzyl)-2-((3-(((5-chloropyridin-2-yl)oxy)methyl)bicyclo[1.1.1]pentan-1-yl)methyl)-2H-pyrazolo[3,4-d]pyrimidin-4-amine N-(6-chloro-2-fluoro-3-methoxybenzyl)-2-((3-(((5-chloropyridin-2-yl)oxy)methyl)bicyclo[1.1.1]pentan-1-yl)

methyl)-2H-pyrazolo[3,4-d]pyrimidin-4-amine was prepared in a similar manner as Example 656. ¹H NMR (400 MHz, CDCl₃) δ 8.52 (s, 1H), 8.01 (s, 1H), 7.82 (s, 1H), 7.48 (d, J=8.7 Hz, 1H), 7.16 (d, J=8.9 Hz, 1H), 6.89 (dd, J=8.8 Hz, 1H), 6.65 (d, J=8.8 Hz, 1H), 5.00 (s, 2H), 4.43 (s, 2H), 4.25 (s, 2H), 3.88 (s, 3H), 1.73 (s, 6H). MS (M+H)⁺ found for C₂₅H₂₃Cl₂FN₆O₂: 529.1, 531.1.

Example 658

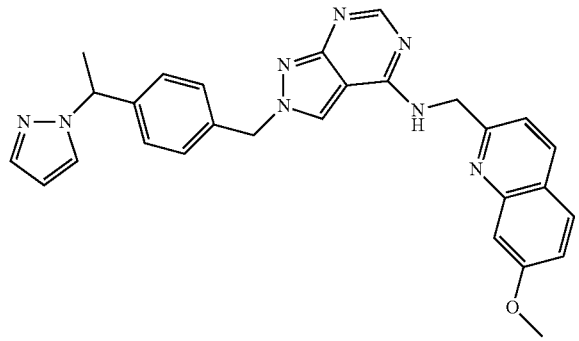 [SMILES: COc1ccc2ccc(CNc3ncnc4nn(Cc5ccc(C(C)n6cccn6)cc5)cc34)nc2c1]

N-[(7-methoxyquinolin-2-yl)methyl]-2-([4-[1-(1H-pyrazol-1-yl)ethyl]phenyl]methyl)-2H-pyrazolo[3,4-d]pyrimidin-4-amine N-[(7-methoxyquinolin-2-yl)methyl]-2-([4-[1-(1H-pyrazol-1-yl)ethyl]phenyl]methyl)-2H-pyrazolo[3,4-d]pyrimidin-4-amine was prepared in a similar manner as Example 594. ¹H-NMR (300 MHz, DMSO): δ 8.90 (brs, 1H), 8.45 (s, 1H), 8.22-8.18 (m, 2H), 7.86-7.83 (m, 2H), 7.45 (s, 1H), 7.36-7.30 (m, 4H), 7.24-7.21 (m, 3H), 6.25 (s, 1H), 5.65-5.55 (m, 3H), 4.93 (d, J=5.7 Hz, 2H), 3.91 (s, 3H), 1.77 (d, J=6.9 Hz, 3H). MS (ESI) m/z 491 [M+H]⁺.

Example 659

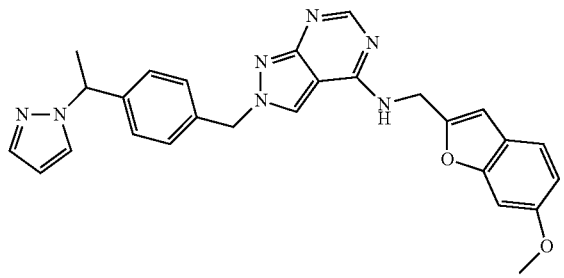 [SMILES: COc1ccc2cc(CNc3ncnc4nn(Cc5ccc(C(C)n6cccn6)cc5)cc34)oc2c1]

N-[(6-methoxy-1-benzofuran-2-yl)methyl]-2-([4-[1-(1H-pyrazol-1-yl)ethyl]phenyl]methyl)-2H-pyrazolo[3,4-d]pyrimidin-4-amine N-[(6-methoxy-1-benzofuran-2-yl)methyl]-2-([4-[1-(1H-pyrazol-1-yl)ethyl]phenyl]methyl)-2H-pyrazolo[3,4-d]pyrimidin-4-amine was prepared in a similar manner as Example 594. ¹H-NMR (300 MHz, DMSO): δ 8.71 (brs, 1H), 8.37 (s, 1H), 8.24 (s, 1H), 7.82 (d, J=2.1 Hz, 1H), 7.44-7.43 (m, 2H), 7.28 (d, J=7.8 Hz, 2H), 7.21 (d, J=8.1 Hz, 2H), 7.14 (d, J=1.2 Hz, 1H), 6.84 (dd, J=8.4 Hz, 2.1 Hz, 1H), 6.70 (s, 1H), 6.24 (t, J=2.1 Hz, 1H), 5.60 (q, J=6.9 Hz, 1H), 5.53 (s, 2H), 4.82 (d, J=5.4 Hz, 2H), 3.77 (s, 3H), 1.76 (d, J=6.9 Hz, 3H). MS (ESI) m/z 480 [M+H]⁺.

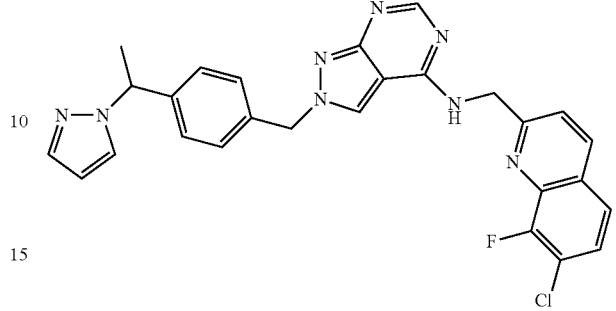

N-[(7-chloro-8-fluoroquinolin-2-yl)methyl]-2-([4-[1-(1H-pyrazol-1-yl)ethyl]phenyl]methyl)-2H-pyrazolo[3,4-d]pyrimidin-4-amine N-[(7-chloro-8-fluoroquinolin-2-yl)methyl]-2-([4-[1-(1H-pyrazol-1-yl)ethyl]phenyl]methyl)-2H-pyrazolo[3,4-d]pyrimidin-4-amine was prepared in a similar manner as Example 594. ¹H-NMR (300 MHz, DMSO-d₆): δ 9.01 (s, 1H), 8.44-8.40 (m, 2H), 8.17 (s, 1H), 7.87-7.83 (m, 2H), 7.74-7.72 (m, 1H), 7.69-7.65 (m, 1H), 7.45 (s, 1H), 7.33 (d, J=7.8 Hz, 2H), 7.24 (d, J=8.1 Hz, 2H), 6.25 (s, 1H), 5.65-5.60 (m, 1H), 5.56 (s, 2H), 4.99 (d, J=6.0 Hz, 2H), 1.78 (d, J=6.9 Hz, 3H). LC-MS (ESI) m/z: calculated for C₂₇H₂₂ClFN₈: 512.16. found: 513 [M+H]⁺.

Example 661

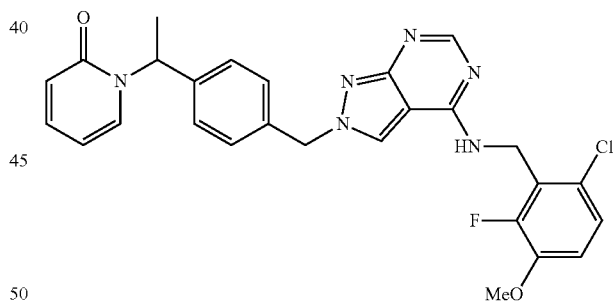

1-(1-[4-[(4-[[(6-chloro-2-fluoro-3-methoxyphenyl)methyl]amino]-2H-pyrazolo[3,4-d]pyrimidin-2-yl)methyl]phenyl]ethyl)-1,2-dihydropyridin-2-one 1-(1-[4-[(4-[[(6-chloro-2-fluoro-3-methoxyphenyl)methyl]amino]-2H-pyrazolo[3,4-d]pyrimidin-2-yl)methyl]phenyl]ethyl)-1,2-dihydropyridin-2-one was prepared in a similar manner as Example 594. ¹H NMR (300 MHz, CDCl₃, ppm): δ 8.50 (s, 1H), 8.03 (s, 1H), 7.32-7.26 (m, 2H), 7.18-7.11 (m, 4H), 6.87 (t, J=8.7 Hz, 1H), 6.58 (d, J=9.0 Hz, 1H), 6.35 (q, J=8.1 Hz, 1H), 6.18 (t, J=6.3 Hz, 1H), 5.40 (s, 2H), 4.98 (s, 2H), 3.86 (s, 3H), 1.69 (d, J=7.2 Hz, 3H). LC-MS (ESI) m/z: calculated for C₂₇H₂₄ClFN₆O₂: 518.16. found: 519 [M+H]⁺.

Example 662

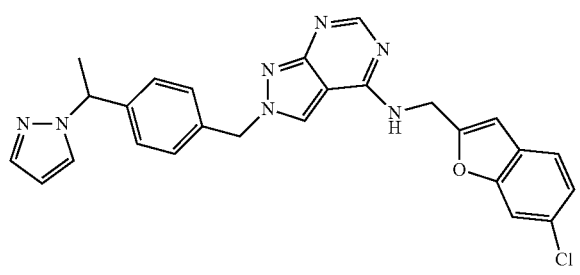 [SMILES: CC(c1ccc(Cn2cc3c(NCc4cc5ccc(Cl)cc5o4)ncnc3n2)cc1)n1cccn1]

N-[(6-chloro-1-benzofuran-2-yl)methyl]-2-([4-[1-(1H-pyrazol-1-yl)ethyl]phenyl]methyl)-2H-pyrazolo[3,4-d]pyrimidin-4-amine N-[(6-chloro-1-benzofuran-2-yl)methyl]-2-([4-[1-(1H-pyrazol-1-yl)ethyl]phenyl]methyl)-2H-pyrazolo[3,4-d]pyrimidin-4-amine was prepared in a similar manner as Example 594. $^1$H-NMR (300 MHz, DMSO-$d_6$): δ 8.79 (brs, 1H), 8.38 (s, 1H), 8.24 (s, 1H), 7.82 (d, J=1.8 Hz, 1H), 7.72 (s, 1H), 7.58 (d, J=8.1 Hz, 1H), 7.44 (s, 1H), 7.31-7.20 (m, 5H), 6.83 (s, 1H), 6.25 (s, 1H), 5.60 (q, J=6.9 Hz, 1H), 5.54 (s, 2H), 4.86 (d, J=5.1 Hz, 2H), 1.76 (d, J=7.2 Hz, 3H). MS (ESI) m/z 484 [M+H]$^+$.

Example 663

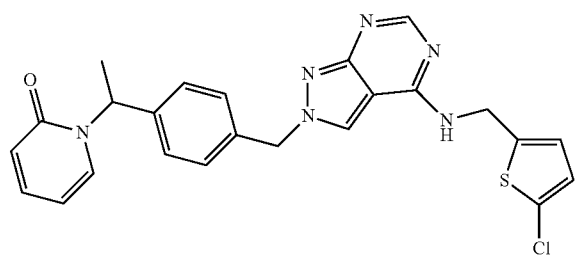 [SMILES: CC(c1ccc(Cn2cc3c(NCc4ccc(Cl)s4)ncnc3n2)cc1)n1ccccc1=O]

1-(1-[4-[(4-[[(5-chlorothiophen-2-yl)methyl]amino]-2H-pyrazolo[3,4-d]pyrimidin-2-yl)methyl]phenyl]ethyl)-1,2-dihydropyridin-2-one 1-(1-[4-[(4-[[(5-chlorothiophen-2-yl)methyl]amino]-2H-pyrazolo[3,4-d]pyrimidin-2-yl)methyl]phenyl]ethyl)-1,2-dihydropyridin-2-one was prepared in a similar manner as Example 594. $^1$H NMR (300 MHz, CDCl$_3$, ppm): δ 8.48 (s, 1H), 7.98 (s, 1H), 7.72 (brs, 1H), 7.34-7.28 (m, 1H), 7.18 (d, J=6.3 Hz, 1H), 7.01-6.92 (m, 4H), 6.81 (d, J=3.6 Hz, 1H), 6.71 (d, J=3.6 Hz, 1H), 6.55 (d, J=9.0 Hz, 1H), 6.26-6.18 (m, 2H), 5.24 (s, 2H), 4.86 (s, 2H), 1.65 (d, J=7.2 Hz, 3H). LC-MS (ESI) m/z: calculated for C$_{24}$H$_{21}$ClN$_6$OS: 476.12. found: 477 [M+H]$^+$.

Example 664

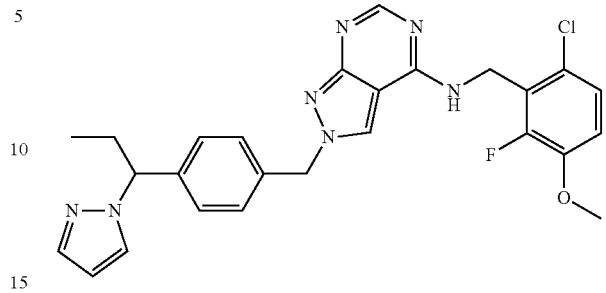

N-[(6-chloro-2-fluoro-3-methoxyphenyl)methyl]-2-([4-[1-(1H-pyrazol-1-yl)propyl]phenyl]methyl)-2H-pyrazolo[3,4-d]pyrimidin-4-amine N-[(6-chloro-2-fluoro-3-methoxyphenyl)methyl]-2-([4-[1-(1H-pyrazol-1-yl)propyl]phenyl]methyl)-2H-pyrazolo[3,4-d]pyrimidin-4-amine was prepared in a similar manner as Example 594. $^1$H NMR (300 MHz, CDCl$_3$, ppm): δ 8.50 (s, 1H), 7.66 (brs, 1H), 7.52 (s, 1H), 7.45 (s, J=1.8 Hz, 1H), 7.20 (s, 4H), 7.14-7.11 (m, 1H), 6.86 (t, J=9.0 Hz, 1H), 6.25 (s, 1H), 5.39 (s, 2H), 5.17-5.12 (m, 1H), 4.96 (s, 2H), 3.86 (s, 3H), 2.43-2.30 (m, 1H), 2.20-2.07 (m, 1H), 0.88 (t, J=7.2 Hz, 3H). LC-MS (ESI) m/z: calculated for C$_{26}$H$_{25}$ClFN$_7$O: 505.18. found: 506[M+H]+.

Example 665

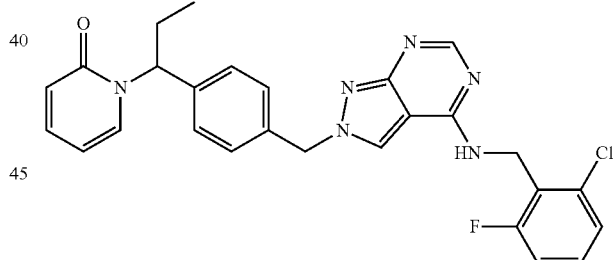

1-(1-[4-[(4-[[(6-chloro-2-fluoro-3-methoxyphenyl)methyl]amino]-2H-pyrazolo[3,4-d]pyrimidin-2-yl)methyl]phenyl]propyl)-1,2-dihydropyridin-2-one 1-(1-[4-[(4-[[(6-chloro-2-fluoro-3-methoxyphenyl)methyl]amino]-2H-pyrazolo[3,4-d]pyrimidin-2-yl)methyl]phenyl]propyl)-1,2-dihydropyridin-2-one was prepared in a similar manner as Example 594. $^1$H NMR (300 MHz, CDCl$_3$, ppm): δ 8.48 (s, 1H), 8.18 (s, 1H), 7.26-7.07 (m, 7H), 6.87 (t, J=9.0 Hz, 1H), 6.56 (d, J=9.0 Hz, 1H), 6.20 (t, J=6.6 Hz, 1H), 6.09 (t, J=8.1 Hz, 1H), 5.35 (s, 2H), 4.99 (s, 2H), 3.86 (s, 3H), 2.20-1.90 (m, 2H), 0.94 (t, J=7.2 Hz, 3H). LC-MS (ESI) m/z: calculated for C$_{28}$H$_{26}$ClFN$_6$O$_2$: 532.18. found: 533 [M+H]$^+$.

Example 666

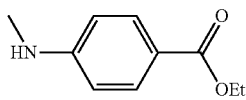

ethyl 4-(methylamino)benzoate Into a 50-mL round-bottom flask, was placed a mixture of ethyl 4-fluorobenzoate (3.4 g, 20.22 mmol, 1.00 equiv), DMSO (20 mL), methanamine hydrochloride (4.0 g, 59.24 mmol, 3.00 equiv) and potassium carbonate (8.3 g, 60.05 mmol, 3.00 equiv). The resulted solution was stirred for 48 h at 80° C. The mixture was diluted with 30 mL of $H_2O$ and extracted with 3×30 mL of ethyl acetate. The organic layers were combined, washed with 3×20 mL of brine, dried over anhydrous sodium sulfate and concentrated under vacuum. This resulted in 3.3 g (91%) of ethyl 4-(methylamino)benzoate as a light yellow solid.

Example 667

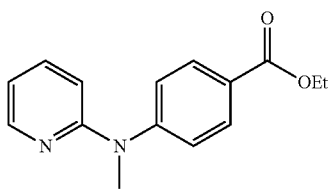 [SMILES: CCOC(=O)c1ccc(N(C)c2ccccn2)cc1]

ethyl 4-[methyl(pyridin-2-yl)amino]benzoate

Into a 25-mL round-bottom flask purged and maintained under an inert atmosphere of nitrogen, was placed a mixture ethyl 4-(methylamino)benzoate (1.0 g, 5.58 mmol, 1.00 equiv)(Example 666), toluene (10 mL), $Pd(OAc)_2$ (150 mg, 0.67 mmol, 0.12 equiv), BINAP (150 mg, 0.24 mmol, 0.04 equiv), 2-bromopyridine (880 mg, 5.57 mmol, 1.00 equiv) and t-BuOK (940 mg, 8.38 mmol, 1.50 equiv). The resulted solution was stirred for 16 h at 110° C. in an oil bath under nitrogen atmosphere. The mixture was concentrated under vacuum. The residue was purified by silica gel column eluted with dichloromethane/methanol=30/1. This resulted in 300 mg (21%) of ethyl 4-[methyl(pyridin-2-yl)amino]benzoate as a green liquid. LC-MS (ESI) m/z: calculated for $C_{15}H_{16}N_2O_2$:256.12. found 257[M+H]$^+$.

Example 668

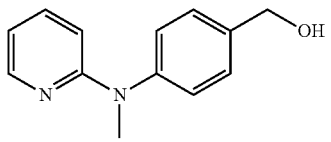 [SMILES: CN(c1ccc(CO)cc1)c1ccccn1]

[4-[methyl(pyridin-2-yl)amino]phenyl]methanol Into a 10-mL round-bottom flask purged and maintained with an inert atmosphere of nitrogen, was placed a solution of ethyl 4-[methyl(pyridin-2-yl)amino]benzoate (300 mg, 1.17 mmol, 1.00 equiv)(Example 667) in THF (3 mL) with stirring at 0° C., to which was added LAH (53.4 mg, 1.41 mmol, 1.20 equiv). The resulted solution was stirred for 1 h at 0° C. The reaction was then quenched by the addition of 1 mL of methanol, followed by 0.5 mL of 5N potassium hydroxide aqueous solution. After filtration, the filtrate was concentrated under reduced pressure. This resulted in 240 mg (96%) of [4-[methyl(pyridin-2-yl)amino]phenyl]methanol as a yellow solid. LC-MS (ESI) m/z: calculated for $C_{13}H_{14}N_2O$: 214.11. found 215[M+H]$^+$.

Example 669

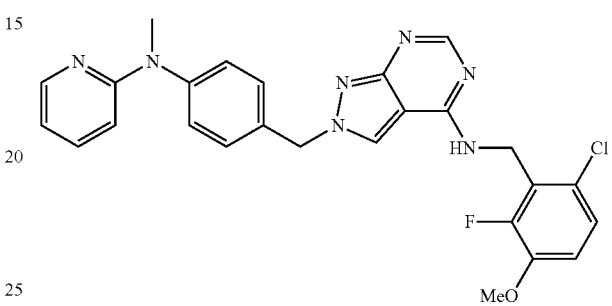

N-[4-[(4-[[(6-chloro-2-fluoro-3-methoxyphenyl)methyl]amino]-2H-pyrazolo[3,4-d]pyrimidin-2-yl)methyl]phenyl]-N-methylpyridin-2-amine N-[4-[(4-[[(6-chloro-2-fluoro-3-methoxyphenyl)methyl]amino]-2H-pyrazolo[3,4-d]pyrimidin-2-yl)methyl]phenyl]-N-methylpyridin-2-amine was prepared in a similar manner as Example 468 using Example 668. $^1$H NMR (300 MHz, DMSO-$d_6$): δ 8.42 (s, 1H), 8.38-8.34 (m, 1H), 8.27 (s, 1H), 8.16 (d, J=4.2 Hz, 1H), 7.45-7.18 (m, 7H), 6.70-6.66 (m, 1H), 6.57 (d, J=8.7 Hz, 1H), 5.55 (s, 2H), 4.77 (d, J=2.1 Hz, 2H), 3.86 (s, 3H), 3.32 (s, 3H). LC-MS (ESI) m/z: calculated for $C_{26}H_{23}ClFN_7O$: 503.16. found 504 [M+H]$^+$. Rt: 1.15.

Example 670

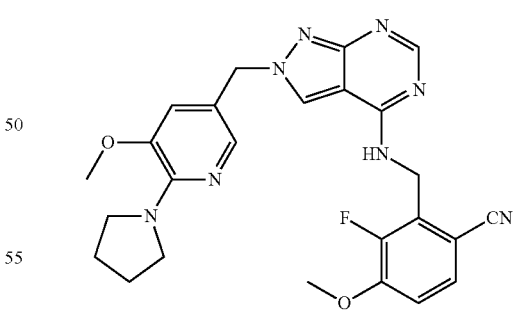

3-fluoro-4-methoxy-2-((2-((5-methoxy-6-(pyrrolidin-1-yl) pyridin-3-yl) methyl)-2H-pyrazolo [3,4-d] pyrimidin-4-ylamino) methyl) benzonitrile 3-fluoro-4-methoxy-2-((2-((5-methoxy-6-(pyrrolidin-1-yl) pyridin-3-yl) methyl)-2H-pyrazolo[3,4-d]pyrimidin-4-ylamino) methyl) benzonitrile was prepared in a similar manner as Example 295. $^1$H NMR (300 MHz, DMSO-$d_6$):

δ 10.01 (s, 1H), 9.88 (s, 1H), 8.95 (s, 1H), 8.70 (s, 1H), 7.72-7.70 (m, 2H), 7.35 (t, J=8.7 Hz, 1H), 7.18 (s, 1H), 5.65 (s, 2H), 5.43 (s, 2H), 3.91 (s, 3H), 3.71 (s, 3H), 3.62 (br. s, 4H), 1.88 (br. s, 4H). LC-MS (ESI) m/z: calculated for $C_{25}H_{25}FN_8O_2$: 488.21. found: 489 [M+H]$^+$.

Example 671

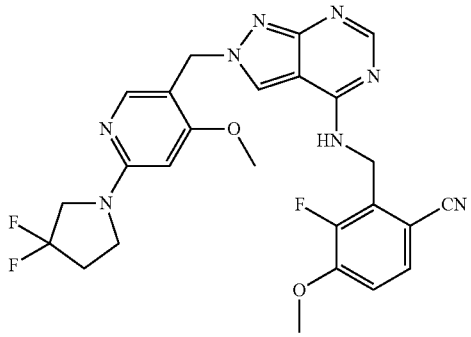 [SMILES: COc1cc(N2CCC(F)(F)C2)ncc1Cn1cc2c(NCc3c(C#N)ccc(OC)c3F)ncnc2n1]

2-((2-((6-(3,3-difluoropyrrolidin-1-yl)-4-methoxy-pyridin-3-yl) methyl)-2H-pyrazolo[3,4-d]pyrimidin-4-ylamino) methyl)-3-fluoro-4-methoxybenzonitrile 2-((2-((6-(3,3-difluoropyrrolidin-1-yl)-4-methoxypyridin-3-yl) methyl)-2H-pyrazolo[3,4-d]pyrimidin-4-ylamino) methyl)-3-fluoro-4-methoxybenzonitrile was prepared in a similar manner as Example 295. $^1$H NMR (300 MHz, DMSO-d$_6$): δ 9.93 (s, 1H), 9.86 (s, 1H), 8.92 (s, 1H), 8.59 (s, 1H), 8.03 (s, 1H), 7.72 (d, J=7.5 Hz, 1H), 7.33 (t, J=8.7 Hz, 1H), 6.16 (s, 1H), 5.63 (s, 2H), 5.36 (s, 2H), 3.98-3.89 (m, 5H), 3.80 (s, 3H), 3.70 (t, J=7.2 Hz, 2H), 2.64-2.57 (m, 2H). LC-MS (ESI) m/z: calculated for $C_{27}H_{24}F_6N_8O_4$: 638.18. found: 525[M-TFA+H]$^+$.

Example 672

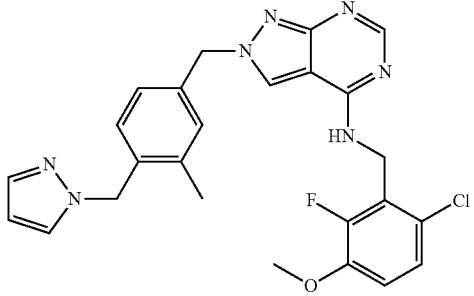 [SMILES: COc1ccc(Cl)c(CNc2ncnc3nn(Cc4ccc(Cn5cccn5)c(C)c4)cc23)c1F]

2-(4-((1H-pyrazol-1-yl)methyl)-3-methylbenzyl)-N-(6-chloro-2-fluoro-3-methoxybenzyl)-2H-pyrazolo[3,4-d]pyrimidin-4-amine 2-(4-((1H-pyrazol-1-yl)methyl)-3-methylbenzyl)-N-(6-chloro-2-fluoro-3-methoxybenzyl)-2H-pyrazolo[3,4-d]pyrimidin-4-amine was prepared similar to Example 594. $^1$H NMR (400 MHz, DMSO-d$_6$) δ 8.27 (dd, J=16.6, 6.7 Hz, 3H), 7.69 (d, J=1.9 Hz, 1H), 7.43 (s, 1H), 7.28 (d, J=9.0 Hz, 1H), 7.23-7.06 (m, 3H), 6.86 (d, J=7.8 Hz, 1H), 6.24 (d, J=2.0 Hz, 1H), 5.45 (s, 2H), 5.30 (s, 2H), 4.76-4.70 (m, 2H), 3.83 (s, 3H), 2.25 (s, 3H). MS (M+H)+ found for $C_{25}H_{23}ClFN_7O$: 494.1.

Example 673

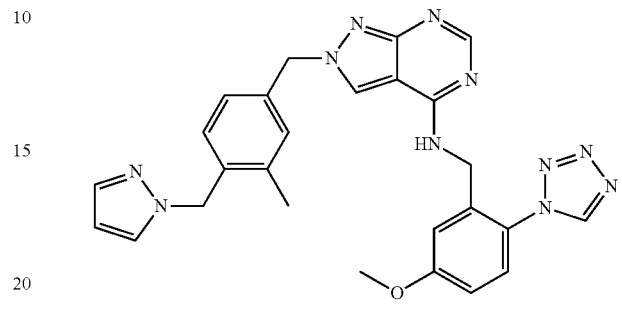

2-(4-((1H-pyrazol-1-yl)methyl)-3-methylbenzyl)-N-(5-methoxy-2-(1H-tetrazol-1-yl)benzyl)-2H-pyrazolo[3,4-d]pyrimidin-4-amine 2-(4-((1H-pyrazol-1-yl)methyl)-3-methylbenzyl)-N-(5-methoxy-2-(1H-tetrazol-1-yl)benzyl)-2H-pyrazolo[3,4-d]pyrimidin-4-amine was prepared similar to Example 247. $^1$H NMR (400 MHz, DMSO-d$_6$) δ 9.75 (d, J=1.3 Hz, 1H), 8.52 (t, J=5.8 Hz, 1H), 8.28 (s, 1H), 8.07 (s, 1H), 7.70 (d, J=2.1 Hz, 1H), 7.52-7.40 (m, 2H), 7.18-7.03 (m, 4H), 6.87 (d, J=7.8 Hz, 1H), 6.24 (t, J=2.0 Hz, 1H), 5.47 (s, 2H), 5.30 (s, 2H), 4.44 (d, J=5.6 Hz, 2H), 3.78 (s, 3H), 2.25 (s, 3H). MS (M+H)+ found for $C_{26}H_{25}N_{11}O$: 508.03.

Example 674

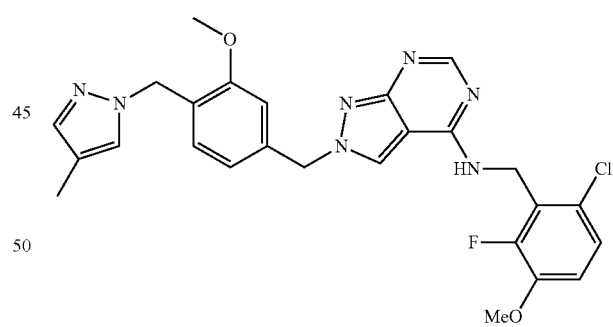

N-[(6-chloro-2-fluoro-3-methoxyphenyl)methyl]-2-([3-methoxy-4-[(4-methyl-1H-pyrazol-1-yl) methyl]phenyl]methyl)-2H-pyrazolo[3,4-d]pyrimidin-4-amine N-[(6-chloro-2-fluoro-3-methoxyphenyl)methyl]-2-([3-methoxy-4-[(4-methyl-1H-pyrazol-1-yl) methyl]phenyl]methyl)-2H-pyrazolo[3,4-d]pyrimidin-4-amine was prepared in a similar manner as Example 504. $^1$H NMR (300 MHz, DMSO-d$_6$): δ 8.31 (s, 1H), 8.26 (s, 2H), 7.44 (s, 1H), 7.33 (d, J=7.5 Hz, 1H), 7.22-7.17 (m, 2H), 7.09 (s, 1H), 6.85-6.78 (m, 2H), 5.50 (s, 2H), 5.16 (s, 2H), 4.74 (s, 2H), 3.85 (s, 3H), 3.80 (s, 3H), 1.98 (s, 3H). LC-MS (ESI) m/z: calculated for $C_{26}H_{25}ClFN_7O_2$: 521.17. found: 522 [M+H]$^+$. Rt: 1.57 min.

Example 675

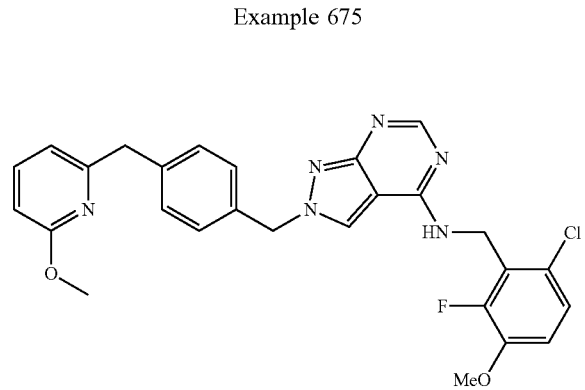

N-[(6-chloro-2-fluoro-3-methoxyphenyl)methyl]-2-([4-[(6-methoxypyridin-2-yl)methyl]phenyl]methyl)-2H-pyrazolo[3,4-d]pyrimidin-4-amine N-[(6-chloro-2-fluoro-3-methoxyphenyl)methyl]-2-([4-[(6-methoxypyridin-2-yl)methyl]phenyl]methyl)-2H-pyrazolo[3,4-d]pyrimidin-4-amine was prepared in a similar manner as Example 647. $^1$H NMR (300 MHz, DMSO-d$_6$): δ 8.29-8.26 (m, 3H), 7.58 (t, J=7.5 Hz, 1H), 7.32-7.17 (m, 6H), 6.80 (d, J=7.2 Hz, 1H), 6.61 (d, J=8.4 Hz, 1H), 5.49 (s, 2H), 4.75 (d, J=2.1 Hz, 2H), 3.96 (s, 2H), 3.86 (s, 3H), 3.81 (s, 3H). LC-MS (ESI) m/z: calculated for $C_{27}H_{24}ClFN_6O_2$: 518.16. found 519 [M+H]$^+$.

Example 676

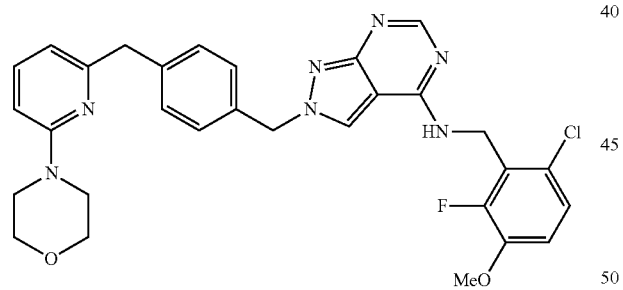

N-[(6-chloro-2-fluoro-3-methoxyphenyl)methyl]-2-[(4-[[6-(morpholin-4-yl)pyridin-2-yl]methyl]phenyl)methyl]-2H-pyrazolo[3,4-d]pyrimidin-4-amine N-[(6-chloro-2-fluoro-3-methoxyphenyl)methyl]-2-[(4-[[6-(morpholin-4-yl)pyridin-2-yl]methyl]phenyl)methyl]-2H-pyrazolo[3,4-d]pyrimidin-4-amine was prepared in a similar manner as Example 647. $^1$H NMR (300 MHz, DMSO-d$_6$): δ 8.30-8.25 (m, 3H), 7.44 (t, J=7.8 Hz, 1H), 7.32-7.17 (m, 6H), 6.61 (d, J=8.4 Hz, 1H), 6.51 (d, J=7.2 Hz, 1H), 5.49 (s, 2H), 4.75 (d, J=2.1 Hz, 2H), 3.87 (s, 2H), 3.85 (s, 3H), 3.67 (t, J=4.5 Hz, 4H), 3.40 (t, J=4.5 Hz, 4H). LC-MS (ESI) m/z: calculated for $C_{30}H_{29}ClFN_7O_2$:573.21. found: 574 [M+H]$^+$.

Example 677

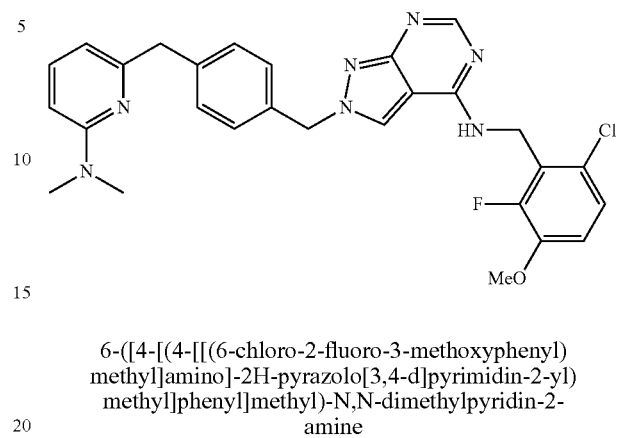

6-([4-[(4-[[(6-chloro-2-fluoro-3-methoxyphenyl)methyl]amino]-2H-pyrazolo[3,4-d]pyrimidin-2-yl)methyl]phenyl]methyl)-N,N-dimethylpyridin-2-amine 6-([4-[(4-[[(6-chloro-2-fluoro-3-methoxyphenyl)methyl]amino]-2H-pyrazolo[3,4-d]pyrimidin-2-yl)methyl]phenyl]methyl)-N,N-dimethylpyridin-2-amine was prepared in a similar manner as Example 647. $^1$H NMR (300 MHz, DMSO-d$_6$): δ 8.30-8.25 (m, 3H), 7.39-7.17 (m, 7H), 6.42-6.37 (m, 2H), 5.48 (s, 2H), 4.75 (d, J=2.1 Hz, 2H), 3.85 (s, 5H), 2.97 (s, 6H). LC-MS (ESI) m/z: calculated for $C_{28}H_{27}ClFN_7O$: 531.19. found: 532 [M+H]$^+$.

Example 680

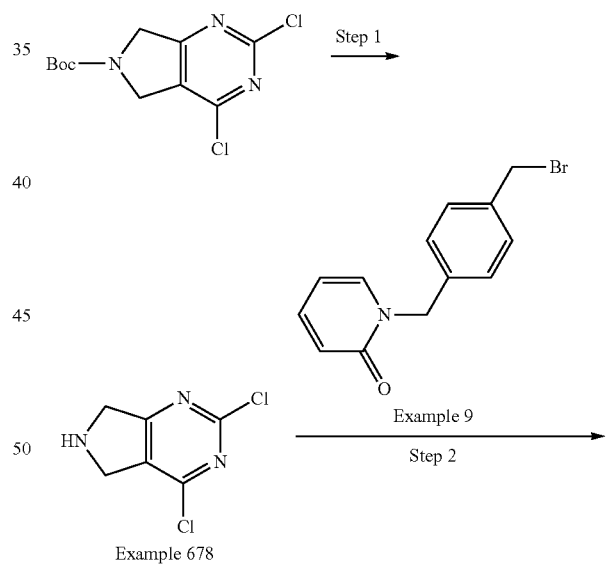

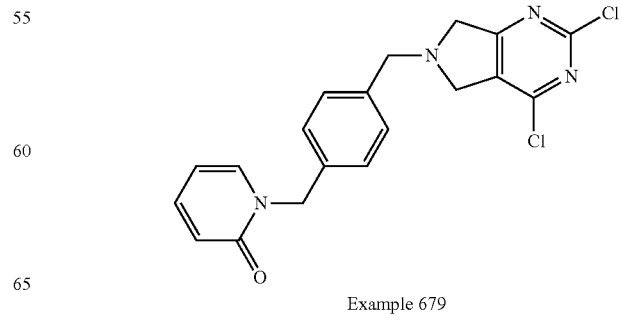

-continued

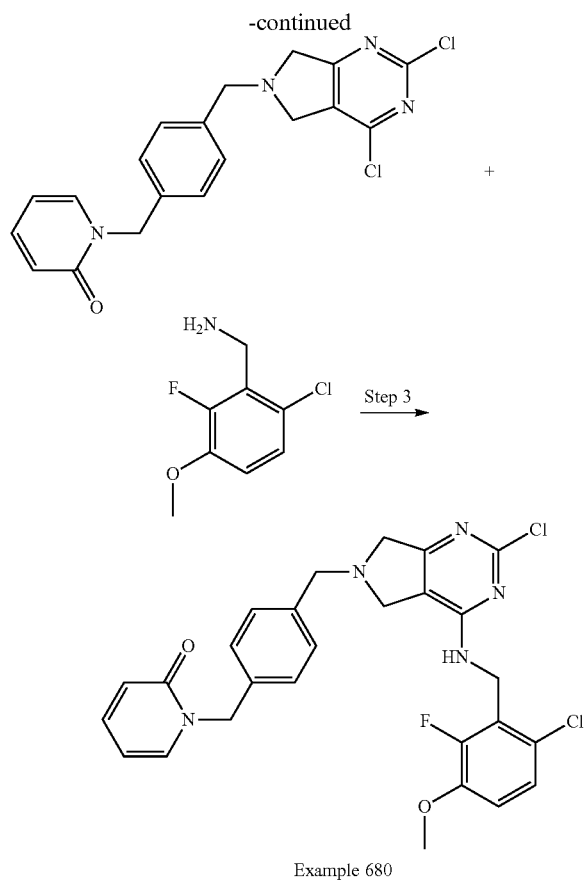

Example 680

Step 1. 2,4-dichloro-6,7-dihydro-5H-pyrrolo[3,4-d]pyrimidine

Trifluoroacetic acid (2.64 ml; 34.47 mmol; 5.00 eq.) was added to a solution of commercial tert-butyl 2,4-dichloro-5H,6H,7H-pyrrolo[3,4-d]pyrimidine-6-carboxylate (2.00 g; 6.89 mmol; 1.00 eq.) in dichloromethane (10.00 ml) and the reaction mixture was left stirring at room temp for 4h. The solvent was removed under vacuum and the residue was further dried under high vacuum. The crude oil solidified and was used as is in the next step.

Step 2. 1-(4-((4-bromo-2-chloro-5,7-dihydro-6H-pyrrolo[3,4-d]pyrimidin-6-yl)methyl)benzyl)pyridin-2(1H)-one. Hunig's base (2.75 ml; 15.79 mmol; 5.00 eq.) was added to a solution of 2,4-dichloro-5H,6H,7H-pyrrolo[3,4-d]pyrimidine (600.00 mg; 3.16 mmol; 1.00 eq.) in 2-methyltetrahydrofuran (3.00 ml) and the reaction mix was stirred until complete dissolution. 1-{[4-(bromomethyl)phenyl]methyl}-1,2-dihydropyridin-2-one (439.11 mg; 1.58 mmol; 0.50 eq.) was added to it and the reaction mix was left stirring overnight at RT. The reaction mix was diluted with water and EtOAc. The organic phase was isolated and the aqueous layer was back extracted with EtOAc. The aqueous layer was back extracted twice and the combined organics were concentrated to dryness. The isolated 1-(4-((4-bromo-2-chloro-5,7-dihydro-6H-pyrrolo[3,4-d]pyrimidin-6-yl)methyl)benzyl)pyridin-2(1H)-one (870 mg) was used as is in the next step. MS (M+H)$^+$ found for $C_{19}H_{16}BrClN_4O$: 388.

Step 3. 1-(4-((2-chloro-4-((6-chloro-2-fluoro-3-methoxybenzyl)amino)-5,7-dihydro-6H-pyrrolo[3,4-d]pyrimidin-6-yl)methyl)benzyl)pyridin-2(1H)-one. Hunig's base (0.02 ml; 0.01 mmol; 1.50 eq.) was added to a solution of 1-(4-((4-bromo-2-chloro-5,7-dihydro-6H-pyrrolo[3,4-d]pyrimidin-6-yl)methyl)benzyl)pyridin-2(1H)-one (25.00 mg; 0.006 mmol; 1.00 eq.) and (6-chloro-2-fluoro-3-methoxyphenyl)methanamine (13.46 mg; 0.007 mol; 1.10 eq.) in N,N-dimethylformamide (1.00 ml) and the reaction mix was heated at 40° C. for 1 h. The reaction mix was diluted with EtOAc and water. The organic layer was isolated and washed with brine, dried (MgSO$_4$) and the solvents removed under vacuum. The crude was purified on a silica gel column using 0-10% MeOH in DCM. The product obtain after concentration of the fractions was suspended in acetonitrile and water, freeze and lyophilized to give the desired 1-(4-((2-chloro-4-((6-chloro-2-fluoro-3-methoxybenzyl)amino)-5,7-dihydro-6H-pyrrolo[3,4-d]pyrimidin-6-yl)methyl)benzyl)pyridin-2(1H)-one (20 mg). $^1$H NMR (400 MHz, DMSO-d$_6$) δ 7.85-7.60 (m, 2H), 7.39 (ddd, J=9.0, 6.6, 2.1 Hz, 1H), 7.30 (d, J=8.0 Hz, 2H), 7.25-7.19 (m, 3H), 7.14 (t, J=8.9 Hz, 1H), 6.19 (d, J=1.4 Hz, OH), 5.04 (s, 2H), 4.53 (dd, J=4.5, 2.0 Hz, 2H), 3.80 (d, J=9.5 Hz, 7H), 3.51 (d, J=2.9 Hz, 2H). MS (M+H)$^+$ found for $C_{27}H_{24}Cl_2FN_5O_2$: 540.2.

Example 681

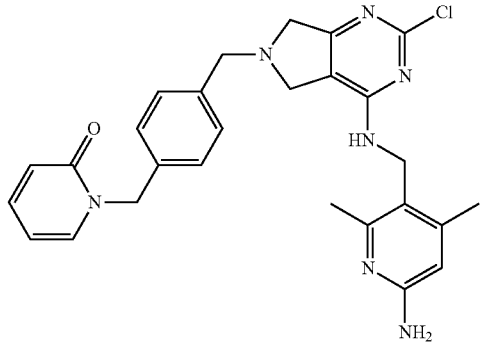 [SMILES: Cc1cc(N)nc(C)c1CNc1nc(Cl)nc2c1CN(Cc1ccc(Cn3ccccc3=O)cc1)C2]

1-(4-((4-(((6-amino-2,4-dimethylpyridin-3-yl)methyl)amino)-2-chloro-5,7-dihydro-6H-pyrrolo[3,4-d]pyrimidin-6-yl)methyl)benzyl)pyridin-2(1H)-one 1-(4-((4-(((6-amino-2,4-dimethylpyridin-3-yl)methyl)amino)-2-chloro-5,7-dihydro-6H-pyrrolo[3,4-d]pyrimidin-6-yl)methyl)benzyl)pyridin-2(1H)-one was prepared in a similar manner as Example 468 using Example 679. $^1$H NMR (400 MHz, DMSO-d$_6$) δ 13.44 (s, 1H), 7.79 (dd, J=6.8, 2.1 Hz, 1H), 7.63 (s, 2H), 7.51-7.37 (m, 3H), 7.32 (d, J=7.7 Hz, 2H), 6.61 (s, 1H), 6.24 (dd, J=6.7, 1.4 Hz, 1H), 5.09 (s, 2H), 4.34 (d, J=4.6 Hz, 4H), 2.34 (s, 3H). MS (M+H)$^+$ found for $C_{27}H_{28}ClN_7O$: 502.2.

423

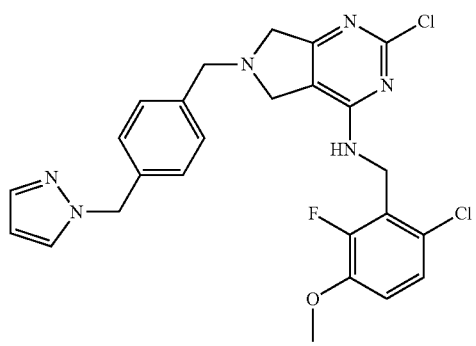 [SMILES: COc1ccc(Cl)c(CNc2nc(Cl)nc3c2CN(Cc2ccc(Cn4cccn4)cc2)C3)c1F]

6-(4-((1H-pyrazol-1-yl)methyl)benzyl)-2-chloro-N-(6-chloro-2-fluoro-3-methoxybenzyl)-6,7-dihydro-5H-pyrrolo[3,4-d]pyrimidin-4-amine 6-(4-((1H-pyrazol-1-yl)methyl)benzyl)-2-chloro-N-(6-chloro-2-fluoro-3-methoxybenzyl)-6,7-dihydro-5H-pyrrolo[3,4-d]pyrimidin-4-amine was prepared in a similar manner as Example 680. $^1$H NMR (400 MHz, DMSO-d$_6$) δ 7.78 (t, J=3.7 Hz, 2H), 7.43 (d, J=1.8 Hz, 1H), 7.29 (d, J=7.9 Hz, 2H), 7.26-7.10 (m, 4H), 6.24 (t, J=2.1 Hz, 1H), 5.28 (s, 2H), 4.54 (dd, J=4.8, 1.9 Hz, 2H), 3.80 (d, J=8.8 Hz, 7H), 3.51 (s, 2H). MS (M+H)$^+$ found for C$_{25}$H$_{23}$Cl$_2$FN$_6$O: 513.5/515.5.

Example 683

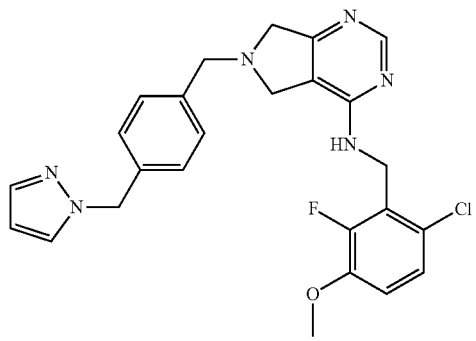 [SMILES: COc1ccc(Cl)c(CNc2ncnc3c2CN(Cc2ccc(Cn4cccn4)cc2)C3)c1F]

6-(4-((1H-pyrazol-1-yl)methyl)benzyl)-N-(6-chloro-2-fluoro-3-methoxybenzyl)-6,7-dihydro-5H-pyrrolo[3,4-d]pyrimidin-4-amine 6-(4-((1H-pyrazol-1-yl)methyl)benzyl)-N-(6-chloro-2-fluoro-3-methoxybenzyl)-6,7-dihydro-5H-pyrrolo[3,4-d]pyrimidin-4-amine was prepared in a similar manner as Example 680. $^1$H NMR (400 MHz, DMSO-d$_6$) δ 8.34 (s, 1H), 7.79 (d, J=2.2 Hz, 1H), 7.43 (d, J=1.8 Hz, 1H), 7.33-7.09 (m, 8H), 6.24 (t, J=2.0 Hz, 1H), 5.28 (s, 2H), 4.58 (dd, J=4.8, 2.0 Hz, 2H), 3.86-3.73 (m, 7H), 3.54 (s, 2H). MS (M+H)$^+$ found for C$_{25}$H$_{24}$ClFN$_6$O: 478.8/480.8.

424

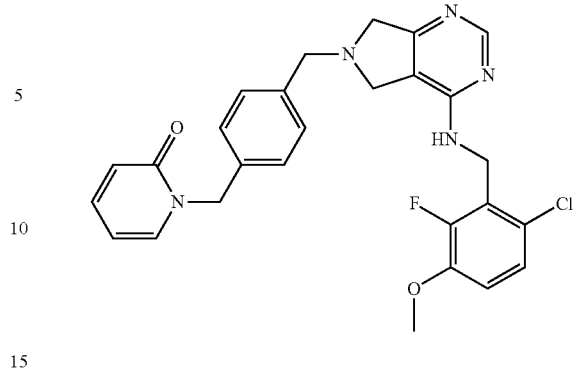

1-(4-((4-((6-chloro-2-fluoro-3-methoxybenzyl)amino)-5,7-dihydro-6H-pyrrolo[3,4-d]pyrimidin-6-yl)methyl)benzyl)pyridin-2(1H)-one 1-(4-((4-((6-chloro-2-fluoro-3-methoxybenzyl)amino)-5,7-dihydro-6H-pyrrolo[3,4-d]pyrimidin-6-yl)methyl)benzyl)pyridin-2(1H)-one was prepared in a similar manner as Example 680. $^1$H NMR (400 MHz, DMSO-d$_6$) δ 8.34 (s, 1H), 7.76 (dd, J=6.6, 2.1 Hz, 1H), 7.46-7.02 (m, 10H), 6.38 (dd, J=9.0, 1.3 Hz, 1H), 6.21 (td, J=6.7, 1.4 Hz, 1H), 5.05 (s, 2H), 4.58 (dd, J=4.6, 2.0 Hz, 2H), 3.88-3.67 (m, 8H), 3.54 (s, 2H). MS (M+H)$^+$ found for C$_{25}$H$_{24}$ClFN$_6$O: 506/508.

Example 685

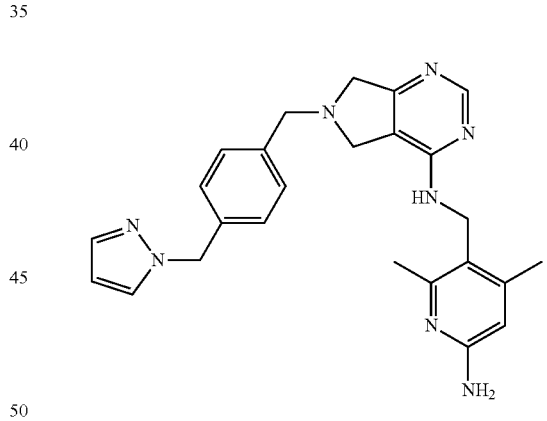

6-(4-((1H-pyrazol-1-yl)methyl)benzyl)-N-((6-amino-2,4-dimethylpyridin-3-yl)methyl)-6,7-dihydro-5H-pyrrolo[3,4-d]pyrimidin-4-amine 6-(4-((1H-pyrazol-1-yl)methyl)benzyl)-N-((6-amino-2,4-dimethylpyridin-3-yl)methyl)-6,7-dihydro-5H-pyrrolo[3,4-d]pyrimidin-4-amine was prepared in a similar manner as Example 681. $^1$H NMR (400 MHz, DMSO-d$_6$) δ 8.34 (s, 1H), 7.80 (d, J=2.3 Hz, 1H), 7.43 (d, J=1.8 Hz, 1H), 7.31 (d, J=7.8 Hz, 2H), 7.17 (d, J=7.9 Hz, 2H), 6.98 (s, 1H), 6.30 (s, 1H), 6.24 (t, J=2.1 Hz, 1H), 5.29 (s, 2H), 4.35 (d, J=4.5 Hz, 2H), 3.82 (d, J=11.1 Hz, 4H), 3.58 (s, 2H), 2.31 (s, 3H), 2.18 (s, 3H). MS (M+H)$^+$ found for C$_{25}$H$_{28}$N$_8$: 441.

Example 686

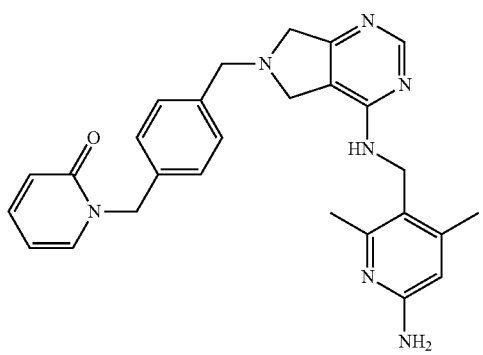 [SMILES: Cc1cc(N)nc(C)c1CNc1ncnc2c1CN(Cc1ccc(Cn3ccccc3=O)cc1)C2]

1-(4-((4-(((6-amino-2,4-dimethylpyridin-3-yl)methyl)amino)-5,7-dihydro-6H-pyrrolo[3,4-d]pyrimidin-6-yl)methyl)benzyl)pyridin-2(1H)-one 1-(4-((4-(((6-amino-2,4-dimethylpyridin-3-yl)methyl)amino)-5,7-dihydro-6H-pyrrolo[3,4-d]pyrimidin-6-yl)methyl)benzyl)pyridin-2(1H)-one was prepared in a similar manner as Example 681. $^1$H NMR (400 MHz, DMSO-d$_6$) δ 8.33 (s, 1H), 7.76 (dd, J=6.8, 2.0 Hz, 1H), 7.39 (ddd, J=8.9, 6.6, 2.1 Hz, 1H), 7.35-7.18 (m, 4H), 6.92 (s, 1H), 6.47-6.32 (m, 1H), 6.25-6.16 (m, 1H), 5.05 (s, 2H), 4.33 (d, J=4.4 Hz, 2H), 3.78 (d, J=10.4 Hz, 4H), 3.55 (s, 2H), 2.24 (s, 3H), 2.11 (s, 3H). MS (M+H)$^+$ found for C$_{27}$H$_{29}$N$_7$O: 468.

Example 687

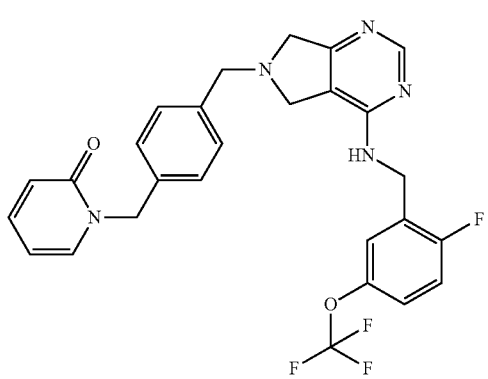 [SMILES: O=c1ccccn1Cc1ccc(CN2Cc3ncnc(NCc4cc(OC(F)(F)F)ccc4F)c3C2)cc1]

1-(4-((4-((2-fluoro-5-(trifluoromethoxy)benzyl)amino)-5,7-dihydro-6H-pyrrolo[3,4-d]pyrimidin-6-yl)methyl)benzyl)pyridin-2(1H)-one. It was prepared following the same synthetic path reported for Example 684 using 2-fluoro-5-(trifluoromethoxy)benzamide instead of 6-chloro-2-fluoro-3-methoxyphenyl)methanamine. $^1$H NMR (400 MHz, DMSO-d$_6$) δ 8.28 (s, 1H), 7.77 (dd, J=6.8, 2.1 Hz, 1H), 7.58 (t, J=5.9 Hz, 1H), 7.47-7.13 (m, 9H), 6.45-6.32 (m, 1H), 6.22 (td, J=6.7, 1.4 Hz, 1H), 5.07 (s, 2H), 4.56 (d, J=5.7 Hz, 2H), 3.84 (s, 2H), 3.79 (d, J=2.5 Hz, 2H), 3.66 (d, J=2.4 Hz, 2H). MS (M+H)$^+$ found for C$_{27}$H$_{23}$F$_4$N$_5$O$_2$: 526.

Example 688

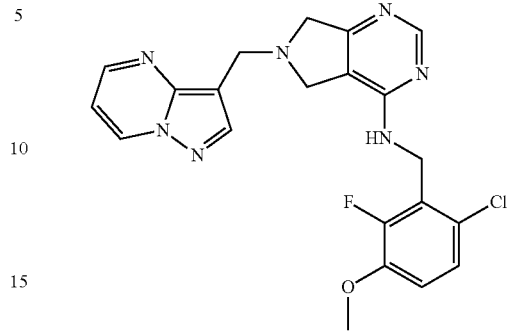

N-(6-chloro-2-fluoro-3-methoxybenzyl)-6-(pyrazolo[1,5-a]pyrimidin-3-ylmethyl)-6,7-dihydro-5H-pyrrolo[3,4-d]pyrimidin-4-amine. Given that the starting N-(6-chloro-2-fluoro-3-methoxybenzyl)-6,7-dihydro-5H-pyrrolo[3,4-d]pyrimidin-4-amine (Example 417) material was a TFA salt, 90 mg of the crude starting material were weighed, assuming that there were ~61 mg of the compound in it. Sodium triacetoxy borohydride (83.55 mg; 0.04 mmol; 2.00 eq.) was added to a solution containing a mixture of the starting amine (60.85 mg; 0.02 mmol; 1.00 eq.) and pyrazolo[1,5-a]pyrimidine-3-carbaldehyde (29.00 mg; 0.02 mmol; 1.00 eq.) in dichloromethane (1.45 ml) and the reaction mix was left stirring at RT overnight. The reaction was quenched by addition of NaHCO$_3$ solution and extracted twice with DCM. The combined organics were dried over Na$_2$SO$_4$, filtered and concentrated. The crude was purified by prep HPLC. The fractions containing the product were concentrated and the residue was taken in acetonitrile/water and freeze dried to give the desired N-(6-chloro-2-fluoro-3-methoxybenzyl)-6-(pyrazolo[1,5-a]pyrimidin-3-ylmethyl)-6,7-dihydro-5H-pyrrolo[3,4-d]pyrimidin-4-amine (53 mg). $^1$H NMR (400 MHz, DMSO-d6) δ 9.05 (dd, J=7.0, 1.7 Hz, 1H), 8.52 (dd, J=4.0, 1.7 Hz, 1H), 8.32 (s, 1H), 8.21 (s, 1H), 7.25-7.18 (m, 2H), 7.13 (t, J=8.9 Hz, 1H), 7.00 (dd, J=7.0, 3.9 Hz, 1H), 4.59 (dd, J=4.7, 2.0 Hz, 2H), 4.03 (s, 2H), 3.81 (s, 5H), 3.65 (d, J=2.4 Hz, 2H). MS (M+H)$^+$ found for C$_{21}$H$_{19}$ClFN$_7$O: 440.

Example 689

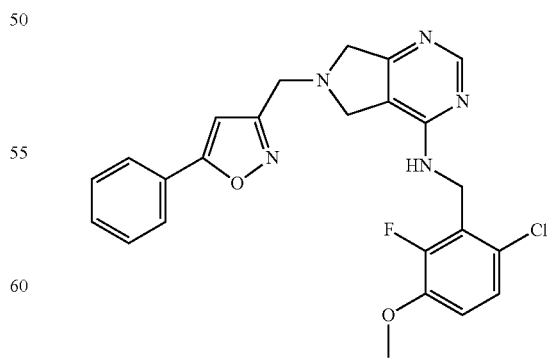

N-(6-chloro-2-fluoro-3-methoxybenzyl)-6-((5-phenylisoxazol-3-yl)methyl)-6,7-dihydro-5H-pyrrolo[3,4-d]pyrimidin-4-amine. It was prepared following the same synthetic path reported for Example 688 using 5-phenylisoxazole-3-carbaldehyde instead of pyrazolo[1,5-a]pyrimidine-3-carbaldehyde. ¹H NMR (400 MHz, DMSO-d6) δ 8.36 (s, 1H), 7.93-7.79 (m, 2H), 7.55-7.40 (m, 3H), 7.30 (t, J=4.7 Hz, 1H), 7.23 (dd, J=9.0, 1.7 Hz, 1H), 7.13 (t, J=8.9 Hz, 1H), 7.06 (s, 1H), 4.61 (dd, J=4.9, 2.0 Hz, 2H), 3.96 (s, 2H), 3.88 (d, J=2.4 Hz, 2H), 3.81 (s, 3H), 3.72 (s, 2H). MS (M+H)⁺ found for $C_{24}H_{21}ClFN_5O_2$: 466/468.

Example 690

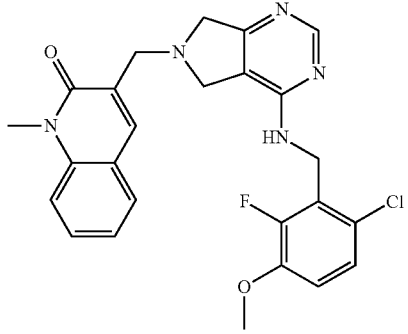 [SMILES: COc1ccc(Cl)c(CNc2ncnc3c2CN(Cc2cc4ccccc4n(C)c2=O)C3)c1F]

Preparation of 3-((4-((6-chloro-2-fluoro-3-methoxybenzyl)amino)-5,7-dihydro-6H-pyrrolo[3,4-d]pyrimidin-6-yl)methyl)-1-methylquinolin-2(1H)-one. It was prepared following the same synthetic path reported for Example 688 using 1-methyl-2-oxo-1,2-dihydroquinoline-3-carbaldehyde instead of pyrazolo[1,5-a]pyrimidine-3-carbaldehyde. ¹H NMR (400 MHz, DMSO-d6) δ 8.37 (s, 1H), 7.93 (s, 1H), 7.77 (dd, J=7.8, 1.5 Hz, 1H), 7.57 (ddd, J=8.6, 7.1, 1.5 Hz, 1H), 7.50 (d, J=8.3 Hz, 1H), 7.31-7.19 (m, 3H), 7.13 (t, J=8.9 Hz, 1H), 4.62 (dd, J=4.8, 2.0 Hz, 2H), 3.89 (t, J=2.3 Hz, 2H), 3.79 (d, J=12.2 Hz, 7H), 3.63 (s, 3H). MS (M+H)⁺ found for $C_{25}H_{23}ClFN_5O_2$: 480.

Example 691

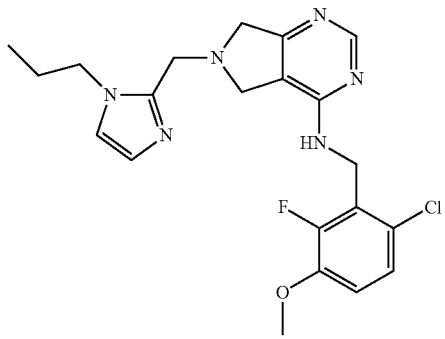 [SMILES: CCCn1ccnc1CN1Cc2ncnc(NCc3c(Cl)ccc(OC)c3F)c2C1]

N-(6-chloro-2-fluoro-3-methoxybenzyl)-6-((1-propyl-1H-imidazol-2-yl)methyl)-6,7-dihydro-5H-pyrrolo[3,4-d]pyrimidin-4-amine. It was prepared following the same synthetic path reported for Example 688 using 1-propyl-1H-imidazole-2-carbaldehyde instead of pyrazolo[1,5-a]pyrimidine-3-carbaldehyde. ¹H NMR (400 MHz, DMSO-d6) δ 8.33 (s, 1H), 7.33 (t, J=4.7 Hz, 1H), 7.23 (dd, J=8.9, 1.7 Hz, 1H), 7.14 (d, J=8.9 Hz, 1H), 7.11 (d, J=1.3 Hz, 1H), 6.76 (d, J=1.2 Hz, 1H), 4.60 (dd, J=4.8, 2.0 Hz, 2H), 3.92 (dd, J=7.9, 6.5 Hz, 2H), 3.87 (s, 2H), 3.82 (s, 3H), 3.77 (t, J=2.3 Hz, 2H), 3.62 (d, J=2.4 Hz, 2H), 1.68 (h, J=7.4 Hz, 2H), 0.80 (t, J=7.4 Hz, 3H). MS (M+H)⁺ found for $C_{21}H_{24}ClFN_6O$: 431

Example 692

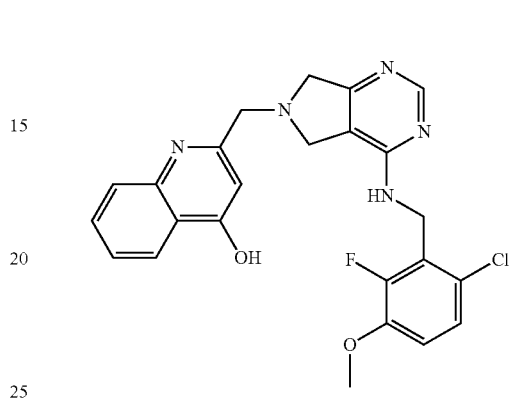

2-((4-((6-chloro-2-fluoro-3-methoxybenzyl)amino)-5,7-dihydro-6H-pyrrolo[3,4-d]pyrimidin-6-yl)methyl)quinolin-4-ol. It was prepared following the same synthetic path reported for Example 688 using 4-hydroxy-2-quinolinecarbaldehyde instead of pyrazolo[1,5-a]pyrimidine-3-carbaldehyde. ¹H NMR (400 MHz, DMSO-d6) δ 11.67 (s, 1H), 8.36 (s, 1H), 7.91 (dd, J=8.1, 1.3 Hz, 1H), 7.49-7.41 (m, 1H), 7.36-7.19 (m, 3H), 7.17-7.06 (m, 2H), 6.54 (d, J=1.8 Hz, 1H), 4.60 (dd, J=4.8, 2.0 Hz, 2H), 4.04 (s, 2H), 3.89 (d, J=2.3 Hz, 2H), 3.81 (s, 3H), 3.66 (t, J=2.2 Hz, 2H). MS (M+H)⁺ found for $C_{24}H_{21}ClFN_5O_2$: 466

Example 693

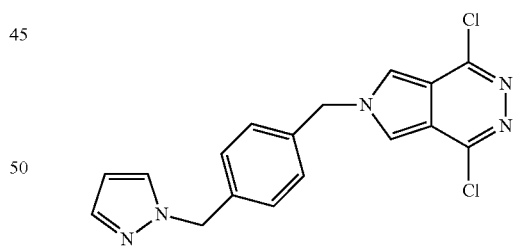

6-(4-((1H-pyrazol-1-yl)methyl)benzyl)-1,4-dichloro-6,7-dihydro-5H-pyrrolo[3,4-d]pyridazine 3,6-dichloro-4,5-dimethylpyridazine (2.00 g; 5.97 mmol; 1.00 eq.) (also containing some 3-bromo-4,5-bis(bromomethyl)-6-chloropyridazine was dissolved in THF (100 ml). Tetrabutylammonium iodide (0.22 g; 0.60 mmol; 0.10 eq.) and disodium carbonate (1.27 g; 11.95 mmol; 2.00 eq.) were added and the mixture was stirred. [4-(1H-pyrazol-1-ylmethyl)phenyl]methanamine (1.12 g; 5.97 mmol; 1.00 eq.) in THF (30 ml) was added in portions. The reaction mixture was warmed to reflux in a 75° C. heat block for 30 h. The solvent was evaporated and the residue was taken up in DCM (200 ml) and water (100 ml). The phases were separated and the organic phase was washed with brine (50 ml), dried over sodium sulfate and evaporated to a residue. The residue was purified by silica gel chromatography (ethyl acetate/hexanes gradient) to give a mixture of 1-{[4-({1,4-dichloro-6H-pyrrolo[3,4-d]pyridazin-6-yl}methyl)phenyl] methyl}-1H-pyrazole and the 1-bromo-4-chloro isomer (0.42 g) as a lightly colored amorphous residue, and a mixture of 6-(4-((1H-pyrazol-1-yl)methyl)benzyl)-1,4-dichloro-6,7-dihydro-5H-pyrrolo[3,4-d]pyridazine and the 1-bromo-4-chloro isomer (0.84 g) as a lightly colored glassy oil.

Example 694

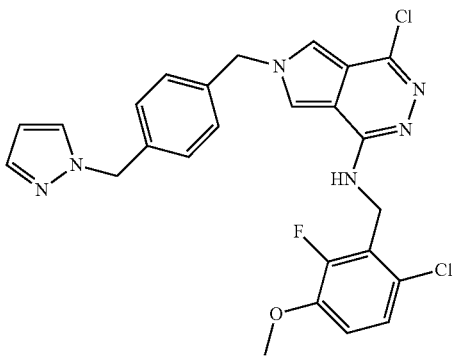 [SMILES: COc1ccc(Cl)c(CNc2nnc(Cl)c3cn(Cc4ccc(Cn5cccn5)cc4)cc23)c1F]

6-(4-((1H-pyrazol-1-yl)methyl)benzyl)-4-chloro-N-(6-chloro-2-fluoro-3-methoxybenzyl)-6H-pyrrolo[3,4-d]pyridazin-1-amine 1-{[4-({1,4-dichloro-6H-pyrrolo[3,4-d]pyridazin-6-yl}methyl)phenyl]methyl}-1H-pyrazole (106.00 mg; 0.30 mmol; 1.00 eq.)(Example 693) (also containing some bromo, chloro isomer) was suspended in 1-butanol (3.5 ml). (6-chloro-2-fluoro-3-methoxyphenyl)methanamine (58.91 mg; 0.31 mmol; 1.05 eq.) and Hunig's base-ethylbis(propan-2-yl)amine (51.54 ul; 0.30 mmol; 1.00 eq.) were added and the reaction was heated in a microwave reactor at 120° C. for 60 m. The reaction was reheated in the microwave at 140° C. for 1 h two times more and was then diluted with acetonitrile (10 ml) and evaporated. The resulting residue was purified by reverse phase chromatography (acetonitrile gradient with 0.1% aqueous formic acid, Waters XSelect CSH column) to give a mixture of 6-(4-((1H-pyrazol-1-yl) methyl)benzyl)-4-chloro-N-(6-chloro-2-fluoro-3-methoxybenzyl)-6H-pyrrolo[3,4-d]pyridazin-1-amine and 6-(4-((1H-pyrazol-1-yl)methyl)benzyl)-4-bromo-N-(6-chloro-2-fluoro-3-methoxybenzyl)-6H-pyrrolo[3,4-d]pyridazin-1-amine (13 mg) as a white solid. $^1$H NMR (400 MHz, CD$_3$OD) δ 7.70-7.64 (m, 2H), 7.58 (d, J=2.1 Hz, 1H), 7.49 (d, J=2.1 Hz, 1H), 7.29-7.17 (m, 5H), 7.11 (t, J=8.9 Hz, 1H), 6.31 (t, J=2.0 Hz, 1H), 5.42 (s, 2H), 5.33 (s, 2H), 4.78 (d, J=2.2 Hz, 2H), 3.88 (s, 3H). MS (M+H)$^+$ found for C$_{25}$H$_{21}$Cl$_2$FN$_6$O: 511.1.

Example 695

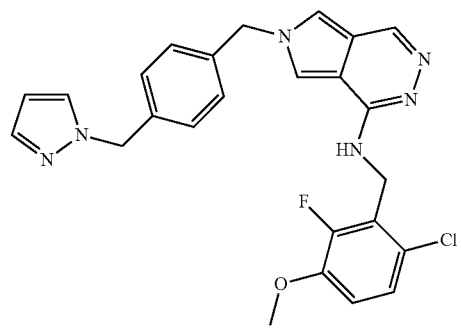 [SMILES: COc1ccc(Cl)c(CNc2nncc3cn(Cc4ccc(Cn5cccn5)cc4)cc23)c1F]

6-(4-((1H-pyrazol-1-yl)methyl)benzyl)-N-(6-chloro-2-fluoro-3-methoxybenzyl)-6H-pyrrolo[3,4-d]pyridazin-1-amine Palladium (7.37 mg; 0.01 mmol; 0.20 eq.) on carbon was combined with 4-chloro-N-[(6-chloro-2-fluoro-3-methoxyphenyl)methyl]-6-{[4-(1H-pyrazol-1-ylmethyl)phenyl] methyl}-6H-pyrrolo[3,4-d]pyridazin-1-amine (17.70 mg; 0.03 mmol; 1.00 eq., also containing some 6-(4-((1H-pyrazol-1-yl)methyl)benzyl)-4-bromo-N-(6-chloro-2-fluoro-3-methoxybenzyl)-6H-pyrrolo[3,4-d]pyridazin-1-amine)(Example 694) in ethanol (3 ml) The flask was charged with H$_2$ gas. After 19 h, more palladium (7.37 mg; 0.01 mmol; 0.20 eq.) was added and stirring was continued for 24 h. The reaction mixture was filtered through Celite and evaporated to a residue which was purified by reverse phase chromatography (acetonitrile gradient with 0.1% aqueous formic acid, Waters XSelect CSH column) to give 6-(4-((1H-pyrazol-1-yl)methyl)benzyl)-N-(6-chloro-2-fluoro-3-methoxybenzyl)-6H-pyrrolo[3,4-d]pyridazin-1-amine (2 mg) as an off-white solid. $^1$H NMR (400 MHz, CD$_3$OD) δ 8.66 (s, 1H), 8.55 (s, 1H), 7.78 (s, 1H), 7.75-7.65 (m, 2H), 7.50 (d, J=2.0 Hz, 1H), 7.30-7.12 (m, 6H), 6.32 (t, J=2.1 Hz, 1H), 5.46 (s, 2H), 5.35 (d, J=5.2 Hz, 2H), 4.82 (d, J=2.1 Hz, 2H), 3.88 (d, J=8.8 Hz, 3H). MS (M+H)$^+$ found for C$_{25}$H$_{22}$ClFN$_6$O: 477.1.

Example 696

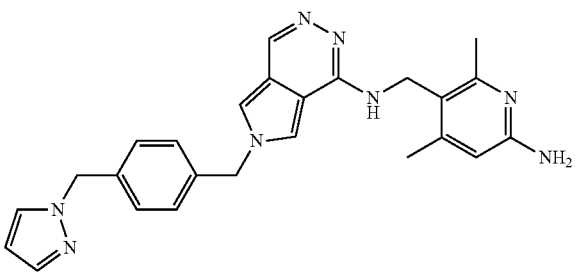 [SMILES: Cc1cc(N)nc(C)c1CNc1nncc2cn(Cc3ccc(Cn4cccn4)cc3)cc12]

6-(4-((1H-pyrazol-1-yl)methyl)benzyl)-N-((6-amino-2,4-dimethylpyridin-3-yl)methyl)-6H-pyrrolo[3,4-d]pyridazin-1-amine 6-(4-((1H-pyrazol-1-yl)methyl)benzyl)-N-((6-amino-2,4-dimethylpyridin-3-yl)methyl)-6H-pyrrolo[3,4-d]pyridazin- 1-amine was prepared in a similar manner as Example 695. $^1$H NMR (400 MHz, CD$_3$OD) δ 8.76 (s, 1H), 7.94 (s, 2H), 7.71 (d, J=2.3 Hz, 1H), 7.51 (d, J=2.0 Hz, 1H), 7.34 (d, J=7.8 Hz, 2H), 7.24 (d, J=7.9 Hz, 2H), 6.76 (s, 1H), 6.33 (t, J=2.1 Hz, 1H), 5.54 (s, 2H), 5.36 (s, 2H), 4.61 (s, 2H), 2.58 (s, 3H), 2.44 (s, 3H). MS (M+H)$^+$ found for C$_{25}$H$_{26}$N$_8$ 439.2.

Example 697

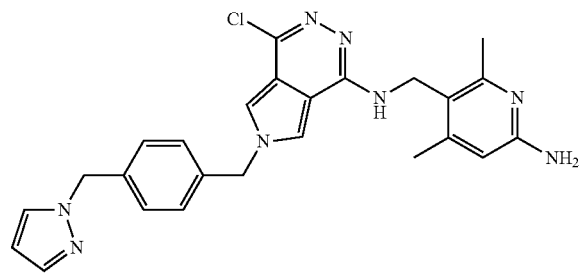 [SMILES: Cc1cc(N)nc(C)c1CNc1nnc(Cl)c2cn(Cc3ccc(Cn4cccn4)cc3)cc12]

6-(4-((1H-pyrazol-1-yl)methyl)benzyl)-N-((6-amino-2,4-dimethylpyridin-3-yl)methyl)-4-chloro-6H-pyrrolo[3,4-d]pyridazin-1-amine 6-(4-((1H-pyrazol-1-yl)methyl)benzyl)-N-((6-amino-2,4-dimethylpyridin-3-yl)methyl)-4-chloro-6H-pyrrolo[3,4-d]pyridazin-1-amine was prepared in a similar manner as Example 695. $^1$H NMR (400 MHz, cd$_3$od) δ 8.32 (s, 1H), 7.73 (d, J=2.0 Hz, 1H), 7.68 (dd, J=7.9, 2.2 Hz, 2H), 7.50 (d, J=1.9 Hz, 1H), 7.35-7.19 (m, 4H), 6.56 (s, 1H), 6.32 (t, J=2.1 Hz, 1H), 5.46 (s, 2H), 5.35 (s, 2H), 4.56 (s, 2H), 2.50 (s, 3H), 2.37 (s, 3H). MS (M+H)$^+$ found for C$_{25}$H$_{25}$ClN$_8$ 473.3.

Example 698

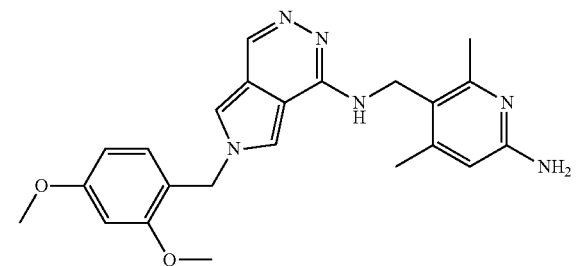 [SMILES: COc1ccc(Cn2cc3cnnc(NCc4c(C)cc(N)nc4C)c3c2)c(OC)c1]

N-((6-amino-2,4-dimethylpyridin-3-yl)methyl)-6-(2,4-dimethoxybenzyl)-6H-pyrrolo[3,4-d]pyridazin-1-amine N-((6-amino-2,4-dimethylpyridin-3-yl)methyl)-6-(2,4-dimethoxybenzyl)-6H-pyrrolo[3,4-d]pyridazin-1-amine was prepared in a similar manner as Example 695. $^1$H NMR (400 MHz, CD$_3$OD) δ 8.64 (s, 1H), 7.93 (s, 1H), 7.77 (d, J=1.9 Hz, 1H), 7.27 (d, J=8.3 Hz, 1H), 6.61-6.51 (m, 2H), 6.42 (s, 1H), 5.38 (s, 2H), 4.56 (s, 2H), 3.83-3.78 (m, 6H), 2.41 (s, 3H), 2.28 (s, 3H). MS (M+H)$^+$ found for C$_{23}$H$_{26}$N$_6$O$_2$: 419.2.

Example 699

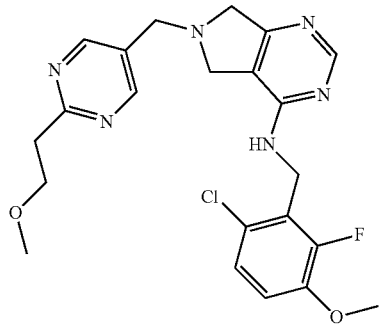 [SMILES: COCCc1ncc(CN2Cc3ncnc(NCc4c(Cl)ccc(OC)c4F)c3C2)cn1]

N-(6-chloro-2-fluoro-3-methoxybenzyl)-6-((2-(2-methoxyethyl)pyrimidin-5-yl)methyl)-6,7-dihydro-5H-pyrrolo[3,4-d]pyrimidin-4-amine N-(6-chloro-2-fluoro-3-methoxybenzyl)-6-((2-(2-methoxyethyl)pyrimidin-5-yl)methyl)-6,7-dihydro-5H-pyrrolo[3,4-d]pyrimidin-4-amine was prepared following the same synthetic path reported for Example 688. $^1$H NMR (400 MHz, CD$_3$OD) δ 8.75 (s, 2H), 8.39 (s, 1H), 7.19 (dd, J=8.9, 1.9 Hz, 1H), 7.07 (t, J=8.9 Hz, 1H), 4.78 (d, J=2.0 Hz, 2H), 3.97 (s, 2H), 3.93-3.86 (m, 7H), 3.83-3.79 (m, 2H), 3.19 (t, J=6.4 Hz, 2H). MS (M+H)$^+$ found for C$_{22}$H$_{24}$ClFN$_6$O$_2$: 459.1.

Example 700

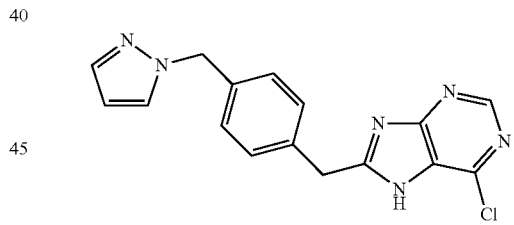

8-(4-((1H-pyrazol-1-yl)methyl)benzyl)-6-chloro-7H-purine

Combined 2-[4-(1H-pyrazol-1-ylmethyl)phenyl]acetic acid (Fichert, Thomas; Yazdanian, Mehran; Proudfoot, John R. Bioorganic and Medicinal Chemistry Letters, 2003, vol. 13, #4 p. 719-722)(400.00 mg; 1.85 mmol; 1.00 eq.) and 6-chloropyrimidine-4,5-diamine (267.42 mg; 1.85 mmol; 1.00 eq.) in POCl$_3$ (5.00 ml). Heated the reaction to 90° C. for 3 hours. Let the reaction cool to rt. Concentrated. Diluted with water, neutralized with sat'd NaHCO3, and extracted with ethyl acetate. Combined organics, dried with MgSO$_4$, filtered, and concentrated. Purified by Biotage silica gel column to afford 8-(4-((1H-pyrazol-1-yl)methyl)benzyl)-6-chloro-7H-purine (319 mgs; 53%). MS (M+H)+ found for C$_{16}$H$_{13}$ClN$_6$ : 325.0.

Example 701

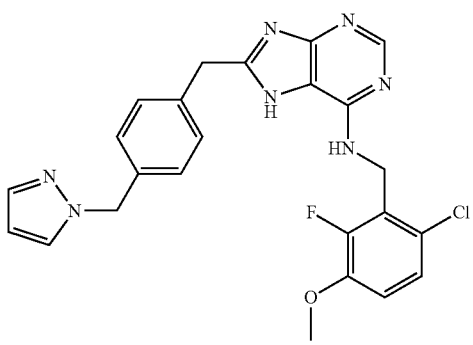 [SMILES: COc1ccc(Cl)c(CNc2ncnc3nc(Cc4ccc(Cn5cccn5)cc4)[nH]c23)c1F]

8-(4-((1H-pyrazol-1-yl)methyl)benzyl)-N-(6-chloro-2-fluoro-3-methoxybenzyl)-7H-purin-6-amine Combined 6-chloro-8-{[4-(1H-pyrazol-1-ylmethyl)phenyl]methyl}-7H-purine (200.00 mg; 0.62 mmol; 1.00 eq.), 6-chloro-2-fluoro-3-methoxybenzylamine (116.77 mg; 0.62 mmol; 1.00 eq.)(Example 700), and Hunig's base (0.21 ml; 1.23 mmol; 2.00 eq.) in acetonitrile (2.00 ml) in a microwave vial. Heated the reaction in a microwave at 100° C. for 15 minutes. Diluted reaction with water, extracted with ethyl acetate, combined organics, dried with MgSO$_4$, filtered and concentrated. Purified by prep HPLC to afford 8-(4-((1H-pyrazol-1-yl)methyl)benzyl)-N-(6-chloro-2-fluoro-3-methoxybenzyl)-7H-purin-6-amine (37 mgs; 12%). $^1$H NMR (400 MHz, Methanol-d$_4$) δ 8.24 (s, 1H), 7.65 (d, J=2.3 Hz, 1H), 7.48 (dd, J=2.0, 0.7 Hz, 1H), 7.31-7.24 (m, 2H), 7.23-7.14 (m, 3H), 7.07 (t, J=8.9 Hz, 1H), 6.29 (t, J=2.2 Hz, 1H), 5.31 (s, 2H), 4.17 (s, 2H), 3.87 (s, 3H). MS (M+H)+ found for C$_{24}$H$_{21}$ClFN$_7$O: 478.0.

Example 702

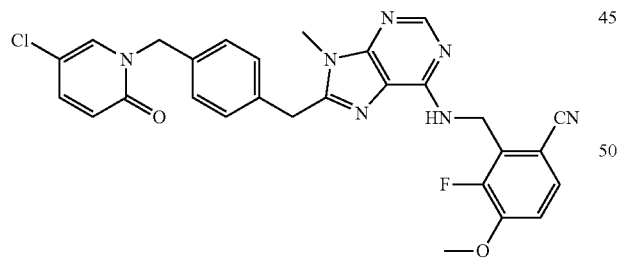

2-(((8-(4-((5-chloro-2-oxopyridin-1(2H)-yl)methyl)benzyl)-9-methyl-9H-purin-6-yl)amino)methyl)-3-fluoro-4-methoxybenzonitrile 2-(((8-(4-((5-chloro-2-oxopyridin-1(2H)-yl)methyl)benzyl)-9-methyl-9H-purin-6-yl)amino)methyl)-3-fluoro-4-methoxybenzonitrile was prepared in a similar manner as Example 701. $^1$H NMR (300 MHz, DMSO-d6): δ 8.83 (br. s, 2H), 8.54 (d, J=9.0 Hz, 2H), 8.01 (d, J=9.6 Hz, 1H), 7.69 (d, J=8.7 Hz, 1H), 7.32-7.21 (m, 5H), 7.11 (d, J=9.6 Hz, 1H), 5.38-5.35 (m, 4H), 4.22 (s, 2H), 3.89 (s, 3H), 3.62 (s, 3H). LC-MS (ESI) m/z: calculated for C$_{30}$H$_{24}$ClF$_4$N$_7$O$_4$: 657.15. found: 544 [M+H]$^+$.

Example 707

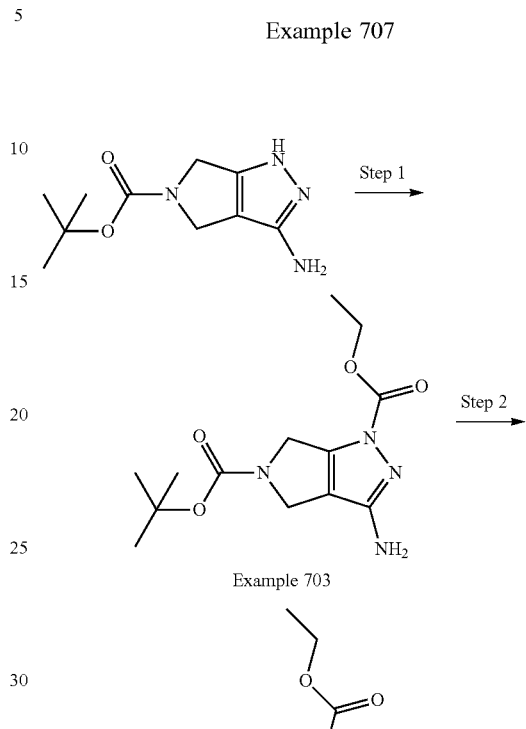

Example 703

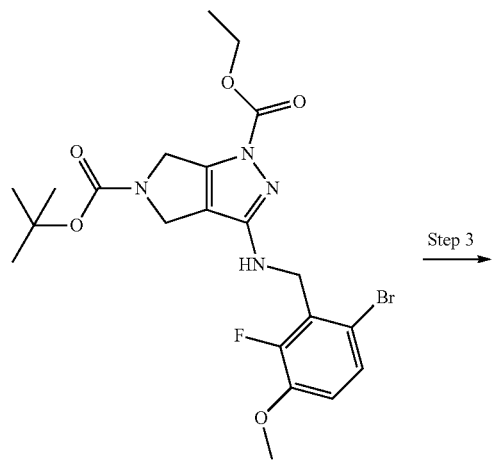

Example 704

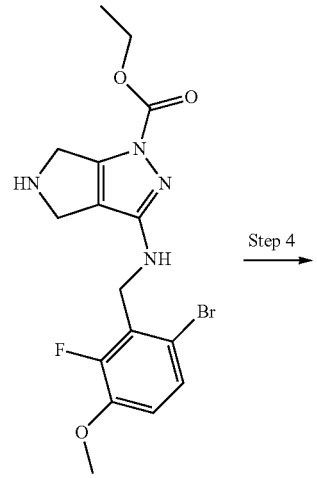

Example 705

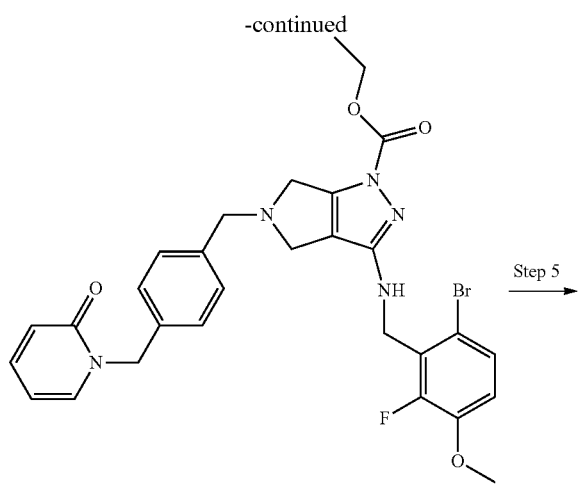

Example 706

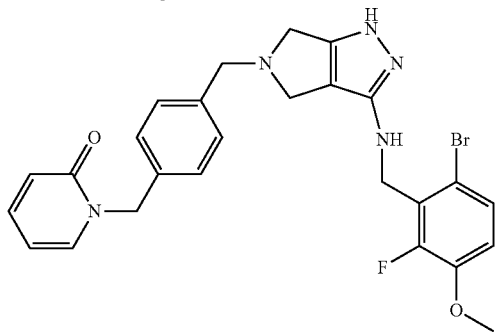

Example 707

Step 1. 5-(tert-butyl) 1-ethyl 3-amino-4,6-dihydropyrrolo[3,4-c]pyrazole-1,5-dicarboxylate. A solution of ethyl chloroformate (0.90 ml; 0.01 mol; 1.05 eq.) in 20 ml of THF was slowly added to a mixture of tert-butyl 3-amino-1H,4H,5H,6H-pyrrolo[3,4-c]pyrazole-5-carboxylate (2.00 g; 0.01 mol; 1.00 eq.) and Hunig's base (8.81 ml; 0.05 mol; 6.00 eq.) in tetrahydrofuran (50.00 ml) at 0-5° C. The reaction was kept at the same temperature for two hours, then allowed to reach room temperature and stirred overnight. The reaction mixture was evaporated to dryness and the resulting residue was partitioned in ethyl acetate and water. The organic phase was separated and the aqueous layer was back extracted with EtOAc. The combined organics were washed with brine, dried over $Na_2SO_4$, filtered and evaporated to dryness. The crude was purified by flash-chromatography using 0-90% EtOAc in hexanes to give the desired 5-(tert-butyl) 1-ethyl 3-amino-4,6-dihydropyrrolo[3,4-c]pyrazole-1,5-dicarboxylate (1.62 g). $^1$H NMR (400 MHz, DMSO-d6) δ 5.67 (d, J=2.2 Hz, 2H), 4.44 (dt, J=10.7, 3.1 Hz, 2H), 4.25 (q, J=7.1 Hz, 2H), 4.15 (dt, J=18.3, 3.2 Hz, 2H), 1.42 (s, 9H), 1.26 (td, J=7.1, 1.4 Hz, 3H). MS (M+H)$^+$ found for $C_{13}H_{20}N_4O_4$: 296.5.

Step 2. 5-(tert-butyl) 1-ethyl 3-((6-bromo-2-fluoro-3-methoxybenzyl)amino)-4,6-dihydropyrrolo[3,4-c]pyrazole-1,5-dicarboxylate. Sodium triacetoxyborohydride (286.09 mg; 0.136 mmol; 2.00 eq.) was added to a solution of 5-(tert-butyl) 1-ethyl 3-amino-4,6-dihydropyrrolo[3,4-c]pyrazole-1,5-dicarboxylate (200.00 mg; 0.06 mmol; 1.00 eq.) and 6-bromo-2-fluoro-3-methoxybenzaldehyde (157.28 mg; 0.06 mmol; 1.00 eq.) in dichloromethane (4.00 ml), followed by the addition of acetic acid (40.53 mg; 0.06 mmol; 1.00 eq.) and the reaction mix was left stirring at RT. After 1 h no traces of product were seen by LCMS. Some molecular sieves were added to the reaction flask and after 1 h a peak corresponding to the desired product was observed. Reaction mix was left stirring overnight. The reaction was quenched by addition of $NaHCO_3$ solution and extracted twice with DCM. The combined organics were dried over $Na_2SO_4$ filtered and concentrated. The crude was purified on silica gel column using 0-100% EtOAc on hexanes to give the desired 5-(tert-butyl) 1-ethyl 3-((6-bromo-2-fluoro-3-methoxybenzyl)amino)-4,6-dihydropyrrolo[3,4-c]pyrazole-1,5-dicarboxylate (70 mg). MS (M+H)$^+$ found for $C_{21}H_{26}BrFN_4O_5$: 513/515.

Step 3. ethyl 3-((6-bromo-2-fluoro-3-methoxybenzyl)amino)-5,6-dihydropyrrolo[3,4-c]pyrazole-1(4H)-carboxylate. Trifluoroacetic acid (0.63 ml; 0.01 mol; 60.00 eq.) was added to a solution of 5-(tert-butyl) 1-ethyl 3-((6-bromo-2-fluoro-3-methoxybenzyl)amino)-4,6-dihydropyrrolo[3,4-c]pyrazole-1,5-dicarboxylate (70.00 mg; 0.02 mmol; 1.00 eq.) in dichloromethane (1.40 ml) and the reaction mixture was left stirring at room temp for 2 h. The solvent was removed under vacuum and the residue was treated with toluene and concentrated. This was repeated a second time and the residue was further dried under high vacuum. The crude was purified on a silica gel column using 0-5% MeOH in DCM to give the desired 3-((6-bromo-2-fluoro-3-methoxybenzyl)amino)-5,6-dihydropyrrolo[3,4-c]pyrazole-1(4H)-carboxylate (34 mg). MS (M+H)$^+$ found for $C_{16}H_{18}BrFN_4O_3$: 414/416.

Step 4. ethyl 3-((6-bromo-2-fluoro-3-methoxybenzyl)amino)-5-(4-((2-oxopyridin-1(2H)-yl)methyl)benzyl)-5,6-dihydropyrrolo[3,4-c]pyrazole-1(4H)-carboxylate 1-{[4-(bromomethyl)phenyl]methyl}-1,2-dihydropyridin-2-one (20.19 mg; 0.07 mmol; 1.00 eq.) and Hunig's base (0.04 ml; 0.22 mmol; 3.00 eq.) were added to a solution of 3-((6-bromo-2-fluoro-3-methoxybenzyl)amino)-5,6-dihydropyrrolo[3,4-c]pyrazole-1(4H)-carboxylate (30.00 mg; 0.07 mmol; 1.00 eq.) in N,N-dimethylformamide (1.00 ml) and the reaction mix was left stirring at RT for 90 minutes. The reaction mix was cooled in an ice bath and treated with water drop wise. The precipitate that appeared was filtered. The solid was dissolved in DCM, loaded onto a silica gel column and eluted with 0-5% MeOH in DCM to give the desired ethyl 3-((6-bromo-2-fluoro-3-methoxybenzyl)amino)-5-(4-((2-oxopyridin-1(2H)-yl)methyl)benzyl)-5,6-dihydropyrrolo[3,4-c]pyrazole-1(4H)-carboxylate (32 mg). MS (M+H)$^+$ found for $C_{29}H_{29}BrFN_5O_4$: 610/612.

Step 5. 1-(4-((3-((6-bromo-2-fluoro-3-methoxybenzyl)amino)-4,6-dihydropyrrolo[3,4-c]pyrazol-5(1H)-yl)methyl)benzyl)pyridin-2(1H)-one. Triethylamine (0.07 ml; 0.49 mmol; 10.00 eq.) was added to a solution of ethyl 3-((6-bromo-2-fluoro-3-methoxybenzyl)amino)-5-(4-((2-oxopyridin-1(2H)-yl)methyl)benzyl)-5,6-dihydropyrrolo[3,4-c]pyrazole-1(4H)-carboxylate (30.00 mg; 0.05 mmol; 1.00 eq.) in methanol (0.90 ml) and the reaction mix was heated at 50° C. overnight. The solvent was removed under vacuum and the residue was purified on a silica gel column using 0-10% MeOH in DCM. The fractions containing the product were combined and concentrated to dryness. The residue was suspended in acetonitrile/water, freeze and lyophilized to give the desired 1-(4-((3-((6-bromo-2-fluoro-3-methoxybenzyl)amino)-4,6-dihydropyrrolo[3,4-c]pyrazol-5(1H)-yl)methyl)benzyl)pyridin-2(1H)-one (21 mg). $^1$H NMR (400 MHz, DMSO-d$_6$) δ 11.20 (s, 1H), 7.76 (dd, J=6.8, 2.1 Hz, 1H), 7.46-7.17 (m, 6H), 7.07 (t, J=8.9 Hz, 1H), 6.39 (ddd, J=9.1, 1.4, 0.7 Hz, 1H), 6.21 (td, J=6.6, 1.4 Hz, 1H), 5.30 (s, 1H), 5.06 (s, 2H), 4.35-4.11 (m, 2H), 3.81 (s, 4H), 3.52 (d, J=21.2 Hz, 3H). MS (M+H)+ found for $C_{21}H_{26}BrFN_4O_5$: 538/540.

All abbreviations used herein have their ordinary scientific meaning as known to the skilled artisan.

From the foregoing it will be appreciated that, although specific embodiments of the invention have been described herein for purposes of illustration, various modifications may be made without deviating from the spirit and scope of the invention.

Throughout the description of this invention, reference is made to various patent applications and publications, each of which are herein incorporated by reference in their entirety.

What is claimed is:
1. A compound of formula I:

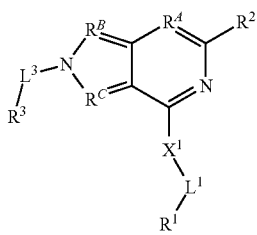

or a tautomer thereof, a pharmaceutically acceptable salt of each thereof, or a pharmaceutically acceptable solvate of each of the foregoing, wherein
each of $R^A$, $R^B$ and $R^C$ independently is N or $CR^{10}$;
$R^{10}$ is hydrogen, halo, hydroxy, optionally substituted $C_1$-$C_6$ alkoxy, or an optionally substituted $C_1$-$C_6$ alkyl;
$X^1$ is S, SO, $SO_2$, or $NR^{15}$;
$R^{15}$ is hydrogen;
each of $L^1$ and $L^3$ independently is $-(L^{11})_m(CO)_n(L^{12})_o-$;
$L^{11}$ and $L^{12}$ each independently are optionally substituted $C_1$-$C_3$ alkylene;
m is 1;
each of n and o is 0;
$R^1$ is $C_6$-$C_{10}$ aryl, 5-10 membered heteroaryl containing up to 3 ring heteroatoms, wherein the heteroatom is selected from the group consisting of O, N and S, and oxidized forms of N and S, a 4-15 membered heterocyclyl containing up to 5 ring heteroatoms, wherein the heteroatom is selected from the group consisting of O, N and S, and oxidized forms of N and S, or a $C_3$-$C_8$ cycloalkyl, wherein the aryl, heteroaryl, heterocyclyl, or cycloalkyl group is optionally substituted;
$R^3$ is substituted $C_6$-$C_{10}$ aryl, 5-10 membered heteroaryl containing up to 3 ring heteroatoms, wherein the heteroatom is selected from the group consisting of O, N and S, and oxidized forms of N and S, a 4-15 membered heterocyclyl containing up to 5 ring heteroatoms, wherein the heteroatom is selected from the group consisting of O, N and S, and oxidized forms of N and S, or a $C_3$-$C_8$ cycloalkyl, wherein the heteroaryl, heterocyclyl, or cycloalkyl group is optionally substituted;
$R^2$ is hydrogen, $-O-R^{30}$, $-NR^{31}R^{32}$, $CONR^{31}R^{32}$, CN, COOH, $NMe_2$, $C_6$-$C_{10}$ aryl, a 5-10 membered heteroaryl containing up to 3 ring heteroatoms, wherein the heteroatom is selected from the group consisting of O, N and S, and oxidized forms of N and S, a 4-15 membered heterocyclyl containing up to 5 ring heteroatoms, wherein the heteroatom is selected from the group consisting of O, N and S, and oxidized forms of N and S, or a $C_3$-$C_8$ cycloalkyl, wherein the aryl, heteroaryl, heterocyclyl, or cycloalkyl group is optionally substituted;
$R^{30}$ is hydrogen or optionally substituted $C_1$-$C_6$ alkyl, $C_3$-$C_8$ cycloalkyl, $C_6$-$C_{10}$ aryl, a 5-10 membered heteroaryl containing up to 3 ring heteroatoms, wherein the heteroatom is selected from the group consisting of O, N and S, and oxidized forms of N and S, or a 4-15 membered heterocyclyl containing up to 5 ring heteroatoms, wherein the heteroatom is selected from the group consisting of O, N and S, and oxidized forms of N and S;
$R^{31}$ is hydrogen; or $R^{32}$ and $R^{31}$ together with the nitrogen atom they are bonded to forms an optionally substituted 4-15 membered heterocyclyl containing up to 5 ring heteroatoms, wherein the heteroatom is selected from the group consisting of O, N and S, and oxidized forms of N and S; and
$R^{32}$ is hydrogen or optionally substituted $C_1$-$C_6$ alkyl.

2. The compound of claim 1 of formula I-A:

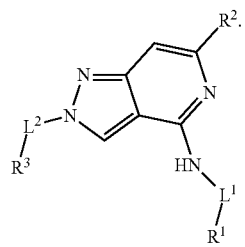

3. The compound of claim 1 of formula I-D:

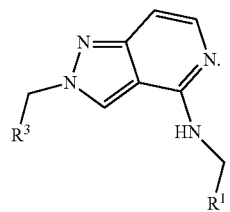

4. The compound of claim 1 of formula I-E:

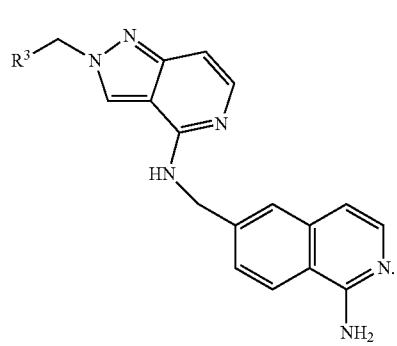

5. The compound of claim 1 of formula I-F:

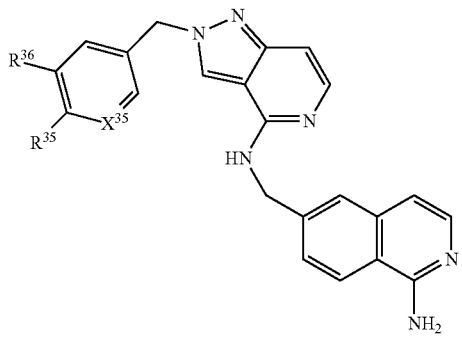

wherein $X^{35}$ is N or CH;
$R^{35}$ is methyl substituted with a 5 membered heteroaryl containing 2 nitrogen atoms, halo, $C_1$-$C_6$ alkoxy, —O-(6 membered heteroaryl containing a single nitrogen atom), or —O-(6 membered heterocyclyl containing a single nitrogen atom); and
$R^{36}$ is hydrogen or methyl, or $R^{35}$ and $R^{36}$ together with the intervening carbon atoms form a 5 membered heteroaryl containing 1-2 nitrogen atoms, wherein the heteroaryl is substituted with 1-2 $C_1$-$C_6$ alkyl groups.

6. The compound of claim 1 of formula I-G:

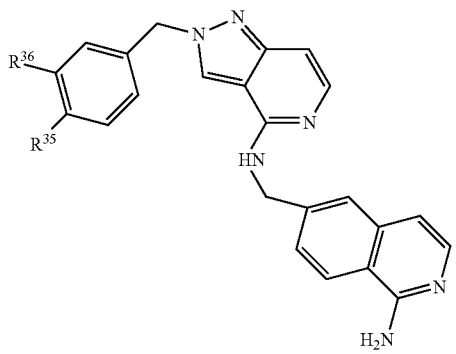

wherein $R^{35}$ is methyl substituted with a 5 membered heteroaryl containing 2 nitrogen atoms, —O-(6 membered heteroaryl containing a single nitrogen atom), or —O-(6 membered heterocyclyl containing a single nitrogen atom); and
$R^{36}$ is hydrogen, or $R^{35}$ and $R^{36}$ together with the intervening carbon atoms form a 5 membered heteroaryl containing 1-2 nitrogen atoms, wherein the heteroaryl is substituted with 1-2 $C_1$-$C_6$ alkyl groups.

7. The compound of claim 1 of formula I-H:

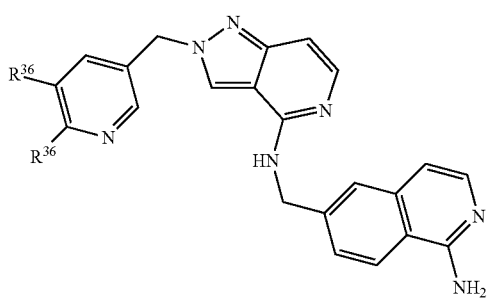

wherein
$R^{35}$ is $C_1$-$C_6$ alkoxy, —O-(6 membered heteroaryl containing a single nitrogen atom), or —O-(6 membered heterocyclyl containing a single nitrogen atom); and
$R^{36}$ is hydrogen or methyl.

8. The compound of claim 1 of the formula:

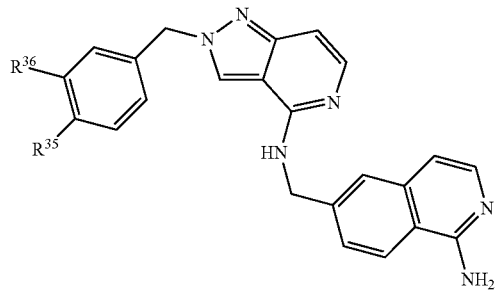

wherein
$R^{35}$ is methyl substituted with a 5 membered heteroaryl containing 2 nitrogen atoms, and
$R^{36}$ is hydrogen, or $R^{35}$ and $R^{36}$ together with the intervening carbon atoms form a 5 membered heteroaryl containing 1-2 nitrogen atoms, wherein the heteroaryl is substituted with 1-2 $C_1$-$C_6$ alkyl groups.

9. The compound of claim 1, wherein $R^A$ is $CR^{10}$.
10. The compound of claim 1, wherein $R^A$ is CH.
11. The compound of claim 1, wherein $R^A$ is N.
12. The compound of claim 1, wherein $R^B$ is N.
13. The compound of claim 1, wherein $R^B$ is $CR^{10}$.
14. The compound of claim 1, wherein $R^B$ is CH.
15. The compound of claim 1, wherein $R^C$ is $CR^{10}$.
16. The compound of claim 1, wherein $R^C$ is CH.
17. The compound of claim 1, wherein $R^C$ is N.
18. The compound of claim 1, wherein $X^1$ is —NH—.
19. The compound of claim 1, wherein $L^1$ is —CH$_2$—.
20. The compound of claim 1, wherein $R^1$ is optionally substituted $C_6$-$C_{10}$ aryl or optionally substituted 5-10 membered heteroaryl.
21. The compound of claim 1, wherein $L^3$ is —CH$_2$—.
22. The compound of claim 1, wherein $R^3$ is substituted $C_6$-$C_{10}$ aryl or optionally substituted 5-10 membered heteroaryl.
23. The compound of claim 1, wherein $R^3$ is 5-10 membered heteroaryl optionally substituted with optionally substituted $C_1$-$C_6$ alkyl groups.
24. The compound of claim 1, wherein $R^3$ is pyridyl optionally substituted with 1-2 substituents selected from amino, halo, $C_1$-$C_6$ alkoxy, —O—$C_3$-$C_8$ cycloalkyl, —O-(5-10 membered heteroaryl), —O—$C_6$-$C_{10}$ aryl, optionally substituted $C_1$-$C_6$ alkyl, $C_6$ $C_{10}$ aryl, 5-10 membered heteroaryl, a 4-15 membered heterocyclyl, and $C_3$-$C_8$ cycloalkyl substituents.
25. The compound of claim 1, wherein $R^2$ is hydrogen.
26. The compound of claim 1, wherein $R^2$ is —$OR^{30}$.
27. The compound of claim 1, wherein $R^2$ is —$NR^{31}R^{32}$.
28. The compound of claim 1, wherein $R^2$ is —$NHR^{32}$, CN, COOH, OH, or $NMe_2$, wherein $R^{32}$ is hydrogen or an optionally substituted $C_1$-$C_6$ alkyl.
29. The compound of claim 1, wherein -$L^3$-$R^3$ is selected from the group consisting of:

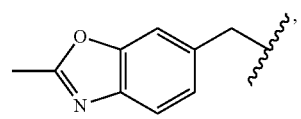

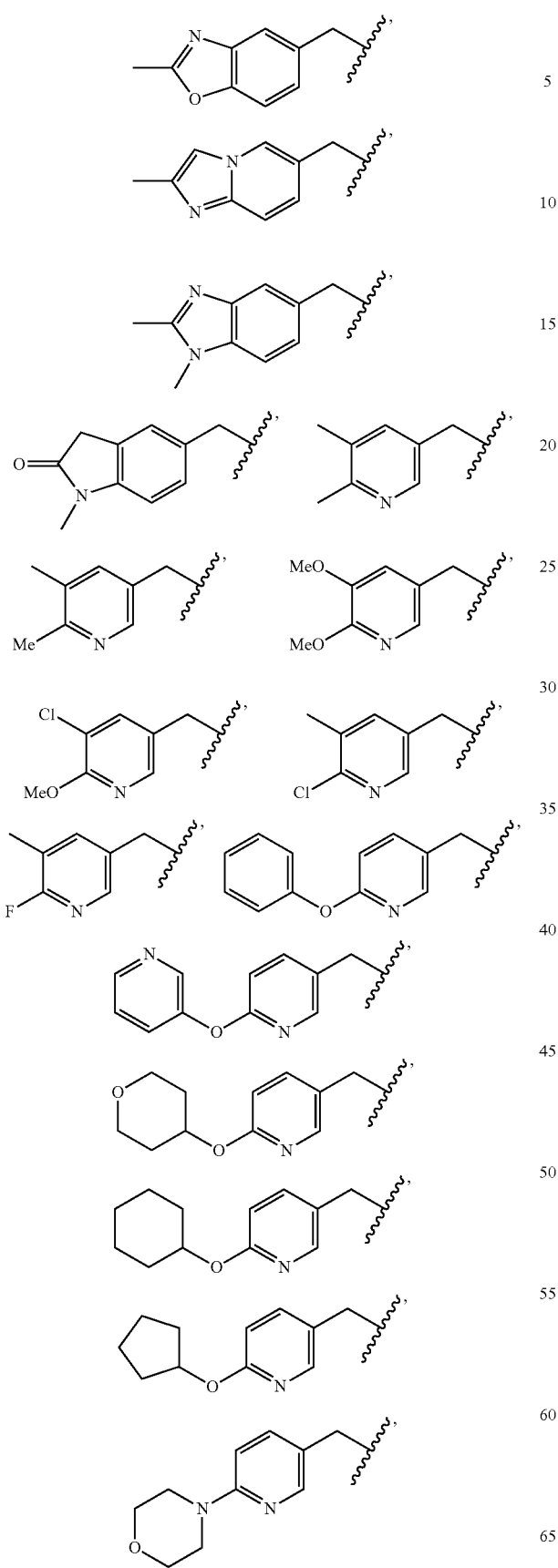
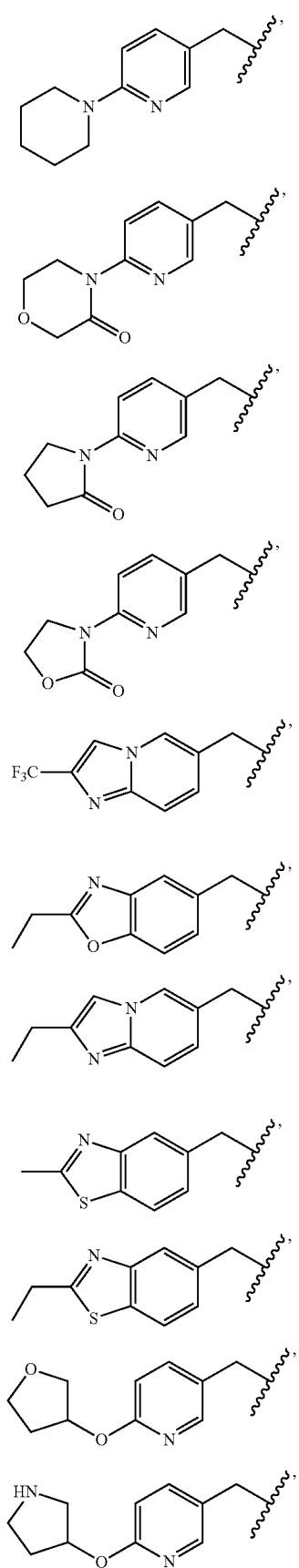

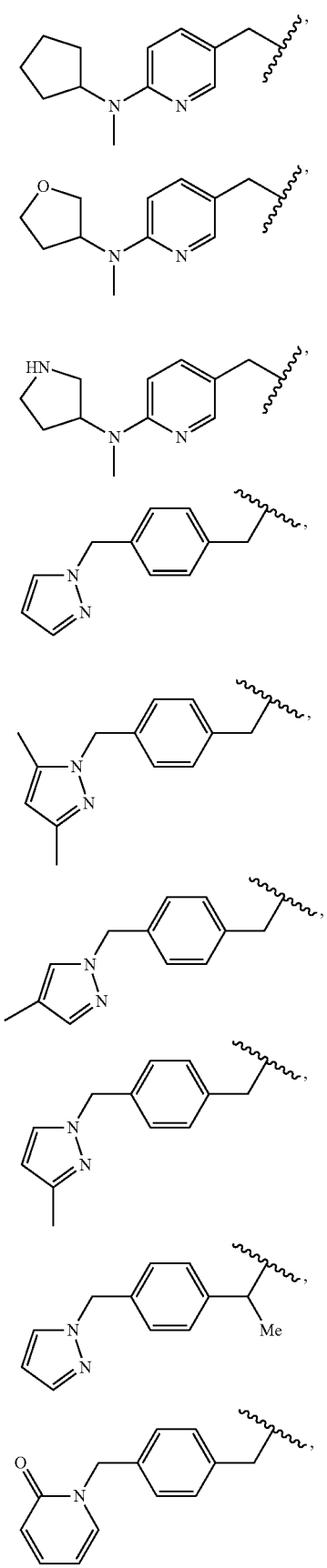
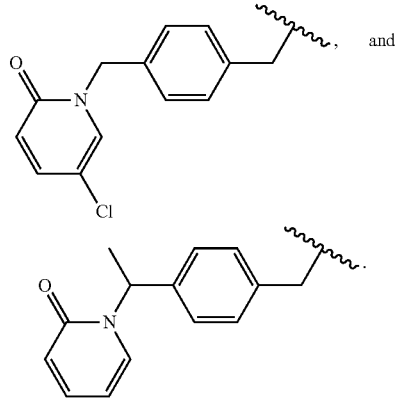
30. The compound of claim 1 wherein -L³-R³ is selected from the group consisting of:
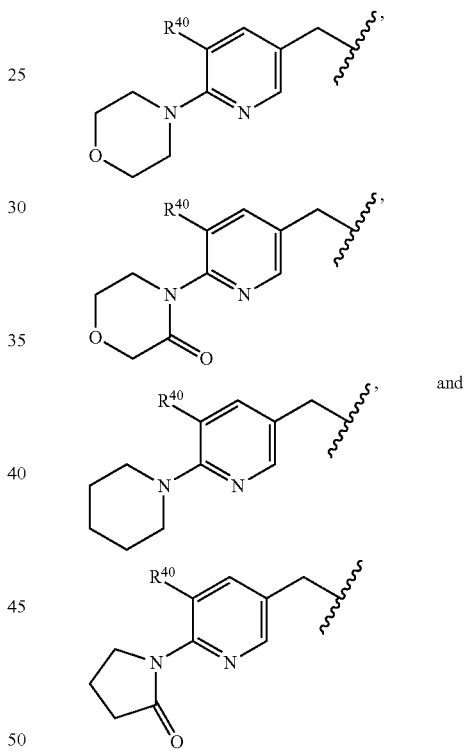
wherein R⁴⁰ is hydrogen.
31. The compound of claim 1, wherein -L¹-R¹ is selected from the group consisting of:
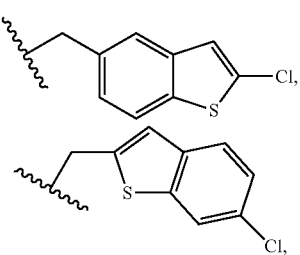

445
-continued
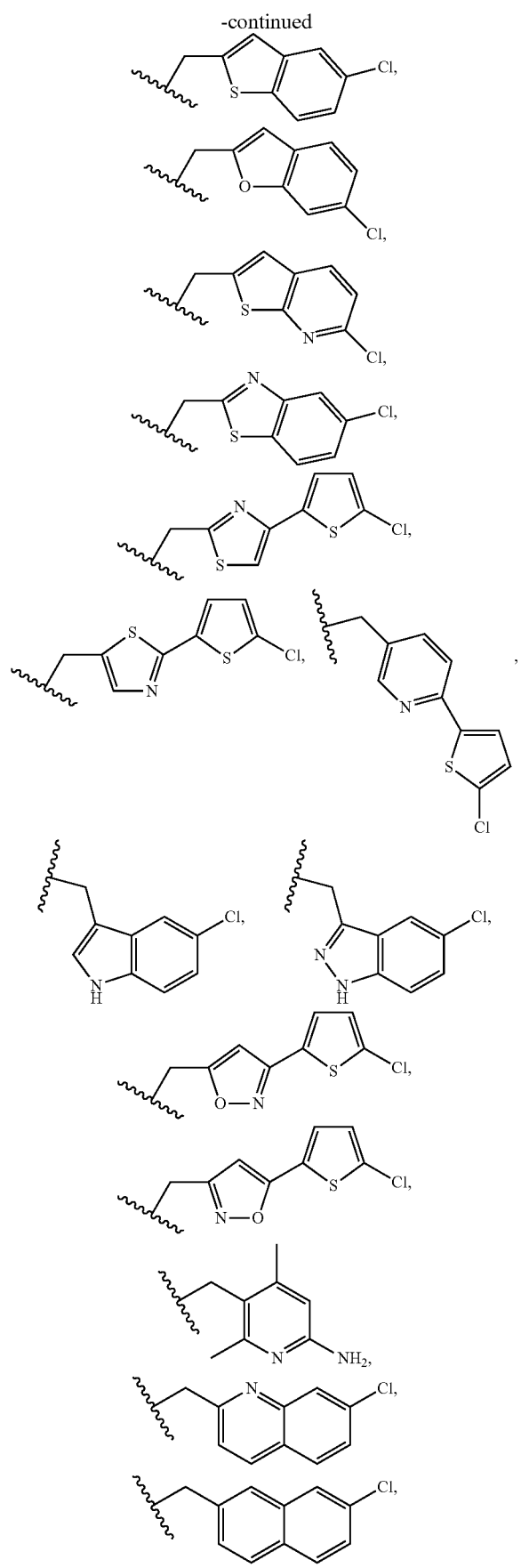
446
-continued
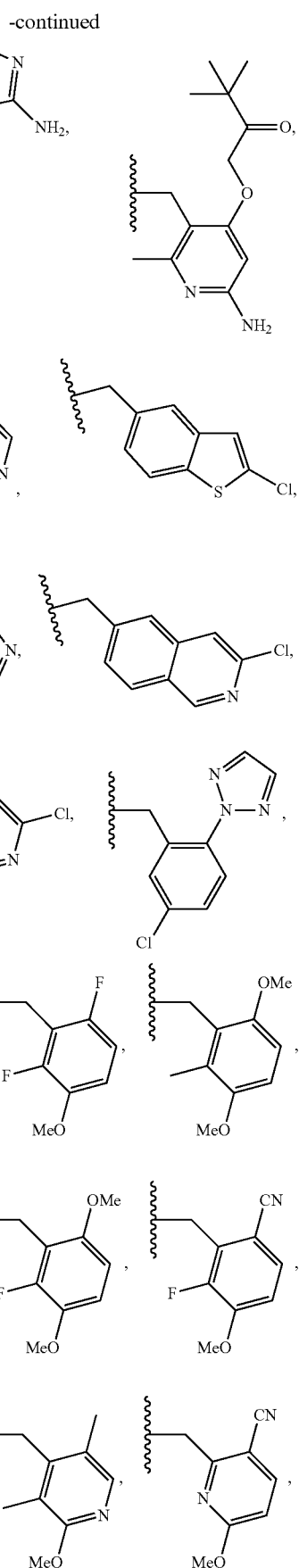

-continued
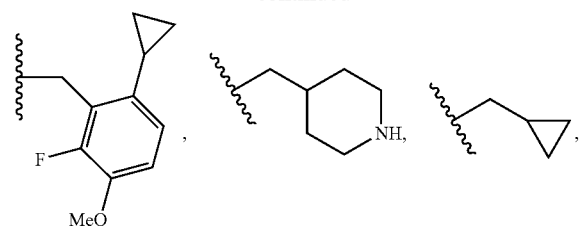
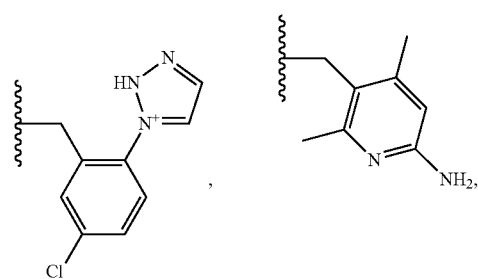
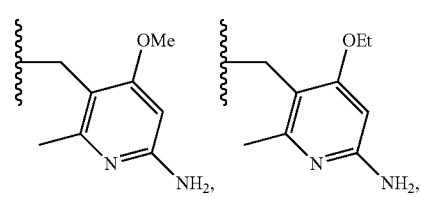
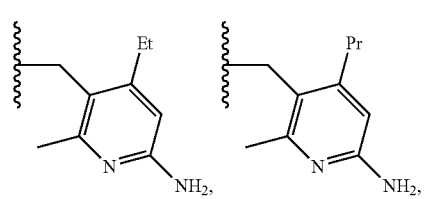
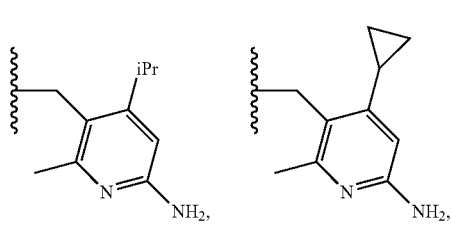
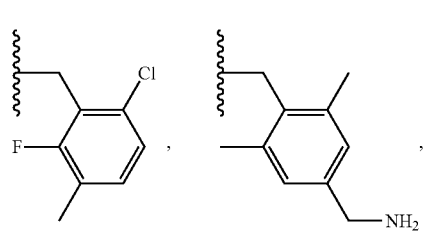
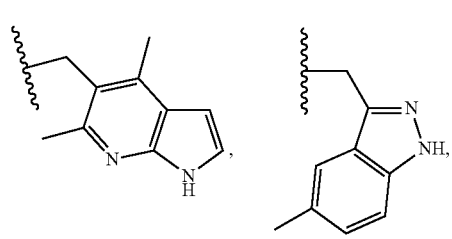
-continued
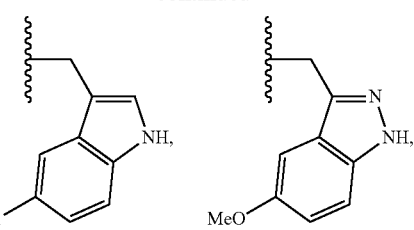
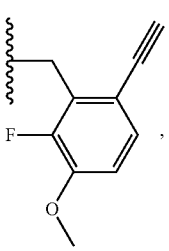
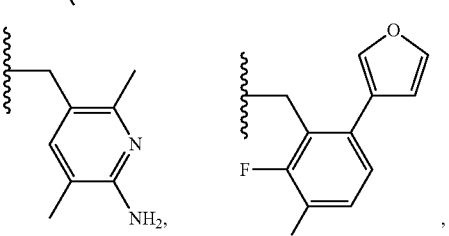
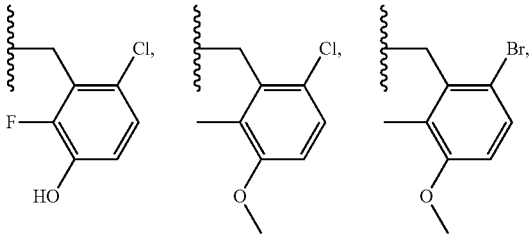
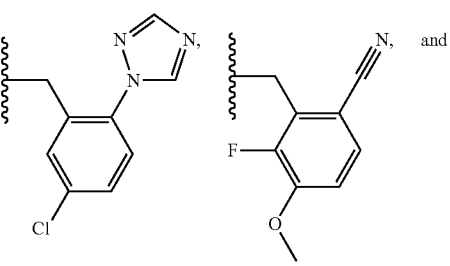
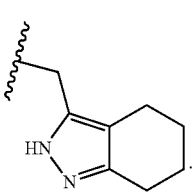
32. The compound of claim 1, wherein $R^2$ is selected from the group consisting of:
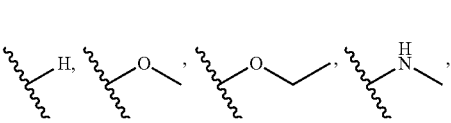
OH, CN, COOH, and NMe$_2$.

33. The compound of claim 1 selected from:
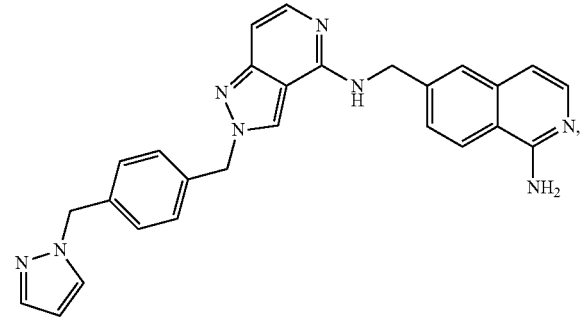
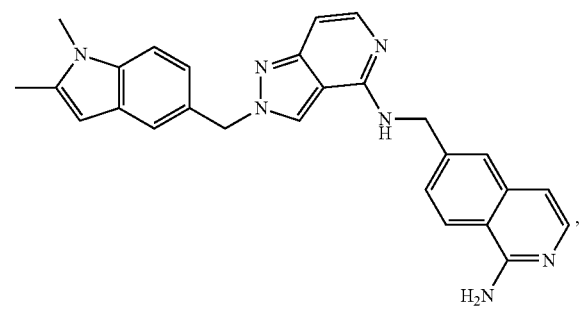
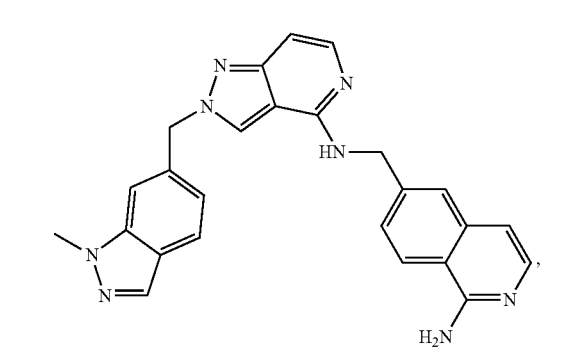
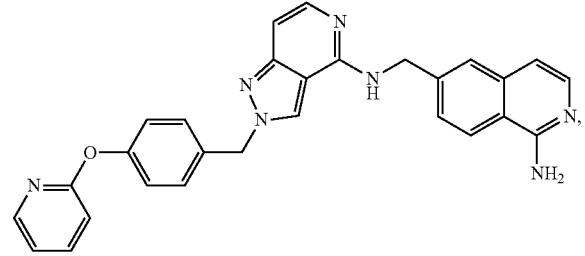
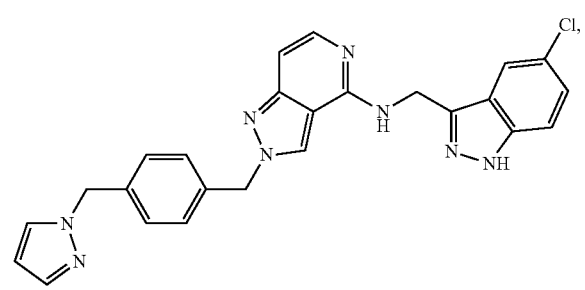
-continued
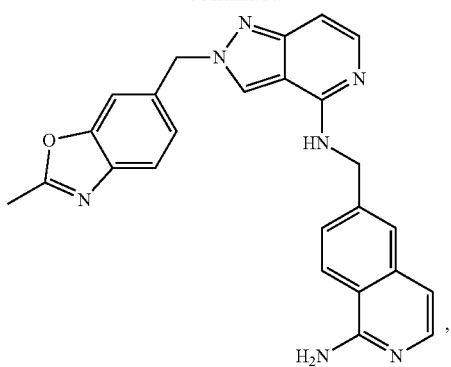
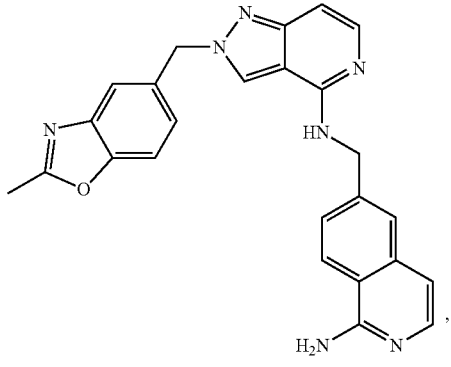
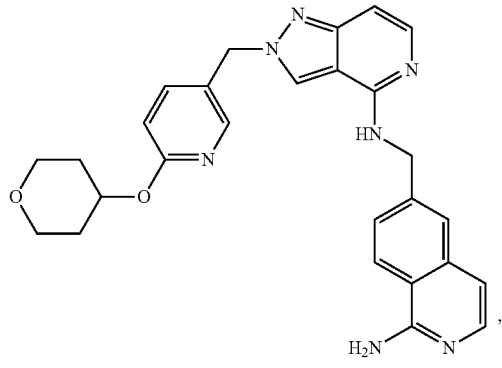
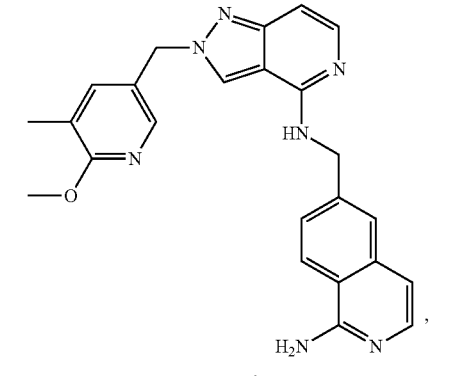
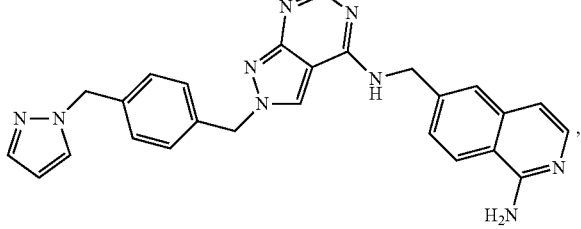

451
-continued
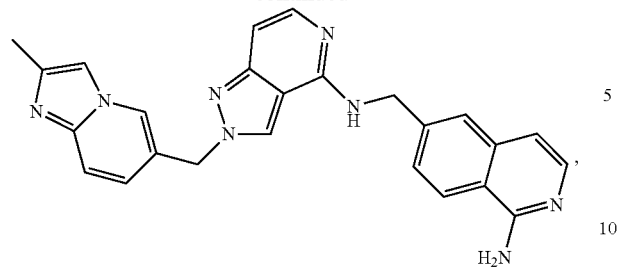
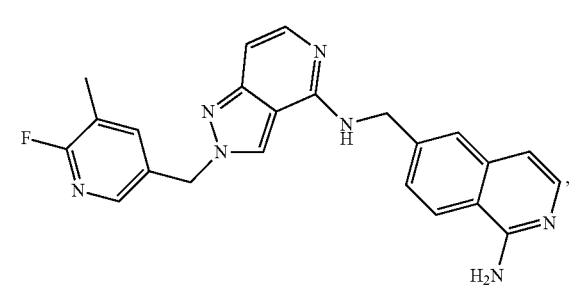
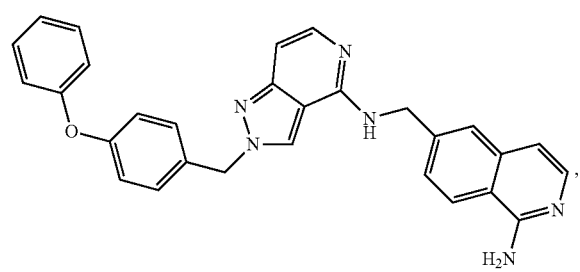
452
-continued
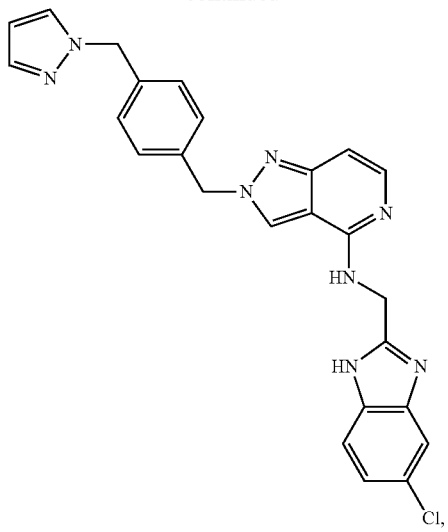
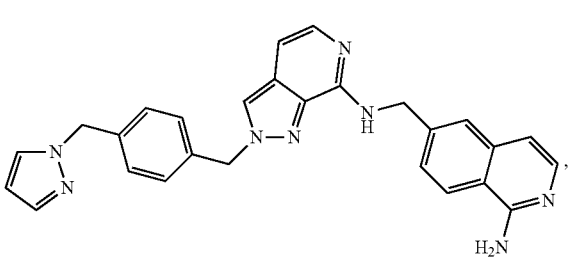
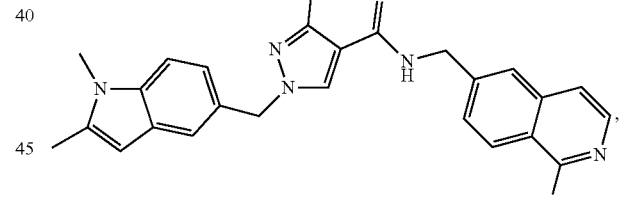
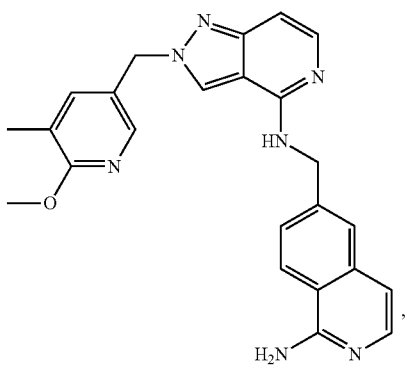

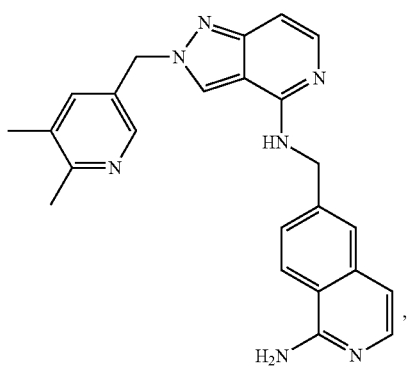

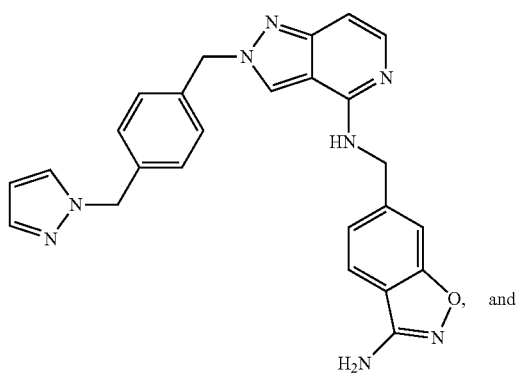

and

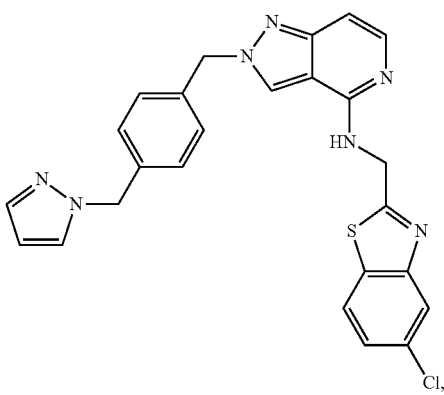

and or a tautomer thereof, a pharmaceutically acceptable salt of each thereof, or a pharmaceutically acceptable solvate of each of the foregoing.

34. The compound of claim 1 of formula:

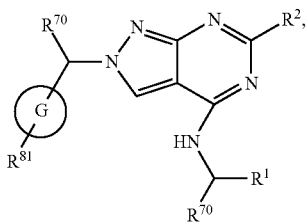

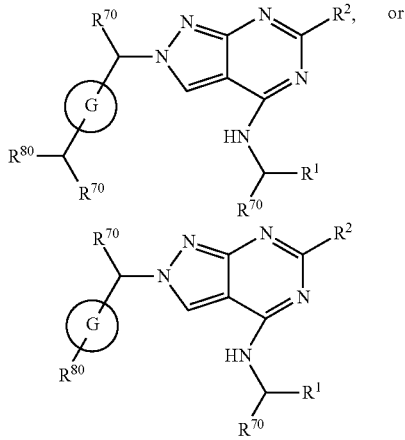

wherein:
G is optionally substituted $C_6$-$C_{10}$ aryl or optionally substituted heteroaryl;
$R^{70}$ is hydrogen;
$R^{80}$ is halo, optionally substituted $C_1$-$C_6$ alkyl, hydroxy, or optionally substituted heteroaryl; and
$R^{81}$ is hydrogen or optionally substituted alkyl.

35. The compound of claim 1 selected from:
6-{[(2-{[4-(1H-pyrazol-1-ylmethyl)phenyl]methyl}-2H-pyrazolo[4,3-c]pyridin-4-yl)amino] methyl}isoquinolin-1-amine;
6-{[(2-{[4-(1H-pyrazol-1-ylmethyl)phenyl]methyl}-2H-pyrazolo[3,4-c]pyridin-7-yl)amino] methyl}isoquinolin-1-amine;
6-[({2-[(1,2-dimethyl-1H-indol-5-yl)methyl]-2H-pyrazolo[4,3-c]pyridin-4-yl}amino)methyl]isoquinolin-1-amine;
6-{[(2-{[4-(1H-pyrazol-1-ylmethyl)phenyl]methyl}-2H-pyrazolo[3,4-d]pyrimidin-4-yl)amino] methyl}isoquinolin-1-amine;
6-[({2-[(1-methyl-1H-indazol-6-yl)methyl]-2H-pyrazolo[4,3-c]pyridin-4-yl}amino)methyl]isoquinolin-1-amine;
6-{[(2-{[4-(pyridin-2-yloxy)phenyl]methyl}-2H-pyrazolo[4,3-c]pyridin-4-yl)amino]methyl}isoquinolin-1-amine;
N-[(5-chloro-1H-indazol-3-yl)methyl]-2-{[4-(1H-pyrazol-1-ylmethyl)phenyl]methyl}-2H-pyrazolo[4,3-c]pyridin-4-amine;
6-[({2-[(2-methyl-1,3-benzoxazol-6-yl)methyl]-2H-pyrazolo[4,3-c]pyridin-4-yl}amino)methyl]isoquinolin-1-amine;
6-[({2-[(2-methyl-1,3-benzoxazol-5-yl)methyl]-2H-pyrazolo[4,3-c]pyridin-4-yl}amino)methyl]isoquinolin-1-amine;
6-{[(2-{[6-(oxan-4-yloxy)pyridin-3-yl]methyl}-2H-pyrazolo[4,3-c]pyridin-4-yl)amino]methyl}isoquinolin-1-amine;
6-[({2-[(6-methoxy-5-methylpyridin-3-yl)methyl]-2H-pyrazolo[4,3-c]pyridin-4-yl}amino)methyl]isoquinolin-1-amine;
6-[({2-[(5,6-dimethylpyridin-3-yl)methyl]-2H-pyrazolo[4,3-c]pyridin-4-yl}amino)methyl]isoquinolin-1-amine;
6-{[(2-{[4-(1H-pyrazol-1-ylmethyl)phenyl]methyl}-2H-pyrazolo[4,3-c]pyridin-4-yl)amino]methyl}-1,2-benzoxazol-3-amine;

N-[(5-chloro-1,3-benzothiazol-2-yl)methyl]-2-{[4-(1H-pyrazol-1-ylmethyl)phenyl]methyl}-2H-pyrazolo[4,3-c]pyridin-4-amine;

N-[(5-chloro-1H-1,3-benzodiazol-2-yl)methyl]-2-{[4-(1H-pyrazol-1-ylmethyl)phenyl]methyl}-2H-pyrazolo[4,3-c]pyridin-4-amine;

4,6-dimethyl-5-{[(2-{[4-(1H-pyrazol-1-ylmethyl)phenyl]methyl}-2H-pyrazolo[3,4-d]pyrimidin-4-yl)amino]methyl}pyridin-2-amine;

N-[(2-chloro-1-benzothiophen-5-yl)methyl]-2-{[4-(1H-pyrazol-1-ylmethyl)phenyl]methyl}-2H-pyrazolo[4,3-c]pyridin-4-amine;

N-[(3-methoxyphenyl)methyl]-2-{[4-(1H-pyrazol-1-ylmethyl)phenyl]methyl}-2H-pyrazolo[3,4-d]pyrimidin-4-amine;

N-[(4-methoxyphenyl)methyl]-2-{[4-(1H-pyrazol-1-ylmethyl)phenyl]methyl}-2H-pyrazolo[3,4-d]pyrimidin-4-amine;

N-[(3-chloro-4-methoxyphenyl)methyl]-2-{[4-(1H-pyrazol-1-ylmethyl)phenyl]methyl}-2H-pyrazolo[3,4-d]pyrimidin-4-amine;

N-[(3,4-dimethoxyphenyl)methyl]-2-{[4-(1H-pyrazol-1-ylmethyl)phenyl]methyl}-2H-pyrazolo[3,4-d]pyrimidin-4-amine;

N-[(3,4-dichlorophenyl)methyl]-2-{[4-(1H-pyrazol-1-ylmethyl)phenyl]methyl}-2H-pyrazolo[3,4-d]pyrimidin-4-amine;

N-[(3,5-dichlorophenyl)methyl]-2-{[4-(1H-pyrazol-1-ylmethyl)phenyl]methyl}-2H-pyrazolo[3,4-d]pyrimidin-4-amine;

N-[(3,5-dimethoxyphenyl)methyl]-2-{[4-(1H-pyrazol-1-ylmethyl)phenyl]methyl}-2H-pyrazolo[3,4-d]pyrimidin-4-amine;

N-[(5-chloro-2-methoxyphenyl)methyl]-2-{[4-(1H-pyrazol-1-ylmethyl)phenyl]methyl}-2H-pyrazolo[3,4-d]pyrimidin-4-amine;

N-[(4-chloro-3-methoxyphenyl)methyl]-2-{[4-(1H-pyrazol-1-ylmethyl)phenyl]methyl}-2H-pyrazolo[3,4-d]pyrimidin-4-amine;

4-methoxy-6-methyl-5-{[(2-{[4-(1H-pyrazol-1-ylmethyl)phenyl]methyl}-2H-pyrazolo[4,3-c]pyridin-4-yl)amino]methyl}pyridin-2-amine;

N-[(2,5-dimethoxyphenyl)methyl]-2-{[4-(1H-pyrazol-1-ylmethyl)phenyl]methyl}-2H-pyrazolo[3,4-d]pyrimidin-4-amine;

N-[(3-chloro-5-methoxyphenyl)methyl]-2-{[4-(1H-pyrazol-1-ylmethyl)phenyl]methyl}-2H-pyrazolo[3,4-d]pyrimidin-4-amine;

N-[(5-methoxy-1H-indazol-3-yl)methyl]-2-{[4-(1H-pyrazol-1-ylmethyl)phenyl]methyl}-2H-pyrazolo[3,4-d]pyrimidin-4-amine;

N-(1H-indazol-3-ylmethyl)-2-{[4-(1H-pyrazol-1-ylmethyl)phenyl]methyl}-2H-pyrazolo[3,4-d]pyrimidin-4-amine;

N-[(2-methoxy-4-methylphenyl)methyl]-2-{[4-(1H-pyrazol-1-ylmethyl)phenyl]methyl}-2H-pyrazolo[3,4-d]pyrimidin-4-amine;

N-[(4-chloro-2-methoxyphenyl)methyl]-2-{[4-(1H-pyrazol-1-ylmethyl)phenyl]methyl}-2H-pyrazolo[3,4-d]pyrimidin-4-amine;

N-[(6-chloro-2-fluoro-3-methoxyphenyl)methyl]-2-{[4-(1H-pyrazol-1-ylmethyl)phenyl]methyl}-2H-pyrazolo[3,4-d]pyrimidin-4-amine;

N-[(2-methoxy-5-methylphenyl)methyl]-2-{[4-(1H-pyrazol-1-ylmethyl)phenyl]methyl}-2H-pyrazolo[3,4-d]pyrimidin-4-amine;

N-[(6-methoxy-2,4-dimethylpyridin-3-yl)methyl]-2-{[4-(1H-pyrazol-1-ylmethyl)phenyl]methyl}-2H-pyrazolo[3,4-d]pyrimidin-4-amine;

2-(2-{[(2-{[4-(1H-pyrazol-1-ylmethyl)phenyl]methyl}-2H-pyrazolo[3,4-d]pyrimidin-4-yl)amino]methyl}phenyl)acetic acid;

2-(5-methoxy-2-{[(2-{[4-(1H-pyrazol-1-ylmethyl)phenyl]methyl}-2H-pyrazolo[3,4-d]pyrimidin-4-yl)amino]methyl}phenoxy)acetic acid;

2-(2-{[(2-{[4-(1H-pyrazol-1-ylmethyl)phenyl]methyl}-2H-pyrazolo[3,4-d]pyrimidin-4-yl)amino]methyl}phenoxy)acetic acid;

N-[(5-methoxy-3-methylpyridin-2-yl)methyl]-2-{[4-(1H-pyrazol-1-ylmethyl)phenyl]methyl}-2H-pyrazolo[3,4-d]pyrimidin-4-amine;

6-methoxy-2-methyl-3-{[(2-{[4-(1H-pyrazol-1-ylmethyl)phenyl]methyl}-2H-pyrazolo[3,4-d]pyrimidin-4-yl)amino]methyl}pyridin-4-ol;

5-chloro-7-{[(2-{[4-(1H-pyrazol-1-ylmethyl)phenyl]methyl}-2H-pyrazolo[3,4-d]pyrimidin-4-yl)amino]methyl}-2,3-dihydro-1,3-benzoxazol-2-one;

N,4,6-trimethyl-5-{[(2-{[4-(1H-pyrazol-1-ylmethyl)phenyl]methyl}-2H-pyrazolo[3,4-d]pyrimidin-4-yl)amino]methyl}pyridin-2-amine;

N,N,4,6-tetramethyl-5-{[(2-{[4-(1H-pyrazol-1-ylmethyl)phenyl]methyl}-2H-pyrazolo[3,4-d]pyrimidin-4-yl)amino]methyl}pyridin-2-amine;

3,6-dimethyl-5-{[(2-{[4-(1H-pyrazol-1-ylmethyl)phenyl]methyl}-2H-pyrazolo[3,4-d]pyrimidin-4-yl)amino]methyl}pyridin-2-amine;

N-[(2-fluoro-3,6-dimethoxyphenyl)methyl]-2-{[4-(1H-pyrazol-1-ylmethyl)phenyl]methyl}-2H-pyrazolo[3,4-d]pyrimidin-4-amine;

N-[(3-bromo-2,6-dimethylphenyl)methyl]-2-{[4-(1H-pyrazol-1-ylmethyl)phenyl]methyl}-2H-pyrazolo[3,4-d]pyrimidin-4-amine;

N-[(2-methoxy-3,5-dimethylpyridin-4-yl)methyl]-2-{[4-(1H-pyrazol-1-ylmethyl)phenyl]methyl}-2H-pyrazolo[3,4-d]pyrimidin-4-amine;

N-[(3-methoxy-2,6-dimethylphenyl)methyl]-2-{[4-(1H-pyrazol-1-ylmethyl)phenyl]methyl}-2H-pyrazolo[3,4-d]pyrimidin-4-amine;

3-fluoro-4-methoxy-2-{[(2-{[4-(1H-pyrazol-1-ylmethyl)phenyl]methyl}-2H-pyrazolo[3,4-d]pyrimidin-4-yl)amino]methyl}benzonitrile;

N-{[6-chloro-2-fluoro-3-(trifluoromethoxy)phenyl]methyl}-2-{[4-(1H-pyrazol-1-ylmethyl)phenyl]methyl}-2H-pyrazolo[3,4-d]pyrimidin-4-amine;

N-[(3,6-dimethoxy-2-methylphenyl)methyl]-2-{[4-(1H-pyrazol-1-ylmethyl)phenyl]methyl}-2H-pyrazolo[3,4-d]pyrimidin-4-amine;

N-[(6-ethynyl-2-fluoro-3-methoxyphenyl)methyl]-2-{[4-(1H-pyrazol-1-ylmethyl)phenyl]methyl}-2H-pyrazolo[3,4-d]pyrimidin-4-amine;

N-[(6-ethyl-2-fluoro-3-methoxyphenyl)methyl]-2-{[4-(1H-pyrazol-1-ylmethyl)phenyl]methyl}-2H-pyrazolo[3,4-d]pyrimidin-4-amine;

N-[(6-bromo-3-methoxy-2-methylphenyl)methyl]-2-{[4-(1H-pyrazol-1-ylmethyl)phenyl]methyl}-2H-pyrazolo[3,4-d]pyrimidin-4-amine;

N-[(6-cyclopropyl-2-fluoro-3-methoxyphenyl)methyl]-2-{[4-(1H-pyrazol-1-ylmethyl)phenyl]methyl}-2H-pyrazolo[3,4-d]pyrimidin-4-amine;

N-{[2-fluoro-6-(furan-3-yl)-3-methoxyphenyl]methyl}-2-{[4-(1H-pyrazol-1-ylmethyl)phenyl]methyl}-2H-pyrazolo[3,4-d]pyrimidin-4-amine;

N-{[4-(aminomethyl)phenyl]methyl}-2-{[4-(1H-pyrazol-1-ylmethyl)phenyl]methyl}-2H-pyrazolo[3,4-d]pyrimidin-4-amine;
N-[(5-methyl-1-benzofuran-4-yl)methyl]-2-{[4-(1H-pyrazol-1-ylmethyl)phenyl]methyl}-2H-pyrazolo[3,4-d]pyrimidin-4-amine;
N-[(5-methyl-1-benzofuran-6-yl)methyl]-2-{[4-(1H-pyrazol-1-ylmethyl)phenyl]methyl}-2H-pyrazolo[3,4-d]pyrimidin-4-amine;
N-{[3-(aminomethyl)phenyl]methyl}-2-{[4-(1H-pyrazol-1-ylmethyl)phenyl]methyl}-2H-pyrazolo[3,4-d]pyrimidin-4-amine;
N-{[2-fluoro-3-methoxy-6-(oxetan-3-ylmethoxy)phenyl]methyl}-2-{[4-(1H-pyrazol-1-ylmethyl)phenyl]methyl}-2H-pyrazolo[3,4-d]pyrimidin-4-amine;
hexyl N-(4,6-dimethyl-5-{[(2-{[4-(1H-pyrazol-1-ylmethyl)phenyl]methyl}-2H-pyrazolo[3,4-d]pyrimidin-4-yl)amino]methyl}pyridin-2-yl)carbamate;
N-{[4-(aminomethyl)-2,6-dimethylphenyl]methyl}-2-{[4-(1H-pyrazol-1-ylmethyl)phenyl]methyl}-2H-pyrazolo[3,4-d]pyrimidin-4-amine;
N-{[2-(aminomethyl)-4,6-dimethylphenyl]methyl}-2-{[4-(1H-pyrazol-1-ylmethyl)phenyl]methyl}-2H-pyrazolo[3,4-d]pyrimidin-4-amine;
1-({4-[(4-{[(6-amino-2,4-dimethylpyridin-3-yl)methyl]amino}-2H-pyrazolo[3,4-d]pyrimidin-2-yl)methyl]phenyl}methyl)-N,N-dimethyl-1H-pyrazole-4-carboxamide;
4,6-dimethyl-5-[({2-[(4-{[4-(morpholine-4-carbonyl)-1H-pyrazol-1-yl]methyl}phenyl)methyl]-2H-pyrazolo[3,4-d]pyrimidin-4-yl}amino)methyl]pyridin-2-amine;
1-({4-[(4-{[(6-amino-2,4-dimethylpyridin-3-yl)methyl]amino}-2H-pyrazolo[3,4-d]pyrimidin-2-yl)methyl]phenyl}methyl)-1H-pyrazole-3-carboxylic acid;
1-({4-[(4-{[(6-amino-2,4-dimethylpyridin-3-yl)methyl]amino}-2H-pyrazolo[3,4-d]pyrimidin-2-yl)methyl]phenyl}methyl)-N,N-dimethyl-1H-pyrazole-3-carboxamide;
1-({4-[(4-{[(6-amino-2,4-dimethylpyridin-3-yl)methyl]amino}-2H-pyrazolo[3,4-d]pyrimidin-2-yl)methyl]phenyl}methyl)-N,N-dimethyl-1H-pyrazole-5-carboxamide;
4,6-dimethyl-5-[({2-[(4-{[4-(trifluoromethyl)-1H-pyrazol-1-yl]methyl}phenyl)methyl]-2H-pyrazolo[3,4-d]pyrimidin-4-yl}amino)methyl]pyridin-2-amine;
5-({[2-({4-[(4-chloro-1H-pyrazol-1-yl)methyl]phenyl}methyl)-2H-pyrazolo[3,4-d]pyrimidin-4-yl]amino}methyl)-4,6-dimethylpyridin-2-amine;
N-[(5-chloro-1H-indazol-3-yl)methyl]-2-({4-[(3,5-dimethyl-1H-pyrazol-1-yl)methyl]phenyl}methyl)-2H-pyrazolo[3,4-d]pyrimidin-4-amine;
N-[(7-chloronaphthalen-2-yl)methyl]-2-({4-[(4-methyl-1H-pyrazol-1-yl)methyl]phenyl}methyl)-2H-pyrazolo[3,4-d]pyrimidin-4-amine;
N-[(7-chloroquinolin-2-yl)methyl]-2-({4-[(4-methyl-1H-pyrazol-1-yl)methyl]phenyl}methyl)-2H-pyrazolo[3,4-d]pyrimidin-4-amine;
N-[(5-chloro-1H-indazol-3-yl)methyl]-2-({4-[(4-methyl-1H-pyrazol-1-yl)methyl]phenyl}methyl)-2H-pyrazolo[3,4-d]pyrimidin-4-amine;
N-[(2,6-difluoro-3-methoxyphenyl)methyl]-2-({4-[(4-methyl-1H-pyrazol-1-yl)methyl]phenyl}methyl)-2H-pyrazolo[3,4-d]pyrimidin-4-amine;
N-[(6-chloro-2-fluoro-3-methoxyphenyl)methyl]-2-({4-[(4-fluoro-1H-pyrazol-1-yl)methyl]phenyl}methyl)-2H-pyrazolo[3,4-d]pyrimidin-4-amine;
N-[(6-cyclopropyl-2-fluoro-3-methoxyphenyl)methyl]-2-({4-[(4-methyl-1H-pyrazol-1-yl)methyl]phenyl}methyl)-2H-pyrazolo[3,4-d]pyrimidin-4-amine;
N-[(6-chloro-2-fluoro-3-methoxyphenyl)methyl]-2-({4-[(4-methyl-1H-pyrazol-1-yl)methyl]phenyl}methyl)-2H-pyrazolo[3,4-d]pyrimidin-4-amine;
N-[(6-chloro-2-fluoro-3-methoxyphenyl)methyl]-2-({4-[(3,5-dimethyl-1H-pyrazol-1-yl)methyl]phenyl}methyl)-2H-pyrazolo[3,4-d]pyrimidin-4-amine;
2-({[2-({4-[(3,5-dimethyl-1H-pyrazol-1-yl)methyl]phenyl}methyl)-2H-pyrazolo[3,4-d]pyrimidin-4-yl]amino}methyl)-3-fluoro-4-methoxybenzonitrile;
1-({4-[(4-{[(6-amino-2,4-dimethylpyridin-3-yl)methyl]amino}-2H-pyrazolo[3,4-d]pyrimidin-2-yl)methyl]phenyl}methyl)-1,2-dihydropyridin-2-one;
1-({4-[(4-{[(5-chloro-1H-indazol-3-yl)methyl]amino}-2H-pyrazolo[3,4-d]pyrimidin-2-yl)methyl]phenyl}methyl)-1,2-dihydropyridin-2-one;
1-({4-[(4-{[(4-methoxyphenyl)methyl]amino}-2H-pyrazolo[3,4-d]pyrimidin-2-yl)methyl]phenyl}methyl)-1,2-dihydropyridin-2-one;
1-({4-[(4-{[(5-methoxy-1H-indazol-3-yl)methyl]amino}-2H-pyrazolo[3,4-d]pyrimidin-2-yl)methyl]phenyl}methyl)-1,2-dihydropyridin-2-one;
1-{[4-({4-[(1H-indazol-3-ylmethyl)amino]-2H-pyrazolo[3,4-d]pyrimidin-2-yl}methyl)phenyl]methyl}-1,2-dihydropyridin-2-one;
1-({4-[(4-{[(7-chloronaphthalen-2-yl)methyl]amino}-2H-pyrazolo[3,4-d]pyrimidin-2-yl)methyl]phenyl}methyl)-1,2-dihydropyridin-2-one;
1-({4-[(4-{[(6-amino-4-methoxy-2-methylpyridin-3-yl)methyl]amino}-2H-pyrazolo[4,3-c]pyridin-2-yl)methyl]phenyl}methyl)-1,2-dihydropyridin-2-one;
1-({4-[(4-{[(5-methyl-1H-indazol-3-yl)methyl]amino}-2H-pyrazolo[3,4-d]pyrimidin-2-yl)methyl]phenyl}methyl)-1,2-dihydropyridin-2-one;
1-({4-[(4-{[(5-chloro-1-methyl-1H-indazol-3-yl)methyl]amino}-2H-pyrazolo[3,4-d]pyrimidin-2-yl)methyl]phenyl}methyl)-1,2-dihydropyridin-2-one;
1-({4-[(4-{[(5-chloro-1H-indol-3-yl)methyl]amino}-2H-pyrazolo[3,4-d]pyrimidin-2-yl)methyl]phenyl}methyl)-1,2-dihydropyridin-2-one;
1-({4-[(4-{[(7-chloroquinolin-2-yl)methyl]amino}-2H-pyrazolo[3,4-d]pyrimidin-2-yl)methyl]phenyl}methyl)-1,2-dihydropyridin-2-one;
1-({4-[(4-{[(6-chloro-1-benzofuran-2-yl)methyl]amino}-2H-pyrazolo[3,4-d]pyrimidin-2-yl)methyl]phenyl}methyl)-1,2-dihydropyridin-2-one;
1-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one;
1-({4-[(4-{[(2-amino-4,6-dimethylpyrimidin-5-yl)methyl]amino}-2H-pyrazolo[3,4-d]pyrimidin-2-yl)methyl]phenyl}methyl)-1,2-dihydropyridin-2-one;
1-{[4-({4-[(4,5,6,7-tetrahydro-1H-indazol-3-ylmethyl)amino]-2H-pyrazolo[3,4-d]pyrimidin-2-yl}methyl)phenyl]methyl}-1,2-dihydropyridin-2-one;
1-({4-[(4-{[(6,6-dimethyl-4,5,6,7-tetrahydro-1H-indazol-3-yl)methyl]amino}-2H-pyrazolo[3,4-d]pyrimidin-2-yl)methyl]phenyl}methyl)-1,2-dihydropyridin-2-one;
1-[(4-{[4-({[4-(5-chlorothiophen-2-yl)-1,3-thiazol-2-yl]methyl}amino)-2H-pyrazolo[3,4-d]pyrimidin-2-yl]methyl}phenyl)methyl]-1,2-dihydropyridin-2-one;

1-{[4-({4-[({7-chloroimidazo[1,2-a]pyridin-2-yl}methyl)amino]-2H-pyrazolo[3,4-d]pyrimidin-2-yl}methyl)phenyl]methyl}-1,2-dihydropyridin-2-one;
1-{[4-({4-[({6-chloroimidazo[1,2-a]pyridin-2-yl}methyl)amino]-2H-pyrazolo[3,4-d]pyrimidin-2-yl}methyl)phenyl]methyl}-1,2-dihydropyridin-2-one;
1-({4-[(4-{[(2,5-dichlorophenyl)methyl]amino}-2H-pyrazolo[3,4-d]pyrimidin-2-yl)methyl]phenyl}methyl)-1,2-dihydropyridin-2-one;
1-({4-[(4-{[(5,5-dimethyl-4,5,6,7-tetrahydro-1H-indazol-3-yl)methyl]amino}-2H-pyrazolo[3,4-d]pyrimidin-2-yl)methyl]phenyl}methyl)-1,2-dihydropyridin-2-one;
1-[(4-{[4-({1H,4H,5H,7H-pyrano[3,4-c]pyrazol-3-ylmethyl}amino)-2H-pyrazolo[3,4-d]pyrimidin-2-yl]methyl}phenyl)methyl]-1,2-dihydropyridin-2-one;
1-{[4-({4-[({6-methoxyimidazo[1,2-a]pyridin-2-yl}methyl)amino]-2H-pyrazolo[3,4-d]pyrimidin-2-yl}methyl)phenyl]methyl}-1,2-dihydropyridin-2-one;
1-[(4-{[4-({[5-chloro-2-(1H-1,2,3-triazol-1-yl)phenyl]methyl}amino)-2H-pyrazolo[3,4-d]pyrimidin-2-yl]methyl}phenyl)methyl]-1,2-dihydropyridin-2-one;
1-[(4-{[4-({[5-chloro-2-(2H-1,2,3-triazol-2-yl)phenyl]methyl}amino)-2H-pyrazolo[3,4-d]pyrimidin-2-yl]methyl}phenyl)methyl]-1,2-dihydropyridin-2-one;
1-({4-[(4-{[(2-fluoro-3-methoxyphenyl)methyl]amino}-2H-pyrazolo[3,4-d]pyrimidin-2-yl)methyl]phenyl}methyl)-1,2-dihydropyridin-2-one;
1-({4-[(4-{[(2,6-difluoro-3-methoxyphenyl)methyl]amino}-2H-pyrazolo[3,4-d]pyrimidin-2-yl)methyl]phenyl}methyl)-1,2-dihydropyridin-2-one;
1-({4-[(4-{[(2,3,6-trifluorophenyl)methyl]amino}-2H-pyrazolo[3,4-d]pyrimidin-2-yl)methyl]phenyl}methyl)-1,2-dihydropyridin-2-one;
1-({4-[(4-{[(2-chloro-6-fluoro-3-methylphenyl)methyl]amino}-2H-pyrazolo[3,4-d]pyrimidin-2-yl)methyl]phenyl}methyl)-1,2-dihydropyridin-2-one;
1-({4-[(4-{[(2,6-difluoro-4-methoxyphenyl)methyl]amino}-2H-pyrazolo[3,4-d]pyrimidin-2-yl)methyl]phenyl}methyl)-1,2-dihydropyridin-2-one;
1-({4-[(4-{[(6-chloro-2-fluoro-3-methylphenyl)methyl]amino}-2H-pyrazolo[3,4-d]pyrimidin-2-yl)methyl]phenyl}methyl)-1,2-dihydropyridin-2-one;
1-[(4-{[4-({[5-chloro-2-(1H-1,2,4-triazol-1-yl)phenyl]methyl}amino)-2H-pyrazolo[3,4-d]pyrimidin-2-yl]methyl}phenyl)methyl]-1,2-dihydropyridin-2-one;
1-{[4-({4-[({5-methyl-1H,4H,5H,6H,7H-pyrazolo[4,3-c]pyridin-3-yl}methyl)amino]-2H-pyrazolo[3,4-d]pyrimidin-2-yl}methyl)phenyl]methyl}-1,2-dihydropyridin-2-one;
7-chloro-2-({[2-({4-[(2-oxo-1,2-dihydropyridin-1-yl)methyl]phenyl}methyl)-2H-pyrazolo[3,4-d]pyrimidin-4-yl]amino}methyl)imidazo[1,2-a]pyridine-3-carbonitrile;
4-methoxy-2-({[2-({4-[(2-oxo-1,2-dihydropyridin-1-yl)methyl]phenyl}methyl)-2H-pyrazolo[3,4-d]pyrimidin-4-yl]amino}methyl)benzonitrile;
1-({4-[(4-{[(6-chloro-1,3-benzoxazol-2-yl)methyl]amino}-2H-pyrazolo[3,4-d]pyrimidin-2-yl)methyl]phenyl}methyl)-1,2-dihydropyridin-2-one;
1-[(4-{[4-({[5-fluoro-2-(morpholin-4-yl)phenyl]methyl}amino)-2H-pyrazolo[3,4-d]pyrimidin-2-yl]methyl}phenyl)methyl]-1,2-dihydropyridin-2-one;
5-({[2-({4-[(2-oxo-1,2-dihydropyridin-1-yl)methyl]phenyl}methyl)-2H-pyrazolo[3,4-d]pyrimidin-4-yl]amino}methyl)-2,3-dihydro-1H-indol-2-one;
5-chloro-3-({[2-({4-[(2-oxo-1,2-dihydropyridin-1-yl)methyl]phenyl}methyl)-2H-pyrazolo[3,4-d]pyrimidin-4-yl]amino}methyl)-1H-indole-2-carbonitrile;
5-chloro-7-({[2-({4-[(2-oxo-1,2-dihydropyridin-1-yl)methyl]phenyl}methyl)-2H-pyrazolo[3,4-d]pyrimidin-4-yl]amino}methyl)-2,3-dihydro-1,3-benzoxazol-2-one;
1-{[4-({4[({6-methyl-1H,4H,5H,6H,7H-pyrazolo[3,4-c]pyridin-3-yl}methyl)amino]-2H-pyrazolo[3,4-d]pyrimidin-2-yl}methyl)phenyl]methyl}-1,2-dihydropyridin-2-one;
1-{[4-({4[({6-chloro-[1,2,4]triazolo[1,5-a]pyridin-2-yl}methyl)amino]-2H-pyrazolo[3,4-d]pyrimidin-2-yl}methyl)phenyl]methyl}-1,2-dihydropyridin-2-one;
6-methoxy-2-({[2-({4-[(2-oxo-1,2-dihydropyridin-1-yl)methyl]phenyl}methyl)-2H-pyrazolo[3,4-d]pyrimidin-4-yl]amino}methyl)pyridine-3-carbonitrile;
1-{[4-({4[({7-chloro-[1,2,4]triazolo[1,5-a]pyridin-2-yl}methyl)amino]-2H-pyrazolo[3,4-d]pyrimidin-2-yl}methyl)phenyl]methyl}-1,2-dihydropyridin-2-one;
4-chloro-2-({[2-({4-[(2-oxo-1,2-dihydropyridin-1-yl)methyl]phenyl}methyl)-2H-pyrazolo[3,4-d]pyrimidin-4-yl]amino}methyl)benzonitrile;
1-[(4-{[4-({[2-fluoro-5-(trifluoromethoxy)phenyl]methyl}amino)-2H-pyrazolo[3,4-d]pyrimidin-2-yl]methyl}phenyl)methyl]-1,2-dihydropyridin-2-one;
1-[(4-{[4-({[2-chloro-5-(difluoromethoxy)phenyl]methyl}amino)-2H-pyrazolo[3,4-d]pyrimidin-2-yl]methyl}phenyl)methyl]-1,2-dihydropyridin-2-one;
1-[(4-{[4-({[6-chloro-2-fluoro-3-(trifluoromethoxy)phenyl]methyl}amino)-2H-pyrazolo[3,4-d]pyrimidin-2-yl]methyl}phenyl)methyl]-1,2-dihydropyridin-2-one;
1-({4-[(4-{[(6-ethynyl-2-fluoro-3-methoxyphenyl)methyl]amino}-2H-pyrazolo[3,4-d]pyrimidin-2-yl)methyl]phenyl}methyl)-1,2-dihydropyridin-2-one;
1-({4-[(4-{[(5-chlorothiophen-2-yl)methyl]amino}-2H-pyrazolo[3,4-d]pyrimidin-2-yl)methyl]phenyl}methyl)-1,2-dihydropyridin-2-one;
3-fluoro-4-methoxy-2-({[2-({4-[(2-oxo-1,2-dihydropyridin-1-yl)methyl]phenyl}methyl)-2H-pyrazolo[3,4-d]pyrimidin-4-yl]amino}methyl)benzonitrile;
1-[(4-{[4-({[4-(aminomethyl)-2,6-dimethylphenyl]methyl}amino)-2H-pyrazolo[3,4-d]pyrimidin-2-yl]methyl}phenyl)methyl]-1,2-dihydropyridin-2-one;
1-[(4-{[4-({[2-(aminomethyl)-4,6-dimethylphenyl]methyl}amino)-2H-pyrazolo[3,4-d]pyrimidin-2-yl]methyl}phenyl)methyl]-1,2-dihydropyridin-2-one;
1-({4-[(4-{[(6-amino-2,4-dimethylpyridin-3-yl)methyl]amino}-2H-pyrazolo[3,4-d]pyrimidin-2-yl)methyl]phenyl}methyl)-5-fluoro-1,2-dihydropyridin-2-one;
1-({4-[(4-{[(6-amino-2,4-dimethylpyridin-3-yl)methyl]amino}-2H-pyrazolo[3,4-d]pyrimidin-2-yl)methyl]phenyl}methyl)-5-chloro-1,2-dihydropyridin-2-one;
5-chloro-1-({4-[(4-{[(4-methoxyphenyl)methyl]amino}-2H-pyrazolo[3,4-d]pyrimidin-2-yl)methyl]phenyl}methyl)-1,2-dihydropyridin-2-one;
5-chloro-1-({4-[(4-{[(5-chloro-3-methylpyridin-2-yl)methyl]amino}-2H-pyrazolo[3,4-d]pyrimidin-2-yl)methyl]phenyl}methyl)-1,2-dihydropyridin-2-one;
5-chloro-1-({4-[(4-{[(5-methoxy-3-methylpyridin-2-yl)methyl]amino}-2H-pyrazolo[3,4-d]pyrimidin-2-yl)methyl]phenyl}methyl)-1,2-dihydropyridin-2-one;
5-chloro-1-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one;

5-chloro-1-({4-[(4-{[(2,6-difluoro-3-methoxyphenyl) methyl]amino}-2H-pyrazolo[3,4-d]pyrimidin-2-yl) methyl]phenyl}methyl)-1,2-dihydropyridin-2-one;
5-chloro-1-({4-[(4-{[(2-fluoro-3-methoxyphenyl)methyl] amino}-2H-pyrazolo[3,4-d]pyrimidin-2-yl)methyl] phenyl}methyl)-1,2-dihydropyridin-2-one;
5-chloro-1-({4-[(4-{[(2-fluoro-5-methoxyphenyl)methyl] amino}-2H-pyrazolo[3,4-d]pyrimidin-2-yl)methyl] phenyl}methyl)-1,2-dihydropyridin-2-one;
5-chloro-1-({4-[(4-{[(6-chloro-2-fluoro-3-hydroxyphenyl)methyl]amino}-2H-pyrazolo[3,4-d]pyrimidin-2-yl)methyl]phenyl}methyl)-1,2-dihydropyridin-2-one;
1-({4-[(4-{[(2-amino-4,6-dimethylpyrimidin-5-yl) methyl]amino}-2H-pyrazolo[3,4-d]pyrimidin-2-yl) methyl]phenyl}methyl)-5-chloro-1,2-dihydropyridin-2-one;
5-chloro-1-({4-[(4-{[(6-methoxy-2,4-dimethylpyridin-3-yl)methyl]amino}-2H-pyrazolo[3,4-d]pyrimidin-2-yl)methyl]phenyl}methyl)-1,2-dihydropyridin-2-one;
5-chloro-1-({4-[(4-{[(6-hydroxy-2,4-dimethylpyridin-3-yl)methyl]amino}-2H-pyrazolo[3,4-d]pyrimidin-2-yl)methyl]phenyl}methyl)-1,2-dihydropyridin-2-one;
5-chloro-1-{[4-({4-[(cyclopropylmethyl)amino]-2H-pyrazolo[3,4-d]pyrimidin-2-yl}methyl)phenyl] methyl}-1,2-dihydropyridin-2-one;
5-chloro-1-{[4-({4-[(piperidin-4-ylmethyl)amino]-2H-pyrazolo[3,4-d]pyrimidin-2-yl}methyl)phenyl] methyl}-1,2-dihydropyridin-2-one;
1-{[4-({4-[(azepan-4-ylmethyl)amino]-2H-pyrazolo[3,4-d]pyrimidin-2-yl}methyl)phenyl]methyl}-5-chloro-1, 2-dihydropyridin-2-one;
5-chloro-1-[(4-{[4-({1H-pyrrolo[2,3-b]pyridin-5-ylmethyl}amino)-2H-pyrazolo[3,4-d]pyrimidin-2-yl] methyl}phenyl)methyl]-1,2-dihydropyridin-2-one;
5-chloro-1-{[4-({4-[({6-methyl-1H-pyrrolo[2,3-b]pyridin-5-yl}methyl)amino]-2H-pyrazolo[3,4-d]pyrimidin-2-yl}methyl)phenyl]methyl}-1,2-dihydropyridin-2-one;
5-chloro-1-{[4-({4-[({4,6-dimethyl-1H-pyrrolo[2,3-b]pyridin-5-yl}methyl)amino]-2H-pyrazolo[3,4-d]pyrimidin-2-yl}methyl)phenyl]methyl}-1,2-dihydropyridin-2-one;
5-{[(6-methoxy-2-{[4-(1H-pyrazol-1-ylmethyl)phenyl] methyl}-2H-pyrazolo[3,4-d]pyrimidin-4-yl)amino] methyl}-4,6-dimethylpyridin-2-amine;
4-{[(6-amino-2,4-dimethylpyridin-3-yl)methyl]amino}-2-{[4-(1H-pyrazol-1-ylmethyl)phenyl]methyl}-2H-pyrazolo[3,4-d]pyrimidine-6-carbonitrile;
4-{[(6-amino-2,4-dimethylpyridin-3-yl)methyl]amino}-2-{[4-(1H-pyrazol-1-ylmethyl)phenyl]methyl}-2H-pyrazolo[3,4-d]pyrimidine-6-carboxylic acid;
4-{[(4-methoxyphenyl)methyl]amino}-2-({4-[(2-oxo-1, 2-dihydropyridin-1-yl)methyl]phenyl}methyl)-2H-pyrazolo[3,4-d]pyrimidine-6-carbonitrile;
4-{[(6-chloro-2-fluoro-3-methoxyphenyl)methyl] amino}-2-{[4-(1H-pyrazol-1-ylmethyl)phenyl] methyl}-2H-pyrazolo[3,4-d]pyrimidine-6-carboxylic acid;
4-{[(6-chloro-2-fluoro-3-methoxyphenyl)methyl] amino}-2-({4-[1-(1H-pyrazol-1-yl)ethyl] phenyl}methyl)-2H-pyrazolo[3,4-d]pyrimidine-6-carboxylic acid;
6-(azetidine-1-carbonyl)-N-[(6-chloro-2-fluoro-3-methoxyphenyl)methyl]-2-({4-[1-(1H-pyrazol-1-yl) ethyl]phenyl}methyl)-2H-pyrazolo[3,4-d]pyrimidin-4-amine;
4-{[(6-chloro-2-fluoro-3-methoxyphenyl)methyl] amino}-2-({4-[1-(1H-pyrazol-1-yl)ethyl] phenyl}methyl)-2H-pyrazolo[3,4-d]pyrimidin-6-ol;
N-[(6-chloro-2-fluoro-3-methoxyphenyl)methyl]-6-{[3-(pyrimidin-5-yl)phenyl]methyl}-6H-pyrrolo [3,4-d]pyrimidin-4-amine;
6-[(4-chloro-1-methyl-1H-pyrazol-3-yl)methyl]-N-[(6-chloro-2-fluoro-3-methoxyphenyl)methyl]-6H-pyrrolo [3,4-d]pyrimidin-4-amine;
5-[(4-{[(6-chloro-2-fluoro-3-methoxyphenyl)methyl] amino}-6H-pyrrolo[3,4-d]pyrimidin-6-yl)methyl]-4-methoxy-N,N-dimethyl-1,3-thiazol-2-amine;
N-[(6-chloro-2-fluoro-3-methoxyphenyl)methyl]-6-{[2-(propan-2-yl)pyrimidin-5-yl]methyl}-6H-pyrrolo [3,4-d]pyrimidin-4-amine;
4-{[(6-chloro-2-fluoro-3-methoxyphenyl)methyl] amino}-2-[(5-methylquinolin-3-yl)methyl]-2H-pyrazolo[3,4-d]pyrimidin-6-ol;
4-{[(6-chloro-2-fluoro-3-methoxyphenyl)methyl] amino}-2-[(3-methylquinolin-5-yl)methyl]-2H-pyrazolo[3,4-d]pyrimidin-6-ol;
4-{[(6-chloro-2-fluoro-3-methoxyphenyl)methyl]amino 1-2-1 [3-methyl-2-(propan-2-yl)imidazo[1,2-a]pyridin-6-yl]methyl}-2H-pyrazolo[3,4-d]pyrimidin-6-ol;
4-{[(6-chloro-2-fluoro-3-methoxyphenyl)methyl] amino}-2-[(2-ethyl-1,4-dimethyl-1H-1,3-benzodiazol-6-yl)methyl]-2H-pyrazolo[3,4-d]pyrimidin-6-ol;
4-{[(6-chloro-2-fluoro-3-methoxyphenyl)methyl] amino}-2-[(6-methylquinolin-3-yl)methyl]-2H-pyrazolo[3,4-d]pyrimidin-6-ol;
4-{[(6-chloro-2-fluoro-3-methoxyphenyl)methyl] amino}-2-[(7-methylquinolin-2-yl)methyl]-2H-pyrazolo[3,4-d]pyrimidin-6-ol;
4-{[(6-chloro-2-fluoro-3-methoxyphenyl)methyl] amino}-2-[(2-methylquinolin-7-yl)methyl]-2H-pyrazolo[3,4-d]pyrimidin-6-ol;
4-{[(6-chloro-2-fluoro-3-methoxyphenyl)methyl] amino}-2-[(2-ethyl-1-methyl-1H-1,3-benzodiazol-6-yl)methyl]-2H-pyrazolo[3,4-d]pyrimidin-6-ol;
4-{[(6-chloro-2-fluoro-3-methoxyphenyl)methyl] amino}-2-[(2-ethyl-1-methyl-1H-1,3-benzodiazol-5-yl)methyl]-2H-pyrazolo[3,4-d]pyrimidin-6-ol;
6-({[2-({2-methylimidazo[1,2-a]pyridin-6-yl}methyl)-2H-pyrazolo[4,3-c]pyridin-4-yl]amino}methyl)isoquinolin-1-amine;
6-[({2-[(1,2-dimethyl-1H-1,3-benzodiazol-5-yl)methyl]-2H-pyrazolo[4,3-c]pyridin-4-yl}amino)methyl]isoquinolin-1-amine;
6-[({2-[(6-chloro-5-methylpyridin-3-yl)methyl]-2H-pyrazolo[4,3-c]pyridin-4-yl}amino)methyl]isoquinolin-1-amine;
6-[({2-[(6-fluoro-5-methylpyridin-3-yl)methyl]-2H-pyrazolo[4,3-c]pyridin-4-yl}amino)methyl]isoquinolin-1-amine;
6-[({2-[(6-phenoxypyridin-3-yl)methyl]-2H-pyrazolo[4, 3-c]pyridin-4-yl}amino)methyl]isoquinolin-1-amine;
6-{[(2-{[6-(pyridin-3-yloxy)pyridin-3-yl]methyl}-2H-pyrazolo[4,3-c]pyridin-4-yl)amino] methyl}isoquinolin-1-amine;
6-{[(2-{[6-(cyclohexyloxy)pyridin-3-yl]methyl}-2H-pyrazolo[4,3-c]pyridin-4-yl)amino] methyl}isoquinolin-1-amine;
6-{[(2-{[6-(cyclopentyloxy)pyridin-3-yl]methyl}-2H-pyrazolo[4,3-c]pyridin-4-yl)amino] methyl}isoquinolin-1-amine;

6-[({2-[(5-chloro-6-methoxypyridin-3-yl)methyl]-2H-pyrazolo[4,3-c]pyridin-4-yl}amino)methyl]isoquinolin-1-amine;

6-{[(2-{[6-(morpholin-4-yl)pyridin-3-yl]methyl}-2H-pyrazolo[4,3-c]pyridin-4-yl)amino]methyl}isoquinolin-1-amine;

6-{[(2-{[6-(piperidin-1-yl)pyridin-3-yl]methyl}-2H-pyrazolo[4,3-c]pyridin-4-yl)amino]methyl}isoquinolin-1-amine;

4,6-dimethyl-5-{[(2-{[5-(piperidin-1-yl)pyrazin-2-yl]methyl}-2H-pyrazolo[3,4-d]pyrimidin-4-yl)amino]methyl}pyridin-2-amine;

5-[(4-{[(6-amino-2,4-dimethylpyridin-3-yl)methyl]amino}-2H-pyrazolo[3,4-d]pyrimidin-2-yl)methyl]-N-cyclopentyl-N-methylpyrazin-2-amine;

5-[({2-[(2-ethyl-1,3-benzoxazol-5-yl)methyl]-2H-pyrazolo[3,4-d]pyrimidin-4-yl}amino)methyl]-4,6-dimethylpyridin-2-amine;

1-{5-[(4-{[(1-aminoisoquinolin-6-yl)methyl]amino}-2H-pyrazolo[4,3-c]pyridin-2-yl)methyl]pyridin-2-yl}pyrrolidin-2-one;

4,6-dimethyl-5-({[2-({2-methylimidazo[1,2-a]pyridin-6-yl}methyl)-2H-pyrazolo[4,3-c]pyridin-4-yl]amino}methyl)pyridin-2-amine;

N-[(2-chloro-1-benzothiophen-5-yl)methyl]-2-({2-methylimidazo[1,2-a]pyridin-6-yl}methyl)-2H-pyrazolo[4,3-c]pyridin-4-amine;

N-[(6-chloro-1-benzofuran-2-yl)methyl]-2-({2-methylimidazo[1,2-a]pyridin-6-yl}methyl)-2H-pyrazolo[4,3-c]pyridin-4-amine;

N-[(5-chloro-1,3-benzothiazol-2-yl)methyl]-2-({2-methylimidazo[1,2-a]pyridin-6-yl}methyl)-2H-pyrazolo[4,3-c]pyridin-4-amine;

N-[(5-chloro-1H-indazol-3-yl)methyl]-2-({2-methylimidazo[1,2-a]pyridin-6-yl}methyl)-2H-pyrazolo[4,3-c]pyridin-4-amine;

6-[({2-[(5,6-dimethoxypyridin-3-yl)methyl]-2H-pyrazolo[4,3-c]pyridin-4-yl}amino)methyl]isoquinolin-1-amine;

N-{[4-(5-chlorothiophen-2-yl)-1,3-thiazol-2-yl]methyl}-2-({2-methylimidazo[1,2-a]pyridin-6-yl}methyl)-2H-pyrazolo[4,3-c]pyridin-4-amine;

4,6-dimethyl-5-{[(2-{[6-(oxolan-3-yloxy)pyridin-3-yl]methyl}-2H-pyrazolo[4,3-c]pyridin-4-yl)amino]methyl}pyridin-2-amine;

4,6-dimethyl-5-[({2-[(2-methyl-1,3-benzoxazol-5-yl)methyl]-2H-pyrazolo[4,3-c]pyridin-4-yl}amino)methyl]pyridin-2-amine;

N-[(7-chloroquinolin-2-yl)methyl]-2-({2-methylimidazo[1,2-a]pyridin-6-yl}methyl)-2H-pyrazolo[4,3-c]pyridin-4-amine;

N-[(6-chloro-1-benzothiophen-2-yl)methyl]-2-({2-methylimidazo[1,2-a]pyridin-6-yl}methyl)-2H-pyrazolo[4,3-c]pyridin-4-amine;

N-[(5-chloro-1-benzothiophen-2-yl)methyl]-2-({2-methylimidazo[1,2-a]pyridin-6-yl}methyl)-2H-pyrazolo[4,3-c]pyridin-4-amine;

4,6-dimethyl-5-[({2-[(2-methyl-1,3-benzoxazol-5-yl)methyl]-2H-pyrazolo[3,4-d]pyrimidin-4-yl}amino)methyl]pyridin-2-amine;

4-{5-[(4-{[(1-aminoisoquinolin-6-yl)methyl]amino}-2H-pyrazolo[4,3-c]pyridin-2-yl)methyl]pyridin-2-yl}morpholin-3-one;

N-[(4-chloro-1-benzothiophen-2-yl)methyl]-2-({2-methylimidazo[1,2-a]pyridin-6-yl}methyl)-2H-pyrazolo[4,3-c]pyridin-4-amine;

N-{[2-(5-chlorothiophen-2-yl)-1,3-thiazol-5-yl]methyl}-2-({2-methylimidazo[1,2-a]pyridin-6-yl}methyl)-2H-pyrazolo[4,3-c]pyridin-4-amine;

1-{[6-amino-2-methyl-3-({[2-({2-methylimidazo[1,2-a]pyridin-6-yl}methyl)-2H-pyrazolo[4,3-c]pyridin-4-yl]amino}methyl)pyridin-4-yl]oxy}-3,3-dimethylbutan-2-one;

4,6-dimethyl-5-{[(2-{[6-(pyrrolidin-3-yloxy)pyridin-3-yl]methyl}-2H-pyrazolo[4,3-c]pyridin-4-yl)amino]methyl}pyridin-2-amine;

4,6-dimethyl-5-[({2-[(2-methyl-1,3-benzothiazol-5-yl)methyl]-2H-pyrazolo[3,4-d]pyrimidin-4-yl}amino)methyl]pyridin-2-amine;

5-[({2-[(2-ethyl-1,3-benzothiazol-5-yl)methyl]-2H-pyrazolo[3,4-d]pyrimidin-4-yl}amino)methyl]-4,6-dimethylpyridin-2-amine;

N-[(3-chloroisoquinolin-6-yl)methyl]-2-({2-methylimidazo[1,2-a]pyridin-6-yl}methyl)-2H-pyrazolo[4,3-c]pyridin-4-amine;

5-{[(2-{[3-fluoro-4-(1H-pyrazol-1-ylmethyl)phenyl]methyl}-2H-pyrazolo[3,4-d]pyrimidin-4-yl)amino]methyl}-4,6-dimethylpyridin-2-amine;

N-{[5-(5-chlorothiophen-2-yl)-1,2-oxazol-3-yl]methyl}-2-({2-methylimidazo[1,2-a]pyridin-6-yl}methyl)-2H-pyrazolo[4,3-c]pyridin-4-amine;

N-[(7-chloronaphthalen-2-yl)methyl]-2-({2-methylimidazo[1,2-a]pyridin-6-yl}methyl)-2H-pyrazolo[4,3-c]pyridin-4-amine;

tert-butyl 2-(5-methoxy-2-{[(2-{[4-(1H-pyrazol-1-ylmethyl)phenyl]methyl}-2H-pyrazolo[3,4-d]pyrimidin-4-yl)amino]methyl}phenoxy)acetate;

4,6-dimethyl-5-({[2-({2-methylimidazo[1,2-a]pyridin-6-yl}methyl)-2H-pyrazolo[3,4-d]pyrimidin-4-yl]amino}methyl)pyridin-2-amine;

5-({[2-({2-ethylimidazo[1,2-a]pyridin-6-yl}methyl)-2H-pyrazolo[3,4-d]pyrimidin-4-yl]amino}methyl)-4,6-dimethylpyridin-2-amine;

1-({4-[(4-{[(6-amino-2,4-dimethylpyridin-3-yl)methyl]amino}-2H-pyrazolo[3,4-d]pyrimidin-2-yl)methyl]phenyl}methyl)pyrrolidin-2-one;

4,6-dimethyl-5-{[(2-{[2-(trifluoromethyl)imidazo[1,2-a]pyridin-6-yl]methyl}-2H-pyrazolo[3,4-d]pyrimidin-4-yl)amino]methyl}pyridin-2-amine;

N-[(3-chloroisoquinolin-6-yl)methyl]-2-{[6-(pyrrolidin-3-yloxy)pyridin-3-yl]methyl}-2H-pyrazolo[4,3-c]pyridin-4-amine;

3-{5-[(4-{[(1-aminoisoquinolin-6-yl)methyl]amino}-2H-pyrazolo[4,3-c]pyridin-2-yl)methyl]pyridin-2-yl}-1,3-oxazolidin-2-one;

N-({6-chlorothieno[2,3-b]pyridin-2-yl}methyl)-2-({2-methylimidazo[1,2-a]pyridin-6-yl}methyl)-2H-pyrazolo[4,3-c]pyridin-4-amine;

6-({[2-({2-methylimidazo[1,2-a]pyridin-6-yl}methyl)-2H-pyrazolo[4,3-c]pyridin-4-yl]amino}methyl)-1,2-benzoxazol-3-amine;

3-chloro-6-({[2-({2-methylimidazo[1,2-a]pyridin-6-yl}methyl)-2H-pyrazolo[4,3-c]pyridin-4-yl]amino}methyl)isoquinolin-1-amine;

5-{[(2-{[3-methoxy-4-(1H-pyrazol-1-ylmethyl)phenyl]methyl}-2H-pyrazolo[3,4-d]pyrimidin-4-yl)amino]methyl}-4,6-dimethylpyridin-2-amine;

5-[({2-[(2-ethyl-7-methyl-1,3-benzoxazol-5-yl)methyl]-2H-pyrazolo[3,4-d]pyrimidin-4-yl}amino)methyl]-4,6-dimethylpyridin-2-amine;

5-[({2-[(2-ethyl-1,3-benzothiazol-5-yl)methyl]-2H-pyrazolo[3,4-d]pyrimidin-4-yl}amino)methyl]-4-methoxy-6-methylpyridin-2-amine;

5-{[(2-{[4-(cyclopentanesulfonyl)phenyl]methyl}-2H-pyrazolo[3,4-d]pyrimidin-4-yl)amino]methyl}-4,6-dimethylpyridin-2-amine;
1-({4-[(4-{[(6-amino-2,4-dimethylpyridin-3-yl)methyl]amino}-2H-pyrazolo[3,4-d]pyrimidin-2-yl)methyl]phenyl}methyl)piperidin-2-one;
4-({4-[(4-{[(6-amino-2,4-dimethylpyridin-3-yl)methyl]amino}-2H-pyrazolo[3,4-d]pyrimidin-2-yl)methyl]phenyl}methyl)morpholin-3-one;
1-({4-[(4-{[(6-amino-2,4-dimethylpyridin-3-yl)methyl]amino}-2H-pyrazolo[3,4-d]pyrimidin-2-yl)methyl]phenyl}methyl)azepan-2-one;
5-({[2-({2-ethyl-3-methylimidazo[1,2-a]pyridin-6-yl}methyl)-2H-pyrazolo[3,4-d]pyrimidin-4-yl]amino}methyl)-4,6-dimethylpyridin-2-amine;
N-[(5-chloro-1H-indazol-3-yl)methyl]-2-{[6-(oxolan-3-ylmethyl)pyridin-3-yl]methyl}-2H-pyrazolo[3,4-d]pyrimidin-4-amine;
N-[(6-chloro-2-fluoro-3-methoxyphenyl)methyl]-2-(quinoxalin-6-ylmethyl)-2H-pyrazolo[3,4-d]pyrimidin-4-amine;
2-[(4-{[(6-amino-2,4-dimethylpyridin-3-yl)methyl]amino}-2H-pyrazolo[3,4-d]pyrimidin-2-yl)methyl]-5-fluorobenzonitrile;
5-[({2-[(2,4-difluorophenyl)methyl]-2H-pyrazolo[3,4-d]pyrimidin-4-yl}amino)methyl]-4,6-dimethylpyridin-2-amine ;
5-[({2-[(2,4-difluorophenyl)methyl]-2H-pyrazolo[3,4-d]pyrimidin-4-yl}amino)methyl]-4,6-dimethylpyrimidin-2-amine;
5-{[(2-{[2-methoxy-4-(trifluoromethyl)phenyl]methyl}-2H-pyrazolo[3,4-d]pyrimidin-4-yl)amino]methyl}-4,6-dimethylpyridin-2-amine;
2-[(4-{[(6-amino-2,4-dimethylpyridin-3-yl)methyl]amino}-2H-pyrazolo[3,4-d]pyrimidin-2-yl)methyl]-5-methoxybenzonitrile;
4,6-dimethyl-5-[({2-[(2-phenyl-1,3-thiazol-4-yl)methyl]-2H-pyrazolo[3,4-d]pyrimidin-4-yl}amino)methyl]pyridin-2-amine;
N-[(6-chloro-2-fluoro-3-methoxyphenyl)methyl]-2-[(2-phenyl-1,3-thiazol-4-yl)methyl]-2H-pyrazolo[3,4-d]pyrimidin-4-amine;
5-[({2-[(2,4-dimethoxyphenyl)methyl]-2H-pyrazolo[3,4-d]pyrimidin-4-yl}amino)methyl]-4,6-dimethylpyridin-2-amine;
5-[({2-[(4-fluoro-2-methoxyphenyl)methyl]-2H-pyrazolo[3,4-d]pyrimidin-4-yl}amino)methyl]-4,6-dimethylpyridin-2-amine;
5-[({2-[(3-fluoropyridin-2-yl)methyl]-2H-pyrazolo[3,4-d]pyrimidin-4-yl}amino)methyl]-4,6-dimethylpyridin-2-amine ;
4,6-dimethyl-5-[({2-[(2-methylquinolin-6-yl)methyl]-2H-pyrazolo[3,4-d]pyrimidin-4-yl}amino)methyl]pyridin-2-amine;
N-[(6-chloro-2-fluoro-3-methoxyphenyl)methyl]-2-({4-[1-(1H-pyrazol-1-yl)ethyl]phenyl}methyl)-2H-pyrazolo[3,4-d]pyrimidin-4-amine;
4,6-dimethyl-5-({[2-({4-[1-(1H-pyrazol-1-yl)ethyl]phenyl}methyl)-2H-pyrazolo[3,4-d]pyrimidin-4-yl]amino}methyl)pyridin-2-amine;
N-[(6-chloro-2-fluoro-3-methoxyphenyl)methyl]-2-({2-ethyl-3-methylimidazo[1,2-a]pyridin-6-yl}methyl)-2H-pyrazolo[3,4-d]pyrimidin-4-amine;
N-[(2,6-difluoro-3-methoxyphenyl)methyl]-2-({2-ethyl-3-methylimidazo[1,2-a]pyridin-6-yl}methyl)-2H-pyrazolo[3,4-d]pyrimidin-4-amine;
4,6-dimethyl-5-[({2-[(2-phenyl-1,3-oxazol-4-yl)methyl]-2H-pyrazolo[3,4-d]pyrimidin-4-yl}amino)methyl]pyridin-2-amine;
N-[(6-chloro-2-fluoro-3-methoxyphenyl)methyl]-2-[(2-phenyl-1,3-oxazol-4-yl)methyl]-2H-pyrazolo[3,4-d]pyrimidin-4-amine;
5-[({2-[(1,2-dimethyl-1H-1,3-benzodiazol-6-yl)methyl]-2H-pyrazolo[3,4-d]pyrimidin-4-yl}amino)methyl]-4,6-dimethylpyridin-2-amine;
5-[({2-[(2-ethyl-1-methyl-1H-1,3-benzodiazol-6-yl)methyl]-2H-pyrazolo[3,4-d]pyrimidin-4-yl}amino)methyl]-4,6-dimethylpyridin-2-amine;
N-[(6-chloro-2-fluoro-3-methoxyphenyl)methyl]-2-{1-[4-(1H-pyrazol-1-ylmethyl)phenyl]ethyl}-2H-pyrazolo[3,4-d]pyrimidin-4-amine;
2-[(4-{[(6-amino-2,4-dimethylpyridin-3-yl)methyl]amino}-2H-pyrazolo[3,4-d]pyrimidin-2-yl)methyl]-5-(trifluoromethyl)benzonitrile;
2-[(4-{[(6-amino-2,4-dimethylpyridin-3-yl)methyl]amino}-2H-pyrazolo[3,4-d]pyrimidin-2-yl)methyl]pyridine-3-carbonitrile;
4,6-dimethyl-5-{[(2-{[3-(trifluoromethyl)pyridin-2-yl]methyl}-2H-pyrazolo[3,4-d]pyrimidin-4-yl)amino]methyl}pyridin-2-amine;
5-({[2-({2,3-dimethylimidazo[1,2-a]pyridin-6-yl}methyl)-2H-pyrazolo[3,4-d]pyrimidin-4-yl]amino}methyl)-4,6-dimethylpyridin-2-amine;
4,6-dimethyl-5-[({2-[(7-methylquinolin-3-yl)methyl]-2H-pyrazolo[3,4-d]pyrimidin-4-yl}amino)methyl]pyridin-2-amine;
1-{4-[(4-{[(6-chloro-2-fluoro-3-methoxyphenyl)methyl]amino}-2H-pyrazolo[3,4-d]pyrimidin-2-yl)methyl]phenyl}-1-(1-methyl-1H-pyrazol-3-yl)ethan-1-ol;
4,6-dimethyl-5-[({2-[(7-methylquinolin-2-yl)methyl]-2H-pyrazolo[3,4-d]pyrimidin-4-yl}amino)methyl]pyridin-2-amine;
4,6-dimethyl-5-[({2-[(2-methylquinolin-7-yl)methyl]-2H-pyrazolo[3,4-d]pyrimidin-4-yl}amino)methyl]pyridin-2-amine;
N-[(2-methoxy-3,5-dimethylpyridin-4-yl)methyl]-2-({4-[1-(1H-pyrazol-1-yl)ethyl]phenyl}methyl)-2H-pyrazolo[3,4-d]pyrimidin-4-amine;
N-[(2-fluoro-3,6-dimethoxyphenyl)methyl]-2-({4-[1-(1H-pyrazol-1-yl)ethyl]phenyl}methyl)-2H-pyrazolo[3,4-d]pyrimidin-4-amine;
1-{4-[(4-{[(6-chloro-2-fluoro-3-methoxyphenyl)methyl]amino}-2H-pyrazolo[3,4-d]pyrimidin-2-yl)methyl]phenyl}-1-(1,3-oxazol-2-yl)ethan-1-ol;
N-[(3-methoxy-2,6-dimethylphenyl)methyl]-2-({4-[1-(1H-pyrazol-1-yl)ethyl]phenyl}methyl)-2H-pyrazolo[3,4-d]pyrimidin-4-amine;
3-fluoro-4-methoxy-2-({[2-({4-[1-(1H-pyrazol-1-yl)ethyl]phenyl}methyl)-2H-pyrazolo[3,4-d]pyrimidin-4-yl]amino}methyl)benzonitrile;
N-[(6-chloro-2-fluoro-3-methoxyphenyl)methyl]-2-({4-[(dimethyl-4H-1,2,4-triazol-4-yl)methyl]phenyl}methyl)-2H-pyrazolo[3,4-d]pyrimidin-4-amine;
N-[(6-chloro-2-fluoro-3-methoxyphenyl)methyl]-2-{3-methoxy-4-(1H-pyrazol-1-ylmethyl)phenyl}-2H-pyrazolo[3,4-d]pyrimidin-4-amine;
N-[(6-chloro-2-fluoro-3-methoxyphenyl)methyl]-2-({4-[(2-methoxypyridin-3-yl)methyl]phenyl}methyl)-2H-pyrazolo[3,4-d]pyrimidin-4-amine;
3-({4-[(4-{[(6-chloro-2-fluoro-3-methoxyphenyl)methyl]amino}-2H-pyrazolo[3,4-d]pyrimidin-2-yl)methyl]phenyl}methyl)-1,2-dihydropyridin-2-one;

1-({4-[(4-{[(6-chloro-2-fluoro-3-methoxyphenyl)methyl] amino}-2H-pyrazolo[3,4-d]pyrimidin-2-yl)methyl] phenyl}methyl)-1,2-dihydropyrimidin-2-one;

N-[(7-chloroquinolin-2-yl)methyl]-2-({4-[1-(1H-pyrazol-1-yl)ethyl]phenyl}methyl)-2H-pyrazolo[3,4-d]pyrimidin-4-amine;

N-[(7-methoxyquinolin-2-yl)methyl]-2-({4-[1-(1H-pyrazol-1-yl)ethyl]phenyl}methyl)-2H-pyrazolo[3,4-d]pyrimidin-4-amine;

N-[(6-methoxy-1-benzofuran-2-yl)methyl]-2-({4-[1-(1H-pyrazol-1-yl)ethyl]phenyl}methyl)-2H-pyrazolo[3,4-d]pyrimidin-4-amine;

N-[(7-chloro-8-fluoroquinolin-2-yl)methyl]-2-({4-[1-(1H-pyrazol-1-yl)ethyl]phenyl}methyl)-2H-pyrazolo[3,4-d]pyrimidin-4-amine;

1-(1-{4-[(4-{[(6-chloro-2-fluoro-3-methoxyphenyl) methyl]amino}-2H-pyrazolo[3,4-d]pyrimidin-2-yl) methyl]phenyl}ethyl)-1,2-dihydropyridin-2-one;

N-[(6-chloro-1-benzofuran-2-yl)methyl]-2-({4-[1-(1H-pyrazol-1-yl)ethyl]phenyl}methyl)-2H-pyrazolo[3,4-d]pyrimidin-4-amine;

1-(1-{4-[(4-{[(5-chlorothiophen-2-yl)methyl]amino}-2H-pyrazolo[3,4-d]pyrimidin-2-yl)methyl] phenyl}ethyl)-1,2-dihydropyridin-2-one;

N-[(6-chloro-2-fluoro-3-methoxyphenyl)methyl]-2-({4-[1-(1H-pyrazol-1-yl)propyl]phenyl}methyl)-2H-pyrazolo[3,4-d]pyrimidin-4-amine;

1-(1-{4-[(4-{[(6-chloro-2-fluoro-3-methoxyphenyl) methyl]amino}-2H-pyrazolo[3,4-d]pyrimidin-2-yl) methyl]phenyl}propyl)-1,2-dihydropyridin-2-one;

N-{4-[(4-{[(6-chloro-2-fluoro-3-methoxyphenyl)methyl] amino}-2H-pyrazolo[3,4-d]pyrimidin-2-yl)methyl] phenyl}-N-methylpyridin-2-amine;

3-fluoro-4-methoxy-2-{[(2-{[5-methoxy-6-(pyrrolidin-1-yl)pyridin-3-yl]methyl}-2H-pyrazolo[3,4-d]pyrimidin-4-yl)amino]methyl}benzonitrile;

2-{[(2-{[6-(3,3-difluoropyrrolidin-1-yl)-4-methoxypyridin-3-yl]methyl}-2H-pyrazolo[3,4-d]pyrimidin-4-yl) amino]methyl}-3-fluoro-4-methoxybenzonitrile;

N-[(6-chloro-2-fluoro-3-methoxyphenyl)methyl]-2-{[3-methyl-4-(1H-pyrazol-1-ylmethyl)phenyl]methyl}-2H-pyrazolo[3,4-d]pyrimidin-4- amine;

N-[(6-chloro-2-fluoro-3-methoxyphenyl)methyl]-2-({3-methoxy-4-[(4-methyl-1H-pyrazol-1-yl)methyl] phenyl}methyl)-2H-pyrazolo[3,4-d]pyrimidin-4-amine;

N-[(6-chloro-2-fluoro-3-methoxyphenyl)methyl]-2-({4-[(6-methoxypyridin-2-yl)methyl]phenyl}methyl)-2H-pyrazolo[3,4-d]pyrimidin-4-amine;

N-[(6-chloro-2-fluoro-3-methoxyphenyl)methyl]-2-[(4-{[6-(morpholin-4-yl)pyridin-2-yl]methyl}phenyl) methyl]-2H-pyrazolo[3,4-d]pyrimidin-4-amine; and 6-({4-[(4-{[(6-chloro-2-fluoro-3-methoxyphenyl) methyl]amino}-2H-pyrazolo[3,4-d]pyrimidin-2-yl) methyl]phenyl}methyl)-N,N-dimethylpyridin-2-amine;

or a pharmaceutically acceptable salt thereof.

36. The compound of claim 1, wherein $L^1$ is —$CHR^{70}$—; and $L^3$ is —$CHR^{70}$—, wherein each $R^{70}$ is hydrogen.

37. A pharmaceutically acceptable composition comprising a compound of claim 1 and at least one pharmaceutically acceptable excipient.

38. A pharmaceutically acceptable composition comprising a compound of claim 34 and at least one pharmaceutically acceptable excipient.

39. A method of inhibiting plasma kallikrein activity in a subject, the method comprising administering to the subject a therapeutically effective amount of the compound of claim 1.

40. A method of treating hereditary angioedema comprising administering to a patient in need thereof a therapeutically effective amount of the compound of claim 1.

* * * * *